US012215093B2

(12) United States Patent
Bravo et al.

(10) Patent No.: US 12,215,093 B2
(45) Date of Patent: *Feb. 4, 2025

(54) BICYCLIC CARBOXAMIDES AND METHODS OF USE THEREOF

(71) Applicant: Tempest Therapeutics, Inc., Brisbane, CA (US)

(72) Inventors: Yalda Bravo, San Diego, CA (US); Austin Chih-Yu Chen, San Marcos, CA (US); Jinyue Ding, Burnaby (CA); Robert Gomez, North Vancouver (CA); Heather Lam, Scarborough (CA); Joe Fred Nagamizo, San Diego, CA (US); Renata Marcella Oballa, Coquitlam (CA); David Andrew Powell, Vancouver (CA); Tao Sheng, Coquitlam (CA)

(73) Assignee: TEMPEST THERAPEUTICS, INC., Brisbane, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/467,022

(22) Filed: Sep. 14, 2023

(65) Prior Publication Data

US 2024/0150316 A1 May 9, 2024

Related U.S. Application Data

(63) Continuation of application No. 17/847,811, filed on Jun. 23, 2022, now Pat. No. 11,795,156, which is a continuation of application No. 17/070,554, filed on Oct. 14, 2020, now Pat. No. 11,472,789, which is a continuation of application No. 16/387,294, filed on Apr. 17, 2019, now Pat. No. 10,968,201.

(60) Provisional application No. 62/746,843, filed on Oct. 17, 2018, provisional application No. 62/659,068, filed on Apr. 17, 2018.

(51) Int. Cl.
| | |
|---|---|
| *C07D 231/56* | (2006.01) |
| *C07D 209/42* | (2006.01) |
| *C07D 401/10* | (2006.01) |
| *C07D 403/10* | (2006.01) |
| *C07D 405/12* | (2006.01) |
| *C07D 417/10* | (2006.01) |
| *C07D 471/04* | (2006.01) |

(52) U.S. Cl.
CPC ......... *C07D 401/10* (2013.01); *C07D 209/42* (2013.01); *C07D 231/56* (2013.01); *C07D 403/10* (2013.01); *C07D 405/12* (2013.01); *C07D 417/10* (2013.01); *C07D 471/04* (2013.01)

(58) Field of Classification Search
CPC .................................................. C07D 231/56
See application file for complete search history.

(56) References Cited

U.S. PATENT DOCUMENTS

| | | | |
|---|---|---|---|
| 7,029,674 B2 | 4/2006 | Carreno et al. |
| 7,488,802 B2 | 2/2009 | Collins et al. |
| 7,521,051 B2 | 4/2009 | Collins et al. |
| 7,803,841 B2 | 9/2010 | Oxford et al. |
| 8,008,449 B2 | 8/2011 | Korman et al. |
| 8,158,671 B2 | 4/2012 | Boyd et al. |
| 8,217,149 B2 | 7/2012 | Irving et al. |
| 8,354,509 B2 | 1/2013 | Carven et al. |
| 8,383,796 B2 | 2/2013 | Korman et al. |
| 8,552,154 B2 | 10/2013 | Freeman et al. |
| 8,617,546 B2 | 12/2013 | Kang et al. |
| 8,685,394 B2 | 4/2014 | Jure-Kunkel |
| 8,709,417 B2 | 4/2014 | Allison et al. |
| 10,968,201 B2 | 4/2021 | Bravo et al. |
| 11,066,405 B2 | 7/2021 | Bravo et al. |
| 11,472,789 B2 | 10/2022 | Bravo et al. |
| 11,638,704 B2 | 5/2023 | Bravo et al. |
| 11,738,009 B2 | 8/2023 | Bravo et al. |
| 11,795,156 B2 | 10/2023 | Bravo et al. |
| 2011/0028463 A1 | 2/2011 | Nozawa et al. |

FOREIGN PATENT DOCUMENTS

| | | |
|---|---|---|
| EP | 2172447 A1 | 4/2010 |
| EP | 2277858 A1 | 1/2011 |
| JP | 2007023028 A | 2/2007 |
| JP | 2017528477 A | 9/2017 |
| WO | WO-2007143825 A1 | 12/2007 |
| WO | WO-2008104055 A1 | 9/2008 |
| WO | WO-2009005076 A1 | 1/2009 |
| WO | WO-2009139373 A1 | 11/2009 |
| WO | WO-2010121382 A1 | 10/2010 |
| WO | WO-2010121385 A1 | 10/2010 |

(Continued)

OTHER PUBLICATIONS

US 11,440,897 B2, 09/2022, Bravo et al. (withdrawn)
No new references cited by the Examiner.*
Abraham et al. Cyclooxygenase-2 selectivity of non-steroidal anti-inflammatory drugs and the risk of myocardial infarction and cerebrovascular accident. Alimet. Pharmacal. Ther. 25:913-924 (2007).
Adams et al. Big opportunities for small molecules in immuno-oncology. Nat Rev Drug Discov. 14:603-622 (2015).
Albu et al. EP4 Antagonism by E7046 diminishes Myeloid immunosuppression and synergizes with Treg-reducing IL-2-Diphtheria toxin fusion protein in restoring anti-tumor immunity. Oncoimmunology 6:e1338239 (2017).
Arosh et al. Molecular and preclinical basis to inhibit PGE2 receptors EP2 and EP4 as a novel nonsteroidal therapy for endometriosis. PNAS USA 112:9716-9721 (2015).

(Continued)

*Primary Examiner* — Shawquia Jackson
(74) *Attorney, Agent, or Firm* — WILSON SONSINI GOODRICH & ROSATI

(57) ABSTRACT

Compounds, compositions and methods are provided for modulating the activity of $EP_2$ and $EP_4$ receptors, and for the treatment, prevention and amelioration of one or more symptoms of diseases or disorders related to the activity of $EP_2$ and $EP_4$ receptors. In certain embodiments, the compounds are antagonists of both the $EP_2$ and $EP_4$ receptors.

18 Claims, 5 Drawing Sheets

(56) References Cited

FOREIGN PATENT DOCUMENTS

| | | |
|---|---|---|
| WO | WO-2012024376 A1 | 2/2012 |
| WO | WO-2017103851 A1 | 6/2017 |
| WO | WO-2018008711 A1 | 1/2018 |
| WO | WO-2018195123 A1 | 10/2018 |
| WO | WO-2019204523 A1 | 10/2019 |

OTHER PUBLICATIONS

Arthritis: Causes, Signs, and Diagnosis [online] retrieved from the internet on Aug. 29, 2021; URL: https://www.healthline.com/health/arthritis.
Bae. Cancer Targeted Drug Delivery. Springer: New York (p. v) (2013).
Banker et al. Modern Pharmaceutics. 3rd ed. Marcel Dekker, New York (pp. 451 & 596) (1996).
Beaumont et al. Design of Ester Prodrugs to Enhance Oral Absorption of Poorly Permeable Compounds: Challenges to the Discovery Scientist. Current Drug Metabolism 4:461-485 (2003).
Benz. The Jeremiah Metzger Lecture Cancer in the Twenty-First Century: An Inside View From an Outsider Transactions of the American Clinical and Climatological Association 128:275-297 (2017).
Berge et al. Pharmaceutical Salts. Journal of Pharmaceutical Sciences 66(1):1-19 (Jan. 1977).
Braun et al. A two-step induction of indoleamine 2,3 dioxygenase (IDO) activity during dendritic-cell maturation. Blood 106(7):2375-2381 (2005).
Cancer [online], retrieved from the Internet on Jul. 6, 2007, URL: http://www.nlm.nih.gov/medlineplus/cancer.html.
Cao et al. Prostaglandin receptor EP4 in abdominal aortic aneurysms. Am J Pathol 181:313-321 (2012).
Chandrasekhar et al. Analgesic and anti-inflammatory properties of novel, selective, and potent EP4 receptor antagonists. Pharmacal Res Perspect. 5(3):e00316 (2017).
Chang et al. Role of prostaglandin E2-dependent angiogenic switch in cyclooxygenase 2-induced breast cancer progression. PNAS USA 101:591-596 (2004).
Chen et al. A novel antagonist of the prostaglandin E(2) EP(4) receptor inhibits Th1 differentiation and Th17 expansion and is orally active in arthritis models. British J. Pharmacol. 160:292 (2010).
Chen et al. Cancer/stroma interplay via cyclooxygenase-2 and indoleamine 2,3-dioxygenase promotes breast cancer progression. Breast Cancer Research 16:410-424 (2014).
Cipollone et al. Association between prostaglandin E receptor subtype EP4 overexpression and unstable phenotype in atherosclerotic plaques in human. Ateriosler Thromb Vasc Biol 25:1925-1931 (2005).
Clark et al. MF498 [N-{[4-(5,9-Diethoxy-6-oxo-6,8-dihydro-7H-pyrrolo[3,4-g]quinolin-7-yl)-3-methylbenzyl]sulfonyl}-2-(2-methoxyphenyl)acetamide], a selective E prostanoid receptor 4 antagonist, relieves joint inflammation and pain in rodent models of rheumatoid and osteoarthritis. J Pharmacal Exp Ther. 325:425-434 (2008).
Colucci et al. Discovery of 4-{1[({144-(trifluoronnethyl)benzy11-1H-indo1-7-yllcarbonyl) amino]cyclopropyl}benzoic acid (MF-766), a highly potent and selective EP4 antagonist for treating inflammatory pain. Bioorganic & Medicinal Chemistry Letters 20(12):3760-3763 (2010).
Damasio. Alzheimer's Disease and Related Dementias. Cecil Textbook of Medicine, 20th edition, 2:1992-1996 (1996).
Damia et al. Contemporary pre-clinical development of anticancer agents—What are the optimal preclinical models? European Journal of Cancer 45:2768-2781 (2009).
Doherty et al. Proneoplastic effects of PGE mediated by EP4 receptor in colorectal cancer. BMC Cancer 9:207 (2009).
Dolgin. Oncogene-specific advocacy groups bring a patient-centric perspective to studies of lung cancer. Nature 587:S16-S17 (2020).
Dounay et al. Challenges and Opportunities in the Discovery of New Therapeutics Targeting the Kynurenine Pathway. J. Med. Chem 58:8762-8782 (2015).
FDA mulls drug to slow late-stage Alzheimer's [online], [retrieved on Sep. 23, 2003]. Retrieved from the internet, URL;http://www.cnn/com/2003/HEALTH/conditions/09/24/alzheimers.drug.ap/index.html.
Ferreira et al. Chapter 6: The Importance of Cancer Cell Lines as in vitro Models in Cancer Methylome Analysis and Anticancer Drugs Testing. Oncogenomics and Cancer Proteomics—Novel Approaches in Biomarkers Discovery and Therapeutic Targets in Cancer Intech pp. 140-166 (2013).
Flesch et al. Novel prostaglandin receptor modulators—Part II: EP receptor modulators; a patent review (2002-2012). Expert Opin Ther Pat 23(2):233-267 (2013).
Freireich et al. Quantitative comparison of toxicity of anticancer agents in mouse, rat, hamster, dog, monkey, and man. Cancer Chemother. Rep. 50:219-244 (1966).
Fulton et al. Targeting Prostaglandin E EP Receptors to Inhibit Metastasis. Cancer Research 66(20):9794-9797 (2006).
Gabitass et al. Elevated myeloid-derived suppressor cells in pancreatic, esophageal and gastric cancer are an independent prognostic factor and are associated with significant elevation of the Th2 cytokine interleukin-13. Cancer Immunol. Immunother. 60:1419-1430 (2011).
Golub et al.; Molecular classification of cancer: class discovery and class prediction by gene expression monitoring. Science. 286(5439):531-537 (1999).
Hata et al. Pharmacology and signaling of prostaglandin receptors: multiple roles in inflammation and immune modulation. Pharmacal. Ther. 103:147-166 (2004).
Hayat. Autophagy Cancer, Other Pathologies, Inflammation, Immunity, Infection, and Aging. Academic Press: Sand Diego 5:xxi (2015).
Hizaki et al. Abortive expansion of the cumulus and impaired fertility in mice lacking the prostaglandin E receptor subtype EP(2). PNAS USA 96:10501-10506 (1999).
Holt et al. Prostaglandin E (PGE) suppresses natural killer cell function primarily through the PGE receptor EP4. Cancer Immunology Immunotherapy 60(11):1577-1586 (2011).
Hoshino et al. Improvement of cognitive function in Alzheimer's disease model mice by genetic and pharmacological inhibition of the EP(4) receptor. J Neurochem. 120:795-805 (2012).
IUPAC-IUB Comm. Biochem. Nomenclature. IUPAC-IUB [International Union of Pure and Applied Chemistry-International Union of Biochemistry] Commission of Biochemical Nomenclature. Abbreviated nomenclature of synthetic polypeptides (polymerized amino acids). Revised recommendations (1971). Biochemistry 11:942-944 (1972).
Jiang et al. Inhibition of the prostaglandin receptor EP2 following status epilepticus reduces delayed mortality and brain inflammation. PNAS USA 110:3591-3596 (2013).
Jiang et al. Prostaglandin receptor EP2 in the crosshairs of anti-inflammation, anti-cancer, and neuroprotection. Trends in Pharm Sci. 34:413-423 (2013).
Jiang et al. Small molecule antagonist reveals seizure-induced mediation of neuronal injury by prostaglandin E2 receptor subtype EP2. PNAS USA 109:3149-3154 (2012).
Jochems et al. The IDO1 selective inhibitor epacadostat enhances dendritic cell immunogenicity and lytic ability of tumor antigen-specific T cells. Oncotarget 7:37762-37772 (2016).
Johnson et al., Relationships between drug activity in NCI preclinical in vitro and in vivo models and early clinical trials. British Journal of Cancer 84(10):1424-1431 (2001).
Kalinski. Regulation of immune responses by prostaglandin E2. J Immunol. 188:21-28 (2012).
Kundu et al. Prostaglandin E receptor EP4 is a therapeutic target in breast cancer cells with stem-like properties. Breast Cancer Research and Treatment 143(1):19-31 (2014).
Lala et al. Role of nitric oxide in tumor progression: Lessons from experimental tumors. Cancer and Metastasis Reviews 17(1):91-106 (1998).

(56) References Cited

OTHER PUBLICATIONS

Layzer. Section Five—Degenerative Diseases of the Nervous System. Cecil Textbook of Medicine, 20th edition, 2:2050-2057 (1996).
Ledford. US cancer institute overhauls cell lines. Nature 530:391 (Feb. 25, 2016).
Legler et al. Prostaglandin E2 at new glance: novel insights in functional diversity offer therapeutic chances. Int. J. Biochem. Cell Biol. 42:198-201 (2010).
Liu et al. Highly efficient route to fused polycyclic aromatics via palladium-catalyzed aryne annulation by aryl halides. J. Org. Chem. 72(1):223-232 (2007).
Ma et al. Definition of Prostaglandin E2-EP2 Signals in the Colon Tumor Microenvironment That Amplify Inflammation and Tumor Growth. Cancer Res. 75:2822-2832 (2015).
Ma et al. Prostaglandin E receptor EP1 suppresses breast cancer metastasis and is linked to survival differences and cancer disparities. Mol. Cancer Res. 8:1310-1318 (2010).
Mahic et al. FOXP3+CD4+CD25+ adaptive regulatory T cells express cyclooxygenase-2 and suppress effector T cells by a prostaglandin E2-dependent mechanism. J. Immunol. 177:246-254 (2011).
Maley et al. Frontiers in Cancer Research Springer pp. 18-19 (2016).
Mao et al. Inhibition of tumor-derived prostaglandin-e2 blocks the induction of myeloid-derived suppressor cells and recovers natural killer cell activity. Clin. Cancer Res. 20:4096-4106 (2014).
Marcias-Perez et al. Mouse EP3 α, β, and γ Receptor Variants Reduce Tumor Cell Proliferation and Tumorigenesis in Vivo. J. Bio. Chem. 283:12538-12545 (2008).
Markovič et al. Structural features of subtype-selective EP receptor modulators. Drug Discovery Today 22(1):57-71 (2016).
Matsumoto et al. Diversification of cyclooxygenase-2-derived prostaglandins in ovulation and implantation. Biol Reprod 64:1557-1565 (2001).
Naing et al. Preclinical investigations and a first-inhuman phase I trial of M4112, the first dual inhibitor of indoleamine 2,3-dioxygenase 1 and tryptophan 2,3-dioxygenase 2, in patients with advanced solid tumors. Journal for ImmunoTherapy of Cancer 8:e000870 (2020).
Nakanishi et al. COX-2 inhibition alters the phenotype of tumor-associated macrophages from M2 to M1 in ApcMin/+ mouse polyps. Carcinogenesis. 32:1333-1339 (2011).
Ocana et al. Preclinical development of molecular targeted agents for cancer. Nat Rev Clin Oncol 8:200-209 (2011).
Ochs et al. Tryptophan-2,3-dioxygenase is regulated by prostaglandin E2 in malignant glioma via a positive signaling loop involving prostaglandin E receptor-4. J. Neurochem. 136:1142-1154 (2016).
PCT/US2018/028034 International Search Report and Written Opinion dated Jul. 6, 2018.
PCT/US2019/027992 International Search Report and Written Opinion dated Jul. 5, 2019.
Platten et al., Cancer immunotherapy by targeting IDO1/TDO and their downstream effectors. Front Immunol. 5:673 (2015).
Prasanna et al. Ocular pharmacokinetics and hypotensive activity of PF-04475270, an EP4 prostaglandin agonist in preclinical models. Experimental Eye Research 89:608-617 (2009).
Qian et al. Macrophage diversity enhances tumor progression and metastasis. Cell. 141:39-51 (2010).
Rautio et al. Prodrugs: design and clinical applications. Nat Rev Drug Discov 7(3):255-270 (2008).

Ravin. Chapter 76: Preformulation. Remington's Pharmaceutical Sciences, 17th ed., Mack Publishing Company, Easton, Pa. (pp. 1409-1423) (1985).
Sharma et al. Cell line-based platforms to evaluate the therapeutic efficacy of candidate anticancer agents. Nature Reviews Cancer 10:241-253 (Apr. 2010).
Shoji et al. Downregulation of prostaglandin E receptor subtype EP3 during colon cancer development. Gut 53:1151-1158 (2004).
Sonoshita et al. Acceleration of intestinal polyposis through prostaglandin receptor EP2 in Apc(Delta 716) knockout mice. Nat. Med. 7:1048-1051 (2001).
Stepan et al., Application of the bicyclo[1.1.1]pentane motif as a nonclassical phenyl ring bioisostere in the design of a potent and orally active γ-secretase inhibitor, J. Med. Chem., 55(7):3414-24 (2012).
Sung et al. Lack of expression of the EP2 but not EP3 receptor for prostaglandin E2 results in suppression of skin tumor development. Cancer Res. 65:9304-9311 (2005).
Sung et al. Overexpression of the prostaglandin E2 receptor EP2 results in enhanced skin tumor development. Oncogene 25:5507-5516 (2006).
Take et al. Prostaglandin E Receptor 4 Antagonist in Cancer Immunotherapy: Mechanisms of Action. Front Immunol 11:324 (2020).
Terada et al. Identification of EP4 as a Potential Target for the Treatment of Castration—Resistant Prostate Cancer Using a Novel Xenograft Model. Cancer Research 70(4):1606-1615 (2010).
U.S. Appl. No. 16/387,294 Office Action dated Mar. 25, 2020.
U.S. Appl. No. 16/387,294 Office Action dated Oct. 4, 2019.
U.S. Appl. No. 16/605,408 Office Action dated Aug. 11, 2022.
U.S. Appl. No. 16/880,756 Office Action dated Jan. 13, 2021.
U.S. Appl. No. 16/880,756 Office Action dated Oct. 20, 2020.
U.S. Appl. No. 17/070,554 Office Action dated Sep. 2, 2021.
U.S. Appl. No. 17/354,010 Office Action dated Aug. 30, 2022.
U.S. Appl. No. 17/847,811 Office Action dated Feb. 27, 2023.
Wang et al. Prostaglandin E Promotes Colorectal Cancer Stem Cell Expansion and Metastasis in Mice. Gastroenterology 149(7):1884-1895 (2015).
Wang et al. The Role of Prostaglandin E(2) in Tumor-Associated Immunosuppression. Trends Mol Med 22:1-3 (2016).
Whiteside et al. Inhibiting the inhibitors: evaluating agents targeting cancer immunosuppression. Expert Opin Biol Ther 10:1019-1035 (2010).
Wiemer et al. A live imaging cell motility screen identifies prostaglandin E2 as a T cell stop signal antagonist. J. Immunology 187:3663 (2011).
Wolff. Burger's Medicinal Chemistry and Drug Discovery. 5th Ed. Part 1, pp. 975-977 (1995).
Yamane et al. Prostaglandin E(2) receptors, EP2 and EP4, differentially modulate TNF-alpha and IL-6 production induced by lipopolysaccharide in mouse peritoneal neutrophils. Biochem. Biophys. Res. Commun. 278:224-228 (2000).
Yang et al. Cancer-associated immunodeficiency and dendritic cell abnormalities mediated by the prostaglandin EP2 receptor. J. Clin. Invest. 111:727-735 (2003).
Zelenay et al. Cyclooxygenase-Dependent Tumor Growth through Evasion of Immunity. Cell 162:1257-1270 (2015).
Cancer [online], retrieved from the Internet on May 3, 2024, URL: http://www.https://en.wikipedia.org/wiki/Cancer.

\* cited by examiner

Start of dosing Day 10 post tumor cell injection

BICYCLIC CARBOXAMIDES AND METHODS OF USE THEREOF

RELATED APPLICATIONS

This application is a continuation of Ser. No. 17/847,811, filed Jun. 23, 2022, which is a continuation of U.S. application Ser. No. 17/070,554, filed Oct. 14, 2020, now U.S. Pat. No. 11,472,789, issued Oct. 18, 2022, which is a continuation of U.S. application Ser. No. 16/387,294, filed Apr. 17, 2019, now U.S. Pat. No. 10,968,201, issued Apr. 6, 2021, which claims the benefit of U.S. Provisional Application Nos. 62/659,068 filed Apr. 17, 2018, and 62/746,843 filed Oct. 17, 2018; the disclosures of the foregoing applications are incorporated herein by reference in their entireties

TECHNICAL FIELD

Compounds, compositions and methods are provided for modulating the activity of $EP_2$ and $EP_4$ receptors, and for the treatment, prevention and amelioration of one or more symptoms of diseases or disorders mediated by the activity of $EP_2$ and $EP_4$ receptors. In certain embodiments, the compounds are antagonists of both the $EP_2$ and $EP_4$ receptors.

BACKGROUND

Prostaglandin $E_2$ ($PGE_2$) is an endogenous bioactive lipid that, through its activation of transmembrane G-protein-coupled receptors (GPCRs) $EP_1$, $EP_2$, $EP_2$ and/or $EP_4$, can elicit a wide range of context-dependent biological responses (Legler, D. F. et al., *Int. J. Biochem. Cell Biol.* 2010, 42, p. 198-201). In particular, while $PGE_2$ acutely favors a pro-inflammatory immune response, persistent and sustained activation of EP receptors in the tumor microenvironment by $PGE_2$ (which is produced in significantly greater quantities by tumor cells (Ochs et al., *J. Neurochem.* 2016, 136, p. 1142-1154; Zelenay, S. et al., *Cell* 2015, 162, p. 1257-1270)), would instead promote the accumulation and enhance the activity of multiple immuno-suppressor cells. These include type-2 tumor associated macrophages (TAMs) (Nakanishi Y et al., *Carcinogenesis.* 2011, 32, p. 1333-1339), $T_{reg}$ cells (Mahic, M. et al., *J. Immunol.* 2011, 177, p. 246-254) and myeloid-derived suppressor cells (MDSCs) (Mao, et al., *Clin. Cancer Res.* 2014, 20, p. 4096-4106; Whiteside, T. L., *Expert Opin. Bio. Th.* 2010, 10, p. 1019-1035). In addition, $PGE_2$ has been reported to induce immune tolerance by inhibiting the accumulation of antigen-presenting dendritic cells (DCs) in tumors, as well as suppressing tumor-infiltrating DC activation (Wang et al., *Trends in Molecular Medicine* 2016, 22, p. 1-3). All these $PGE_2$-mediated immune cell repolarization would conspire to facilitate the escape of tumor cells from immune surveillance (Adams et al., *Nat Rev Drug Discov.* 2015, 14, p. 603-622). Indeed, one of the major hallmarks of an immunosuppressive tumor microenvironment is the presence of a large amount of MDSCs and TAMs which, in turn, are significantly associated with poor overall survival in patients with gastric, ovarian, breast, bladder, hepatocellular carcinoma (HCC), head-and-neck, and other types of cancers (Qian et al., *Cell.* 2010, 141, p. 39-51; Gabitass et al., *Cancer Immunol. Immunother.* 2011, 60, p. 1419-1430).

While the relative contributions of each of the EP receptor subtypes in mediating the plethora of immune-suppressive effects of $PGE_2$ have remained an area of active research (Kalinski, P. *J Immunol.* 2012, 188, p. 21-28), there is a general consensus that the $EP_4$ receptor; which is highly expressed in myeloid cells, tumor cells, and T lymphocytes, plays an important role in enhancing various tumor survival pathways and in blunting both innate and adaptive anti-tumor immune responses (Albu, D. I. et al., *Oncoimmunology* 2017, 6, e1338239, and the references therein). One such tumor pro-survival pathway was recently revealed to be $EP_4$-mediated upregulation of indoleamine 2,3-dioxygenase (IDO) and tryptophan 2,3-deoxygenase (TDO) activity; via its stimulation by tumor-secreted $PGE_2$, in the tumor microenvironment (Ochs et al., *J. Neurochem.* 2016, 136, p. 1142-1154; Chen. J.-Y. et al., *Breast Cancer Research.* 2014, 16, p. 410-424). Since tryptophan; the substrate of the IDO and TDO enzymes, is essential for the proliferation and activation of cytotoxic $T_{eff}$ cells and kynurenine; the product of the IDO and TDO enzymes, is essential for the proliferation and activation of immunosuppressive $T_{reg}$ cells (Dounay, A. B. et al., *J. Med. Chem.* 2015, 58, p. 8762-8782), inhibition of the IDO and/or TDO activity represents a promising avenue for the treatment of various cancers (Jochems, C. et al., *Oncotarget* 2016, 7, p. 37762-37772). In fact, significantly increased overall response rates in patients with advanced stage IIIB or IV melanoma have been reported with epacadostat, a potent and selective IDO inhibitor from Incyte, when used in combination with pembrolizumab. Indeed, in light of this and other observations and studies, selective $EP_4$-antagonists are being evaluated for the treatment of advanced cancer; both as a single agent and in combination with other anti-cancer therapies.

It has been established that $PGE_2$-stimulation of $EP_2$ plays an important role in the regulation of maternal-fetal tolerance (Matsumoto et al., *Biology of Reproduction* 2001, 64, p. 1557-1565; Hizaki et al., *Proc. Natl. Acad. Sci. U.S.A.* 1999, 96, p. 10501-10506) and $EP_2$-selective antagonists are currently in development for use as an on-demand contraception (Lindenthal, B. et al., U.S. Pat. No. 9,655,887). More recently, research has also begun to unravel how tumor cells can hijack the very same $PGE_2$-$EP_2$ machinery as a way of creating an immune-tolerant environment within which tumor cells can proliferate and thrive (Jiang, J and Dingledine, R. *Trends in Pharm Sci.* 2013, 34, p. 413-423, and the reference therein). For example, it has been shown that induction of IDO activity during dendritic cell maturation is driven mostly via $EP_2$ (Braun, D. et al., *Blood* 2005, 106, p. 2375-2381) and that $EP_2$-activation downregulates TNF-α production by immune cells such as neutrophils and macrophages (Yamane, et al., *Biochem. Biophys. Res. Commun.* 2000, 278. p. 224-228), as well as IFNγ synthesis by natural killer T-cells (Oxford. A. W. et al., U.S. Pat. No. 7,803,841). Indeed, genetic ablation of the $EP_2$ receptor has been demonstrated to attenuate tumor growth and prolong survival in syngeneic mouse tumor models (Yang, L. et al., *J. Clin. Invest.* 2003, 111, p. 727-735; Sonoshita, M. et al. *Nat. Med.* 2001, 7, p. 1048-1051; Sung Y.-M. et al., *Cancer Res.* 2005, 65, p. 9304-9311; Sung Y.-M. et al., *Oncogene* 2006, 25, p. 5507-5516; Narumiya, S. et al., *Cancer Res.* 2015, 75, p. 2822-2832).

While $EP_2$ and $EP_4$ both signal via stimulatory G proteins to which they are coupled, $EP_1$ and $EP_3$ receptors, on the other hand, are both coupled to inhibitory G proteins (Hata. A. N. Breyer, R. M. *Pharmacol. Ther.* 2004, 103, p. 147-166). Indeed, $EP_1$ has been reported to function as a metastasis suppressor and that loss of nuclear $EP_1$ expression in breast cancer patients is associated with poorer overall prognosis (Ma, et al., *Mol. Cancer Res.* 2010, 8, p. 1310-1318). Furthermore, $EP_3$ expression is found to be decreased in mice and human colon and breast cancer when compared with normal healthy tissue (Shoji, Y. et al., *Gut* 2004, 53, p. 1151-1158; Chang, S. H. et al., *Proc. Natl. Acad. Sci. U.S.A.* 2004, 101, p. 591-596), and that increasing $EP_3$ expression in these very same tumor cells actually reduced their tumorigenic potential in vivo (Marcias-Perez, I. M. et al., *J. Bio. Chem.* 2008, 283, p. 12538-12545). Therefore, it serves to reason that the selective and simultaneous blockade of $EP_2$ and $EP_4$ signaling by a small molecule antagonist would constitute the most effective therapeutic strategy for cancer treatment vs a non-selective blockade of $PGE_2$ production by way of COX-2 inhibitors; especially in recognition of the latter's detrimental cardiovascular and cerebrovascular side effects (Abraham, N. S. et al., *Alimet. Pharmacol. Ther.* 2007, 25, p. 913-924).

Selective and dual $EP_2$ and/or $EP_4$ antagonists may be useful in the treatment of other diseases and disorders. $EP_4$ antagonists have been shown to be effective in relieving joint inflammation and pain in rodent models of rheumatoid arthritis and ostcoarthritis (Clark P. et al., *J Pharmacol Exp Ther.* 2008, 325, p. 425-434). $EP_4$ antagonists have also been shown to be efficacious in rodent models of autoimmune disease (Chandrasekhar S. et al., *Pharmacol Res Perspect.* 2017, 5(3), p. e00316).

As $PGE_2$ is a major prostaglandin which has been shown to mediate proinflammatory functions through $EP_2$ receptors, $EP_2$ antagonists may show utility as a therapeutic agent for certain chronic inflammatory diseases, particularly inflammatory neurodegenerative diseases such as epilepsy, Alzheimer's disease (AD), Parkinson's disease (PD), amyotrophic lateral sclerosis (ALS) and traumatic brain injury (TBI) (Jiang J. et al., *Proc. Natl. Acad. Sci. U.S.A.* 2012, 109, p. 3149-3154; Jiang J. et al., *Proc. Natl. Acad. Sci. U.S.A.* 2013, 110, p. 3591-3596). The $EP_4$ antagonist ONO-AE3-208 decreased amyloid-β and improved behavioral performance in a murine model of Alzheimer's disease (Hoshino T. et al., *J Neurochem.* 2012, 120, p. 795-805).

$EP_2$ and $EP_4$ are highly expressed in endometriosis and there is data that suggests that $EP_2/EP_4$ inhibition may serve as nonsteroidal therapy for endometriosis (Arosh J. A. et al., *Proc. Natl. Acad. Sci. U.S.A.* 2015, 112, p. 9716-9721).

The $EP_4$ pathway is also implicated in vascular disease. The $EP_4$ antagonist ONO-AE3-208 was found to decrease vascular inflammation and to reduce the incidence and severity of abdominal aortic aneurism in the angiotensin 11 mouse model (Cao R. et al., *Am J Pathol* 2012 181, p. 313-321). $EP_4$ overexpression has been associated with enhanced inflammatory reaction in atherosclerotic plaques and $EP_4$ antagonism has been suggested as a therapy for atherosclerosis and the prevention of acute ischemic syndromes (Cipollone F. et al., *Arteriosclerosis, Thrombosis, and Vascular Biology* 2005, 25, p. 1925-1931).

There remains a need to provide novel classes of compounds that are useful in the treatment of EP2 and EP4 receptor-mediated diseases. Such classes of compounds have the potential to be useful in the treatment of inflammatory disease, autoimmune disease, neurodegenerative disease, cardiovascular disease and cancer.

SUMMARY

Provided herein are compounds of Formula (I) or a pharmaceutically acceptable salt, solvate, solvate of the salt, hydrate, single stereoisomer, mixture of stereoisomers, racemic mixture of stereoisomers, or prodrug thereof. In certain embodiments, the compounds are modulators of both the $EP_2$ and $EP_4$ receptors. In certain embodiments, the compounds are useful as potent and selective antagonists of both the $EP_2$ and $EP_4$ receptors, and in this regard, will confer therapeutic benefits associated with the selective blockade of $PGE_2$-mediated signaling.

In certain embodiments, provided herein are compound having the Formula (I), or a pharmaceutically acceptable salt, solvate, solvate of the salt, hydrate, a single stereoisomer, a mixture of stereoisomers, a racemic mixture of stereoisomers, or prodrug thereof:

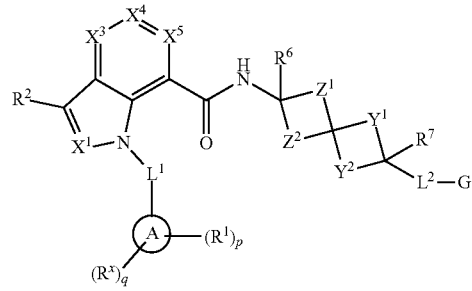

Formula (I)

wherein:
  $X^1$ is N or CH;
  $X^3$ is N or $CR^3$;
  $X^4$ is N or $CR^4$;
  $X^5$ is N or $CR^5$;
  wherein no more than two of $X^3$, $X^4$ and $X_5$ are N;
  $L^1$ is —$(CR^b{}_2)_t$—;
  Ring A is optionally deuterated aryl;
  each $R^1$ is independently $C_2$-$C_9$ alkyl, $C_2$-$C_9$ alkenyl, $C_2$-$C_9$ alkynyl, cycloalkyl, heterocyclyl, aryl, heteroaryl, or —$OR^{8'}$, wherein $C_2$-$C_9$ alkyl, $C_2$-$C_9$ alkenyl, $C_2$-$C_9$ alkynyl, cycloalkyl, heterocyclyl, aryl, and heteroaryl are optionally deuterated and optionally substituted with one, two, or three $R^y$;
  or two $R^1$ substituents on adjacent atoms of Ring A are taken together with the atom to which they are attached to form an aromatic or non-aromatic ring containing 0-2 heteroatoms selected from the group consisting of —O—, =N—, —$NR^{10}$—, —S—, and —$S(O)_2$—, wherein the aromatic or non-aromatic ring is optionally deuterated and optionally substituted with one, two, or three $R^y$;
  each $R^{8'}$ is independently hydrogen, alkyl, haloalkyl, cycloalkyl, heterocyclyl, aryl, or heteroaryl, wherein cycloalkyl, heterocyclyl, aryl, and heteroaryl are optionally substituted with one, two, or three groups selected from halogen, alkyl, and haloalkyl;
  each $R^y$ is independently alkyl, haloalkyl, cycloalkyl, cycloalkylalkyl, heterocyclyl, heterocyclylalkyl, halogen, —$OR^8$, —$NR^8R^9$, —CN, —$C(O)R^{11}$, —$C(O)NR^8R^9$, —$NR^8C(O)R^{11}$, —$NR^8C(O)OR^9$, —$NR^{10}C(O)NR^8R^9$, —$OC(O)NR^8R^9$, —$S(O)_2R^{11}$, —$S(O)R^{11}$, —$SR^8$, —$S(O)_2NR^8R^9$, —$S(O)NR^8R^9$, —$NR^8S(O)R^{11}$, —$NR^8S(O)_2R^{11}$, or —$NR^{10}S(O)_2NR^8R^9$; wherein alkyl is optionally substituted with —$OR^8$ or —$NR^8R^9$ and wherein cycloalkyl and heterocyclyl are optionally substituted with one, two, or three groups selected from halogen, alkyl, and haloalkyl;
  each $R^x$ is independently halogen, methyl, $C_1$haloalkyl, or —CN;

$R^2$, $R^3$, $R^4$, and $R^5$ are each independently hydrogen, alkyl, halogen, —$OR^8$, —$NR^8R^9$, —$SR^8$, —$S(O)R^{11}$, —$S(O)_2R^{11}$, —CN, cycloalkyl, or haloalkyl;

$R^6$ is hydrogen, deuterium, alkyl, or haloalkyl;

$R^7$ is hydrogen, deuterium, halogen, alkyl, alkoxy, haloalkoxy, hydroxyl, or haloalkyl;

each $R^8$ and each $R^9$ are independently hydrogen, deuterium, alkyl, deuterated alkyl, haloalkyl, cycloalkyl, heterocyclyl, aryl, or heteroaryl, wherein cycloalkyl, heterocyclyl, aryl, and heteroaryl are optionally substituted with one, two, or three groups selected from halogen, alkyl, and haloalkyl; or $R^8$ and $R^9$, together with the atom or atoms to which they are attached, form a heterocyclyl optionally substituted with one, two, or three groups selected from halogen, alkyl, and haloalkyl;

each $R^{10}$ is independently hydrogen, deuterium, alkyl or deuterated alkyl;

each $R^{11}$ is independently alkyl, deuterated alkyl, haloalkyl, cycloalkyl, heterocyclyl, aryl, or heteroaryl, wherein cycloalkyl, heterocyclyl, aryl, and heteroaryl are optionally substituted with one, two, or three groups selected from halogen, alkyl, and haloalkyl;

$Y^1$ and $Y^2$ are each independently a bond or —$(CR^a{}_2)_a$—, provided that $Y^1$ and $Y^2$ are not both a bond;

$Z^1$ and $Z^2$ are each —$CR^a{}_2$—;

$L^2$ is $(CR^c{}_2)_m$—;

G is —$C(O)OR^{12}$, —$C(O)NHOH$, —$SO_3H$, —$SO_2NH_2$, —$SO_2NHR^d$, —$SO_2NHC(O)R^d$, —$NHC(O)NHSO_2R^d$, -1H-tetrazolyl, —$P(O)(OH)_2$, -1,2,4-oxadiazol-5(4H)-one, -tetrazol-5(4H)-one, or —$C(O)NHSO_2R^d$;

$R^{12}$ is selected from hydrogen, $C_1$-$C_6$alkyl, aryl, aralkyl, $CH(R^{13})OC(=O)R^{14}$, $CH(R^{13})OC(=O)OR^{14}$ and a (5-alkyl-2-oxo-1,3-dioxolen-4-yl)methyl group having the following formula

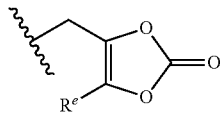

wherein $R^e$ is $C_1$-$C_6$ alkyl;

$R^{13}$ is hydrogen or $C_1$-$C_6$ alkyl;

$R^{14}$ is $C_1$-$C_6$ alkyl or $C_3$-$C_6$-cycloalkyl;

each $R^a$ is independently hydrogen, deuterium, optionally deuterated alkyl, halogen, or haloalkyl;

each $R^b$ is independently hydrogen, deuterium, optionally alkyl or haloalkyl, or two $R^b$s, together with the carbon atom to which they are attached, form optionally cycloalkyl or heterocyclyl;

each $R^c$ is independently hydrogen or halogen;

$R^d$ is alkyl, haloalkyl, cycloalkyl, aryl, or heteroaryl;

m is 0, 1, or 2;

each n is independently 1, 2, or 3;

p is 1 or 2;

q is 0, 1, or 2; and t is 1, 2 or 3.

In one embodiment, the compound provided herein is a compound of Formula (I). In one embodiment, the compound provided herein is a pharmaceutically acceptable salt of the compound of Formula (I). In one embodiment, provided herein is a solvate of the compound of Formula (I). In one embodiment, provided herein is a solvate of the pharmaceutically acceptable salt of the compound of Formula (I). In one embodiment, provided herein is a hydrate of the compound of Formula (I). In one embodiment, provided herein is an isotopic variant of the compound of Formula (I). In one embodiment, provided herein is a deuterated compound of Formula (I). In one embodiment, provided herein is a prodrug of the compound of Formula (I).

Also provided are pharmaceutical compositions formulated for administration by an appropriate route and formulations comprising effective concentrations of one or more of the compounds provided herein, or pharmaceutically acceptable salts, solvates, solvates of pharmaceutically acceptable salts, hydrates, and prodrugs thereof and optionally comprising at least one pharmaceutically acceptable carrier.

In certain embodiments, the compounds are useful for the treatment, prevention or amelioration of cancer, arthritis, pain, endometriosis, neurodegenerative disease, and cardiovascular disease.

In an aspect, the present disclosure provides a method for the treatment of cancer in a patient comprising administering to the patient a compound or pharmaceutical composition as described herein. In some embodiments, the cancer is selected from glioblastoma bone cancer, head and neck cancer, melanoma, basal cell carcinoma, squamous cell carcinoma, adenocarcinoma, oral cancer, esophageal cancer, gastric cancer, intestinal cancer, colon cancer, bladder cancer, hepatocellular carcinoma, renal cell carcinoma, pancreatic cancer, ovarian cancer, cervical cancer, lung cancer, breast cancer, and prostate cancer. In some embodiments, the cancer is selected from colon cancer, bladder cancer, hepatocellular carcinoma, pancreatic cancer, ovarian cancer, cervical cancer, lung cancer, breast cancer and prostate cancer.

In another aspect, the present disclosure provides a compound or pharmaceutical composition (e.g., as described herein) for use in the treatment of cancer. In some embodiments, the cancer is selected from glioblastoma bone cancer, head and neck cancer, melanoma, basal cell carcinoma, squamous cell carcinoma, adenocarcinoma, oral cancer, esophageal cancer, gastric cancer, intestinal cancer, colon cancer, bladder cancer, hepatocellular carcinoma, renal cell carcinoma, pancreatic cancer, ovarian cancer, cervical cancer, lung cancer, breast cancer, and prostate cancer. In some embodiments, the cancer is selected from colon cancer, bladder cancer, hepatocellular carcinoma, pancreatic cancer, ovarian cancer, cervical cancer, lung cancer, breast cancer and prostate cancer.

In another aspect, the present disclosure provides a method of treating a neurodegenerative disease in a patient comprising administering to the patient a compound or pharmaceutical composition as described herein. In some embodiments, the neurodegenerative disease is selected from epilepsy, Alzheimer's disease (AD), Parkinson's disease (PD), amyotrophic lateral sclerosis (ALS) and traumatic brain injury (TBI).

In another aspect, the present disclosure provides a method of treating arthritis or inflammatory pain in a patient comprising administering to the patient a compound or pharmaceutical composition as described herein.

In certain embodiments, the compounds are useful as pharmaceutically acceptable compositions and useful in the treatment of various diseases; in particular cancer, both alone or in combination with radiation, antibodies to cytotoxic t-lymphocyte antigen 4 (i.e. anti-CTLA4 agents such as ipilimumab, or the like), antibodies to programmed death-ligand 1 (i.e. anti-PD-L1 agents such as atezolizumab, avelumab, or the like), antibodies to programmed cell death protein 1 (i.e. anti-PD-1 agents such as nivolumab, pembrolizumab, or the like), activators of stimulator of interferon genes pathway (i.e. STING activators such as ADU-S100, MK-1454, or the like) and cytotoxic agents (i.e. alkylating agents such as cisplatin, dacarbazine, chlorambucil, or the like; anti-metabolites such as methotrexate, fludarabine, gemcitabine, or the like; anti-microtubule agents such as vinblastine, paclitaxel, or the like; topoisomerase inhibitors such as topotecan, doxorubicin, or the like; and others). Also provided herein are processes for the preparation of the compounds of this intervention, as well as for the preparation of intermediates useful for the synthesis of the compounds of Formula (I).

These and other aspects of the subject matter described herein will become evident upon reference to the following detailed description.

DETAILED DESCRIPTION OF THE INVENTION

Figure 1:
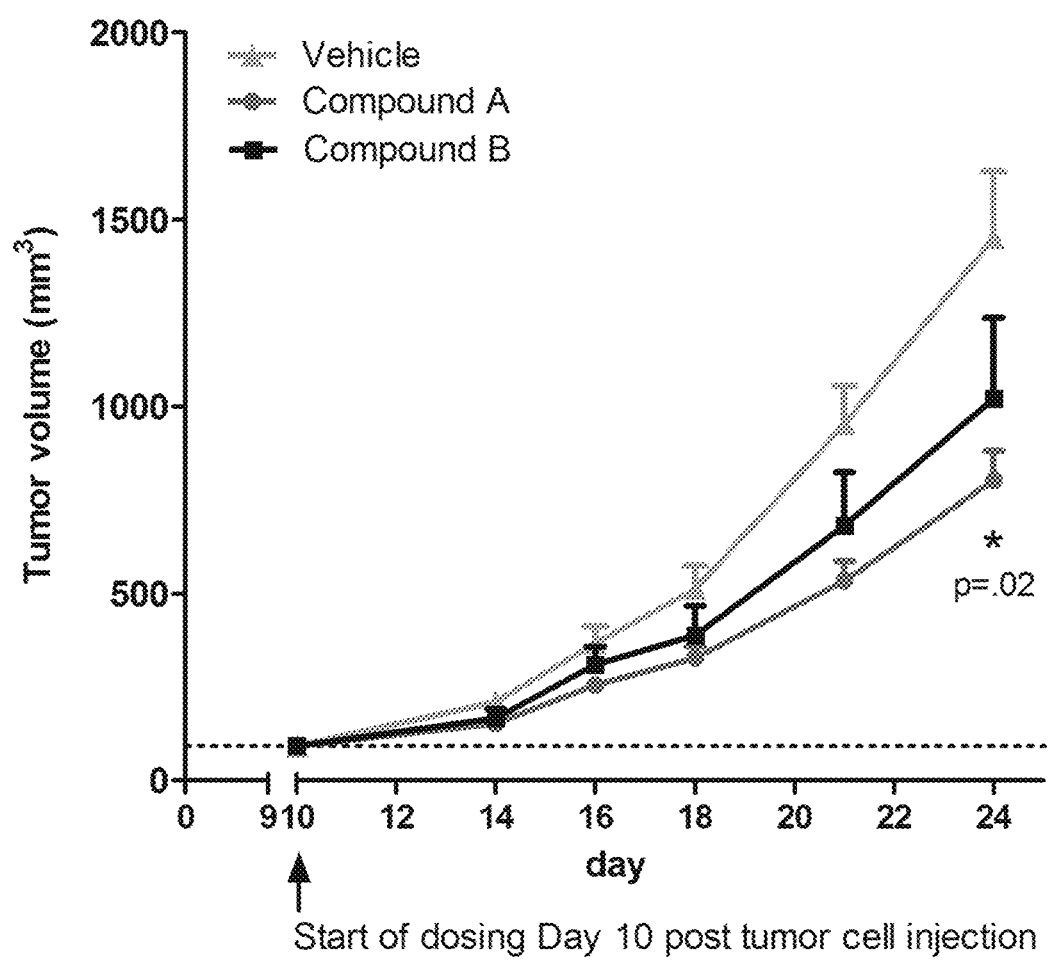
FIG. 1 depicts animal tumor growth delay in syngeneic CT26 colon carcinoma mouse model. CT26 tumor bearing mice treated p.o., b.i.d with 50 mg/kg of one of the compounds of Formula (I) (Compound A) for 14 days resulted in a statistically significant (p=0.02) reduction in tumor size compared to animals treated with vehicle or an internal EP4 selective compound (Compound B).

Provided herein are compounds of Formula (I) that have activity as $EP_2$ and $EP_4$ receptor modulators, including as antagonists of both the $EP_2$ and $EP_4$ receptors. Provided further are methods for modulating the activity of $EP_2$ and $EP_4$ receptors and for the treatment, prevention and amelioration of one or more symptoms of diseases or disorders that are modulated by the $EP_2$ and $EP_4$ receptors; and pharmaceutical compositions and dosage forms useful for such methods. The compounds, compositions and methods are described in detail in the sections below.

A. DEFINITIONS

Unless defined otherwise, all technical and scientific terms used herein have the same meaning as is commonly understood by one of ordinary skill in the art. All patents, applications, published applications and other publications referenced herein are incorporated by reference in their entirety unless stated otherwise. In the event that there is a plurality of definitions for a term herein, those in this section prevail unless stated otherwise. The term "patient" includes mammals such as mice, rats, cows, sheep, pigs, rabbits, goats, horses, monkeys, dogs, cats, and humans, including neonatal, infant, juvenile, adolescent, adult or geriatric patients.

The term "halo", "halogen" or "halide" as used herein and unless otherwise indicated, refers to any radical of fluorine, chlorine, bromine or iodine.

The term "alkyl" as used herein and unless otherwise indicated, refers to a saturated hydrocarbon chain that may be a straight chain or branched chain, containing the indicated number of carbon atoms or otherwise having from one to ten, one to eight, one to six or one to four carbon atoms, and which is attached to the rest of the molecule by a single bond. In certain embodiments, the hydrocarbon chain is optionally deuterated. For example, $C_1$-$C_6$ alkyl indicates that the group may have from 1 to 6 (inclusive) carbon atoms in it. In some embodiments, an alkyl is a $C_1$-$C_6$ alkyl which represents a straight-chain or branched saturated hydrocarbon radical having 1 to 6 carbon atoms. Examples of alkyl include without limitation methyl, ethyl, n-propyl, isopropyl, n-butyl, isobutyl, sec-butyl, and tert-butyl.

The term "cycloalkyl" as used herein and unless otherwise indicated, refers to a monocyclic, bicyclic, tricyclic or other polycyclic hydrocarbon group having the indicated number of ring carbon atoms or otherwise having three to ten carbon atoms and which are fully saturated or partially unsaturated. Multicyclic cycloalkyl may be fused, bridged or spiro-ring systems. Cycloalkyl groups include, but are not limited to, cyclopropyl, cyclobutyl, cyclopentyl, cyclohexyl, cycloheptyl, cyclooctyl, norbornyl, and partially unsaturated hydrocarbon rings such as cyclobutylene, cyclopentene and cyclohexene. In some embodiments, cycloalkyl is a monocyclic $C_3$-$C_8$ cycloalkyl.

The term "haloalkyl" as used herein and unless otherwise indicated, refers to an alkyl group in which at least one hydrogen atom is replaced by a halogen. In some embodiments, more than one hydrogen atom (e.g., 2, 3, 4, 5 or 6) are replaced by halogens. In these embodiments, the hydrogen atoms can each be replaced by the same halogen (e.g., fluoro) or the hydrogen atoms can be replaced by a combination of different halogens (e.g., fluoro and chloro). "Haloalkyl" also includes alkyl moieties in which all hydrogens have been replaced by halogens (sometimes referred to herein as perhaloalkyl, e.g., perfluoroalkyl, such as trifluoromethyl).

The term "alkoxy" as used herein and unless otherwise indicated, refers to a group of formula —O-(alkyl). Alkoxy can be, for example, methoxy, ethoxy, n-propoxy, isopropoxy, n-butoxy, iso-butoxy, sec-butoxy, n-pentoxy, 2-pentoxy, 3-pentoxy, or hexyloxy. Likewise, the term "thioalkoxy" refers to a group of formula —S-(alkyl). The terms "haloalkoxy" and "thiohaloalkoxy" refer to —O-(haloalkyl) and —S-(haloalkyl), respectively.

The term "aralkyl" as used herein and unless otherwise indicated, refers to an alkyl moiety in which an alkyl hydrogen atom is replaced by an aryl group. One of the carbons of the alkyl moiety serves as the point of attachment of the aralkyl group to another moiety. Non-limiting examples of "aralkyl" include benzyl, 2-phenylethyl, and 3-phenylpropyl groups.

The term "alkenyl" as used herein and unless otherwise indicated, refers to a straight or branched hydrocarbon chain containing the indicated number of carbon atoms or otherwise having from two to ten, two to eight or two to six carbon atoms, having one or more carbon-carbon double bonds and which is attached to the rest of the molecule by a single bond or a double bond. Alkenyl groups can include, e.g., vinyl, allyl, 1-butenyl, and 2-hexenyl. In some embodiments, an alkenyl is a $C_2$-$C_6$ alkenyl.

The term "alkynyl" as used herein and unless otherwise indicated, refers to a straight or branched hydrocarbon chain containing the indicated number of carbon atoms or otherwise having from two to ten, two to eight or two to six carbon atoms and having one or more carbon-carbon triple bonds. Alkynyl groups can include. e.g., ethynyl, propargyl, 1-butynyl, and 2-hexynyl. In some embodiments, an alkynyl is a $C_2$-$C_6$ alkynyl.

The term "cycloalkylalkyl" as used herein and unless otherwise indicated, refers to a monovalent alkyl group substituted with cycloalkyl.

The term "deuterium" as used herein and unless otherwise indicated, refers to the heavy isotope of hydrogen represented by the symbol D or $^2H$. As used herein, when a particular position in a compound is designated as "deuterated" or as having deuterium, it is understood that the compound is an isotopically enriched compound and the presence of deuterium at that position in the compound is substantially greater than its natural abundance of 0.0156%.

The term "enantiomerically pure" or "pure enantiomer" as used herein denotes that the compound comprises more than 75% by weight, more than 80% by weight, more than 85% by weight, more than 90% by weight, more than 91% by weight, more than 92% by weight, more than 93% by weight, more than 94% by weight, more than 95% by weight, more than 96% by weight, more than 97% by weight, more than 98% by weight, more than 98.5% by weight, more than 99% by weight, more than 99.2% by weight, more than 99.5% by weight, more than 99.6% by weight, more than 99.7% by weight, more than 99.8% by weight or more than 99.9% by weight, of a single enantiomer to the exclusion of its corresponding non-superimposable mirror image.

The term "heterocycle", "heterocyclyl" or "heterocyclic" as used herein and unless otherwise indicated, represents a stable 4-, 5-, 6- or 7-membered monocyclic- or a stable 6-, 7-, 8-, 9-, 10-, 11-, or 12-membered bicyclic heterocyclic ring system which comprises at least one non-aromatic (i.e. saturated or partially unsaturated) ring which consists of carbon atoms and from one to four, preferably up to three, heteroatoms selected from the group consisting of N, O and S, wherein the nitrogen and sulfur atoms may optionally be oxidized as N-oxide, sulfoxide or sulfone, and wherein the nitrogen atom may optionally be quaternized. A heterocycle can be bonded via a ring carbon atom or, if available, via a ring nitrogen atom. Bicyclic heterocyclic ring systems may be fused, bridged, or spiro-bicyclic heterocyclic ring system(s). In some embodiments, heterocyclyl is monocyclic having 4 to 7, preferably 4 to 6, ring atoms, of which 1 or 2 are heteroatoms independently selected from the group consisting of N, O and S. In some embodiments, a heterocyclyl group is bicyclic, and in which case, the second ring may be an aromatic or a non-aromatic ring which consists of carbon atoms and from one to four, preferably up to three, heteroatoms independently selected from the group consisting of N, O and S, or the second ring may be a benzene ring, or a "cycloalkyl", or a "cycloalkenyl", as defined herein. Examples of such heterocyclic groups include, but are not limited to azetidine, chroman, dihydrofuran, dihydropyran, dioxane, dioxolane, hexahydroazepine, imidazolidine, imidazoline, indoline, isochroman, isoindoline, isothiazoline, isothiazolidine, isoxazoline, isoxazolidine, morpholine, oxazoline, oxazolidine, oxetane, piperazine, piperidine, dihydropyridine, tetrahydropyridine, dihydropyridazine, pyran, pyrazolidine, pyrazoline, pyrrolidine, pyrroline, tetrahydrofuran, tetrahydropyran, thiamorpholine, tetrahydrothiophene, thiazoline, thiazolidine, thiomorpholine, thietane, thiolane, sulfolane, 1,3-dioxolane, 1,3-oxazolidine, 1,3-thiazolidine, tetrahydrothiopyran, tetrahydrotriazine, 1,3-dioxane, 1,4-dioxane, hexahydrotriazine, tetrahydro-oxazine, tetrahydropyrimidine, perhydroazepine, perhydro-1,4-diazepine, perhydro-1,4-oxazepine, 7-azabicyclo[2.2.1]heptane, 3-azabicyclo[3.2.0]heptane, 7-azabicyclo[4.1.0]heptane, 2,5-diazabicyclo[2.2.1]heptane, 2-oxa-5-azabicyclo[2.2.1]heptane, tropane, 2-oxa-6-azaspiro[3.3]heptane, dihydrobenzofuran, dihydrobenzimidazolyl, dihydrobenzoxazole, and dihydrobenzothiazolyl, and N-oxides or sulfones or sulfoxides thereof.

The term "heterocyclylalkyl" as used herein and unless otherwise indicated, refers to a monovalent alkyl group substituted with heterocyclyl.

The term "aryl" as used herein and unless otherwise indicated, is intended to mean any stable monocyclic or bicyclic carbon ring of up to 6 members in each ring, wherein at least one ring is aromatic. Examples of aryl include phenyl, naphthyl, tetrahydronaphthyl, indanyl, or biphenyl.

The term "heteroaryl", as used herein and unless otherwise indicated, represents a stable 5-, 6- or 7-membered monocyclic- or stable 9- or 10-membered fused bicyclic ring system which comprises at least one aromatic ring, which consists of carbon atoms and from one to four, preferably up to three, heteroatoms selected from the group consisting of N, O and S wherein the nitrogen and sulfur heteroatoms may optionally be oxidized, and the nitrogen heteroatom may optionally be quaternized. In the case of a "heteroaryl" which is a bicyclic group, the second ring need not be aromatic and need not comprise a heteroatom. Accordingly, bicyclic "heteroaryl" includes, for example, a stable 5- or 6-membered monocyclic aromatic ring consisting of carbon atoms and from one to four, preferably up to three, heteroatoms, as defined immediately above, fused to a benzene ring, or a second monocyclic "heteroaryl", or a "heterocyclyl", a "cycloalkyl", or a "cycloalkenyl", as defined above. Examples of heteroaryl groups include, but are not limited to, benzimidazole, benzopyrazole, benzisothiazole, benzisoxazole, benzofuran, isobenzofuran, benzothiazole, benzothiophene, benzotriazole, benzoxazole, furan, furazan, imidazole, indazole, indole, indolizine, isoquinoline, isothiazole, isoxazole, naphthyridine, oxadiazole, oxazole, phthalazine, pteridine, purine, pyrazine, pyrazole, pyridazine, pyridine, pyrimidine, pyrrole, quinazoline, quinoline, quinoxaline, tetrazole, thiadiazole, thiazole, thiophene, triazine, triazole, benzimidazole, benzothiadiazole, isoindole, pyrrolo pyridines, imidazopyridines such as imidazo[1,2-a]pyridine, pyrazolopyridine, pyrrolopyrimidine and N-oxides thereof.

The term "hydrate" as used herein and unless otherwise indicated, refers to a compound provided herein or a salt thereof, that further includes a stoichiometric or non-stoichiometric amount of water bound by non-covalent intermolecular forces.

The term "solvate" as used herein and unless otherwise indicated, refers to a solvate formed from the association of one or more solvent molecules to a compound provided herein. The term "solvate" includes hydrates (e.g., monohydrate, dehydrate, trihydrate, and the like).

The term "treating", "treat", or "treatment" refers generally to controlling, alleviating, ameliorating, slowing the progress of or eliminating a named condition once the condition has been established. In addition to its customary meaning, the term "preventing", "prevent", or "prevention" also refers to delaying the onset of, or reducing the risk of developing a named condition or of a process that can lead to the condition, or the recurrence of symptoms of a condition.

The term "therapeutically effective amount" or "effective amount" is an amount sufficient to effect beneficial or desired clinical results. An effective amount can be administered in one or more administrations. An effective amount is typically sufficient to palliate, ameliorate, stabilize, reverse, slow or delay the progression of the disease state.

Unless stated otherwise or specifically described, it is understood that substitutions where present can occur on any atom of the alkyl, alkenyl, alkynyl, cycloalkyl, heterocyclyl, aryl or heteroaryl groups.

Unless specifically stated otherwise, where a compound may assume alternative tautomeric or stereoisomeric forms, all alternative isomers are intended to be encompassed within the scope of the claimed subject matter. For example, unless specifically stated otherwise, the compounds provided herein may be enantiomerically pure, or be enantiomeric mixtures.

In the description herein, if there is any discrepancy between a chemical name and chemical structure, the chemical structure controls.

B. COMPOUNDS

Described herein are compounds of Formula (I) that are antagonists of both the $EP_2$ and $EP_4$ receptors. These compounds, and compositions comprising these compounds, are useful for the treatment of cancer, arthritis, pain, endometriosis, neurodegenerative disease and cardiovascular disease.

In some embodiments, provided herein are compounds having the Formula (I), or a pharmaceutically acceptable salt, solvate, solvate of the salt, hydrate, a single stereoisomer, a mixture of stereoisomers, a racemic mixture of stereoisomers, or prodrug thereof:

Formula (I)

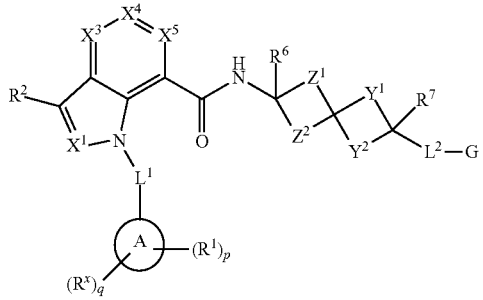

wherein:
$X^1$ is N or CH;
$X^3$ is N or $CR^3$;
$X^4$ is N or $CR^4$;
$X^5$ is N or $CR^5$;

wherein no more than two of $X^3$, $X^4$ and $X^5$ are N;
$L^1$ is —$(CR^b_2)_t$—;
Ring A is optionally deuterated aryl;
each $R^1$ is independently $C_2$-$C_9$alkyl, $C_2$-$C_9$alkenyl, $C_2$-$C_9$alkynyl, cycloalkyl, heterocyclyl, aryl, heteroaryl, or —$OR^{8'}$, wherein $C_2$-$C_9$alkyl, $C_2$-$C_9$alkenyl, $C_2$-$C_9$alkynyl, cycloalkyl, heterocyclyl, aryl, and heteroaryl are optionally deuterated and optionally substituted with one, two, or three $R^y$;
or two $R^1$ substituents on adjacent atoms of Ring A are taken together with the atom to which they are attached to form an aromatic or non-aromatic ring containing 0-2 heteroatoms selected from the group consisting of —O—, =N—, —$NR^{10}$—, —S—, and —$S(O)_2$—, wherein the aromatic or non-aromatic ring is optionally deuterated and optionally substituted with one, two, or three $R^y$;
each $R^{8'}$ is independently hydrogen, alkyl, haloalkyl, cycloalkyl, heterocyclyl, aryl, or heteroaryl, wherein cycloalkyl, heterocyclyl, aryl, and heteroaryl are optionally substituted with one, two, or three groups selected from halogen, alkyl, and haloalkyl;
each $R^y$ is independently alkyl, haloalkyl, cycloalkyl, cycloalkylalkyl, heterocyclyl, heterocyclylalkyl, halogen, —$OR^8$, —$NR^8R^9$, —CN, —$C(O)R^{11}$, —$C(O)NR^8R^9$, —$NR^8C(O)R^{11}$, —$NR^8C(O)OR^9$, —$NR^{10}C(O)NR^8R^9$, —$OC(O)NR^8R^9$, —$S(O)_2R^{11}$, —$S(O)R^{11}$, —$SR^8$, —$S(O)_2NR^8R^9$, —$S(O)NR^8R^9$, —$NR^8S(O)R^{11}$, —$NR^8S(O)_2R^{11}$, or —$NR^{10}S(O)_2NR^8R^9$; wherein alkyl is optionally substituted with —$OR^8$ or —$NR^8R^9$ and wherein cycloalkyl and heterocyclyl are optionally substituted with one, two, or three groups selected from halogen, alkyl, and haloalkyl;
each $R^x$ is independently halogen, methyl, $C_1$haloalkyl, or —CN;
$R^2$, $R^3$, $R^4$, and $R^5$ are each independently hydrogen, alkyl, halogen, —$OR^8$, —$NR^8R^9$, —$SR^8$, —$S(O)R^{11}$, —$S(O)_2R^{11}$, —CN, cycloalkyl, or haloalkyl;
$R^6$ is hydrogen, deuterium, alkyl, or haloalkyl;
$R^7$ is hydrogen, deuterium, halogen, optionally deuterated alkyl, alkoxy, haloalkoxy, hydroxyl, or haloalkyl;
each $R^8$ and each $R^9$ are independently hydrogen, deuterium, alkyl, deuterated alkyl, haloalkyl, cycloalkyl, heterocyclyl, aryl, or heteroaryl, wherein cycloalkyl, heterocyclyl, aryl, and heteroaryl are optionally substituted with one, two, or three groups selected from halogen, alkyl, and haloalkyl; or
$R^8$ and $R^9$, together with the atom or atoms to which they are attached, form a heterocyclyl optionally substituted with one, two, or three groups selected from halogen, alkyl, and haloalkyl;
each $R^{10}$ is independently hydrogen, deuterium, alkyl or deuterated alkyl;
each $R^{11}$ is independently alkyl, deuterated alkyl, haloalkyl, cycloalkyl, heterocyclyl, aryl, or heteroaryl, wherein cycloalkyl, heterocyclyl, aryl, and heteroaryl are optionally substituted with one, two, or three groups selected from halogen, alkyl, and haloalkyl;
$Y^1$ and $Y^2$ are each independently a bond or —$(CR^a_2)_n$—, provided that $Y^1$ and $Y^2$ are not both a bond;
$Z^1$ and $Z^2$ are each —$CR^a_2$—;
$L^2$ is —$(CR^c_2)_m$—;
G is —$C(O)OR^{12}$, —$C(O)NHOH$, —$SO_3H$, —$SO_2NH_2$, —$SO_2NHR^d$, —$SO_2NHC(O)R^d$, —$NHC(O)NHSO_2R^d$, -1H-tetrazolyl, —$P(O)(OH)_2$, -1,2,4-oxadiazol-5(4H)-one, -tetrazol-5(4H)-one, or —$C(O)NHSO_2R^d$;

each $R^a$ is independently hydrogen, deuterium, optionally deuterated alkyl, halogen, or haloalkyl;

each $R^b$ is independently hydrogen, deuterium, optionally deuterated alkyl or haloalkyl, or two $R^b$s, together with the carbon atom to which they are attached, form optionally deuterated cycloalkyl or heterocyclyl;

each $R^c$ is independently hydrogen, deuterium or halogen;

$R^d$ is alkyl, haloalkyl, cycloalkyl, aryl, or heteroaryl;

$R^{12}$ is selected from H, $C_1$-$C_6$alkyl, aryl, aralkyl, $CH(R^{13})OC(=O)R^{14}$, $CH(R^{13})OC(=O)OR^{14}$ and a (5-alkyl-2-oxo-1,3-dioxolen-4-yl)methyl group having the following formula:

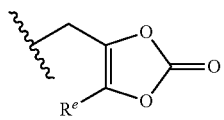

wherein $R^e$ is $C_1$-$C_6$alkyl;

$R^{13}$ is hydrogen or $C_1$-$C_6$ alkyl;

$R^{14}$ is $C_1$-$C_6$alkyl or $C_3$-$C_6$-cycloalkyl;

m is 0, 1, or 2;

each n is independently 1, 2, or 3;

p is 1 or 2;

q is 0, 1, or 2; and t is 1, 2 or 3.

A compound having the Formula (I), or a pharmaceutically acceptable salt, solvate, solvate of the salt, hydrate, a single stereoisomer, a mixture of stereoisomers, a racemic mixture of stereoisomers, or prodrug thereof:

Formula (I)

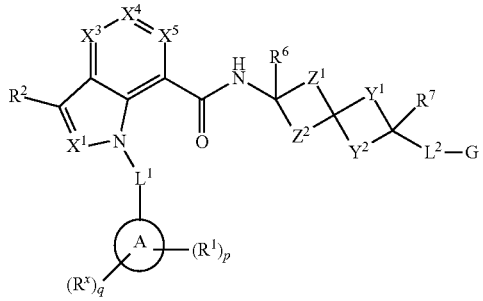

wherein:

$X^1$ is N or CH;

$X^3$ is N or $CR^3$;

$X^4$ is N or $CR^4$;

$X^5$ is N or $CR^5$;

wherein no more than two of $X^3$, $X^4$ and $X^5$ are N;

$L^1$ is —$(CR^b_2)_t$—;

Ring A is aryl;

each $R^1$ is independently $C_2$-$C_9$alkyl, $C_2$-$C_9$alkenyl, $C_2$-$C_9$alkynyl, cycloalkyl, heterocyclyl, aryl, heteroaryl, or —$OR^{8'}$, wherein $C_2$-$C_9$alkyl, $C_2$-$C_9$alkenyl, $C_2$-$C_9$alkynyl, cycloalkyl, heterocyclyl, aryl, and heteroaryl are optionally substituted with one, two, or three $R^y$;

or two $R^1$ substituents on adjacent atoms of Ring A are taken together with the atom to which they are attached to form an aromatic or non-aromatic ring containing 0-2 heteroatoms selected from the group consisting of —O—, —$NR^{10}$—, —S—, and —$S(O)_2$—, wherein the aromatic or non-aromatic ring is optionally substituted with one, two, or three $R^y$;

each $R^{8'}$ is independently hydrogen, alkyl, haloalkyl, cycloalkyl, heterocyclyl, aryl, or heteroaryl, wherein cycloalkyl, heterocyclyl, aryl, and heteroaryl are optionally substituted with one, two, or three groups selected from halogen, alkyl, and haloalkyl;

each $R^y$ is independently alkyl, haloalkyl, cycloalkyl, cycloalkylalkyl, heterocyclyl, heterocyclylalkyl, halogen, —$OR^8$, —$NR^8R^9$, —CN, —$C(O)R^{11}$, —$C(O)NR^8R^9$, —$NR^8C(O)R^{11}$, —$NR^8C(O)OR^9$, —$NR^{10}C(O)NR^8R^9$, —$OC(O)NR^8R^9$, —$S(O)_2R^{11}$, —$S(O)R^{11}$, —$SR^8$, —$S(O)_2NR^8R^9$, —$S(O)NR^8R^9$, —$NR^8S(O)R^{11}$, —$NR^8S(O)_2R^{11}$, or —$NR^{10}S(O)_2NR^8R^9$; wherein alkyl is optionally substituted with —$OR^8$ or —$NR^8R^9$ and wherein cycloalkyl and heterocyclyl are optionally substituted with one, two, or three groups selected from halogen, alkyl, and haloalkyl;

each $R^x$ is independently halogen, methyl, $C_1$haloalkyl, or —CN;

$R^2$, $R^3$, $R^4$, and $R^5$ are each independently hydrogen, alkyl, halogen, —$OR^8$, —CN, cycloalkyl, or haloalkyl;

$R^6$ is hydrogen, deuterium, alkyl, or haloalkyl;

$R^7$ is hydrogen, deuterium, halogen, alkyl, alkoxy, haloalkoxy, hydroxyl, or haloalkyl;

each $R^8$ and each $R^9$ are independently hydrogen, alkyl, deuterated alkyl, haloalkyl, cycloalkyl, heterocyclyl, aryl, or heteroaryl, wherein cycloalkyl, heterocyclyl, aryl, and heteroaryl are optionally substituted with one, two, or three groups selected from halogen, alkyl, and haloalkyl; or $R^8$ and $R^9$, together with the atom or atoms to which they are attached, form a heterocyclyl optionally substituted with one, two, or three groups selected from halogen, alkyl, and haloalkyl;

each $R^{10}$ is independently hydrogen or alkyl;

each $R^{11}$ is independently alkyl, haloalkyl, cycloalkyl, heterocyclyl, aryl, or heteroaryl, wherein cycloalkyl, heterocyclyl, aryl, and heteroaryl are optionally substituted with one, two, or three groups selected from halogen, alkyl, and haloalkyl;

$Y^1$ and $Y^2$ are each independently a bond or —$(CR^a_2)_n$—, provided that $Y^1$ and $Y^2$ are not both a bond;

$Z^1$ and $Z^2$ are each —$CR^a_2$—, $L^2$ is —$(CR^c_2)_m$—;

G is —$C(O)OR^{12}$, —$C(O)NHOH$, —$SO_3H$, —$SO_2NH_2$, —$SO_2NHR^d$, —$SO_2NHC(O)R^d$, —$NHC(O)NHSO_2R^d$, -1H-tetrazolyl, —$P(O)(OH)_2$, -1,2,4-oxadiazol-5(4H)-one, -tetrazol-5(4H)-one, or —$C(O)NHSO_2R^d$;

$R^{12}$ is selected from hydrogen, $C_1$-$C_6$ alkyl, aryl, aralkyl, $CH(R^{13})OC(=O)R^{14}$, $CH(R^{13})OC(=O)OR^{14}$ and a (5-alkyl-2-oxo-1,3-dioxolen-4-yl)methyl group having the following formula:

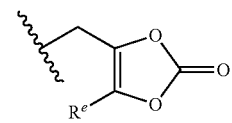

wherein $R^e$ is $C_1$-$C_6$alkyl;

$R^{13}$ is hydrogen or $C_1$-$C_6$ alkyl;

$R^{14}$ is $C_1$-$C_6$ alkyl or $C_3$-$C_6$-cycloalkyl;

each $R^a$ is independently hydrogen, deuterium, alkyl, halogen, or haloalkyl;

each $R^b$ is independently hydrogen, deuterium, alkyl or haloalkyl, or two $R^b$s, together with the carbon atom to which they are attached, form cycloalkyl;

each $R^c$ is independently hydrogen or halogen;

$R^d$ is alkyl, haloalkyl, cycloalkyl, aryl, or heteroaryl;

m is 0, 1, or 2;

each n is independently 1, 2, or 3;

p is 1 or 2;

q is 0, 1, or 2; and t is 1, 2 or 3.

In some embodiments, provided herein are compounds having the Formula (I), or a pharmaceutically acceptable salt, solvate, solvate of the salt, hydrate, a single stereoisomer, a mixture of stereoisomers, a racemic mixture of stereoisomers, or prodrug thereof:

Formula (I)

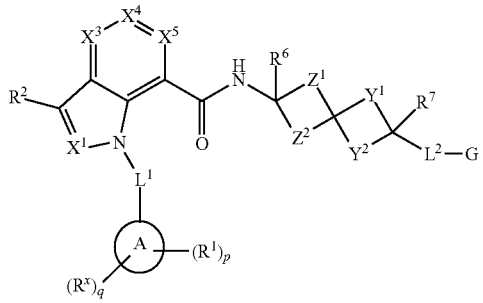

wherein:

$X^1$ is N or CH;

$X^3$ is N or $CR^3$;

$X^4$ is N or $CR^4$;

$X^5$ is N or $CR^5$;

wherein no more than two of $X^3$, $X^4$ and $X^5$ are N;

$L^1$ is $-(CR^b_2)_t-$;

Ring A is aryl;

each $R^1$ is independently $C_2$-$C_9$alkyl, $C_2$-$C_9$alkenyl, $C_2$-$C_9$alkynyl, cycloalkyl, heterocyclyl, aryl, heteroaryl, or $-OR^{8'}$, wherein $C_2$-$C_9$alkyl, $C_2$-$C_9$alkenyl, $C_2$-$C_9$alkynyl, cycloalkyl, heterocyclyl, aryl, and heteroaryl are optionally substituted with one, two, or three $R^y$;

or two $R^1$ substituents on adjacent atoms of Ring A are taken together with the atom to which they are attached to form an aromatic or non-aromatic ring containing 0-2 heteroatoms selected from the group consisting of $-O-$, $-NR^{10}-$, $-S-$, and $-S(O)_2-$, wherein the aromatic or non-aromatic ring is optionally substituted with one, two, or three $R^y$;

each $R^{8'}$ is independently hydrogen, alkyl, haloalkyl, cycloalkyl, heterocyclyl, aryl, or heteroaryl, wherein cycloalkyl, heterocyclyl, aryl, and heteroaryl are optionally substituted with one, two, or three groups selected from halogen, alkyl, and haloalkyl;

each $R^y$ is independently alkyl, haloalkyl, cycloalkyl, cycloalkylalkyl, heterocyclyl, heterocyclylalkyl, halogen, $-OR^8$, $-NR^8R^9$, $-CN$, $-C(O)R^{11}$, $-C(O)NR^8R^9$, $-NR^8C(O)R^{11}$, $-NR^8C(O)OR^9$, $-NR^{10}C(O)NR^8R^9$, $-OC(O)NR^8R^9$, $-S(O)_2R^{11}$, $-S(O)R^{11}$, $-SR^8$, $-S(O)_2NR^8R^9$, $-NR^8S(O)_2R^{11}$, or $-NR^{10}S(O)_2NR^8R^9$;

wherein alkyl is optionally substituted with $-OR^8$ or $-NR^8R^9$ and wherein cycloalkyl and heterocyclyl are optionally substituted with one, two, or three groups selected from halogen, alkyl, and haloalkyl;

each $R^x$ is independently halogen, methyl, $C_1$haloalkyl, or $-CN$;

$R^2$, $R^3$, $R^4$, and $R^5$ are each independently hydrogen, alkyl, halogen, $-OR^8$, $-CN$, cycloalkyl, or haloalkyl;

$R^6$ is hydrogen, deuterium, alkyl, or haloalkyl;

$R^7$ is hydrogen, deuterium, halogen, alkyl, alkoxy, haloalkoxy, hydroxyl, or haloalkyl;

each $R^8$ and each $R^9$ are independently hydrogen, alkyl, haloalkyl, cycloalkyl, heterocyclyl, aryl, or heteroaryl, wherein cycloalkyl, heterocyclyl, aryl, and heteroaryl are optionally substituted with one, two, or three groups selected from halogen, alkyl, and haloalkyl; or $R^8$ and $R^9$, together with the atom or atoms to which they are attached, form a heterocyclyl optionally substituted with one, two, or three groups selected from halogen, alkyl, and haloalkyl;

each $R^{10}$ is independently hydrogen or alkyl;

each $R^{11}$ is independently alkyl, haloalkyl, cycloalkyl, heterocyclyl, aryl, or heteroaryl, wherein cycloalkyl, heterocyclyl, aryl, and heteroaryl are optionally substituted with one, two, or three groups selected from halogen, alkyl, and haloalkyl;

$Y^1$ and $Y^2$ are each independently a bond or $-(CR^a_2)_n-$, provided that $Y^1$ and $Y^2$ are not both a bond, $Z^1$ and $Z^2$ are each $-CR^a_2-$;

$L^2$ is $(CR^c_2)_m-$;

G is $-C(O)OR^{12}$, $-C(O)NHOH$, $-SO_3H$, $-SO_2NH_2$, $-SO_2NHR^d$, $-SO_2NHC(O)R^d$, $-NHC(O)NHSO_2R^d$, -1H-tetrazolyl, $-P(O)(OH)_2$, -1,2,4-oxadiazol-5(4H)-one, -tetrazol-5(4H)-one, or $-C(O)NHSO_2R^d$;

$R^{12}$ is selected from H, $C_1$-$C_6$ alkyl, aryl, aralkyl, $CH(R^{13})OC(=O)R^{14}$, $CH(R^{13})OC(=O)OR^{14}$ and a (5-alkyl-2-oxo-1,3-dioxolen-4-yl)methyl group having the following formula:

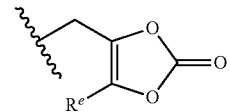

wherein $R^e$ is $C_1$-$C_6$alkyl;

$R^{13}$ is hydrogen or $C_1$-$C_6$ alkyl;

$R^{14}$ is $C_1$-$C_6$ alkyl or $C_1$-$C_6$-cycloalkyl;

each $R^a$ is independently hydrogen, deuterium, alkyl, halogen, or haloalkyl;

each $R^b$ is independently hydrogen or deuterium;

each $R^c$ is independently hydrogen or halogen;

$R^d$ is alkyl, haloalkyl, cycloalkyl, aryl, or heteroaryl;

m is 0, 1, or 2;

each n is independently 1, 2, or 3;

p is 1 or 2;

q is 0, 1, or 2; and t is 1, 2 or 3.

In certain embodiments, provided herein are compounds of Formula (I) wherein t is 1. In certain embodiments, provided herein are compounds of Formula (I) wherein m is 0 and t is 1. In certain embodiments, provided herein are compounds of Formula (I) wherein m is 0, q is 0 and t is 1.

In certain embodiments, provided herein are compounds of Formula (I) wherein $R^1$ is hydrogen or deuterium. In certain embodiments, provided herein are compounds of Formula (I) wherein $R^a$ is hydrogen.

In certain embodiments, $X^3$ is $CR^3$; $X^4$ is N or $CR^4$; $X^5$ is N or $CR^5$; $R^3$, $R^4$, and $R^5$ are each independently hydrogen, alkyl, halogen, —$OR^8$, —CN, cycloalkyl, or haloalkyl; and each $R^8$ is independently hydrogen, alkyl, haloalkyl, cycloalkyl, heterocyclyl, aryl, or heteroaryl, wherein cycloalkyl, heterocyclyl, aryl, and heteroaryl are optionally substituted with one, two, or three groups selected from halogen, alkyl, and haloalkyl.

In certain embodiments, $X^3$ is $CR^3$; $X^4$ is N or $CR^4$; $X^5$ is N or $CR^5$; $R^3$, $R^4$, and $R^5$ are each independently hydrogen, alkyl, halogen, —$OR^8$, —$NR^8R^9$, —$SR^8$, —$S(O)R^{11}$, —$S(O)_2R^{11}$, —CN, cycloalkyl, or haloalkyl; and each $R^8$ and each $R^9$ are independently hydrogen, deuterium, alkyl, deuterated alkyl, haloalkyl, cycloalkyl, heterocyclyl, aryl, or heteroaryl, wherein cycloalkyl, heterocyclyl, aryl, and heteroaryl are optionally substituted with one, two, or three groups selected from halogen, alkyl, and haloalkyl; or $R^8$ and $R^9$, together with the atom or atoms to which they are attached, form a heterocyclyl optionally substituted with one, two, or three groups selected from halogen, alkyl, and haloalkyl; each $R^{10}$ is independently hydrogen, deuterium, alkyl or deuterated alkyl; and each $R^{11}$ is independently alkyl, deuterated alkyl, haloalkyl, cycloalkyl, heterocyclyl, aryl, or heteroaryl, wherein cycloalkyl, heterocyclyl, aryl, and heteroaryl are optionally substituted with one, two, or three groups selected from halogen, alkyl, and haloalkyl.

In certain embodiments, one of $R^3$, $R^4$ and $R^5$ is alkyl, halogen, —$OR^8$, —$NR^8R^9$, —$SR^8$, —$S(O)R^{11}$, —$S(O)_2R^{11}$, —CN, cycloalkyl, or haloalkyl and the remainder of $R^3$, $R^4$, and $R^5$, when present, is hydrogen; and each $R^8$ and each $R^9$ are independently hydrogen, alkyl, deuterated alkyl, haloalkyl, cycloalkyl, heterocyclyl, aryl, or heteroaryl, wherein cycloalkyl, heterocyclyl, aryl, and heteroaryl are optionally substituted with one, two, or three groups selected from halogen, alkyl, and haloalkyl; or $R^8$ and $R^9$, together with the atom or atoms to which they are attached, form a heterocyclyl optionally substituted with one, two, or three groups selected from halogen, alkyl, and haloalkyl; each $R^{10}$ is independently hydrogen, deuterium, alkyl or deuterated alkyl; and each $R^{11}$ is independently alkyl, deuterated alkyl, haloalkyl, cycloalkyl, heterocyclyl, aryl, or heteroaryl, wherein cycloalkyl, heterocyclyl, aryl, and heteroaryl are optionally substituted with one, two, or three groups selected from halogen, alkyl, and haloalkyl. In certain embodiments, one of $R^3$, $R^4$ and $R^5$ is alkyl, halogen, —$OR^8$, —CN, cycloalkyl, or haloalkyl and the remainder of $R^3$, $R^4$, and $R^5$, when present, is hydrogen; and $R^8$ is independently hydrogen, alkyl, deuterated alkyl, haloalkyl, cycloalkyl, heterocyclyl, aryl, or heteroaryl, wherein cycloalkyl, heterocyclyl, aryl, and heteroaryl are optionally substituted with one, two, or three groups selected from halogen, alkyl, and haloalkyl. In certain embodiments, one of $R^3$, $R^4$, and $R^5$ is halogen and the remainder of $R^3$, $R^4$, and $R^5$, when present, is hydrogen. In certain embodiments, $X^3$ is $CR^3$; $X^4$ is N or $CR^4$; $X^5$ is N or $CR^5$; one of $R^3$, $R^4$ and $R^5$ is halogen and the remainder of $R^3$, $R^4$ and $R^5$, when present, is each independently hydrogen, alkyl, halogen, —$OR^8$, —CN, cycloalkyl, or haloalkyl; and each $R^8$ is independently hydrogen, alkyl, deuterated alkyl, haloalkyl, cycloalkyl, heterocyclyl, aryl, or heteroaryl, wherein the cycloalkyl, heterocyclyl, aryl, and heteroaryl, are optionally substituted with one, two, or three groups selected from halogen, alkyl, and haloalkyl.

In certain embodiments, $X^3$ is $CR^3$; $X^4$ is N or $CR^4$; $X^5$ is N or $CR^5$; and $R^3$, $R^4$, and $R^5$ are each independently hydrogen or halogen. In certain embodiments, one of $R^3$ and $R^4$ is halogen and the other of $R^3$ and $R^4$, when present, is hydrogen, and $R^5$, when present, is hydrogen. In certain embodiments, $R^3$ is halogen. In certain embodiments, $R^4$ is halogen. In certain embodiments, $R^3$ is halogen and $R^4$, and $R^5$ are hydrogen. In certain embodiments, $R^4$ is halogen and $R^3$ and $R^5$ are hydrogen. In certain embodiments, $X^1$ is CH and no more than one of $X^3$, $X^4$ and $X^5$ is N.

In certain embodiments, $X^1$ is CH or N; one of $X^3$, $X^4$ and $X^5$ is N and the remainder of $X^3$, $X^4$ and $X^5$ is CH. In certain embodiments, $X^1$ is CH; one of $X^3$, $X^4$ and $X^5$ is N and the remainder of $X^3$, $X^4$ and $X^5$ is CH.

In certain embodiments, $X^1$ is CH or N; $X^3$ is $CR^3$; $X^4$ is $CR^4$; $X^5$ is $CR^5$; $R^3$, $R^4$, and $R^5$ are each independently hydrogen, alkyl, halogen, —$OR^8$, —$NR^8R^9$, —$SR^8$, —$S(O)R^{11}$, —$S(O)_2R^{11}$, —CN, cycloalkyl, or haloalkyl; and each $R^8$ and each $R^9$ are independently hydrogen, alkyl, haloalkyl, cycloalkyl, heterocyclyl, aryl, or heteroaryl, wherein cycloalkyl, heterocyclyl, aryl, and heteroaryl are optionally substituted with one, two, or three groups selected from halogen, alkyl, and haloalkyl; or $R^8$ and $R^9$, together with the atom or atoms to which they are attached, form a heterocyclyl optionally substituted with one, two, or three groups selected from halogen, alkyl, and haloalkyl; and each $R^{11}$ is independently alkyl, deuterated alkyl, haloalkyl, cycloalkyl, heterocyclyl, aryl, or heteroaryl, wherein cycloalkyl, heterocyclyl, aryl, and heteroaryl are optionally substituted with one, two, or three groups selected from halogen, alkyl, and haloalkyl. In certain embodiments, $X^1$ is CH; $X^3$ is $CR^3$; $X^4$ is $CR^4$; $X^5$ is $CR^5$; $R^3$, $R^4$, and $R^5$ are each independently hydrogen, alkyl, halogen, —$OR^8$, —$NR^8R^9$, —$SR^8$, —$S(O)R^{11}$, —$S(O)_2R^{11}$, —CN, cycloalkyl, or haloalkyl; and each $R^8$ and each $R^9$ are independently hydrogen, deuterium, alkyl, deuterated alkyl, haloalkyl, cycloalkyl, heterocyclyl, aryl, or heteroaryl, wherein cycloalkyl, heterocyclyl, aryl, and heteroaryl are optionally substituted with one, two, or three groups selected from halogen, alkyl, and haloalkyl; or $R^8$ and $R^9$, together with the atom or atoms to which they are attached, form a heterocyclyl optionally substituted with one, two, or three groups selected from halogen, alkyl, and haloalkyl; and each $R^{11}$ is independently alkyl, deuterated alkyl, haloalkyl, cycloalkyl, heterocyclyl, aryl, or heteroaryl, wherein cycloalkyl, heterocyclyl, aryl, and heteroaryl are optionally substituted with one, two, or three groups selected from halogen, alkyl, and haloalkyl. In certain embodiments, $X^1$ is N; $X^3$ is $CR^3$; $X^4$ is $CR^4$; $X^5$ is $CR^5$; $R^3$, $R^4$, and $R^5$ are each independently hydrogen, alkyl, halogen, —$OR^8$, —$NR^8R^9$, —$SR^8$, —$S(O)R^{11}$, —$S(O)_2R^{11}$, —CN, cycloalkyl, or haloalkyl; and each $R^8$ and each $R^9$ are independently hydrogen, deuterium, alkyl, deuterated alkyl, haloalkyl, cycloalkyl, heterocyclyl, aryl, or heteroaryl, wherein cycloalkyl, heterocyclyl, aryl, and heteroaryl are optionally substituted with one, two, or three groups selected from halogen, alkyl, and haloalkyl; or $R^8$ and $R^9$, together with the atom or atoms to which they are attached, form a heterocyclyl optionally substituted with one, two, or three groups selected from halogen, alkyl, and haloalkyl; and each $R^{11}$ is independently alkyl, deuterated alkyl, haloalkyl, cycloalkyl, heterocyclyl, aryl, or heteroaryl, wherein cycloalkyl, aryl, and heteroaryl are optionally substituted with one, two, or three groups selected from halogen, alkyl, and haloalkyl.

In certain embodiments, one of $R^3$, $R^4$ and $R^5$ is alkyl, halogen, —$OR^8$, —CN, cycloalkyl, or haloalkyl and the remainder of $R^3$, $R^4$, and $R^5$, when present, is hydrogen; and $R^8$ is independently hydrogen, alkyl, deuterated alkyl, haloalkyl, cycloalkyl, heterocyclyl, aryl, or heteroaryl, wherein cycloalkyl, heterocyclyl, aryl, and heteroaryl are optionally substituted with one, two, or three groups selected from halogen, alkyl, and haloalkyl. In certain embodiments, $X^1$ is CH or N; $X^3$ is $CR^3$; $X^4$ is $CR^4$; $X^5$ is $CR^5$; $R^3$, $R^4$, and $R^5$ are each independently hydrogen, alkyl, halogen, $-OR^8$, $-CN$, cycloalkyl, or haloalkyl; and each $R^8$ is independently hydrogen, alkyl, haloalkyl, cycloalkyl, heterocyclyl, aryl, or heteroaryl, wherein cycloalkyl, heterocyclyl, aryl, and heteroaryl are optionally substituted with one, two, or three groups selected from halogen, alkyl, and haloalkyl. In certain embodiments, $X^1$ is CH; $X^3$ is $CR^3$; $X^4$ is $CR^4$; $X^5$ is $CR^5$; $R^3$, $R^4$, and $R^5$ are each independently hydrogen, alkyl, halogen, $-OR^8$, $-NR^8R^9$, $-SR^8$, $-S(O)R^{11}$, $-S(O)_2R^{11}$, $-CN$, cycloalkyl, or haloalkyl; and each $R^8$ is independently hydrogen, alkyl, haloalkyl, cycloalkyl, heterocyclyl, aryl, or heteroaryl, wherein cycloalkyl, heterocyclyl, aryl, and heteroaryl are optionally substituted with one, two, or three groups selected from halogen, alkyl, and haloalkyl. In certain embodiments, $X^1$ is CH; $X^3$ is CR; $X^4$ is $CR^4$; $X^5$ is $CR^5$; $R^3$, $R^4$, and $R^5$ are each independently hydrogen, alkyl, halogen, $-OR^8$, $-CN$, cycloalkyl, or haloalkyl; and each $R^8$ is independently hydrogen, alkyl, haloalkyl, cycloalkyl, heterocyclyl, aryl, or heteroaryl, wherein cycloalkyl, heterocyclyl, aryl, and heteroaryl are optionally substituted with one, two, or three groups selected from halogen, alkyl, and haloalkyl.

In certain embodiments, $X^1$ is CH or N; $X^3$ is $CR^3$; $X^4$ and $X^5$ are CH; $R^3$ is hydrogen, alkyl, halogen, $-OR^8$, $-CN$, cycloalkyl, or haloalkyl; and $R^8$ is hydrogen, alkyl, haloalkyl, cycloalkyl, heterocyclyl, aryl, or heteroaryl, wherein cycloalkyl, heterocyclyl, aryl, and heteroaryl are optionally substituted with one, two, or three groups selected from halogen, alkyl, and haloalkyl. In certain embodiments, $X^1$ is CH; $X^3$ is $CR^3$; $X^1$ and $X^5$ are CH; $R^3$ is hydrogen, alkyl, halogen, $-OR$, $-CN$, cycloalkyl, or haloalkyl; and $R^8$ is hydrogen, alkyl, haloalkyl, cycloalkyl, heterocyclyl, aryl, or heteroaryl, wherein cycloalkyl, heterocyclyl, aryl, and heteroaryl are optionally substituted with one, two, or three groups selected from halogen, alkyl, and haloalkyl.

In certain embodiments, $X^1$ is CH or N; one of $X^3$, $X^4$ and $X^5$ is N and the remainder of $X^3$, $X^4$ and $X^5$ is CH. In certain embodiments, $X^1$ is CH; one of $X^3$, $X^4$ and $X^5$ is N and the remainder of $X^3$, $X^4$ and $X^5$ is CH.

In certain embodiments, $X^1$ is CH or N; $X^3$ is N; $X^4$ is $CR^4$ and $X^5$ is $CR^5$; $R^4$ and $R^5$ are each independently hydrogen, alkyl, halogen. $-OR^8$, $-CN$, cycloalkyl, or haloalkyl; and each $R^8$ is independently hydrogen, alkyl, haloalkyl, cycloalkyl, heterocyclyl, aryl, or heteroaryl, wherein cycloalkyl, heterocyclyl, aryl, and heteroaryl are optionally substituted with one, two, or three groups selected from halogen, alkyl, and haloalkyl. In certain embodiments, $X^1$ is CH or N; $X^3$ is N; $X^4$ is CH and $X^5$ is CH.

In certain embodiments, $X^1$ is CH or N; $X^3$ is $CR^3$; $X^4$ is N; $X^5$ is $CR^5$; $R^3$ and $R^5$ are each independently hydrogen, alkyl, halogen, $-OR^8$, $-CN$, cycloalkyl, or haloalkyl; and each $R^8$ is independently hydrogen, alkyl, haloalkyl, cycloalkyl, heterocyclyl, aryl, or heteroaryl, wherein cycloalkyl, heterocyclyl, aryl, and heteroaryl are optionally substituted with one, two, or three groups selected from halogen, alkyl, and haloalkyl. In certain embodiments, $X^1$ is CH or N; $X^3$ is CH; $X^4$ is N; $X^5$ is CH.

In certain embodiments, $X^1$ is CH or N; $X^3$ is $CR^3$; $X^4$ is $CR^4$; $X^5$ is N; $R^3$ and $R^4$ are each independently hydrogen, alkyl, halogen, $-OR$, $-CN$, cycloalkyl, or haloalkyl; and each $R^8$ is independently hydrogen, alkyl, haloalkyl, cycloalkyl, heterocyclyl, aryl, or heteroaryl, wherein cycloalkyl, heterocyclyl, aryl, and heteroaryl are optionally substituted with one, two, or three groups selected from halogen, alkyl, and haloalkyl. In certain embodiments, $X^1$ is CH or N; $X^3$ and $X^4$ are both CH and $X^5$ is N.

In some embodiments, each $R^1$ is independently heterocyclyl, aryl, heteroaryl, or $-OR^{8'}$, wherein heterocyclyl, aryl, and heteroaryl are each independently optionally substituted with one, two, or three $R^y$; each $R^y$ is independently alkyl, haloalkyl, cycloalkyl, cycloalkylalkyl, heterocyclyl, heterocyclylalkyl, halogen, $-OR^8$, $-NR^8R^9$, $-CN$, $-C(O)R^{11}$, $-C(O)NR^8R^9$, $-NR^8C(O)R^{11}$, $-NR^8C(O)OR^9$, $-NR^{10}C(O)NR^8R^9$, $-OC(O)NR^8R^9$, $-S(O)_2R^{11}$, $-S(O)R^{11}$, $-SR^8$, $-S(O)_2NR^8R^9$, $-NR^8S(O)_2R^{11}$, or $-NR^{10}S(O)_2NR^8R^9$; wherein alkyl is optionally substituted with $-OR^8$ or $-NR^8R^9$ and wherein cycloalkyl and heterocyclyl are optionally substituted with one, two, or three groups selected from halogen, alkyl, and haloalkyl; each $R^8$ and each $R^9$ are independently hydrogen, alkyl, haloalkyl, cycloalkyl, heterocyclyl, aryl, or heteroaryl, wherein cycloalkyl, heterocyclyl, aryl, and heteroaryl are optionally substituted with one, two, or three groups selected from halogen, alkyl, and haloalkyl; or $R^8$ and $R^9$, together with the atom or atoms to which they are attached, form a heterocyclyl optionally substituted with one, two, or three groups selected from halogen, alkyl, and haloalkyl; each $R^{10}$ is independently hydrogen or alkyl; each $R^{11}$ is independently alkyl, haloalkyl, cycloalkyl, heterocyclyl, aryl, or heteroaryl, wherein cycloalkyl, heterocyclyl, aryl, and heteroaryl are optionally substituted with one, two, or three groups selected from halogen, alkyl, and haloalkyl; and each $R^{8'}$ is independently hydrogen, alkyl, haloalkyl, cycloalkyl, heterocyclyl, aryl, or heteroaryl, wherein cycloalkyl, heterocyclyl, aryl, and heteroaryl are each independently optionally substituted with one, two, or three groups selected from halogen, alkyl, and haloalkyl.

In certain embodiments, each $R^1$ is independently cycloalkyl heterocyclyl, aryl, heteroaryl, or $-OR^{8'}$, wherein the cycloalkyl, heterocyclyl, aryl, and heteroaryl are each independently optionally substituted with one, two, or three $R^y$; each $R^{8'}$ is independently hydrogen, alkyl, haloalkyl, cycloalkyl, heterocyclyl, aryl, or heteroaryl, wherein cycloalkyl, heterocyclyl, aryl, and heteroaryl are optionally substituted with one, two, or three groups selected from halogen, alkyl, and haloalkyl and each $R^y$ is independently alkyl, haloalkyl, cycloalkyl, cycloalkylalkyl, heterocyclyl, heterocyclylalkyl, halogen, $-OR^8$, $-NR^8R^9$, $-CN$, $-C(O)R^{11}$, $-C(O)NR^8R^9$, $-NR^8C(O)R^{11}$, $-NR^8C(O)OR^9$, $-NR^{10}C(O)NR^8R^9$, $-OC(O)NR^8R^9$, $-S(O)_2R^{11}$, $-S(O)R^{11}$, $-SR^8$, $-S(O)_2NR^8R^9$, $-S(O)NR^8R^9$, $-NR^8S(O)R^{11}$, $-NR^8S(O)_2R^{11}$, or $-NR^{10}S(O)_2NR^8R^9$; wherein alkyl is optionally substituted with $-OR^8$ or $-NR^8R^9$ and wherein cycloalkyl and heterocyclyl are optionally substituted with one, two, or three groups selected from halogen, alkyl, and haloalkyl, and the other variables are as described elsewhere herein. In certain embodiments, each $R^1$ is independently cycloalkyl heterocyclyl, aryl, heteroaryl, or $-OR^{8'}$, wherein the cycloalkyl, heterocyclyl, aryl, and heteroaryl are each independently optionally deuterated and optionally substituted with one, two, or three $R^y$; each $R^{8'}$ is independently hydrogen, alkyl, haloalkyl, cycloalkyl, heterocyclyl, aryl, or heteroaryl, wherein cycloalkyl, heterocyclyl, aryl, and heteroaryl are optionally substituted with one, two, or three groups selected from halogen, alkyl, and haloalkyl and each $R^y$ is independently alkyl, haloalkyl, cycloalkyl, cycloalkylalkyl, heterocyclyl, heterocyclylalkyl, halogen, $-OR^8$, $-NR^8R^9$, $-CN$, $-C(O)R^{11}$, $-C(O)NR^8R^9$, $-NR^8C(O)R^{11}$, $-NR^8C(O)OR^9$, $-NR^{10}C(O)NR^8R^9$, $-OC(O)NR^8R^9$, $-S(O)_2R^{11}$, $-S(O)R^{11}$, $-SR^8$, $-S(O)_2NR^8R^9$, $-S(O)NR^8R^9$, —NR$^8$S(O)R$^{11}$, —NR$^8$S(O)$_2$R$^{11}$, or —NR$^{10}$S(O)$_2$NR$^8$R$^9$; wherein alkyl is optionally substituted with —OR$^8$ or —NR$^8$R$^9$ and wherein cycloalkyl and heterocyclyl are optionally substituted with one, two, or three groups selected from halogen, alkyl, and haloalkyl, and the other variables are as described elsewhere herein. In certain embodiments, each R$^1$ is independently cycloalkyl heterocyclyl, aryl or heteroaryl wherein the cycloalkyl, heterocyclyl, aryl, and heteroaryl are each independently optionally substituted with one, two, or three R$^y$; each R$^y$ is independently alkyl, haloalkyl, cycloalkyl, cycloalkylalkyl, heterocyclyl, heterocyclylalkyl, halogen, —OR$^8$, —NR$^8$R$^9$, —CN, —C(O)R$^{11}$, —C(O)NR$^8$R$^9$, —NR$^8$C(O)R$^{11}$, —NR$^8$C(O)OR$^9$, —NR$^{10}$C(O)NR$^8$R$^9$, —OC(O)NR$^8$R$^9$, —S(O)$_2$R$^{11}$, —S(O)R$^{11}$, —SR$^8$, —S(O)$_2$NR$^8$R$^9$, —S(O)NR$^8$R$^9$, —NR$^8$S(O)R$^{11}$, —NR$^8$S(O)$_2$R$^{11}$, or —NR$^{10}$S(O)$_2$NR$^8$R$^9$; wherein alkyl is optionally substituted with —OR$^8$ or —NR$^8$R$^9$ and wherein cycloalkyl and heterocyclyl are optionally substituted with one, two, or three groups selected from halogen, alkyl, and haloalkyl, and the other variables are as described elsewhere herein. In certain embodiments, each R$^1$ is independently cycloalkyl heterocyclyl, aryl or heteroaryl wherein the cycloalkyl, heterocyclyl, aryl, and heteroaryl are each independently optionally deuterated and optionally substituted with one, two, or three R$^y$; each R$^y$ is independently alkyl, haloalkyl, cycloalkyl, cycloalkylalkyl, heterocyclyl, heterocyclylalkyl, halogen, —OR$^8$, —NR$^8$R$^9$, —CN, —C(O)R$^{11}$, —C(O)N$^8$R$^9$, —NR$^8$C(O)R$^{11}$, —NR$^8$C(O)OR$^9$, —NR$^{10}$C(O)NR$^8$R$^9$, —OC(O)NR$^8$R$^9$, —S(O)$_2$R$^{11}$, —S(O)R$^{11}$, —SR$^8$, —S(O)$_2$NR$^8$R$^9$, —S(O)NR$^8$R$^9$, —NR$^8$S(O)R$^{11}$, —NR$^8$S(O)$_2$R$^{11}$, or —NR$^{10}$S(O)$_2$NR$^8$R$^9$; wherein alkyl is optionally substituted with —OR$^8$ or —NR$^8$R$^9$ and wherein cycloalkyl and heterocyclyl are optionally substituted with one, two, or three groups selected from halogen, alkyl, and haloalkyl, and the other variables are as described elsewhere herein. In certain embodiments, R$^1$ is aryl or heteroaryl optionally substituted with one, two, or three R$^y$. In certain embodiments, R$^1$ is cycloalkyl or aryl optionally substituted with one, two or three R$^y$. In certain embodiments, p is 1 and R$^1$ is alkoxy, haloalkoxy or aryl optionally substituted with one, two or three R$^y$. In certain embodiments, p is 1 and R$^1$ is aryl optionally substituted with one, two or three R$^y$. In certain embodiments, R$^1$ is aryl optionally substituted with one, two, or three R$^y$. In certain embodiments, R$^1$ is phenyl optionally substituted with one, two, or three R$^y$. In certain embodiments, Ring A is phenyl, p is 1 and R$^1$ is alkoxy, haloalkoxy orss phenyl optionally substituted with one, two or three R$^y$. In certain embodiments, Ring A is phenyl, p is 1 and R$^1$ is phenyl optionally substituted with one, two or three R$^y$.

In certain embodiments, q is 0. In certain embodiments, q is 0 or 1. In certain embodiments, m is 0, q is 0, and t is 1.

In certain embodiments, R$^3$ is hydrogen, halogen, cyano or methoxy. In certain embodiments, R$^3$ is hydrogen or halogen.

In certain embodiments, G is —C(O)OH, —C(O)NHOH, —SO$_3$H, —SO$_2$NH$_2$, —SO$_2$NHR$^d$, —SO$_2$NHC(O)R$^d$, —NHC(O)NHSO$_2$R$^d$, -1H-tetrazolyl, —P(O)(OH)$_2$, -1,2,4-oxadiazol-5(4H)-one, -tetrazol-5(4H)-one, or —C(O)NHSO$_2$R$^d$ and R$^d$ is alkyl, haloalkyl, cycloalkyl, aryl, or heteroaryl. In certain embodiments, G is —COOH, -1H-tetrazolyl, -1,2,4-oxadiazol-5(4H)-one or -tetrazol-5(4H)-one. In certain embodiments, G is —COOH or -1H-tetrazolyl.

In some embodiments,

X$^1$ is N or CH;
X$^3$ is N or CR$^3$;
X$^4$ is N or CH;
X$^5$ is N or CH;
wherein no more than two of X$^3$, X$^4$ and X$^5$ are N;
L$^1$ is —(CH$_2$)—;
Ring A is phenyl;
each R$^1$ is independently C$_2$-C$_9$ alkyl, C$_2$-C$_9$ alkenyl, C$_2$-C$_9$ alkynyl, cycloalkyl, heterocyclyl, aryl, heteroaryl, or —OR$^{8'}$, wherein C$_2$-C$_9$ alkyl, C$_2$-C$_9$ alkenyl, C$_2$-C$_9$alkynyl, cycloalkyl, heterocyclyl, aryl, and heteroaryl are optionally substituted with one, two, or three R$^y$;
or two R$^1$ substituents on adjacent atoms of Ring A are taken together with the atom to which they are attached to form an aromatic or non-aromatic ring containing 0-2 heteroatoms selected from the group consisting of —O—, —NR$^{10}$—, —S—, and —S(O)$_2$—, wherein the aromatic or non-aromatic ring is optionally substituted with one, two, or three R$^y$;
each R$^{8'}$ is independently hydrogen, alkyl, haloalkyl, cycloalkyl, or heterocyclyl, wherein cycloalkyl and heterocyclyl are optionally substituted with one, two, or three groups selected from halogen, alkyl, and haloalkyl;
each R$^y$ is independently alkyl, haloalkyl, cycloalkyl, cycloalkylalkyl, heterocyclyl, heterocyclylalkyl, halogen, —OR$^8$, —NR$^8$R$^9$, —CN, —C(O)R$^{11}$, —C(O)NR$^8$R$^9$, —NRC(O)R$^{11}$, —NR$^8$C(O)OR$^9$, —NR$^{10}$C(O)NR$^8$R$^9$, —OC(O)NR$^8$R$^9$, —S(O)$_2$R$^{11}$, —S(O)R$^{11}$, —SR$^8$, —S(O)$_2$NR$^8$R$^9$, —NR$^8$S(O)$_2$R$^{11}$, or —NR$^{10}$S(O)$_2$NR$^8$R$^9$; wherein alkyl is optionally substituted with —OR$^8$ or —NR$^8$R$^9$ and wherein cycloalkyl and heterocyclyl are optionally substituted with one, two, or three groups selected from halogen, alkyl, and haloalkyl;
each R$^x$ is independently halogen, methyl, C$_1$ haloalkyl, or —CN;
R$^2$ is hydrogen;
R$^3$ is hydrogen, halogen, —OR$^8$, cycloalkyl, haloalkyl, or —CN;
R$^6$ is hydrogen;
R$^7$ is hydrogen, deuterium, halogen, alkyl, alkoxy, haloalkoxy, hydroxyl, or haloalkyl;
each R$^8$ and each R$^9$ are independently hydrogen, alkyl, haloalkyl, cycloalkyl, or heterocyclyl, wherein cycloalkyl and heterocyclyl are optionally substituted with one, two, or three groups selected from halogen, alkyl, and haloalkyl; or
R$^8$ and R$^9$, together with the atom or atoms to which they are attached, form a heterocyclyl optionally substituted with one, two, or three groups selected from halogen, alkyl, and haloalkyl;
each R$^{10}$ is independently hydrogen or alkyl;
each R$^{11}$ is independently alkyl, haloalkyl, cycloalkyl, or heterocyclyl, wherein cycloalkyl and heterocyclyl are optionally substituted with one, two, or three groups selected from halogen, alkyl, and haloalkyl;
Y$^1$ and Y$^2$ are each —CH—;
Z$^1$ and Z$^2$ are each —CH$_2$—;
L$^2$ is —(CH$_2$)$_m$— or —(CF$_2$)$_m$—;
G is —C(O)OH, —C(O)NHOH, —SO$_3$H, —SO$_2$NH$_2$, —SO$_2$NHR$^d$, —SO$_2$NHC(O)R$^d$, —NHC(O)NHSO$_2$R$^d$, -1H-tetrazolyl, —P(O)(OH)$_2$, -1,2,4-oxadiazol-5(4H)-one, -tetrazol-5(4H)-one, or —C(O)NHSO$_2$R$^d$;
R$^d$ is alkyl, haloalkyl, cycloalkyl, aryl, or heteroaryl;
m is 0 or 1;
p is 1 or 2, and
q is 0, 1, or 2.

In some embodiments,
$X^1$ is N or CH;
$X^3$ is N or $CR^3$;
$X^4$ is N or CH;
$X^5$ is N or CH;
provided that no more than two of $X^3$, $X^4$ and $X^5$ are N;
$L^1$ is —(CH$_2$)—;
Ring A is phenyl;
each $R^1$ is independently $C_2$-$C_9$ alkyl, $C_3$-$C_9$ cycloalkyl, heterocyclyl, aryl, heteroaryl, or —$OR^{8'}$, wherein $C_2$-$C_9$ alkyl, $C_3$-$C_9$ cycloalkyl, heterocyclyl, aryl, and heteroaryl are optionally substituted with one, two, or three $R^y$;
each $R^{8'}$ is independently hydrogen, alkyl, haloalkyl, cycloalkyl, or heterocyclyl, wherein cycloalkyl and heterocyclyl are optionally substituted with one, two, or three groups selected from halogen, alkyl, and haloalkyl;
each $R^y$ is independently alkyl, haloalkyl, cycloalkyl, cycloalkylalkyl, heterocyclyl, heterocyclylalkyl, halogen, —$OR^8$, —$NR^8R^9$, —CN; wherein alkyl is optionally substituted with —$OR^8$ or —$NR^8R^9$ and wherein cycloalkyl and heterocyclyl are optionally substituted with one, two, or three groups selected from halogen, alkyl, and haloalkyl;
each $R^x$ is independently halogen, methyl, $C_1$ haloalkyl, or —CN;
$R^2$ is hydrogen;
$R^3$ is hydrogen, halogen, —$OR^8$, cycloalkyl, haloalkyl, or —CN;
$R^6$ is hydrogen;
$R^7$ is hydrogen, deuterium, halogen, alkyl, alkoxy, haloalkoxy, hydroxyl, or haloalkyl;
each $R^8$ and each $R^9$ are independently hydrogen, alkyl, haloalkyl, cycloalkyl, or heterocyclyl, wherein cycloalkyl and heterocyclyl are optionally substituted with one, two, or three groups selected from halogen, alkyl, and haloalkyl; or
$R^8$ and $R^9$ together with the atom or atoms to which they are attached, form a heterocyclyl optionally substituted with one, two, or three groups selected from halogen, alkyl, and haloalkyl;
$Y^1$ and $Y^2$ are each —CH$_2$—;
$Z^1$ and $Z^2$ are each —CH$_2$—;
$L^2$ is —(CH$_2$)$_m$—;
G is —C(O)OH, —C(O)NHOH, —SO$_3$H, —SO$_2$NH$_2$, —SO$_2$NHR$^d$, —SO$_2$NHC(O)R$^d$, —NHC(O)NHSO$_2$R$^d$, -1H-tetrazolyl, —P(O)(OH)$_2$, -1,2,4-oxadiazol-5(4H)-one, -tetrazol-5(4H)-one, or —C(O)NHSO$_2$R$^d$—
$R^d$ is alkyl, haloalkyl, or cycloalkyl;
m is 0;
p is 1; and
q is 0 or 1.
In some embodiments,
$X^1$ is N or CH;
$X^3$ is $CR^3$;
$X^4$ is CH;
$X^5$ is CH;
$L^1$ is —(CH$_2$)—;
Ring A is phenyl;
each $R^1$ is independently $C_2$-$C_9$ alkyl, $C_3$-$C_9$ cycloalkyl, heterocyclyl, aryl, heteroaryl, or —$OR^{8'}$, wherein $C_2$-$C_9$ alkyl, $C_3$-$C_9$ cycloalkyl, heterocyclyl, aryl, and heteroaryl are optionally substituted with one or two $R^y$;

or two $R^1$ substituents on adjacent atoms of Ring A are taken together with the atom to which they are attached to form an aromatic ring, wherein the aromatic ring is optionally substituted with one or two $R^y$;
each $R^{8'}$ is independently hydrogen, alkyl, haloalkyl, cycloalkyl, or heterocyclyl, wherein cycloalkyl and heterocyclyl are optionally substituted with one, two, or three groups selected from halogen, alkyl, and haloalkyl;
each $R^y$ is independently alkyl, haloalkyl, cycloalkyl, cycloalkylalkyl, heterocyclyl, heterocyclylalkyl, halogen, —$OR^8$, —$NR^8R^9$, —CN;
each $R^x$ is independently halogen, methyl, —CF$_3$, —CHF$_2$, —CH$_2$F, or —CN;
$R^2$ is hydrogen;
$R^3$ is hydrogen, halogen, —OR, cycloalkyl, haloalkyl, or —CN;
$R^6$ is hydrogen;
$R^7$ is hydrogen, deuterium, halogen, alkyl, alkoxy, haloalkoxy, hydroxyl, or haloalkyl;
each $R^8$ and each $R^9$ are independently hydrogen, alkyl, cycloalkyl, or heterocyclyl, wherein cycloalkyl and heterocyclyl are optionally substituted with one, two, or three groups selected from halogen, alkyl, and haloalkyl;
$Y^1$ and $Y^2$ are each —CH$_2$—;
$Z^1$ and $Z^2$ are each —CH$_2$—,
$L^2$ is —(CH$_2$)$_m$—;
G is —C(O)OH;
m is 0 or 1;
p is 1 or 2; and
q is 0 or 1.
In certain embodiments, $R^7$ is hydrogen, deuterium, halogen, alkyl or hydroxyl. In certain embodiments, $R^7$ is hydrogen, deuterium, halogen or alkyl. In certain embodiments, $R^7$ is hydrogen or deuterium.

In some embodiments, provided herein are compounds of Formula (I), or a pharmaceutically acceptable salt, solvate, solvate of the salt, hydrate, a single stereoisomer, a mixture of stereoisomers, a racemic mixture of stereoisomers, or prodrug thereof, having the Formula (II):

(II)

In certain embodiments, provided herein are compounds of Formula (II) wherein:
$X^3$ is $CR^3$;
$X^4$ is N or $CR^4$;
$X^5$ is N or $CR^5$;
$R^3$, $R^4$, and $R^5$ are each independently hydrogen, alkyl, halogen, —$OR^8$, —CN, cycloalkyl, or haloalkyl; and
each $R^8$ is independently hydrogen, alkyl, haloalkyl, cycloalkyl, heterocyclyl, aryl, or heteroaryl, wherein cycloalkyl, heterocyclyl, aryl, and heteroaryl are optionally substituted with one, two, or three groups selected from halogen, alkyl, and haloalkyl. In certain embodiments, provided herein are compounds of Formula (II) wherein:

$X^3$ is $CR^3$;

$X^4$ is N or $CR^4$;

$X^5$ is N or $CR^5$;

$R^3$, $R^4$, and $R^5$ are each independently hydrogen, alkyl, halogen, —$OR^8$, —$NR^8R^9$, —$SR^8$, —$S(O)R^{11}$, —$S(O)_2R^{11}$, —CN, cycloalkyl, or haloalkyl; and each $R^8$ and each $R^9$ are independently hydrogen, deuterium, alkyl, deuterated alkyl, haloalkyl, cycloalkyl, heterocyclyl, aryl, or heteroaryl, wherein cycloalkyl, heterocyclyl, aryl, and heteroaryl are optionally substituted with one, two, or three groups selected from halogen, alkyl, and haloalkyl; or $R^8$ and $R^9$, together with the atom or atoms to which they are attached, form a heterocyclyl optionally substituted with one, two, or three groups selected from halogen, alkyl, and haloalkyl;

each $R^{10}$ is independently hydrogen, deuterium, alkyl or deuterated alkyl; and each $R^{11}$ is independently alkyl, deuterated alkyl, haloalkyl, cycloalkyl, heterocyclyl, aryl, or heteroaryl, wherein cycloalkyl, heterocyclyl, aryl, and heteroaryl are optionally substituted with one, two, or three groups selected from halogen, alkyl, and haloalkyl.

In certain embodiments, provided herein are compounds of Formula (II) wherein:

$X^3$ is $CR^3$;

$X^4$ is N or $CR^4$;

$X^5$ is N or $CR^5$;

one of $R^3$, $R^4$ and $R^5$ is halogen and the remainder of $R^3$, $R^4$ and $R^5$, when present, is each independently hydrogen, alkyl, halogen, —$OR^8$, —CN, cycloalkyl, or haloalkyl;

and each $R^8$ is independently hydrogen, alkyl, deuterated alkyl, haloalkyl, cycloalkyl, heterocyclyl, aryl, or heteroaryl, wherein cycloalkyl, heterocyclyl, aryl, and heteroaryl are optionally substituted with one, two, or three groups selected from halogen, alkyl, and haloalkyl. In certain embodiments, provided herein are compounds of Formula (II) wherein:

$X^3$ is $CR^3$;

$X^4$ is N or $CR^4$;

$X^5$ is N or $CR^5$;

one of $R^3$, $R^4$ and $R^5$ is halogen and the remainder of $R^3$, $R^4$ and $R^5$, when present, is each independently hydrogen, alkyl, halogen, —OR, —$NR^8R^9$, —$SR^8$, —$S(O)R^{11}$, —$S(O)_2R^{11}$, —CN, cycloalkyl, or haloalkyl;

each $R^8$ and each $R^9$ are independently hydrogen, deuterium, alkyl, deuterated alkyl, haloalkyl, cycloalkyl, heterocyclyl, aryl, or heteroaryl, wherein cycloalkyl, heterocyclyl, aryl, and heteroaryl are optionally substituted with one, two, or three groups selected from halogen, alkyl, and haloalkyl; or $R^8$ and $R^9$, together with the atom or atoms to which they are attached, form a heterocyclyl optionally substituted with one, two, or three groups selected from halogen, alkyl, and haloalkyl;

each $R^{10}$ is independently hydrogen, deuterium, alkyl or deuterated alkyl; and each $R^{11}$ is independently alkyl, deuterated alkyl, haloalkyl, cycloalkyl, heterocyclyl, aryl, or heteroaryl, wherein cycloalkyl, heterocyclyl, aryl, and heteroaryl are optionally substituted with one, two, or three groups selected from halogen, alkyl, and haloalkyl. In certain embodiments, provided herein are compounds of Formula (II) wherein $X^3$ is $CR^3$; $X^4$ is N or $CR^4$; $X^5$ is N or $CR^5$; one of $R^3$, $R^4$ and $R^5$ is halogen and the remainder of $R^3$, $R^4$ and $R^5$, when present, is each hydrogen. In certain embodiments, provided herein are compounds of Formula (II) wherein $X^3$ is $CR^3$; $X^4$ is N or $CR^4$; $X^5$ is N or $CR^5$; one of $R^3$ and $R^4$ is halogen and the other of $R^3$ and $R^4$, when present, is hydrogen, alkyl, halogen, —$OR^8$, —CN, cycloalkyl, or haloalkyl; $R^5$, when present, is hydrogen, alkyl, halogen, —OR, —CN, cycloalkyl, or haloalkyl and $R^8$ is hydrogen, alkyl, deuterated alkyl, haloalkyl, cycloalkyl, heterocyclyl, aryl, or heteroaryl, wherein cycloalkyl, heterocyclyl, aryl, and heteroaryl are optionally substituted with one, two, or three groups selected from halogen, alkyl, and haloalkyl. In certain embodiments, provided herein are compounds of Formula (II) wherein $X^3$ is $CR^3$; $X^4$ is N or $CR^4$; $X^5$ is N or $CR^5$; one of $R^3$ and $R^4$ is halogen and the other of $R^3$ and $R^4$, when present, is hydrogen and $R^5$ is hydrogen.

In certain embodiments, provided herein are compounds of Formula (II), wherein $X^1$ is CH and no more than one of $X^3$, $X^4$ and $X^5$ is N.

In certain embodiments, provided herein are compounds of Formula (II) wherein $X^1$ is CH or N; one of $X^3$, $X^4$ and $X^5$ is N and the remainder of $X^3$, $X^4$ and $X^5$ is CH. In certain embodiments, $X^1$ is CH; one of $X^3$, $X^4$ and $X^5$ is N and the remainder of $X^3$, $X^4$ and $X^5$ is CH.

In certain embodiments, provided herein are compounds of Formula (II) wherein $X^1$ is CH or N; $X^3$ is $CR^3$; $X^4$ is $CR^4$; $X^5$ is $CR^5$; $R^3$, $R^4$, and $R^5$ are each independently hydrogen, alkyl, halogen, —$OR^8$, —CN, cycloalkyl, or haloalkyl; and each $R^8$ is independently hydrogen, alkyl, haloalkyl, cycloalkyl, heterocyclyl, aryl, or heteroaryl, wherein cycloalkyl, heterocyclyl, aryl, and heteroaryl are optionally substituted with one, two, or three groups selected from halogen, alkyl, and haloalkyl. In certain embodiments, provided herein are compounds of Formula (II) wherein $X^1$ is CH; $X^3$ is $CR^3$; $X^4$ is $CR^4$; $X^5$ is $CR^5$; $R^3$, $R^4$, and $R^5$ are each independently hydrogen, alkyl, halogen, —$OR^8$, —CN, cycloalkyl, or haloalkyl; and each $R^8$ is independently hydrogen, alkyl, haloalkyl, cycloalkyl, heterocyclyl, aryl, or heteroaryl, wherein cycloalkyl, heterocyclyl, aryl, and heteroaryl are optionally substituted with one, two, or three groups selected from halogen, alkyl, and haloalkyl.

In certain embodiments, provided herein are compounds of Formula (II) wherein $X^1$ is CH or N; $X^3$ is $CR^3$; $X^4$ and $X^5$ are CH; $R^3$ is hydrogen, alkyl, halogen, —$OR^8$, —CN, cycloalkyl, or haloalkyl; and $R^8$ is hydrogen, alkyl, haloalkyl, cycloalkyl, heterocyclyl, aryl, or heteroaryl, wherein cycloalkyl, heterocyclyl, aryl, and heteroaryl are optionally substituted with one, two, or three groups selected from halogen, alkyl, and haloalkyl. In certain embodiments, provided herein are compounds of Formula (II) wherein $X^1$ is CH; $X^3$ is $CR^3$; $X^4$ and $X^5$ are CH; $R^3$ is hydrogen, alkyl, halogen, —$OR^8$, —CN, cycloalkyl, or haloalkyl; and $R^8$ is hydrogen, alkyl, haloalkyl, cycloalkyl, heterocyclyl, aryl, or heteroaryl, wherein cycloalkyl, heterocyclyl, aryl, and heteroaryl are optionally substituted with one, two, or three groups selected from halogen, alkyl, and haloalkyl.

In certain embodiments, provided herein are compounds of Formula (II) wherein $X^1$ is CH or N; $X^3$ is N; $X^4$ is $CR^4$ and $X^5$ is $CR^5$; $R^4$ and $R^5$ are each independently hydrogen, alkyl, halogen, —$OR^8$, —CN, cycloalkyl, or haloalkyl; and each $R^8$ is independently hydrogen, alkyl, haloalkyl, cycloalkyl, heterocyclyl, aryl, or heteroaryl, wherein cycloalkyl, heterocyclyl, aryl, and heteroaryl are optionally substituted with one, two, or three groups selected from halogen, alkyl, and haloalkyl. In certain embodiments, $X^1$ is CH or N; $X^3$ is N; $X^4$ and $X^5$ are both CH.

In certain embodiments, provided herein are compounds of Formula (II) wherein $X^1$ is CH or N; $X^3$ is CR, $X^4$ is N; $X^5$ is $CR^5$; $R^3$ and $R^5$ are each independently hydrogen, alkyl, halogen, —$OR^8$, —CN, cycloalkyl, or haloalkyl; and each $R^8$ is independently hydrogen, alkyl, haloalkyl, cycloalkyl, heterocyclyl, aryl, or heteroaryl, wherein cycloalkyl, heterocyclyl, aryl, and heteroaryl are optionally substituted with one, two, or three groups selected from halogen, alkyl, and haloalkyl. In certain embodiments, $X^1$ is CH or N; $X^3$ is CH; $X^4$ is N; $X^5$ is CH.

In certain embodiments, provided herein are compounds of Formula (II) wherein $X^1$ is CH or N; $X^3$ is $CR^3$; $X^4$ is $CR^4$; $X^5$ is N; $R^3$ and $R^4$ are each independently hydrogen, alkyl, halogen, —$OR^8$, —CN, cycloalkyl, or haloalkyl; and each $R^8$ is independently hydrogen, alkyl, haloalkyl, cycloalkyl, heterocyclyl, aryl, or heteroaryl, wherein cycloalkyl, heterocyclyl, aryl, and heteroaryl are optionally substituted with one, two, or three groups selected from halogen, alkyl, and haloalkyl. In certain embodiments, $X^1$ is CH or N; $X^3$ and $X^4$ are both CH and $X^5$ is N.

In certain embodiments, provided herein are compounds of Formula (II) wherein $R^1$ is independently cycloalkyl, heterocyclyl, aryl, heteroaryl, or —$OR^{8'}$, wherein cycloalkyl, heterocyclyl, aryl, and heteroaryl are each independently optionally substituted with one, two, or three $R^y$;
  each $R^y$ is independently alkyl, haloalkyl, cycloalkyl, cycloalkylalkyl, heterocyclyl, heterocyclylalkyl, halogen, —$OR^8$, —$NR^8R^9$, —CN, —$C(O)R^{11}$, —$C(O)NR^8R^9$, —$NR^8C(O)R^{11}$, —$NR^8C(O)OR^9$, —$NR^{10}C(O)NR^8R^9$, —$OC(O)NR^8R^9$, —$S(O)_2R^{11}$, —$S(O)R^{11}$, —$SR^8$, —$S(O)_2NR^8R^9$, —$S(O)NR^8R^9$, —$NR^8S(O)R^{11}$, —$NR^8S(O)_2R^{11}$, or —$NR^{10}S(O)_2NR^8R^9$; wherein alkyl is optionally substituted with —$OR^8$ or —$NR^8R^9$ and wherein cycloalkyl and heterocyclyl are optionally substituted with one, two, or three groups selected from halogen, alkyl, and haloalkyl;
  each $R^8$ and each $R^9$ are independently hydrogen, alkyl, haloalkyl, cycloalkyl, heterocyclyl, aryl, or heteroaryl, wherein cycloalkyl, heterocyclyl, aryl, and heteroaryl are optionally substituted with one, two, or three groups selected from halogen, alkyl, and haloalkyl; or
  $R^8$ and $R^9$, together with the atom or atoms to which they are attached, form a heterocyclyl optionally substituted with one, two, or three groups selected from halogen, alkyl, and haloalkyl;
  each $R^{10}$ is independently hydrogen or alkyl;
  each $R^{11}$ is independently alkyl, haloalkyl, cycloalkyl, heterocyclyl, aryl, or heteroaryl, wherein cycloalkyl, heterocyclyl, aryl, and heteroaryl are optionally substituted with one, two, or three groups selected from halogen, alkyl, and haloalkyl; and
  each $R^{8'}$ is independently hydrogen, alkyl, haloalkyl, cycloalkyl, heterocyclyl, aryl, or heteroaryl, wherein cycloalkyl, heterocyclyl, aryl, and heteroaryl are each independently optionally substituted with one, two, or three groups selected from halogen, alkyl, and haloalkyl.

In certain embodiments, provided herein are compounds of Formula (II) wherein each $R^1$ is independently heterocyclyl, aryl, heteroaryl, or —$OR^{8'}$, wherein the heterocyclyl, aryl, and heteroaryl are each independently optionally substituted with one, two, or three $R^y$; each $R^{8'}$ is independently hydrogen, alkyl, haloalkyl, cycloalkyl, heterocyclyl, aryl, or heteroaryl, wherein cycloalkyl, heterocyclyl, aryl, and heteroaryl are optionally substituted with one, two, or three groups selected from halogen, alkyl, and haloalkyl and each $R^y$ is independently alkyl, haloalkyl, cycloalkyl, cycloalkylalkyl, heterocyclyl, heterocyclylalkyl, halogen, —$OR^8$, —$NR^8R^9$, —CN, —$C(O)R^{11}$, —$C(O)NR^8R^9$, —$NR^8C(O)R^{11}$, —$NR^8C(O)OR^9$, —$NR^{10}C(O)NR^8R^9$, —$OC(O)NR^8R^9$, —$S(O)_2R^{11}$, —$S(O)R^{11}$, —$SR^8$, —$S(O)_2NR^8R^9$, —$NR^8S(O)_2R^{11}$, or —$NR^{10}S(O)_2NR^8R^9$; wherein alkyl is optionally substituted with —$OR^8$ or —$NR^8R^9$ and wherein cycloalkyl and heterocyclyl are optionally substituted with one, two, or three groups selected from halogen, alkyl, and haloalkyl; each $R^8$ and each $R^9$ are independently hydrogen, alkyl, haloalkyl, cycloalkyl, heterocyclyl, aryl, or heteroaryl, wherein cycloalkyl, heterocyclyl, aryl, and heteroaryl are optionally substituted with one, two, or three groups selected from halogen, alkyl, and haloalkyl; or $R^8$ and $R^9$, together with the atom or atoms to which they are attached, form a heterocyclyl optionally substituted with one, two, or three groups selected from halogen, alkyl, and haloalkyl; and each $R^{10}$ is independently hydrogen or alkyl.

In certain embodiments, provided herein are compounds of Formula (II) wherein $R^7$ is hydrogen, deuterium, halogen, alkyl or hydroxyl. In certain embodiments, $R^7$ is hydrogen, deuterium, halogen or alkyl.

In certain embodiments, provided herein are compounds of Formula (II) wherein q is 0. In certain embodiments, provided herein are compounds of Formula (II) wherein q is 0 or 1.

In certain embodiments, provided herein are compounds of Formula (II) wherein t is 1. In certain embodiments, t is 1 and q is 0 or 1. In certain embodiments, t is 1 and q is 0.

In certain embodiments, provided herein are compounds of Formula (II) wherein G is —C(O)OH, —C(O)NHOH, —$SO_3H$, —$SO_2NH_2$, —$SO_2NHR^d$, —$SO_2NHC(O)R^d$, —$NHC(O)NHSO_2R^d$, -1H-tetrazolyl, —$P(O)(OH)_2$, -1,2,4-oxadiazol-5(4H)-one, -tetrazol-5(4H)-one, or —C(O)NHSO_2R^d$ and $R^d$ is alkyl, haloalkyl, cycloalkyl, aryl, or heteroaryl. In certain embodiments, provided herein are compounds of Formula (II) wherein G is —COOH, -1H-tetrazolyl, -1,2,4-oxadiazol-5(4H)-one or -tetrazol-5(4H)-one. In certain embodiments, G is —COOH or -1H-tetrazolyl.

In some embodiments, a compound of Formula (I), or a pharmaceutically acceptable salt, solvate, solvate of the salt, hydrate, a single stereoisomer, a mixture of stereoisomers, a racemic mixture of stereoisomers, or prodrug thereof, has the structure of Formula (IIa) or (IIb):

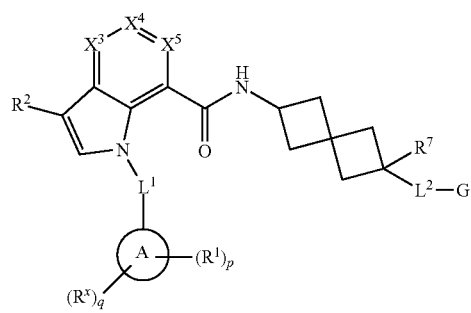

(IIa)

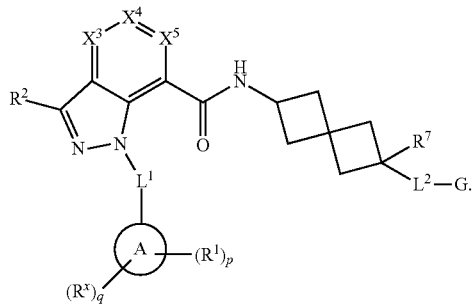

(IIb)

In some embodiments, a compound of Formula (I), or a pharmaceutically acceptable salt, solvate, solvate of the salt, hydrate, a single stereoisomer, a mixture of stereoisomers, a racemic mixture of stereoisomers, an isotopic variant or prodrug thereof, has the structure of Formula (IIc):

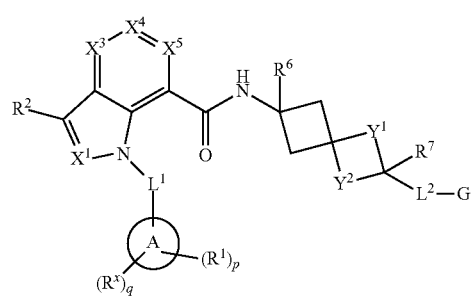

(IIc)

wherein the variables are as provided elsewhere herein for Formula (I) or (II).

In certain embodiments, provided herein are compounds of Formula (I), (II) or (IIc) wherein $L^1$ is —$CR^b_2$—; each $R^b$ is independently hydrogen, deuterium, optionally deuterated alkyl or haloalkyl or two $R^b$s, together with the carbon atom to which they are attached, form optionally deuterated cycloalkyl or heterocyclyl and the the other variables are as provided elsewhere herein for Formula (I) or (II). In certain embodiments, provided herein are compounds of Formula (I), (II) or (IIc) wherein $L^1$ is —$CR^b_2$—; each $R^b$ is independently hydrogen, deuterium, optionally deuterated alkyl or haloalkyl or two $R^b$s, together with the carbon atom to which they are attached, form optionally deuterated $C_3$-$C_6$ cycloalkyl or 4-6 membered heterocyclyl with one heteroatom, and the other variables are as provided elsewhere herein for Formula (I) or (II). In certain embodiments, provided herein are compounds of Formula (I), (II) or (IIc) wherein $L^1$ is —$CR^b_2$—; each $R^b$ is independently hydrogen, deuterium, optionally deuterated alkyl or haloalkyl or two $R^b$s, together with the carbon atom to which they are attached, form optionally deuterated $C_3$-$C_4$ cycloalkyl or 4-membered heterocyclyl with one heteroatom, and the other variables are as provided elsewhere herein for Formula (I) or (II).

In certain embodiments, provided herein are compounds of Formula (IIc) wherein $L^1$ is —$CR^b_2$—; each $R^b$ is independently hydrogen, alkyl or haloalkyl and the remaining variables are as provided elsewhere herein for Formula (I) or (II). In certain embodiments, each $R^b$ is independently hydrogen, deuterium, optionally deuterated alkyl or haloalkyl.

In some embodiments, a compound of Formula (I), or a pharmaceutically acceptable salt, solvate, solvate of the salt, hydrate, a single stereoisomer, a mixture of stereoisomers, a racemic mixture of stereoisomers, or prodrug thereof, has the structure of Formula (III):

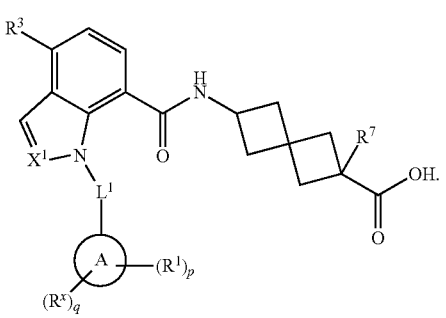

(III)

In some embodiments, a compound of Formula (I), or a pharmaceutically acceptable salt, solvate, solvate of the salt, hydrate, a single stereoisomer, a mixture of stereoisomers, a racemic mixture of stereoisomers, or prodrug thereof, has the structure of Formula (IIIa):

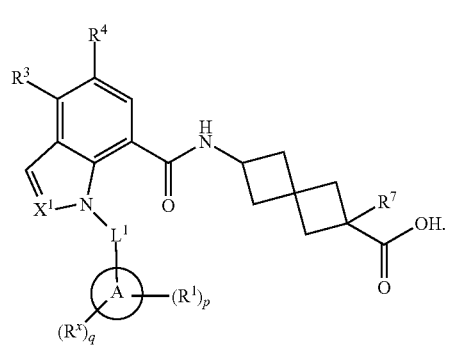

(IIIa)

In some embodiments, a compound of Formula (I), or a pharmaceutically acceptable salt, solvate, solvate of the salt, hydrate, a single stereoisomer, a mixture of stereoisomers, a racemic mixture of stereoisomers, isotopic variant or prodrug thereof, has the structure of Formula (IIIb):

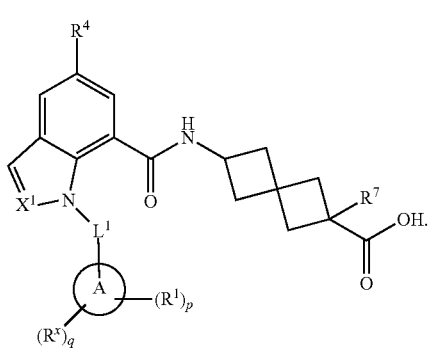

(IIIb)

In some embodiments, provided herein are compounds of Formula (I), (II), (IIa), (IIb), (III), (IIIa) wherein t is 1. In some embodiments, provided herein are compounds of Formula (I), (II), (IIa), (IIb), (III), (IIIa) wherein q is 0 or 1 and t is 1. In some embodiments, a compound of Formula (I), or a pharmaceutically acceptable salt, solvate, solvate of the salt, hydrate, a single stereoisomer, a mixture of stereoisomers, a racemic mixture of stereoisomers, or prodrug thereof, has the structure of Formula (IV):

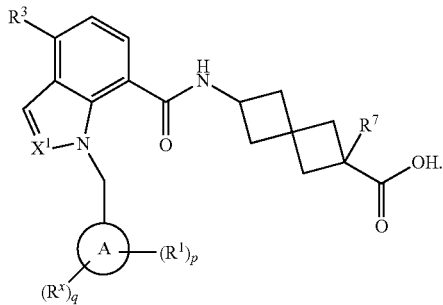

(IV)

In some embodiments, a compound of Formula (I), or a pharmaceutically acceptable salt, solvate, solvate of the salt, hydrate, a single stereoisomer, a mixture of stereoisomers, a racemic mixture of stereoisomers, or prodrug thereof, has the structure of Formula (IVa):

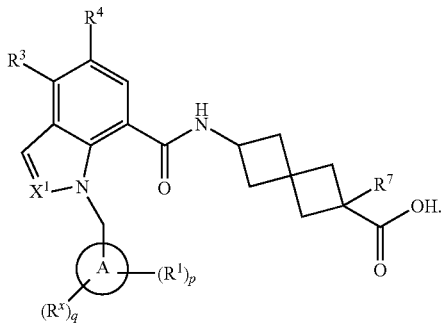

(IVa)

In some embodiments, a compound of Formula (I), or a pharmaceutically acceptable salt, solvate, solvate of the salt, hydrate, a single stereoisomer, a mixture of stereoisomers, a racemic mixture of stereoisomers, or prodrug thereof, has the structure of Formula (IV):

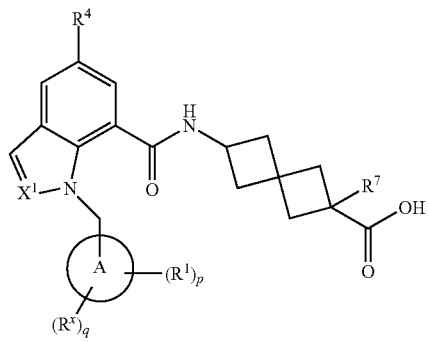

(IVb)

In some embodiments, a compound of Formula (I), or a pharmaceutically acceptable salt, solvate, solvate of the salt, hydrate, a single stereoisomer, a mixture of stereoisomers, a racemic mixture of stereoisomers, or prodrug thereof, has the structure of Formula (V):

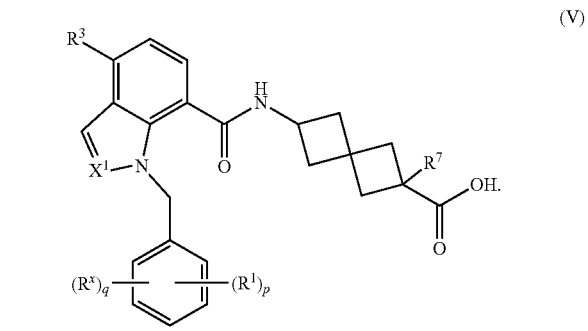

(V)

In some embodiments, a compound of Formula (I), or a pharmaceutically, acceptable salt, solvate, solvate of the salt, hydrate, a single stereoisomer, a mixture of stereoisomers, a racemic mixture of stereoisomers, or prodrug thereof, has the structure of Formula (Va):

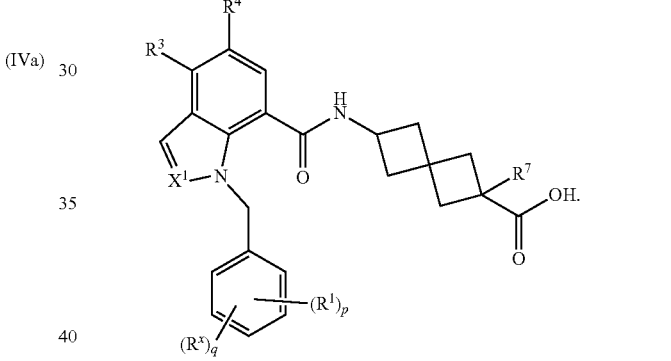

(Va)

In some embodiments, a compound of Formula (I), or a pharmaceutically acceptable salt, solvate, solvate of the salt, hydrate, a single stereoisomer, a mixture of stereoisomers, a racemic mixture of stereoisomers, or prodrug thereof, has the structure of Formula (Vb):

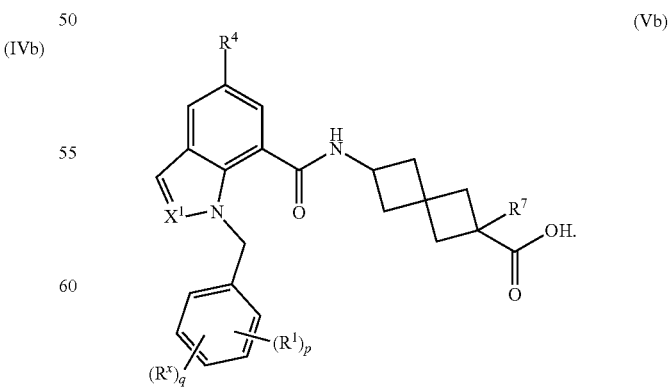

(Vb)

In some embodiments, provided herein are compounds having the Formula (I), or a pharmaceutically acceptable salt, solvate, solvate of the salt, hydrate, a single stereoisomer, a mixture of stereoisomers, a racemic mixture of stereoisomers, isotopic variants or prodrug thereof:

Formula (I)

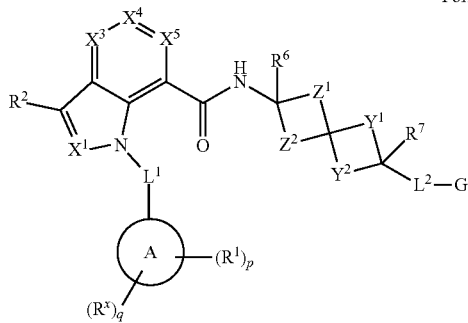

wherein:
$X^1$ is N or CH;
$X^3$ is N or $CR^3$;
$X^4$ is N or $CR^4$;
$X^5$ is N or $CR^5$;
wherein no more than two of $X^3$, $X^4$ and $X^5$ are N;
$L^1$ is $—(CR^b_2)_t—$;
Ring A is aryl;
each $R^1$ is independently $C_2$-$C_9$alkyl, $C_2$-$C_9$alkenyl, $C_2$-$C_6$alkynyl, cycloalkyl, heterocyclyl, aryl, heteroaryl, or $—OR^{8'}$, wherein $C_2$-$C_9$alkyl, $C_2$-$C_9$alkenyl, $C_2$-$C_9$alkynyl, cycloalkyl, heterocyclyl, aryl, and heteroaryl are optionally substituted with one, two, or three $R^y$;
or two $R^1$ substituents on adjacent atoms of Ring A are taken together with the atom to which they are attached to form an aromatic or non-aromatic ring containing 0-2 heteroatoms selected from the group consisting of $—O—$, $=N—$, $—NR^{10}—$, $—S—$, and $—S(O)_2—$, wherein the aromatic or non-aromatic ring is optionally deuterated and optionally substituted with one, two, or three $R^y$;
each $R^{8'}$ is independently hydrogen, alkyl, haloalkyl, cycloalkyl, heterocyclyl, aryl, or heteroaryl, wherein cycloalkyl, heterocyclyl, aryl, and heteroaryl arm optionally substituted with one, two, or three groups selected from halogen, alkyl, and haloalkyl;
each $R^y$ is independently alkyl, haloalkyl, cycloalkyl, cycloalkylalkyl, heterocyclyl, heterocyclylalkyl, halogen, $—OR^8$, $—NR^8R^9$, $—CN$, $—C(O)R^{11}$, $—C(O)NR^8R^9$, $—NR^8C(O)R^{11}$, $—NR^8C(O)OR^9$, $—NR^{10}C(O)NR^8R^9$, $—OC(O)NR^8R^9$, $—S(O)_2R^{11}$, $—S(O)R^{11}$, $—SR^8$, $—S(O)_2NR^8R^9$, $—S(O)NR^8R^9$, $—NR^8S(O)R^{11}$, $—NR^8S(O)_2R^{11}$, or $—NR^{10}S(O)_2NR^8R^9$; wherein the alkyl is optionally substituted with $—OR^8$ or $—NR^8R^9$ and wherein the cycloalkyl and heterocyclyl are optionally substituted with one, two, or three groups selected from halogen, alkyl, and haloalkyl;
each $R^x$ is independently halogen, methyl, $C_1$haloalkyl, or $—CN$;
$R^2$, $R^3$, $R^4$, and $R^5$ are each independently hydrogen, alkyl, halogen, $—OR^8$, $—NR^8R^9$, $—SR^8$, $—S(O)R^{11}$, $—S(O)_2R^{11}$, $—CN$, cycloalkyl, or haloalkyl;
$R^6$ is hydrogen, alkyl, or haloalkyl;
$R^7$ is hydrogen, halogen, alkyl, alkoxy, haloalkoxy, hydroxyl, or haloalkyl;

each $R^8$ and each $R^9$ are independently hydrogen, alkyl, haloalkyl, cycloalkyl, heterocyclyl, aryl, or heteroaryl, wherein cycloalkyl, heterocyclyl, aryl, and heteroaryl are optionally substituted with one, two, or three groups selected from halogen, alkyl, and haloalkyl; or
$R^8$ and $R^9$, together with the atom or atoms to which they are attached, form a heterocyclyl optionally substituted with one, two, or three groups selected from halogen, alkyl, and haloalkyl;
each $R^{10}$ is independently hydrogen or alkyl;
each $R^{11}$ is independently alkyl, haloalkyl, cycloalkyl, heterocyclyl, aryl, or heteroaryl, wherein cycloalkyl, heterocyclyl, aryl, and heteroaryl are optionally substituted with one, two, or three groups selected from halogen, alkyl, and haloalkyl;
$Y^1$ and $Y^2$ are each independently a bond or $—(CR^a_2)_n—$, provided that $Y^1$ and $Y^2$ are not both a bond;
$Z^1$ and $Z^2$ are each $—CR^a_2—$;
$L^2$ is $—(CR^c_2)_m—$;
G is $—C(O)OR^{12}$, $—C(O)NHOH$, $—SO_3H$, $—SO_2NH_2$, $—SO_2NHR^d$, $—SO_2NHC(O)R^d$, $—NHC(O)NHSO_2R^d$, -1H-tetrazolyl, $—P(O)(OH)_2$, -1,2,4-oxadiazol-5(4H)-one, -tetrazol-5(4H)-one, or $—C(O)NHSO_2R^d$;
$R^2$ is selected from H, $C_1$-$C_6$ alkyl, aryl, aralkyl, $CH(R^{13})OC(=O)R^{14}$, $CH(R^{13})OC(=O)OR^{14}$ and a (5-alkyl-2-oxo-1,3-dioxolen-4-yl)methyl group having the following formula:

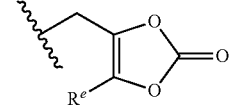

wherein $R^e$ is $C_1$-$C_6$ alkyl;
$R^{13}$ is hydrogen or $C_1$-$C_6$ alkyl;
$R^{14}$ is $C_1$-$C_6$ alkyl or $C_3$-$C_6$-cycloalkyl;
each $R^a$ is independently hydrogen, alkyl, halogen, or haloalkyl;
each $R^b$ is independently hydrogen, alkyl or haloalkyl, or two $R^b$s, together with the carbon atom to which they are attached, form cycloalkyl or heterocyclyl;
each $R^c$ is independently hydrogen or halogen;
$R^d$ is alkyl, haloalkyl, cycloalkyl, aryl, or heteroaryl;
m is 0, 1, or 2;
each n is independently 1, 2, or 3;
p is 1 or 2;
q is 0, 1, or 2; and
t is 1, 2 or 3.
In some embodiments, provided herein are compounds having the Formula (I) wherein:
$L^1$ is $—(CR^b_2)_t—$;
Ring A is optionally deuterated aryl;
each $R^1$ is independently $C_2$-$C_9$alkyl, $C_2$-$C_9$alkenyl, $C_2$-$C_9$alkynyl, cycloalkyl, heterocyclyl, aryl, heteroaryl or $—OR^{8'}$, wherein $C_2$-$C_9$alkyl, $C_2$-$C_9$alkenyl, $C_2$-$C_9$alkynyl, cycloalkyl, heterocyclyl, aryl, and heteroaryl are optionally deuterated and optionally substituted with one, two, or three $R^y$;
or two $R^1$ substituents on adjacent atoms of Ring A are taken together with the atom to which they are attached to form an aromatic or non-aromatic ring containing 0-2 heteroatoms selected from the group consisting of $—O—$, $=N—$, $—NR^{10}—$, $—S—$, and $—S(O)_2—$, wherein the aromatic or non-aromatic ring is optionally deuterated and optionally substituted with one, two, or three $R^y$;

$R^2$, $R^3$, $R^4$, and $R^5$ are each independently hydrogen, alkyl, halogen, —OR, —$NR^8R^9$, —$SR^8$, —$S(O)R^{11}$, —$S(O)_2R^{11}$, —CN, cycloalkyl, or haloalkyl;

$R^7$ is hydrogen, deuterium, halogen, optionally deuterated alkyl, alkoxy, haloalkoxy, hydroxyl, or haloalkyl;

each $R^8$ and each $R^9$ are independently hydrogen, deuterium, alkyl, deuterated alkyl, haloalkyl, cycloalkyl, heterocyclyl, aryl, or heteroaryl, wherein cycloalkyl, heterocyclyl, aryl, and heteroaryl are optionally substituted with one, two, or three groups selected from halogen, alkyl, and haloalkyl; or $R^8$ and $R^9$, together with the atom or atoms to which they are attached, form a heterocyclyl optionally substituted with one, two, or three groups selected from halogen, alkyl, and haloalkyl;

each $R^{10}$ is independently hydrogen, deuterium, alkyl or deuterated alkyl;

each $R^{11}$ is independently alkyl, deuterated alkyl, haloalkyl, cycloalkyl, heterocyclyl, aryl, or heteroaryl, wherein cycloalkyl, heterocyclyl, aryl, and heteroaryl are optionally substituted with one, two, or three groups selected from halogen, alkyl, and haloalkyl;

$Y^1$ and $Y^2$ are each independently a bond or —$(CR^a_2)_n$—, provided that $Y^1$ and $Y^2$ are not both a bond;

$Z^1$ and $Z^2$ are each —$CR^a_2$—;

$L^2$ is —$(CR^c_2)_m$—;

each $R^a$ is independently hydrogen, deuterium, optionally deuterated alkyl, halogen, or haloalkyl;

each $R^b$ is independently hydrogen, deuterium, optionally deuterated alkyl or haloalkyl, or two $R^b$s, together with the carbon atom to which they are attached, form optionally deuterated cycloalkyl or heterocyclyl;

each $R^c$ is independently hydrogen, deuterium or halogen;

m is 0, 1, or 2;

each n is independently 1, 2, or 3;

p is 1 or 2;

q is 0, 1, or 2; and t is 1, 2 or 3.

In some embodiments, provided herein are compounds of Formula (I) wherein the compound is selected from:

6-(4-Fluoro-1-(4-(trifluoromethoxy)benzyl)-1H-indole-7-carboxamido)spiro[3.3]heptane-2-carboxylic acid (Example 1);

($R_a$)-6-(4-Fluoro-1-(4-(trifluoromethoxy)benzyl)-1H-indole-7-carboxamido)spiro[3.3]heptane-2-carboxylic acid;

($S_a$)-6-(4-Fluoro-1-(4-(trifluoromethoxy)benzyl)-1H-indole-7-carboxamido)spiro[3.3]heptane-2-carboxylic acid (Example 8);

6-(1-(4-(tert-butyl)benzyl)-4-fluoro-1H-indole-7-carboxamido)spiro[3.3]heptane-2-carboxylic acid (Example 2);

($R_a$)-6-(1-(4-(tert-butyl)benzyl)-4-fluoro-1H-indole-7-carboxamido)spiro[3.3]heptane-2-carboxylic acid;

($S_a$)-6-(1-(4-(tert-butyl)benzyl)-4-fluoro-1H-indole-7-carboxamido)spiro[3.3]heptane-2-carboxylic acid;

6-(1-([1,1'-biphenyl]-4-ylmethyl)-4-fluoro-1H-indole-7-carboxamido)spiro[3.3]heptane-2-carboxylic acid (Example 3);

($R_a$)-6-(1-([1,1'-biphenyl]-4-ylmethyl)-4-fluoro-1H-indole-7-carboxamido)spiro[3.3]heptane-2-carboxylic acid;

($S_a$)-6-(1-([1,1'-biphenyl]-4-ylmethyl)-4-fluoro-1H-indole-7-carboxamido)spiro[3.3]heptane-2-carboxylic acid (Example 9);

6-(4-fluoro-1-(naphthalen-2-ylmethyl)-1H-indole-7-carboxamido)spiro[3.3]heptane-2-carboxylic acid (Example 4);

($R_a$)-6-(4-fluoro-1-(naphthalen-2-ylmethyl)-1H-indole-7-carboxamido)spiro[3.3]heptane-2-carboxylic acid;

($S_a$)-6-(4-fluoro-1-(naphthalen-2-ylmethyl)-1H-indole-7-carboxamido)spiro[3.3]heptane-2-carboxylic acid (Example 26);

6-(4-fluoro-1-((6-fluoronaphthalen-2-yl)methyl)-1H-indole-7-carboxamido)spiro[3.3]heptane-2-carboxylic acid (Example 5);

($R_a$)-6-(4-fluoro-1-((6-fluoronaphthalen-2-yl)methyl)-1H-indole-7-carboxamido)spiro[3.3]heptane-2-carboxylic acid;

($S_a$)-6-(4-fluoro-1-((6-fluoronaphthalen-2-yl)methyl)-1H-indole-7-carboxamido)spiro[3.3]heptane-2-carboxylic acid (Example 37);

6-(4-bromo-1-(4-(tert-butyl)benzyl)-1H-indole-7-carboxamido)spiro[3.3]heptane-2-carboxylic acid (Example 6);

($R_a$)-6-(4-bromo-1-(4-(tert-butyl)benzyl)-1H-indole-7-carboxamido)spiro[3.3]heptane-2-carboxylic acid;

($S_a$)-6-(4-bromo-1-(4-(tert-butyl)benzyl)-1H-indole-7-carboxamido)spiro[3.3]heptane-2-carboxylic acid;

6-(1-(4-(tert-Butyl)benzyl)-4-chloro-1H-indole-7-carboxamido)spiro[3.3]heptane-2-carboxylic acid (Example 7);

($R_a$)-6-(1-(4-(tert-Butyl)benzyl)-4-chloro-1H-indole-7-carboxamido)spiro[3.3]heptane-2-carboxylic acid;

($S_a$)-6-(1-(4-(tert-Butyl)benzyl)-4-chloro-1H-indole-7-carboxamido)spiro[3.3]heptane-2-carboxylic acid;

6-(4-Fluoro-1-((2-fluoro-[1,1'-biphenyl]-4-yl)methyl)-1H-indole-7-carboxamido)spiro[3.3]heptane-2-carboxylic acid (Example 10);

($R_a$)-6-(4-Fluoro-1-((2-fluoro-[1,1'-biphenyl]-4-yl)methyl)-1H-indole-7-carboxamido)spiro[3.3]heptane-2-carboxylic acid;

($S_a$)-6-(4-Fluoro-1-((2-fluoro-[1,1'-biphenyl]-4-yl)methyl)-1H-indole-7-carboxamido)spiro[3.3]heptane-2-carboxylic acid (Example 65);

6-(4-Fluoro-1-(4-(pyridin-4-yl)benzyl)-1H-indole-7-carboxamido)spiro[3.3]heptane-2-carboxylic acid (Example 11);

($R_a$)-6-(4-Fluoro-1-(4-(pyridin-4-yl)benzyl)-1H-indole-7-carboxamido)spiro[3.3]heptane-2-carboxylic acid;

($S_a$)-6-(4-Fluoro-1-(4-(pyridin-4-yl)benzyl)-1H-indole-7-carboxamido)spiro[3.3]heptane-2-carboxylic acid (Example 24);

6-(4-fluoro-1-((4'-methoxy-[1,1'-biphenyl]-4-yl)methyl)-1H-indole-7-carboxamido)spiro[3.3]heptane-2-carboxylic acid (Example 12);

($R_a$)-6-(4-fluoro-1-((4'-methoxy-[1,1'-biphenyl]-4-yl)methyl)-1H-indole-7-carboxamido)spiro[3.3]heptane-2-carboxylic acid;

($S_a$)-6-(4-fluoro-1-((4'-methoxy-[1,1'-biphenyl]-4-yl)methyl)-1H-indole-7-carboxamido)spiro[3.3]heptane-2-carboxylic acid (Example 51);

6-(1-((4'-cyano-[1,1'-biphenyl]-4-yl)methyl)-4-fluoro-1H-indole-7-carboxamido)spiro[3.3]heptane-2-carboxylic acid (Example 13);

($R_a$)-6-(1-((4'-cyano-[1,1'-biphenyl]-4-yl)methyl)-4-fluoro-1H-indole-7-carboxamido)spiro[3.3]heptane-2-carboxylic acid;

($S_a$)-6-(1-((4'-cyano-[1,1'-biphenyl]-4-yl)methyl)-4-fluoro-1H-indole-7-carboxamido)spiro[3.3]heptane-2-carboxylic acid;

6-(4-fluoro-1-((3'-methoxy-[1,1'-biphenyl]-4-yl)methyl)-1H-indole-7-carboxamido)spiro[3.3]heptane-2-carboxylic acid (Example 14);

(R$_a$)-6-(4-fluoro-1-((3'-methoxy-[1,1'-biphenyl]-4-yl)methyl)-1H-indole-7-carboxamido)spiro[3.3]heptane-2-carboxylic acid;
(S$_a$)-6-(4-fluoro-1-((3'-methoxy-[1,1'-biphenyl]-4-yl)methyl)-1H-indole-7-carboxamido)spiro[3.3]heptane-2-carboxylic acid;
6-(1-((3'-cyano-[1,1'-biphenyl]-4-yl)methyl)-4-fluoro-1H-indole-7-carboxamido)spiro[3.3]heptane-2-carboxylic acid (Example 15);
(R$_a$)-6-(1-((3'-cyano-[1,1'-biphenyl]-4-yl)methyl)-4-fluoro-1H-indole-7-carboxamido)spiro[3.3]heptane-2-carboxylic acid;
(S$_a$)-6-(1-((3'-cyano-[1,1'-biphenyl]-4-yl)methyl)-4-fluoro-1H-indole-7-carboxamido)spiro[3.3]heptane-2-carboxylic acid (Example 55);
6-(4-fluoro-1-((3'-fluoro-4'-methoxy-[1,1'-biphenyl]-4-yl)methyl)-1H-indole-7-carboxamido)spiro[3.3]heptane-2-carboxylic acid (Example 16);
(R$_a$)-6-(4-fluoro-1-((3'-fluoro-4'-methoxy-[1,1'-biphenyl]-4-yl)methyl)-1H-indole-7-carboxamido)spiro[3.3]heptane-2-carboxylic acid;
(S$_a$)-6-(4-fluoro-1-((3'-fluoro-4'-methoxy-[1,1'-biphenyl]-4-yl)methyl)-1H-indole-7-carboxamido)spiro[3.3]heptane-2-carboxylic acid (Example 47);
6-(1-(4-(5-Chloro-6-methoxypyridin-3-yl)benzyl)-4-fluoro-1H-indole-7-carboxamido)spiro[3.3]heptane-2-carboxylic acid (Example 17);
(R$_a$)-6-(1-(4-(5-Chloro-6-methoxypyridin-3-yl)benzyl)-4-fluoro-1H-indole-7-carboxamido)spiro[3.3]heptane-2-carboxylic acid;
(S$_a$)-6-(1-(4-(5-Chloro-6-methoxypyridin-3-yl)benzyl)-4-fluoro-1H-indole-7-carboxamido)spiro[3.3]heptane-2-carboxylic acid;
6-(4-fluoro-1-((2'-methoxy-[1,1'-biphenyl]-4-yl)methyl)-1H-indole-7-carboxamido)spiro[3.3]heptane-2-carboxylic acid (Example 18);
(R$_a$)-6-(4-fluoro-1-((2'-methoxy-[1,1'-biphenyl]-4-yl)methyl)-1H-indole-7-carboxamido)spiro[3.3]heptane-2-carboxylic acid;
(S$_a$)-6-(4-fluoro-1-((2'-methoxy-[1,1'-biphenyl]-4-yl)methyl)-1H-indole-7-carboxamido)spiro[3.3]heptane-2-carboxylic acid;
6-(4-fluoro-1-((4'-fluoro-3'-methoxy-[1,1'-biphenyl]-4-yl)methyl)-1H-indole-7-carboxamido)spiro[3.3]heptane-2-carboxylic acid (Example 19);
(R$_a$)-6-(4-fluoro-1-((4'-fluoro-3'-methoxy-[1,1'-biphenyl]-4-yl)methyl)-1H-indole-7-carboxamido)spiro[3.3]heptane-2-carboxylic acid;
(S$_a$)-6-(4-fluoro-1-((4'-fluoro-3'-methoxy-[1,1'-biphenyl]-4-yl)methyl)-1H-indole-7-carboxamido)spiro[3.3]heptane-2-carboxylic acid (Example 46);
6-(1-((3'-cyano-5'-methoxy-[1,1'-biphenyl]-4-yl)methyl)-4-fluoro-1H-indole-7-carboxamido)spiro[3.3]heptane-2-carboxylic acid (Example 20);
(R$_a$)-6-(1-((3'-cyano-5'-methoxy-[1,1'-biphenyl]-4-yl)methyl)-4-fluoro-1H-indole-7-carboxamido)spiro[3.3]heptane-2-carboxylic acid;
(S$_a$)-6-(1-((3'-cyano-5'-methoxy-[1,1'-biphenyl]-4-yl)methyl)-4-fluoro-H-indole-7-carboxamido)spiro[3.3]heptane-2-carboxylic acid (Example 49);
6-(1-((3'-Chloro-4'-(oxetan-3-yloxy)-[1,1'-biphenyl]-4-yl)methyl)-4-fluoro-1H-indole-7-carboxamido)spiro[3.3]heptane-2-carboxylic acid (Example 21);
(R$_a$)-6-(1-(3'-Chloro-4'-(oxetan-3-yloxy)-[1,1'-biphenyl]-4-yl)methyl)-1H-indole-7-carboxamido)spiro[3.3]heptane-2-carboxylic acid;
(S$_a$)-6-(1-((3'-Chloro-4'-(oxetan-3-yloxy)-[1,1'-biphenyl]-4-yl)methyl)-4-fluoro-1H-indole-7-carboxamido)spiro[3.3]heptane-2-carboxylic acid;
6-(1-(4-(2-(dimethylamino)pyridin-4-yl)benzyl)-4-fluoro-1H-indole-7-carboxamido)spiro[3.3]heptane-2-carboxylic acid (Example 22);
(R$_a$)-6-(1-(4-(2-(dimethylamino)pyridin-4-yl)benzyl)-4-fluoro-1H-indole-7-carboxamido)spiro[3.3]heptane-2-carboxylic acid;
(S$_a$)-6-(1-(4-(2-(dimethylamino)pyridin-4-yl)benzyl)-4-fluoro-1H-indole-7-carboxamido)spiro[3.3]heptane-2-carboxylic acid;
6-(4-Fluoro-1-((4'-(oxetan-3-yloxy)-[1,1'-biphenyl]-4-yl)methyl)-1H-indole-7-carboxamido)spiro[3.3]heptane-2-carboxylic acid (Example 23);
(R$_a$)-6-(4-Fluoro-1-((4'-(oxetan-3-yloxy)-[1,1'-biphenyl]-4-yl)methyl)-1H-indole-7-carboxamido)spiro[3.3]heptane-2-carboxylic acid;
(S$_a$)-6-(4-Fluoro-1-((4'-(oxetan-3-yloxy)-[1,1'-biphenyl]-4-yl)methyl)-1H-indole-7-carboxamido)spiro[3.3]heptane-2-carboxylic acid;
6-(1-(3'-Chloro-4'-methoxy-[1,1'-biphenyl]-4-yl)methyl)-4-fluoro-1H-indole-7-carboxamido)spiro[3.3]heptane-2-carboxylic acid;
(R$_a$)-6-(1-((3'-Chloro-4'-methoxy-[1,1'-biphenyl]-4-yl)methyl)-4-fluoro-1H-indole-7-carboxamido)spiro[3.3]heptane-2-carboxylic acid;
(S$_a$)-6-(1-((3'-Chloro-4'-methoxy-[1,1'-biphenyl]-4-yl)methyl)-4-fluoro-1H-indole-7-carboxamido)spiro[3.3]heptane-2-carboxylic acid (Example 25);
6-(1-(4-(tert-Butyl)benzyl)-4-cyano-1H-indole-7-carboxamido)spiro[3.3]heptane-2-carboxylic acid (Example 27);
(R$_a$)-6-(1-(4-(tert-Butyl)benzyl)-4-cyano-1H-indole-7-carboxamido)spiro[3.3]heptane-2-carboxylic acid;
(S$_a$)-6-(1-(4-(tert-Butyl)benzyl)-4-cyano-1H-indole-7-carboxamido)spiro[3.3]heptane-2-carboxylic acid;
6-(1-(4-(cyclopentyloxy)benzyl)-4-fluoro-1H-indole-7-carboxamido)spiro[3.3]heptane-2-carboxylic acid (Example 28);
(R$_a$)-6-(1-(4-(cyclopentyloxy)benzyl)-4-fluoro-1H-indole-7-carboxamido)spiro[3.3]heptane-2-carboxylic acid;
(S$_a$)-6-(1-(4-(cyclopentyloxy)benzyl)-4-fluoro-1H-indole-7-carboxamido)spiro[3.3]heptane-2-carboxylic acid;
6-(1-(4-(cyclohexyloxy)benzyl)-4-fluoro-1H-indole-7-carboxamido)spiro[3.3]heptane-2-carboxylic acid (Example 29);
(R$_a$)-6-(1-(4-(cyclohexyloxy)benzyl)-4-fluoro-1H-indole-7-carboxamido)spiro[3.3]heptane-2-carboxylic acid;
(S$_a$)-6-(1-(4-(cyclohexyloxy)benzyl)-4-fluoro-1H-indole-7-carboxamido)spiro[3.3]heptane-2-carboxylic acid;
6-(4-fluoro-1-(4-((tetrahydro-2H-pyran-4-yl)oxy)benzyl)-1H-indole-7-carboxamido)spiro[3.3]heptane-2-carboxylic acid (Example 30);
(R$_a$)-6-(4-fluoro-1-(4-((tetrahydro-2H-pyran-4-yl)oxy)benzyl)-1H-indole-7-carboxamido)spiro[3.3]heptane-2-carboxylic acid;
(S$_a$)-6-(4-fluoro-1-(4-((tetrahydro-2H-pyran-4-yl)oxy)benzyl)-1H-indole-7-carboxamido)spiro[3.3]heptane-2-carboxylic acid;
6-(4-Fluoro-1-(4-morpholinobenzyl)-1H-indole-7-carboxamido)spiro[3.3]heptane-2-carboxylic acid (Example 31);
(R$_a$)-6-(4-Fluoro-1-(4-morpholinobenzyl)-1H-indole-7-carboxamido)spiro[3.3]heptane-2-carboxylic acid;
(S$_a$)-6-(4-Fluoro-1-(4-morpholinobenzyl)-1H-indole-7-carboxamido)spiro[3.3]heptane-2-carboxylic acid;

6-(1-(4-(Trifluoromethoxy)benzyl)-1H-indazole-7-carboxamido)spiro[3.3]heptane-2-carboxylic acid (Example 32);
($R_a$)-6-(1-(4-(Trifluoromethoxy)benzyl)-1H-indazole-7-carboxamido)spiro[3.3]heptane-2-carboxylic acid;
($S_a$)-6-(1-(4-(Trifluoromethoxy)benzyl)-1H-indazole-7-carboxamido)spiro[3.3]heptane-2-carboxylic acid;
6-(1-([1,1'-biphenyl]-4-ylmethyl)-1H-indazole-7-carboxamido)spiro[3.3]heptane-2-carboxylic acid (Example 33);
($R_a$)-6-(1-([1,1'-biphenyl]-4-ylmethyl)-1H-indazole-7-carboxamido)spiro[3.3]heptane-2-carboxylic acid;
($S_a$)-6-(1-([1,1'-biphenyl]-4-ylmethyl)-1H-indazole-7-carboxamido)spiro[3.3]heptane-2-carboxylic acid;
6-(1-([1,1'-biphenyl]-4-ylmethyl)-4-fluoro-1H-indazole-7-carboxamido)spiro[3.3]heptane-2-carboxylic acid (Example 34);
($R_a$)-6-(1-([1,1'-biphenyl]-4-ylmethyl)-4-fluoro-1H-indazole-7-carboxamido)spiro[3.3]heptane-2-carboxylic acid;
($S_a$)-6-(1-([1,1'-biphenyl]-4-ylmethyl)-4-fluoro-1H-indazole-7-carboxamido)spiro[3.3]heptane-2-carboxylic acid;
6-(4-fluoro-1-((3'-fluoro-[1,1'-biphenyl]-4-yl)methyl)-1H-indole-7-carboxamido)spiro[3.3]heptane-2-carboxylic acid (Example 35);
($R_a$)-6-(4-fluoro-1-((3'-fluoro-[1,1'-biphenyl]-4-yl)methyl)-1H-indole-7-carboxamido)spiro[3.3]heptane-2-carboxylic acid;
($S_a$)-6-(4-fluoro-1-((3'-fluoro-[1,1'-biphenyl]-4-yl)methyl)-1H-indole-7-carboxamido)spiro[3.3]heptane-2-carboxylic acid (Example 45);
6-(1-(4-(2-ethoxypyridin-4-yl)benzyl)-4-fluoro-1H-indole-7-carboxamido)spiro[3.3]heptane-2-carboxylic acid (Example 36);
($R_a$)-6-(1-(4-(2-ethoxy pyridin-4-yl)benzyl)-4-fluoro-1H-indole-7-carboxamido)spiro[3.3]heptane-2-carboxylic acid;
($S_a$)-6-(1-(4-(2-ethoxypyridin-4-yl)benzyl)-4-fluoro-1H-indole-7-carboxamido)spiro[3.3]heptane-2-carboxylic acid (Example 48);
6-(4-fluoro-1-((6-methoxynaphthalen-2-yl)methyl)-1H-indole-7-carboxamido)spiro[3.3]heptane-2-carboxylic acid;
($R_a$)-6-(4-fluoro-1-((6-methoxynaphthalen-2-yl)methyl)-1H-indole-7-carboxamido)spiro[3.3]heptane-2-carboxylic acid;
($S_a$)-6-(4-fluoro-1-((6-methoxynaphthalen-2-yl)methyl)-1H-indole-7-carboxamido)spiro[3.3]heptane-2-carboxylic acid (Example 38);
6-(4-fluoro-1-((5-methoxynaphthalen-2-yl)methyl)-1H-indole-7-carboxamido)spiro[3.3]heptane-2-carboxylic acid;
($R_a$)-6-(4-fluoro-1-((5-methoxynaphthalen-2-yl)methyl)-1H-indole-7-carboxamido)spiro[3.3]heptane-2-carboxylic acid;
($S_a$)-6-(4-fluoro-1-((5-methoxynaphthalen-2-yl)methyl)-1H-indole-7-carboxamido)spiro[3.3]heptane-2-carboxylic acid (Example 39);
6-(4-fluoro-1-((7-methoxynaphthalen-2-yl)methyl)-1H-indole-7-carboxamido)spiro[3.3]heptane-2-carboxylic acid;
($R_a$)-6-(4-fluoro-1-((7-methoxynaphthalen-2-yl)methyl)-1H-indole-7-carboxamido)spiro[3.3]heptane-2-carboxylic acid;
($S_a$)-6-(4-fluoro-1-((7-methoxynaphthalen-2-yl)methyl)-1H-indole-7-carboxamido)spiro[3.3]heptane-2-carboxylic acid (Example 40);
6-(1-((6-cyanonaphthalen-2-yl)methyl)-4-fluoro-1H-indole-7-carboxamido)spiro[3.3]heptane-2-carboxylic acid;
($R_a$)-6-(1-((6-cyanonaphthalen-2-yl)methyl)-4-fluoro-1H-indole-7-carboxamido)spiro[3.3]heptane-2-carboxylic acid;
($S_a$)-6-(1-((6-cyanonaphthalen-2-yl)methyl)-4-fluoro-1H-indole-7-carboxamido)spiro[3.3]heptane-2-carboxylic acid (Example 41);
6-(1-((6-bromonaphthalen-2-yl)methyl)-4-fluoro-1H-indole-7-carboxamido)spiro[3.3]heptane-2-carboxylic acid;
($R_a$)-6-(1-((6-bromonaphthalen-2-yl)methyl)-4-fluoro-1H-indole-7-carboxamido)spiro[3.3]heptane-2-carboxylic acid;
($S_a$)-6-(1-((6-bromonaphthalen-2-yl)methyl)-4-fluoro-1H-indole-7-carboxamido)spiro[3.3]heptane-2-carboxylic acid (Example 42);
6-(1-((5-bromonaphthalen-2-yl)methyl)-4-fluoro-1H-indole-7-carboxamido)spiro[3.3]heptane-2-carboxylic acid;
($R_a$)-6-(1-((5-bromonaphthalen-2-yl)methyl)-4-fluoro-1H-indole-7-carboxamido)spiro[3.3]heptane-2-carboxylic acid;
($S_a$)-6-(1-((5-bromonaphthalen-2-yl)methyl)-4-fluoro-1H-indole-7-carboxamido)spiro[3.3]heptane-2-carboxylic acid (Example 43);
6-(1-((7-bromonaphthalen-2-yl)methyl)-4-fluoro-1H-indole-7-carboxamido)spiro[3.3]heptane-2-carboxylic acid;
($R_a$)-6-(1-((7-bromonaphthalen-2-yl)methyl)-4-fluoro-1H-indole-7-carboxamido)spiro[3.3]heptane-2-carboxylic acid;
($S_a$)-6-(1-((7-bromonaphthalen-2-yl)methyl)-4-fluoro-1H-indole-7-carboxamido)spiro[3.3]heptane-2-carboxylic acid (Example 44);
6-(1-((3'-(difluoromethoxy)-[1,1'-biphenyl]-4-yl)methyl)-4-fluoro-1H-indole-7-carboxamido)spiro[3.3]heptane-2-carboxylic acid;
($R_a$)-6-(1-((3'-(difluoromethoxy)-[1,1'-biphenyl]-4-yl)methyl)-4-fluoro-1H-indole-7-carboxamido)spiro[3.3]heptane-2-carboxylic acid;
($S_a$)-6-(1-((3'-(difluoromethoxy)-[1,1'-biphenyl]-4-yl)methyl)-4-fluoro-1H-indole-7-carboxamido)spiro[3.3]heptane-2-carboxylic acid (Example 50);
6-(4-fluoro-1-((3'-methoxy-$d_3$-[1,1'-biphenyl]-4-yl)methyl)-1H-indole-7-carboxamido)spiro[3.3]heptane-2-carboxylic acid;
($R_a$)-6-(4-fluoro-1-((3'-methoxy-$d_3$-[1,1'-biphenyl]-4-yl)methyl)-1H-indole-7-carboxamido)spiro[3.3]heptane-2-carboxylic acid;
($S_a$)-6-(4-fluoro-1-((3'-methoxy-$d_3$-[1,1'-biphenyl]-4-yl)methyl)-1H-indole-7-carboxamido)spiro[3.3]heptane-2-carboxylic acid (Example 52);
6-(4-fluoro-1-((3'-fluoro-5'-methoxy-[1,1'-biphenyl]-4-yl)methyl)-FH-indole-7-carboxamido)spiro[3.3]heptane-2-carboxylic acid;
($R_a$)-6-(4-fluoro-1-((3'-fluoro-5'-methoxy-[1,1'-biphenyl]-4-yl)methyl)-1H-indole-7-carboxamido)spiro[3.3]heptane-2-carboxylic acid;
($S_a$)-6-(4-fluoro-1-((3'-fluoro-5'-methoxy-[1,1'-biphenyl]-4-yl)methyl)-1H-indole-7-carboxamido)spiro[3.3]heptane-2-carboxylic acid (Example 53);
6-(1-((3'-ethoxy-[1,1'-biphenyl]-4-yl)methyl)-4-fluoro-1H-indole-7-carboxamido)spiro[3.3]heptane-2-carboxylic acid;
($R_a$)-6-(1-((3'-ethoxy-[1,1'-biphenyl]-4-yl)methyl)-4-fluoro-1H-indole-7-carboxamido)spiro[3.3]heptane-2-carboxylic acid;
($S_a$)-6-(1-((3'-ethoxy-[1,1'-biphenyl]-4-yl)methyl)-4-fluoro-1H-indole-7-carboxamido)spiro[3.3]heptane-2-carboxylic acid (Example 54);

6-(1-(4-(6-ethoxypyridin-2-yl)benzyl)-4-fluoro-1H-indole-7-carboxamido)spiro[3.3]heptane-2-carboxylic acid;
($R_a$)-6-(1-(4-(6-ethoxypyridin-2-yl)benzyl)-4-fluoro-1H-indole-7-carboxamido)spiro[3.3]heptane-2-carboxylic acid;
($S_a$)-6-(1-(4-(6-ethoxypyridin-2-yl)benzyl)-4-fluoro-1H-indole-7-carboxamido)spiro[3.3]heptane-2-carboxylic acid (Example 56);
6-(4-fluoro-1-((3'-(oxetane-3-yloxy)-[1,1'-biphenyl]-4-yl)methyl)-1H-indole-7-carboxamido)spiro[3.3]heptane-2-carboxylic acid;
($R_a$)-6-(4-fluoro-1-((3'-(oxetane-3-yloxy)-[1,1'-biphenyl]-4-yl)methyl)-1H-indole-7-carboxamido)spiro[3.3]heptane-2-carboxylic acid;
($S_a$)-6-(4-fluoro-1-((3'-(oxetane-3-yloxy)-[1,1'-biphenyl]-4-yl)methyl)-1H-indole-7-carboxamido)spiro[3.3]heptane-2-carboxylic acid (Example 57);
6-(1-(4-(2-ethoxypyrimidin-4-yl)benzyl)-4-fluoro-1H-indole-7-carboxamido)spiro[3.3]heptane-2-carboxylic acid;
($R_a$)-6-(1-(4-(2-ethoxypyrimidin-4-yl)benzyl)-4-fluoro-1H-indole-7-carboxamido)spiro[3.3]heptane-2-carboxylic acid;
($S_a$)-6-(1-(4-(2-ethoxypyrimidin-4-yl)benzyl)-4-fluoro-1H-indole-7-carboxamido)spiro[3.3]heptane-2-carboxylic acid (Example 58);
6-(1-(4-(4-cyano-6-methoxypyridin-2-yl)benzyl)-4-fluoro-1H-indole-7-carboxamido)spiro[3.3]heptane-2-carboxylic acid;
($R_a$)-6-(1-(4-(4-cyano-6-methoxypyridin-2-yl)benzyl)-4-fluoro-1H-indole-7-carboxamido)spiro[3.3]heptane-2-carboxylic acid;
($S_a$)-6-(1-(4-(4-cyano-6-methoxypyridin-2-yl)benzyl)-4-fluoro-1H-indole-7-carboxamido)spiro[3.3]heptane-2-carboxylic acid (Example 59);
6-(4-fluoro-1-(4-(2-(methylcarbamoyl)pyridin-4-yl)benzyl)-1H-indole-7-carboxamido)spiro[3.3]heptane-2-carboxylic acid;
($R_a$)-6-(4-fluoro-1-(4-(2-(methylcarbamoyl)pyridin-4-yl)benzyl)-1H-indole-7-carboxamido)spiro[3.3]heptane-2-carboxylic acid;
($S_a$)-6-(4-fluoro-1-(4-(2-(methylcarbamoyl)pyridin-4-yl)benzyl)-1H-indole-7-carboxamido)spiro[3.3]heptane-2-carboxylic acid (Example 60);
6-(1-(4-(2-(ethylcarbamoyl)pyridin-4-yl)benzyl)-4-fluoro-1H-indole-7-carboxamido)spiro[3.3]heptane-2-carboxylic acid;
($R_a$)-6-(1-(4-(2-(ethylcarbamoyl)pyridin-4-yl)benzyl)-4-fluoro-1H-indole-7-carboxamido)spiro[3.3]heptane-2-carboxylic acid;
($S_a$)-6-(1-(4-(2-(ethylcarbamoyl)pyridin-4-yl)benzyl)-4-fluoro-1H-indole-7-carboxamido)spiro[3.3]heptane-2-carboxylic acid (Example 61);
6-(4-fluoro-1-(4-(6-(methylcarbamoyl)pyridin-2-yl)benzyl)-1H-indole-7-carboxamido)spiro[3.3]heptane-2-carboxylic acid;
($R_a$)-6-(4-fluoro-1-(4-(6-(methylcarbamoyl)pyridin-2-yl)benzyl)-1H-indole-7-carboxamido)spiro[3.3]heptane-2-carboxylic acid;
($S_a$)-6-(4-fluoro-1-(4-(6-(methylcarbamoyl)pyridin-2-yl)benzyl)-1H-indole-7-carboxamido)spiro[3.3]heptane-2-carboxylic acid (Example 62);
6-(4-fluoro-1-(4-(6-(methylcarbamoyl)pyridin-3-yl)benzyl)-1H-indole-7-carboxamido)spiro[3.3]heptane-2-carboxylic acid;
($R_a$)-6-(4-fluoro-1-(4-(6-(methylcarbamoyl)pyridin-3-yl)benzyl)-1H-indole-7-carboxamido)spiro[3.3]heptane-2-carboxylic acid;
($S_a$)-6-(4-fluoro-1-(4-(6-(methylcarbamoyl)pyridin-3-yl)benzyl)-1H-indole-7-carboxamido)spiro[3.3]heptane-2-carboxylic acid (Example 63);
6-(1-(4-(2-(difluoromethyl)pyridin-4-yl)benzyl)-4-fluoro-1H-indole-7-carboxamido)spiro[3.3]heptane-2-carboxylic acid;
($R_a$)-6-(1-(4-(2-(difluoromethyl)pyridin-4-yl)benzyl)-4-fluoro-1H-indole-7-carboxamido)spiro[3.3]heptane-2-carboxylic acid;
($S_a$)-6-(1-(4-(2-(difluoromethyl)pyridin-4-yl)benzyl)-4-fluoro-1H-indole-7-carboxamido)spiro[3.3]heptane-2-carboxylic acid (Example 64);
6-(4-fluoro-1-((3-fluoro-[1,1'-biphenyl]-4-yl)methyl)-1H-indole-7-carboxamido)spiro[3.3]heptane-2-carboxylic acid;
($R_a$)-6-(4-fluoro-1-((3-fluoro-[1,1'-biphenyl]-4-yl)methyl)-1H-indole-7-carboxamido)spiro[3.3]heptane-2-carboxylic acid;
($S_a$)-6-(4-fluoro-1-((3-fluoro-[1,1'-biphenyl]-4-yl)methyl)-1H-indole-7-carboxamido)spiro[3.3]heptane-2-carboxylic acid (Example 66);
6-(4-chloro-1-(4-(pyridin-4-yl)benzyl)-1H-indole-7-carboxamido)spiro[3.3]heptane-2-carboxylic acid;
($R_a$)-6-(4-chloro-1-(4-(pyridin-4-yl)benzyl)-1H-indole-7-carboxamido)spiro[3.3]heptane-2-carboxylic acid;
($S_a$)-6-4-chloro-1-(4-(pyridin-4-yl)benzyl)-1H-indole-7-carboxamido)spiro[3.3]heptane-2-carboxylic acid (Example 67);
6-(1-([1,1'-biphenyl]-4-ylmethyl)-4-chloro-1H-indole-7-carboxamido)spiro[3.3]heptane-2-carboxylic acid;
($R_a$)-6-(1-([1,1'-biphenyl]-4-ylmethyl)-4-chloro-1H-indole-7-carboxamido)spiro[3.3]heptane-2-carboxylic acid;
($S_a$)-6-(1-([1,1'-biphenyl]-4-ylmethyl)-4-chloro-1H-indole-7-carboxamido)spiro[3.3]heptane-2-carboxylic acid (Example 68);
6-(4-chloro-1-(4-(2-methoxypyridin-4-yl)benzyl)-1H-indole-7-carboxamido)spiro[3.3]heptane-2-carboxylic acid;
($R_a$)-6-(4-chloro-1-(4-(2-methoxypyridin-4-yl)benzyl)-1H-indole-7-carboxamido)spiro[3.3]heptane-2-carboxylic acid;
($S_a$)-6-(4-chloro-1-(4-(2-methoxypyridin-4-yl)benzyl)-1H-indole-7-carboxamido)spiro[3.3]heptane-2-carboxylic acid (Example 69);
6-(4-chloro-1-(4-(2-ethoxypyridin-4-yl)benzyl)-1H-indole-7-carboxamido)spiro[3.3]heptane-2-carboxylic acid;
($R_a$)-6-(4-chloro-1-(4-(2-ethoxypyridin-4-yl)benzyl)-1H-indole-7-carboxamido)spiro[3.3]heptane-2-carboxylic acid;
($S_a$)-6-(4-chloro-1-(4-(2-ethoxypyridin-4-yl)benzyl)-1H-indole-7-carboxamido)spiro[3.3]heptane-2-carboxylic acid (Example 70);
6-(4-chloro-1-(4-morpholinobenzyl)-1H-indole-7-carboxamido)spiro[3.3]heptane-2-carboxylic acid;
($R_a$)-6-(4-chloro-1-(4-morpholinobenzyl)-1H-indole-7-carboxamido)spiro[3.3]heptane-2-carboxylic acid;
($S_a$)-6-(4-chloro-1-(4-morpholinobenzyl)-1H-indole-7-carboxamido)spiro[3.3]heptane-2-carboxylic acid (Example 71);
6-(1-(4-((1R,5S)-3-azabicyclo[3.1.0]hexan-3-yl)benzyl)-4-chloro-1H-indazole-7-carboxamido)spiro[3.3]heptane-2-carboxylic acid;
($R_a$)-6-(1-(4-((1R,5S)-3-azabicyclo[3.1.0]hexan-3-yl)benzyl)-4-chloro-1H-indazole-7-carboxamido)spiro[3.3]heptane-2-carboxylic acid;
($S_a$)-6-(1-(4-((1R,5S)-3-azabicyclo[3.1.0]hexan-3-yl)benzyl)-4-chloro-1H-indazole-7-carboxamido)spiro[3.3]heptane-2-carboxylic acid (Example 72);

6-(1-(4-(1H-pyrazol-1-yl)benzyl)-4-chloro-1H-indazole-7-carboxamido)spiro[3.3]heptane-2-carboxylic acid;
(R$_a$)-6-(1-(4-(1H-pyrazol-1-yl)benzyl)-4-chloro-1H-indazole-7-carboxamido)spiro[3.3]heptane-2-carboxylic acid;
(S$_a$)-6-(1(4-(F H-pyrazol-1-yl)benzyl)-4-chloro-1H-indazole-7-carboxamido)spiro[3.3]heptane-2-carboxylic acid (Example 73);
6-(4-chloro-1-(4-(3,3-difluoropyrrolidin-1-yl)benzyl)-1H-indazole-7-carboxamido)spiro[3.3]heptane-2-carboxylic acid;
(R$_a$)-6-(4-chloro-1-(4-(3,3-difluoropyrrolidin-1-yl)benzyl)-1H-indazole-7-carboxamido)spiro[3.3]heptane-2-carboxylic acid;
(S$_a$)-6-(4-chloro-1-(4-(3,3-difluoropyrrolidin-1-yl)benzyl)-1H-indazole-7-carboxamido)spiro[3.3]heptane-2-carboxylic acid (Example 74);
6-(1-(4-((1R,5S)-3-azabicyclo[3.1.0]hexan-3-yl)-3-fluorobenzyl)-4-chloro-1H-indazole-7-carboxamido)spiro[3.3]heptane-2-carboxylic acid;
(R$_a$)-6-(1-(4-((1R,5S)-3-azabicyclo[3.1.0]hexan-3-yl)-3-fluorobenzyl)-4-chloro-1H-indazole-7-carboxamido)spiro[3.3]heptane-2-carboxylic acid;
(S$_a$)-6-(1-(4-((1R,5S)-3-azabicyclo[3.1.0]hexan-3-yl)-3-fluorobenzyl)-4-chloro-1H-indazole-7-carboxamido)spiro[3.3]heptane-2-carboxylic acid (Example 75);
6-(4-chloro-1-(4-(1-(difluoromethyl)-3-azabicyclo[3.1.0]hexan-3-yl)-3-fluorobenzyl)-1H-indazole-7-carboxamido)spiro[3.3]heptane-2-carboxylic acid;
(R$_a$)-6-(4-chloro-1-(4-((racemic)-1-(difluoromethyl)-3-azabicyclo[3.1.0]hexan-3-yl)-3-fluorobenzyl)-1H-indazole-7-carboxamido)spiro[3.3]heptane-2-carboxylic acid;
(S$_a$)-6-(4-chloro-1-(4-((racemic)-1-(difluoromethyl)-3-azabicyclo[3.1.0]hexan-3-yl)-3-fluorobenzyl)-1H-indazole-7-carboxamido)spiro[3.3]heptane-2-carboxylic acid (Example 76);
6-(1-(1-(4-((1R,5S)-3-azabicyclo[3.1.0]hexan-3-yl)phenyl)ethyl)-4-chloro-1H-indazole-7-carboxamido)spiro[3.3]heptane-2-carboxylic acid;
(R$_a$)-6-(1-((racemic)-1-(4-((1R,5S)-3-azabicyclo[3.1.0]hexan-3-yl)phenyl)ethyl)-4-chloro-1H-indazole-7-carboxamido)spiro[3.3]heptane-2-carboxylic acid;
(S$_a$)-6-(1-((racemic)-1-(4-((1R,5S)-3-azabicyclo[3.1.0]hexan-3-yl)phenyl)ethyl)-4-chloro-1H-indazole-7-carboxamido)spiro[3.3]heptane-2-carboxylic acid (Example 77);
(R$_a$)-6-(1-((R)-1-(4-((1R,5S)-3-azabicyclo[3.1.0]hexan-3-yl)phenyl)ethyl)-4-chloro-1H-indazole-7-carboxamido)spiro[3.3]heptane-2-carboxylic acid;
(R$_a$)-6-(1-((S)-1-(4-((1R,5S)-3-azabicyclo[3.1.0]hexan-3-yl)phenyl)ethyl)-4-chloro-1H-indazole-7-carboxamido)spiro[3.3]heptane-2-carboxylic acid;
(S$_a$)-6-(1-((R)-1-(4-((1R,5S)-3-azabicyclo[3.1.0]hexan-3-yl)phenyl)ethyl)-4-chloro-1H-indazole-7-carboxamido)spiro[3.3]heptane-2-carboxylic acid (Example 132);
(S$_a$)-6-(1-((S)-1-(4-((1R,5S)-3-azabicyclo[3.1.0]hexan-3-yl)phenyl)ethyl)-4-chloro-1H-indazole-7-carboxamido)spiro[3.3]heptane-2-carboxylic acid (Example 132);
6-(4-chloro-1-(4-(2-methoxypyridin-4-yl)benzyl)-1H-indazole-7-carboxamido)spiro[3.3]heptane-2-carboxylic acid;
(R$_a$)-6-(4-chloro-1-(4-(2-methoxypyridin-4-yl)benzyl)-1H-indazole-7-carboxamido)spiro[3.3]heptane-2-carboxylic acid;
(S$_a$)-6-(4-chloro-1-(4-(2-methoxypyridin-4-yl)benzyl)-1H-indazole-7-carboxamido)spiro[3.3]heptane-2-carboxylic acid (Example 78);
6-(4-chloro-1-(4-(2-ethoxypyridin-4-yl)benzyl)-1H-indazole-7-carboxamido)spiro[3.3]heptane-2-carboxylic acid;
(R$_a$)-6-(4-chloro-1-(4-(2-ethoxypyridin-4-yl)benzyl)-1H-indazole-7-carboxamido)spiro[3.3]heptane-2-carboxylic acid;
(S$_a$)-6-(4-chloro-1-(4-(2-ethoxypyridin-4-yl)benzyl)-1H-indazole-7-carboxamido)spiro[3.3]heptane-2-carboxylic acid (Example 79);
6-(4-chloro-1-(4-(6-ethoxypyridin-2-yl)benzyl)-1H-indazole-7-carboxamido)spiro[3.3]heptane-2-carboxylic acid;
(R$_a$)-6-(4-chloro-1-(4-(6-ethoxypyridin-2-yl)benzyl)-1H-indazole-7-carboxamido)spiro[3.3]heptane-2-carboxylic acid;
6-(4-chloro-1-((3'-cyano-[1,1'-biphenyl]-4-yl)methyl)-1H-indazole-7-carboxamido)spiro[3.3]heptane-2-carboxylic acid;
(R$_a$)-6-(4-chloro-1-((3'-cyano-[1,1'-biphenyl]-4-yl)methyl)-1H-indazole-7-carboxamido)spiro[3.3]heptane-2-carboxylic acid;
(S$_a$)-6-(4-chloro-1-((3'-cyano-[1,1'-biphenyl]-4-yl)methyl)-1H-indazole-7-carboxamido)spiro[3.3]heptane-2-carboxylic acid (Example 80);
6-(4-chloro-1-((2-fluoro-2'3'4'5'-tetrahydro-[1,1'-biphenyl]-4-yl)methyl)-1H-indazole-7-carboxamido)spiro[3.3]heptane-2-carboxylic acid;
(R$_a$)-6-(4-chloro-1-((2-fluoro-2'3'4'5'-tetrahydro-[1,1'-biphenyl]-4-yl)methyl)-1H-indazole-7-carboxamido)spiro[3.3]heptane-2-carboxylic acid;
(S$_a$)-6-(4-chloro-1-((2-fluoro-2'3'4'5'-tetrahydro-[1,1'-biphenyl]-4-yl)methyl)-1H-indazole-7-carboxamido)spiro[3.3]heptane-2-carboxylic acid (Example 81);
6-(4-chloro-1-(4-(cyclopent-1-en-1-yl)-3-fluorobenzyl)-1H-indazole-7-carboxamido)spiro[3.3]heptane-2-carboxylic acid;
(R$_a$)-6-(4-chloro-1-(4-(cyclopent-1-en-1-yl)-3-fluorobenzyl)-1H-indazole-7-carboxamido)spiro[3.3]heptane-2-carboxylic acid;
(S$_a$)-6-(4-chloro-1-(4-(cyclopent-1-en-1-yl)-3-fluorobenzyl)-1H-indazole-7-carboxamido)spiro[3.3]heptane-2-carboxylic acid (Example 82);
(S$_a$)-6-(4-chloro-1-(4-(6-ethoxypyridin-2-yl)benzyl)-1H-indazole-7-carboxamido)spiro[3.3]heptane-2-carboxylic acid (Example 83);
6-(4-chloro-1-(4-(2-ethoxypyrimidin-6-yl)benzyl)-1H-indazole-7-carboxamido)spiro[3.3]heptane-2-carboxylic acid;
(R$_a$)-6-(4-chloro-1-(4-(2-ethoxypyrimidin-6-yl)benzyl)-1H-indazole-7-carboxamido)spiro[3.3]heptane-2-carboxylic acid;
(S$_a$)-6-(4-chloro-1-(4-(2-ethoxypyrimidin-6-yl)benzyl)-1H-indazole-7-carboxamido)spiro[3.3]heptane-2-carboxylic acid (Example 84);
6-(4-chloro-1-(4-(6-(methylcarbamoyl)pyridin-2-yl)benzyl)-1H-indazole-7-carboxamido)spiro[3.3]heptane-2-carboxylic acid;
(R$_a$)-6-(4-chloro-1-(4-(6-(methylcarbamoyl)pyridin-2-yl)benzyl)-1H-indazole-7-carboxamido)spiro[3.3]heptane-2-carboxylic acid;
(S$_a$)-6-(4-chloro-1-(4-(6-(methylcarbamoyl)pyridin-2-yl)benzyl)-1H-indazole-7-carboxamido)spiro[3.3]heptane-2-carboxylic acid (Example 85);
6-(4-chloro-1-(4-(6-(trifluoromethoxy)pyridin-2-yl)benzyl)-1H-indazole-7-carboxamido)spiro[3.3]heptane-2-carboxylic acid;
(R$_a$)-6-(4-chloro-1-(4-(6-(trifluoromethoxy)pyridin-2-yl)benzyl)-1H-indazole-7-carboxamido)spiro[3.3]heptane-2-carboxylic acid;
(S$_a$)-6-(4-chloro-1-(4-(6-(trifluoromethoxy)pyridin-2-yl)benzyl)-1H-indazole-7-carboxamido)spiro[3.3]heptane-2-carboxylic acid (Example 86);

6-(4-chloro-1-(4-(thiazol-2-yl)benzyl)-1H-indazole-7-carboxamido)spiro[3.3]heptane-2-carboxylic acid;

($R_a$)-6-(4-chloro-1-(4-(thiazol-2-yl)benzyl)-1H-indazole-7-carboxamido)spiro[3.3]heptane-2-carboxylic acid;

($S_a$)-6-(4-chloro-1-(4-(thiazol-2-yl)benzyl)-1H-indazole-7-carboxamido)spiro[3.3]heptane-2-carboxylic acid (Example 87);

6-(1-([1,1'-biphenyl]-4-ylmethyl)-4-methoxy-1H-pyrrolo[3,2-c]pyridine-7-carboxamido)spiro[3.3]heptane-2-carboxylic acid;

($R_a$)-6-(1-([1,1'-biphenyl]-4-ylmethyl)-4-methoxy-1H-pyrrolo[3,2-c]pyridine-7-carboxamido)spiro[3.3]heptane-2-carboxylic acid;

($S_a$)-6-(1-([1,1'-biphenyl]-4-ylmethyl)-4-methoxy-1H-pyrrolo[3,2-c]pyridine-7-carboxamido)spiro[3.3]heptane-2-carboxylic acid (Example 88);

6-(1-(4-(2-ethoxypyridin-4-yl)benzyl)-4-methoxy-1H-pyrrolo[3,2-c]pyridine-7-carboxamido)spiro[3.3]heptane-2-carboxylic acid;

($R_a$)-6-(1-(4-(2-ethoxypyridin-4-yl)benzyl)-4-methoxy-1H-pyrrolo[3,2-c]pyridine-7-carboxamido)spiro[3.3]heptane-2-carboxylic acid;

($S_a$)-6-(1-(4-(2-ethoxypyridin-4-yl)benzyl)-4-methoxy-1H-pyrrolo[3,2-c]pyridine-7-carboxamido)spiro[3.3]heptane-2-carboxylic acid (Example 89);

6-(1-([1,1'-biphenyl]-4-ylmethyl)-4-ethoxy-1H-pyrrolo[3,2-c]pyridine-7-carboxamido)spiro[3.3]heptane-2-carboxylic acid;

($R_a$)-6-(1-([1,1'-biphenyl]-4-ylmethyl)-4-ethoxy-1H-pyrrolo[3,2-c]pyridine-7-carboxamido)spiro[3.3]heptane-2-carboxylic acid;

($S_a$)-6-(1-([1,1'-biphenyl]-4-ylmethyl)-4-ethoxy-1H-pyrrolo[3,2-c]pyridine-7-carboxamido)spiro[3.3]heptane-2-carboxylic acid (Example 90);

6-(1-(4-(6-ethoxypyridin-3-yl)benzyl)-4-methoxy-1H-pyrrolo[3,2-c]pyridine-7-carboxamido)spiro[3.3]heptane-2-carboxylic acid;

($R_a$)-6-(1-(4-(6-ethoxypyridin-3-yl)benzyl)-4-methoxy-1H-pyrrolo[3,2-c]pyridine-7-carboxamido)spiro[3.3]heptane-2-carboxylic acid;

($S_0$)-6-(1-(4-(6-ethoxypyridin-3-yl)benzyl)-4-methoxy-1H-pyrrolo[3,2-c]pyridine-7-carboxamido)spiro[3.3]heptane-2-carboxylic acid (Example 91);

6-(4-methoxy-1-(4-(6-methoxypyridin-2-yl)benzyl)-1H-pyrrolo[3,2-c]pyridine-7-carboxamido)spiro[3.3]heptane-2-carboxylic acid;

($R_a$)-6-(4-methoxy-1-(4-(6-methoxypyridin-2-yl)benzyl)-1H-pyrrolo[3,2-c]pyridine-7-carboxamido)spiro[3.3]heptane-2-carboxylic acid;

($S_a$)-6-(4-methoxy-1-(4-(6-methoxypyridin-2-yl)benzyl)-1H-pyrrolo[3,2-c]pyridine-7-carboxamido)spiro[3.3]heptane-2-carboxylic acid (Example 92);

6-(1-([1,1'-biphenyl]-4-ylmethyl)-5-chloro-1H-indazole-7-carboxamido)spiro[3.3]heptane-2-carboxylic acid;

($R_a$)-6-(1-([1,1'-biphenyl]-4-ylmethyl)-5-chloro-1H-indazole-7-carboxamido)spiro[3.3]heptane-2-carboxylic acid;

($S_a$)-6-(1-([1,1'-biphenyl]-4-ylmethyl)-5-chloro-1H-indazole-7-carboxamido)spiro[3.3]heptane-2-carboxylic acid (Example 93);

6-(1-([1,1'-biphenyl]-4-ylmethyl)-4-chloro-1H-indazole-7-carboxamido)spiro[3.3]heptane-2-carboxylic acid;

($R_a$)-6-(1-([1,1'-biphenyl]-4-ylmethyl)-4-chloro-1H-indazole-7-carboxamido)spiro[3.3]heptane-2-carboxylic acid;

($S_a$)-6-(1-([1,1'-biphenyl]-4-ylmethyl)-4-chloro-1H-indazole-7-carboxamido)spiro[3.3]heptane-2-carboxylic acid (Example 94);

6-(4-chloro-1-(4-(trifluoromethoxy)benzyl)-1H-indazole-7-carboxamido)spiro[3.3]heptane-2-carboxylic acid;

($R_a$)-6-(4-chloro-1-(4-(trifluoromethoxy)benzyl)-1H-indazole-7-carboxamido)spiro[3.3]heptane-2-carboxylic acid;

($S_a$)-6-(4-chloro-1-(4-(trifluoromethoxy)benzyl)-1H-indazole-7-carboxamido)spiro[3.3]heptane-2-carboxylic acid (Example 95);

6-(4-chloro-1-(naphthalen-2-ylmethyl)-1H-indazole-7-carboxamido)spiro[3.3]heptane-2-carboxylic acid (Example 96);

($R_a$)-6-(4-chloro-1-(naphthalen-2-ylmethyl)-1H-indazole-7-carboxamido)spiro[3.3]heptane-2-carboxylic acid;

($S_a$)-6-(4-chloro-1-(naphthalen-2-ylmethyl)-1H-indazole-7-carboxamido)spiro[3.3]heptane-2-carboxylic acid (Example 96);

6-(4-chloro-1-(4-isopropylbenzyl)-1H-indazole-7-carboxamido)spiro[3.3]heptane-2-carboxylic acid;

($R_a$)-6-(4-chloro-1-(4-isopropylbenzyl)-1H-indazole-7-carboxamido)spiro[3.3]heptane-2-carboxylic acid;

($S_a$)-6-(4-chloro-1-(4-isopropylbenzyl)-1H-indazole-7-carboxamido)spiro[3.3]heptane-2-carboxylic acid (Example 97);

6-(4-chloro-1-(4-cyclopropylbenzyl)-1H-indazole-7-carboxamido)spiro[3.3]heptane-2-carboxylic acid;

($R_a$)-6-(4-chloro-1-(4-cyclopropylbenzyl)-1H-indazole-7-carboxamido)spiro[3.3]heptane-2-carboxylic acid;

($S_a$)-6-(4-chloro-1-(4-cyclopropylbenzyl)-1H-indazole-7-carboxamido)spiro[3.3]heptane-2-carboxylic acid (Example 98);

6-(4-chloro-1-(4-(tert-butyl)benzyl)-1H-indazole-7-carboxamido)spiro[3.3]heptane-2-carboxylic acid;

($R_a$)-6-(4-chloro-1-(4-(tert-butyl)benzyl)-1H-indazole-7-carboxamido)spiro[3.3]heptane-2-carboxylic acid;

($S_a$)-6-(4-chloro-1-(4-(tert-butyl)benzyl)-1H-indazole-7-carboxamido)spiro[3.3]heptane-2-carboxylic acid (Example 99);

6-(1-([1,1'-biphenyl]-4-ylmethyl)-4-fluoro-1H-indole-7-carboxamido)-2-methylspiro[3.3]heptane-2-carboxylic acid (Example 100);

($R_a$)-6-(1-([1,1'-biphenyl]-4-ylmethyl)-4-fluoro-1H-indole-7-carboxamido)-2-methylspiro[3.3]heptane-2-carboxylic acid;

($S_a$)-6-(1-([1,1'-biphenyl]-4-ylmethyl)-4-fluoro-1H-indole-7-carboxamido)-2-methylspiro[3.3]heptane-2-carboxylic acid;

6-(1-([1,1'-biphenyl]-4-ylmethyl)-4-fluoro-1H-indole-7-carboxamido)-2-deuterospiro[3.3]heptane-2-carboxylic acid (Example 101);

($R_a$)-6-(1-([1,1'-biphenyl]-4-ylmethyl)-4-fluoro-1H-indole-7-carboxamido)-2-deuterospiro[3.3]heptane-2-carboxylic acid;

($S_a$)-6-(1-([1,1'-biphenyl]-4-ylmethyl)-4-fluoro-1H-indole-7-carboxamido)-2-deuterospiro[3.3]heptane-2-carboxylic acid (Example 105);

6-(4-chloro-1-(4-(2-(methylcarbamoyl)pyridin-4-yl)benzyl)-1H-indazole-7-carboxamido)-2-fluorospiro[3.3]heptane-2-carboxylic acid (Example 102);

($R_a$)-6-(4-chloro-1-(4-(2-(methylcarbamoyl)pyridin-4-yl)benzyl)-1H-indazole-7-carboxamido)-2-fluorospiro[3.3]heptane-2-carboxylic acid;

($S_a$)-6-(4-chloro-1-(4-(2-(methylcarbamoyl)pyridin-4-yl)benzyl)-1H-indazole-7-carboxamido)-2-fluorospiro[3.3]heptane-2-carboxylic acid;

2-(6-(1-([1,1'-biphenyl]-4-ylmethyl)-4-fluoro-1H-indole-7-carboxamido)spiro[3.3]heptan-2-yl)acetic acid (Example 106);

(R$_a$)-2-(6-(1-([1,1'-biphenyl]-4-ylmethyl)-4-fluoro-1H-indole-7-carboxamido)spiro[3.3]heptan-2-yl)acetic acid (Example 104);

(S$_a$)-2-(6-(1-([1,1'-biphenyl]-4-ylmethyl)-4-fluoro-1H-indole-7-carboxamido)spiro[3.3]heptan-2-yl)acetic acid (Example 103);

2-(6-(1-([1,1'-biphenyl]-4-ylmethyl)-5-fluoro-1H-indazole-7-carboxamido)spiro[3.3]heptan-2-yl)acetic acid (Example 107);

(R$_a$)-2-(6(1-([1,1'-biphenyl]-4-ylmethyl)-5-fluoro-1H-indazole-7-carboxamido)spiro[3.3]heptan-2-yl)acetic acid;

(S$_a$)-2-(6-(1-([1,1'-biphenyl]-4-ylmethyl)-5-fluoro-1H-indazole-7-carboxamido)spiro[3.3]heptan-2-yl)acetic acid;

2-(6-(1-([1,1'-biphenyl]-4-ylmethyl)-4-methoxy-1H-pyrrolo[3,2-c]pyridine-7-carboxamido)spiro[3.3]heptan-2-yl)acetic acid (Example 108);

(R$_a$)-2-(6-(1-([1,1'-biphenyl]-4-ylmethyl)-4-methoxy-1H-pyrrolo[3,2-c]pyridine-7-carboxamido)spiro[3.3]heptan-2-yl)acetic acid;

(S$_a$)-2-(6-(1-([1,1'-biphenyl]-4-ylmethyl)-4-methoxy-1H-pyrrolo[3,2-c]pyridine-7-carboxamido)spiro[3.3]heptan-2-yl)acetic acid;

2-(6-(1-([1,1'-biphenyl]-4-ylmethyl)-4-chloro-1H-indazole-7-carboxamido)spiro[3.3]heptan-2-yl)acetic acid (Example 109);

(R$_a$)-2-(6-(1-([1,1'-biphenyl]-4-ylmethyl)-4-chloro-1H-indazole-7-carboxamido)spiro[3.3]heptan-2-yl)acetic acid;

(S$_a$)-2-(6-(1-([1,1'-biphenyl]-4-ylmethyl)-4-chloro-1H-indazole-7-carboxamido)spiro[3.3]heptan-2-yl)acetic acid;

2-(6-(1-([1,1'-biphenyl]-4-ylmethyl)-5-chloro-1H-indazole-7-carboxamido)spiro[3.3]heptan-2-yl)acetic acid (Example 110);

(R$_a$)-2-(6-(1-([1,1'-biphenyl]-4-ylmethyl)-5-chloro-1H-indazole-7-carboxamido)spiro[3.3]heptan-2-yl)acetic acid;

(S$_a$)-2-(6-(1-([1,1'-biphenyl]-4-ylmethyl)-5-chloro-1H-indazole-7-carboxamido)spiro[3.3]heptan-2-yl)acetic acid;

4-fluoro-N-(6-((methylsulfonyl)carbamoyl)spiro[3.3]heptan-2-yl)-1-(4-(trifluoromethoxy)benzyl)-1H-indole-7-carboxamide;

(R$_a$)-4-fluoro-N-(6-((methylsulfonyl)carbamoyl)spiro[3.3]heptan-2-yl)-1-(4-(trifluoromethoxy)benzyl)-1H-indole-7-carboxamide;

(S$_a$)-4-fluoro-N-(6-((methylsulfonyl)carbamoyl)spiro[3.3]heptan-2-yl)-1-(4-(trifluoromethoxy)benzyl)-1H-indole-7-carboxamide (Example 111);

6-(1-(1-([1,1'-biphenyl]-4-yl)-ethyl)-1H-indazole-7-carboxamido)spiro[3.3]heptane-2-carboxylic acid;

(R$_a$)-6-(1-((racemic)-1-([1,1'-biphenyl]-4-yl)-ethyl)-1H-indazole-7-carboxamido)spiro[3.3]heptane-2-carboxylic acid;

(S$_a$)-6-(1-((racemic)-1-([1,1'-biphenyl]-4-yl)-ethyl)-1H-indazole-7-carboxamido)spiro[3.3]heptane-2-carboxylic acid (Example 112);

(R$_a$)-6-(1-((R)-1-([1,1'-biphenyl]-4-yl)-ethyl)-1H-indazole-7-carboxamido)spiro[3.3]heptane-2-carboxylic acid;

(R$_a$)-6-(1-((S)-1-([1,1'-biphenyl]-4-yl)-ethyl)-1H-indazole-7-carboxamido)spiro[3.3]heptane-2-carboxylic acid;

(S$_a$)-6-(1-((R)-1-([1,1'-biphenyl]-4-yl)-ethyl)-1H-indazole-7-carboxamido)spiro[3.3]heptane-2-carboxylic acid (Example 125);

(S$_a$)-6-(1-((S)-1-([1,1'-biphenyl]-4-yl)-ethyl)-1H-indazole-7-carboxamido)spiro[3.3]heptane-2-carboxylic acid (Example 125);

6-(1-(1-(3'-methoxy-[1,1'-biphenyl]-4-yl)-ethyl)-1H-indazole-7-carboxamido)spiro[3.3]heptane-2-carboxylic acid;

(R$_a$)-6-(1-((racemic)-1-(3'-methoxy-[1,1'-biphenyl]-4-yl)-ethyl)-1H-indazole-7-carboxamido)spiro[3.3]heptane-2-carboxylic acid;

(S$_a$)-6-(1-((racemic)-1-(3'-methoxy-[1,1'-biphenyl]-4-yl)-ethyl)-1H-indazole-7-carboxamido)spiro[3.3]heptane-2-carboxylic acid (Example 113);

(R$_a$)-6-(1-((R)-1-(3'-methoxy-[1,1'-biphenyl]-4-yl)-ethyl)-1H-indazole-7-carboxamido)spiro[3.3]heptane-2-carboxylic acid;

(R$_a$)-6-(1-((S)-1-(3'-methoxy-[1,1'-biphenyl]-4-yl)-ethyl)-1H-indazole-7-carboxamido)spiro[3.3]heptane-2-carboxylic acid;

(S$_a$)-6-(1-((R)-1-(3'-methoxy-[1,1'-biphenyl]-4-yl)-ethyl)-1H-indazole-7-carboxamido)spiro[3.3]heptane-2-carboxylic acid;

(S$_a$)-6-(1-((S)-1-(3'-methoxy-[1,1'-biphenyl]-4-yl)-ethyl)-1H-indazole-7-carboxamido)spiro[3.3]heptane-2-carboxylic acid;

6-(1-(1-(3'-cyano-5'-methoxy-[1,1'-biphenyl]-4-yl)-ethyl)-1H-indazole-7-carboxamido)spiro[3.3]heptane-2-carboxylic acid;

(R$_a$)-6-(1-((racemic)-1-(3'-cyano-5'-methoxy-[1,1'-biphenyl]-4-yl)-ethyl)-1H-indazole-7-carboxamido)spiro[3.3]heptane-2-carboxylic acid;

(S$_a$)-6-(1-((racemic)-1-(3'-cyano-5'-methoxy-[1,1'-biphenyl]-4-yl)-ethyl)-1H-indazole-7-carboxamido)spiro[3.3]heptane-2-carboxylic acid (Example 114);

(R$_a$)-6-(1-((R)-1-(3'-cyano-5'-methoxy-[1,1'-biphenyl]-4-yl)-ethyl)-1H-indazole-7-carboxamido)spiro[3.3]heptane-2-carboxylic acid;

(R$_a$)-6-(1-((S)-1-(3'-cyano-5'-methoxy-[1,1'-biphenyl]-4-yl)-ethyl)-1H-indazole-7-carboxamido)spiro[3.3]heptane-2-carboxylic acid;

(S$_a$)-6-(1-((R)-1-(3'-cyano-5'-methoxy-[1,1'-biphenyl]-4-yl)-ethyl)-1H-indazole-7-carboxamido)spiro[3.3]heptane-2-carboxylic acid (Example 126);

(S$_a$)-6-(1-((S)-1-(3'-cyano-5'-methoxy-[1,1'-biphenyl]-4-yl)-ethyl)-1H-indazole-7-carboxamido)spiro[3.3]heptane-2-carboxylic acid (Example 126);

6-(1-(1-(4-(2-ethoxypyridin-4-yl)phenyl)-ethyl)-1H-indazole-7-carboxamido)spiro[3.3]heptane-2-carboxylic acid;

(R$_a$)-6-(1-((racemic)-1-(4-(2-ethoxypyridin-4-yl)phenyl)-ethyl)-1H-indazole-7-carboxamido)spiro[3.3]heptane-2-carboxylic acid;

(S$_a$)-6-(1-((racemic)-1-(4-(2-ethoxypyridin-4-yl)phenyl)-ethyl)-1H-indazole-7-carboxamido)spiro[3.3]heptane-2-carboxylic acid (Example 115);

(R$_a$)-6-(1-((R)-1-(4-(2-ethoxypyridin-4-yl)phenyl)-ethyl)-1H-indazole-7-carboxamido)spiro[3.3]heptane-2-carboxylic acid;

(R$_a$)-6-(1-((S)-1-(4-(2-ethoxypyridin-4-yl)phenyl)-ethyl)-1H-indazole-7-carboxamido)spiro[3.3]heptane-2-carboxylic acid;

(S$_a$)-6-(1-((R)-1-(4-(2-ethoxypyridin-4-yl)phenyl)-ethyl)-1H-indazole-7-carboxamido)spiro[3.3]heptane-2-carboxylic acid;

(S$_a$)-64(1-((S)-1-(4-(2-ethoxypyridin-4-yl)phenyl)-ethyl)-1H-indazole-7-carboxamido)spiro[3.3]heptane-2-carboxylic acid;

6-(1-(1-([1,1'-biphenyl]-4-yl)-ethyl)-4-fluoro-1H-indole-7-carboxamido)spiro[3.3]heptane-2-carboxylic acid;

(R$_a$)-6-(1-((racemic)-1-([1,1'-biphenyl]-4-yl)-ethyl)-4-fluoro-1H-indole-7-carboxamido)spiro[3.3]heptane-2-carboxylic acid;

(S$_a$)-6-(1-((racemic)-1-([1,1'-biphenyl]-4-yl)-ethyl)-4-fluoro-1H-indole-7-carboxamido)spiro[3.3]heptane-2-carboxylic acid (Example 116);

($R_a$)-6-(1-((S)-1-([1,1'-biphenyl]-4-yl)-ethyl)-4-fluoro-1H-indole-7-carboxamido)spiro[3.3]heptane-2-carboxylic acid;

($R_a$)-6-(1-((R)-1-([1,1'-biphenyl]-4-yl)-ethyl)-4-fluoro-1H-indole-7-carboxamido)spiro[3.3]heptane-2-carboxylic acid;

($S_a$)-6-(1-((R)-1-([1,1'-biphenyl]-4-yl)-ethyl)-4-fluoro-1H-indole-7-carboxamido)spiro[3.3]heptane-2-carboxylic acid (Example 127);

($S_a$)-6-(1-((S)-1-([1,1'-biphenyl]-4-yl)-ethyl)-4-fluoro-1H-indole-7-carboxamido)spiro[3.3]heptane-2-carboxylic acid (Example 127);

6-(4-fluoro-1-(1-(3'-methoxy-[1,1'-biphenyl]-4-yl)-ethyl)-1H-indole-7-carboxamido)spiro[3.3]heptane-2-carboxylic acid;

($R_a$)-6-(4-fluoro-1-((racemic)-1-(3'-methoxy-[1,1'-biphenyl]-4-yl)-ethyl)-1H-indole-7-carboxamido)spiro[3.3]heptane-2-carboxylic acid;

($S_a$)-6-(4-fluoro-1-((racemic)-1-(3'-methoxy-[1,1'-biphenyl]-4-yl)-ethyl)-1H-indole-7-carboxamido)spiro[3.3]heptane-2-carboxylic acid (Example 117);

($R_a$)-6-(4-fluoro-1-((R)-1-(3'-methoxy-[1,1'-biphenyl]-4-yl)-ethyl)-1H-indole-7-carboxamido)spiro[3.3]heptane-2-carboxylic acid;

($R_a$)-6-(4-fluoro-1-((S)-1-(3'-methoxy-[1,1'-biphenyl]-4-yl)-ethyl)-1H-indole-7-carboxamido)spiro[3.3]heptane-2-carboxylic acid;

($S_a$)-6-(4-fluoro-1-((R)-1-(3'-methoxy-[1,1'-biphenyl]-4-yl)-ethyl)-1H-indole-7-carboxamido)spiro[3.3]heptane-2-carboxylic acid Example 128);

($S_a$)-6(4-fluoro-1-((S)-(3'-methoxy-[1,1'-biphenyl]-4-yl)-ethyl)-1H-indole-7-carboxamido)spiro[3.3]heptane-2-carboxylic acid (Example 128);

6-(1-(1-(4-(2-ethoxypyridin-4-yl)phenyl)-ethyl)-4-fluoro-1H-indole-7-carboxamido)spiro[3.3]heptane-2-carboxylic acid;

($R_a$)-6-(1-((racemic)-1-(4-(2-ethoxypyridin-4-yl)phenyl)-ethyl)-4-fluoro-1H-indole-7-carboxamido)spiro[3.3]heptane-2-carboxylic acid;

($S_a$)-6-(1-((racemic)-1-(4-(2-ethoxypyridin-4-yl)phenyl)-ethyl)-4-fluoro-1H-indole-7-carboxamido)spiro[3.3]heptane-2-carboxylic acid (Example 118);

($R_a$)-6-(1-((R)-1-(4(2-ethoxypyridin-4-yl)phenyl)-ethyl)-4-fluoro-1H-indole-7-carboxamido)spiro[3.3]heptane-2-carboxylic acid;

($R_a$)-6-(1-((S)-1-(4-(2-ethoxypyridin-4-yl)phenyl)-ethyl)-4-fluoro-1H-indole-7-carboxamido)spiro[3.3]heptane-2-carboxylic acid;

($S_a$)-6-(1-((R)-1-(4-(2-ethoxypyridin-4-yl)phenyl)-ethyl)-4-fluoro-1H-indole-7-carboxamido)spiro[3.3]heptane-2-carboxylic acid (Example 129);

($S_a$)-6-(1-((S)-1-(4-(2-ethoxypyridin-4-yl)phenyl)-ethyl)-4-fluoro-1H-indole-7-carboxamido)spiro[3.3]heptane-2-carboxylic acid (Example 129);

6-(4-fluoro-1-(1-(4-(6-methoxypyridin-3-yl)phenyl)-ethyl)-1H-indole-7-carboxamido)spiro[3.3]heptane-2-carboxylic acid;

($R_a$)-6-(4-fluoro-1-((racemic)-1-(4-(6-methoxypyridin-3-yl)phenyl)-ethyl)-1H-indole-7-carboxamido)spiro[3.3]heptane-2-carboxylic acid;

($S_a$)-6-(4-fluoro-1-((racemic)-1-(4-(6-methoxypyridin-3-yl)phenyl)-ethyl)-1H-indole-7-carboxamido)spiro[3.3]heptane-2-carboxylic acid (Example 119);

($R_a$)-6-(4-fluoro-1-((R)-1-(4-(6-methoxypyridin-3-yl)phenyl)-ethyl)-1H-indole-7-carboxamido)spiro[3.3]heptane-2-carboxylic acid;

($R_a$)-6-(4-fluoro-1-((S)-1-(4-(6-methoxypyridin-3-yl)phenyl)-ethyl)-1H-indole-7-carboxamido)spiro[3.3]heptane-2-carboxylic acid;

($S_a$)-6-(4-fluoro-1-((R)-1-(4-(6-methoxypyridin-3-yl)phenyl)-ethyl)-1H-indole-7-carboxamido)spiro[3.3]heptane-2-carboxylic acid;

($S_a$)-6-(4-fluoro-1-((S)-1-(4-(6-methoxypyridin-3-yl)phenyl)-ethyl)-1H-indole-7-carboxamido)spiro[3.3]heptane-2-carboxylic acid;

6-(1-(1-(4-(5-chloro-6-methoxypyridin-3-yl)phenyl)-ethyl)-4-fluoro-1H-indole-7-carboxamido)spiro[3.3]heptane-2-carboxylic acid;

($R_a$)-6-(1-((racemic)-1-(4-(5-chloro-6-methoxypyridin-3-yl)phenyl)-ethyl)-4-fluoro-1H-indole-7-carboxamido)spiro[3.3]heptane-2-carboxylic acid;

($S_a$)-6-(1-((racemic)-1-(4-(5-chloro-6-methoxypyridin-3-yl)phenyl)-ethyl)-4-fluoro-1H-indole-7-carboxamido)spiro[3.3]heptane-2-carboxylic acid (Example 120);

($R_a$)-6-(1-((R)-1-(4-(5-chloro-6-methoxypyridin-3-yl)phenyl)-ethyl)-4-fluoro-1H-indole-7-carboxamido)spiro[3.3]heptane-2-carboxylic acid;

($R_a$)-6-(1-((S)-1-(4-(5-chloro-6-methoxypyridin-3-yl)phenyl)-ethyl)-4-fluoro-1H-indole-7-carboxamido)spiro[3.3]heptane-2-carboxylic acid;

($S_a$)-6-(1-((R)-1-(4-(5-chloro-6-methoxypyridin-3-yl)phenyl)-ethyl)-4-fluoro-1H-indole-7-carboxamido)spiro[3.3]heptane-2-carboxylic acid;

($S_a$)-6-(1-((S)-1-(4-(5-chloro-6-methoxypyridin-3-yl)phenyl)-ethyl)-4-fluoro-1H-indole-7-carboxamido)spiro[3.3]heptane-2-carboxylic acid;

6-(1-(1-([1,1'-biphenyl]-4-yl)-ethyl)-4-chloro-1H-indazole-7-carboxamido)spiro[3.3]heptane-2-carboxylic acid;

($R_a$)-6-(1-((racemic)-1-([1,1'-biphenyl]-4-yl)-ethyl)-4-chloro-1H-indazole-7-carboxamido)spiro[3.3]heptane-2-carboxylic acid;

($S_a$)-6-(1-((racemic)-1-([1,1'-biphenyl]-4-yl)-ethyl)-4-chloro-1H-indazole-7-carboxamido)spiro[3.3]heptane-2-carboxylic acid (Example 121);

($R_a$)-6-(1-((R)-1-([1,1'-biphenyl]-4-yl)-ethyl)-4-chloro-1H-indazole-7-carboxamido)spiro[3.3]heptane-2-carboxylic acid;

($R_a$)-6-(1-((S)-1-([1,1'-biphenyl]-4-yl)-ethyl)-4-chloro-1H-indazole-7-carboxamido)spiro[3.3]heptane-2-carboxylic acid;

($S_a$)-6-(1-((R)-1-([1,1'-biphenyl]-4-yl)-ethyl)-4-chloro-1H-indazole-7-carboxamido)spiro[3.3]heptane-2-carboxylic acid (Example 130);

($S_a$)-6-(1-((S)-1-([1,1'-biphenyl]-4-yl)-ethyl)-4-chloro-1H-indazole-7-carboxamido)spiro[3.3]heptane-2-carboxylic acid (Example 130);

6-(4-chloro-1-(1-(3'-methoxy-[1,1'-biphenyl]-4-yl)-ethyl)-1H-indazole-7-carboxamido)spiro[3.3]heptane-2-carboxylic acid;

($R_a$)-6-(4-chloro-1-((racemic)-1-(3'-methoxy-[1,1'-biphenyl]-4-yl)-ethyl)-1H-indazole-7-carboxamido)spiro[3.3]heptane-2-carboxylic acid;

($S_a$)-6-(4-chloro-1-((racemic)-1-(3'-methoxy-[1,1'-biphenyl]-4-yl)-ethyl)-1H-indazole-7-carboxamido)spiro[3.3]heptane-2-carboxylic acid (Example 122);

($R_a$)-6-(4-chloro-1-((R)-1-(3'-methoxy-[1,1'-biphenyl]-4-yl)-ethyl)-1H-indazole-7-carboxamido)spiro[3.3]heptane-2-carboxylic acid;

($R_a$)-6-(4-chloro-1-(S)-1-(3'-methoxy-[1,1'-biphenyl]-4-yl)-ethyl)-1H-indazole-7-carboxamido)spiro[3.3]heptane-2-carboxylic acid;

($S_a$)-6-(4-chloro-1-((R)-1-(3'-methoxy-[1,1'-biphenyl]-4-yl)-ethyl)-1H-indazole-7-carboxamido)spiro[3.3]heptane-2-carboxylic acid;

($S_a$)-6-(4-chloro-1-((S)-1-(3'-methoxy-[1,1'-biphenyl]-4-yl)-ethyl)-1H-indazole-7-carboxamido)spiro[3.3]heptane-2-carboxylic acid;

6-(4-chloro-1-(1-(3'-cyano-5'-methoxy-[1,1'-biphenyl]-4-yl)-ethyl)-1H-indazole-7-carboxamido)spiro[3.3]heptane-2-carboxylic acid;

($R_a$)-6-(4-chloro-1-((racemic)-1-(3'-cyano-5'-methoxy-[1,1'-biphenyl]-4-yl)-ethyl)-1H-indazole-7-carboxamido)spiro[3.3]heptane-2-carboxylic acid;

($S_a$)-6-(4-chloro-1-((racemic)-1-(3'-cyano-5'-methoxy-[1,1'-biphenyl]-4-yl)-ethyl)-1H-indazole-7-carboxamido)spiro[3.3]heptane-2-carboxylic acid (Example 123);

($R_a$)-6-(4-chloro-1-((R)-1-(3'-cyano-5'-methoxy-[1,1'-biphenyl]-4-yl)-ethyl)-1H-indazole-7-carboxamido)spiro[3.3]heptane-2-carboxylic acid;

($R_a$)-6-(4-chloro-1-((S)-1-(3'-cyano-5'-methoxy-[1,1'-biphenyl]-4-yl)-ethyl)-1H-indazole-7-carboxamido)spiro[3.3]heptane-2-carboxylic acid;

($S_a$)-6-(4-chloro-1-((R)-1-(3'-cyano-5'-methoxy-[1,1'-biphenyl]-4-yl)-ethyl)-1H-indazole-7-carboxamido)spiro[3.3]heptane-2-carboxylic acid;

($S_a$)-6-(4-chloro-1-((S)-1-(3'-cyano-5'-methoxy-[1,1'-biphenyl]-4-yl)-ethyl)-1H-indazole-7-carboxamido)spiro[3.3]heptane-2-carboxylic acid;

6-(4-chloro-1-(1-(4-(2-ethoxypyridin-4-yl)phenyl)-ethyl)-1H-indazole-7-carboxamido)spiro[3.3]heptane-2-carboxylic acid;

($R_a$)-6-(4-chloro-1-((racemic)-1-(4-(2-ethoxypyridin-4-yl)phenyl)-ethyl)-1H-indazole-7-carboxamido)spiro[3.3]heptane-2-carboxylic acid;

($S_a$)-6-(4-chloro-1-((racemic)-1-(4-(2-ethoxypyridin-4-yl)phenyl)-ethyl)-1H-indazole-7-carboxamido)spiro[3.3]heptane-2-carboxylic acid (Example 124);

($R_a$)-6-(4-chloro-1-((R)-1-(4-(2-ethoxypyridin-4-yl)phenyl)-ethyl)-1H-indazole-7-carboxamido)spiro[3.3]heptane-2-carboxylic acid;

($R_a$)-6-(4-chloro-1-((S)-1-(4-(2-ethoxypyridin-4-yl)phenyl)-ethyl)-H-indazole-7-carboxamido)spiro[3.3]heptane-2-carboxylic acid;

($S_a$)-6-(4-chloro-1-((R)-1-(4-(2-ethoxypyridin-4-yl)phenyl)-ethyl)-1H-indazole-7-carboxamido)spiro[3.3]heptane-2-carboxylic acid (Example 131);

($S_a$)-6-(4-chloro-1-((S)-1-(4-(2-ethoxypyridin-4-yl)phenyl)-ethyl)-1H-indazole-7-carboxamido)spiro[3.3]heptane-2-carboxylic acid (Example 131);

6-(1-(1-(4-(6-ethoxypyridin-2-yl)phenyl)-ethyl)-1H-indazole-7-carboxamido)spiro[3.3]heptane-2-carboxylic acid;

($R_a$)-6-(1-((racemic)-1-(4-(6-ethoxypyridin-2-yl)phenyl)-ethyl)-1H-indazole-7-carboxamido)spiro[3.3]heptane-2-carboxylic acid;

($S_a$)-6-(1-((racemic)-1-(4-(6-ethoxypyridin-2-yl)phenyl)-ethyl)-1H-indazole-7-carboxamido)spiro[3.3]heptane-2-carboxylic acid (Example 133);

($R_a$)-6-(1-((R)-1-(4-(6-ethoxypyridin-2-yl)phenyl)-ethyl)-1H-indazole-7-carboxamido)spiro[3.3]heptane-2-carboxylic acid;

($R_a$)-6-(1-((S)-1-(4-(6-ethoxypyridin-2-yl)phenyl)-ethyl)-1H-indazole-7-carboxamido)spiro[3.3]heptane-2-carboxylic acid;

($S_a$)-6-(1-((R)-1-(4-(6-ethoxypyridin-2-yl)phenyl)-ethyl)-1H-indazole-7-carboxamido)spiro[3.3]heptane-2-carboxylic acid;

($S_a$)-6-(1-((S)-1-(4-(6-ethoxypyridin-2-yl)phenyl)-ethyl)-1H-indazole-7-carboxamido)spiro[3.3]heptane-2-carboxylic acid;

6-(4-chloro-1-(1-(4-(6-ethoxypyridin-2-yl)phenyl)-ethyl)-1H-indazole-7-carboxamido)spiro[3.3]heptane-2-carboxylic acid;

($R_a$)-6-(4-chloro-1-((racemic)-1-(4-(6-ethoxypyridin-2-yl)phenyl)-ethyl)-1H-indazole-7-carboxamido)spiro[3.3]heptane-2-carboxylic acid;

($S_a$)-6-(4-chloro-1-((racemic)-1-(4-(6-ethoxypyridin-2-yl)phenyl)-ethyl)-1H-indazole-7-carboxamido)spiro[3.3]heptane-2-carboxylic acid (Example 134);

($R_a$)-6-(4-chloro-1-((R)-1-(4-(6-ethoxypyridin-2-yl)phenyl)-ethyl)-1H-indazole-7-carboxamido)spiro[3.3]heptane-2-carboxylic acid;

($R_a$)-6-(4-chloro-1-((S)-1-(4-(6-ethoxypyridin-2-yl)phenyl)-ethyl)-1H-indazole-7-carboxamido)spiro[3.3]heptane-2-carboxylic acid;

($S_a$)-6-(4-chloro-1-((R)-1-(4-(6-ethoxypyridin-2-yl)phenyl)-ethyl)-1H-indazole-7-carboxamido)spiro[3.3]heptane-2-carboxylic acid;

($S_a$)-6-(4-chloro-1-((S)-1-(4-(6-ethoxypyridin-2-yl)phenyl)-ethyl)-1H-indazole-7-carboxamido)spiro[3.3]heptane-2-carboxylic acid;

6-(5-chloro-1-(4-(2-methoxypyridin-4-yl)benzyl)-1H-indazole-7-carboxamido)spiro[3.3]heptane-2-carboxylic acid;

($R_a$)-6-(5-chloro-1-(4-(2-methoxypyridin-4-yl)benzyl)-1H-indazole-7-carboxamido)spiro[3.3]heptane-2-carboxylic acid;

($S_a$)-6-(5-chloro-1-(4-(2-methoxypyridin-4-yl)benzyl)-1H-indazole-7-carboxamido)spiro[3.3]heptane-2-carboxylic acid (Example 135);

6-(5-chloro-1-(4-(2-ethoxypyridin-4-yl)benzyl)-1H-indazole-7-carboxamido)spiro[3.3]heptane-2-carboxylic acid;

($R_a$)-6-(5-chloro-1-(4-(2-ethoxypyridin-4-yl)benzyl)-1H-indazole-7-carboxamido)spiro[3.3]heptane-2-carboxylic acid;

($S_a$)-6-(5-chloro-1-(4-(2-ethoxypyridin-4-yl)benzyl)-1H-indazole-7-carboxamido)spiro[3.3]heptane-2-carboxylic acid (Example 136);

2-(6-(4-fluoro-1-(4-(2-methoxyquinolin-6-yl)benzyl)-1H-indole-7-carboxamido)spiro[3.3]heptan-2-yl)acetic acid;

($R_a$)-2-(6-(4-fluoro-1-(4-(2-methoxyquinolin-6-yl)benzyl)-1H-indole-7-carboxamido)spiro[3.3]heptan-2-yl)acetic acid;

($S_a$)-2-(6-(4-fluoro-1-(4-(2-methoxyquinolin-6-yl)benzyl)-1H-indole-7-carboxamido)spiro[3.3]heptan-2-yl)acetic acid; (Example 137)

2-(6-(4-fluoro-1-(4-(6-methoxypyridin-3-yl)benzyl)-1H-indole-7-carboxamido)spiro[3.3]heptan-2-yl)acetic acid;

($R_a$)-2-(6-(4-fluoro-1-(4-(6-methoxypyridin-3-yl)benzyl)-1H-indole-7-carboxamido)spiro[3.3]heptan-2-yl)acetic acid; (Example 138)

($S_a$)-2-(6-(4-fluoro-1-(4-(6-methoxypyridin-3-yl)benzyl)-1H-indole-7-carboxamido)spiro[3.3]heptan-2-yl)acetic acid;

2-(6-(4-fluoro-1-(4-(2-methoxypyridin-4-yl)benzyl)-1H-indole-7-carboxamido)spiro[3.3]heptan-2-yl)acetic acid;

($R_a$)-2-(6-(4-fluoro-1-(4-(2-methoxypyridin-4-yl)benzyl)-1H-indole-7-carboxamido)spiro[3.3]heptan-2-yl)acetic acid; (Example 139)

($S_a$)-2-(6(4-fluoro-1-(4-(2-methoxypyridin-4-yl)benzyl)-1H-indole-7-carboxamido)spiro[3.3]heptan-2-yl)acetic acid;

2-(6-(4-fluoro-1-(4-(2-methoxyquinolin-6-yl)benzyl)-1H-indole-7-carboxamido)spiro[3.3]heptan-2-yl)acetic acid;

(R$_a$)-2-(6-(4-fluoro-1-(4-(2-methoxyquinolin-6-yl)benzyl)-1H-indole-7-carboxamido)spiro[3.3]heptan-2-yl)acetic acid; (Example 140)

(S$_a$)-2-(6-(4-fluoro-1-(4-(2-methoxyquinolin-6-yl)benzyl)-1H-indole-7-carboxamido)spiro[3.3]heptan-2-yl)acetic acid;

2-(6-(1-([1,1'-biphenyl]-4-ylmethyl)-4-chloro-1H-indazole-7-carboxamido)spiro[3.3]heptan-2-yl)acetic acid;

(S$_a$)-2-(6-(1-([1,1'-biphenyl]-4-ylmethyl)-4-chloro-1H-indazole-7-carboxamido)spiro[3.3]heptan-2-yl)acetic acid; (Example 141)

(R$_a$)-2-(6-(1-([1,1'-biphenyl]-4-ylmethyl)-4-chloro-1H-indazole-7-carboxamido)spiro[3.3]heptan-2-yl)acetic acid; (Example 142)

2-(6-(4-chloro-1-((2'-fluoro-[1,1'-biphenyl]-4-yl)methyl)-1H-indazole-7-carboxamido)spiro[3.3]heptan-2-yl)acetic acid;

(R$_a$)-2-(6-(4-chloro-1-((2'-fluoro-[1,1'-biphenyl]-4-yl)methyl)-1H-indazole-7-carboxamido)spiro[3.3]heptan-2-yl)acetic acid; (Example 143)

(S$_a$)-2-(6-(4-chloro-1-((2'-fluoro-[1,1'-biphenyl]-4-yl)methyl)-1H-indazole-7-carboxamido)spiro[3.3]heptan-2-yl)acetic acid;

2-(6-(4-chloro-1-((3'-cyano-[1,1'-biphenyl]-4-yl)methyl)-1H-indazole-7-carboxamido)spiro[3.3]heptan-2-yl)acetic acid;

(R$_a$)-2-(6-(4-chloro-1-((3'-cyano-[1,1'-biphenyl]-4-yl)methyl)-1H-indazole-7-carboxamido)spiro[3.3]heptan-2-yl)acetic acid; (Example 144)

(S$_a$)-2-(6-(4-chloro-1-((3'-cyano-[1,1'-biphenyl]-4-yl)methyl)-1H-indazole-7-carboxamido)spiro[3.3]heptan-2-yl)acetic acid;

2-(6-(4-chloro-1-((4'-cyano-[1,1'-biphenyl]-4-yl)methyl)-1H-indazole-7-carboxamido)spiro[3.3]heptan-2-yl)acetic acid;

(R$_a$)-2-(6-(4-chloro-1-((4'-cyano-[1,1'-biphenyl]-4-yl)methyl)-1H-indazole-7-carboxamido)spiro[3.3]heptan-2-yl)acetic acid; (Example 145)

(S$_a$)-2-(6-(4-chloro-1-((4'-cyano-[1,1'-biphenyl]-4-yl)methyl)-1H-indazole-7-carboxamido)spiro[3.3]heptan-2-yl)acetic acid;

2-(6-(4-chloro-1-(4-(2-methoxyquinolin-6-yl)benzyl)-1H-indazole-7-carboxamido)spiro[3.3]heptan-2-yl)acetic acid;

(R$_a$)-2-(6-(4-chloro-1-(4-(2-methoxyquinolin-6-yl)benzyl)-1H-indazole-7-carboxamido)spiro[3.3]heptan-2-yl)acetic acid; (Example 146)

(S$_a$)-2-(6-(4-chloro-1-(4-(2-methoxyquinolin-6-yl)benzyl)-1H-indazole-7-carboxamido)spiro[3.3]heptan-2-yl)acetic acid;

2-(6-(5-chloro-1-(4-(2-methoxyquinolin-6-yl)benzyl)-1H-indazole-7-carboxamido)spiro[3.3]heptan-2-yl)acetic acid;

(R$_a$)-2-(6-(5-chloro-1-(4-(2-methoxyquinolin-6-yl)benzyl)-1H-indazole-7-carboxamido)spiro[3.3]heptan-2-yl)acetic acid; (Example 147)

(S$_a$)-2-(6-(5-chloro-1-(4-(2-methoxyquinolin-6-yl)benzyl)-1H-indazole-7-carboxamido)spiro[3.3]heptan-2-yl)acetic acid;

2-(6-(1-([1,1'-biphenyl]-4-ylmethyl)-5-chloro-1H-indazole-7-carboxamido)spiro[3.3]heptan-2-yl)acetic acid;

(R$_a$)-2-(6-(1-([1,1'-biphenyl]-4-ylmethyl)-5-chloro-1H-indazole-7-carboxamido)spiro[3.3]heptan-2-yl)acetic acid;

(S$_a$)-2-(6-(1-([1,1'-biphenyl]-4-ylmethyl)-5-chloro-1H-indazole-7-carboxamido)spiro[3.3]heptan-2-yl)acetic acid; (Example 148)

2-(6-(4-chloro-1-(4-(6-methoxypyridin-2-yl)benzyl)-1H-indazole-7-carboxamido)spiro[3.3]heptan-2-yl)acetic acid;

(R$_a$)-2-(6-(4-chloro-1-(4-(6-methoxypyridin-2-yl)benzyl)-1H-indazole-7-carboxamido)spiro[3.3]heptan-2-yl)acetic acid; (Example 149)

(S$_a$)-2-(6-(4-chloro-1-(4-(6-methoxypyridin-2-yl)benzyl)-1H-indazole-7-carboxamido)spiro[3.3]heptan-2-yl)acetic acid;

2-(6-(4-fluoro-1-(4-(6-methoxypyridin-2-yl)benzyl)-1H-indole-7-carboxamido)spiro[3.3]heptan-2-yl)acetic acid;

(R$_a$)-2-(6-(4-fluoro-1-(4-(6-methoxypyridin-2-yl)benzyl)-1H-indole-7-carboxamido)spiro[3.3]heptan-2-yl)acetic acid; (Example 150)

(S$_a$)-2-(6-(4-fluoro-1-(4-(6-methoxypyridin-2-yl)benzyl)-1H-indole-7-carboxamido)spiro[3.3]heptan-2-yl)acetic acid;

2-(6-(5-chloro-1-((2-fluoro-[1,1'-biphenyl]-4-yl)methyl)-1H-indazole-7-carboxamido)spiro[3.3]heptan-2-yl)acetic acid;

(R$_a$)-2-(6-(5-chloro-1-((2-fluoro-[1,1'-biphenyl]-4-yl)methyl)-1H-indazole-7-carboxamido)spiro[3.3]heptan-2-yl)acetic acid; (Example 151)

(S$_a$)-2-(6-(5-chloro-1-((2-fluoro-[1,1'-biphenyl]-4-yl)methyl)-1H-indazole-7-carboxamido)spiro[3.3]heptan-2-yl)acetic acid; (Example 152)

6-(5-chloro-1-((2-fluoro-[1,1'-biphenyl]-4-yl)methyl)-1H-indazole-7-carboxamido)spiro[3.3]heptane-2-carboxylic acid;

(R$_a$)-6-(5-chloro-1-((2-fluoro-[1,1'-biphenyl]-4-yl)methyl)-1H-indazole-7-carboxamido)spiro[3.3]heptane-2-carboxylic acid;

(S$_a$)-6-(5-chloro-1-((2-fluoro-[1,1'-biphenyl]-4-yl)methyl)-1H-indazole-7-carboxamido)spiro[3.3]heptane-2-carboxylic acid; (Example 153)

6-(5-chloro-1-(3-fluoro-4-(2-methoxypyridin-4-yl)benzyl)-1H-indazole-7-carboxamido)spiro[3.3]heptane-2-carboxylic acid;

(R$_a$)-6-(5-chloro-1-(3-fluoro-4-(2-methoxypyridin-4-yl)benzyl)-1H-indazole-7-carboxamido)spiro[3.3]heptane-2-carboxylic acid;

(S$_a$)-6-(5-chloro-1-(3-fluoro-4-(2-methoxypyridin-4-yl)benzyl)-1H-indazole-7-carboxamido)spiro[3.3]heptane-2-carboxylic acid; (Example 154)

6-(5-chloro-1-((3-fluoro-[1,1'-biphenyl]-4-yl)methyl)-1H-indazole-7-carboxamido)spiro[3.3]heptane-2-carboxylic acid;

(R$_a$)-6-(5-chloro-1-((3-fluoro-[1,1'-biphenyl]-4-yl)methyl)-1H-indazole-7-carboxamido)spiro[3.3]heptane-2-carboxylic acid;

(S$_a$)-6-(5-chloro-1-((3-fluoro-[1,1'-biphenyl]-4-yl)methyl)-1H-indazole-7-carboxamido)spiro[3.3]heptane-2-carboxylic acid; (Example 155)

6-(5-chloro-1-(2-fluoro-4-(2-methoxypyridin-4-yl)benzyl)-1H-indazole-7-carboxamido)spiro[3.3]heptane-2-carboxylic acid;

(R$_a$)-6-(5-chloro-1-(2-fluoro-4-(2-methoxypyridin-4-yl)benzyl)-1H-indazole-7-carboxamido)spiro[3.3]heptane-2-carboxylic acid;

(S$_a$)-6-(5-chloro-1-(2-fluoro-4-(2-methoxypyridin-4-yl)benzyl)-1H-indazole-7-carboxamido)spiro[3.3]heptane-2-carboxylic acid; (Example 156)

6-(1-(([1,1'-biphenyl]-4-yl-2,3,5,6-d4)methyl-d2)-4-chloro-1H-indazole-7-carboxamido)spiro[3.3]heptane-2-carboxylic acid;

(R$_a$)-6-(1-(([1,1'-biphenyl]-4-yl-2,3,5,6-d4)methyl-d2)-4-chloro-1H-indazole-7-carboxamido)spiro[3.3]heptane-2-carboxylic acid;

($S_a$)-6-(1-((([1,1'-biphenyl]-4-yl-2,3,5,6-d4)methyl-d2)-4-chloro-1H-indazole-7-carboxamido)spiro[3.3]heptane-2-carboxylic acid; (Example 157)

6-(1-([1,1'-biphenyl]-4-ylmethyl)-5-bromo-1H-indazole-7-carboxamido)spiro[3.3]heptane-2-carboxylic acid;

($R_a$)-6-(1-([1,1'-biphenyl]-4-ylmethyl)-5-bromo-1H-indazole-7-carboxamido)spiro[3.3]heptane-2-carboxylic acid;

($S_a$)-6-(1-([1,1'-biphenyl]-4-ylmethyl)-5-bromo-1H-indazole-7-carboxamido)spiro[3.3]heptane-2-carboxylic acid; (Example 158)

6-(1-([1,1'-biphenyl]-4-ylmethyl)-5-methoxy-1H-indazole-7-carboxamido)spiro[3.3]heptane-2-carboxylic acid;

($R_a$)-6-(1-([1,1'-biphenyl]-4-ylmethyl)-5-methoxy-1H-indazole-7-carboxamido)spiro[3.3]heptane-2-carboxylic acid;

($S_a$)-6-(1-([1,1'-biphenyl]-4-ylmethyl)-5-methoxy-1H-indazole-7-carboxamido)spiro[3.3]heptane-2-carboxylic acid; (Example 159)

6-(1-([1,1'-biphenyl]-4-ylmethyl)-5-methyl-1H-indazole-7-carboxamido)spiro[3.3]heptane-2-carboxylic acid;

($R_a$)-6-(1-([1,1'-biphenyl]-4-ylmethyl)-5-methyl-1H-indazole-7-carboxamido)spiro[3.3]heptane-2-carboxylic acid;

($S_a$)-6-(1-([1,1'-biphenyl]-4-ylmethyl)-5-methyl-1H-indazole-7-carboxamido)spiro[3.3]heptane-2-carboxylic acid; (Example 160)

2-(6-(1-([1,1'-biphenyl]-4-ylmethyl)-4-methoxy-1H-indazole-7-carboxamido)spiro[3.3]heptan-2-yl)acetic acid;

($R_a$)-2-(6-(1-([1,1'-biphenyl]-4-ylmethyl)-4-methoxy-1H-indazole-7-carboxamido)spiro[3.3]heptan-2-yl)acetic acid;

($S_a$)-2-(6-(1-([1,1'-biphenyl]-4-ylmethyl)-4-methoxy-1H-indazole-7-carboxamido)spiro[3.3]heptan-2-yl)acetic acid; (Example 161)

2-(6-(1-([1,1'-biphenyl]-4-ylmethyl)-4-(difluoromethoxy)-1H-indazole-7-carboxamido)spiro[3.3]heptan-2-yl)acetic acid;

($R_a$)-2-(6-(1-([1,1'-biphenyl]-4-ylmethyl)-4-(difluoromethoxy)-1H-indazole-7-carboxamido)spiro[3.3]heptan-2-yl)acetic acid;

($S_a$)-2-(6-(1-([1,1'-biphenyl]-4-ylmethyl)-4-(difluoromethoxy)-1H-indazole-7-carboxamido)spiro[3.3]heptan-2-yl)acetic acid; (Example 162)

6-(1-([1,1'-biphenyl]-4-ylmethyl)-5-(difluoromethoxy)-1H-indazole-7-carboxamido)spiro[3.3]heptane-2-carboxylic acid;

($R_a$)-6-(1-([1,1'-biphenyl]-4-ylmethyl)-5-(difluoromethoxy)-1H-indazole-7-carboxamido)spiro[3.3]heptane-2-carboxylic acid;

($S_a$)-6-(1-([1,1'-biphenyl]-4-ylmethyl)-5-(difluoromethoxy)-1H-indazole-7-carboxamido)spiro[3.3]heptane-2-carboxylic acid; (Example 163)

2-(6-(1-([1,1'-biphenyl]-4-ylmethyl)-5-methoxy-1H-indazole-7-carboxamido)spiro[3.3]heptan-2-yl)acetic acid;

($R_a$)-2-(6-(1-([1,1'-biphenyl]-4-ylmethyl)-5-methoxy-1H-indazole-7-carboxamido)spiro[3.3]heptan-2-yl)acetic acid; (Example 164)

($S_a$)-2-(6-(1-([1,1'-biphenyl]-4-ylmethyl)-5-methoxy-1H-indazole-7-carboxamido)spiro[3.3]heptan-2-yl)acetic acid;

2-(6-(1-([1,1'-biphenyl]-4-ylmethyl)-5-(difluoromethoxy)-1H-indazole-7-carboxamido)spiro[3.3]heptan-2-yl)acetic acid;

($R_a$)-2-(6-(1-([1,1'-biphenyl]-4-ylmethyl)-5-(difluoromethoxy)-1H-indazole-7-carboxamido)spiro[3.3]heptan-2-yl)acetic acid; (Example 165)

($S_a$)-2-(6-(1-([1,1'-biphenyl]-4-ylmethyl)-5-(difluoromethoxy)-1H-indazole-7-carboxamido)spiro[3.3]heptan-2-yl)acetic acid;

6-(1-(1-([1,1'-biphenyl]-4-yl)ethyl-1,2,2,2-d4)-4-chloro-H-indazole-7-carboxamido)spiro[3.3]heptane-2-carboxylic acid;

($R_a$)-6-(1-((racemic)-1-([1,1'-biphenyl]-4-yl)ethyl-1,2,2,2-d4)-4-chloro-1H-indazole-7-carboxamido)spiro[3.3]heptane-2-carboxylic acid;

($S_a$)-6-(1-((racemic)-1-([1,1'-biphenyl]-4-yl)ethyl-1,2,2,2-d4)-4-chloro-1H-indazole-7-carboxamido)spiro[3.3]heptane-2-carboxylic acid; (Example 166)

6-(1-((R) or (S)-1-([1,1'-biphenyl]-4-yl)ethyl-1,2,2,2-d4)-4-chloro-1H-indazole-7-carboxamido)spiro[3.3]heptane-2-carboxylic acid;

($R_a$)-6-(1-((R) or (S)-1-([1,1'-biphenyl]-4-yl)ethyl-1,2,2,2-d4)-4-chloro-1H-indazole-7-carboxamido)spiro[3.3]heptane-2-carboxylic acid;

($S_a$)-6-(1-((R) or (S)-1-([1,1'-biphenyl]-4-yl)ethyl-1,2,2,2-d4)-4-chloro-1H-indazole-7-carboxamido)spiro[3.3]heptane-2-carboxylic acid; (Example 167)

6-(1-(1-([1,1'-biphenyl]-4-yl)ethyl-1,2,2,2-d4)-1H-indazole-7-carboxamido)spiro[3.3]heptane-2-carboxylic acid;

($R_a$)-6-(1-((racemic)-1-([1,1'-biphenyl]-4-yl)ethyl-1,2,2,2-d4)-1H-indazole-7-carboxamido)spiro[3.3]heptane-2-carboxylic acid;

($S_a$)-6-(1-((racemic)-1-([1,1'-biphenyl]-4-yl)ethyl-1,2,2,2-d4)-1H-indazole-7-carboxamido)spiro[3.3]heptane-2-carboxylic acid; (Example 168)

($R_a$)-6-(1-((R) or (S)-1-([1,1'-biphenyl]-4-yl)ethyl-1,2,2,2-d4)-1H-indazole-7-carboxamido)spiro[3.3]heptane-2-carboxylic acid;

($S_a$)-6-(1-((R) or (S)-1-([1,1'-biphenyl]-4-yl)ethyl-1,2,2,2-d4)-1H-indazole-7-carboxamido)spiro[3.3]heptane-2-carboxylic acid; (Example 169)

2-(6-(1-([1,1'-biphenyl]-4-ylmethyl)-5-chloro-4-fluoro-1H-indazole-7-carboxamido)spiro[3.3]heptan-2-yl)acetic acid;

($R_a$)-2-(6-(1-([1,1'-biphenyl]-4-ylmethyl)-5-chloro-4-fluoro-1H-indazole-7-carboxamido)spiro[3.3]heptan-2-yl)acetic acid; (Example 170)

($S_a$)-2-(6-(1-([1,1'-biphenyl]-4-ylmethyl)-5-chloro-4-fluoro-1H-indazole-7-carboxamido)spiro[3.3]heptan-2-yl)acetic acid;

2-(6-(1-([1,1'-biphenyl]-4-ylmethyl)-5-chloro-4-methoxy-1H-indazole-7-carboxamido)spiro[3.3]heptan-2-yl)acetic acid;

($R_a$)-2-(6-(1-([1,1'-biphenyl]-4-ylmethyl)-5-chloro-4-methoxy-1H-indazole-7-carboxamido)spiro[3.3]heptan-2-yl)acetic acid; (Example 171)

($S_a$)-2-(6-(1-([1,1'-biphenyl]-4-ylmethyl)-5-chloro-4-methoxy-1H-indazole-7-carboxamido)spiro[3.3]heptan-2-yl)acetic acid; (Example 171)

6-(4-chloro-1-(4-cyclobutyl-3-fluorobenzyl)-1H-indazole-7-carboxamido)spiro[3.3]heptane-2-carboxylic acid;

($R_a$)-6-(4-chloro-1-(4-cyclobutyl-3-fluorobenzyl)-1H-indazole-7-carboxamido)spiro[3.3]heptane-2-carboxylic acid;

($S_a$)-6-(4-chloro-1-(4-cyclobutyl-3-fluorobenzyl)-1H-indazole-7-carboxamido)spiro[3.3]heptane-2-carboxylic acid; (Example 172)

6-(1-(1-([1,1'-biphenyl]-4-yl)ethyl)-5-chloro-1H-indazole-7-carboxamido)spiro[3.3]heptane-2-carboxylic acid;

($R_a$)-6-(1-((racemic)1-([1,1'-biphenyl]-4-yl)ethyl)-5-chloro-1H-indazole-7-carboxamido)spiro[3.3]heptane-2-carboxylic acid;

($S_a$)-6-(1-((racemic)1-([1,1'-biphenyl]-4-yl)ethyl)-5-chloro-1H-indazole-7-carboxamido)spiro[3.3]heptane-2-carboxylic acid; (Example 173)

6-(1-(1-([1,1'-biphenyl]-4-yl)ethyl)-5-chloro-1H-indazole-7-carboxamido)spiro[3.3]heptane-2-carboxylic acid;

($R_a$)-6-(1-((R)-1-[1,1'-biphenyl]-4-yl)ethyl)-5-chloro-1H-indazole-7-carboxamido)spiro[3.3]heptane-2-carboxylic acid;

($S_a$)-6-(1-((S)-1-([1,1'-biphenyl]-4-yl)ethyl)-5-chloro-1H-indazole-7-carboxamido)spiro[3.3]heptane-2-carboxylic acid;

6-(4-chloro-1-((2-methoxyquinolin-7-yl)methyl)-1H-indazole-7-carboxamido)spiro[3.3]heptane-2-carboxylic acid;

($R_a$)-6-(4-chloro-1-((2-methoxyquinolin-7-yl)methyl)-1H-indazole-7-carboxamido)spiro[3.3]heptane-2-carboxylic acid;

($S_a$)-6-(4-chloro-1-((2-methoxyquinolin-7-yl)methyl)-1H-indazole-7-carboxamido)spiro[3.3]heptane-2-carboxylic acid; (Example 175)

6-(1-(3-([1,1'-biphenyl]-4-yl)oxetan-3-yl)-4-chloro-1H-indazole-7-carboxamido)spiro[3.3]heptane-2-carboxylic acid;

($R_a$)-6-(1-(3-([1,1'-biphenyl]-4-yl)oxetan-3-yl)-4-chloro-1H-indazole-7-carboxamido)spiro[3.3]heptane-2-carboxylic acid;

($S_a$)-6-(1-(3-([1,1'-biphenyl]-4-yl)oxetan-3-yl)-4-chloro-1H-indazole-7-carboxamido)spiro[3.3]heptane-2-carboxylic acid; (Example 176).

Any combination of the groups described above for the various variables is contemplated herein. Throughout the specification, groups and substituents thereof are chosen by one skilled in the field to provide stable moieties and compounds.

The compounds of this disclosure may contain one or more stereogenic centers and thus occur as racemates and racemic mixtures, enantiomerically enriched mixtures, single enantiomers, individual diastereomers and diastereomeric mixtures. The compounds of the present disclosure may, either by nature of stereogenic centers or by restricted rotation, be present in the form of isomers (e.g., enantiomers, diastereomers).

It will also be appreciated that when two or more stereogenic centers are present in the compounds of the disclosure, several diastereomers and enantiomers of the exemplified structures will often be possible. It is intended that pure stereoisomers, pure diastereomers, pure enantiomers, and mixtures thereof, are within the scope of the disclosure. When compounds contain stereochemistry, the compounds are designated as '(racemic)' or "rac" if the stereoisomers have not been resolved and '(R) or (S)' if the stereoisomers have been resolved. In certain embodiments, the compounds disclosed herein contain axial chirality, particularly in the case of the spirocyclic[3.3]heptane containing compounds. These have also been designed as either '($R_a$) or ($S_a$)' when there is a single stereoisomer, where the 'a' denotes axial chirality.

All isomers, whether separated, pure, partially pure, or in racemic mixture, of the compounds of this disclosure are encompassed within the scope of this disclosure. The purification of said isomers and the separation of said isomeric mixtures may be accomplished by various methods. For example, diastereomeric mixtures can be separated into the individual isomers by chromatographic processes or crystallization, and racemates can be separated into the respective enantiomers either by chromatographic processes on chiral phases or by resolution.

The compounds of the present disclosure include all cis, trans, syn, anti, entgegen (E), and zusammen (Z) isomers as well as mixtures thereof. The compounds of the present disclosure may also be represented in multiple tautomeric forms, in such instances, the present disclosure expressly includes all tautomeric forms of the compounds described herein, even though only a single tautomeric form may be represented. In addition, where a term used in the present disclosure encompasses a group that may tautomerize, all tautomeric forms are expressly included thereunder. For example, hydroxy substituted heteroaryl includes 2-hydroxypyridine as well as 2-pyridone, 1-hydroxyisoquinoline as well as 1-oxo-1,2-dihydroisoquinoline, and the like. All such isomeric forms of such compounds are expressly included in the present disclosure.

The compounds of the present disclosure include the compounds themselves, as well as their salts, solvate, solvate of the salt and their prodrugs, if applicable. Salts for the purposes of the present disclosure are preferably pharmaceutically acceptable salts of the compounds according to the present disclosure. Salts which are not themselves suitable for pharmaceutical uses but can be used, for example, for isolation or purification of the compounds according to the disclosure are also included. A salt, for example, can be formed between an anion and a positively charged substituent (e.g., amino) on a compound described herein. Suitable anions include chloride, bromide, iodide, sulfate, nitrate, phosphate, citrate, methanesulfonate, trifluoroacetate, and acetate. Likewise, a salt can also be formed between a cation and a negatively charged substituent (e.g., carboxylate) on a compound described herein. Suitable cations include sodium ion, potassium ion, magnesium ion, calcium ion, and an ammonium cation such as tetramethylammonium ion.

As used herein, "pharmaceutically acceptable salts" refer to derivatives wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. When the compound of the present disclosure is basic, pharmaceutically acceptable salts include non-toxic salts or quaternary ammonium salts of the parent compound formed, for example, from non-toxic inorganic or organic acids. For example, such non-toxic salts include those derived from inorganic acids such as hydrochloric, hydrobromic, sulfonic, sulfuric, sulfamic, phosphoric, nitric and the like; and the salts prepared from organic acids such as acetic, propionic, succinic, glycolic, stearic, lactic, malic, tartaric, citric, ascorbic, maleic, hydroxymaleic, phenylacetic, glutamic, benzoic, salicylic, sulfanilic, 2-acetoxybenzoic, fumaric, benzenesulfonic, toluenesulfonic, naphthalenedisulfonic, methanesulfonic, ethanesulfonic, ethanedisulfonic, camphorsulfonic, gluconic, mandelic, mucic, pantothenic, oxalic, isethionic, and the like.

When the compound of the present disclosure is acidic, salts may be prepared from pharmaceutically acceptable non-toxic bases, including inorganic and organic bases. Such salts that may be prepared include lithium salt, sodium salt, potassium salt, magnesium salt, calcium salt, dicyclohexylamine salt, N-methyl-D-glucamine salt, tris(hydroxymethyl)methylamine salt, arginine salt, lysine salt, and the like.

Lists of suitable salts may be found in Remington's Pharmaceutical Sciences, 17th ed., Mack Publishing Company, Easton, Pa., 1985, p. 1418; S. M. Berge et al., "Pharmaceutical Salts", J. Pharm. Sci. 1977, 66, 1-19; and "Pharmaceutical Salts: Properties. Selection, and Use. A Handbook"; Wermuth, C. G. and Stahl, P. H. (eds.) Verlag Helvetica Chimica Acta, Zurich, 2002 [ISBN 3-906390-26-8]; each of which is incorporated herein by reference in its entirety.

Solvates in the context of the present disclosure are designated as those forms of the compounds according to the present disclosure which form a complex in the solid or liquid state by stoichiometric coordination with solvent molecules. Hydrates are a specific form of solvates, in which the coordination takes place with water. The formation of solvates is described in greater detail in "Solvents and Solvent Effects in Organic Chemistry"; Reichardt, C. and Welton T.; John Wiley & Sons, 2011 [ISBN: 978-3-527-32473-6], the contents of which is incorporated herein by reference in its entirety.

The present disclosure also encompasses all suitable isotopic variants of the compounds according to the present disclosure, whether radioactive or not. An isotopic variant of a compound according to the present disclosure is understood to mean a compound in which at least one atom within the compound according to the present disclosure has been exchanged for another atom of the same atomic number, but with a different atomic mass than the atomic mass which usually or predominantly occurs in nature. Examples of isotopes which can be incorporated into a compound according to the present disclosure are those of hydrogen, carbon, nitrogen, oxygen, fluorine, chlorine, bromine and iodine, such as $^2$H (deuterium), $^3$H (tritium), $^{13}$C, $^{14}$C, $^{15}$N, $^{17}$O, $^{18}$O, $^{18}$F, $^{36}$Cl, $^{82}$Br, $^{123}$I, $^{124}$I, $^{125}$I, $^{129}$I and $^{131}$I. Particular isotopic variants of a compound according to the present disclosure, especially those in which one or more radioactive isotopes have been incorporated, may be beneficial, for example, for the examination of the mechanism of action or of the active compound distribution in the body. Compounds labelled with $^3$H, $^{14}$C and/or $^{18}$F isotopes are suitable for this purpose. In addition, the incorporation of isotopes, for example of deuterium, can lead to particular therapeutic benefits as a consequence of greater metabolic stability of the compound, for example an extension of the half-life in the body or a reduction in the active dose required. In some embodiments, hydrogen atoms of the compounds described herein may be replaced with deuterium atoms. In certain embodiments, "deuterated" as applied to a chemical group and unless otherwise indicated, refers to a chemical group that is isotopically enriched with deuterium in an amount substantially greater than its natural abundance. Isotopic variants of the compounds according to the present disclosure can be prepared by various, including, for example, the methods described below and in the working examples, by using corresponding isotopic modifications of the particular reagents and/or starting compounds therein.

The present disclosure includes within its scope prodrugs of the compounds of Formulas (I), (II), (IIa), (IIb), (III), (IIIa), (IV), (IVa), (V), and (Va). Prodrugs are generally drug precursors that, following administration to a subject are converted to an active, or a more active species via some process, such as conversion by chemical hydrolysis or a metabolic pathway. Thus, in the methods of treatment of the present disclosure, the terms "administration of" or "administering a" compound shall encompass the treatment of the various conditions described with the compound specifically disclosed or with a compound which may not be specifically disclosed, but which converts to the specified compound in vivo after administration to the patient. Procedures for the selection and preparation of suitable prodrug derivatives are described, for example, in "Design of Prodrugs," ed. H. Bundgaard, Elsevier, 1985 (Amsterdam, NL). Examples of prodrugs include $C_1$-$C_6$ alkyl esters of carboxylic acid group, which, upon administration to a subject, are capable of providing active compounds.

C. FORMULATION

The term "pharmaceutical composition" as used herein is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present disclosure encompass any composition made by admixing a compound of the present disclosure, or a pharmaceutically acceptable salt, or solvate or solvate of the salt thereof, and a pharmaceutically acceptable carrier.

The term "pharmaceutically acceptable carrier" refers to a carrier or an adjuvant that may be administered to a patient, together with a compound of the present disclosure, or a pharmaceutically acceptable salt, solvate, salt of the solvate or prodrug thereof, and which does not destroy the pharmacological activity thereof and is nontoxic when administered in doses sufficient to deliver a therapeutic amount of the compound.

The amount administered depends on the compound formulation, route of administration, etc. and is generally empirically determined, and variations will necessarily occur depending on the target, the host, and the route of administration, etc. Generally, the quantity of active compound in a unit dose of preparation may be varied or adjusted from about 1 milligram (mg) to about 100 mg or from about 1 mg to about 1000 mg, according to the particular application. For convenience, the total daily dosage may be divided and administered in portions during the day.

Pharmaceutical compositions of the present disclosure for injection comprise pharmaceutically acceptable sterile aqueous or non-aqueous solutions, dispersions, suspensions or emulsions as well as sterile powders for reconstitution into sterile injectable solutions or dispersions just prior to use. Examples of suitable aqueous and non-aqueous carriers, diluents, solvents or vehicles include water, ethanol, polyols (such as glycerol, propylene glycol, polyethylene glycol, and the like), and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

These pharmaceutical compositions may also contain adjuvants such as preservative, wetting agents, emulsifying agents, and dispersing agents. Prevention of the action of micro-organisms may be ensured by the inclusion of various antibacterial and antifungal agents, for example, paraben, chlorobutanol, phenol sorbic acid, and the like. It may also be desirable to include isotonic agents such as sugars, sodium chloride, and the like. Prolonged absorption of the injectable pharmaceutical form may be brought about by the inclusion of agents that delay absorption such as aluminum monostearate and gelatin. The compounds can be incorporated into slow release or targeted delivery systems such as polymer matrices, liposomes, and microspheres. Such formulations may provide more effective distribution of the compounds.

The pharmaceutical compositions that are injectable formulations can be sterilized, for example, by filtration through a bacterial-retaining filter, or by incorporating sterilizing agents in the form of sterile solid pharmaceutical compositions that can be dissolved or dispersed in sterile water or other sterile injectable medium prior to use.

Solid dosage forms of the instant pharmaceutical compositions for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid pharmaceutical compositions of a similar type may also be employed as fillers in soft and hard-filled gelatin capsules using such excipients as lactose or milk sugar as well as high molecular weight polyethylene glycols and the like.

The solid dosage forms of the instant pharmaceutical compositions of tablets, dragées. capsules, pills, and granules can be prepared with coatings and shells such as enteric coatings and other pharmaceutical coatings. They may optionally contain opacifying agents and can also be of a formulation that they release the active ingredient(s) only, or preferentially, in a certain part of the intestinal tract, optionally, in a delayed manner. Examples of embedding pharmaceutical compositions which can be used include polymeric substances and waxes.

The active compounds can also be in microencapsulated form, if appropriate, with one or more of the above-mentioned excipients.

Liquid dosage forms of the instant pharmaceutical compositions for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, coin, germ, olive, castor, and sesame oils), glycerol, tetrahydrofurfuryl alcohol, polyethylene glycols and fatty acid esters of sorbitan, and mixtures thereof.

Besides inert diluents, the oral pharmaceutical compositions can also include adjuvants such as wetting agents, emulsifying and suspending agents, sweetening, flavoring, and perfuming agents.

Suspensions of the instant compounds, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, and tragacanth, and mixtures thereof.

Pharmaceutical compositions for rectal or vaginal administration are preferably suppositories which can be prepared by mixing the compounds with suitable non-irritating excipients or carriers such as cocoa butter, polyethylene glycol or a suppository wax which are solid at room temperature but liquid at body temperature and therefore melt in the rectum or vaginal cavity and release the active compound.

Dosage forms for topical administration of a compound or pharmaceutical composition of the present disclosure include powders, patches, sprays, ointments and inhalants. The active compound is mixed under sterile conditions with a pharmaceutically acceptable carrier and any preservatives, buffers, or propellants which may be required.

The compounds and compositions described herein can, for example, be administered orally, parenterally (e.g., subcutaneously, intracutaneously, intravenously, intramuscularly, intraarticularly, intraarterially, intrasynovially, intrasternally, intrathecally, intralesionally, and by intracranial injection or infusion techniques), by inhalation spray, topically, rectally, nasally, buccally, vaginally, via an implanted reservoir, by injection, subdermally, intratumorally, intraperitoneally, transmucosally, or in an ophthalmic preparation, with a dosage ranging from about 0.01 milligrams per kilogram (mg/kg) to about 1000 mg/kg, (e.g., from about 0.01 to about 100 mg/kg, from about 0.1 to about 100 mg/kg) every 4 to 120 hours, or according to the requirements of the particular drug, dosage form, and/or route of administration. The interrelationship of dosages for animals and humans (based on milligrams per meter squared of body surface) is described by Freireich et al., Cancer Chemother. Rep. 50, 219-244 (1966). Body surface area may be approximately determined from height and weight of the patient. See, e.g., Scientific Tables, Geigy Pharmaceuticals, Ardsley, N.Y., 537 (1970). In certain embodiments, the compositions are administered by oral administration or by injection. The methods herein contemplate administration of an effective amount of compound or compound composition to achieve a desired or stated effect. Typically, the pharmaceutical compositions of the present disclosure will be administered from about 1 to about 6 times per day or alternatively, as a continuous infusion. Such administration can be used as a chronic or acute therapy.

Lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, and the judgment of the treating physician.

Dosage forms include from about 0.001 mg to about 2,000 mg (including, from about 0.001 mg to about 1,000 mg, from about 0.001 mg to about 500 mg, from about 0.01 mg to about 250 mg) of a compound of any of Formulas (I), (II), (IIa), (IIb), (III), (IIIa), (IV), (IVa), (V), and (Va) or a salt (e.g., a pharmaceutically acceptable salt) thereof as defined anywhere herein. The dosage forms can further include a pharmaceutically acceptable carrier and/or an additional therapeutic agent.

Appropriate dosage levels may be determined by any suitable method. Preferably, the active substance is administered at a frequency of 1 to 4 times per day for topical administration, or less often if a drug delivery system is used. Nevertheless, actual dosage levels and time course of administration of the active ingredients in the pharmaceutical compositions of the present disclosure may be varied so as to obtain an amount of the active ingredient which is effective to achieve a desired therapeutic response for a particular patient, composition and mode of administration, without being intolerably toxic to the patient. In certain cases, dosages may deviate from the stated amounts, in particular as a function of age, gender, body weight, diet and general health status of the patient, route of administration, individual response to the active ingredient, nature of the preparation, and time or interval over which administration takes place. Thus, it may be satisfactory in some cases to manage with less than the aforementioned minimum amount, whereas in other cases the stated upper limit may be exceeded. It may in the event of administration of larger amounts be advisable to divide these into multiple individual doses spread over the day.

D. COMBINATION THERAPY

In one aspect the compounds of the present disclosure may be co-administered with one or more additional agents used in the treatment of cancer. The additional agents include, but are not limited to: alkylating agents such as cyclophosphamide, chlorambucil, meclorethamine, ifosfamide, or melphalan; antimetabolites such as methotrexate, cytarabine, gemcitabine, fludarabine, 6-mercaptopurine, azathioprene, or 5-fluorouracil; antimitotic agents such as vincristine, vinblastine, vindesine, vinorelbine, paclitaxel, or docetaxel; platinum derivatives such as cisplatin, carboplatin or oxaliplatin; hormone therapeutics such as tamoxifen; aromatase inhibitors such as bicalutamide, anastrozole, exemestane or letrozole; signaling inhibitors such as imatinib (tyrosine kinase inhibitor; Gleevac), gefitinib (EGFR inhibitor; Iressa) or erlotinib (receptor TKI, which acts on EGFR; Tarceva); monoclonal antibodies such as trastuzumab, pertuzumab, inotuzumab, or ozogamicins, as well as their antibody-drug conjugates such as ado-trastuzumab emtansine; antiangiogenic agents such as bevacizumab, sorafenib (tyrosine protein kinase), pazopanib or sunitinib (receptor tyrosine kinase inhibitor); tivozanib, axitinib, and cediranib; biologic response modifiers such as interferon-alpha; topoisomerase inhibitors such as camptothecins (including irinotecan and topotecan), amsacrine, etoposide, etoposide phosphate, or teniposide; anthracyclines such as doxorubicin, daunorubicin, epirubicin, idarubicin, sabarubicin, aclarubicin, carubicin and valrubicin; other cytotoxic agents such as actinomycin, bleomycin, plicamycin or mitomycin; mTOR inhibitors such as rapamycin, temsirolimus and everolimus; STING activators such as ADU-S100 and MK-1454; IDO inhibitors such as epacadostat, indoximod, or BMS-986205; and antibody therapy such as CTLA4 antibody therapy, PD-L1 antibody therapy, and PD-1 antibody therapy.

"CTLA4 antibody" or "anti-CTLA4" refers to an antibody or antibodies directed towards cytotoxic t-lymphocyte antigen 4 (CTLA4). Exemplary antibodies include, but are not limited to, antibodies that are CTLA4 antagonists or the CTLA4 antibodies as set forth in U.S. Pat. Nos. 8,685,394 and 8,709,417. Some embodiments of the antibody include ipilimumab (YERVOY®, Bristol-Myers Squibb) and CP-675,206 (tremelimumab, Pfizer). In a particular embodiment, the antibody is ipilimumab.

"PD-L1 antibody" or "anti-PD-L1" refers to an antibody directed towards programmed death ligand 1 (PD-L1). Exemplary antibodies include, but are not limited to, the antibodies set forth in U.S. Pat. Nos. 8,217,149, 8,383,796, 8,552,154 and 8,617,546. Some embodiments of the antibody include avelumab (Merck KGA/Pfizer), durvalumab (AstraZeneca) and atezolizumab (TECENTRIQ®, Roche). In a particular embodiment, the antibody is atezolizumab.

"PD-1 antibody" or "anti-PD-1" refers to an antibody directed towards programmed death protein 1 (PD-1). Exemplary antibodies include, but are not limited to, the antibodies set forth in U.S. Pat. Nos. 7,029,674, 7,488,802, 7,521,051, 8,008,449, 8,354,509, 8,617,546 and 8,709,417. Particular embodiments of the antibody include nivolumab (OPDIVO®, Bristol-Myers Squibb), and pembrolizumab (KEYTRUDA®, Merck).

The terms "antibody" and "antibodies" as used herein is inclusive of all types of immunoglobulins, including IgG, IgM, IgA, IgD, and IgE, or fragments thereof, that may be appropriate for the medical uses disclosed herein. The antibodies may be monoclonal or polyclonal and may be of any species of origin, including, for example, mouse, rat, rabbit, horse, or human. Antibody fragments that retain specific binding to the protein or epitope, for example, CTLA4, PD-L1 or PD-1, bound by the antibody used in the present disclosure are included within the scope of the term "antibody." The antibodies may be chimeric or humanized, particularly when they are used for therapeutic purposes. Antibodies and antibody fragments may be obtained or prepared using various methods.

In certain embodiments, the additional agents may be administered separately from the compounds of the present disclosure as part of a multiple dose regimen (e.g., sequentially, or on different overlapping schedules with the administration of one or more compounds of Formulas (I), (II), (IIa), (IIb), (III), (IIIa), (IV), (IVa), (V), and (Va). In other embodiments, these agents may be part of a single dosage form, mixed together with the compounds of the present disclosure in a single composition. In still another embodiment, these agents can be given as a separate dose that is administered at about the same time as one or more compounds of Formulas (I), (II), (IIa), (IIb), (III), (IIIa), (IV), (IVa), (V), and (Va) are administered (e.g., simultaneously with the administration of one or more compounds of any of Formulas (I), (II), (IIa), (IIb), (III), (IIIa), (IV), (IVa), (V), and (Va)). In some embodiments, at least one of the therapeutic agents in the combination therapy is administered using the same dosage regimen (dose, frequency and duration of treatment) that is typically employed when the agent is used as monotherapy for treating the same cancer. In other embodiments, the patient receives a lower total amount of at least one of the therapeutic agents in the combination therapy than when the agent is used as monotherapy, e.g., smaller doses, less frequent doses, and/or shorter treatment duration.

When the compositions of the present disclosure include a combination of a compound of the formulae described herein and one or more additional agents, both the compound and the additional agent can be present at dosage levels of between about 1 to 100%, and more preferably between about 5 to 95% of the dosage normally administered in a monotherapy regimen.

E. EVALUATION OF THE ACTIVITY OF THE COMPOUNDS

Standard physiological, pharmacological and biochemical procedures are available for testing the compounds to identify those that possess biological activity as $EP_2$ and $EP_4$ receptor modulators, or as $EP_2$ and $EP_4$ receptor antagonists.

In Vitro Assay: The compounds in the present disclosure were tested in a functional calcium flux assay using stably transfected HEK293 cells. Cells transfected with $EP_1$, $EP_2$, $EP_3$ and $EP_4$ were purchased from Eurofins Discovery Services (St. Charles, Missouri). Each receptor subtype has an additional promiscuous G protein added in order to couple the aforementioned receptor to the calcium signaling pathway. The parental cell line used also expresses a novel variant of clytin, a calcium-activated photo-protein, to enable sensitive luminescent detection. Briefly, cells were plated at 50,000 cells-per-well in black, clear bottom 96-well plates. The plated cells were allowed to sit at room temperature for 30 min prior to transferring to a humidified, 37° C., 5% $CO_2$ incubator for 18 to 24 h. Assay buffer (HBSS with 20 mM HEPES) and loading buffer (assay buffer plus 10 μM coelenterazine) were prepared on the day of the assay. Assays were performed by aspirating media from the assay plate and washing once with assay buffer, then replacing with loading buffer and allowing the cells to incubate for 1.5 h at room temperature. Compounds were prepared in assay buffer at a 3× final concentration in non-binding plates. Compounds were added to the cell plates and incubated for 30 min at room temperature. The prostanoid receptor ligand $PGE_2$ was prepared at a 4× dilution ratio for a final concentration of 10 nM. Plates were run on a Flexstation™ using a 100 ms integration luminescence protocol for a total of 60 sec with ligand addition at 15 sec. Data were obtained from relative light units as measured by area under the curve.

TABLE 1

Calcium Flux Data Against $EP_2$ and $EP_4$ for Described Examples

| Example | $EP_2$ $Ca^{2+}$-flux assay $IC_{50}$ (nM) | $EP_4$ $Ca^{2+}$-flux assay $IC_{50}$ (nM) |
|---|---|---|
| 1 | 34 | <1 |
| 2 | 30 | <1 |
| 3 | <25 | <1 |
| 4 | <25 | 17 |
| 5 | <25 | <1 |
| 6 | 32 | <1 |
| 7 | <25 | <1 |
| 8 | 43 | <1 |
| 9 | <25 | <1 |
| 10 | <25 | <1 |
| 11 | 70 | <1 |
| 12 | <25 | <1 |
| 13 | 39 | <1 |
| 14 | <25 | <1 |
| 15 | <25 | <1 |
| 16 | <25 | <1 |
| 17 | <25 | 7 |
| 18 | 34 | <1 |
| 19 | <25 | <1 |
| 20 | <25 | <1 |
| 21 | 51 | 1 |
| 22 | 78 | <1 |
| 23 | 60 | 1 |
| 24 | 100 | 2 |
| 25 | <25 | <1 |
| 26 | 34 | <1 |
| 27 | 45 | <1 |
| 28 | 84 | 4 |
| 29 | 76 | 32 |
| 30 | 39 | 36 |
| 31 | 44 | <1 |
| 32 | <25 | <1 |
| 33 | <25 | 3 |
| 34 | <25 | <1 |

TABLE 1-continued

Calcium Flux Data Against $EP_2$ and $EP_4$ for Described Examples

| Example | $EP_2$ $Ca^{2+}$-flux assay $IC_{50}$ (nM) | $EP_4$ $Ca^{2+}$-flux assay $IC_{50}$ (nM) |
|---|---|---|
| 35 | 34 | <1 |
| 36 | 72 | <1 |
| 37 | 70 | <1 |
| 38 | <25 | <1 |
| 39 | 46 | <1 |
| 40 | <25 | <1 |
| 41 | 95 | <1 |
| 42 | 37 | <1 |
| 43 | <25 | <1 |
| 44 | 30 | <1 |
| 45 | 62 | <1 |
| 46 | 88 | <1 |
| 47 | 79 | <1 |
| 48 | 27 | <1 |
| 49 | <25 | <1 |
| 50 | 67 | <1 |
| 51 | <25 | <1 |
| 52 | <25 | <1 |
| 53 | <25 | <1 |
| 54 | 43 | <1 |
| 55 | 46 | <1 |
| 56 | 76 | <1 |
| 57 | 99 | <1 |
| 58 | 95 | 2.4 |
| 59 | 51 | 2.5 |
| 60 | 40 | <1 |
| 61 | <25 | <1 |
| 62 | 54 | <1 |
| 63 | 90 | <1 |
| 64 | 48 | <1 |
| 65 | 43 | 3.0 |
| 66 | <25 | <1 |
| 67 | 100 | 6.6 |
| 68 | <25 | <1 |
| 69 | 33 | 2.2 |
| 70 | <25 | <1 |
| 71 | 94 | <1 |
| 72 | <25 | 4.1 |
| 73 | 71 | 1.3 |
| 74 | <25 | 1.2 |
| 75 | <25 | 1.4 |
| 76 | 56 | <1 |
| 77 | 71 | <1 |
| 78 | 99 | 4.4 |
| 79 | <25 | <1 |
| 80 | 55 | 1.1 |
| 81 | <25 | <1 |
| 82 | <25 | <1 |
| 83 | <25 | <1 |
| 84 | <25 | <1 |
| 85 | 30 | <1 |
| 86 | 36 | 1.8 |
| 87 | 65 | 3.8 |
| 88 | 29 | <1 |
| 89 | 97 | 1.3 |
| 90 | 57 | <1 |
| 91 | 59 | <1 |
| 92 | <25 | <1 |
| 93 | 28 | 11 |
| 94 | <25 | <1 |
| 95 | 83 | 9.0 |
| 96 | <25 | <1 |
| 97 | 60 | <1 |
| 98 | 42 | <1 |
| 99 | 45 | <1 |
| 100 | 91 | <1 |
| 101 | 44 | <1 |
| 102 | 81 | 8.9 |
| 103 | <25 | <1 |
| 104 | <25 | <1 |
| 105 | <25 | <1 |
| 106 | <25 | <1 |
| 107 | 33 | <1 |
| 108 | <25 | <1 |

TABLE 1-continued

Calcium Flux Data Against $EP_2$ and $EP_4$ for Described Examples

| Example | $EP_2$ $Ca^{2+}$-flux assay $IC_{50}$ (nM) | $EP_4$ $Ca^{2+}$-flux assay $IC_{50}$ (nM) |
|---|---|---|
| 109 | <25 | 5.2 |
| 110 | <25 | <1 |
| 111 | 38 | 1.2 |
| 112 | <25 | 1.8 |
| 113 | <25 | 1.3 |
| 114 | 57 | 5.5 |
| 115 | 69 | 2.9 |
| 116 | <25 | 2.8 |
| 117 | 87 | 14 |
| 118 | 31 | 2.6 |
| 119 | 59 | 3.8 |
| 120 | <25 | 11 |
| 121 | <25 | 6.6 |
| 122 | <25 | 4.7 |
| 123 | 60 | 12 |
| 124 | <25 | 3.9 |
| 125 | <25 | <1 |
| 126 | <25 | <1 |
| 127 | <25 | 1.2 |
| 128 | <25 | 1.9 |
| 129 | 61 | 3.0 |
| 130 | <25 | <1 |
| 131 | <25 | <1 |
| 132 | <25 | 2.2 |
| 133 | 65 | <1 |
| 134 | <25 | 1.3 |
| 135 | <25 | <1 |
| 136 | <25 | <1 |
| 137 | 64 | 3.2 |
| 138 | 25 | <1 |
| 139 | <25 | <1 |
| 140 | <25 | <1 |
| 141 | <25 | 3.8 |
| 142 | 40 | 17.3 |
| 143 | 35 | <1 |
| 144 | <25 | <1 |
| 145 | 100 | <1 |
| 146 | 82 | <1 |
| 147 | <25 | <1 |
| 148 | <25 | 1.4 |
| 149 | 38 | <1 |
| 150 | 61 | <1 |
| 151 | <25 | <1 |
| 152 | 49 | <1 |
| 153 | 95 | <1 |
| 154 | <25 | 2.8 |
| 155 | 44 | 2.6 |
| 156 | <25 | <1 |
| 157 | <25 | <1 |
| 158 | 64 | <1 |
| 159 | 65 | <1 |
| 160 | 56 | 4.0 |
| 161 | 63 | <1 |
| 162 | 52 | 1.2 |
| 163 | 30 | <1 |
| 164 | <25 | <1 |
| 165 | <25 | 1.0 |
| 166 | 26 | 3.9 |
| 167 | 41 | 3.5 |
| 168 | 28 | 1.2 |
| 169 | 63 | 1.5 |
| 170 | <25 | 5.1 |
| 171 | <25 | 1.4 |
| 172 | <25 | 2.1 |
| 173 | <25 | 7.2 |
| 174 | <25 | 6.4 |
| 175 | <25 | 5.6 |
| 176 | <25 | 2.9 |

In certain embodiments, the compounds provided herein have an $EP_2$ $Ca^{2+}$-flux assay $IC^{50}$ of less than 50 nM and an $EP_4$ $Ca^{2+}$-flux assay $IC_{50}$ of less than 10 nM. In certain embodiments, the compounds provided herein have an $EP_2$ $Ca^{2+}$-flux assay $IC_{50}$ of less than 50 nM and an $EP_4$ $Ca^{2+}$-flux assay $IC_{50}$ of less than 1 nM. In certain embodiments, the compounds provided herein have an $EP_2$ $Ca^{2+}$-flux assay $IC_{50}$ of less than 25 nM and an $EP_4$ $Ca^{2+}$-flux assay $IC_{50}$ of less than 10 nM. In certain embodiments, the compounds provided herein have an $EP_2$ $Ca^{2+}$-flux assay $IC_{50}$ of less than 25 nM and an $EP_4$ $Ca^{2+}$-flux assay $IC_{50}$ of less than 1 nM.

Efficacy Evaluation in syngeneic CT26 colon carcinoma mouse model: A compound of Formula (I) designated Compound A was evaluated and compared to Compound B, an internal selective EP4 antagonist, for efficacy in the CT26 colon carcinoma mouse model.

Cell culture: CT26 cells were obtained from American Type Tissue Culture (ATCC catalog #CRL-2638). Cells were thawed quickly at 37° C. and placed in RPMI-1640 with 10% FBS, and passaged every 3 days. Cells were expanded for a minimum of 3 passages and harvested 2 days after the last passage at 50% confluency for cell implantation. Cells were harvested for implantation, washed in DPBS, and re-suspended in DPBS at a concentration of 20E6 cells/ml and placed on ice.

Implantation: Seven to eight week old female Balb-c mice from Harlan Laboratories were allowed to acclimate for 1 week prior to cell implantation. The left flank of each animal was shaved 3 days prior to cell injection. Harvested CT26 cells were gently swirled and re-suspended with a pipette before each injection. Fifty microliters of cell suspension, containing 1E6 cells, was injected subcutaneously into the left flank of each animal. Tumors were measured with calipers on day 10 and randomized into two groups of n=10 animals, containing an average tumor size of 93 mm³. Volume calculations were based on the formula: (width²*length)/2.

Drug Treatment: Animals with average tumor size of 93 mm³ were divided into vehicle Compound A, or Compound B groups with an n=10 per group, methylcellulose (cP 400; Sigma) was used as the vehicle and prepared at 0.5% weight/volume in sterile water. Compound A was prepared in 0.5% methyl cellulose at a concentration of 5 mg/ml. Animals were dosed p.o., b.i.d with 10 ml/kg of vehicle, 50 mg/kg of Compound A, or 30 mg/kg of Compound B. Mice were weighed every 3 days to account for adjustments in dosing volume. Dosing began on day 10 after implantation and continued for 14 days after which animals were sacrificed.

Tumor Volume Measurements: Beginning on day 10 tumors were measured every 2-3 days for 14 days using calipers and volume calculated based on the formula: (width²*length)/2. Data was plotted in Prism (GraphPad). Study was terminated when tumors in vehicle treated group reached an average size of ~1500 mm³ and animals were moribund.

Statistical Analysis: Statistical analysis was performed in Prism using t-test or two-way ANOVA where appropriate. Where *p<0.05, **p<0.01.

Figure 2A:
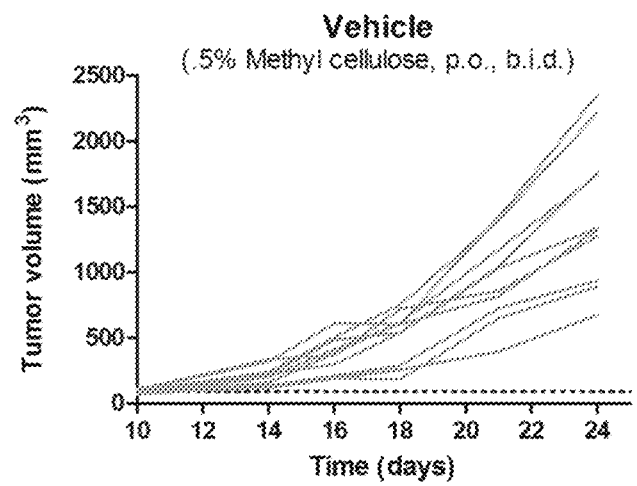
FIG. 2A-C depict Spider plots of individual CT26 tumor bearing mice treated with one of the compounds of Formula (I) (Compound A) for 14 days (FIG. 2B) which also demonstrate significant tumor growth inhibition compared to animals treated with vehicle (FIG. 2A) or an internal EP4 selective compound Compound B (FIG. 2C).
Figure 2B:
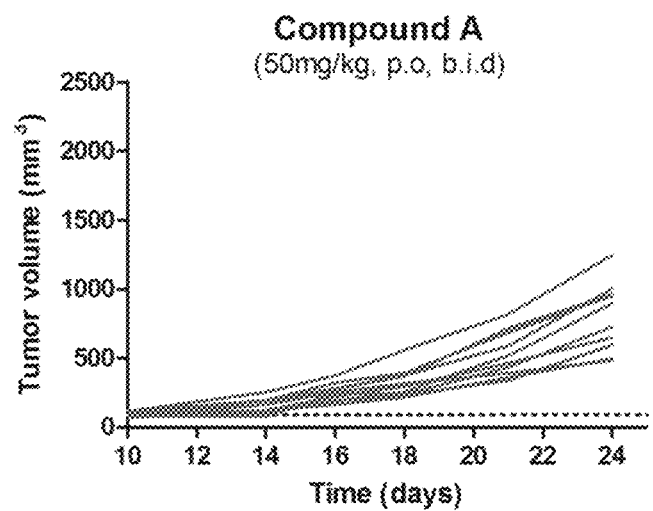
Figure 2C:
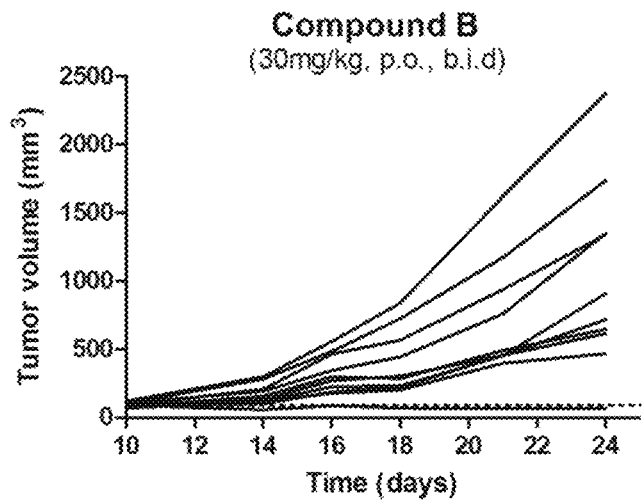

Results: CT26 tumor bearing mice treated with 50 mg/kg of the dual EP2/4 antagonist Compound A (p.o., b.i.d) for 14 days resulted in a statistically significant (p=0.02 by One-Way ANOVA) reduction in tumor size compared to vehicle or Compound B treated animals (FIG. 1). Spider plots (FIG. 2A-C) also demonstrate significant tumor growth inhibition in individual CT26 tumor bearing mice treated with Compound A for 14 days. After 14 days of dosing with vehicle Compound A, or Compound B, animals were sacrificed and tumors were weighed and percent tumor volume increase was calculated. Mice treated with 50 mg/kg of Compound A for 14 days had a statistically significant (p<0.05) 2-fold reduction in tumor weight and a statistically significant (p<0.05) 1.8-fold decrease in percent tumor volume compared to CT26 tumor bearing mice treated with vehicle or Compound B. Data are presented as mean f SEM of n=10 animals/group.

Figure 3:
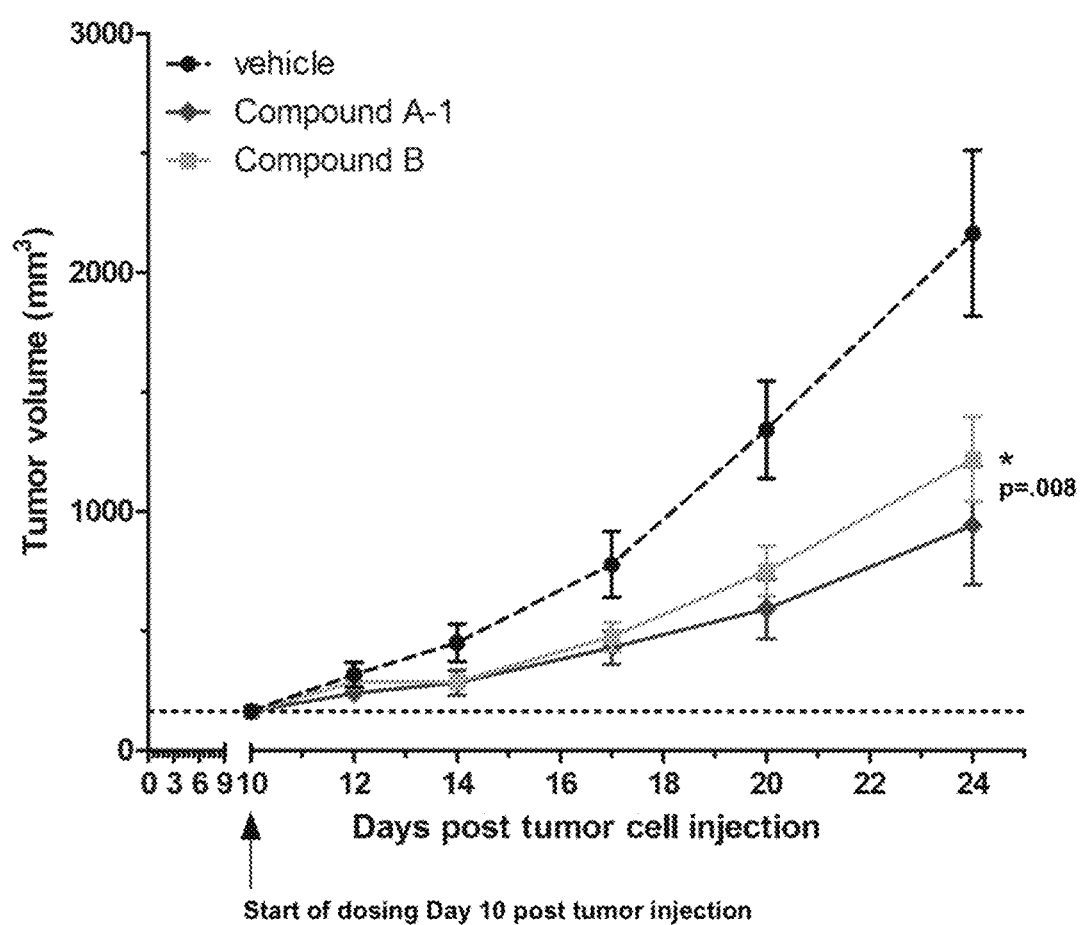
FIG. 3 depicts animal tumor growth delay in syngeneic CT26 colon carcinoma mouse model. CT26 tumor bearing mice treated p.o., b.i.d with 30 mg/kg of one of the compounds of Formula (I) (Compound A-1) for 14 days resulted in a statistically significant (p=0.008) reduction in tumor size compared to animals treated with vehicle or an internal EP4 selective compound (Compound B).
Figure 4A:
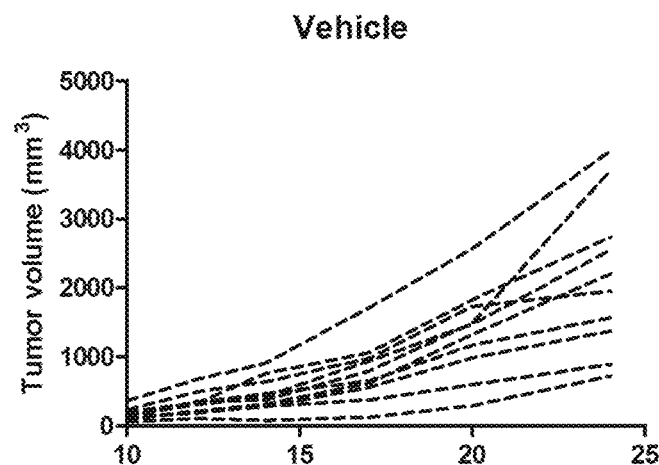
FIG. 4A-C depict Spider plots of individual CT26 tumor bearing mice treated with one of the compounds of Formula (I) (Compound A-1) for 14 days (FIG. 2B) which also demonstrate significant tumor growth inhibition compared to animals treated with vehicle (FIG. 4A) or an internal EP4 selective compound Compound B (FIG. 4C).
Figure 4B:
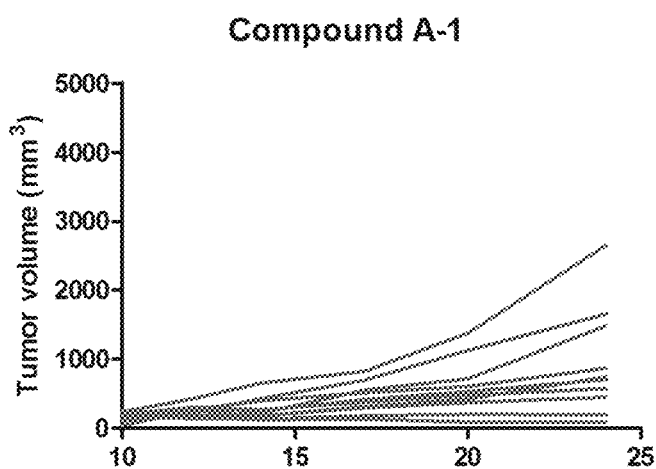
Figure 4C:
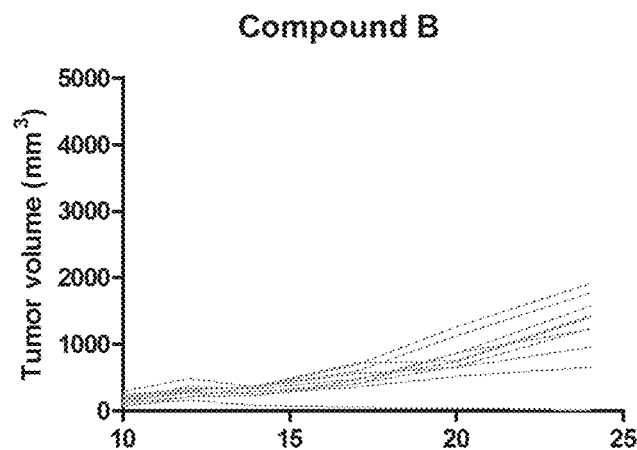
Figure 5:
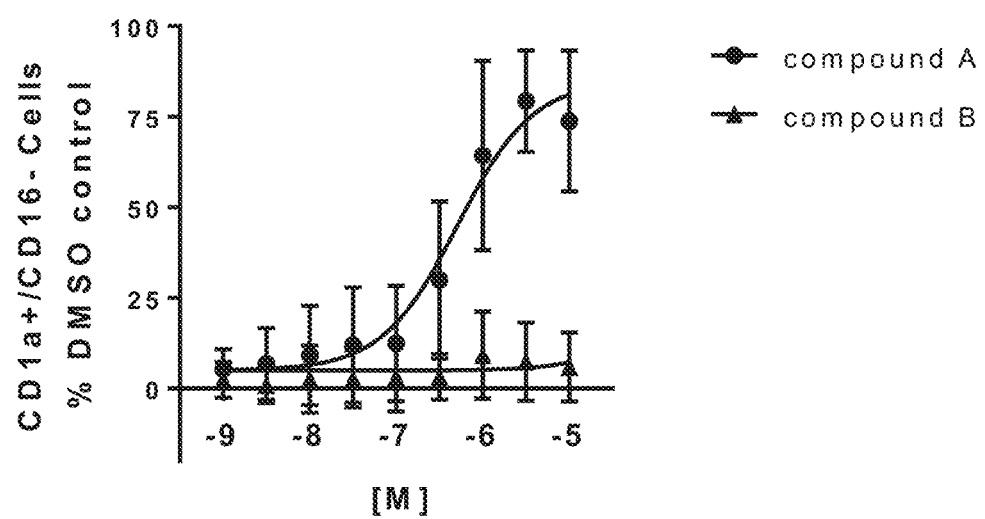
FIG. 5 depicts the $EC_{50}$ for restoration of the $CD1a^+$/$CD16^-$ DCs phenotype for one of the compounds of Formula (I) (Compound A) in the dendritic cell differentiation assay.

Another compound of Formula (I) designated Compound A-1 was also evaluated in the syngeneic CT26 colon carcinoma mouse model using the same procedure, except that the starting average tumor size was 163 mm$^3$. Compound A-1 was prepared in 0.5% methyl cellulose at a concentration of 3 mg/ml. Animals were dosed p.o., b.i.d with 10 ml/kg of vehicle, 30 mg/kg of Compound A-1, or 30 mg/kg of Compound B. CT26 tumor bearing mice treated with 30 mg/kg of Compound A-1 (p.o., b.i.d) for 14 days resulted in a statistically significant (p=0.008 by One-Way ANOVA) reduction in tumor size compared to vehicle treated animals as well as an improved reduction in tumor growth compared to Compound B (30 mg/kg, p.o., q.d) treated animals (FIG. 3). Spider plots (FIG. 4A-C) also demonstrate significant tumor growth inhibition in individual CT26 tumor bearing mice treated with Compound A-1 for 14 days. After 14 days of dosing with vehicle Compound A-1, or Compound B, animals were sacrificed and tumors were weighed and percent tumor volume increase was calculated. Mice treated with 30 mg/kg of Compound A-1 for 14 days had a statistically significant (p<0.03) 2.2-fold reduction and a 1.5-fold reduction in tumor weight compared to vehicle and Compound B, respectively. Percent tumor volume increase was also reduced significantly (p<0.009, One-Way ANOVA) in Compound A-1 treated animals with a 2.57-fold and 1.5-fold decrease decrease in percent tumor volume compared to CT26 tumor bearing mice treated with vehicle or Compound B, respectively. Data are presented as mean±SEM of n=10 animals/group.

Dendritic Cell (DC) differentiation assay: A compound of Formula (I) designated Compound A, was evaluated in a DC differentiation assay and compared against an internal selective EP4 antagonist, Compound B.

Blood of healthy volunteers was purchased from the San Diego Blood Bank. PBMCs were isolated using a Ficoll gradient (VWR International; CAT #95021-205). Monocytes were isolated from PBMCs using CD14-beads (Miltenyi; CAT #130-050-201) as per the manufacturer's instructions.

CD14+ cells were plated at 1.5×10$^{\wedge}6$ cells/well in a 12-well plate in 1.5 ml of media (RPMI 1640 medium (Gibco CAT #11875-093) supplemented with: 50 μM 2-mercaptoethanol (Sigma. CAT #M7522), 5 ml of HEPES, stock is 100× (1M) (Thermo Fisher CAT #15630080), 5 ml of penicillin, streptomycin, L-glutamine, stock is 100× (Thermo Fisher CAT #10378016), and 10% FCS heat inactivated (Invitrogen; 10082-147)). At day 0 of culture DMSO only was added to the control well. Prostaglandin E$_2$ (PGE$_2$) only control was added at 30 nM final concentration (Sigma Aldrich, CAT #P6532) to a separate control well. A dose response of the EP2/4 dual antagonist, (Compound A) and an EP4-selective antagonist (Compound B) was added to the cultures plus PGE$_2$ at 30 nM. The final concentration of DMSO in compound was 0.1% and 0.1% DMSO was used as vehicle control. IL-4 50 ng/ml (R&D Systems, #204-IL-050/CF) and 20 ng/ml GMCSF (R&D Systems; #215-GM-050/CF) were added to the cells on day 0 and 2 of culture. Cells were incubated in a 37° C./5% CO$_2$ incubator. Immature dendritic cells (DCs) were harvested at day 5 of culture and analyzed for cell surface antigen expression by flow cytometry.

DCs were collected and stained using the following antibodies all purchased from BD Biosciences: fluorescein isothiocyanate (FITC)-conjugated Isotype control (CAT #555748); R-phycoerythrin (PE)-conjugated isotype control (CAT #559320); CD1a-FITC (CAT #555806); CD16-PE (CAT #62293); CD163-PE (CAT #556018). The cells were incubated with antibodies for 20 min on ice in the dark and washed 3 times with PBS/10% FCS using 2000 rpm 2 min. After the last wash cells were fixed using 2% PFA/PBS and analyzed by flow cytometry using the Accuri C6 (Accuri). Data was analyzed by using the CFlowPlus software (Accuri).

PGE$_2$ caused a downregulation of CD1a$^+$/CD16$^-$ DCs and this level was set as 0%. The level in the absence of PGE$_2$ (with DMSO control) was set as 100%. CD163 is a marker for M2 macrophages, which is upregulated by PGE$_2$. For analysis of CD163$^+$ cells, the level of the PGE$_2$ control cells was set at 100% and the DMSO control was set as 0%. DCs were generated and evaluated from 20 different donors.

Results: PGE$_2$ reduced the number of CD1a+/CD16$^-$ DCs in all 20 donors tested and this was reversed by the EP2/4 dual antagonist (Compound A) in all 20 donors. Compound B, the internal EP4-selective antagonist, did not show reversal of the PGE$_2$ mediated reduction in CD1a+/CD16$^-$ cells. PGE$_2$ increased the percentage of CD163$^+$ cells in 15/20 donors and in all those cases, the EP2/4 dual antagonist (Compound A) caused a reduction of CD163$^+$ cells back to baseline levels, whereas the EP4-selective antagonist (Compound B) did not. The EC$_{50}$ for restoration of the CD1a$^+$/CD16$^-$ DCs phenotype for Compound A is 511 nM (FIG. 3) and the IC$_{50}$ for inhibition of the CD163$^+$ macrophage phenotype is 367 nM.

F. METHODS OF USE

In certain embodiments, provided herein are methods of using a compound of any of Formulas (I), (II), (IIa), (IIb), (III), (IIIa), (IV), (IVa), (V), and (Va) for the treatment, prevention or amelioration of cancer, arthritis, pain, endometriosis, neurodegenerative disease and cardiovascular disease.

In one aspect, the present disclosure provides for a method of treating cancer comprising administering to a patient in need thereof a therapeutically effective amount of a compound of any of Formulas (I), (II), (IIa), (IIb), (III), (IIIa), (IV), (IVa), (V), and (Va), or a pharmaceutically acceptable salt, solvate, solvate of a salt, or a prodrug thereof. In some embodiments the cancers include, but are not limited to: brain cancer including glioblastoma and medulloblastoma, bone cancer, sarcoma, head and neck cancer, retinoblastoma, thyroid cancer, leukemia including acute myeloid leukemia, skin cancer including melanoma, basal cell carcinoma, squamous cell carcinoma, adenocarcinoma, oral cancer, esophageal cancer, stomach cancer, gastric cancer, bile duct cancer, intestinal cancer, colon cancer, colorectal cancer, bladder cancer, liver cancer including hepatocellular carcinoma, renal cancer including renal cell carcinoma, pancreatic cancer, ovarian cancer, endometrial cancer, cervical cancer, uterine cancer, ureteral cancer, lung cancer, breast cancer, and prostate cancer. In certain embodiments, the cancer is glioblastoma, medulloblastoma, head and neck cancer, skin cancer including melanoma, basal cell carcinoma and squamous cell carcinoma, esophageal cancer, gastric cancer, colorectal cancer, liver cancer, pancreatic cancer, ovarian cancer, endometrial cancer, ureteral cancer, lung cancer, breast cancer, and prostate cancer.

In certain embodiments, the cancer is esophageal cancer, gastric cancer, colorectal cancer, pancreatic cancer, breast cancer or ovarian cancer.

In one aspect, provided herein are methods for the treatment of arthritis including rheumatoid arthritis and osteoarthritis. In another aspect, provided herein are methods for the treatment of pain, including acute and chronic pain, and including joint paint caused by arthritis or joint inflammation. In yet another aspect, provided herein are methods for the treatment of endometriosis. In yet another aspect, provided herein are methods for the treatment of neurodegenerative disease including epilepsy, Alzheimer's disease (AD). Parkinson's disease (PD), amyotrophic lateral sclerosis (ALS) and traumatic brain injury (TBI). In yet another aspect, provided herein are methods for the treatment of cardiovascular disease including coronary artery disease such as myocardial infarction and cerebrovascular disease such as stroke.

In some embodiments the disclosure is directed to a method of preventing the onset of and/or recurrence of cancer. In another embodiment, provided herein are methods of preventing the onset and/or recurrence of neurodegenerative disease. In another embodiment, provided herein are methods of preventing the onset and/or recurrence of arthritis. In yet another embodiment, provided herein are methods for preventing the onset and/or recurrence of cardiovascular disease.

G. PREPARATION OF THE COMPOUNDS

The starting materials used for the synthesis are either synthesized or obtained from commercial sources, such as, but not limited to, Sigma-Aldrich, Combi-Blocks, Fluka, Acros Organics, Alfa Aesar. Enamine, PharmaBlock, VWR Scientific, and the like. The reversed phase and normal phase chromatography columns were purchased from Teledyne ISCO, Inc. (NE). Nuclear Magnetic Resonance (NMR) analysis was conducted using a Bruker Fourier 300 MHz spectrometer or Bruker Avance DRX400 spectrometer with an appropriate deuterated solvent. LCMS spectra were obtained on either a Shimazu LCMS-2020 Series mass spectrometer using Electrospray Ionization (ESI) and a Luna $C_{18}$ 5 µM, 2.0×50 mm column, eluting with 95:5 to 0:100 $H_2O$:MeCN+0.1% formic acid at a flow rate of 0.7 mL/min over 3.5 minutes, or a Waters Acquity UPLC with a QDA MS detector using a Waters C18 BEH 1.7 µM, 2.1×50 mm column, eluting with 95:5 to 0:100 $H_2O$:MeCN+0.1% formic acid at a flow rate of 0.6 mL/min over 3.5 minutes. The QDA MS detector was set up to scan under both positive and negative mode ions ranging from 100-1200 Daltons. General methods for the preparation of compounds can be modified by the use of appropriate reagents and conditions for the introduction of the various moieties found in the structures as provided herein.

Standard abbreviations and acronyms as defined in *J. Org. Chem.* 2007 72(1):223A-24A are used herein. Other abbreviations and acronyms used herein are as follows:

TABLE 2

| Abbreviations | |
|---|---|
| Ac | acetate |
| DCM | dichloromethane |
| DIAD | di-iso-propyl azodicarboxylate |
| DIPEA | di-iso-propyl ethyl amine |
| dppf | 1,1'-bis(diphenylphosphino)ferrocene |

TABLE 2-continued

| Abbreviations | |
|---|---|
| ee | enantiomeric excess |
| $EN(iPr)_2$ | di-iso-propyl ethylamine |
| EtOAc | ethyl acetate |
| G2 | second generation pre-catalyst |
| G3 | third generation pre-catalyst |
| HATU | 1-[bis(dimethylamino)methylene]-1H-1,2,3-triazolo[4,5-b]pyridinium 3-oxide hexafluorophosphate |
| HBSS | Hank's balanced salt solution |
| HEPES | 4-(2-hydroxyethyl)-1-piperazine ethanesulfonic acid |
| iPr | iso-propyl |
| LCMS | liquid chromatography - mass spectrometry |
| M + 1 | parent mass + 1 dalton |
| M + Na | parent mass + 1 sodium ion |
| MeCN | acetonitrile |
| MeOH | methanol |
| mm | millimeter |
| NFSI | N-fluorobenzenesulfonimide |
| nM | nanomolar |
| p | pentet |
| Pd/C | palladium on carbon |
| RuPhos | 2-dicyclohexylphosphino-2',6'-di-iso-propoxybiphenyl |
| sat. | saturated |
| $scCO_2$ | supercritical carbon dioxide |
| SFC | supercritical fluid chromatography |
| tBuXPhos | 2-di-(tert-butyl)phosphino-2',4',6'-tri-iso-propylbiphenyl |
| µm | micrometer |
| XPhos | 2-dicyclohexylphosphino-2',4',6'-tri-iso-propylbiphenyl |

General Synthetic Scheme

In some embodiments, compounds described herein can be prepared as outlined in the following general synthetic schemes.

General Structure

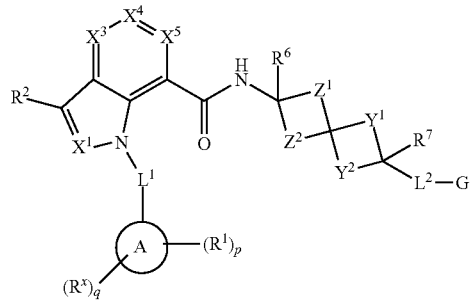

Method 1: Synthesis of Carboxylic Acid (A)

The heterocyclic ester 1 can be N-alkylated with the alkylating agent 2 (wherein X is a leaving group such as iodide, bromide, chloride, mesylate or the like) in DMF at 0-22° C. using an appropriate base such as sodium tert-pentoxide, cesium carbonate or the like to provide 3. This ester may be hydrolyzed using an agent such as lithium hydroxide, sodium hydroxide or the like in THF/MeOH to give the corresponding carboxylic acid 4. This acid can be coupled to the aminoester 5 using standard amide coupling conditions such as HATU and Hünig's base in DMF to provide the ester 6. The racemic ester 6 derived from the racemate of ester 5 may be hydrolyzed using lithium hydroxide, sodium hydroxide or the like to provide racemic carboxylic acid A. The ester 6 that is derived from a single enantiomer of 5 may be hydrolyzed using appropriate conditions (e.g. trimethyltin hydroxide in dichloroethane at 80° C.) to provide the carboxylic acid A without loss of enantiopurity. The racemic mixture of A may be resolved into both enantiomers using known methods such as chromatography using chiral columns such as ChiralPak OD, ChiralPak AD or the like.

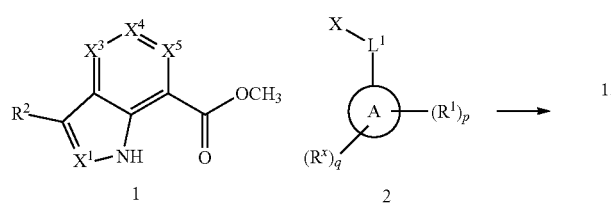

1        2

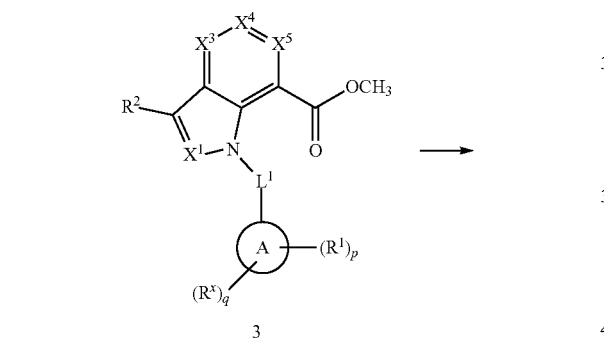

3

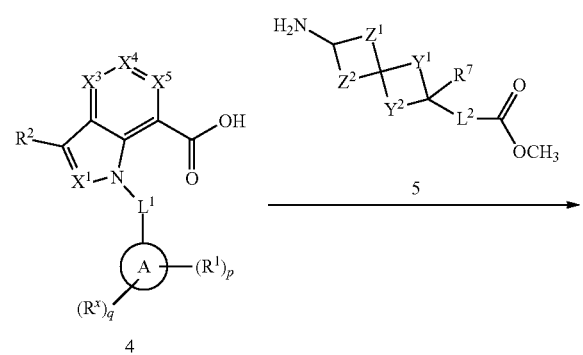

4        5

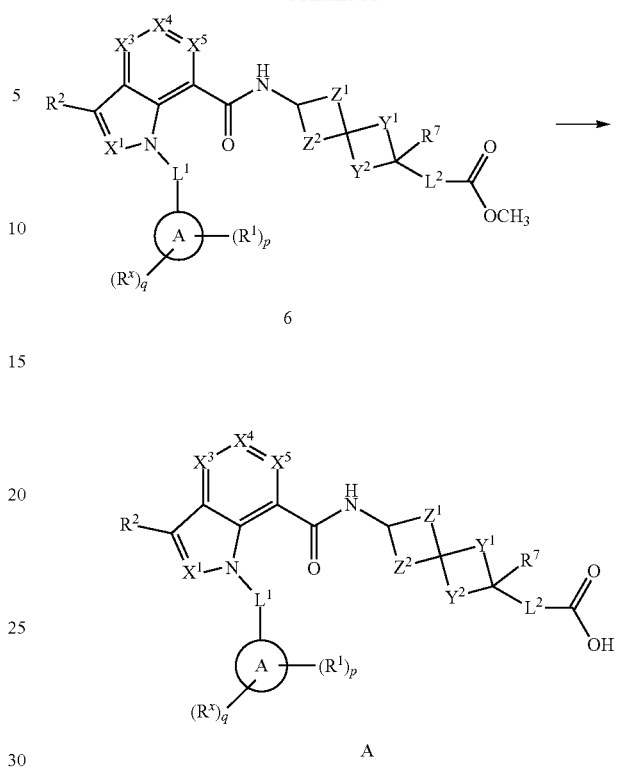

6

A

Method 2: Synthesis of Biaryl (B)

In embodiments where $R^1$ is an appropriately functionalized aryl or heteroaryl, the target biaryl B can be formed from the palladium-catalyzed cross coupling between the aryl halide 7 and (hetero)aryl boronic acids or (hetero)aryl boronate esters. This reaction may utilize XPhos palladacycle Gen 3, Pd(dppf)Cl$_2$ or any other suitable palladium ligand complexes. These reactions are best earned out in the presence of abase such as K$_3$PO$_4$, Na$_2$CO$_3$ or the like, and can be heated at 100 to 150° C. for 10-40 minutes in a microwave reactor or for 2-18 hours in an oil bath. Alternatively, it may be more advantageous to first convert aryl halide 7 into the corresponding aryl pinacol boronate ester or boronic acid 8, using, for example, borylation conditions (i.e. heating at 80° C. with a catalytic quantity of Pd(dppf) Cl$_2$, potassium acetate, and bis(pinacolato)diboron in dioxane, or the like), to enable its subsequent cross coupling to an appropriately functionalized (hetero)aryl halide. A single enantiomer may be provided by standard methods, such as chromatography of B utilizing an appropriate chiral column such as ChiralPak OD ChiralPak AD or the like. Alternately, a single enantiomer may be obtained by utilizing a single enantiomer of in the synthesis of 7 or 8. In addition to boronic acids and boronates, other organometallic cross-coupling agents, such as organotin, organosilicon, organozinc and organomagensium reagents are known to participate as suitable coupling reagents in the Scheme below.

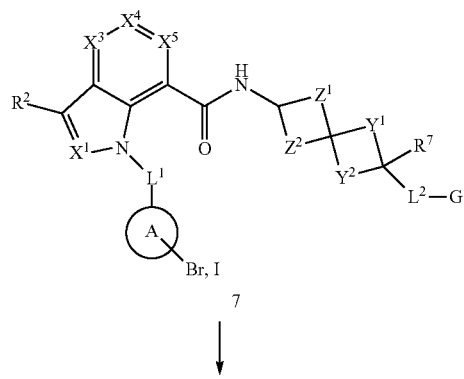

7

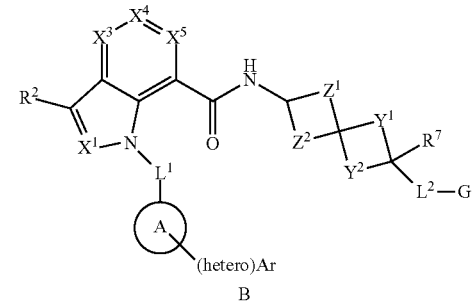

B

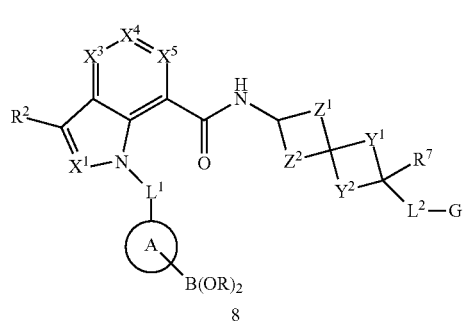  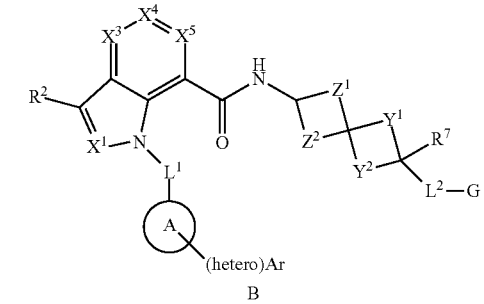

8

B

Method 3: Synthesis of Arylamine (C)

The arylamine C can be prepared by the palladium-catalyzed cross coupling reaction of the aryl halide 7 with an appropriately functionalized primary or secondary amine in the presence of bases such as sodium tert-pentoxide, sodium hexamethyldisilazide, or the like at 120° C. for 30 minutes in a microwave reactor or for 10-18 hours in an oil bath. A single enantiomer may be provided by chromatography of C utilizing an appropriate chiral column such as ChiralPak OD, ChiralPak AD or the like. Alternately, a single enantiomer of C may be obtained by utilizing a single enantiomer of 5 in the synthesis of 7.

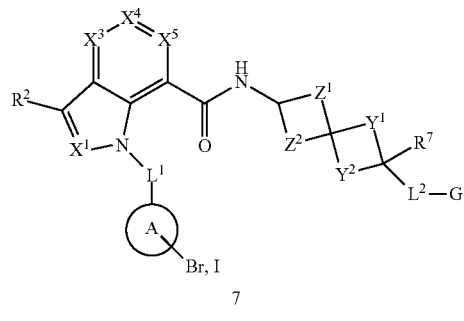 

7

-continued

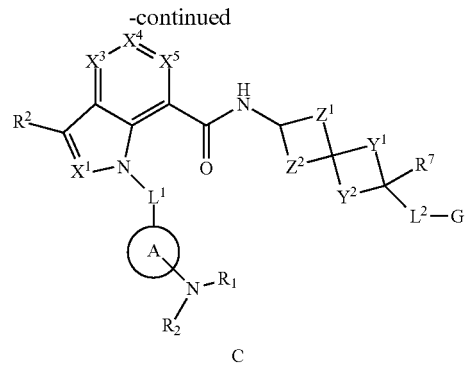

C

Method 4: Synthesis of Arylether (D)

The arylether 10 can be prepared using the Mitsunobu reaction of phenol 9 with an alkyl alcohol under standard conditions (i.e. di-iso-propyl azodicarboxylate and triphenylphosphine, diethyl azodicarboxylate and tri-butyl-phosphine, or the like). The arylether D can then be readily accessed by hydrolysis of 10 using standard saponification conditions, such as aqueous lithium hydroxide in THF/MeOH, or the like. A single enantiomer may be provided by standard methods for chiral separation, including chromatography of D utilizing an appropriate chiral column such as ChiralPak OD, ChiralPak AD or the like. Alternately, a single enantiomer of D may be obtained by utilizing a single enantiomer of 5 in the synthesis of 9.

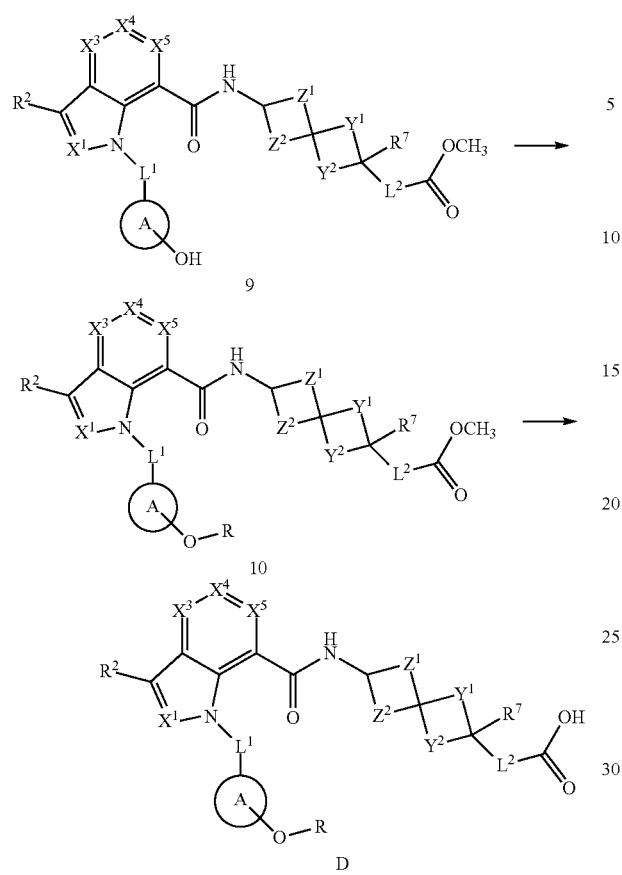

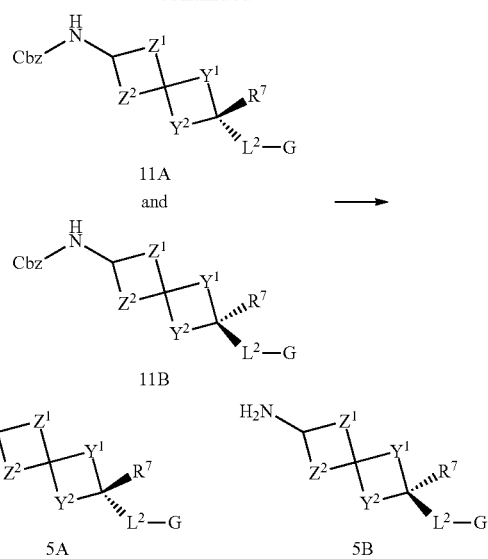

Method 5: Resolution of Amine (5)

The amine 5 can be reacted with a protecting group, such as Cbz-Cl in the presence of appropriate bases such as Hünig's base, triethylamine or the like, to provide the Cbz carbamate 11. The enantiomers of 11 can then be separated by chromatography on a suitable chiral column such as ChiralPak OD, ChiralPac AD or the like. Each of the enantiomers, 11A and 11B, can then be deprotected to afford the primary amine, using suitable conditions for the particular protecting group. For a Cbz group, this would entail hydrogenation using, for example, palladium on carbon in EtOAc, to provide the single enantiomers 5A and 5B. These enantiomers can also be independently treated with an acid such as HCl to provide the corresponding salts of 5A and 5B as solids for ease of handling.

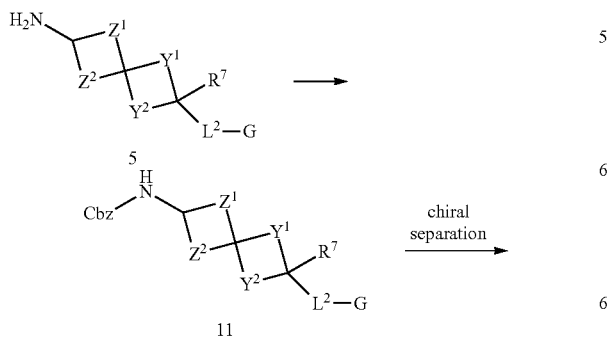

Method 6: Alpha Alkylation of Ester (15)

The ester 12 can be protected as the bisbenzylamine 13 by alkylation of the primary amine with benzyl bromide using potassium carbonate as the base. This ester can be deprotonated using lithium tetramethylpiperidide in THF and then quenched with $R^7$—X (where X is a suitable leaving group) to provide compound 14 where $R^7$ can be deutero, alkyl, fluoro or hydroxyl. Primary amine 15 can then be readily revealed from ester 14 using, for example, palladium hydroxide as catalyst and hexafluoroisopropanol as solvent under a hydrogen atmosphere.

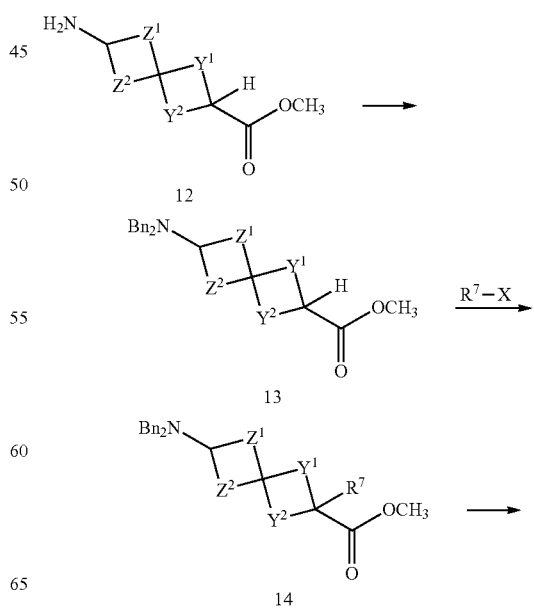

-continued

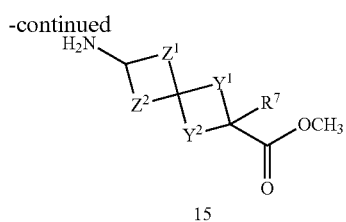

15

Method 7: Late Stage Functionalization of Amide (16)

In instances where $X^3$, $X^4$ or $X^5$ in compound 16 is C—Br or C—I, it may be deemed desirable to effect its transformation into, for example, cyanide 17 or alkyl ether 18. Such functional group conversion can be readily realized using metal-catalyzed reactions. Examples of such conversions include, but are not limited to, (a) cyanation using zinc cyanide as the coupling partner and tBuXPhos palladacycle Gen 3 as the catalyst; and (b) aliphatic alcohol as the coupling partner, cesium carbonate as the base, CuI as the metal catalyst and 3,4,7,8-tetramethyl-1,10-phenanthroline as the ligand.

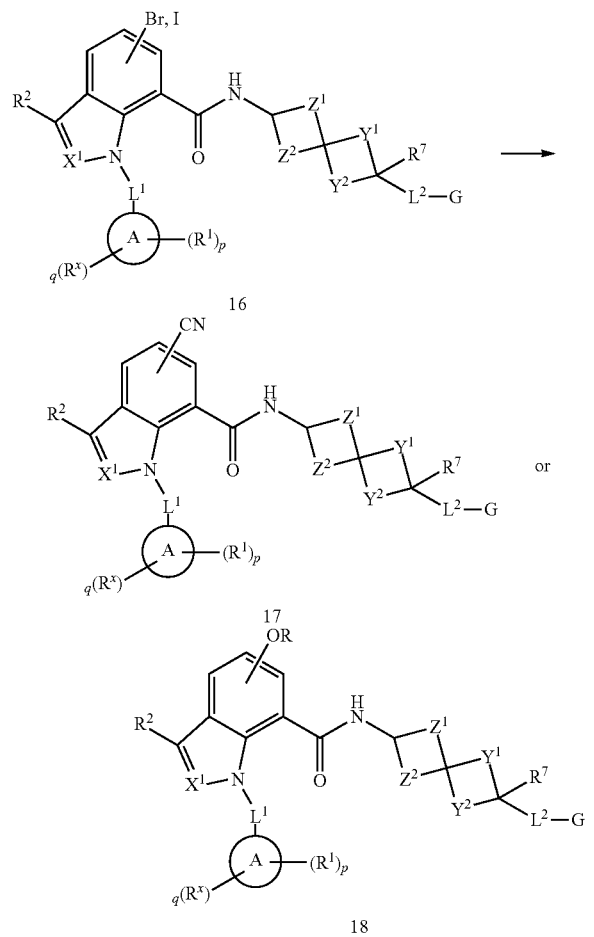

The general synthetic schemes above have been described in an illustrative manner, and is intended to be in the nature of description rather than of limitation. Thus, it will be appreciated that conditions such as choice of solvent, temperature of reaction, volumes, reaction time may vary while still producing the desired compounds. In addition, it will be appreciated that many of the reagents provided in the following examples may be substituted with other suitable reagents (See, e.g., *Smith & March, Advanced Organic Chemistry*, 7th Ed. (2013)). Such changes and modifications, including without limitation, those relating to the chemical structures, substituents, derivatives, intermediates, syntheses, formulations and/or methods of use provided herein, may be made without departing from the spirit and scope thereof.

H. EXAMPLES

Intermediate A: Preparation of 4-Fluoro-1-(4-(trifluoromethoxy)benzyl)-1H-indole-7-carboxylic acid

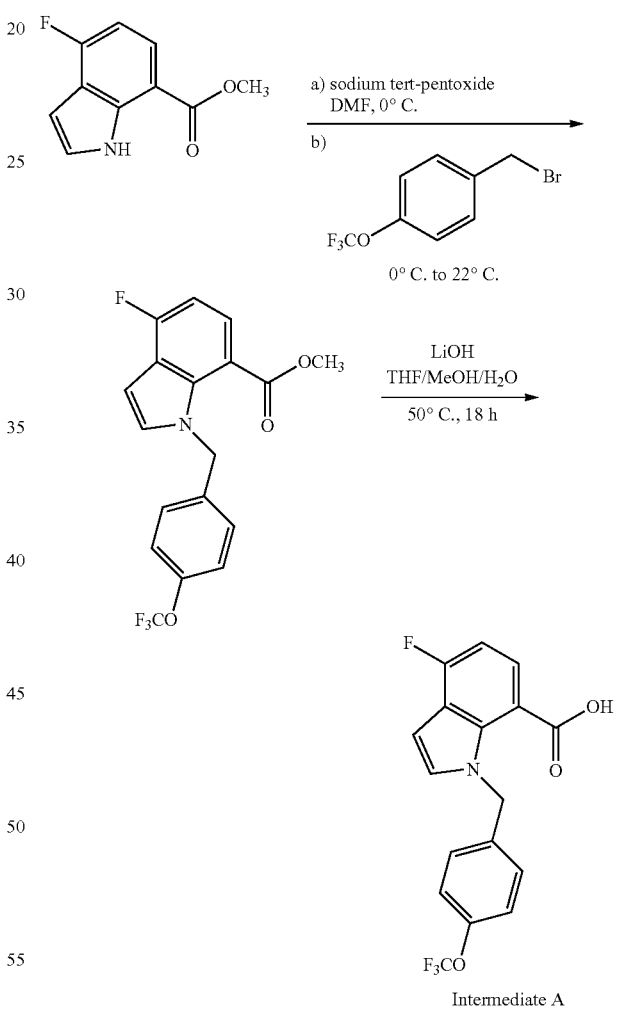

Step 1: Preparation of methyl 4-fluoro-1-(4-(trifluoromethoxy)benzyl)-1H-indole-7-carboxylate To a solution of methyl 4-fluoro-1H-indole-7-carboxylate (1 equiv, PharmaBlock, CAS #313337-35-8) in DMF (0.1 M) cooled over an ice bath was added sodium tert-pentoxide (1.5 equiv) and the mixture was stirred at 0° C. for 30 minutes. After this time, 1-(bromomethyl)-4-(trifluoromethoxy)benzene (1.2 equiv. Aldrich, CAS #50824-05-0) was added drop-wise via syringe over 5 minutes, the ice bath was removed and the mixture was allowed to stir at 22° C. for 1.25 hours. LCMS analysis at this time revealed complete conversion to product. The mixture was quenched with sat. aqueous NH$_4$Cl solution and extracted with Et$_2$O (3×). The combined organic extracts were washed with brine (1×) and concentrated under reduced pressure. The resulting residue was loaded onto a silica gel pre-cartridge and then dried under vacuum. This pre-absorbed material was purified by column chromatography using a Teledyne ISCO silica cartridge eluting with 0% to 40% EtOAc in hexanes as a gradient. The fractions from the major peak which elutes at 15% EtOAc were combined and concentrated under vacuum to provide the title compound as a solid (75% yield).

Step 2: Preparation of 4-fluoro-1-(4-(trifluoromethoxy)benzyl)-1H-indole-7-carboxylic acid Into a sample vial equipped with a magnetic stir bar and under N$_2$ was added methyl 4-fluoro-1-[[4-(trifluoromethoxy)phenyl]methyl]indole-7-carboxylate (1 equiv), THF (0.2 M) and MeOH (0.2 M). The solution was treated with 1.0 M aqueous LiOH solution (2.5 equiv) and the resulting solution was heated to 50° C. for 18 hours. The reaction mixture was concentrated under reduced pressure to remove the THF and MeOH and then acidified to pH=4 with 10% aqueous citric acid. The resulting suspension was poured into a Cl-phase separatory cartridge and extracted with CH$_2$Cl$_2$ (3×). The combined organic extracts were concentrated under reduced pressure to provide the title compound (99%).

Intermediate B: Preparation of 1-(4-Bromobenzyl)-4-fluoro-1H-indole-7-carboxylic acid

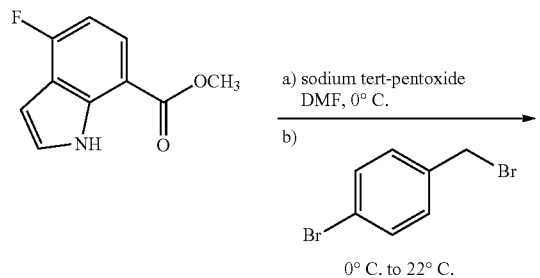

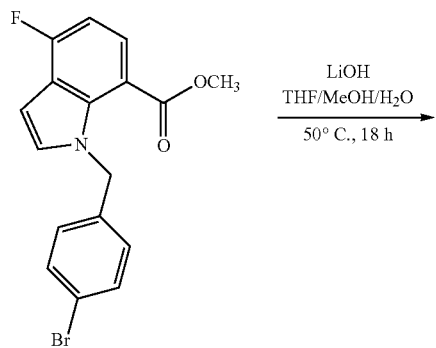

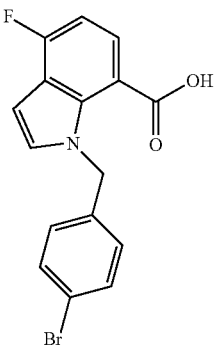

Intermediate B

Step 1: Preparation of methyl 1-(4-bromobenzyl)-4-fluoro-1H-indole-7-carboxylate In a round-bottom flask equipped with a magnetic stir bar was added methyl 4-fluoro-1H-indole-7-carboxylate (1.0 equiv, PharmaBlock, CAS #313337-35-8) and DMF (0.5 M). The mixture was cooled to 0° C. in an ice bath. Sodium tert-pentoxide (1.1 equiv) was added and the reaction was stirred at 0° C. for 20 minutes. After this time, 1-bromo-4-(bromomethyl)benzene (1.0 equiv, Combi-Blocks, CAS #589-15-1) was added portion-wise while stirring in the ice bath. The reaction was allowed to warm to 22° C. and stirred overnight for 18 hours. LCMS indicated the reaction was complete. The mixture was partitioned between water and EtOAc. The aqueous layer was further extracted with EtOAc. The combined organic extracts were washed with brine, dried over MgSO$_4$, filtered and concentrated under vacuum for 30 minutes. The resulting crude oil was loaded onto a silica gel pre-cartridge using CH$_2$Cl$_2$ and dried under high vacuum for 1 hour. After this time, this pre-absorbed material was purified by column chromatography using a Teledyne ISCO cartridge eluting with 0% to 20% EtOAc in hexanes as a gradient over 20 minutes. The fractions from the first peak eluting at 11% EtOAc in hexanes were combined and concentrated under vacuum. The title product was obtained as a colorless oil (56% yield). LCMS (ESI+): 364 (M+1)$^+$.

Step 2: Preparation of 1-(4-bromobenzyl)-4-fluoro-1H-indole-7-carboxylic acid

Into a round-bottom flask equipped with a magnetic stir bar was added methyl 1-(4-bromobenzyl)-4-fluoro-1H-indole-7-carboxylate (1.0 equiv), THF (0.4 M), MeOH (0.4 M) and 1.0 M aqueous LiOH (2.5 equiv). The reaction mixture was stirred at 50° C. for 18 hours. LCMS analysis revealed conversion to product. The reaction mixture was concentrated to remove most of the THF and MeOH. The resulting solution was acidified to pH=2-3 with 1.0 M aqueous HCl solution. An off-white solid precipitate which was collected by vacuum filtration, washed twice with water and air dried overnight. LCMS indicated no product remained in the mother liquor. The title product was obtained as a crystalline solid (98% yield). LCMS (ESI+): 350 (M+1)$^+$.

Intermediate C: Preparation of (racemic)-6-(1-(4-Bromobenzyl)-4-fluoro-1H-indole-7-carboxamido)-spiro[3.3]heptane-2-carboxylic acid

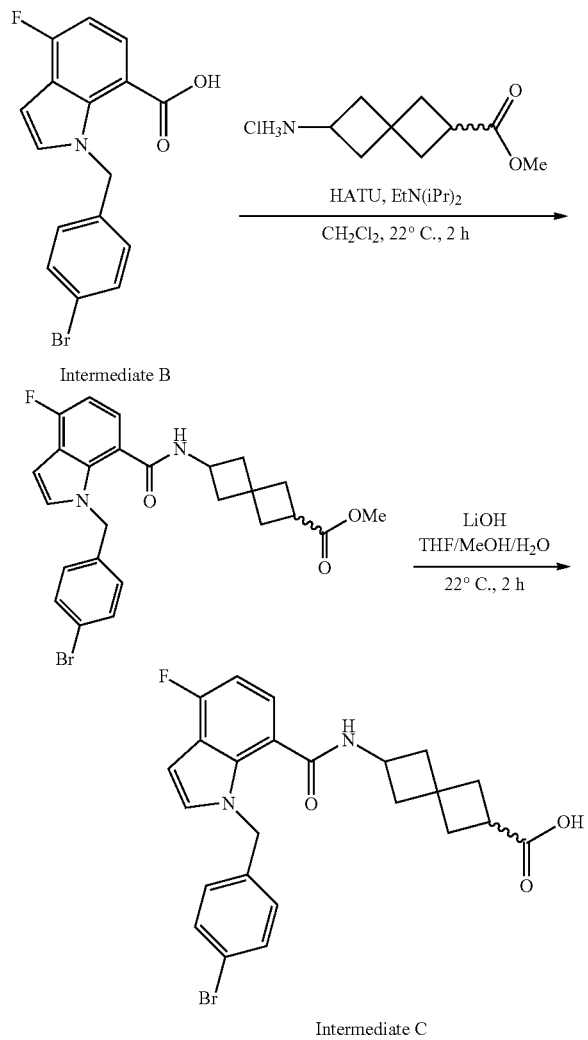

Intermediate B

Intermediate C

Step 1: Preparation of (racemic)-methyl 6-(1-(4-bromobenzyl)-4-fluoro-1H-indole-7-carboxamido)spiro[3.3]heptane-2-carboxylate Into a round-bottom flask equipped with a magnetic stir bar was added Intermediate B (1.0 equiv), (racemic)-methyl 2-aminospiro[3.3]heptane-6-carboxylate hydrochloride (1.3 equiv, Enamine. CAS #1808249-67-3), HATU (1.5 equiv) and CH₂Cl₂ (0.3 M). To the reaction mixture was added Hünig's base (4 equiv). The solution was stirred at 22° C. for 2 hours. LCMS indicated reaction was complete. This solution was concentrated, diluted with water and extracted twice with EtOAc. The combined extracts were washed with sat. aqueous NaHCO₃ solution, 1 M aqueous HCl solution and then brine. The organic extracts were dried over MgSO₄, filtered and concentrated under vacuum. The resulting white solid was dissolved in EtOAc and loaded onto a silica gel pre-cartridge. The pre-cartridge was air dried for 15 minutes and dried under high vacuum for 30 minutes. This pre-absorbed material was purified by column chromatography using a Teledyne ISCO silica cartridge eluting with a gradient of 0% to 100% EtOAc in hexanes over 20 minutes. The product-containing peak eluted between 90-100% EtOAc in hexanes. The desired fractions were combined and concentrated under vacuum. The title product was obtained as a white crystalline solid (91% yield). LCMS (ESI+): 501 (M+1)⁺.

Step 2: Preparation of (racemic)-6-(1-(4-bromobenzyl)-4-fluoro-1H-indole-7-carboxamido)spiro[3.3]heptane-2-carboxylic acid Into a round-bottom flask equipped with a magnetic stir bar was added (racemic)-methyl 6-(1-(4-bromobenzyl)-4-fluoro-1H-indole-7-carboxamido)spiro[3.3]heptane-2-carboxylate (1.0 equiv), THF (0.6 M), MeOH (0.6 M) and 1.0 M aqueous LiOH solution (2.5 equiv). The reaction mixture was stirred at 22° C. for 2 hours. LCMS analysis revealed complete conversion to product. The reaction mixture was concentrated to remove most of the THF and MeOH. The resulting solution was acidified using 1 M aqueous HCl solution to pH=2-3. The resulting suspension was partitioned in water and EtOAc and the aqueous layer was back extracted with EtOAc. The combined organic extracts were washed with brine, dried with MgSO₄, filtered and concentrated under vacuum. The title product was obtained as a white solid (98% yield). LCMS (ESI+): 486 (M+1)⁺.

Intermediate D: Preparation of 4-Fluoro-1-(4-iodobenzyl)-1H-indole-7-carboxylic acid

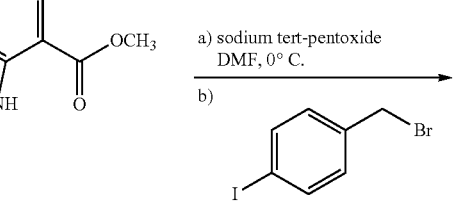

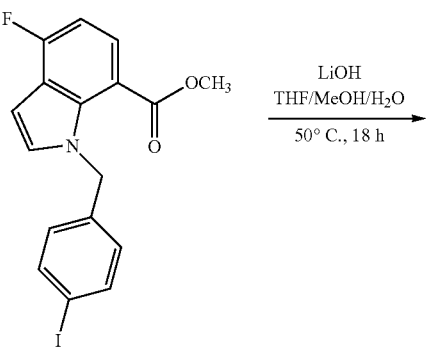

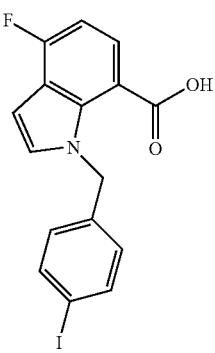

Intermediate D

The title compound was prepared in a similar manner to Intermediate B replacing 1-bromo-4-(bromomethyl)benzene with 1-iodo-4-(bromomethyl)benzene (Combi-Blocks, CAS #16004-15-2). LCMS (ESI+): 396 (M+1)⁺.

Intermediate E: Preparation of (racemic)-6-(4-Fluoro-1-(4-(4,4,5,5-tetramethyl-1,3,2-dioxaborolan-2-yl)benzyl)-1H-indole-7-carboxamido)spiro[3.3]heptane-2-carboxylic acid

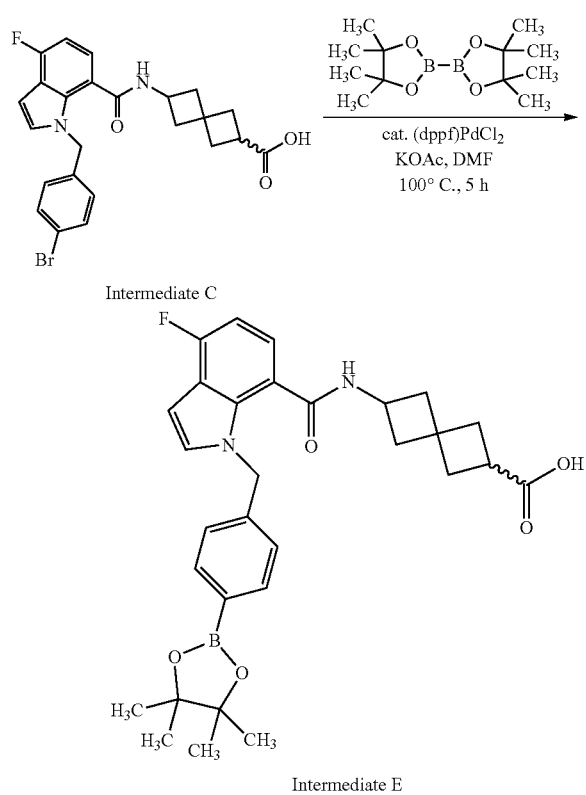

Intermediate C

Intermediate E

To a degassed mixture of 4,4,5,5-tetramethyl-2-(4,4,5,5-tetramethyl-1,3,2-dioxaborolan-2-yl)-1,3,2-dioxaborolane (1.2 equiv), Intermediate C (1 equiv) and potassium acetate (3 equiv) in DMF (0.3 M) was added [1,1'-bis(diphenylphosphino)ferrocene]palladium dichloride•dichloromethane complex (0.05 equiv, Strem CAS #95464-05-4). The mixture was purged under N₂ and then heated to 100° C. for 5 hours. The reaction mixture was diluted with water (3 volumes) and extracted with EtOAc (3×). The combined organic layers were washed with brine, dried over MgSO₄, filtered and concentrated under reduced pressure. This residue was purified by column chromatography using a Teledyne ISCO silica cartridge eluting with 0 to 100% EtOAc in hexanes gradient. The fractions from the major peak which eluted at 55% EtOAc in hexanes were combined and concentrated under vacuum to provide the title compound as a white foam (75% yield).

Intermediate F: Preparation of (R$_a$) or (S$_a$)-Methyl 6-aminospiro[3.3]heptane-2-carboxylate hydrochloride

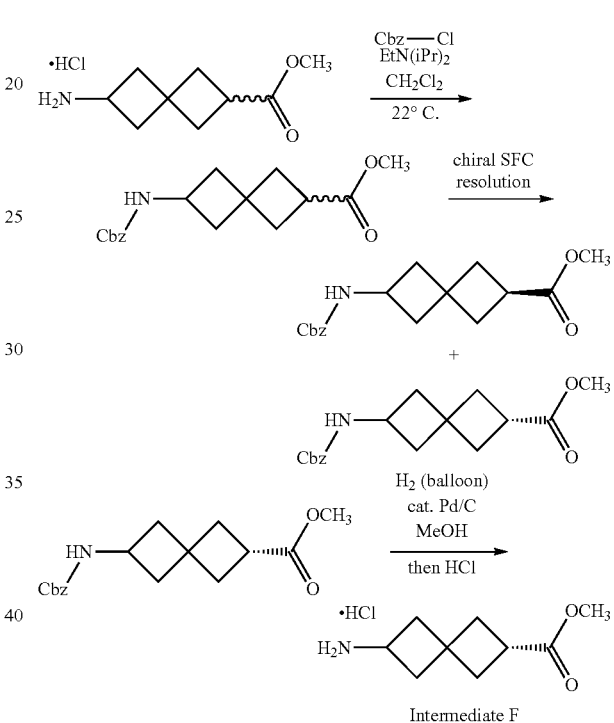

Intermediate F

Step 1: Preparation of (racemic)-methyl 6-(((benzyloxy)carbonyl)amino)-spiro[3.3]heptane-2-carboxylate Into a round-bottom flask equipped with a magnetic stir bar and under N₂ was added (racemic)-methyl 2-aminospiro[3.3]heptane-6-carboxylate hydrochloride salt (1.0 equiv, Enamine, CAS #1808249-67-3), benzyl chloroformate (1.5 equiv), CH₂Cl₂ (0.5 M) and Hunig's base (3 equiv). The reaction mixture was stirred at 22° C. for 2 hours. LCMS analysis revealed product formation. The reaction mixture was quenched with sat. aqueous NH₄Cl solution and extracted with CH₂Cl₂ (2×). The combined organic layers were washed with brine, dried over MgSO₄, filtered and concentrated under reduced pressure. Purification by column chromatography through silica gel on the Teledyne ISCO Rf eluting with 0% to 50% EtOAc in hexanes as a gradient over 25 minutes. The product containing fractions were concentrated and dried under vacuum for 3 hours. The title product was obtained as a colorless oil (94% yield).

Step 2: Chiral Resolution of (R$_a$) or (S$_a$)-methyl 6-(((benzyloxy)carbonyl)amino)-spiro[3.3]heptane-2-carboxylate The enantiomers were separated by supercritical fluid chiral chromatography on a 20 µm ChiralPac AD column (50×500 mm), eluting with 10% MeOH at a flow rate of 18 mL/min over 10 minutes, maintaining a column temperature of 35° C. The first eluting peak had a retention time of 2.23 minutes and the second eluting enantiomer at 2.53 minutes. The first eluting enantiomer was determined to be the more active enantiomer.

Step 3: Preparation of (R$_a$) or (S$_a$)-methyl 6-aminospiro[3.3]heptane-2-carboxylate hydrochloride To a degassed solution of (R$_a$) or (S$_a$)-methyl 2-(benzyloxycarbonylamino)spiro[3.3]heptane-6-carboxylate (1 equiv) in EtOAc was added 10% palladium on carbon (10% by weight, 0.1 equiv). This mixture was degassed, evacuated and then placed under a balloon of hydrogen gas and stirred at 22° C. for 16 hours. This mixture was filtered through celite and the pad was rinsed with CH$_2$Cl$_2$. The combined filtrates were concentrated under vacuum. This oil residue was dissolved in Et$_2$O and then acidified with 4 M HCl in dioxane to pH=4. The resulting suspension was further diluted with Et$_2$O and then filtered, washed with Et$_2$O and then dried under high vacuum to provide the title compound as a white solid (65% yield).

Intermediate G: Preparation of 2-(Bromomethyl)-6-fluoronaphthalene

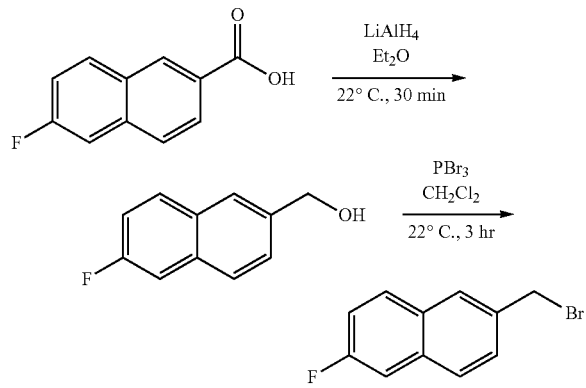

Intermediate G

Step 1: Preparation of (6-fluoronaphthalen-2-yl)methanol

To a solution of LiAlH$_4$ (2.0 equiv) in ether (0.5 M) was added 6-fluoro-2-naphthoic acid (1.0 equiv, CombiBlocks, CASS #5043-01-6). The mixture was stirred for 30 minutes and then cooled in an ice bath and quenched with H$_2$O dropwise. The mixture was further stirred for 40 minutes, filtered and concentrated under vacuum to provide the title compound.

Step 2: Preparation of 2-(bromomethyl)-6-fluoronaphthalene

To a solution of (6-fluoronaphthalen-2-yl)methanol (1.0 equiv) in CH$_2$Cl$_2$ (0.2 M) was added PBr$_3$. The mixture was stirred for 3 hours at 22° C. and then cooled in an ice bath and quenched with 1 M aqueous NaHCO$_3$ solution. The reaction was extracted with CH$_2$Cl$_2$, the organic layer was dried over MgSO$_4$, and then concentrated under vacuum to provide the title compound.

Intermediate H: Preparation of (racemic)-Methyl 6-amino-2-fluorospiro[3.3]heptane-2-carboxylate

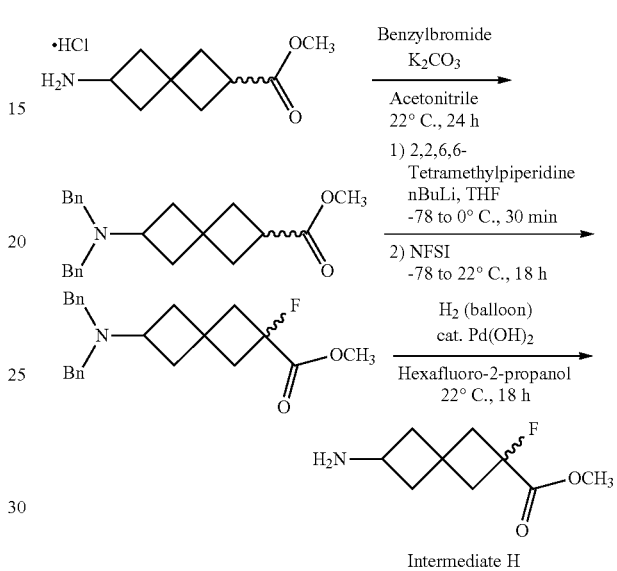

Intermediate H

Step 1: Preparation of (racemic)-methyl 6-(dibenzylamino)spiro[3.3]heptane-2-carboxylate Into a round-bottom flask equipped with a magnetic stir bar was added (racemic)-methyl 2-aminospiro[3.3]heptane-6-carboxylate hydrochloride salt (1.0 equiv, Enamine, CAS #1808249-67-3), benzyl bromide (2 equiv), potassium carbonate (5 equiv) and acetonitrile (0.3 M) under N$_2$ purge. The reaction mixture was stirred at 22° C. for 24 hours. LCMS analysis confirmed product formation. The reaction mixture was partitioned between sat. aqueous NaHCO$_3$ and CH$_2$Cl$_2$. The aqueous layer was separated and back extracted with CH$_2$Cl$_2$ (2×). The combined organic layers were washed with further brine, dried over MgSO$_4$, filtered and the filtrate concentrated in vacuo. The resulting colorless oil was dried under high vacuum overnight to afford the title product as a white solid. This was used directly in the next step without further purification.

Step 2: Preparation of (racemic)-methyl 6-(dibenzylamino)-2-fluorospiro[3.3]heptane-2-carboxylate Into a flame-dried round-bottom flask equipped with a magnetic stir bar was added 2,2,6,6-tetramethylpiperidine (1.5 equiv) and THF (0.4 M) under N$_2$. The mixture was cooled to −78° C. before n-butyl lithium in hexanes (2.5 M, 1.5 equiv) was added dropwise over a period of 5 min. The resulting yellow mixture was stirred in at −78° C. for another 30 min before it was added drop-wise to another flame-dried flask containing a THF (0.4 M) solution of methyl 2-(dibenzylamino)-spiro[3.3]heptane-6-carboxylate (1.0 equiv). The reaction mixture was stirred for another 30 min at −78° C.

N-fluorobenzenesulfonimide (1.3 equiv) was then added and the reaction mixture was allowed to warm slowly to room temperature overnight. LCMS analysis revealed product formation. The reaction was cooled to 0° C. and quenched by the careful addition of sat. aqueous $NH_4Cl$. The volatiles were then removed in vacuo and the resulting residue was poured into a separatory funnel and partitioned between with EtOAc and sat. aqueous $NaHCO_3$. The organic layer was separated, washed sequentially with sat. aqueous $NaHCO_3$ and brine, dried over $MgSO_4$, filtered and the filtrate concentrated in vacuo. The crude yellow oil thus obtained was purified by reverse-phase column chromatography using a C18 cartridge on an automated Teledyne ISCO Rf machine, eluting with 5% to 40% acetonitrile in water+0.1% formic acid as a gradient over 25 minutes. The desired fractions were combined and concentrated in vacuo. The resulting residue was partitioned between sat. aqueous $NaHCO_3$ and $CH_2Cl_2$. The aqueous layer was separated and back extracted with $CH_2Cl_2$. The organic layers were combined, dried over $MgSO_4$, and filtered. Concentration of the filtrate in vacuo afforded the title product as a yellow oil (35% yield over two steps).

Step 3: Preparation of (racemic)-methyl 6-amino-2-fluorospiro[3.3]heptane-2-carboxylate Into a round-bottom flask equipped with a magnetic stir bar was added methyl 6-(dibenzylamino)-2-fluorospiro[3.3]heptane-2-carboxylate (1.0 equiv) and hexafluoro-2-propanol (0.15 M). The mixture was thoroughly degassed via sub-surface bubbling with $N_2$ before $Pd(OH)_2$ (20% wt. loading, 0.1 equiv) was added. The resulting suspension was evacuated and then thoroughly purged with $H_2$. The reaction mixture was then stirred at 22° C. for 18 hours under a static hydrogen atmosphere maintained by a balloon. This mixture was filtered through a pad of celite and the insoluble was washed further with $CH_2Cl_2$. Concentration of the combined filtrate in vacuo afforded the title compound as a yellow oil.

Intermediate I: Preparation of (racemic)-Methyl 6-amino-2-methylspiro[3.3]heptane-2-carboxylate

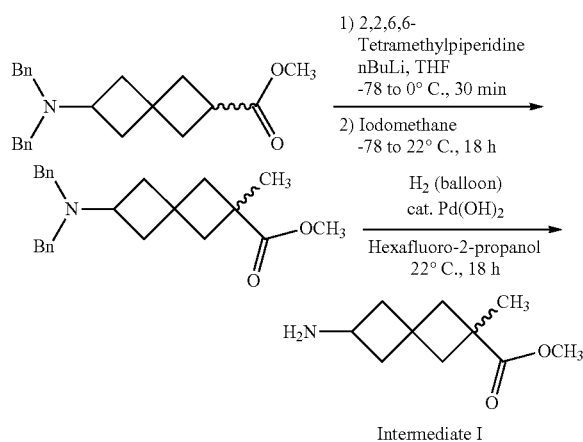

Intermediate I

The title compound was prepared in a similar manner to Intermediate H replacing N-fluorobenzenesulfonimide with iodomethane in Step 2.

Intermediate J: Preparation of (racemic)-Methyl 6-amino-2-deuterospiro[3.3]heptane-2-carboxylate

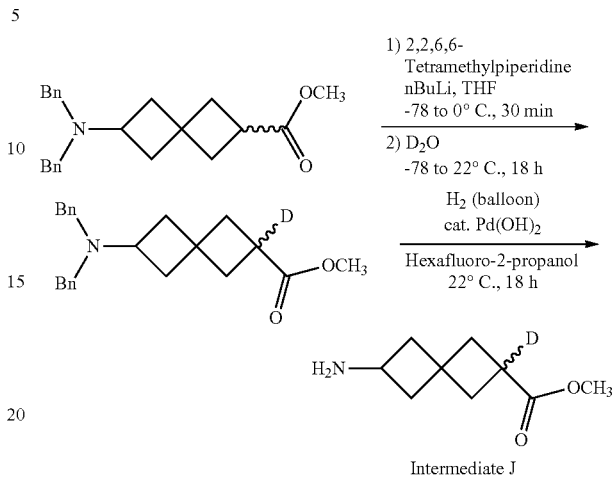

Intermediate J

The title compound was prepared in a similar manner to Intermediate H replacing N-fluorobenzenesulfonimide with $D_2O$ (2.5 equiv. Cambridge Isotope, D, 99.96%) in Step 2.

Intermediate K: Preparation of (racemic)-2-(6-Aminospiro[3.3]heptan-2-yl)acetonitrile hydrochloride

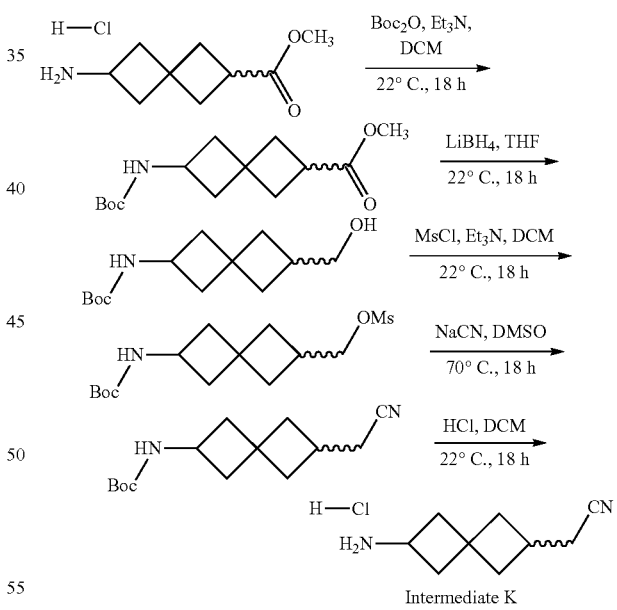

Intermediate K

Step 1: Preparation of (racemic)-methyl 6-((tert-butoxycarbonyl)amino)spiro[3.3]heptane-2-carboxylate Into a round-bottom flask equipped with a magnetic stir bar was added (racemic)-methyl 2-aminospiro[3.3]heptane-6-carboxylate hydrochloride salt (1.0 equiv, Enamine, CAS #1808249-67-3), di-tert-butyl dicarbonate (1.2 equiv), $CH_2Cl_2$ (0.2 M) and $Et_3N$ (4 equiv) under $N_2$. The reaction mixture was stirred at 22° C. for 18 hours. LCMS analysis revealed product formation. The reaction mixture was quenched with sat. aqueous NH₄Cl solution and extracted with CH₂Cl₂ (2×). The combined organic layers were washed with brine, dried over MgSO₄, filtered and the filtrate concentrated in vacuo. The crude product mixture thus obtained was purified by column chromatography through silica gel on the Teledyne ISCO Rf system (gradient elution, 0% to 50% EtOAc in hexanes). The product-containing fractions were combined, concentrated and dried under high vacuum. The title product was obtained as a colorless oil.

Step 2: Preparation of (racemic)-tert-butyl (6-(hydroxymethyl)spiro[3.3]heptan-2-yl)carbamate Into a round-bottom flask equipped with a magnetic stir bar was added (racemic)-methyl 6-((tert-butoxycarbonyl)amino)spiro[3.3]heptane-2-carboxylate (1.0 equiv) and THF (0.2 M). The reaction mixture was cooled to 0° C. before lithium borohydride (7.0 equiv, 2.0 M in THF) was added drop-wise. The reaction mixture was stirred at 0° C. for 30 minutes, then at 22° C. for 18 hours. LCMS analysis revealed product formation. The reaction mixture was cooled to 0° C., quenched with sat. aqueous NH₄Cl solution and extracted with EtOAc (3×). The combined organic layers were washed with brine, dried over Na₂SO₄, filtered, and the filtrate concentrated in vacuo. The crude product mixture thus obtained was purified by column chromatography through silica gel on the Teledyne ISCO Rf system (gradient elution, 0% to 50% EtOAc in hexanes). The product-containing fractions were combined, concentrated and dried under high vacuum to afford the title compound as a white solid.

Step 3: Preparation of (racemic)-(6-((tert-butoxycarbonyl)amino)spiro[3.3]heptan-2-yl)methyl methanesulfonate Into a round-bottom flask equipped with a magnetic stir bar and under N₂ was added (racemic)-tert-butyl (6-(hydroxymethyl)spiro[3.3]heptan-2-yl)carbamate (1.0 equiv). Et₃N (2.0 equiv) and CH₂Cl₂ (0.2 M). To the reaction mixture was added drop-wise methanesulfonyl chloride (1.3 equiv) and the resulting mixture was stirred at 22° C. for 18 hours. LCMS analysis revealed complete conversion to the desired product. The mixture was poured into a separatory funnel containing water and extracted with CH₂Cl₂ (3×). The combined organic extracts were washed further with brine, dried over Na₂SO₄, and filtered. Concentration of the filtrate in vacuo yielded the title compound as a yellow oil.

Step 4: Preparation of (racemic)-tert-butyl (6-(cyanomethyl)spiro[3.3]heptan-2-yl)carbamate Into a round-bottom flask equipped with a magnetic stir bar and under N₂ was added (racemic)-(6-((tert-butoxycarbonyl)amino)spiro[3.3]heptan-2-yl)methyl methanesulfonate (1.0 equiv), sodium cyanide (2.5 equiv) and DMSO (0.2 M). The reaction suspension was heated at 70° C. for 18 hours. LCMS analysis revealed complete conversion to the desired product. The mixture was cooled to RT, poured into a separatory funnel containing water and extracted with EtOAc (3×). The combined organic layers were washed further with brine (2×), dried over Na₂SO₄, filtered and the filtrate concentrated in vacuo. The crude product mixture thus obtained was purified by column chromatography through silica gel on the Teledyne ISCO Rf system (gradient elution, 0% to 50% EtOAc in hexanes). The product-containing fractions were combined, concentrated and dried under high vacuum to afford the title compound as a white solid.

Step 5: Preparation of (racemic)-2-(6-aminospiro[3.3]heptan-2-yl)acetonitrile hydrochloride Into a round-bottom flask equipped with a magnetic stir bar and under N₂ was added (racemic)-tert-butyl (6-(cyanomethyl)spiro[3.3]heptan-2-yl)carbamate (1.0 equiv) and CH₂Cl₂ (0.2 M). To the reaction mixture was then added dropwise HCl (15 equiv, 4.0 M in 1,4-dioxane) and the reaction was stirred at 22° C. for 18 hours. LCMS analysis revealed complete conversion to the desired product. The reaction mixture was concentrated under reduced pressure and then dried under high vacuum to give the title compound.

Intermediate (S$_a$)-L: Preparation of (S$_a$)-Ethyl 2-(6-aminospiro[3.3]heptan-2-yl)acetate hydrochloride

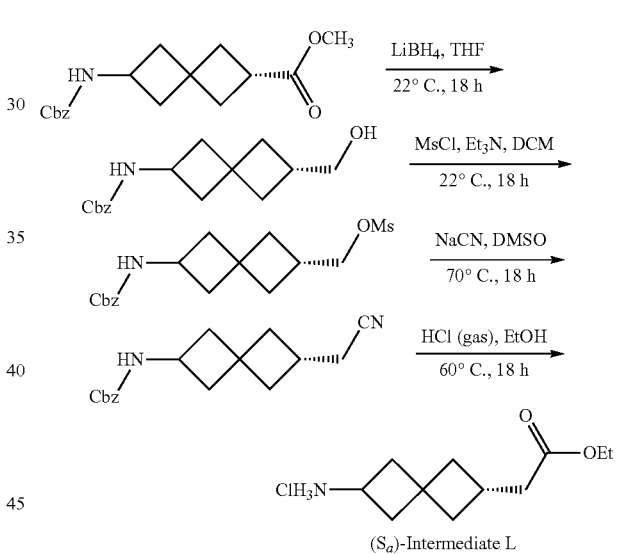

(S$_a$)-Intermediate L

Step 1: Preparation of S$_a$)-benzyl (6-(hydroxymethyl)spiro[3.3]heptan-2-yl)carbamate Into a round-bottom flask equipped with a magnetic stir bar and under N₂ was added (S$_a$)-methyl 6-(((benzyloxy)carbonyl)amino)-spiro[3.3]heptane-2-carboxylate (1.0 equiv, Intermediate F, Step 2) and THF (0.25 M). The reaction mixture was cooled to 0° C. before lithium borohydride (7.0 equiv, 2.0 M in THF) was added drop-wise. The reaction mixture was stirred at 0° C. for 30 minutes and then at 22° C. for 18 hours. LCMS analysis revealed product formation. The reaction mixture was cooled to 0° C. carefully quenched with 1 M aqueous HCl solution and extracted with EtOAc (3×). The combined organic layers were washed with brine, dried over Na₂SO₄, and filtered. Concentration of the filtrate in vacuo furnished the title compound as a colorless oil.

93

Step 2: Preparation of (S$_a$)-(6-(((benzyloxy)carbonyl)amino)spiro[3.3]heptan-2-yl)methyl methanesulfonate Into a round-bottom flask equipped with a magnetic stir bar and under N$_2$ was added (S$_a$)-benzyl (6-(hydroxymethyl)spiro[3.3]heptan-2-yl)carbamate (1.0 equiv), Et$_3$N (2.0 equiv) and CH$_2$Cl$_2$ (0.2 M). To the reaction mixture was added dropwise methanesulfonyl chloride (1.3 equiv) and the resulting mixture was stirred at 22° C. for 18 hours. LCMS analysis revealed complete conversion to the desired product. The mixture was poured into a separatory funnel containing water and extracted with CH$_2$Cl$_2$ (3×). The combined organic extracts were washed further with brine, dried over Na$_2$SO$_4$, and filtered. Concentration of the filtrate in vacuo yielded the title compound as a yellow oil.

Step 3: Preparation of (S$_a$)-benzyl (6-(cyanomethyl)spiro[3.3]heptan-2-yl)carbamate Into a round-bottom flask equipped with a magnetic stir bar and under N$_2$ was added (S$_a$)-(6-(((benzyloxy)carbonyl)amino)spiro[3.3]heptan-2-yl)methyl methanesulfonate (1.0 equiv), sodium cyanide (2.5 equiv) and DMSO (0.2 M). The reaction suspension was heated at 70° C. for 18 hours. LCMS analysis revealed complete conversion to the desired product. The mixture was cooled to RT, poured into a separatory funnel containing water and extracted with EtOAc (3×). The combined organic layers were washed further with brine (2×), dried over Na$_2$SO$_4$, filtered and the filtrate concentrated in vacuo. The crude product mixture thus obtained was purified by column chromatography through silica gel on the Teledyne ISCO Rf system (gradient elution, 0% to 50% EtOAc in hexanes). The product-containing fractions were combined, concentrated and dried under high vacuum to afford the title compound as a white solid (93% yield over 3 steps).

Step 4: Preparation of (S$_a$)-ethyl 2-(6-aminospiro[3.3]heptan-2-yl)acetate hydrochloride Into a thick-walled reaction flask equipped with a magnetic stir bar and a Teflon screw cap was added (S$_a$)-benzyl (6-(cyanomethyl)spiro[3.3]heptan-2-yl)carbamate (1.0 equiv) and ethanol (0.2 M). The reaction mixture was bubbled with a vigorous stream of HCl gas for 5 minutes. The reaction flask was then tightly sealed and heated at 60° C. for 18 hours. LCMS analysis revealed complete conversion to the desired product. The mixture was then cooled to RT, carefully vented and the volatiles were removed in vacuo. The crude product thus obtained was then thoroughly triturated with methyl tert-butyl ether and then vacuum filtered. The solid thus obtained was washed further with cold methyl tert-butyl ether and drying until constant weight to afford the title compound as a white solid.

Intermediate (R$_a$)-L: Preparation of (R$_a$)-Ethyl 2-(6-aminospiro[3.3]heptan-2-yl)acetate hydrochloride

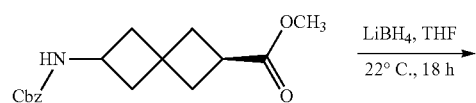

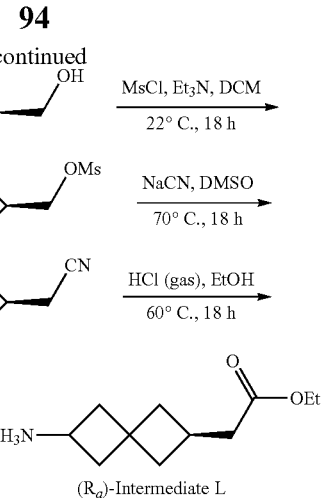

(R$_a$)-Intermediate L

The title compound was prepared in a similar manner to Intermediate (S$_a$)-L replacing (S$_a$)-methyl 6-(((benzyloxy)carbonyl)amino)-spiro[3.3]heptane-2-carboxylate in the first step with (S$_a$)-methyl 6-(((benzyloxy)carbonyl)amino)-spiro[3.3]heptane-2-carboxylate.

Intermediate M: Preparation of Methyl 4-chloro-1H-indazole-7-carboxylate

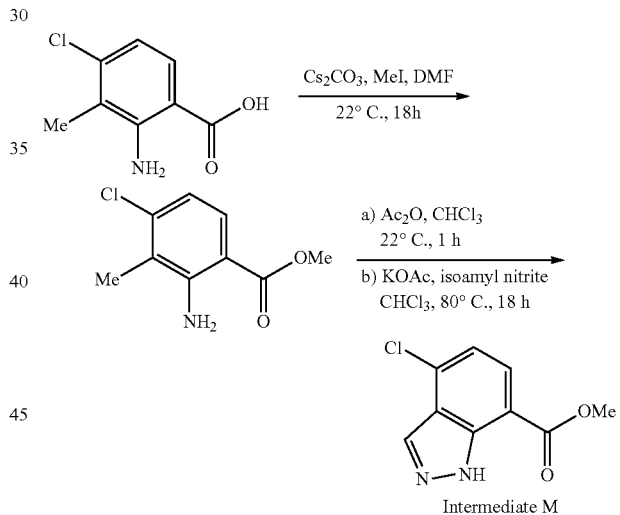

Intermediate M

Step 1: Preparation of methyl 2-amino-4-chloro-3-methylbenzoate

Into a round-bottom flask equipped with a magnetic stir bar and under N$_2$ was combined 2-amino-4-chloro-3-methylbenzoic acid (1 equiv, Enamine, CAS #98968-68-4) and cesium carbonate (1.5 equiv) in DMF (0.43 M). To this reaction suspension was added iodomethane (1.2 equiv) and the mixture was stirred at 22° C. for 18 hours. LCMS analysis at this time revealed complete conversion to the desired product. The mixture was poured into a separatory funnel containing brine and extracted with EtOAc (3). The combined organic extracts were washed with brine (1×), dried over MgSO$_4$, filtered and the filtrate concentrated in vacuo. The resulting residue was loaded onto a silica gel pre-cartridge and then dried under vacuum. This pre-absorbed material was purified by column chromatography using a Teledyne ISCO silica cartridge eluting with 0% to 40% EtOAc in hexanes as a gradient to provide the title compound as a light yellow solid.

Step 2: Preparation of methyl 4-chloro-1H-indazole-7-carboxylate

Into a round-bottom flask equipped with a magnetic stir bar and under N₂ was combined methyl 2-amino-4-chloro-3-methylbenzoate (1 equiv) and acetic anhydride (1.2 equiv) in chloroform (0.17 M). The resulting solution was then stirred a 22° C. for 1 hour. After this time, potassium acetate (0.3 equiv) and iso-amyl nitrite (2.2 equiv) were added in one rapid portion to the reaction flask. A reflux condenser was attached and the yellow reaction suspension was heated at reflux for 18 hours. LCMS analysis at this time revealed complete conversion to the desired product. The reaction mixture was then cooled to 22° C. and poured into a separatory funnel containing water. The aqueous layer was separated and extracted further with dichloromethane (3×). The combined organic extracts were washed with brine (1×), dried over MgSO₄, filtered and the filtrate concentrated in vacuo. The resulting residue was then triturated with ether and vacuum filtered. The solid thus obtained was washed further with cold ether and dried until constant weight to afford the title compound as a light yellow solid.

Intermediate N: Preparation of Methyl 5-chloro-1H-indazole-7-carboxylate

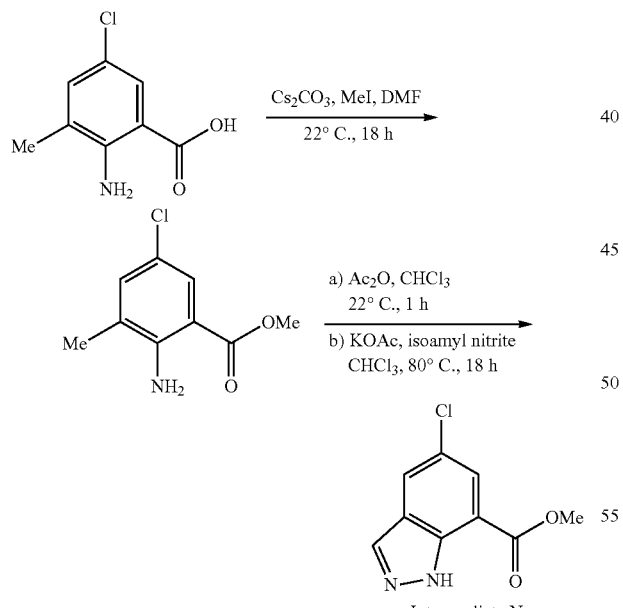

The title compound was prepared in a similar manner to Intermediate M replacing 2-amino-4-chloro-3-methylbenzoic acid with 2-amino-5-chloro-3-methylbenzoic acid (1 equiv, Enamine, CAS #20776-67-4) in Step 1.

Intermediate O: Preparation of Methyl 5-fluoro-1H-indazole-7-carboxylate

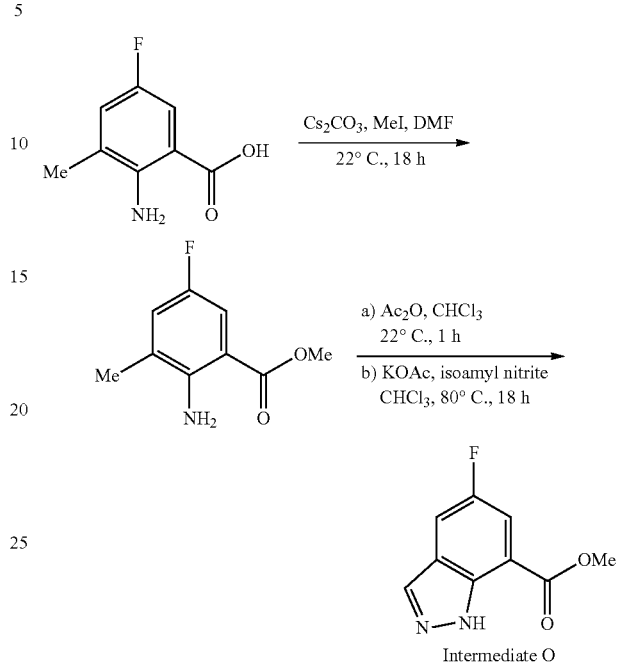

The title compound was prepared in a similar manner to Intermediate M replacing 2-amino-4-chloro-3-methylbenzoic acid with 2-amino-5-fluoro-3-methylbenzoic acid (1 equiv, Enamine, EN300-59603) in Step 1.

Intermediate P: Preparation of 1-(4-Bromobenzyl)-4-methoxy-1H-pyrrolo[3,2-c]pyridine-7-carboxylic acid

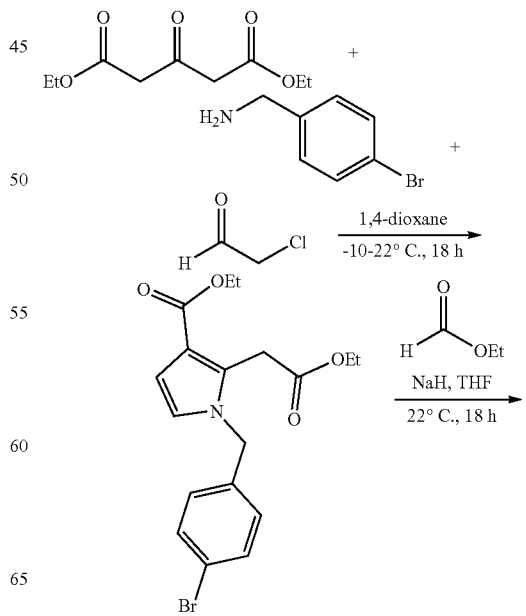

97
-continued

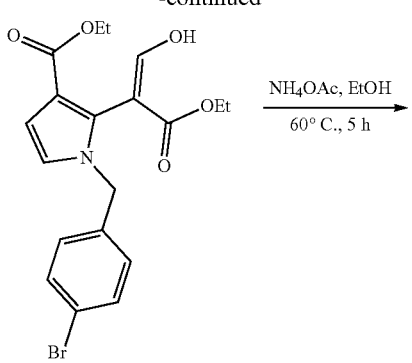

NH₄OAc, EtOH
60° C., 5 h

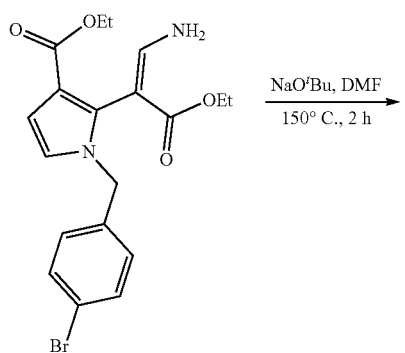

NaO'Bu, DMF
150° C., 2 h

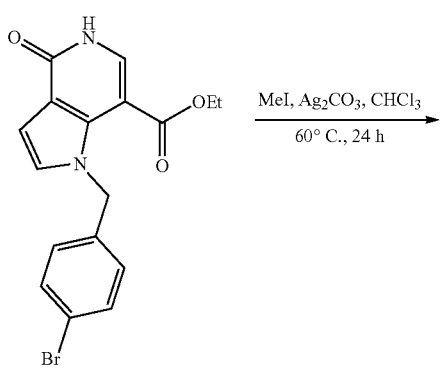

MeI, Ag₂CO₃, CHCl₃
60° C., 24 h

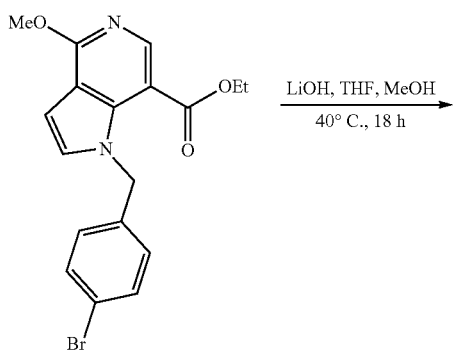

LiOH, THF, MeOH
40° C., 18 h

98
-continued

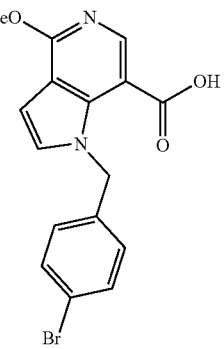

Intermediate P

Step 1: Preparation of ethyl 1-(4-bromobenzyl)-2-(2-ethoxy-2-oxoethyl)-1H-pyrrole-3-carboxylate Into a round-bottom flask equipped with a magnetic stir bar and under N₂ was added 4-bromobenzylamine (5.0 equiv) and 1,4-dioxane (2.5 M). To this was then added dropwise a 1,4-dioxane (2.5 M) solution of diethyl 1,3-acetonedicarboxylate (1.0 equiv) at −10° C. and the resulting reaction mixture was allowed to warm slowly to 0° C. over 30 minutes. Chloroacetaldehyde (1.7 equiv, 45% w/w in water) was then added drop-wise over 1.5 hours at a rate that maintained the internal reaction temperature below 15° C. The cooling bath was then removed and the reaction suspension was stirred at 22° C. for 18 hours. LCMS analysis revealed product formation. The volatiles were then evaporated in vacuo and the resulting residue was partitioned between EtOAc and 2 M aqueous HCl solution. The aqueous layer was separated and back extracted with EtOAc (2×). The combined organic extracts were washed further with brine, dried over Na₂SO₄, filtered and the filtrate concentrated in vacuo. The crude product thus obtained was then purified by column chromatography through silica gel on the Teledyne ISCO Rf (gradient elution, 0% to 30% EtOAc in hexanes). The product-containing fractions were combined and concentrated in vacuo to furnish the title compound as a white solid.

Step 2: Preparation of ethyl (Z)-1-(4-bromobenzyl)-2-(3-ethoxy-1-hydroxy-3-oxoprop-1-en-2-yl)-1H-pyrrole-3-carboxylate Into a round-bottom flask equipped with a magnetic stir bar and under N₂ was added ethyl 1-(4-bromobenzyl)-2-(2-ethoxy-2-oxoethyl)-1H-pyrrole-3-carboxylate (1.0 equiv) and THF (0.15 M). To this reaction mixture was added sodium hydride (4.0 equiv, 60% dispersion over oil) in three portions over 15 minutes. The reaction suspension was stirred for an additional 20 minutes before ethyl formate (2.0 equiv) was added. After 2 hours, more ethyl formate (2.0 equiv) was added and the reaction mixture was stirred at 22° C. for 16 hours. The reaction was then carefully quenched at 0° C. with a minimum amount of ethanol. The volatiles were evaporated and the resulting residue was partitioned between EtOAc and sat. aqueous NH₄Cl solution. The aqueous layer was separated and back extracted with EtOAc (2×). The combined organic layers were washed with brine, dried over Na₂SO₄, filtered and the filtrate concentrated in vacuo. The crude product thus obtained was then purified by column chromatography through silica gel on the Teledyne ISCO Rf (gradient elution, 0% to 50% EtOAc in hexanes). The product-containing fractions were combined and concentrated in vacuo to furnish the title compound.

Step 3: Preparation of ethyl (Z)-2-(1-amino-3-ethoxy-3-oxoprop-1-en-2-yl)-1-(4-bromobenzyl)-1H-pyrrole-3-carboxylate Into a round-bottom flask equipped with a magnetic stir bar and under $N_2$ was added ethyl (Z)-1-(4-bromobenzyl)-2-(3-ethoxy-1-hydroxy-3-oxoprop-1-en-2-yl)-H-pyrrole-3-carboxylate (1.0 equiv), ammonium acetate (4.75 equiv) and ethanol (0.2 M). The reaction mixture was heated at 60° C. for 5 hours. LCMS analysis revealed complete conversion to the desired product. The volatiles were then evaporated in vacuo and the resulting residue was partitioned between EtOAc and water. The aqueous layer was separated and back extracted with EtOAc (2×). The combined organic layers were washed further with brine, dried over $Na_2SO_4$ and filtered. Concentration of the filtrate in vacuo afforded the title compound.

Step 4: Preparation of ethyl 1-(4-bromobenzyl)-4-oxo-4,5-dihydro-1H-pyrrolo[3,2-c]pyridine-7-carboxylate Into a round-bottom flask equipped with a magnetic stir bar and under $N_2$ was added ethyl (Z)-2-(1-amino-3-ethoxy-3-oxoprop-1-en-2-yl)-1-(4-bromobenzyl)-1H-pyrrole-3-carboxylate (1.0 equiv), sodium tert-butoxide (0.5 equiv) and DMF (0.25 M). The reaction mixture was heated at 150° C. for 2 hours. LCMS analysis revealed successful product formation. The reaction mixture was cooled to RT, poured into a separatory funnel containing 1 M aqueous HCl solution and extracted with EtOAc (3×). The combined organic extracts were washed sequentially with water and brine, dried over $Na_2SO_4$, filtered and the filtrate concentrated in vacuo. The crude product thus obtained was then purified by column chromatography through silica gel on the Teledyne ISCO Rf (gradient elution, 0% to 100% EtOAc in hexanes). The product-containing fractions were combined and concentrated in vacuo to furnish the title compound.

Step 5: Preparation of ethyl 1-(4-bromobenzyl)-4-methoxy-1H-pyrrolo[3,2-c]pyridine-7-carboxylate Into a round-bottom flask equipped with a magnetic stir bar and under $N_2$ was added ethyl 1-(4-bromobenzyl)-4-oxo-4,5-dihydro-1H-pyrrolo[3,2-c]pyridine-7-carboxylate (1.0 equiv), silver carbonate (2.0 equiv) and chloroform (0.1 M). Iodomethane (2.0 equiv) was added drop-wise over a period of 5 min and the reaction suspension was heated at 60° C. for 18 hours. More iodomethane (2.0 equiv) was added at this time and the reaction suspension was heated at 60° C. for another 6 hours. LCMS analysis revealed complete conversion to the desired product. This reaction suspension was then cooled to 22° C. and filtered through a pad of celite. The insolubles were washed with $CH_2Cl_2$ and the filtrate thus obtained was concentrated in vacuo. The crude product thus obtained was then purified by column chromatography through silica gel on the Teledyne ISCO Rf (gradient elution, 0% to 100% EtOAc in hexanes). The product-containing fractions were combined and concentrated in vacuo to furnish the title compound.

Step 6: Preparation of 1-(4-bromobenzyl)-4-methoxy-1H-pyrrolo[3,2-c]pyridine-7-carboxylic acid Into a round-bottom flask equipped with a magnetic stir bar and under $N_2$ was added ethyl 1-(4-bromobenzyl)-4-methoxy-1H-pyrrolo[3,2-c]pyridine-7-carboxylate (1.0 equiv), THF (0.09 M) and methanol (0.17 M). To this was then added 1 M aqueous lithium hydroxide solution (3.0 equiv) and the resulting mixture was heated at 40° C. for 18 hours. LCMS analysis revealed complete conversion to the desired product. The reaction mixture was cooled to RT, carefully neutralized with 1 M aqueous HCl solution and extracted with $CH_2Cl_2$ (3×). The combined organic extracts were washed with brine, dried over $Na_2SO_4$, and filtered. Concentration of the filtrate in vacuo furnished the title compound as a white solid.

Intermediate Q: Preparation of 1-(4-Bromobenzyl)-4-ethoxy-1H-pyrrolo[3,2-c]pyridine-7-carboxylic acid

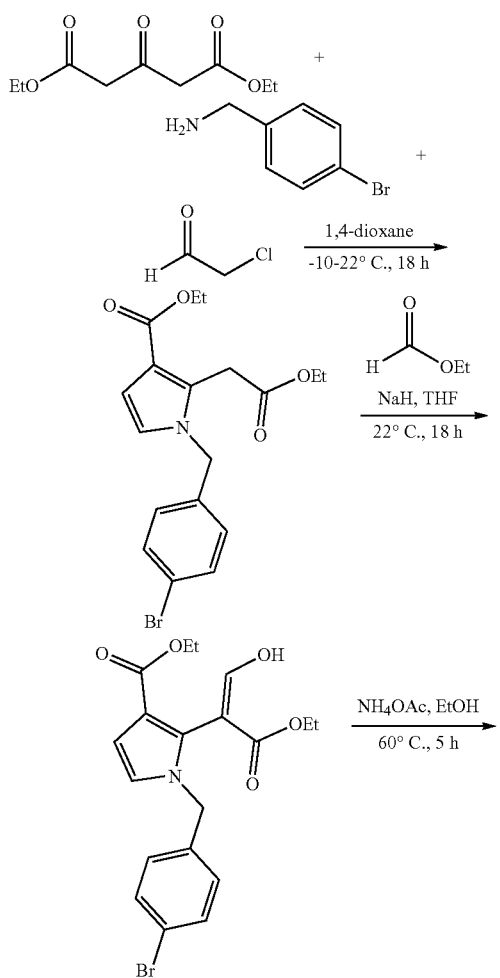

-continued

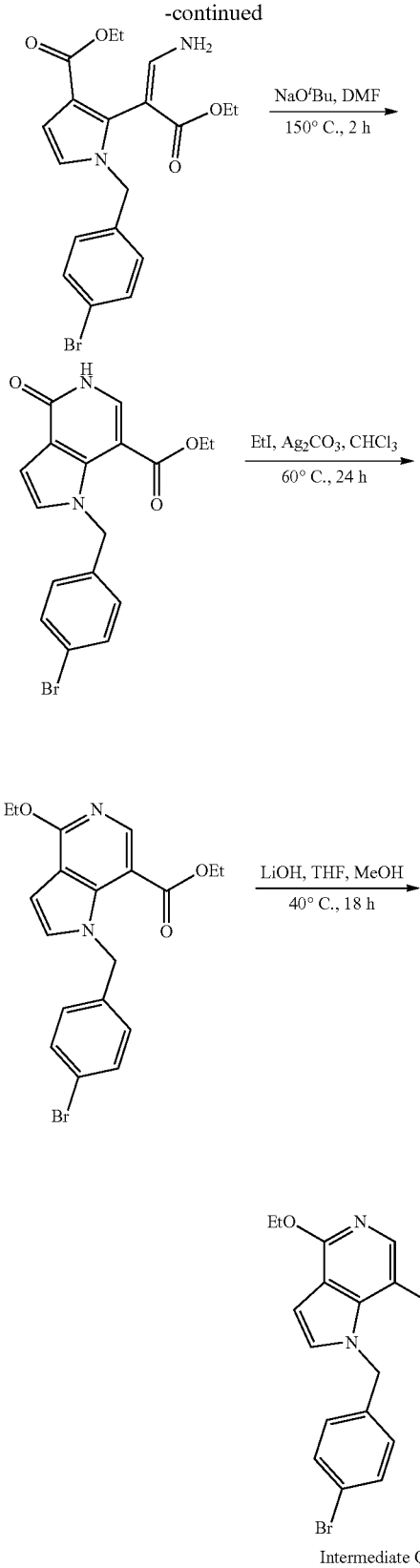

Intermediate R: Preparation of (S_a)-6-(1-(4-Bromobenzyl)-4-fluoro-1H-indole-7-carboxamido)spiro[3.3]heptane-2-carboxylic acid

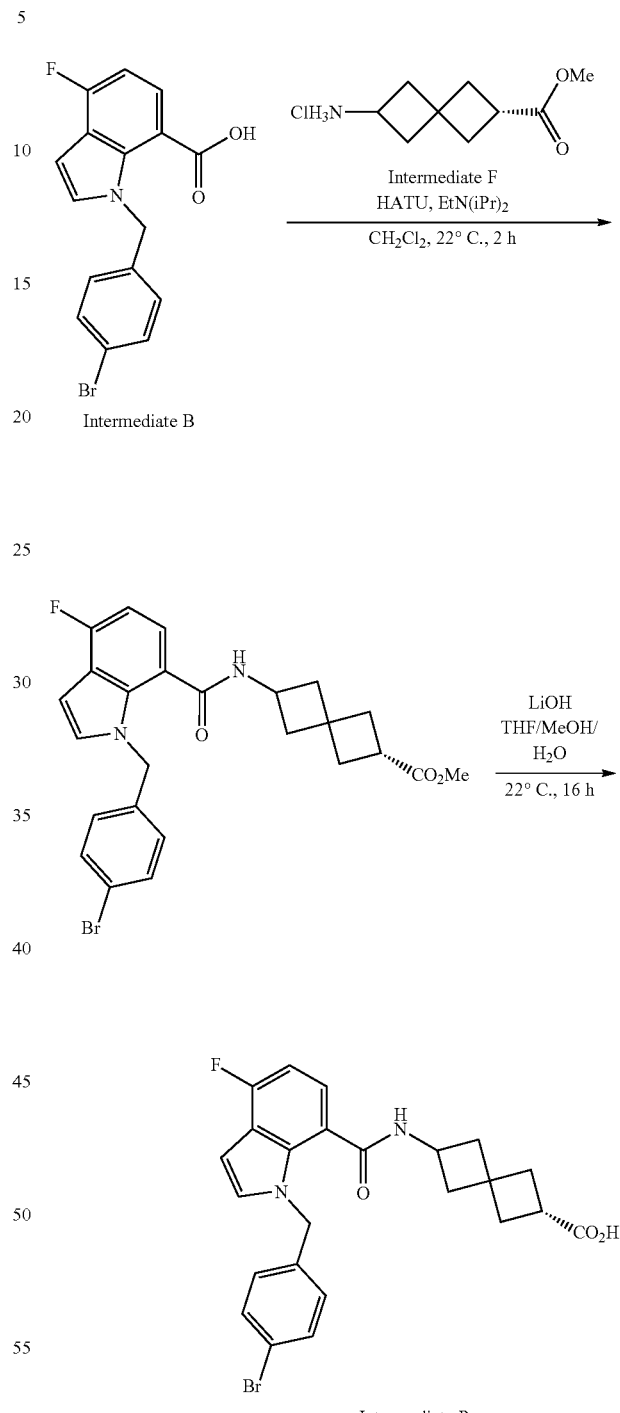

The title compound was prepared in a similar manner to Intermediate P replacing iodomethane with iodoethane in Step 5.

The title compound was prepared in a similar manner to Intermediate C but replacing (racemic)-methyl 2-aminospiro[3.3]heptane-6-carboxylate hydrochloride with (S_a)-methyl 2-aminospiro[3.3]heptane-6-carboxylate hydrochloride (Intermediate F).

Intermediate S: Preparation of (S$_a$)-6-(4-Fluoro-1-(4-iodobenzyl)-1H-indole-7-carboxamido)spiro[3.3]heptane-2-carboxylic acid

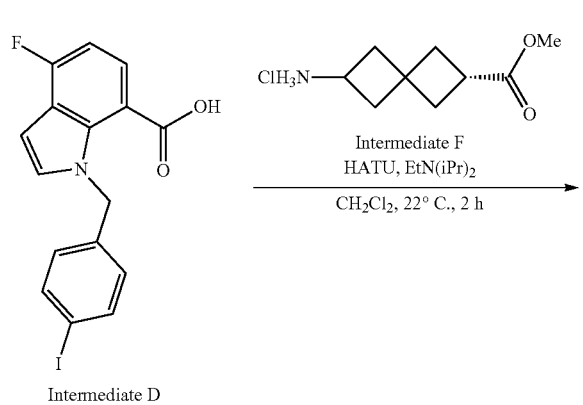

Intermediate D

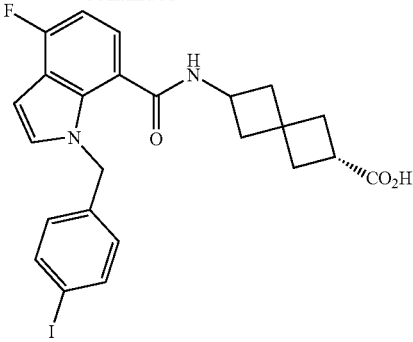

Intermediate F

HATU, EtN(iPr)$_2$
CH$_2$Cl$_2$, 22° C., 2 h

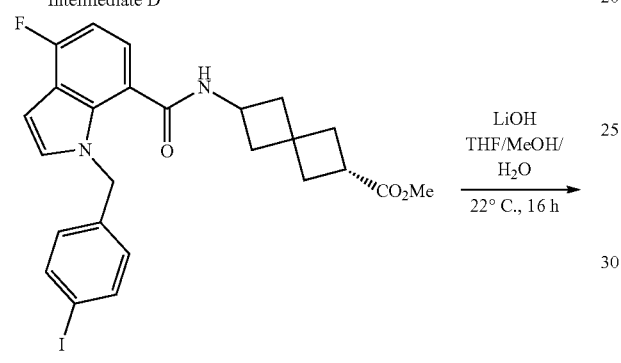

LiOH
THF/MeOH/
H$_2$O
22° C., 16 h

Intermediate S

The title compound was prepared in a similar manner to Intermediate R but replacing Intermediate B with Intermediate D.

Intermediate T: Preparation of (S$_a$)-6-(4-Fluoro-1-(4-(4,4,5,5-tetramethyl-1,3,2-dioxaborolan-2-yl)benzyl)-1H-indole-7-carboxamido)spiro[3.3]heptane-2-carboxylic acid

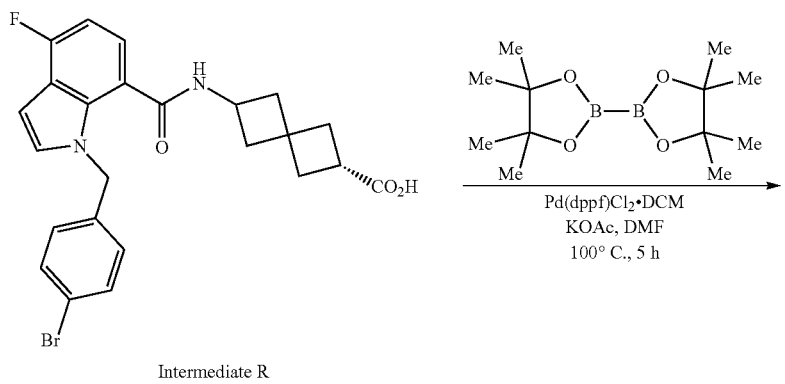

Intermediate R

Pd(dppf)Cl$_2$·DCM
KOAc, DMF
100° C., 5 h

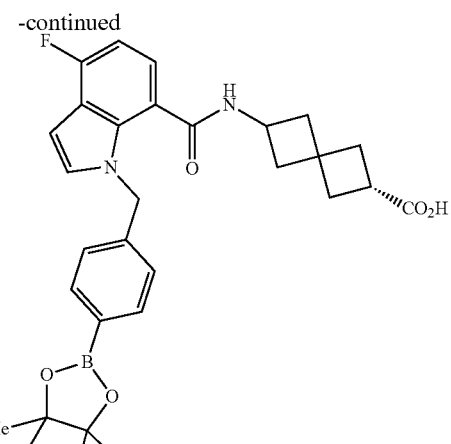

Intermediate T

The title compound was prepared in a similar manner to Intermediate E but replacing Intermediate C with Intermediate R.

Intermediate U: Preparation of (S$_a$)-6-(1-(4-Bromo-3-fluorobenzyl)-4-fluoro-1H-indole-7-carboxamido)spiro[3.3]heptane-2-carboxylic acid

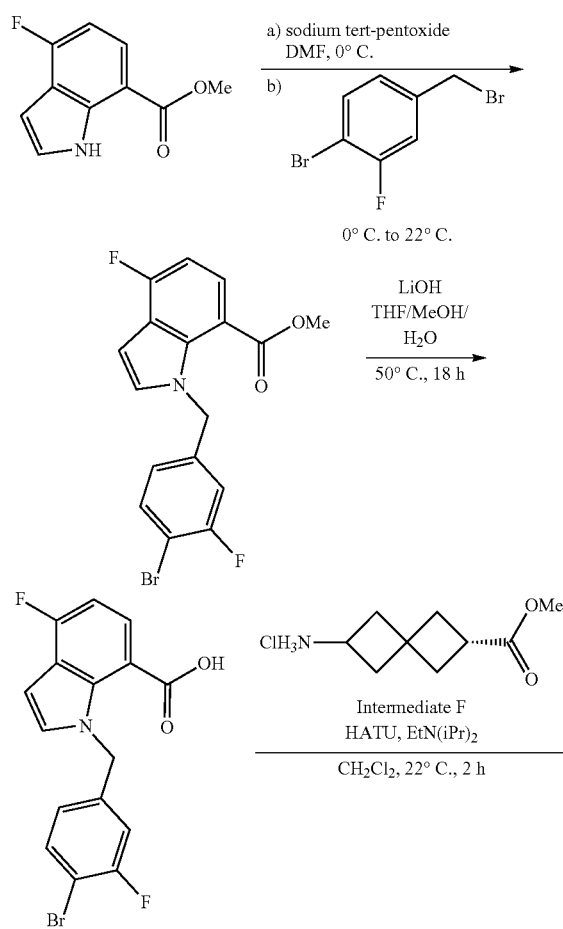

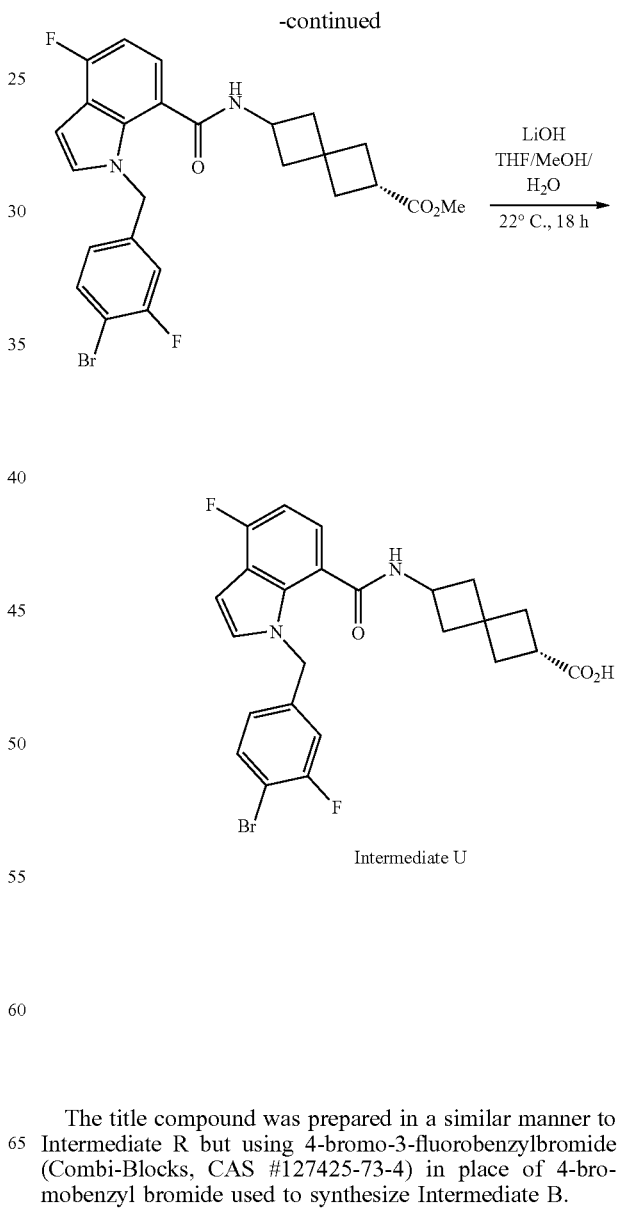

Intermediate U

The title compound was prepared in a similar manner to Intermediate R but using 4-bromo-3-fluorobenzylbromide (Combi-Blocks, CAS #127425-73-4) in place of 4-bromobenzyl bromide used to synthesize Intermediate B.

Intermediate V: Preparation of (S$_a$)-6-(1-(4-Bromo-2-fluorobenzyl)-4-fluoro-1H-indole-7-carboxamido)spiro[3.3]heptane-2-carboxylic acid

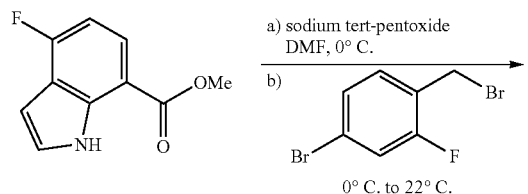

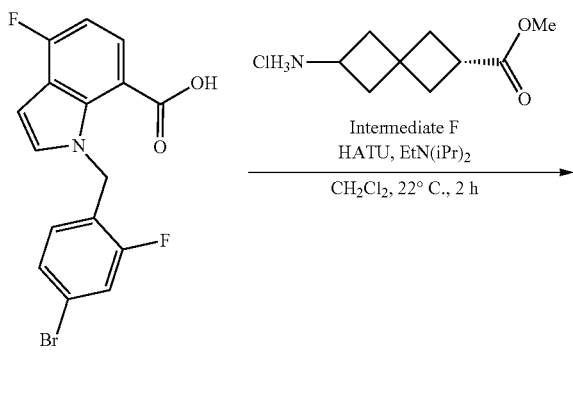

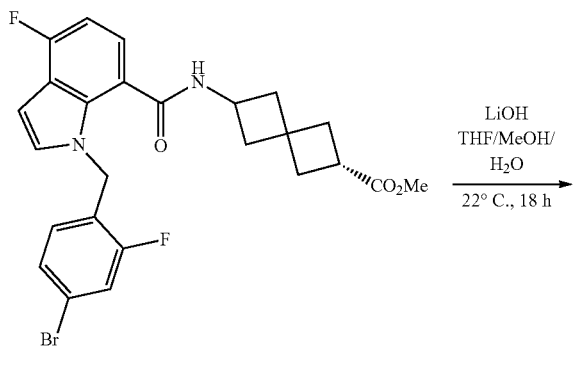

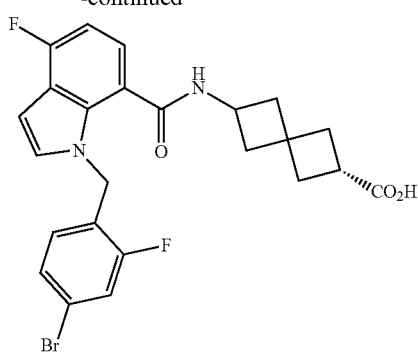

Intermediate V

The title compound was prepared in a similar manner to Intermediate R but using 4-bromo-2-fluorobenzylbromide (Combi-Blocks, CAS #76283-09-5) in place of 4-bromobenzyl bromide used to synthesize Intermediate B.

Intermediate W: Preparation of (S$_a$)-6-(1-(4-Bromobenzyl)-4-chloro-1H-indole-7-carboxamido)spiro[3.3]heptane-2-carboxylic acid

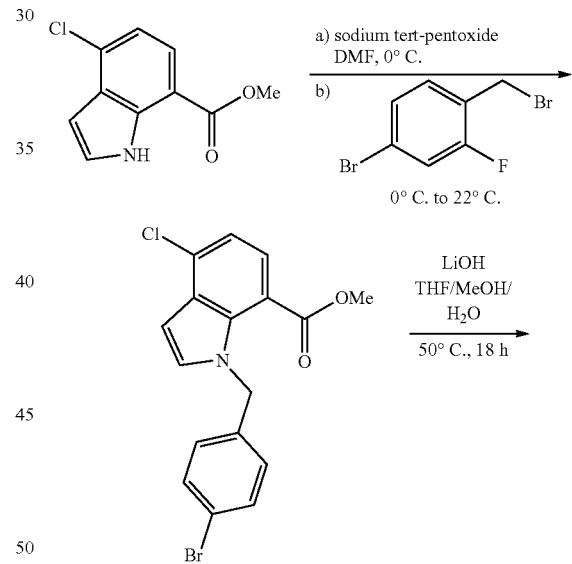

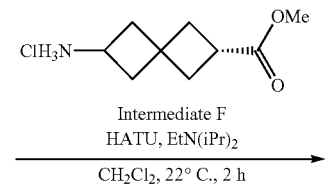

-continued

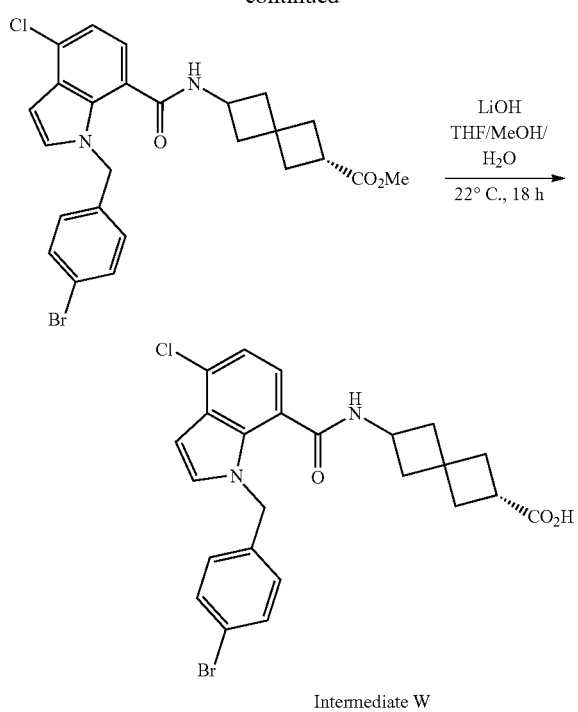

Intermediate W

The title compound was prepared in a similar manner to Intermediate R but using methyl 4-chloro-1H-indole-7-carboxylate (Enamine, CAS #142741345-3) in place of methyl 4-fluoro-H-indole-7-carboxylate used to synthesize Intermediate B.

Intermediate X: Preparation of ($S_a$)-6-(4-Chloro-1-(4-iodobenzyl)-1H-indazole-7-carboxamido)spiro[3.3]heptane-2-carboxylic acid

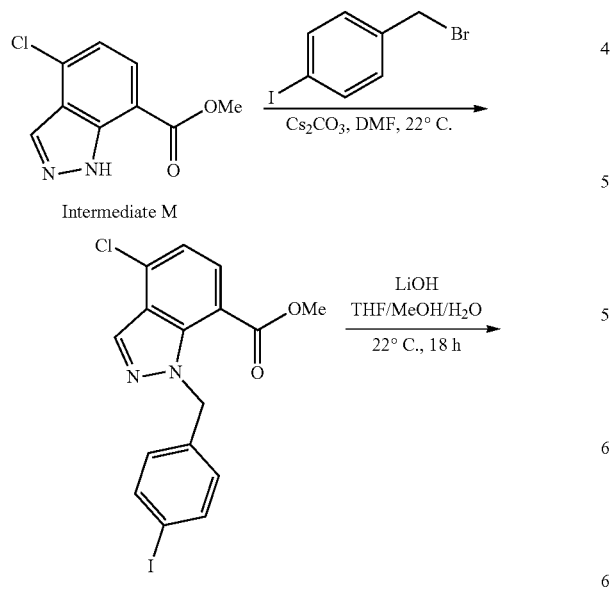

-continued

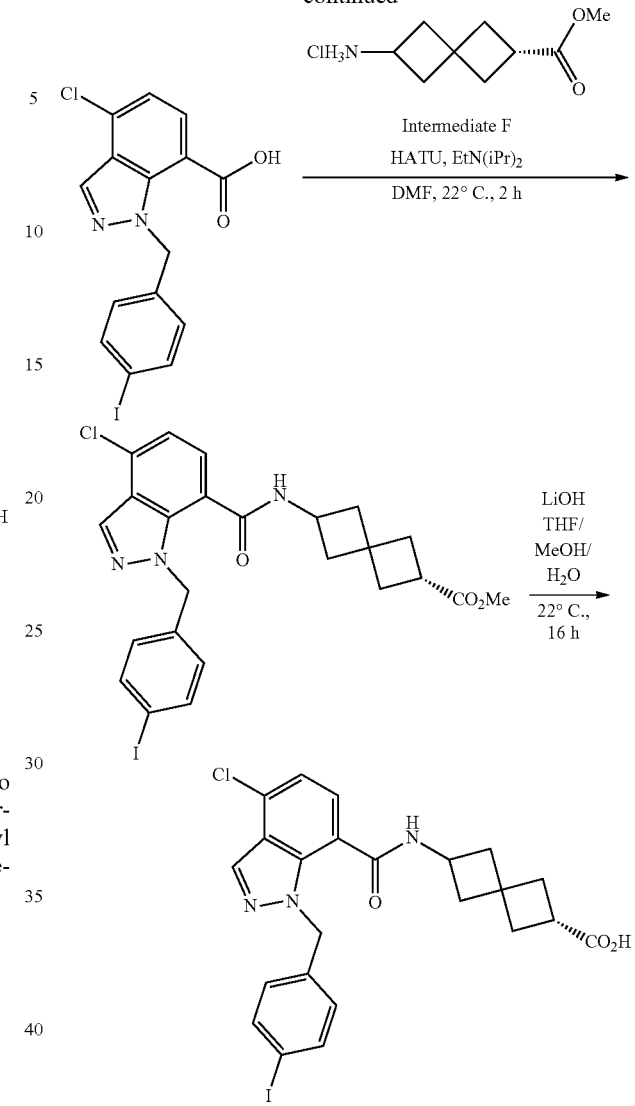

Intermediate X

Step 1: Preparation of methyl 4-chloro-1-(4-iodobenzyl)-1H-indazole-7-carboxylate In a round-bottom flask equipped with a magnetic stir bar was suspended Intermediate M (1.0 equiv) and cesium carbonate (3 equiv) in DMF (0.53 M). This suspension was cooled to 0° C. and then added 1-(bromomethyl)-4-iodobenzene (1.2 equiv) portion-wise over a period of 5 minutes. The resulting reaction mixture was allowed to warm to 22° C. over 16 hours. The reaction was then carefully quenched with the addition of ice-water and extracted with tert-butyl methyl ether. The combined organic extracts were washed further with water and brine, dried over $MgSO_4$, treated with activated charcoal and filtered through a pad of celite. Concentration of the filtrate thus obtained in vacuo furnished the crude reaction product as a red oil. Purification by column chromatography through silica gel on the Teledyne ISCO Rf (gradient elution with 10% to 70% EtOAc in hexanes) afforded the title compound as a pale yellow oil that solidified upon standing.

Step 2: Preparation of 4-chloro-1-(4-iodobenzyl)-1H-indazole-7-carboxylic acid Into a glass round-bottom flask equipped with a magnetic stir bar was dissolved methyl 4-chloro-1-(4-iodobenzyl)-1H-indazole-7-carboxylate (1 equiv) in a 3:2 (v/v) solution (0.15 M) of THF and MeOH. To this was then added 2.0 M aqueous LiOH solution (3 equiv) and the resulting solution was stirred at 22° C. for 18 hours. The reaction mixture was then carefully neutralized with the drop-wise addition of 1 M aqueous HCl solution (3 equiv). The resulting suspension was extracted with EtOAc. The combined organic extracts were washed further with water and brine, dried over MgSO$_4$ and filtered. Concentration of the filtrate thus obtained in vacuo furnished the crude reaction product as a pale yellow semi-solid. Trituration of the crude product in tert-butyl methyl ether and hexanes afforded the title compound as an off-white solid.

Step 3: Preparation of (S$_a$)-methyl 6-(4-chloro-1-(4-iodobenzyl)-1H-indazole-7-carboxamido)spiro[3.3]heptane-2-carboxylate In a round-bottom flask equipped with a magnetic stir bar was dissolved 4-chloro-1-(4-iodobenzyl)-1H-indazole-7-carboxylic acid (1 equiv), Intermediate F (1.2 equiv) and HATU (1.5 equiv) in DMF (0.18 M). To this was then added Hünig's base (5 equiv) and the resulting yellow solution was allowed to stir at 22° C. for 2 hours. The crude reaction mixture was diluted with tert-butyl methyl ether and washed sequentially with water, 1 M aqueous HCl solution, 1 M aqueous NaOH solution, water and brine. The organic extract was dried over MgSO$_4$, filtered and the filtrate concentrated in vacuo. Purification by column chromatography through silica gel on the Teledyne ISCO Rf (gradient elution with 10% to 70% EtOAc in hexanes) afforded the title compound.

Step 4: Preparation of (S$_a$)-6-(4-chloro-1-(4-iodobenzyl)-1H-indazole-7-carboxamido)spiro[3.3]heptane-2-carboxylic acid Into a round-bottom flask equipped with a magnetic stir bar was dissolved (S$_a$)-methyl 6-(4-chloro-1-(4-iodobenzyl)-1H-indazole-7-carboxamido)spiro[3.3]heptane-2-carboxylate (1 equiv) in a 3:2 (v/v) solution (0.1 M) of THF and MeOH. To this was then added 2.0 M aqueous LiOH solution (3 equiv) and the resulting solution was stirred at 22° C. for 16 hours. The reaction mixture was then carefully neutralized with the drop-wise addition of 1 M aqueous HCl solution (3 equiv). The resulting suspension was extracted with EtOAc. The combined organic extracts were washed further with water and brine, dried over MgSO$_4$, and filtered. Concentration of the filtrate thus obtained in vacuo furnished the crude reaction product as a beige solid. Trituration of the crude product in tert-butyl methyl ether and hexanes afforded the title compound as an off-white, solid.

Intermediate Y: Preparation of (S$_a$)-6-(4-Chloro-1-(3-fluoro-4-iodobenzyl)-1H-indazole-7-carboxamido)spiro[3.3]heptane-2-carboxylic acid

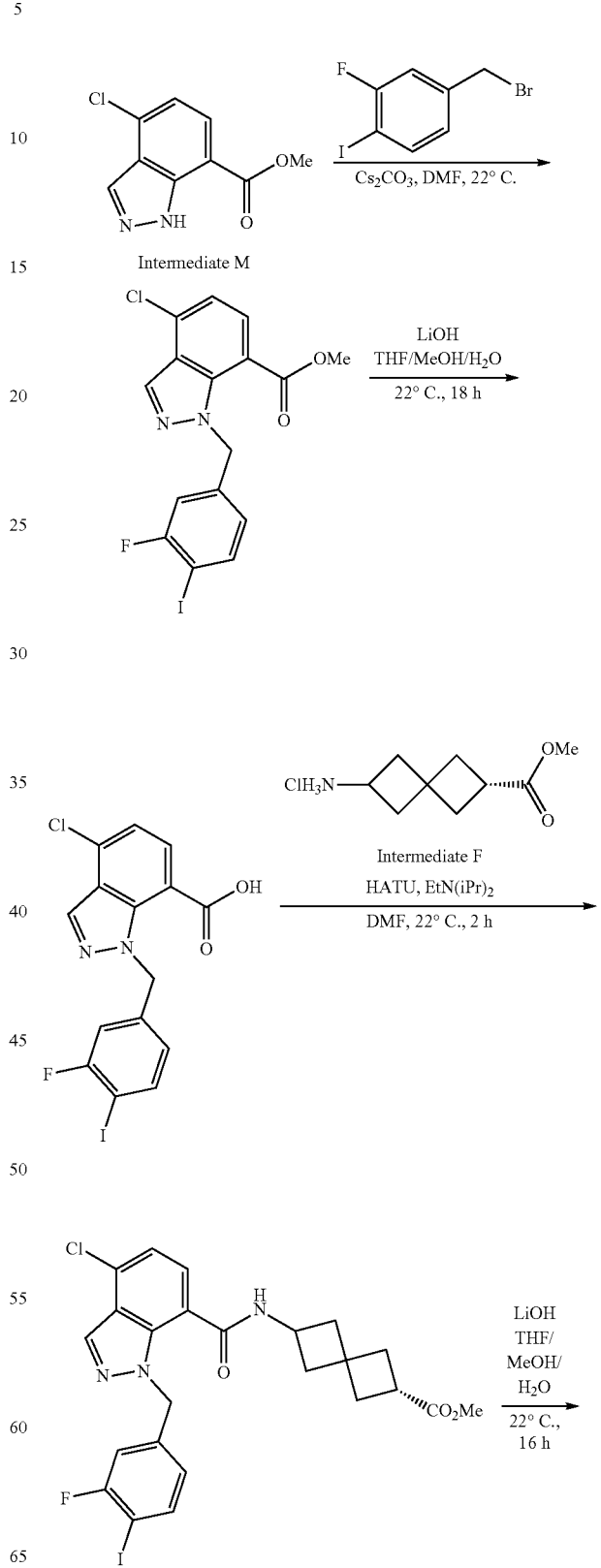

113

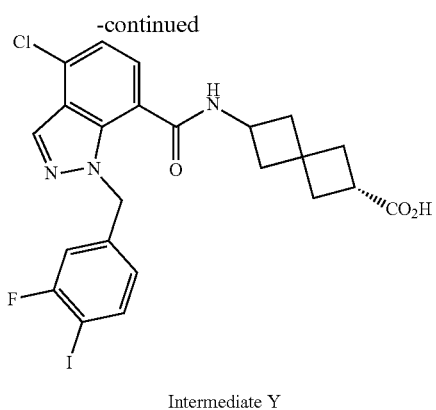

Intermediate Y

The title compound was prepared in a similar manner to Intermediate X but replacing 4-iodobenzyl bromide with 3-fluoro-4-iodobenzyl bromide (Astatech, CAS #1022931-83-4) in Step 1.

Intermediate Z: Preparation of (S$_a$)-6-(1-(4-Bromobenzyl)-4-chloro-1H-indazole-7-carboxamido)spiro[3.3]heptane-2-carboxylic acid

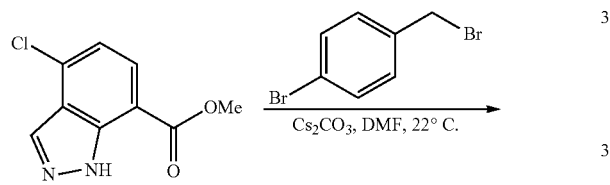

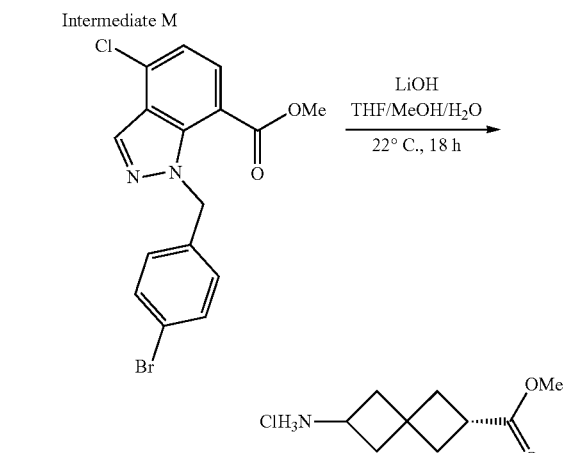

114

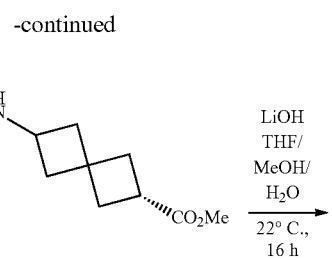

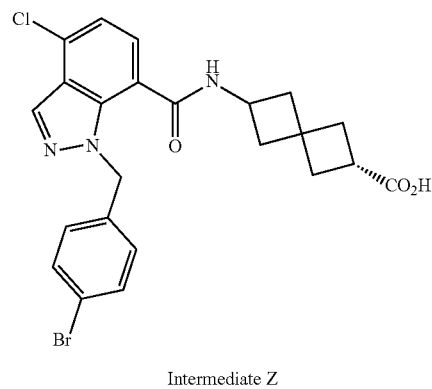

Intermediate Z

The title compound was prepared in a similar manner to Intermediate X but replacing 4-iodobenzyl bromide with 4-bromobenzyl bromide in Step 1.

Intermediate AA: Preparation of (S$_a$)-6-(4-Chloro-1-(4-(4,4,5,5-tetramethyl-1,3,2-dioxaborolan-2-yl)benzyl)-1H-indazole-7-carboxamido)spiro[3.3]heptane-2-carboxylic acid

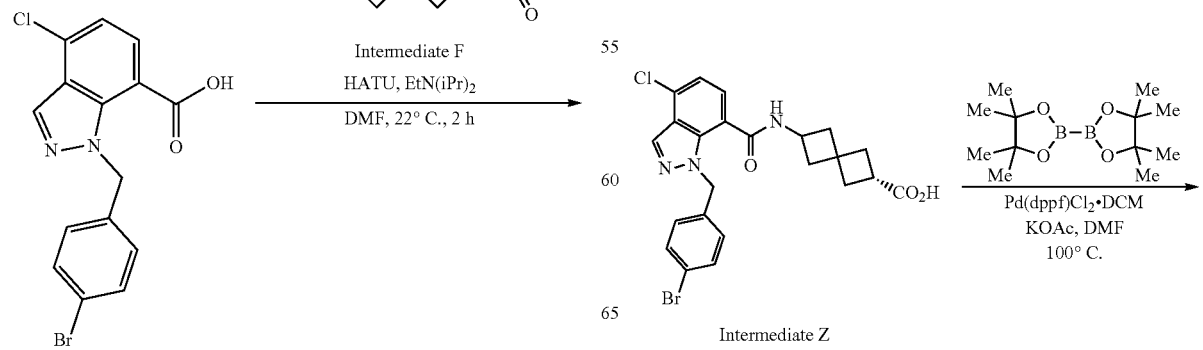

Intermediate Z

115

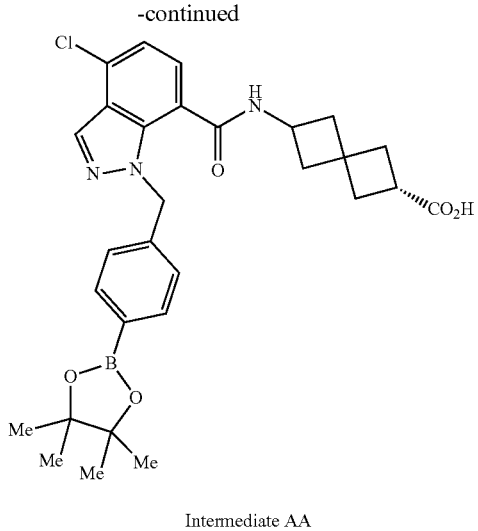

Intermediate AA

The title compound was prepared in a similar manner to Intermediate E but replacing Intermediate C with Intermediate Z.

Intermediate BB: Preparation of (S$_a$)-6-(1-(1-(4-Bromophenyl)ethyl)-1H-indazole-7-carboxamido)spiro[3.3]heptane-2-carboxylic acid

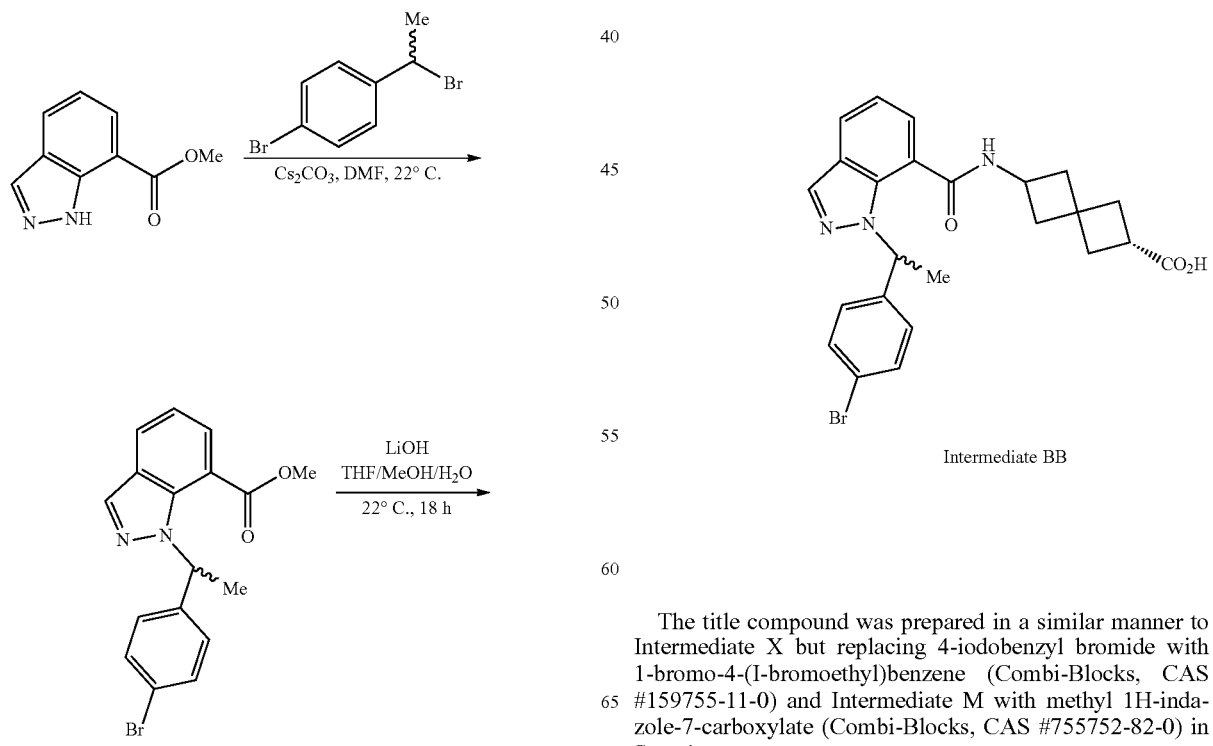

116

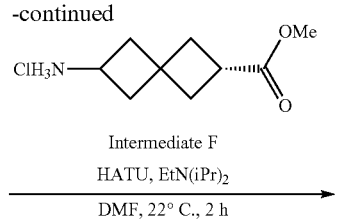

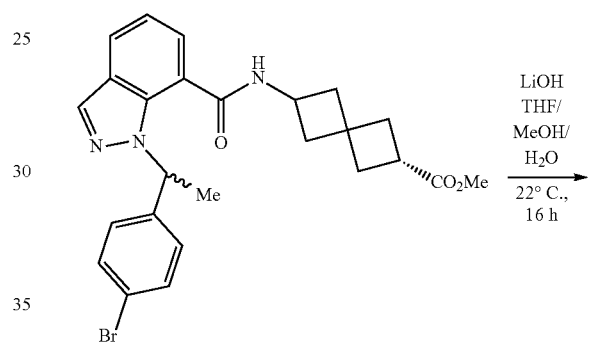

Intermediate BB

The title compound was prepared in a similar manner to Intermediate X but replacing 4-iodobenzyl bromide with 1-bromo-4-(1-bromoethyl)benzene (Combi-Blocks, CAS #159755-11-0) and Intermediate M with methyl 1H-indazole-7-carboxylate (Combi-Blocks, CAS #755752-82-0) in Step 1.

Intermediate CC: Preparation of (S$_a$)-6-(1-(1-(4-Bromophenyl)ethyl)-4-chloro-1H-indazole-7-carboxamido)spiro[3.3]heptane-2-carboxylic acid

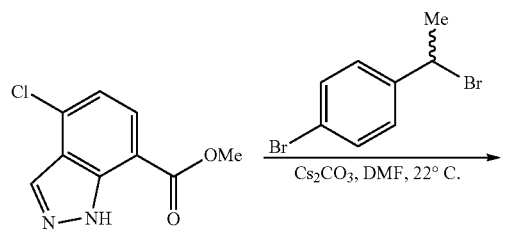

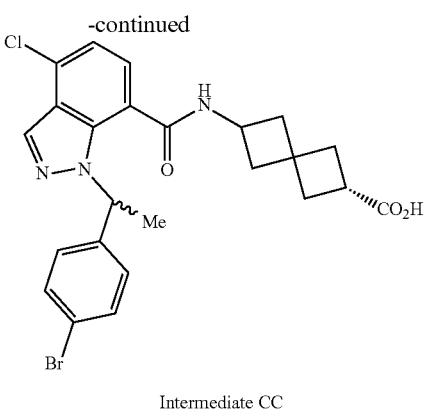

Intermediate CC

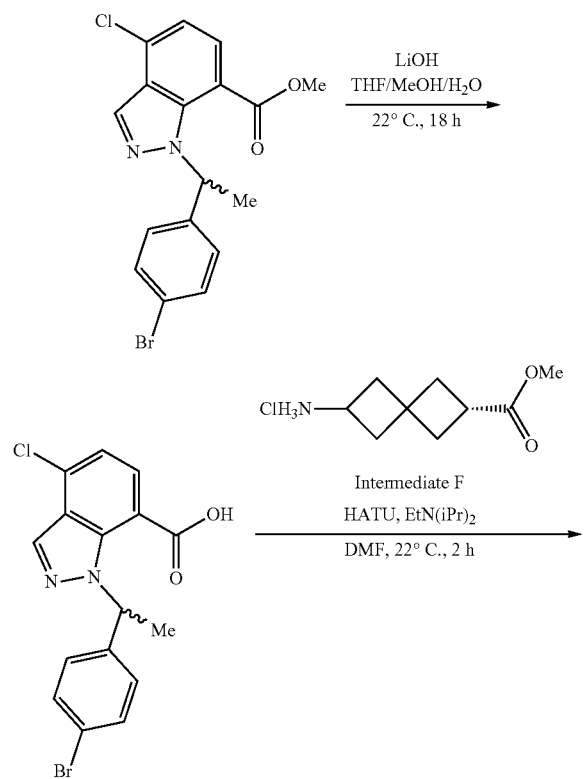

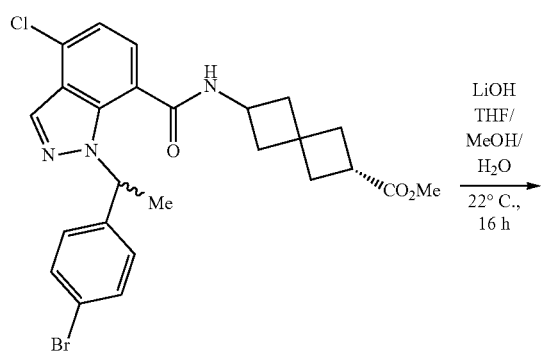

The title compound was prepared in a similar manner to Intermediate X but replacing 4-iodobenzyl bromide with 1-bromo-4-(1-bromoethyl)benzene (Combi-Blocks, CAS #159755-11-0) in Step 1.

Intermediate DD: Preparation of (S$_a$)-6-(1-(1-(4-Bromophenyl)ethyl)-4-fluoro-1H-indole-7-carboxamido)spiro[3.3]heptane-2-carboxylic acid

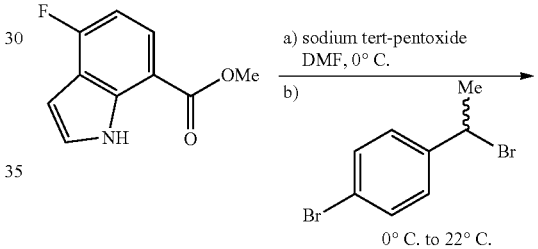

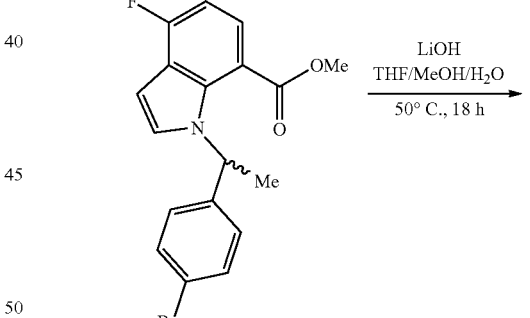

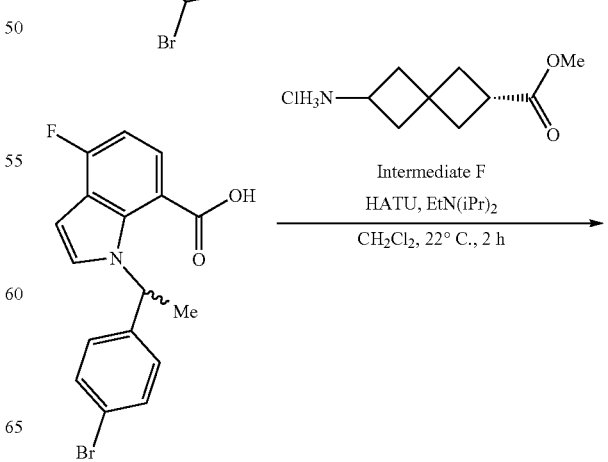

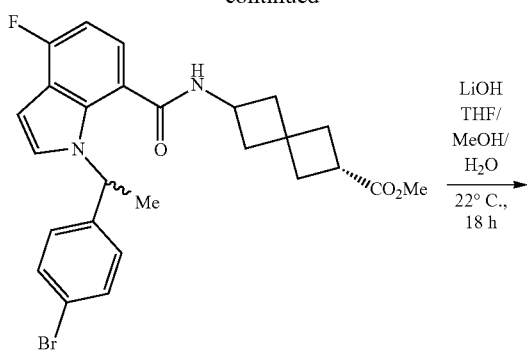

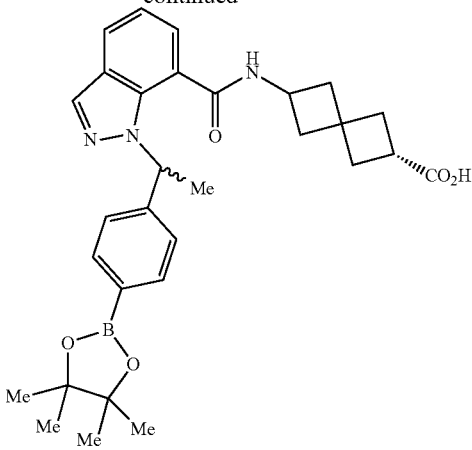

Intermediate EE

The title compound was prepared in a similar manner to Intermediate E but replacing Intermediate C with Intermediate BB.

Intermediate FF: Preparation of (S$_a$)-6-(4-Chloro-1-(1-(4-(4,4,5,5-tetramethyl-1,3,2-dioxaborolan-2-yl)phenyl)ethyl)-1H-indazole-7-carboxamido)spiro[3.3]heptane-2-carboxylic acid

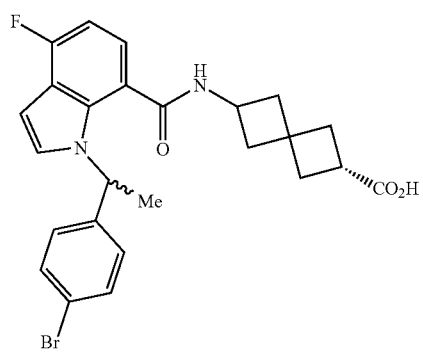

Intermediate DD

The title compound was prepared in a similar manner to Intermediate R but using 1-bromo-4-(1-bromoethyl)benzene (Combi-Blocks, CAS #159755-11-0) in place of 4-bromobenzyl bromide used to synthesize Intermediate B.

Intermediate EE: Preparation of (S$_a$)-6-(1-(1-(4-(4,4,5,5-Tetramethyl-1,3,2-dioxaborolan-2-yl)phenyl)ethyl)-1H-indazole-7-carboxamido)spiro[3.3]heptane-2-carboxylic acid

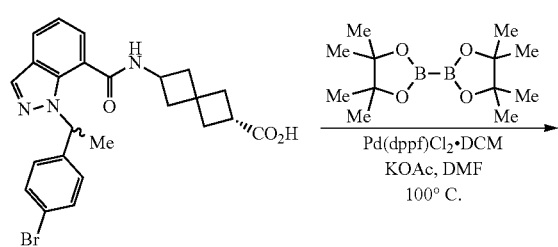

Intermediate BB

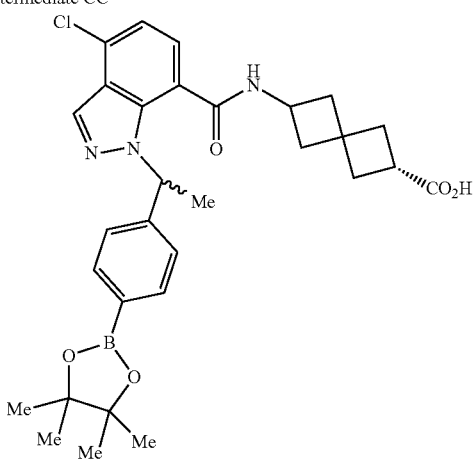

Intermediate FF

The title compound was prepared in a similar manner to Intermediate E but replacing Intermediate C with Intermediate CC.

Intermediate GG: Preparation of (S<sub>a</sub>)-6-(1-(4-Bromobenzyl)-4-methoxy-1H-pyrrolo[3,2-c]pyridine-7-carboxamido)spiro[3.3]heptane-2-carboxylic acid

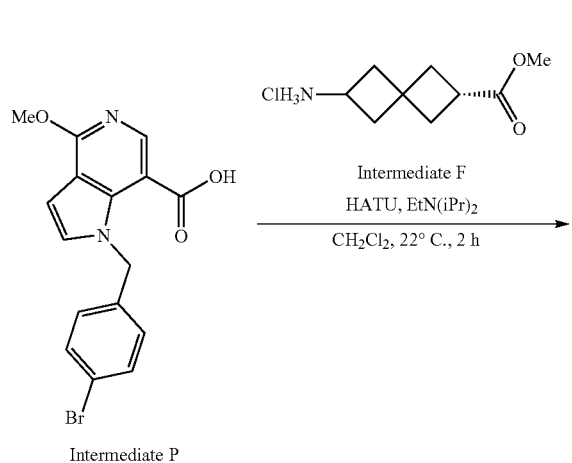

Intermediate P

Intermediate HH: Preparation of (S<sub>a</sub>)-6-(1-(4-Bromobenzyl)-4-ethoxy-1H-pyrrolo[3,2-c]pyridine-7-carboxamido)spiro[3.3]heptane-2-carboxylic acid

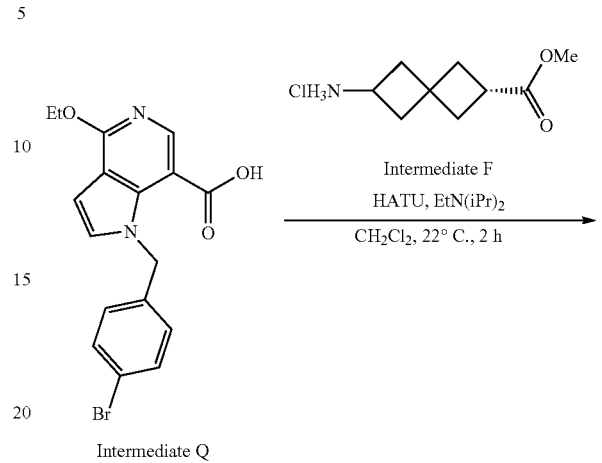

Intermediate Q

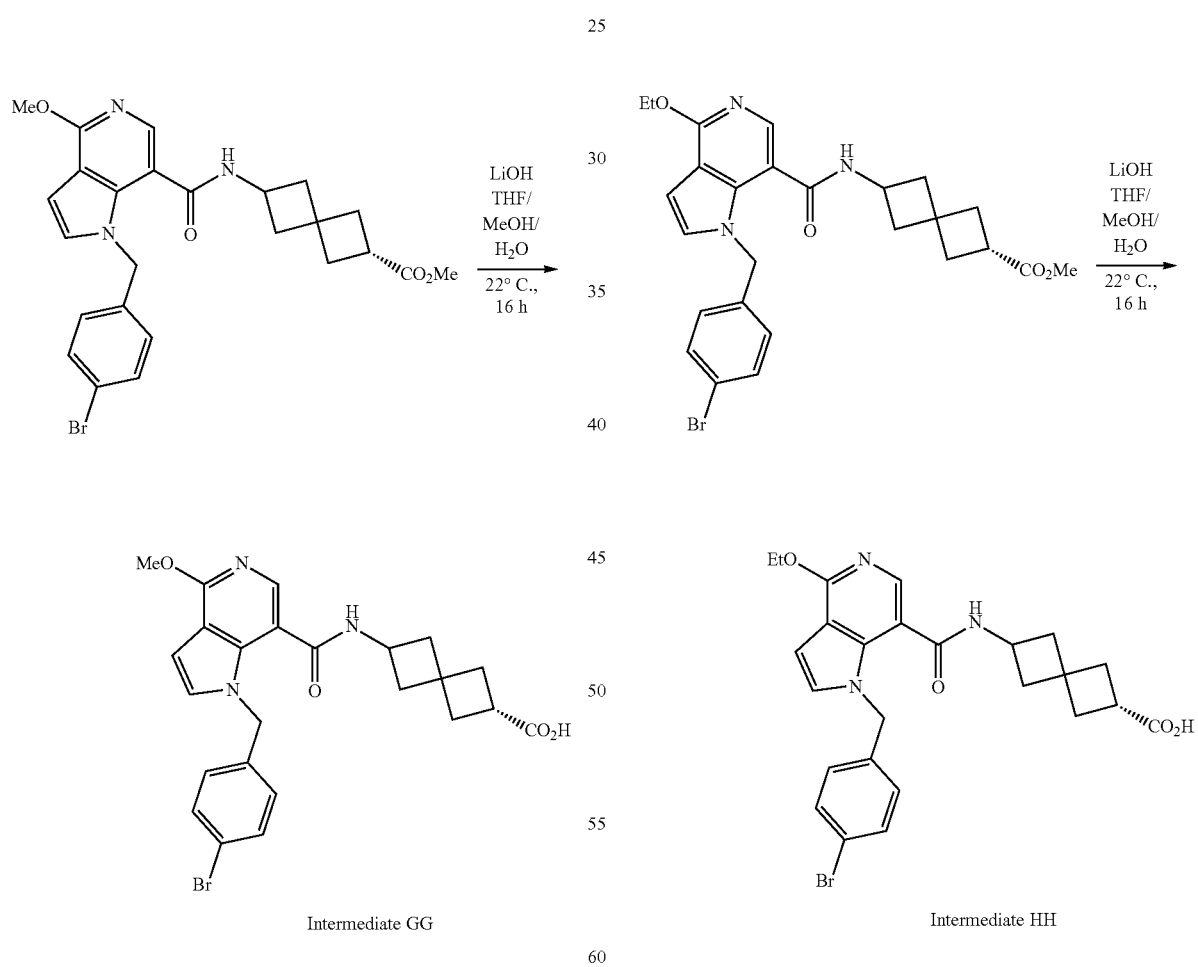

The title compound was prepared in a similar manner to Intermediate R but replacing Intermediate B with Intermediate P.

The title compound was prepared in a similar manner to Intermediate R but replacing Intermediate B with Intermediate Q.

Intermediate II: Preparation of (S$_a$)-6-(4-Methoxy-1-(4-(4,4,5,5-tetramethyl-1,3,2-dioxaborolan-2-yl)benzyl)-1H-pyrrolo[3,2-c]pyridine-7-carboxamido)spiro[3.3]heptane-2-carboxylic acid

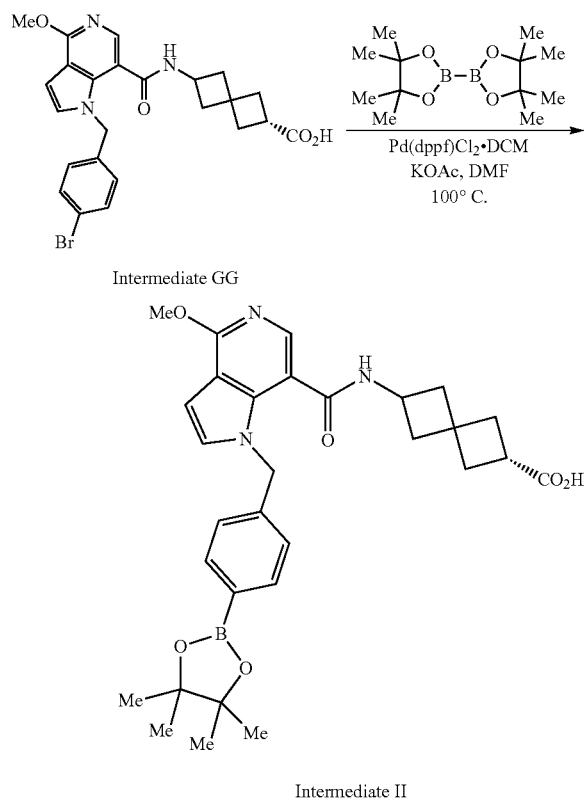

The title compound was prepared in a similar manner to Intermediate E but replacing Intermediate C with Intermediate GG.

Intermediate JJ: Preparation of (S$_a$)-6-(1-(1-(4-Iodophenyl)ethyl)-4-chloro-1H-indazole-7-carboxamido)spiro[3.3]heptane-2-carboxylic acid

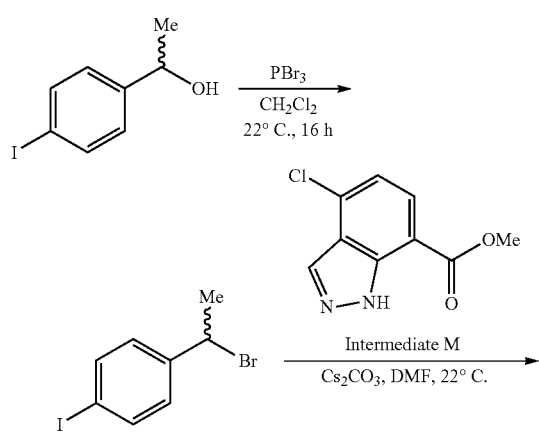

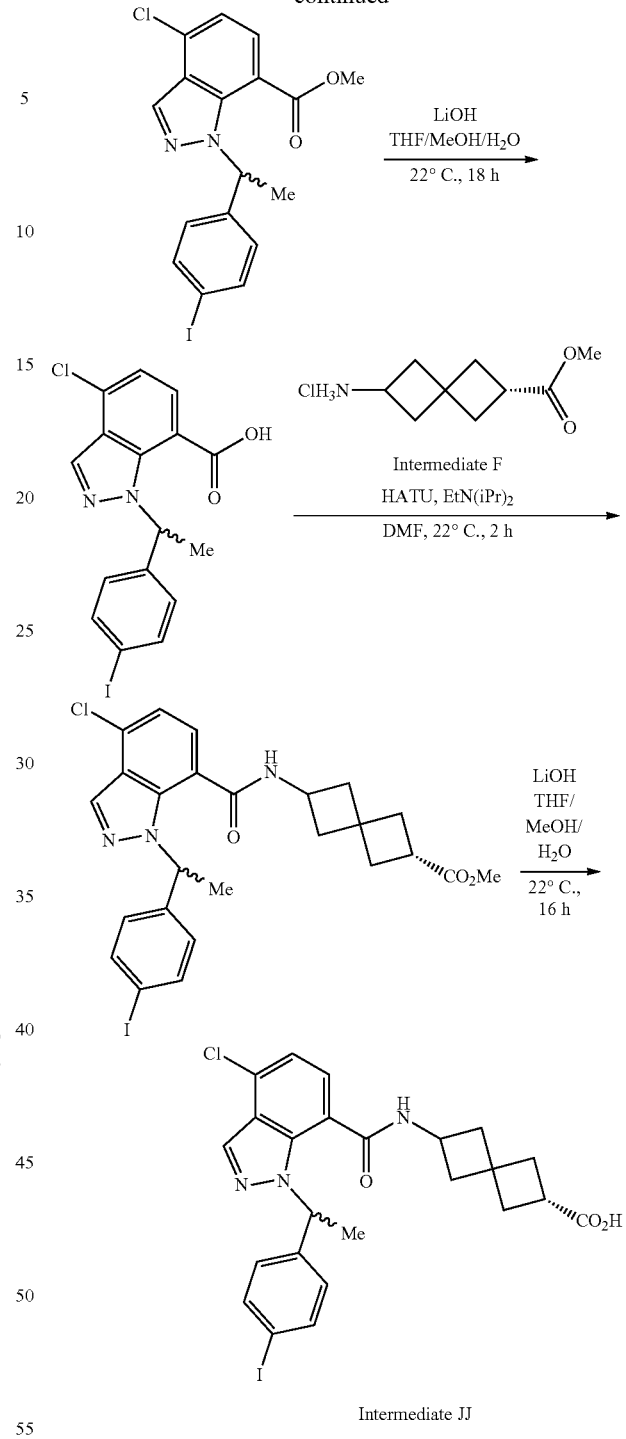

The title compound was prepared in a similar manner to Intermediate X but replacing 4-iodobenzyl bromide with 1-(1-bromoethyl)-4-iodobenzene in Step 1. 1-(1-Bromoethyl)-4-iodobenzene was itself prepared in a similar manner to Intermediate G, but replacing (6-fluoronaphthalen-2-yl)methanol with 1-(4-iodophenyl)ethan-1-ol (Enamine, CAS #53207-29-7) in Step 2.

Intermediate KK: Preparation of (S$_a$)-2-(6-(1-(4-Bromobenzyl)-4-fluoro-1H-indole-7-carboxamido)spiro[3.3]heptan-2-yl)acetic acid Intermediate LL: Preparation of (R$_a$)-2-(6-(1-(4-Bromobenzyl)-4-fluoro-1H-indole-7-carboxamido)spiro[3.3]heptan-2-yl)acetic acid

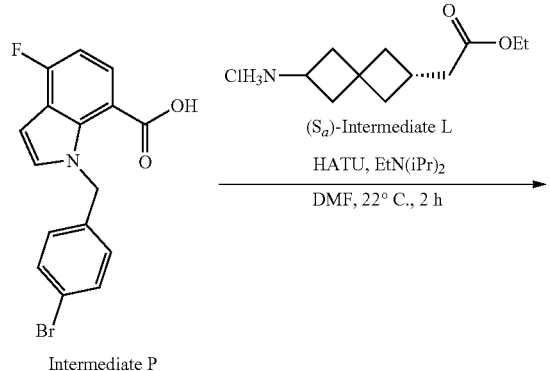
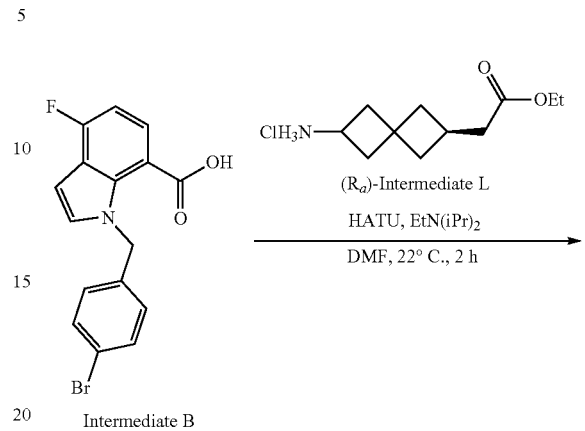
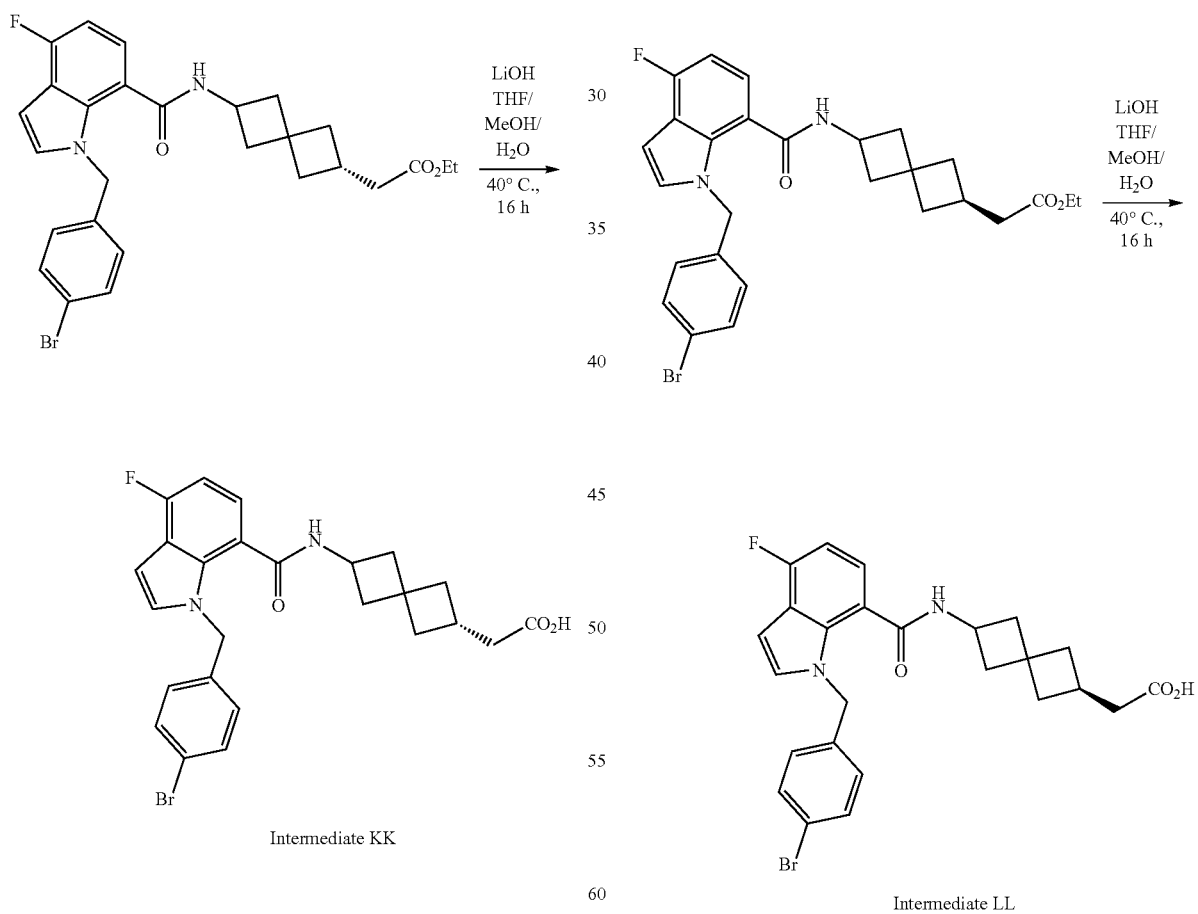

The title compound was prepared in a similar manner to Intermediate C but replacing (racemic)-methyl 2-aminospiro[3.3]heptane-6-carboxylate hydrochloride with (S$_a$)-ethyl 2-(6-aminospiro[3.3]heptan-2-yl)acetate hydrochloride (Intermediate (Sa)-L).

The title compound was prepared in a similar manner to Intermediate C but replacing (racemic)-methyl 2-aminospiro[3.3]heptane-6-carboxylate hydrochloride with (R$_a$)-Ethyl 2-(6-aminospiro[3.3]heptan-2-yl)acetate hydrochloride (Intermediate (Ra)-L).

Intermediate MM: Preparation of (S$_a$)-2-(6-(1-(4-Bromobenzyl)-4-chloro-1H-indazole-7-carboxamido)spiro[3.3]heptan-2-yl)acetic acid

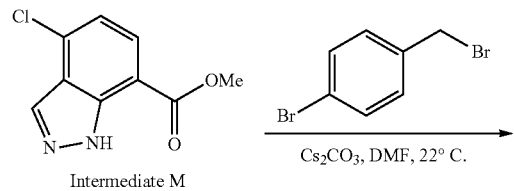
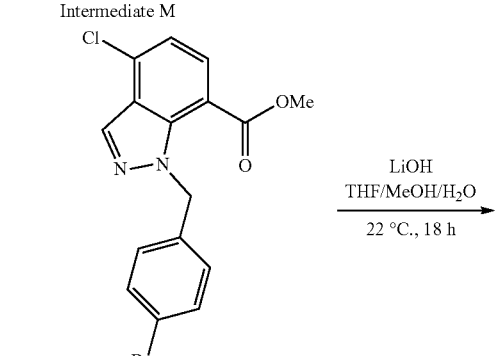
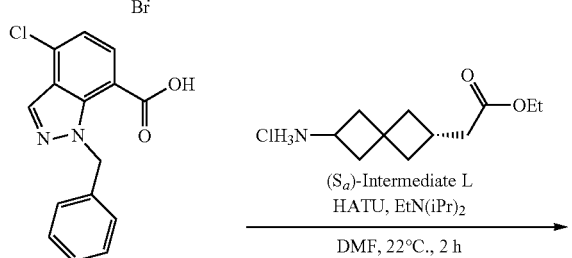
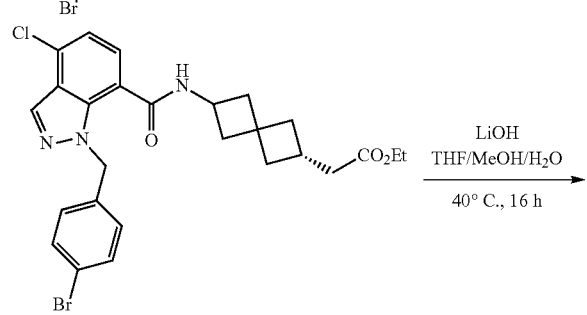
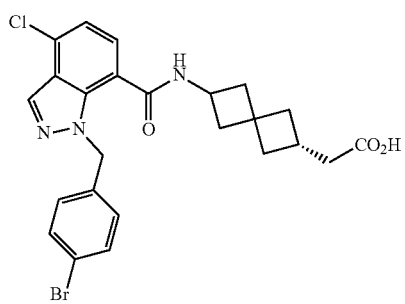

Intermediate MM

The title compound was prepared in a similar manner to Intermediate X but replacing 4-iodobenzyl bromide with 4-bromobenzyl bromide in Step 1 and replacing Intermediate F with Intermediate (S$_a$)-L in Step 3.

Intermediate NN: Preparation of (R$_a$)-2-(6-(1-(4-Bromobenzyl)-4-chloro-1H-indazole-7-carboxamido)spiro[3.3]heptan-2-yl)acetic acid

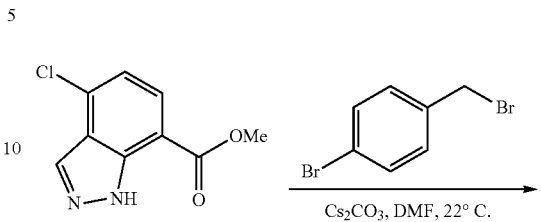
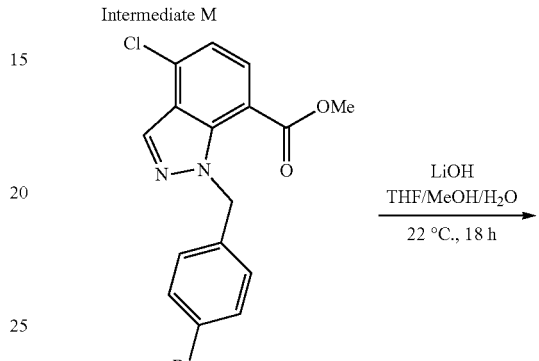
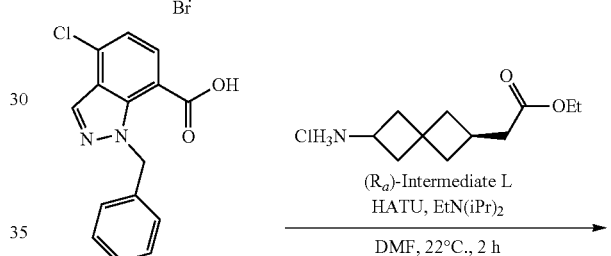
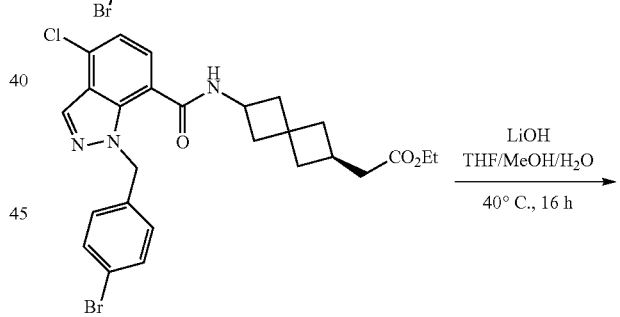
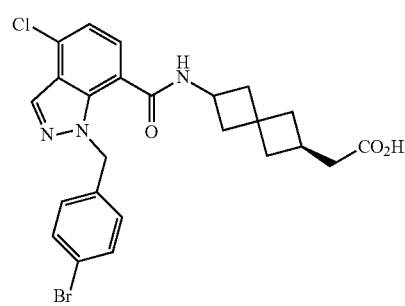

Intermediate NN

The title compound was prepared in a similar manner to Intermediate X but replacing 4-iodobenzyl bromide with 4-bromobenzyl bromide in Step 1 and replacing Intermediate F with Intermediate (R$_a$)-L in Step 3.

Intermediate OO: Preparation of (R$_a$)-2-(6-(1-(4-Bromobenzyl)-5-chloro-1H-indazole-7-carboxamido)spiro[3.3]heptan-2-yl)acetic acid

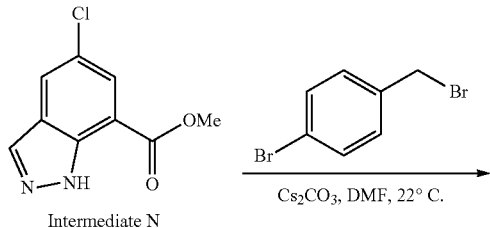

Intermediate N

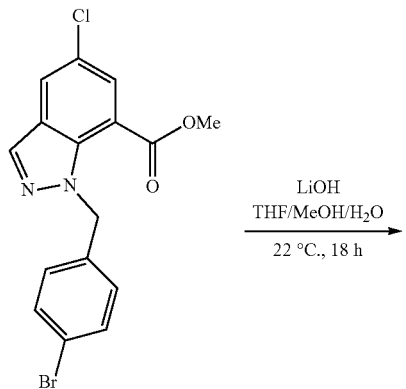

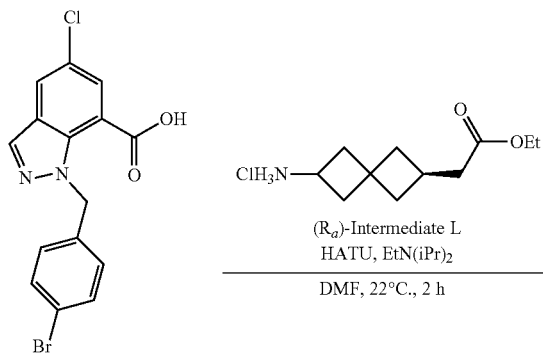

(R$_a$)-Intermediate L
HATU, EtN(iPr)$_2$
DMF, 22°C., 2 h

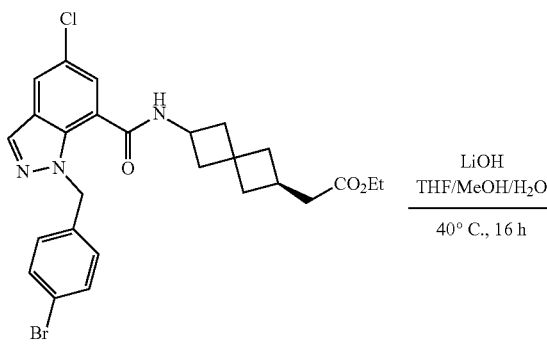

LiOH
THF/MeOH/H$_2$O
40° C., 16 h

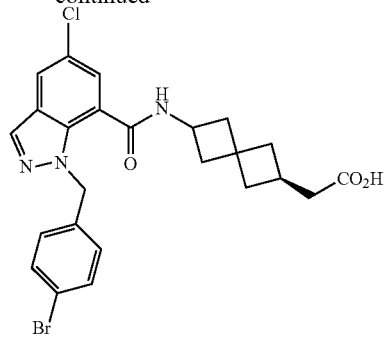

Intermediate OO

The title compound was prepared in a similar manner to Intermediate X but replacing Intermediate M with Intermediate N and replacing 4-iodobenzyl bromide with 4-bromobenzyl bromide in Step 1 and replacing Intermediate F with Intermediate (R$_a$)-L in Step 3.

Intermediate PP: Preparation of (S$_a$)-2-(6-(1-(4-Bromobenzyl)-5-chloro-1H-indazole-7-carboxamido)spiro[3.3]heptan-2-yl)acetic acid

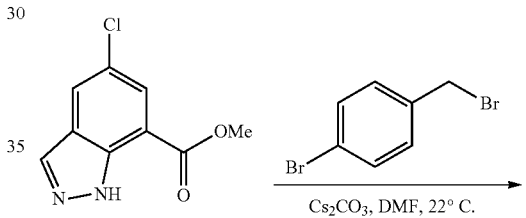

Intermediate N

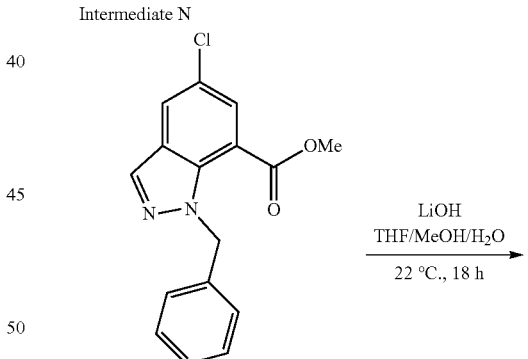

LiOH
THF/MeOH/H$_2$O
22 °C., 18 h

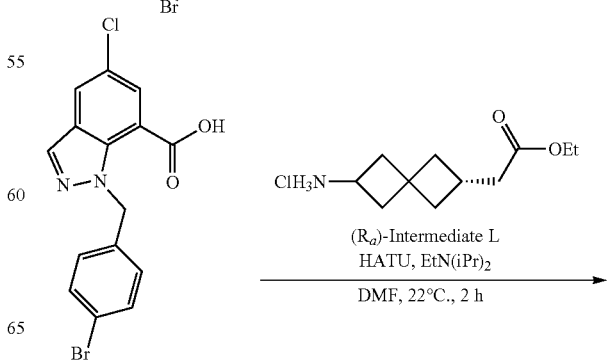

(R$_a$)-Intermediate L
HATU, EtN(iPr)$_2$
DMF, 22°C., 2 h

131

-continued

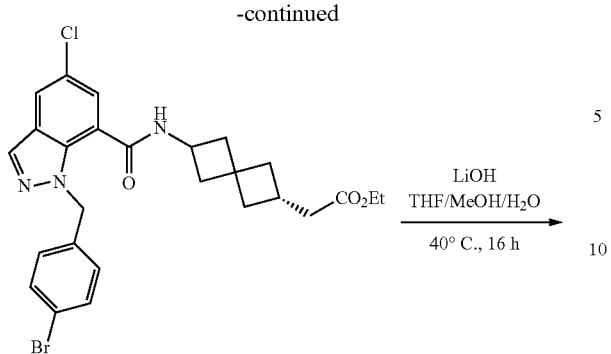

LiOH
THF/MeOH/H$_2$O
————————→
40° C., 16 h

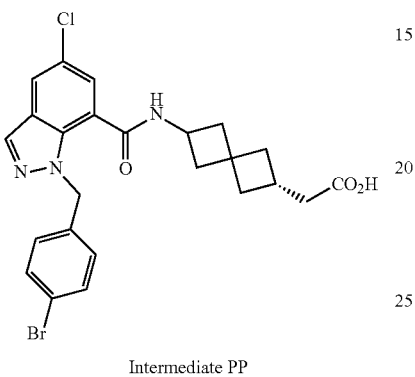

Intermediate PP

132

The title compound was prepared in a similar manner to Intermediate X but replacing Intermediate M with Intermediate N and replacing 4-iodobenzyl bromide with 4-bromobenzyl bromide in Step 1 and replacing Intermediate F with Intermediate (S$_a$)-L in Step 3.

Intermediate QQ: Preparation of (R$_a$)-2-(6-(4-Chloro-1-(4-(4,4,5,5-tetramethyl-1,3,2-dioxaborolan-2-yl)benzyl)-1H-indazole-7-carboxamido)spiro[3.3]heptan-2-yl)acetic acid

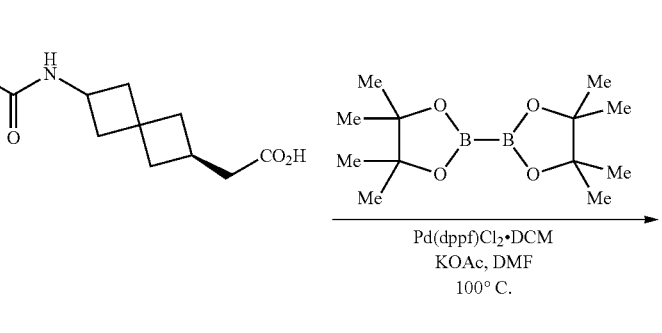

Intermediate NN

Pd(dppf)Cl$_2$•DCM
KOAc, DMF
100° C.

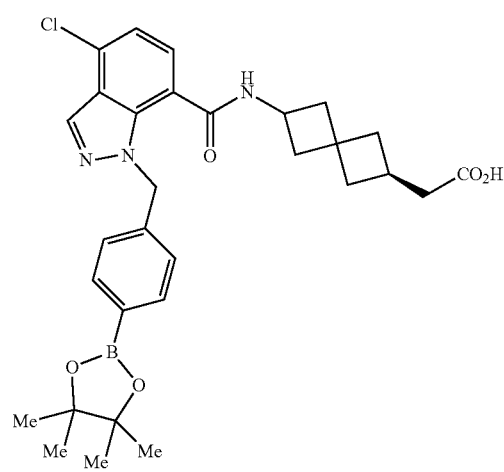

Intermediate QQ

The title compound was prepared in a similar manner to Intermediate E but replacing Intermediate C with Intermediate NN.

Intermediate RR: Preparation of $(R_a)$-2-(6-(4-fluoro-1-(4-(4,4,5,5-tetramethyl-1,3,2-dioxaborolan-2-yl)benzyl)-1H-indole-7-carboxamido)spiro[3.3]heptan-2-yl)acetic acid

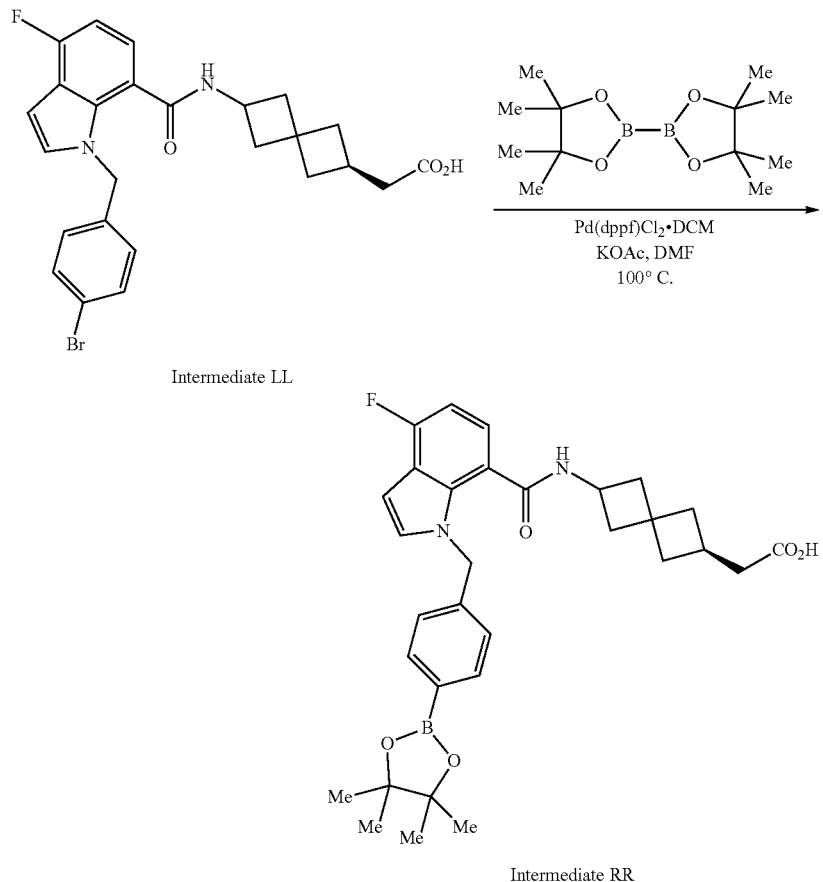

The title compound was prepared in a similar manner to Intermediate E but replacing Intermediate C with Intermediate LL.

Intermediate SS: Preparation of $(S_a)$-2-(6-(5-Chloro-1-(3-fluoro-4-iodobenzyl)-1H-indazole-7-carboxamido)spiro[3.3]heptan-2-yl)acetic acid

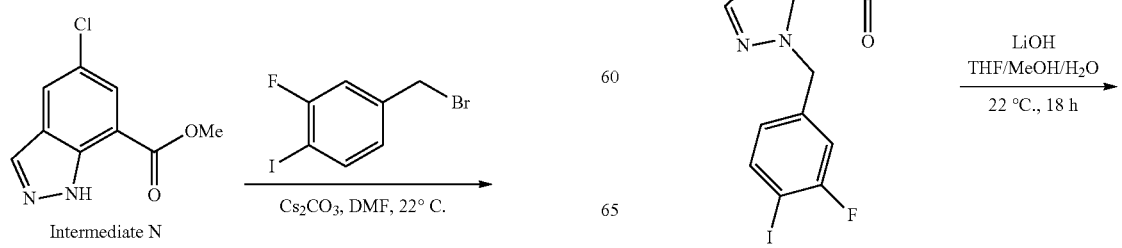

135

-continued

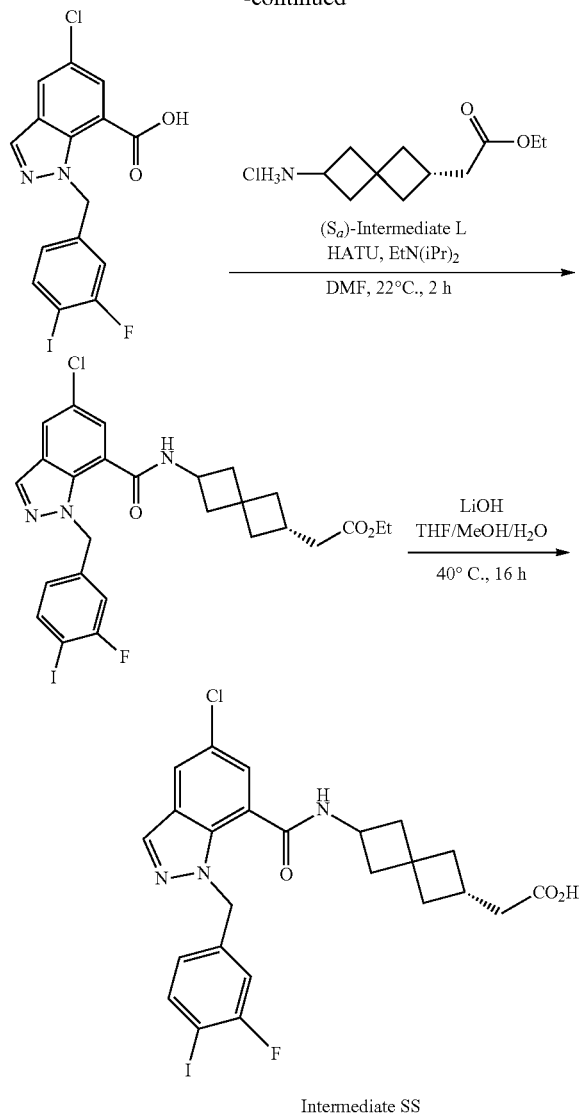

The title compound was prepared in a similar manner to Intermediate X but replacing Intermediate M with Intermediate N and replacing 4-iodobenzyl bromide with 3-fluoro-4-iodobenzyl bromide in Step 1 and replacing Intermediate F with Intermediate ($S_a$)-L in Step 3.

Intermediate TT: Preparation of ($R_a$)-2-(6-(5-Chloro-1-(3-fluoro-4-iodobenzyl)-1H-indazole-7-carboxamido)spiro[3.3]heptan-2-yl)acetic acid

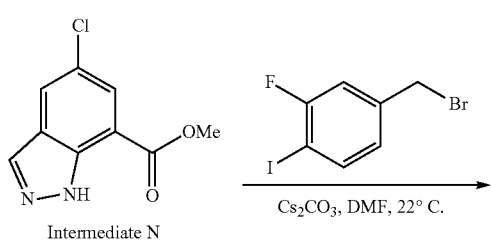

136

-continued

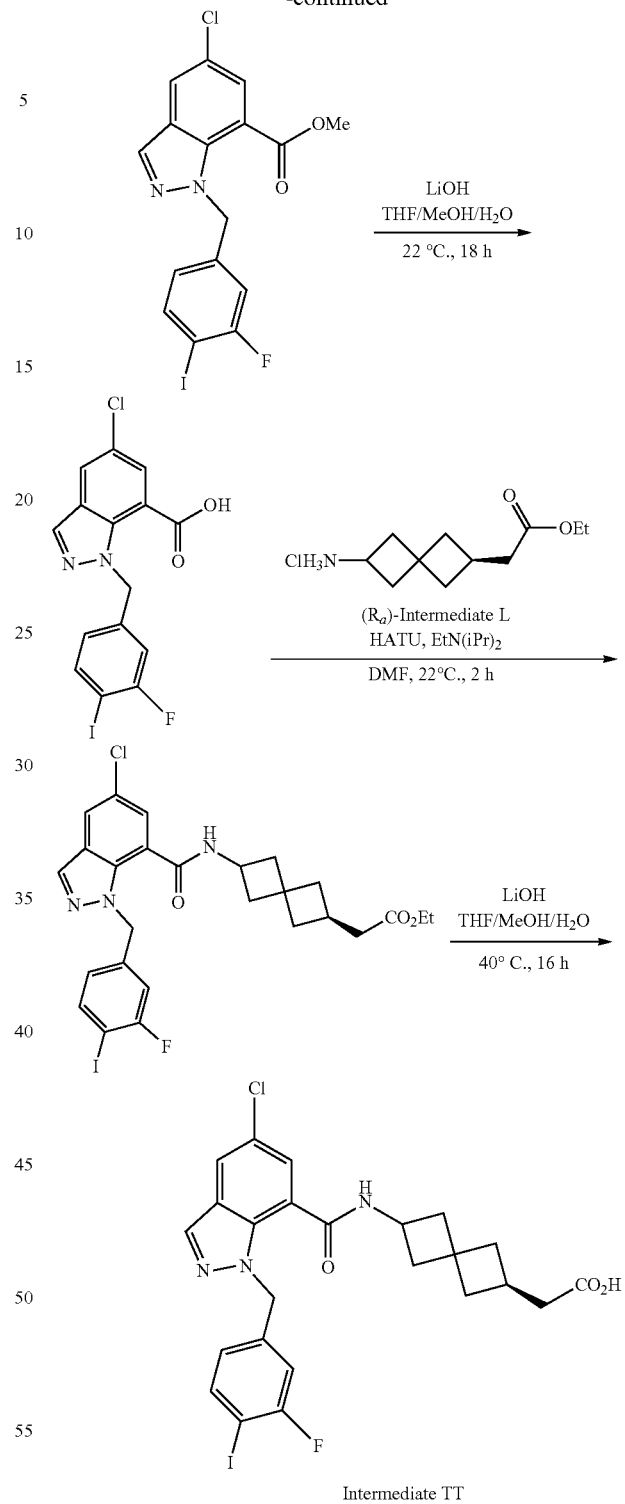

The title compound was prepared in a similar manner to Intermediate X but replacing Intermediate M with Intermediate N and replacing 4-iodobenzyl bromide with 3-fluoro-4-iodobenzyl bromide in Step 1 and replacing Intermediate F with Intermediate ($R_a$)-L in Step 3.

Intermediate UU: Preparation of (S$_a$)-6-(5-Chloro-1-(3-fluoro-4-iodobenzyl)-1H-indazole-7-carboxamido)spiro[3.3]heptane-2-carboxylic acid

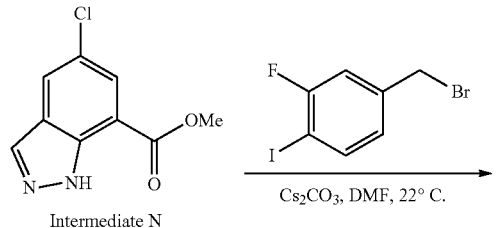

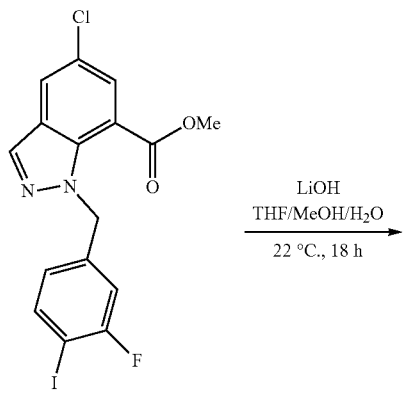

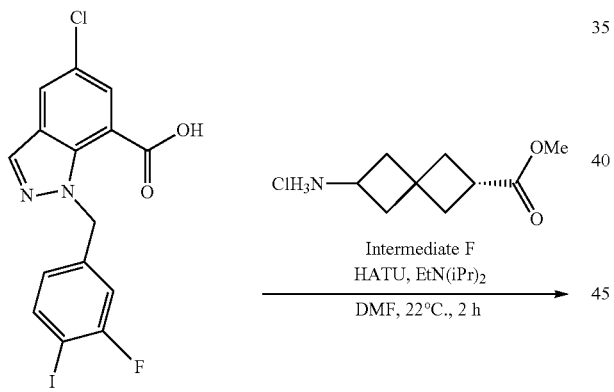

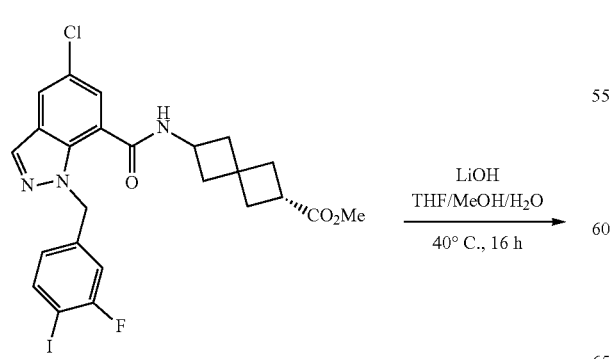

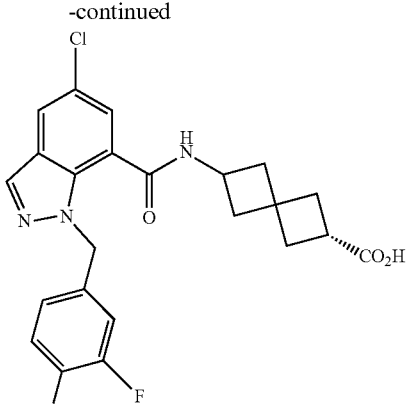

Intermediate UU

The title compound was prepared in a similar manner to Intermediate X but replacing Intermediate M with Intermediate N and replacing 4-iodobenzyl bromide with 3-fluoro-4-iodobenzyl bromide in Step 1.

Intermediate VV: Preparation of (S$_a$)-6-(1-(4-Bromo-2-fluorobenzyl)-5-chloro-1H-indazole-7-carboxamido)spiro[3.3]heptane-2-carboxylic acid

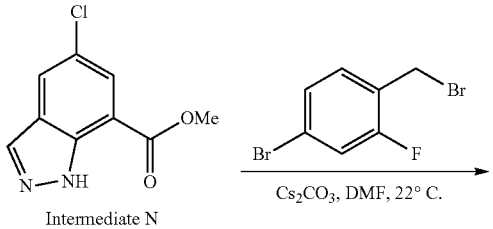

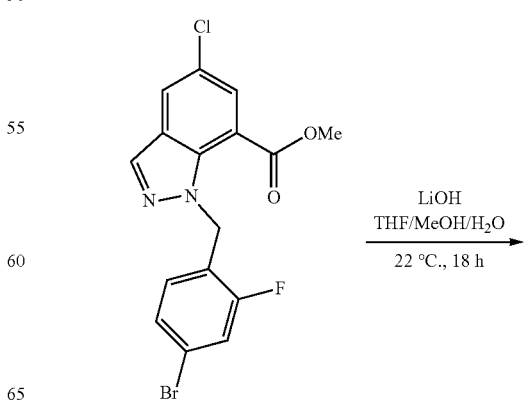

-continued

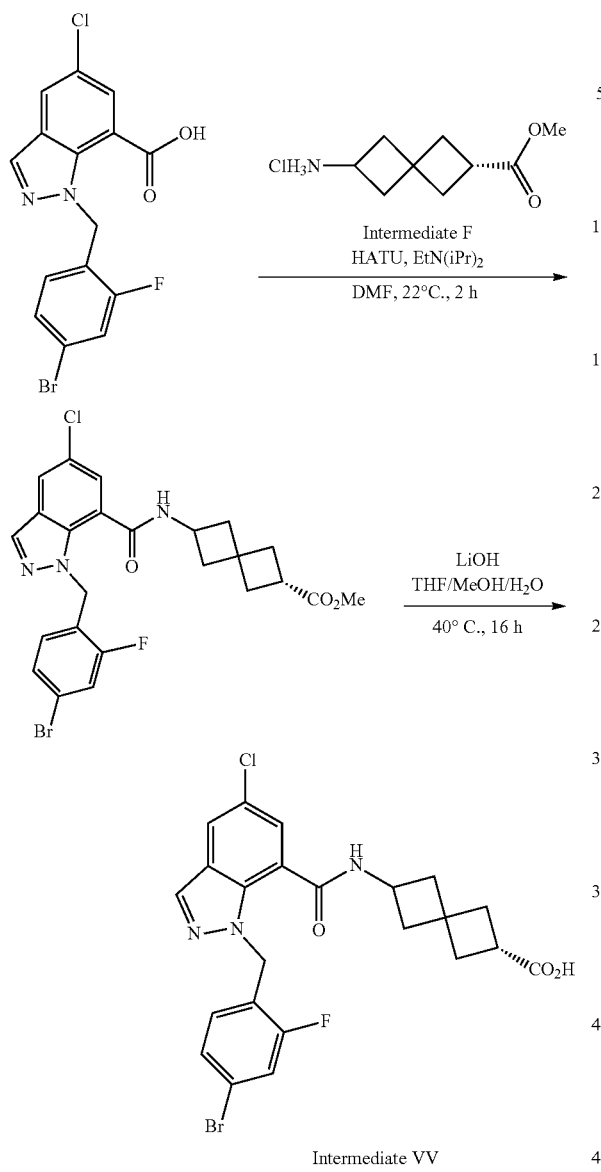

The title compound was prepared in a similar manner to Intermediate X but replacing Intermediate M with Intermediate N and replacing 4-iodobenzyl bromide with 4-bromo-2-fluorobenzyl bromide in Step 1.

Intermediate WW: Preparation of 1-(Bromomethyl-$d_2$)-4-iodobenzene-2,3,5,6-$d_4$

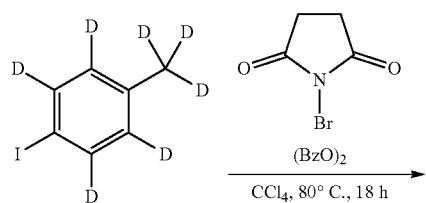

-continued

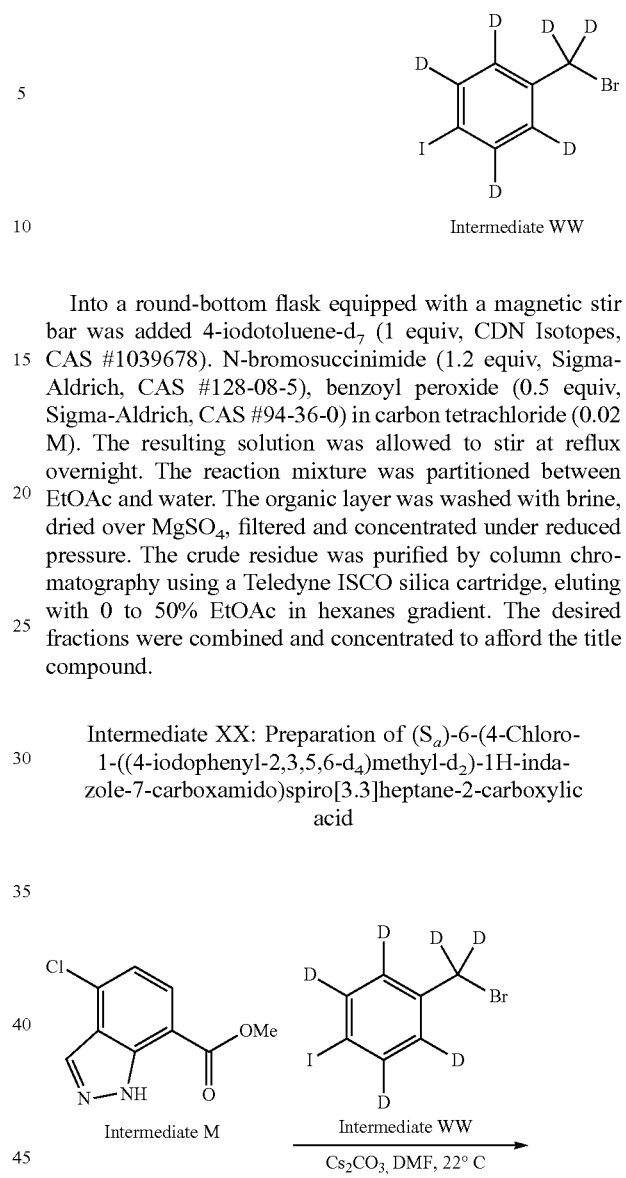

Into a round-bottom flask equipped with a magnetic stir bar was added 4-iodotoluene-$d_7$ (1 equiv, CDN Isotopes, CAS #1039678). N-bromosuccinimide (1.2 equiv, Sigma-Aldrich, CAS #128-08-5), benzoyl peroxide (0.5 equiv, Sigma-Aldrich, CAS #94-36-0) in carbon tetrachloride (0.02 M). The resulting solution was allowed to stir at reflux overnight. The reaction mixture was partitioned between EtOAc and water. The organic layer was washed with brine, dried over MgSO$_4$, filtered and concentrated under reduced pressure. The crude residue was purified by column chromatography using a Teledyne ISCO silica cartridge, eluting with 0 to 50% EtOAc in hexanes gradient. The desired fractions were combined and concentrated to afford the title compound.

Intermediate XX: Preparation of ($S_a$)-6-(4-Chloro-1-((4-iodophenyl-2,3,5,6-$d_4$)methyl-$d_2$)-1H-indazole-7-carboxamido)spiro[3.3]heptane-2-carboxylic acid

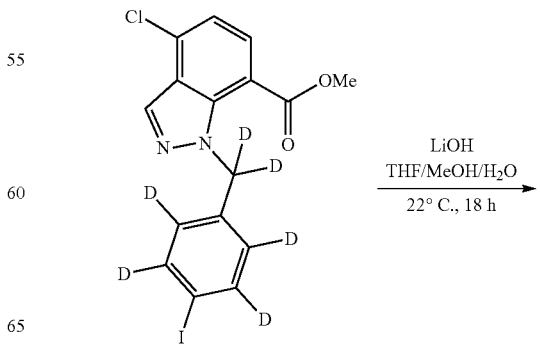

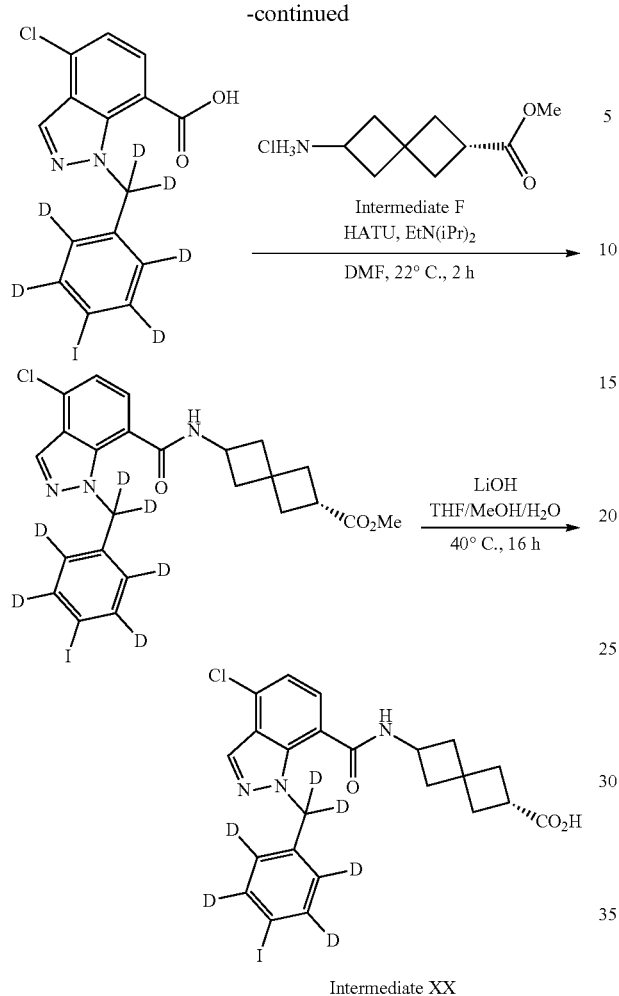

Intermediate XX

The title compound was prepared in a similar manner to Intermediate X but replacing Intermediate M with Intermediate N and replacing 4-iodobenzyl bromide with Intermediate WW in Step 1.

Intermediate YY: Preparation of methyl 1-([1,1'-biphenyl]-4-ylmethyl)-5-(difluoromethoxy)-1H-indazole-7-carboxylate

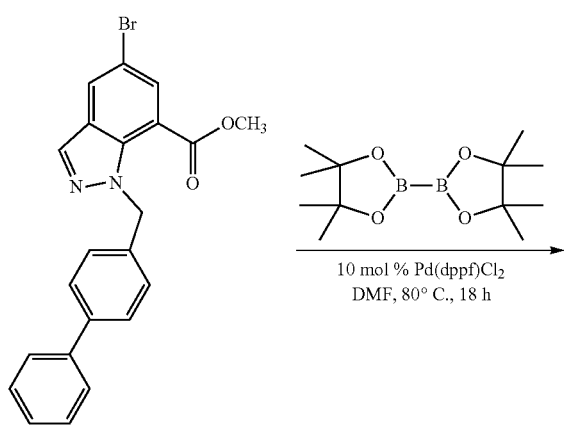

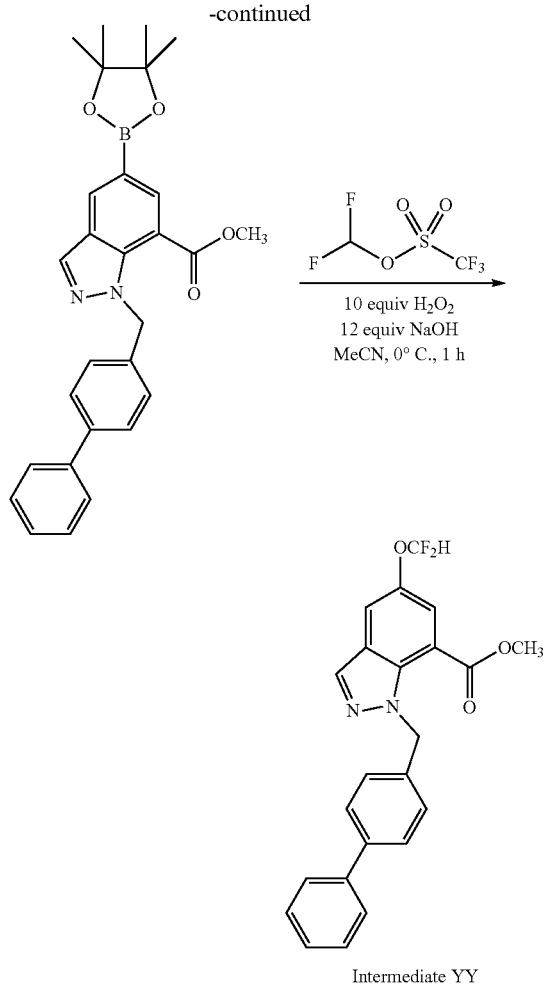

Intermediate YY

Step 1: Preparation of methyl 1-([1,1'-biphenyl]-4-ylmethyl)-5-bromo-1H-indazole-7-carboxylate This compound was prepared in similar manner to the first step of Intermediate A, but utilizing the commercially available methyl 5-bromo-1H-indazole-7-carboxylate and 4-(bromomethyl)-1,1'-biphenyl. The desired product was obtained as a white solid after purification by column chromatography through silica gel on the Teledyne ISCO Rf (gradient elution with 10% to 70% EtOAc in hexanes).

Step 2: Preparation of methyl 1-([1,1'-biphenyl]-4-ylmethyl)-5-(4,4,5,5-tetramethyl-1,3,2-dioxaborolan-2-yl)-1H-indazole-7-carboxylate Into a round-bottom flask equipped with a magnetic stirbar and under $N_2$ was added methyl 1-([1,1'-biphenyl]-4-ylmethyl)-5-bromo-1H-indazole-7-carboxylate (1.0 equiv), PdCl$_2$(dppf) catalyst (0.1 equiv), potassium acetate (3.0 equiv), bis(pinacoloto)diboron (1.5 equiv) and DMF (0.2 M). The resulting mixture was degassed with a steady flow of $N_2$ for 15 minutes and then heated to 80° C. for 18 h overnight. The reaction mixture was loaded onto a silica gel pre-cartridge and dried and purified by column chromatography through silica gel on the Teledyne ISCO Rf (gradient elution with 10% to 70% EtOAc in hexanes). The product containing fractions were dried under vacuum to afford a white solid (86% yield).

Step 3: Preparation of methyl 1-([1,1'-biphenyl]-4-ylmethyl)-5-(difluoromethoxy)-1H-indazole-7-carboxylate Into a round-bottom flask equipped with a magnetic stir bar was added methyl 1-([1,1'-biphenyl]-4-ylmethyl)-5-(4,4,5,5-tetramethyl-1,3,2-dioxaborolan-2-yl)-1H-indazole-7-carboxylate (1.0 equiv), MeCN (0.2 M) and hydrogen peroxide (30% in water, 10 equiv). The reaction mixture was stirred at room temperature for 15 minutes after which LCMS analysis reveals formation of the phenol product. The reaction mixture was concentrated to remove the MeCN and the aqueous mixture was poured into a Cl-phase separatory cartridge and extracted with CH$_2$Cl$_2$ (3×). The combined organic layers were concentrated under reduced pressure and the residue was diluted in 2:1 MeCN:water (0.3 M) and solid potassium hydroxide (12 equiv) was added and the mixture was stirred until a solution. At this stage, difluoromethyl triflate (3.0 equiv, CAS #1885-46-7) was added and the mixture was stirred at room temperature for 15 minutes. LCMS analysis of the mixture reveals product formation, but remaining phenol. The mixture was quenched with water (2-volumes) and concentrated under reduced pressure. The residue was poured into a Cl-phase separatory cartridge, extracted with CH$_2$Cl$_2$ (3×), and loaded onto a silica gel column. Purification by column chromatography through silica gel on the Teledyne ISCO Rf (gradient elution with 10% to 50% EtOAc in hexanes) afforded the desired product as a colourless oil (10% yield).

Intermediate ZZ: Preparation of Methyl 1-([1,1'-biphenyl]-4-ylmethyl)-4-(difluoromethoxy)-1H-indazole-7-carboxylate

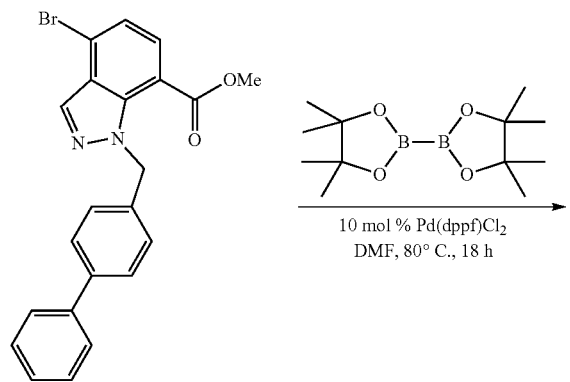

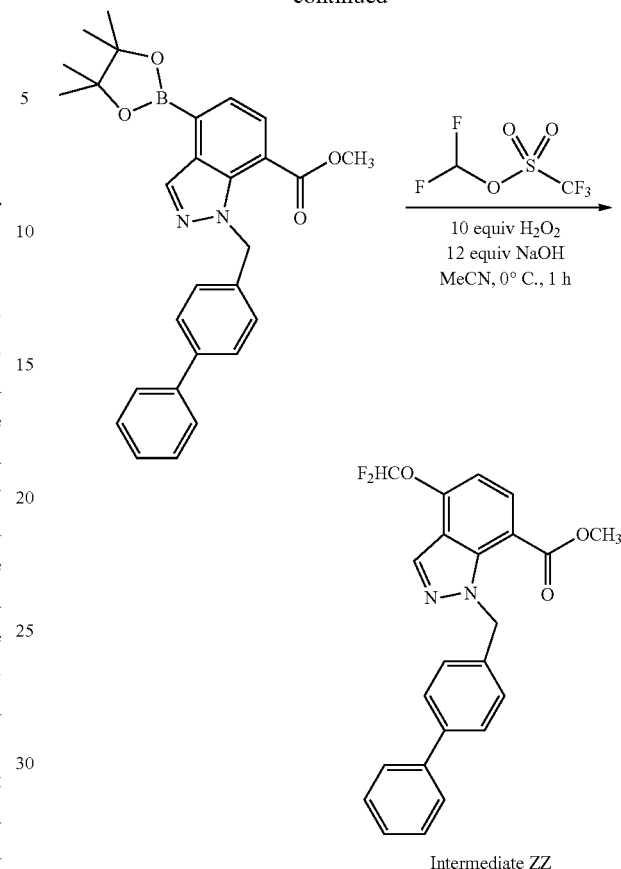

Intermediate ZZ

The title compound was prepared in a similar manner to Intermediate YY, but replacing methyl 1-([1,1'-biphenyl]-4-ylmethyl)-5-bromo-1H-indazole-7-carboxylate with methyl 1-([1,1'-biphenyl]-4-ylmethyl)-4-bromo-1H-indazole-7-carboxylate; which was made in a similar manner to the first step of Intermediate X, utilizing the commercially available methyl 4-bromo-1H-indazole-7-carboxylate and 4-(bromomethyl)-1,1'-biphenyl.

Intermediate aaa: Preparation of Methyl 1-([1,1'-biphenyl]-4-ylmethyl)-4-methoxy-1H-indazole-7-carboxylate

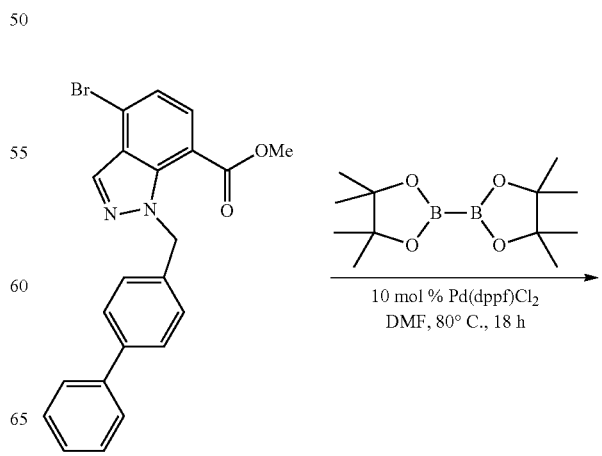

-continued

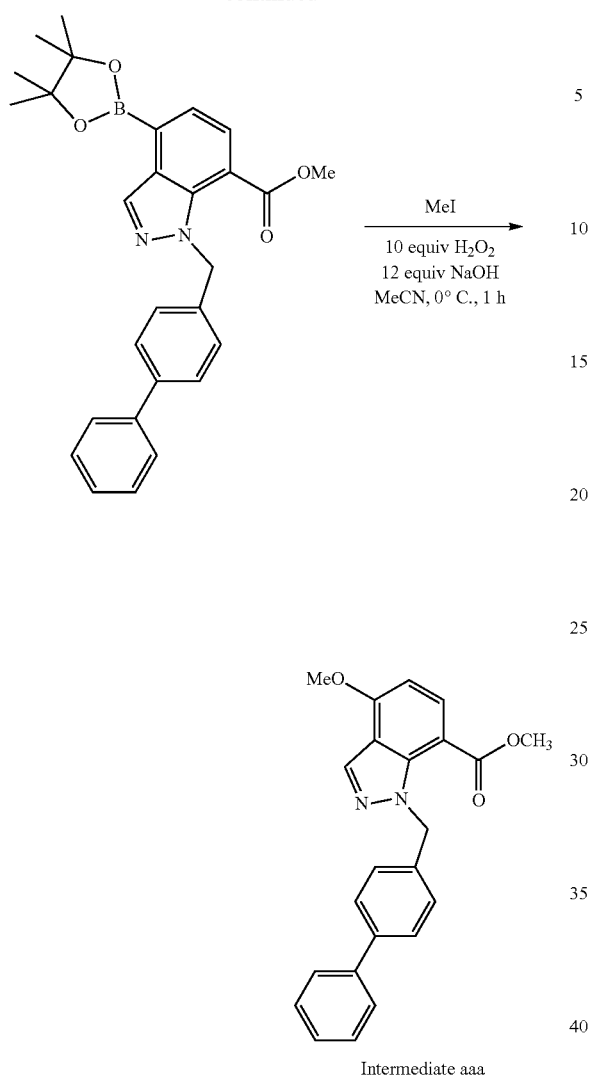

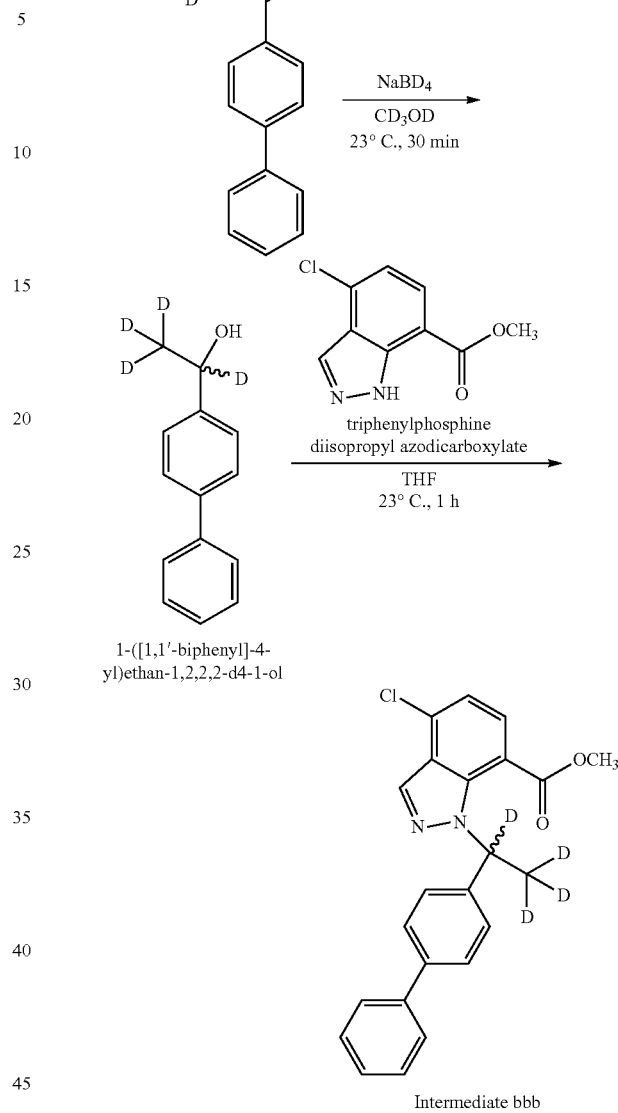

The title compound was prepared in a similar manner to Intermediate ZZ, but replacing difluoromethyl triflate with methyl iodide in Step 2.

Intermediate bbb: Preparation of methyl 1-(1-([1,1'-biphenyl]-4-yl)ethyl-1,2,2,2-$d_4$)-4-chloro-1H-indazole-7-carboxylate

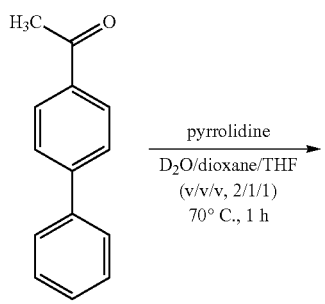

Step 1: Preparation of 1-([1,1'-biphenyl]-4-yl)ethan-1-one-2,2,2-$d_3$

Into a round-bottom flask equipped with a magnetic stirbar and under $N_2$ was added 1-(4-phenylphenyl)ethanone (1.0 equiv), pyrrolidine (0.1 equiv) and $D_2O$ (D, 99.96%, Cambridge Isotope Laboratories)/THF/dioxane (0.3 M, v/v/v=2/1/1). The resulting mixture was stirred at 70° C. for 1 h. LCMS indicated completion of reaction. The reaction mixture was loaded onto a silica gel pre-cartridge and dried and purified by column chromatography through silica gel on the Teledyne ISCO Rf (gradient elution with 10% to 70% EtOAc in hexanes). The product containing fractions were dried under vacuum to afford a white solid (96% yield).

Step 2: Preparation of 1-([1,1'-biphenyl]-4-yl)ethan-1,2,2,2-$d_4$-1-ol

Into a round-bottom flask equipped with a magnetic stirbar and under $N_2$ was added 2,2,2-trideuterio-1-(4-phenylphenyl)ethanone (1.0 equiv) and CD$_3$OD (0.5 M). NaBD$_4$ (1.5 equiv) was added portion-wise. The reaction mixture was loaded onto a silica gel pre-cartridge and dried and purified by column chromatography through silica gel on the Teledyne ISCO Rf (gradient elution with 0% to 100% EtOAc in hexanes). The product containing fractions were dried under vacuum to afford a white solid (98% yield).

Step 3: Preparation of methyl 1-(1-([1,1'-biphenyl]-4-yl)ethyl-1,2,2,2-d$_4$)-4-chloro-1H-indazole-7-carboxylate Into a reaction vail equipped with a magnetic stir bar was added 1-([1,1'-biphenyl]-4-yl)ethan-1,2,2,2-d$_4$-1-ol (1.5 equiv), methyl 4-chloro-1H-indazole-7-carboxylate (1.0 equiv), triphenylphosphine (1.3 equiv) and THF (0.3 M). The mixture was cooled over an ice bath, added diisopropyl azodicarboxylate (1.2 equiv) dropwise and stirred for 10 minutes as the reactants dissolved. After this time, the cooling bath was removed and the mixture was stirred for an additional 1 hour. LC-MS indicated completion of reaction. The reaction mixture was loaded onto a silica gel pre-cartridge and dried. Purification by column chromatography through silica gel on the Teledyne ISCO Rf (gradient elution with 0% to 80% EtOAc in hexanes) afforded the desired product (68% yield).

Intermediate ccc: Preparation of methyl 1-(1-([1,1'-biphenyl]-4-yl)ethyl-1,2,2,2-d$_4$)-1H-indazole-7-carboxylate

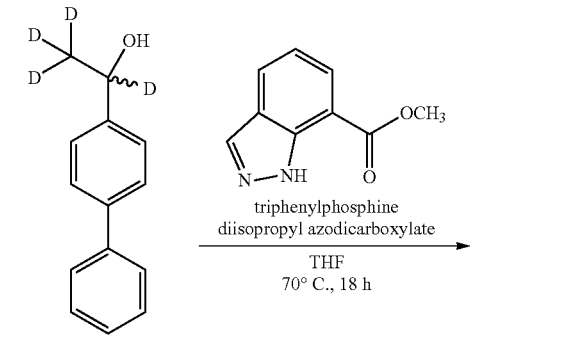

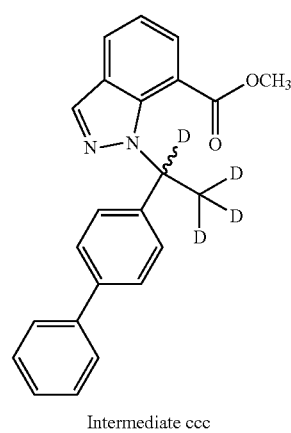

Intermediate ccc

Step 1: Preparation of methyl 1-(1-([1,1'-biphenyl]-4-yl)ethyl-1,2,2,2-d$_4$)-1H-indazole-7-carboxylate Into a reaction vail equipped with a magnetic stir bar was added 1-([1,1'-biphenyl]-4-yl)ethan-1,2,2,2-d$_4$-1-ol (1.5 equiv), methyl 1H-indazole-7-carboxylate (1.0 equiv), triphenylphosphine (1.3 equiv) and THF (0.3 M). The mixture was cooled over an ice bath, added diisopropyl azodicarboxylate (1.2 equiv) dropwise and stirred for 10 minutes as the reactants dissolved. After this time, the cooling bath was removed and the mixture was heated at 70° C. for 18 hours. LC-MS indicated completion of reaction. The reaction mixture was loaded onto a silica gel pre-cartridge and dried. Purification by column chromatography through silica gel on the Teledyne ISCO Rf (gradient elution with 0% to 60% EtOAc in hexanes) afforded the desired product (28% yield).

Intermediate ddd: Preparation of 2-Amino-5-chloro-4-fluoro-3-methylbenzoic acid

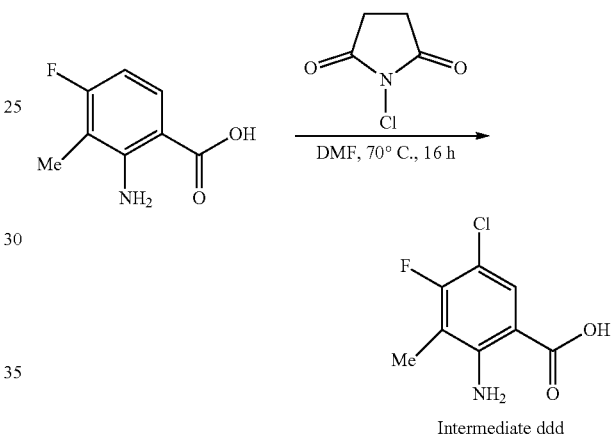

Intermediate ddd

To a solution of 2-amino-4-fluoro-3-methylbenzoic acid (1 equiv, Enamine, CAS #129833-28-9) in DMF (0.12 M) was added N-chlorosuccinimide (1 equiv, Sigma-Aldrich, CAS #128-09-6) at 22° C. The resulting solution was stirred and heated to 70° C. for 16 hours. LCMS analysis revealed product formation. The reaction mixture was partitioned between EtOAc and water. The organic layer was washed with brine, dried over MgSO$_4$, filtered and concentrated under reduced pressure. The crude residue was purified by column chromatography using a Teledyne ISCO silica cartridge, eluting with 0 to 100% EtOAc in hexanes gradient. The desired fractions were combined and concentrated to afford the title compound (58% yield).

Intermediate eee: Preparation of Methyl 5-chloro-4-fluoro-1H-indazole-7-carboxylate

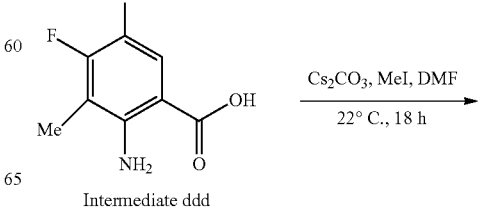

Intermediate ddd

-continued

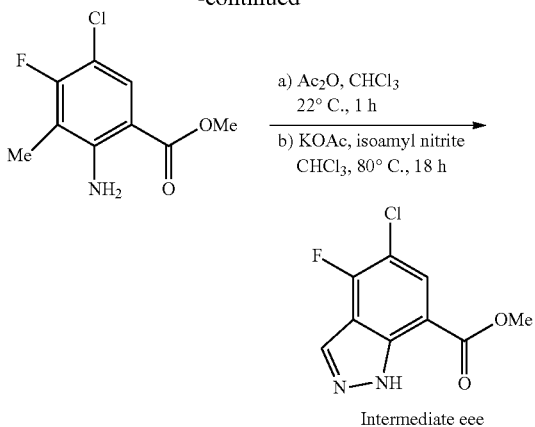

The title compound was prepared in a similar manner to Intermediate M replacing 2-amino-4-chloro-3-methylbenzoic acid with Intermediate ddd in Step 1.

Intermediate fff: Preparation of Methyl 4-chloro-1-(4-cyclobutyl-3-fluorobenzyl)-1H-indazole-7-carboxylate

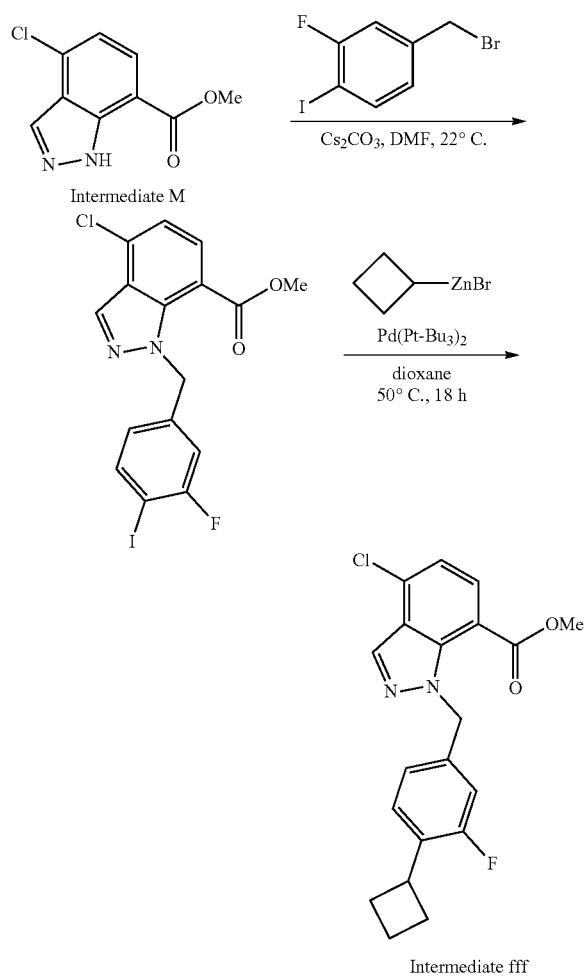

Step 1: Preparation of Methyl 4-chloro-1-(3-fluoro-4-iodobenzyl)-1H-indazole-7-carboxylate Prepared in a similar manner to Intermediate Y Step 1.

Step 2: Preparation of Methyl 4-chloro-1-(4-cyclobutyl-3-fluorobenzyl)-1H-indole-7-carboxylate Into a round-bottom flask equipped with a magnetic stir bar was added methyl 4-chloro-1-(3-fluoro-4-iodobenzyl)-1H-indazole-7-carboxylate (I equiv) and Bis(tri-tert-butylphosphine)palladium(0) (0.1 equiv. Apollo Scientific. CAS #53199-31-8) in dioxane (0.06 M). The resulting suspension was sub-surface purged with nitrogen gas for ten minutes and then charged with cyclobutylzinc bromide (1.5 equiv, 0.5M in THF, Rieke Metals, CAS #1019205-65-2). The flask was sealed and stirred overnight at 50° C. LCMS analysis revealed lots of remaining starting material. Added another portion of catalyst, subsurface purged with $N_2$ gas, added 2.5 equiv of zincate, stirred overnight at 50° C. LCMS analysis revealed good product formation. The reaction mixture was partitioned between EtOAc and 1 N HCl. The organic layer was washed with 1N NaOH, brine, dried over $MgSO_4$, filtered and concentrated under reduced pressure. The crude residue was purified by column chromatography using a Teledyne ISCO silica cartridge, eluting with 0 to 50% EtOAc in hexanes gradient. The desired fractions were combined and concentrated to afford the title compound.

Intermediate ggg: Preparation of $(S_a)$-6-(1-(1-(4-Bromophenyl)ethyl)-5-chloro-1H-indazole-7-carboxamido)spiro[3.3]heptane-2-carboxylic acid

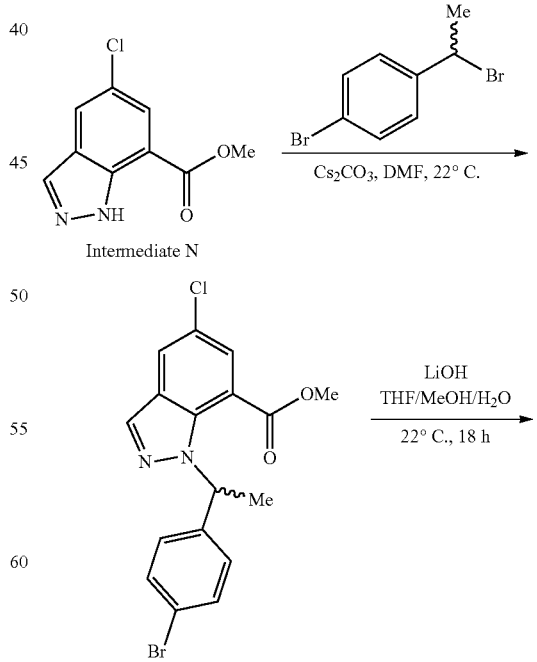

151
-continued

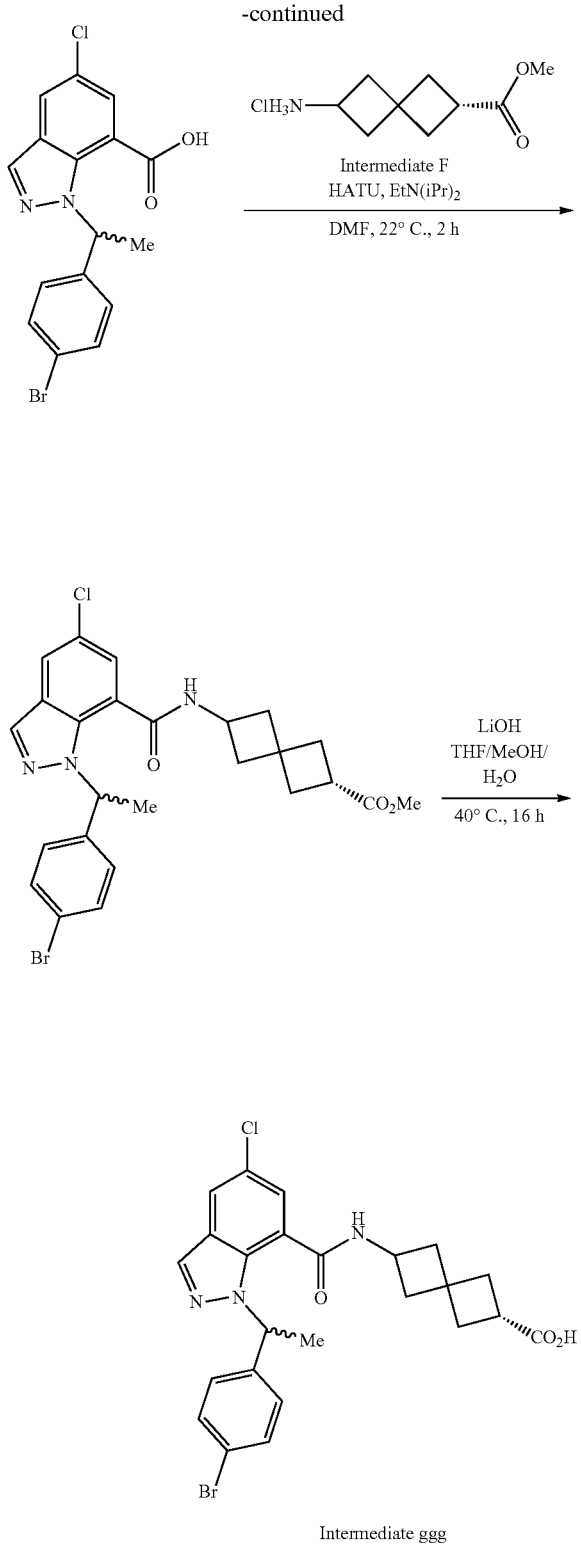

The title compound was prepared in a similar manner to Intermediate X but replacing Intermediate M with Intermediate N and 4-iodobenzyl bromide with 1-bromo-4-(1-bromoethyl)benzene (Combi-Blocks, CAS #159755-11-0) in Step 1.

152
Example 1

Preparation of (racemic)-6-(4-Fluoro-1-(4-(trifluoromethoxy)benzyl)-1H-indole-7-carboxamido)spiro[3.3]heptane-2-carboxylic acid

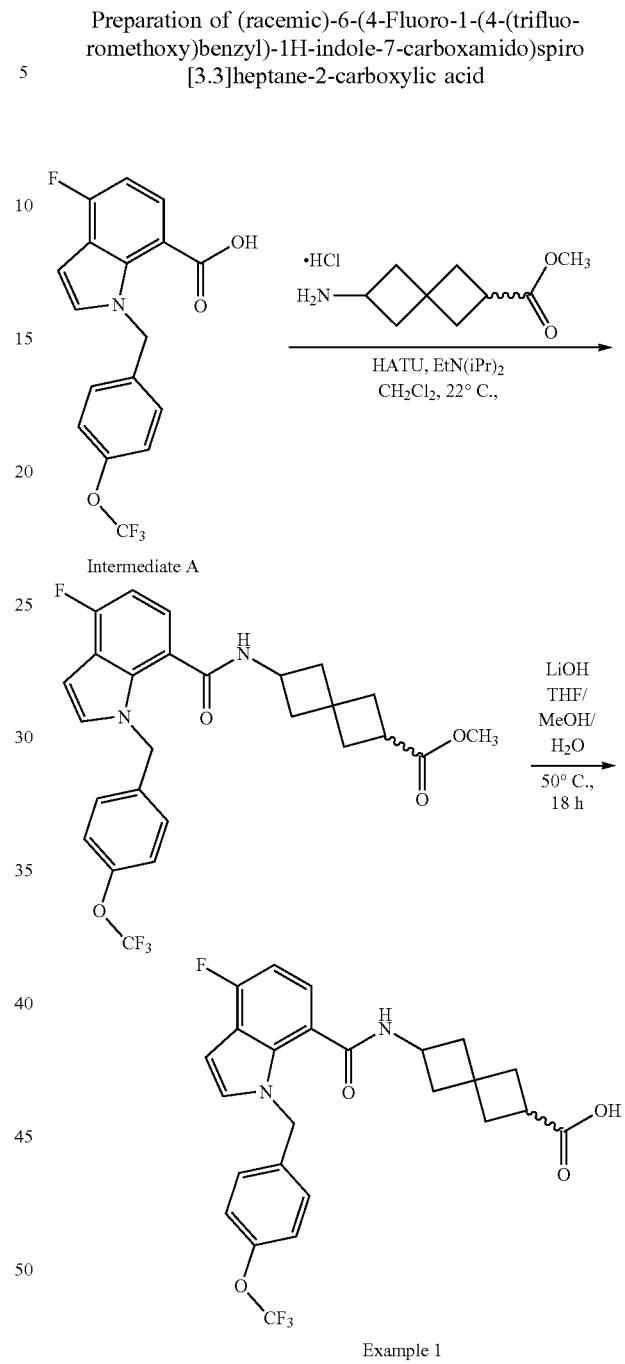

Step 1: Preparation of (racemic)-methyl 6-(4-fluoro-1-(4-(trifluoromethoxy)benzyl)-1H-indole-7-carboxamido)spiro[3.3]heptane-2-carboxylate Into a sample vial equipped with a magnetic stir bar and under $N_2$ was added Intermediate A (1.0 equiv), HATU (1.2 equiv), (racemic)-methyl 6-aminospiro[3.3]heptane-2-carboxylate hydrochloride salt (1.1 equiv, Enamine, CAS #1808249-67-3) and dichloromethane (0.25 M). The suspension was stirred at 22° C. for 10 minutes, then treated with Hünig's base (3.0 equiv) and stirred at 22° C. for 2 hours. LCMS analysis after this time revealed complete conversion of starting material. The reaction mixture was quenched with sat. aqueous NH₄Cl solution and poured into a Cl-phase separatory cartridge and extracted with CH₂Cl₂ (3×). The combined organic layers were concentrated and loaded directly onto a silica gel pre-cartridge and dried. Purification by column chromatography through silica gel, using an automated Teledyne ISCO Rf machine, eluting with 5% to 75% EtOAc in hexanes as a gradient over 20 minutes. The desired fractions were combined, concentrated under reduced pressure and dried under vacuum to afford a white solid (77% yield). LCMS (ESI+): 505 (M+1)⁺.

Step 2: Preparation of (racemic)-6-(4-fluoro-1-(4-(trifluoromethoxy)benzyl)-1H-indole-7-carboxamido)spiro[3.3]heptane-2-carboxylic acid To a solution of methyl 6-(4-fluoro-1-(4-(trifluoromethoxy)benzyl)-1H-indole-7-carboxamido)spiro[3.3]heptane-2-carboxylate in MeOH (0.4 M) and THF (0.4 M) was added a 1.0 M aqueous LiOH solution (2.5 equiv). The solution was heated to 50° C. on a heating block for 18 h overnight. The resulting solution was cooled to 22° C., quenched with 10% aqueous citric acid solution (5 mL) and poured into a Cl-phase separatory cartridge. The aqueous layer was extracted with CH₂Cl₂ (3×) and the combined organic layers were concentrated under reduced pressure. Purification by reverse-phase column chromatography using a C18 cartridge on an automated Teledyne ISCO Rf machine, eluting with 5% to 80% acetonitrile in water+0.1% formic acid as a gradient over 20 minutes. The desired fractions were combined, concentrated and dried under vacuum to afford a white solid (71% yield). ¹H NMR (400 MHz, d₆-DMSO) δ 12.01 (bs, 1H), 8.43 (d, J=7.5 Hz, 1H), 7.62 (d, J=3.5 Hz, 1H), 7.20 (d, J=8.5 Hz, 2H), 7.07 (dd, J=8.0, 5.5 Hz, 1H), 6.92 (d, J=8.5 Hz, 2H), 6.83 (dd, J=10.0, 8.0 Hz, 1H), 6.66 (d, J=3.5 Hz, 1H), 5.60 (s, 2H), 4.14-4.08 (m, 1H), 2.92-2.83 (m, 1H), 2.25-2.07 (m, 6H), 1.98-1.66 (m, 2H). LCMS (ESI+): 491 (M+1)⁺.

The following compounds were prepared in a similar manner to Example 1, substituting 4-trifluoromethoxybenzyl bromide with a series of commercially available benzyl bromides in the preparation of Intermediate A. Example 5 was prepared in a similar manner to Example 1, substituting 4-trifluoromethoxybenzyl bromide with Intermediate G.

| Example | Structure and Name | MW | MS (ESI⁺) |
|---|---|---|---|
| Example 2 | 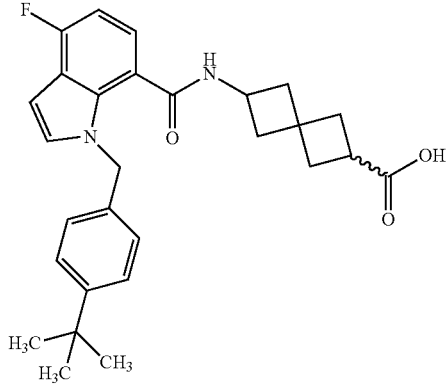 [SMILES: CC(C)(C)c1ccc(Cn2ccc3c(F)ccc(C(=O)NC4CC5(C4)CC(C(=O)O)C5)c32)cc1]<br>(racemic)-6-(1-(4-(tert-butyl)benzyl)-4-fluoro-1H-indole-7-carboxamido)spiro[3.3]heptane-2-carboxylic acid | 462.56 | 463 (M + 1)⁺ |
| Example 3 | 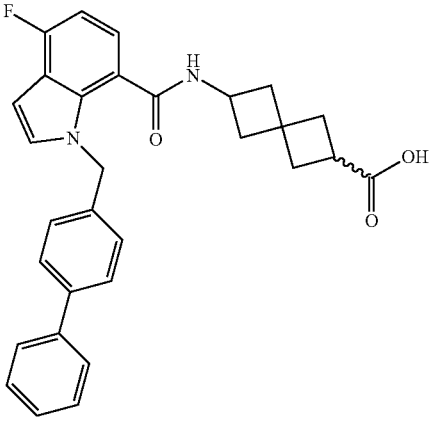 [SMILES: O=C(NC1CC2(C1)CC(C(=O)O)C2)c1ccc(F)c2ccn(Cc3ccc(-c4ccccc4)cc3)c12]<br>(racemic)-6-(1-([1,1'-biphenyl]-4-ylmethyl)-4-fluoro-1H-indole-7-carboxamido)spiro[3.3]heptane-2-carboxylic acid | 482.56 | 483 (M + 1)⁺ |

| Example | Structure and Name | MW | MS (ESI+) |
|---|---|---|---|
| Example 4 | 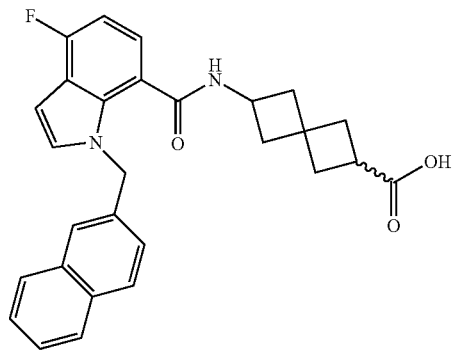 [SMILES: O=C(NC1CC2(C1)CC(C(=O)O)C2)c1ccc(F)c2ccn(Cc3ccc4ccccc4c3)c12]<br>(racemic)-6-(4-fluoro-1-(naphthalen-2-ylmethyl)-1H-indole-7-carboxamido)spiro[3.3]heptane-2-carboxylic acid | 456.52 | 457 (M + 1)+ |
| Example 5 | 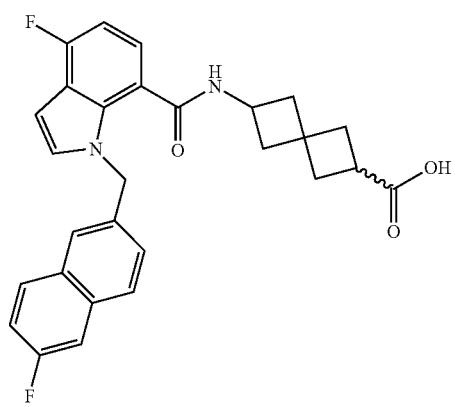 [SMILES: O=C(NC1CC2(C1)CC(C(=O)O)C2)c1ccc(F)c2ccn(Cc3ccc4cc(F)ccc4c3)c12]<br>(racemic)-6-(4-fluoro-1-((6-fluoronaphthalen-2-yl)methyl)-1H-indole-7-carboxamido)spiro[3.3]heptane-2-carboxylic acid | 474.51 | 475 (M + 1)+ |

Example 6

Preparation of (racemic)-6-(4-bromo-1-(4-(tert-butyl)benzyl)-1H-indole-7-carboxamido)spiro[3.3]heptane-2-carboxylic acid

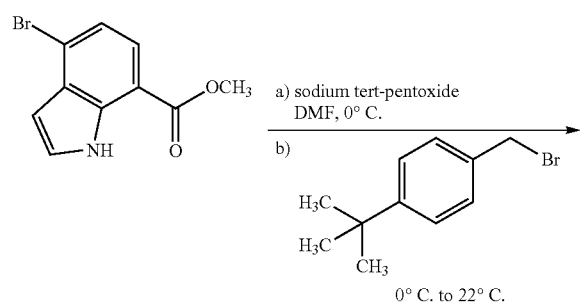

-continued

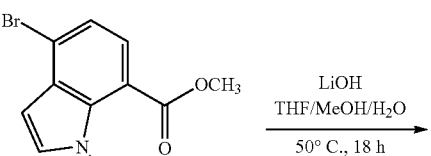

157
-continued
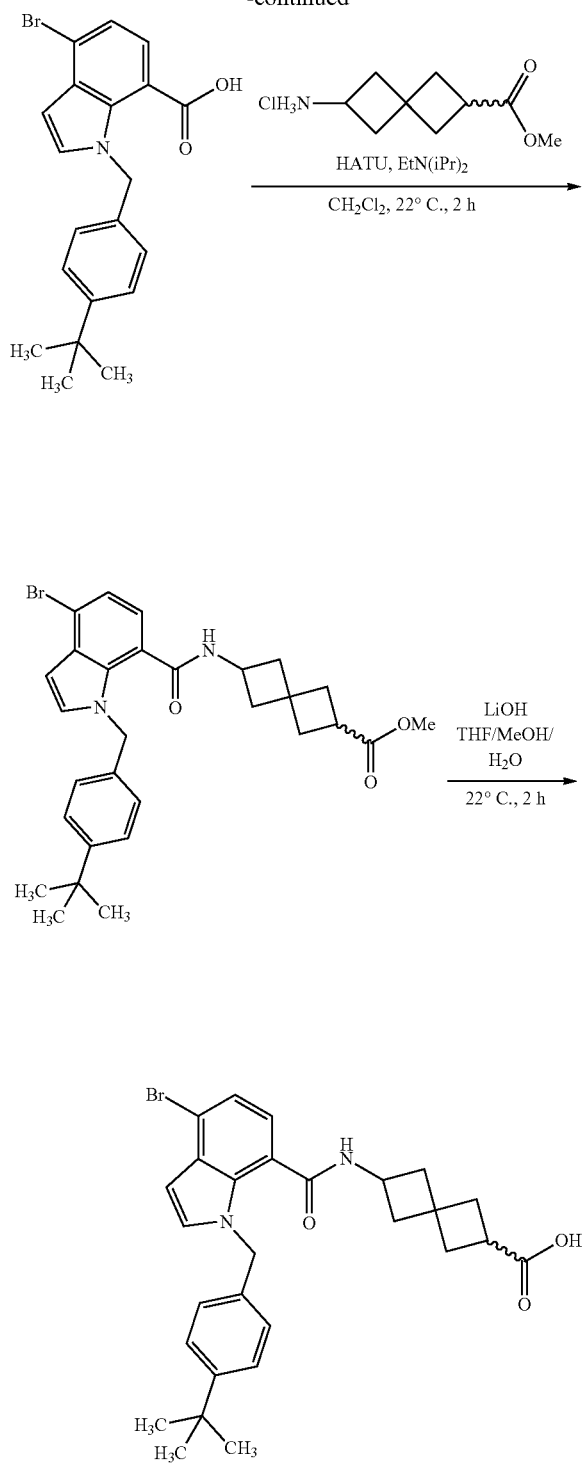
158
Example 7
Preparation of (racemic)-6-(1-(4-(tert-Butyl)benzyl)-4-chloro-1H-indole-7-carboxamido)spiro[3.3]heptane-2-carboxylic acid
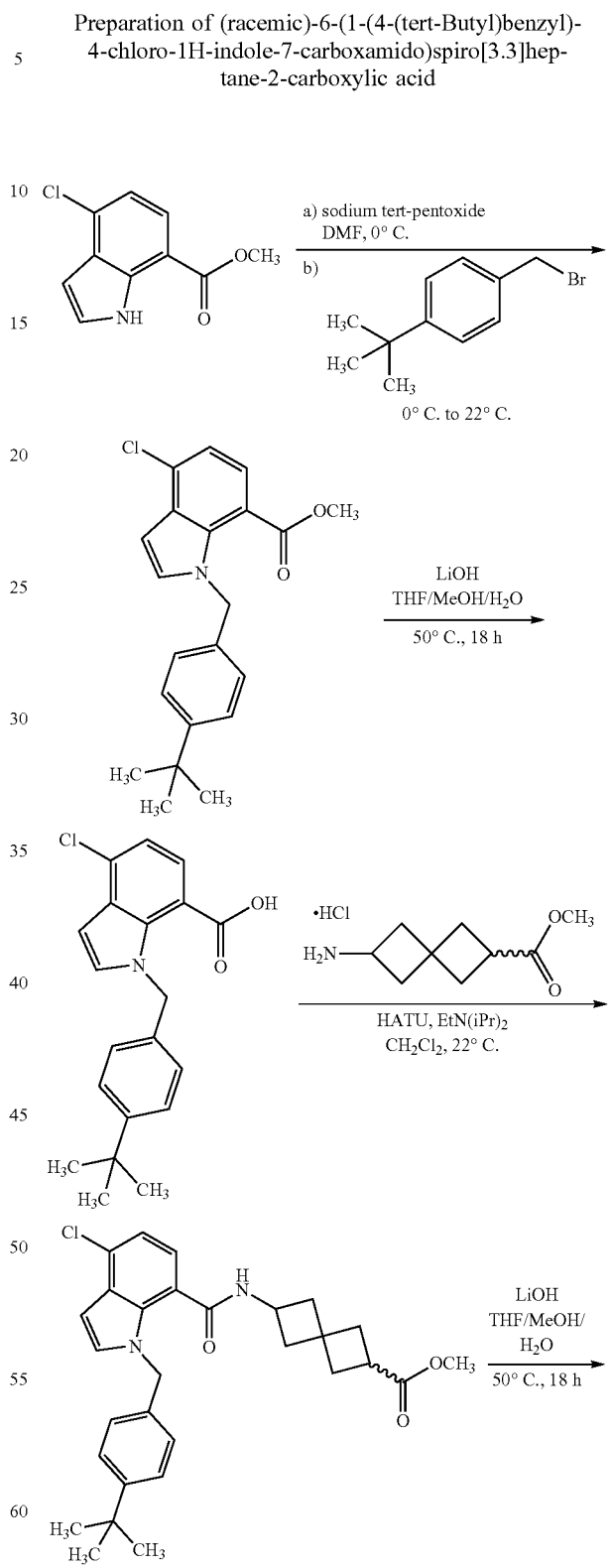
Example 6
The title compound was prepared in a similar manner to Intermediate B and C, steps 1-3, replacing methyl 4-fluoro-1H-indole-7-carboxylate with methyl 4-bromo-1H-indole-7-carboxylate (Ark Pharm, CAS #1224724-39-3) in step 1 of Intermediate B. LCMS (ESI+): 523/525 (M+1)⁺.

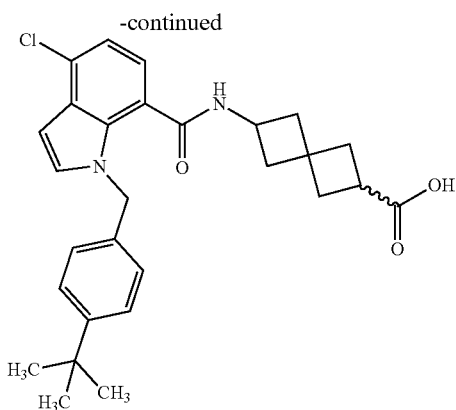

Example 7

Step 1: Preparation of methyl 1-(4-(tert-butyl)benzyl)-4-chloro-1H-indole-7-carboxylate Into a sample vial equipped with a magnetic stir bar and under $N_2$ was added methyl 4-chloro-1H-indole-7-carboxylate (1.0 equiv, Enamine, CAS #1427413-45-3), sodium tert-pentoxide (1.5 equiv) and DMF (0.4 M). The solution was cooled to 0° C. in an ice bath and treated with 4-tert-butylbenzyl bromide (1.2 equiv, Aldrich, CAS #18880-00-7) and the mixture was allowed to warm to 22° C. for 18 hours overnight. The reaction mixture was quenched with sat. aqueous $NH_4Cl$ solution and poured into a Cl-phase separatory cartridge and extracted with $CH_2Cl_2$ (3×). The combined organic layers were concentrated and loaded directly onto a silica gel pre-cartridge and dried. Purification by column chromatography through silica gel, using an automated Teledyne ISCO Rf machine, eluting with 0% to 50% EtOAc in hexanes as a gradient over 25 minutes. The desired fractions were combined, concentrated under reduced pressure and dried under vacuum to afford a clear oil (29% yield). LCMS (ESI+): 355 (M+1)$^+$.

Step 2: Preparation of 1-(4-tert-butyl)benzyl)-4-chloro-1H-indole-7-carboxylic acid A solution of methyl 1-(4-(tert-butyl)benzyl)-4-chloro-1H-indole-7-carboxylate (1.0 equiv) in a mixture of THF (0.4 M) and MeOH (0.4 M) was treated with 1.0 M aqueous LiOH solution (2.5 equiv) and heated on an aluminum block to 50° C. for 18 hours. The resulting solution was cooled to 22° C. and quenched with 10% aqueous citric acid solution (5 mL) and poured into a Cl-phase separatory cartridge. The aqueous layer was extracted with $CH_2Cl_2$ (3×) and the combined organic layers were concentrated under reduced pressure. Purification by reverse-phase column chromatography using a C18 cartridge on an automated Teledyne ISCO Rf machine, eluting with 5% to 70% acetonitrile in water+0.1% formic acid as a gradient over 25 minutes. The desired fractions were combined, concentrated and dried under vacuum to afford a white solid (94% yield).

Step 3: Preparation of (racemic)-methyl 6-(1-(4-(tert-butyl)benzyl)-4-chloro-1H-indole-7-carboxamido)spiro[3.3]heptane-2-carboxylate Into a 20 mL sample vial equipped with a magnetic stir and under $N_2$ was added 1-(4-(tert-butyl)benzyl)-4-chloro-1H-indole-7-carboxylic acid (1.0 equiv), HATU (1.2 equiv) and dichloromethane (0.3 M). The solution was stirred at 22° C. for 10 minutes and then treated with (racemic)-methyl 6-aminospiro[3.3]heptane-2-carboxylate hydrochloride salt (1.1 equiv, Enamine, CAS #1808249-67-3) and then Hünig's base (3.0 equiv) and stirred at 22° C. for 2 hours. LCMS analysis after this time revealed complete conversion of starting material. The reaction mixture was quenched with sat. aqueous $NH_4Cl$ solution and poured into a Cl-phase separatory cartridge and extracted with $CH_2Cl_2$ (3×). The combined organic layers were concentrated and loaded directly onto a silica gel pre-cartridge and dried. Purification by column chromatography through silica gel, using an automated Teledyne ISCO Rf machine, eluting with 0% to 40% EtOAc in hexanes as a gradient over 25 minutes. The desired fractions were combined, concentrated under reduced pressure and dried under vacuum to afford an off-white solid (96% yield). LCMS (ESI+): 493 (M+1)$^+$.

Step 4: Preparation of (racemic)-6-(1-(4-(tert-butyl)benzyl)-4-chloro-1H-indole-7-carboxamido)spiro[3.3]heptane-2-carboxylic acid Into a 20 mL sample vial equipped with a magnetic stir bar and under $N_2$ was added methyl 6-(1-(4-(tert-butyl)benzyl)-4-chloro-1H-indole-7-carboxamido)spiro[3.3]heptane-2-carboxylate (1.0 equiv), THF (0.4 M) and MeOH (0.4 M). The solution was treated with 1.0 M aqueous LiOH solution (2.5 equiv) and heated to 50° C. for 18 h using an aluminum block. The reaction mixture was quenched with 10% aqueous citric acid solution (2 mL) and concentrated under reduced pressure. The residue was loaded onto a C18 pre-cartridge and dried under vacuum. Purification by reverse-phase column chromatography using a C18 cartridge on an automated Teledyne ISCO Rf machine, eluting with 5% to 70% acetonitrile in water+0.1% formic acid as a gradient over 20 minutes. The desired fractions were combined, concentrated and dried under vacuum to afford the title compound as a white solid (70% yield). $^1$H NMR (400 MHz, $d_6$-DMSO) δ 12.02 (s, 1H), 8.50 (d, J=7.5 Hz, 1H), 7.65 (d, J=3.0 Hz, 1H), 7.21 (d, J=8.0 Hz, 2H), 7.12-7.04 (m, 2H), 6.80 (d, J=8.0 Hz, 2H), 6.61 (d, J=3.0 Hz, 1H), 5.49 (s, 2H), 4.16 (apparent pentet, J=8.0 Hz, 1H), 2.92-2.84 (m, 1H), 2.29-1.94 (m, 6H), 1.82-1.71 (m, 2H), 1.19 (s, 9H). LCMS (ESI+): 479 (M+1)$^+$.

Example 8

Preparation of ($S_a$)-6-(4-Fluoro-1-(4-(trifluoromethoxy)benzyl)-1H-indole-7-carboxamido)spiro[3.3]heptane-2-carboxylic acid (Second Eluting Enantiomer)

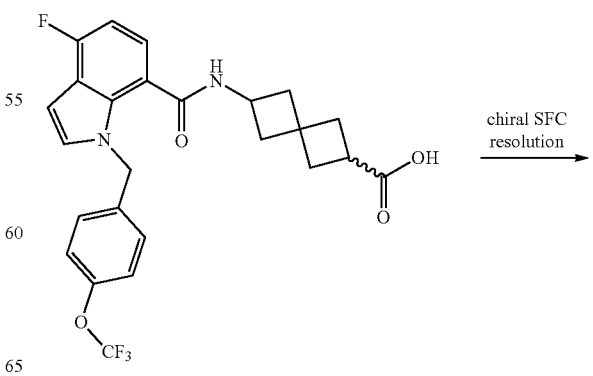

chiral SFC resolution →

Example 1

161

-continued

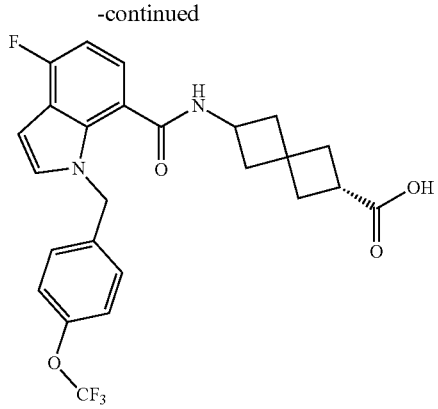

Example 8

The compound Example 1 was resolved into both enantiomers using chiral SFC. The enantiomers were separated using a 5 μm ChiralPac IC column (10×250 mm), eluting with 30% iPrOH at a flow rate of 10 mL/min over 15 minutes, maintaining a column temperature of 35° C. The first eluting peak had a retention time of 7.4 minutes and the second eluting enantiomer at 9.9 minutes. The second eluting enantiomer, Example 8, was determined to be the more active enantiomer. LCMS (ESI+): 491 (M+1)$^+$.

Alternate procedure to prepare Example 8: (S$_a$)-6-(4-fluoro-1-(4-(trifluoromethoxy)benzyl)-1H-indole-7-carboxamido)spiro[3.3]heptane-2-carboxylic acid (second eluting enantiomer) using chiral Intermediate F.

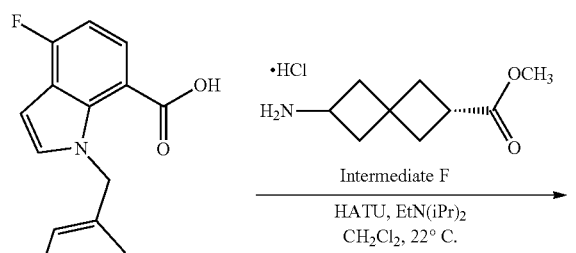

Intermediate A

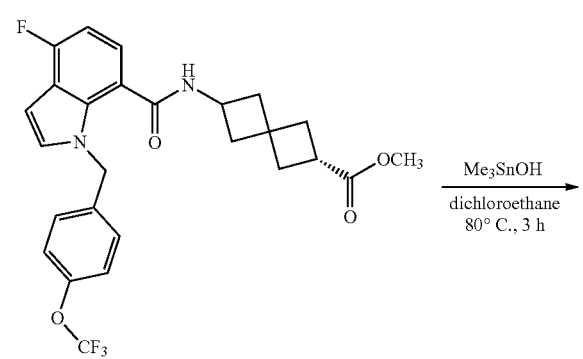

162

-continued

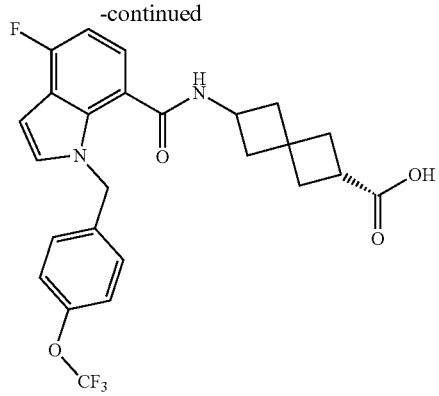

Example 8

Step 1: Preparation of (S$_a$)-methyl 6-(4-fluoro-1-(4-(trifluoromethoxy)benzyl)-1H-indole-7-carboxamido)spiro[3.3]heptane-2-carboxylate Into a sample vial equipped with a magnetic stir bar and under N$_2$ was added Intermediate A (1.0 equiv), HATU (1.2 equiv), first eluting enantiomer Intermediate F (1.2 equiv) and dichloromethane (0.25 M). The suspension was stirred at 22° C. for 10 minutes, treated with Hunig's base (3.0 equiv) and stirred at 22° C. for 2 hours. LCMS analysis after this time revealed complete conversion of starting material. The reaction mixture was quenched with sat. aqueous NH$_4$Cl solution and poured into a Cl-phase separatory cartridge and extracted with CH$_2$Cl$_2$ (3). The combined organic layers were concentrated and loaded directly onto a silica gel pre-cartridge and dried under vacuum. Purification by column chromatography through silica gel, using an automated Teledyne ISCO Rf machine, eluting with 5% to 75% EtOAc in hexanes as a gradient over 20 minutes. The desired fractions were combined, concentrated under reduced pressure and dried under vacuum to afford the title compound as a white solid (90% yield). LCMS (ESI+): 505 (M+1)$^+$.

Step 2: Preparation of (S$_a$)-6-(4-fluoro-1-(4-(trifluoromethoxy)benzyl)-1H-indole-7-carboxamido)spiro[3.3]heptane-2-carboxylic acid A solution of (S$_a$)-methyl 6-(4-fluoro-1-(4-(trifluoromethoxy)benzyl)-1H-indole-7-carboxamido)spiro[3.3] heptane-2-carboxylate (1 equiv), trimethyltin hydroxide (5.0 equiv, Alfa, CAS #56-24-6) and dichloroethane (0.2 M) was heated to 80° C. in an oil bath for 3 hours. The resulting solution was cooled to 22° C. and quenched with 10% aqueous citric acid solution and poured into a Cl-phase separatory cartridge. The aqueous layer was extracted with CH$_2$Cl$_2$ (3×) and the combined organic layers were concentrated under reduced pressure. Purification by reverse-phase column chromatography using a C18 cartridge on an automated Teledyne ISCO Rf machine, eluting with 5% to 80% acetonitrile in water+0.1% formic acid as a gradient over 20 minutes. The desired fractions were combined, concentrated and dried under vacuum to afford the title compound as a white solid (70% yield). LCMS (ESI+): 491 (M+1)$^+$. Chiral SFC analysis revealed no epimerization had occurred and the material maintained an enantiopurity of >99%.

Example 9

Preparation of (S$_a$)-6-(1-([1,1'-Biphenyl]-4-ylmethyl)-4-fluoro-1H-indole-7-carboxamido)spiro[3.3]heptane-2-carboxylic acid (Second Eluting Enantiomer)

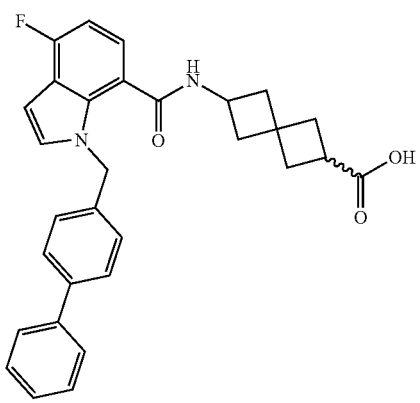

Example 3 chiral SFC resolution

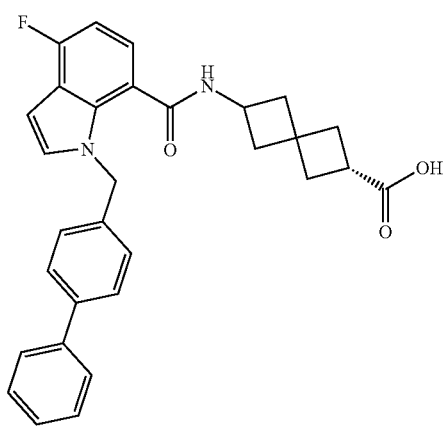

Example 9

The racemic compound, Example 3, was resolved into both enantiomers using chiral SFC. The enantiomers were separated using a 5 μm ChiralPac OJ column (10×250 mm), eluting with 55% MeOH at a flow rate of 10 mL/min over 10 minutes, maintaining a column temperature of 35° C. The first eluting peak had a retention time of 4.1 minutes and the second eluting enantiomer at 5.3 minutes. The second eluting enantiomer, Example 9, was determined to be the more active enantiomer. $^1$H NMR (400 MHz, d$_6$-DMSO) δ 12.05 (s, 1H), 8.49 (d, J=7.5 Hz, 1H), 7.65 (d, J=7.5 Hz, 1H), 7.55 (d, J=8.0 Hz, 2H), 7.49 (d, J=8.0 Hz, 2H), 7.41 (t, J=7.5 Hz, 2H), 7.31 (t, J=7.5 Hz, 1H), 7.08 (dd, J=8.0, 5.5 Hz, 1H), 6.97 (d, J=8.0 Hz, 2H), 6.85-6.80 (m, 1H), 6.66 (d, J=3.0 Hz, 1H), 5.60 (s, 2H), 4.25-4.15 (m, 1H), 2.92-2.84 (m, 1H), 2.37-2.17 (m, 2H), 2.21-2.10 (m, 2H), 2.07-1.89 (m, 2H), 1.82-1.74 (m, 2H). LCMS (ESI+): 483 (M+1)$^+$.

Example 10

Preparation of (racemic)-6-(4-Fluoro-1-((2-fluoro-[1,1'-biphenyl]-4-yl)methyl)-1H-indole-7-carboxamido)spiro[3.3]heptane-2-carboxylic acid

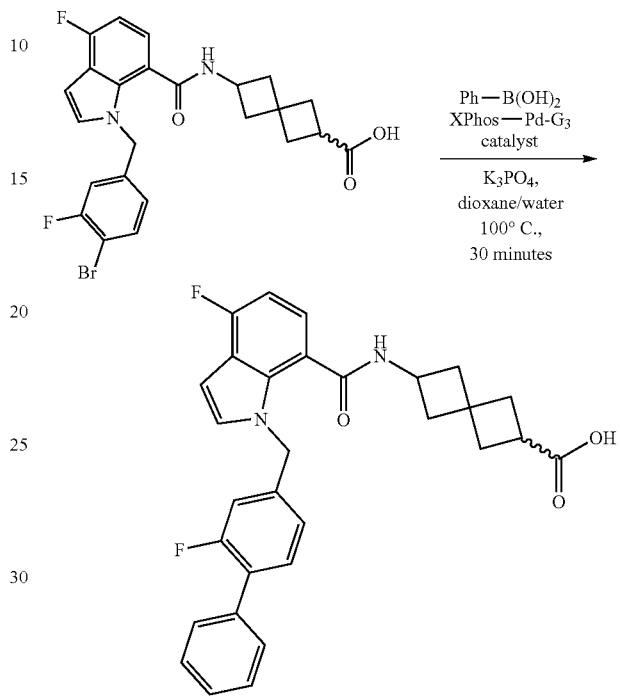

Example 10

Steps 1-4: Preparation of (racemic)-6-(1-(4-bromo-3-fluorobenzyl)-4-fluoro-1H-indole-7-carboxamido)spiro[3.3]heptane-2-carboxylic acid Prepared in a similar manner to Intermediate B and C using 1-bromo-4-(bromomethyl)-2-fluorobenzene (Aldrich, CAS #76283-09-5) in place of 4-bromobenzyl bromide in step 1 of Intermediate B.

Step 5: Preparation of (racemic)-6-(4-fluoro-1-((2-fluoro-[1,1'-biphenyl]-4-yl)methyl)-1H-indole-7-carboxamido)spiro[3.3]heptane-2-carboxylic acid Into a microwave vial equipped with a magnetic stir bar was added (racemic)-6-(1-(4-bromo-3-fluorobenzyl)-4-fluoro-1H-indole-7-carboxamido)spiro[3.3]heptane-2-carboxylic acid (1.0 equiv), XPhos-Pd-G3 catalyst (0.02 equiv. Strem, CAS #1445085-55-1), phenylboronic acid (1.5 equiv), potassium phosphate (3.0 equiv) and dioxane:water (10:1, 0.3 M). The vial was sealed and purged with a steady flow of N$_2$ for 15 minutes. The vial was heated in a microwave reactor at 100° C. for 30 minutes, cooled to room temperature and loaded directly onto a C18 silica gel pre-cartridge and dried under vacuum. Purification by reverse-phase column chromatography using a C18 cartridge on an automated Teledyne ISCO Rf machine, eluting with 5% to 80% acetonitrile in water+0.1% formic acid as a gradient over 20 minutes. The desired fractions were combined,

Example 11

Preparation of (racemic)-6-(4-Fluoro-1-(4-(pyridin-4-yl)benzyl)-1H-indole-7-carboxamido)spiro[3.3]heptane-2-carboxylic acid

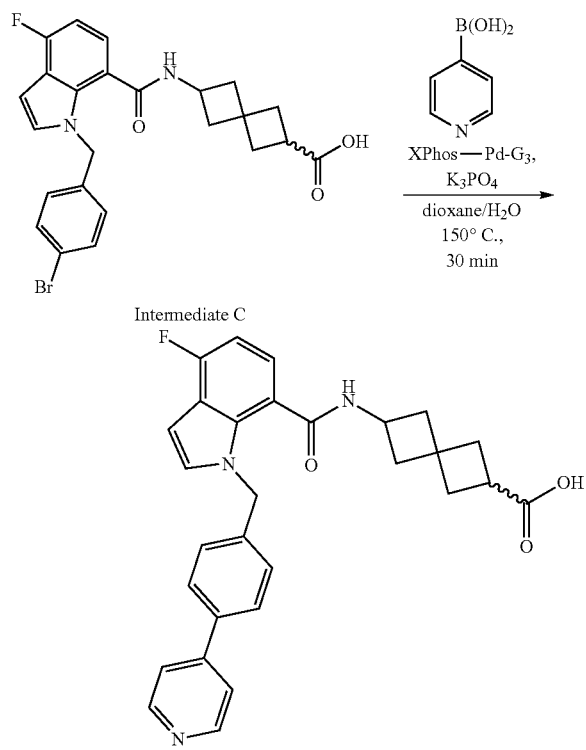

Example 11

In a microwave vial equipped with a magnetic stir bar was added Intermediate C (1 equiv), 4-pyridinylboronic acid (3.0 equiv), and XPhos-Pd-G3 catalyst (0.1 equiv, Strem, CAS #1445085-55-1) and the vial was sealed with a Teflon cap. The vial was evacuated and back-filled with $N_2$ atmosphere three times. The vial was then placed under vacuum before the addition of a 2 M aqueous $K_3PO_4$ solution (3.0 equiv) and dioxane (0.14 M). The vial was heated to 150° C. for 30 min in a microwave reactor. The resulting reaction mixture was allowed to cool to 22° C. and then directly subjected to purification by reverse-phase column chromatography using a C18 cartridge on an automated Teledyne ISCO Rf machine, eluting with 10% to 100% acetonitrile in water+ 0.1% formic acid as a gradient. Fractions with the desired product were combined and lyophilized to afford the title compound as a white powder (26% yield). $^1$H NMR (400 MHz, $d_6$-DMSO) δ 8.58 (d, J=5.5 Hz, 2H), 8.47 (d, J=7.5 Hz, 1H), 7.77-7.56 (m, 5H), 7.08 (dd, J=8.0, 5.5 Hz, 1H), 6.99 (d, J=8.0 Hz, 2H), 6.83 (dd, J=10.0, 8.0 Hz, 1H), 6.67 (d, J=3.5 Hz, 1H), 5.63 (s, 2H), 4.17-4.15 (m, 1H), 2.87 (apparent pentet, J=8.5 Hz, 1H), 2.37-1.87 (m, 6H), 1.84-1.68 (m, 2H). LCMS (ESI+): 484 (M+1)$^+$.

Compounds in the following table were made in a similar manner to Example 11. Reactions were run using Intermediate C and the corresponding commercially available boronic acid or boronate ester at temperatures ranging from 120-150° C. for durations ranging from 10-30 minutes in a microwave reactor.

| Example | Structure and Name | MW | MS (ESI+) |
|---|---|---|---|
| Example 12 | (racemic)-6-(4-fluoro-1-((4'-methoxy-[1,1'-biphenyl]-4-yl)methyl)-1H-indole-7-carboxamido)spiro[3.3]heptane-2-carboxylic acid | 512.21 | 535 (M + Na)$^+$ |

-continued

| Example | Structure and Name | MW | MS (ESI+) |
|---|---|---|---|
| Example 13 | 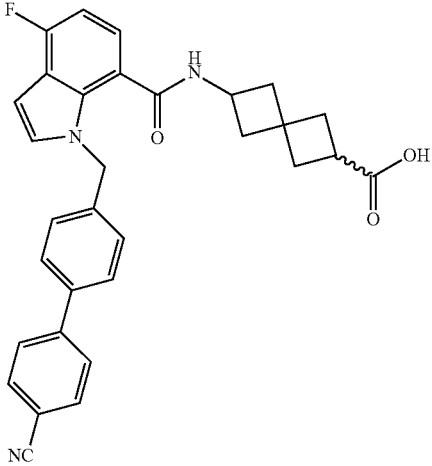 [SMILES: N#Cc1ccc(-c2ccc(Cn3ccc4c(F)ccc(C(=O)NC5CC6(C5)CC(C(=O)O)C6)c43)cc2)cc1]<br>(racemic)-6-(1-((4'-cyano-[1,1'-biphenyl]-4-yl)methyl)-4-fluoro-1H-indole-7-carboxamido)spiro[3.3]heptane-2-carboxylic acid | 507.57 | 508 (M + 1)+ |
| Example 14 | 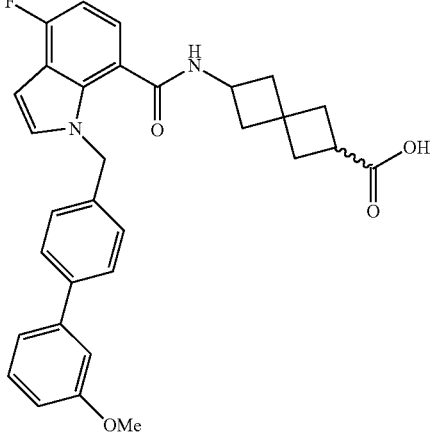<br>(racemic)-6-(4-fluoro-1-((3'-methoxy-[1,1'-biphenyl]-4-yl)methyl)-1H-indole-7-carboxamido)spiro[3.3]heptane-2-carboxylic acid | 512.21 | 513 (M + 1)+ |
| Example 15 | 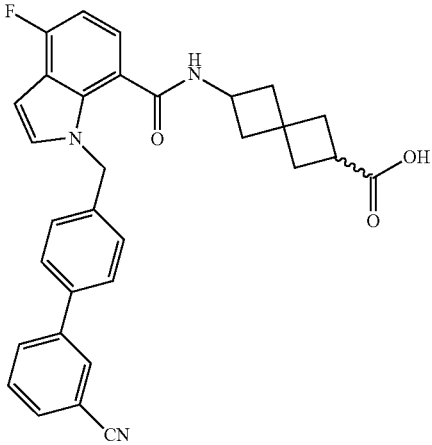 [SMILES: N#Cc1cccc(-c2ccc(Cn3ccc4c(F)ccc(C(=O)NC5CC6(C5)CC(C(=O)O)C6)c43)cc2)c1]<br>(racemic)-6-(1-((3'-cyano-[1,1'-biphenyl]-4-yl)methyl)-4-fluoro-1H-indole-7-carboxamido)spiro[3.3]heptane-2-carboxylic acid | 507.56 | 508 (M + 1)+ |

-continued

| Example | Structure and Name | MW | MS (ESI+) |
|---|---|---|---|
| Example 16 | 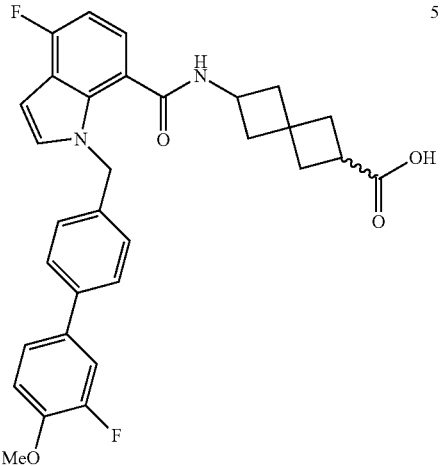 [SMILES: COc1ccc(-c2ccc(Cn3ccc4c(F)ccc(C(=O)NC5CC6(C5)CC(C(=O)O)C6)c43)cc2)cc1F]<br>(racemic)-6-(4-fluoro-1-((3'-fluoro-4'-methoxy-[1,1'-biphenyl]-4-yl)methyl)-1H-indole-7-carboxamido)spiro[3.3]heptane-2-carboxylic acid | 530.57 | 531 (M + 1)+ |

Example 17

Preparation of (racemic)-6-(1-(4-(5-Chloro-6-methoxypyridin-3-yl)benzyl)-4-fluoro-1H-indole-7-carboxamido)spiro[3.3]heptane-2-carboxylic acid

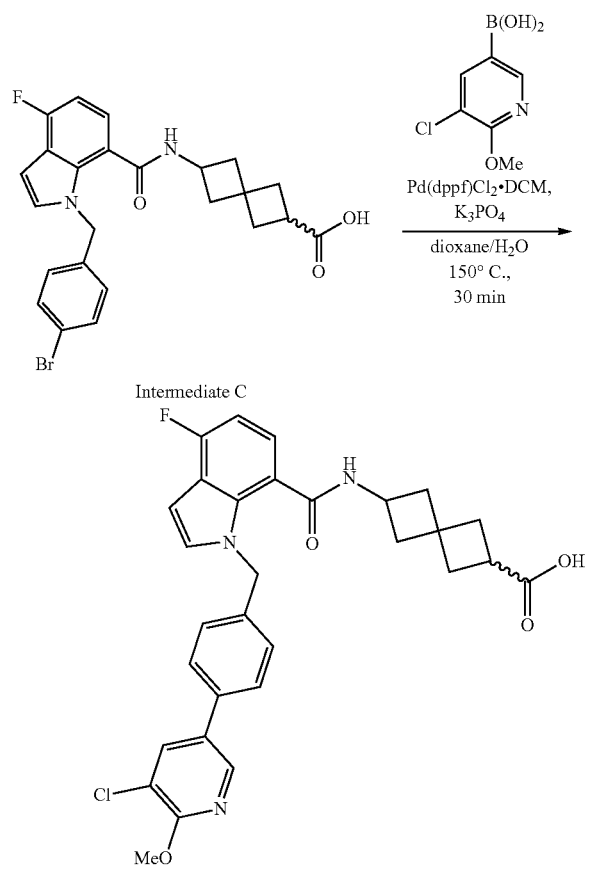

Example 17

In a microwave vial equipped with a magnetic stir bar was added Intermediate C (1.0 equiv), (5-chloro-6-methoxypyridin-3-yl)boronic acid (2.0 equiv, CombiBlocks. CAS #942438-89-3) and Pd(dppf)Cl$_2$ dichloromethane adduct (0.1 equiv, Strem CAS #95464-05-4) and the vial was sealed with a Teflon cap. The vial was evacuated and back-filled with a N$_2$ atmosphere three times. The vial was then placed under vacuum before the addition of a 2 M aqueous solution of K$_3$PO$_4$ (3.0 equiv) and dioxane (0.14 M). The vial was heated to 130° C. for 20 min in a microwave reactor. The resulting reaction mixture was allowed to cool to 22° C. and then directly subjected to purification by reverse-phase column chromatography using a C18 cartridge on an automated Teledyne ISCO Rf machine, eluting with 10% to 100% acetonitrile in water+0.1% formic acid as a gradient over 20 minutes. Fractions with the desired product were combined and lyophilized to afford the title compound as a white powder. $^1$H NMR (400 MHz, d$_6$-DMSO) δ 8.49 (d, J=7.5 Hz, 1H), 8.37 (d, J=2.0 Hz, 1H), 8.11 (d, J=2.0 Hz, 1H), 7.65 (d, J=3.0 Hz, 1H), 7.55 (d, J=8.0 Hz, 2H), 7.08 (dd, J=8.0, 5.5 Hz, 1H), 6.96 (d, J=8.0 Hz, 2H), 6.82 (dd, J=8.5, 1.0 Hz, 1H), 6.66 (d, J=3.0 Hz, 1H), 5.59 (s, 2H), 4.19-4.17 (m, 1H), 3.94 (s, 3H), 2.87 (apparent pentet, J=8.5 Hz, 1H), 2.41-2.09 (m, 4H), 2.08-1.86 (m, 2H), 1.83-1.76 (m, 2H). LCMS (ESI+): 548 (M+1)+.

Compounds in the following table were made in a similar manner to Example 17. Reactions were run using the Intermediate C and the corresponding commercially available boronic acid at temperatures ranging from 100-130° C. for durations ranging from 10-30 min in a microwave reactor.

| Example | Structure and Name | MW | MS (ESI+) |
|---|---|---|---|
| Example 18 | 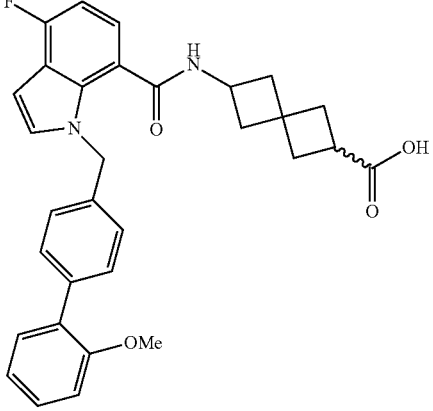<br>(racemic)-6-(4-fluoro-1-((2'-methoxy-[1,1'-biphenyl]-4-yl)methyl)-1H-indole-7-carboxamido)spiro[3.3]heptane-2-carboxylic acid | 512.21 | 535 (M + Na)+ |
| Example 19 | 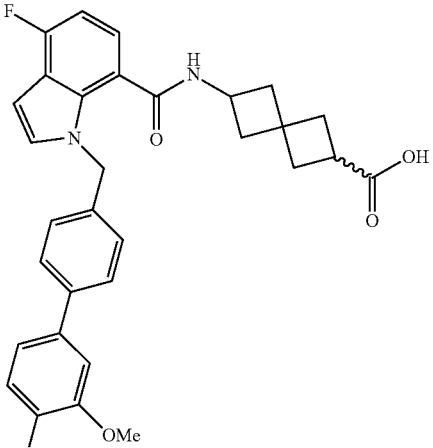<br>(racemic)-6-(4-fluoro-1-((4'-fluoro-3'-methoxy-[1,1'-biphenyl]-4-yl)methyl)-1H-indole-7-carboxamido)spiro[3.3]heptane-2-carboxylic acid | 530.57 | 531 (M + 1)+ |
| Example 20 | 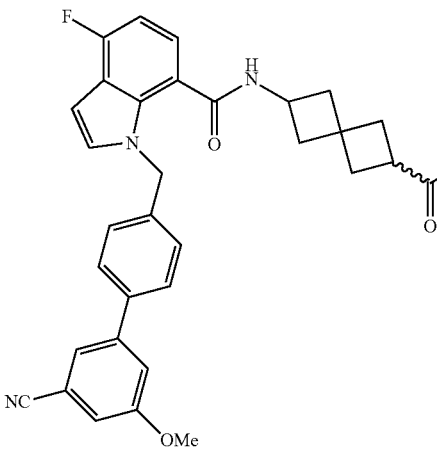<br>(racemic)-6-(1-((3'-cyano-5'-methoxy-[1,1'-biphenyl]-4-yl)methyl)-4-fluoro-1H-indole-7-carboxamido)spiro[3.3]heptane-2-carboxylic acid | 537.59 | 538 (M + 1)+ |

Example 21

Preparation of (racemic)-6-(1-((3'-Chloro-4'-(oxetan-3-yloxy)-[1,1'-biphenyl]-4-yl)methyl)-4-fluoro-1H-indole-7-carboxamido)spiro[3.3]heptane-2-carboxylic acid

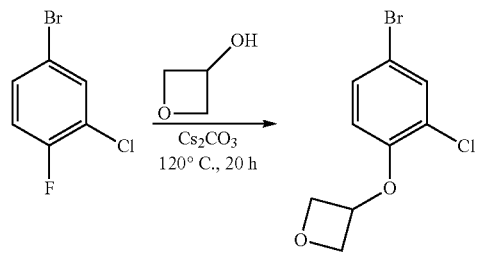

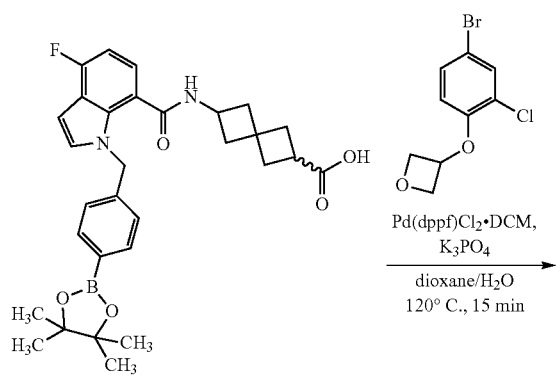

Intermediate E

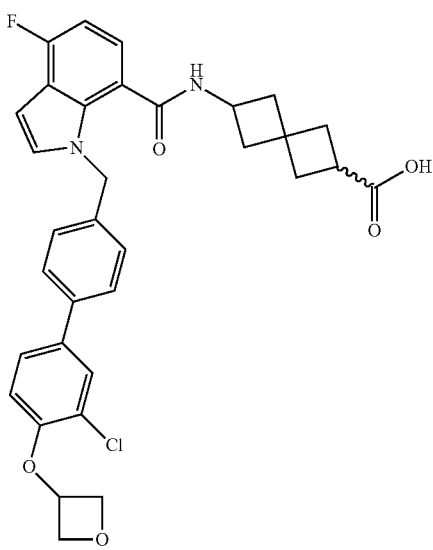

Example 21

Step 1: Preparation of 3-(4-bromo-2-chlorophenoxy)oxetane

In a microwave vial equipped with a stir bar, 4-bromo-2-chloro-1-fluorobenzene (1 equiv, Combi-Blocks. CAS #60811-21-4), oxetan-3-ol (10 equiv) and $Cs_2CO_3$ (1 equiv) were combined. The vial was sealed, degassed and heated to 120° C. for 20 hours in an oil bath. The reaction mixture was purified by reverse-phase column chromatography using a C18 cartridge on an automated Teledyne ISCO Rf machine, eluting with 10% to 100% acetonitrile in water+0.1% formic acid as a gradient over 20 minutes. The fractions containing the desired compound were combined and concentrated under vacuum to provide the title compound.

Step 2: Preparation of (racemic)-6-(1-((3'-chloro-4'-(oxetan-3-yloxy)-[1,1'-biphenyl]-4-yl)methyl)-4-fluoro-1H-indole-7-carboxamido)spiro[3.3]heptane-2-carboxylic acid In a microwave vial equipped with a magnetic stir bar was combined Intermediate E (1.0 equiv), 3-(4-bromo-2-chlorophenoxy)oxetane (1.0 equiv), and Pd(dppf)$Cl_2$·dichloromethane adduct (0.1 equiv). The vial was sealed with a Teflon cap. The vial was evacuated under vacuum and back-filled with a $N_2$ atmosphere three times. The vial was then placed under vacuum before the addition of a 2 M aqueous solution of $K_3PO_4$ (3.0 equiv) and dioxane (0.06 M). The vial was heated to 120° C. for 15 min in a microwave reactor. The resulting reaction mixture was allowed to cool to 22° C. and then directly subjected to reverse-phase column chromatography using a C18 cartridge on an automated Teledyne ISCO Rf machine, eluting with 10% to 100% acetonitrile in water+0.1% formic acid as a gradient over 20 minutes. Fractions with the desired product were combined and lyophilized to afford the title compound as a white powder. $^1$H NMR (400 MHz, $d_6$-DMSO) δ 12.07 (br s, 1H), 8.46 (d, J=7.5 Hz, 1H), 7.65 (d, J=2.5 Hz, 1H), 7.64 (d, J=3.5 Hz, 1H), 7.47 (d, J=8.0 Hz, 2H), 7.44 (d, J=2.5 Hz, 1H), 7.08 (dd, J=8.0, 5.5 Hz, 1H), 6.93 (d, J=8.0 Hz, 2H), 6.87-6.76 (m, 2H), 6.65 (d, J=3.0 Hz, 1H), 5.58 (s, 2H), 5.36 (d, J=6.0 Hz, 1H), 4.93 (t, J=6.5 Hz, 2H), 4.56 (dd, J=7.5, 5.0 Hz, 2H), 4.19-4.17 (m, 1H), 2.88 (apparent pentet, J=8.5 Hz, 1H), 2.38-2.08 (m, 4H), 2.08-1.89 (m, 2H), 1.87-1.59 (m, 2H). LCMS (ESI+): 589 (M+1)$^+$.

Compounds in this table were made in a similar manner to Step 2, Example 21. Reactions were run using Intermediate E and the corresponding aryl halide at temperatures ranging from 100-130° C. for durations ranging from 10-30 min in a microwave reactor.

| Example | Structure and Name | MW | MS (ESI+) |
|---|---|---|---|
| Example 22 | 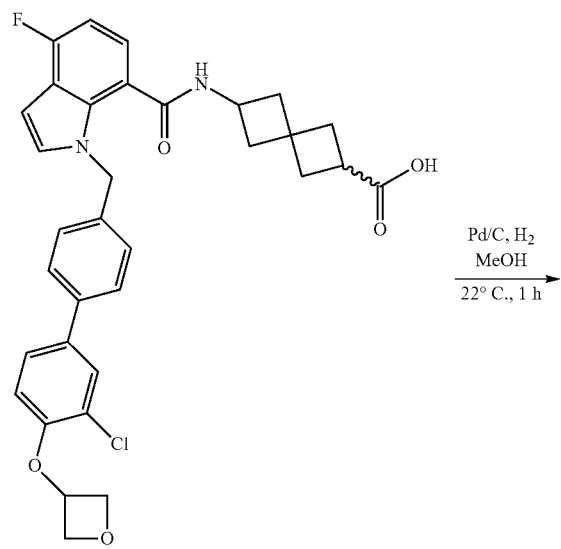 (racemic)-6-(1-(4-(2-(dimethylamino)pyridin-4-yl)benzyl)-4-fluoro-1H-indole-7-carboxamido)spiro[3.3]heptane-2-carboxylic acid | 526.60 | 527 (M + 1)+ |

Example 23

Preparation of (racemic)-6-(4-Fluoro-1-((4'-(oxetan-3-yloxy)-[1,1'-biphenyl]-4-yl)methyl)-1H-indole-7-carboxamido)spiro[3.3]heptane-2-carboxylic acid

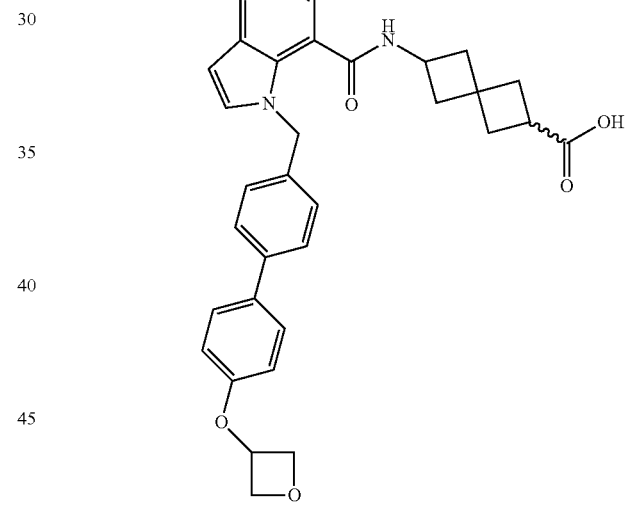

To a solution of Example 21 (1.0 equiv) in MeOH (0.008 M) was added 10% Pd/C (10% wt/wt to compound). The vessel was evacuated and then stirred under an atmospheric pressure of $H_2$ at 22° C. for 1 hour. The resulting reaction mixture was directly subjected to reverse-phase column chromatography using a C18 cartridge on an automated Teledyne ISCO Rf machine, eluting with 10% to 100% acetonitrile in water+0.1% formic acid as a gradient over 20 minutes. Fractions with the desired product were combined and lyophilized to afford the title compound as a white powder. $^1$H NMR (400 MHz, $d_6$-DMSO) δ 8.49 (d, J=8.0 Hz, 1H), 7.64 (d, J=3.5 Hz, 1H), 7.48 (d, J=8.5 Hz, 2H), 7.42 (d, J=8.0 Hz, 2H), 7.08 (dd, J=8.0, 5.5 Hz, 1H), 6.94 (d, J=8.0 Hz, 2H), 6.88-6.76 (m, 3H), 6.65 (d, J=3.0 Hz, 1H), 5.57 (s, 2H), 5.28 (t, J=6.0 Hz, 1H), 4.90 (t, J=6.5 Hz, 2H), 4.52 (dd, J=5.5, 1.5 Hz, 2H), 4.19-4.17 (m, 1H), 2.87

(apparent pentet, J=8.5 Hz, 1H), 2.38-2.09 (m, 4H), 2.08-1.90 (m, 2H), 1.88-1.70 (m, 2H). LCMS (ESI+): 555 (M+1)⁺.

Example 24

Preparation of (S$_a$)-6-(4-Fluoro-1-(4-(pyridin-4-yl)benzyl)-1H-indole-7-carboxamido)spiro[3.3]heptane-2-carboxylic acid

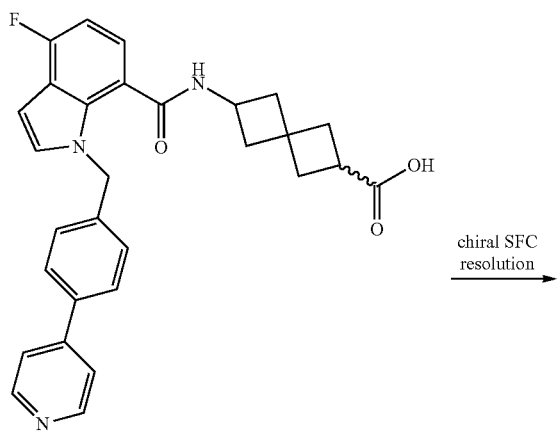

Example 11

↓ chiral SFC resolution

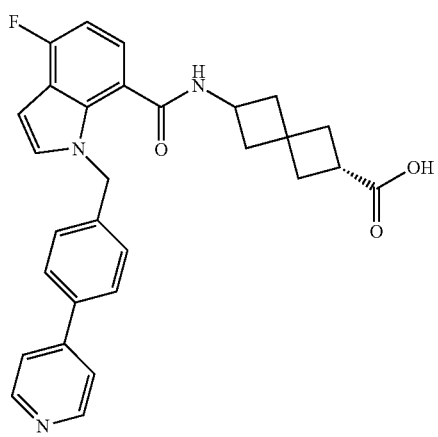

Example 24

Compound Example 11 was resolved into both enantiomers by chiral SFC using a ChiralPak AD column (4.6×150 mm) with a gradient of 5% to 55% MeOH+0.1 mM ammonium formate in scCO₂. The second eluting enantiomer, Example 24, was determined to be the more active enantiomer. ¹H NMR (400 MHz, d₆-DMSO) δ 8.58 (d, J=5.5 Hz, 2H), 8.47 (d, J=7.5 Hz, 1H), 7.77-7.56 (m, 5H), 7.08 (dd, J=8.0, 5.5 Hz, 1H), 6.99 (d, J=8.0 Hz, 2H), 6.83 (dd, J=10.0, 8.0 Hz, 1H), 6.67 (d, J=3.5 Hz, 1H), 5.63 (s, 2H), 4.17-4.15 (m, 1H), 2.87 (apparent pentet, J=8.5 Hz, 1H), 2.37-1.87 (m, 6H), 1.84-1.68 (m, 2H). LCMS (ESI+): 484 (M+1)⁺.

Example 25

Preparation of (S$_a$)-6-(1-((3'-Chloro-4'-methoxy-[1,1'-biphenyl]-4-yl)methyl)-4-fluoro-1H-indole-7-carboxamido)spiro[3.3]heptane-2-carboxylic acid

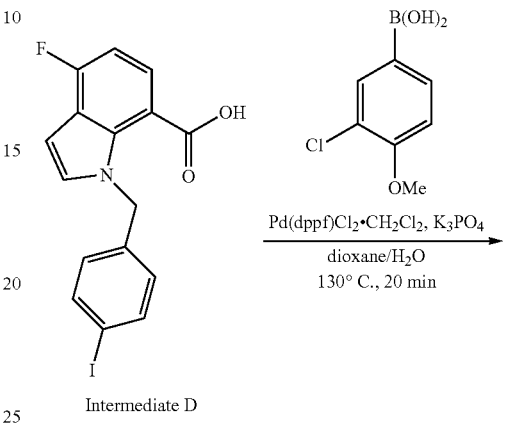

Intermediate D

Pd(dppf)Cl₂·CH₂Cl₂, K₃PO₄
dioxane/H₂O
130° C., 20 min

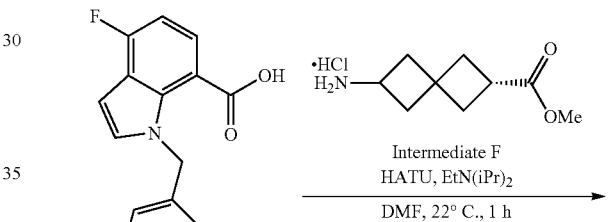

Intermediate F
HATU, EtN(iPr)₂
DMF, 22° C., 1 h

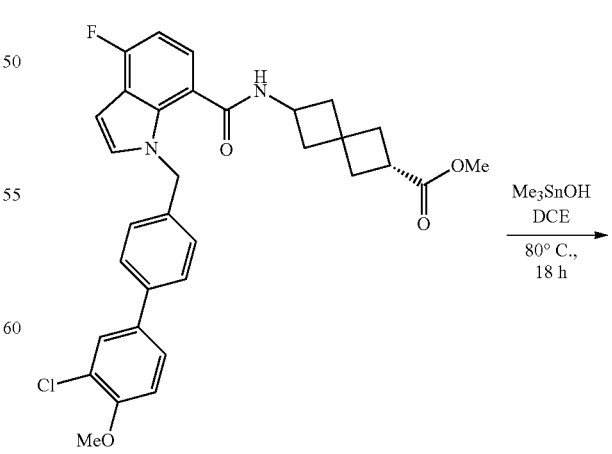

Me₃SnOH
DCE
80° C.,
18 h

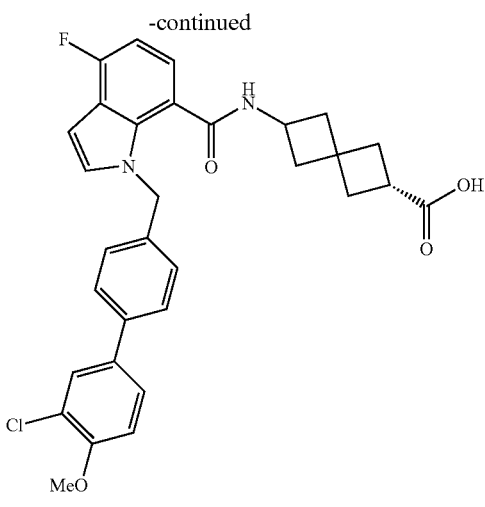

Example 25

Step 1: Preparation of 1-((3'-chloro-4'-methoxy-[1,1'-biphenyl]-4-yl)methyl)-4-fluoro-1H-indole-7-carboxylic acid In a microwave vial equipped with a magnetic stir bar, Intermediate D (1.0 equiv), 3-chloro-4-methoxy phenylboronic acid (2.0 equiv, CombiBlock, CAS #175883-60-0), and Pd(dppf)Cl$_2$·dichloromethane adduct (0.1 equiv) were combined and sealed with a Teflon cap. The vial was evacuated and back-filled with a N$_2$ atmosphere three times. The vial was then placed under vacuum before the addition of a 2 M aqueous K$_3$PO$_4$ solution (3.0 equiv) and dioxane (0.14 M). The vial was heated to 130° C. for 20 min in a microwave reactor. The resulting reaction mixture was allowed to cool to 22° C. and then directly subjected to purification by reverse-phase column chromatography using a C18 cartridge on an automated Teledyne ISCO Rf machine, eluting with 10% to 100% acetonitrile in water+0.1% formic acid as a gradient over 20 minutes. Fractions with the desired product were combined and concentrated under vacuum to afford the title compound as an off-white powder.

Step 2: Preparation of (S %)-methyl 6-(1-((3'-chloro-4'-methoxy-[1,1'-biphenyl]-4-yl)methyl)-4-fluoro-1H-indole-7-carboxamido)spiro[3.3]heptane-2-carboxylate To a solution of 1-((3'-chloro-4'-methoxy-[1,1'-biphenyl]-4-yl)methyl)-4-fluoro-1H-indole-7-carboxylic acid in DMF (0.1 M) was added Intermediate F (1.0 equiv), HATU (1.5 equiv) and Hünig's base (3 equiv). The mixture was stirred at 22° C. for 1 hour and then subjected to purification by reverse-phase column chromatography using a C18 cartridge on an automated Teledyne ISCO Rf machine, eluting with 10% to 100% acetonitrile in water+0.1% formic acid as a gradient over 20 minutes. Fractions with the desired product were combined and concentrated under vacuum to afford the title compound as an off-white solid.

Step 3: Preparation of (S$_a$)-6-(1-((3'-chloro-4'-methoxy-[1,1'-biphenyl]-4-yl)methyl)-4-fluoro-1H-indole-7-carboxamido)spiro[3.3]heptane-2-carboxylic acid In a microwave vial equipped with a stir bar, (S$_a$)-methyl 6-(1-((3'-chloro-4'-methoxy-[1,1'-biphenyl]-4-yl)methyl)-4-fluoro-1H-indole-7-carboxamido)spiro[3.3]heptane-2-carboxylate (1.0 equiv) and trimethyltin hydroxide (5 equiv) were suspended in dichloroethane (0.05 M). The vial was sealed and then heated to 80° C. for 18 hours. The vial was opened, 1.0 M aqueous citric acid was added, the mixture was stirred for 10 minutes and then extracted with CH$_2$Cl$_2$. The organic layer was dried over MgSO$_4$ and then concentrated under vacuum to obtain a brown solid. The solid was subjected to purification by reverse-phase column chromatography using a C18 cartridge on an automated Teledyne ISCO Rf machine, eluting with 10% to 100% acetonitrile in water+0.1% formic acid as a gradient over 20 minutes. Fractions with the desired product were lyophilized to afford the title compound as a white powder. $^1$H NMR (400 MHz, d$_6$-DMSO) δ 8.47 (d, J=7.5 Hz, 1H), 7.64 (d, J=3.0 Hz, 1H), 7.61 (d, J=2.0 Hz, 1H), 7.51 (dd, J=8.5, 2.0 Hz, 1H), 7.47 (d, J=8.0 Hz, 2H), 7.18 (d, J=8.5 Hz, 1H), 7.08 (dd, J=8.0, 5.5 Hz, 1H), 6.93 (d, J=8.0 Hz, 2H), 6.82 (dd, J=8.0, 1.5 Hz, 1H), 6.66 (d, J=3.0 Hz, 1H), 5.58 (s, 2H), 4.19-4.17 (m, 1H), 3.85 (s, 3H), 2.87 (apparent pentet, J=8.5 Hz, 1H), 2.37-2.08 (m, 2H), 2.07-1.88 (m, 3H), 1.85-1.70 (m, 3H). LCMS (ESI+): 547 (M+1)$^+$.

Example 26

Preparation of (S$_a$)-6-(4-Fluoro-1-(naphthalen-2-ylmethyl)-1H-indole-7-carboxamido)spiro[3.3]heptane-2-carboxylic acid

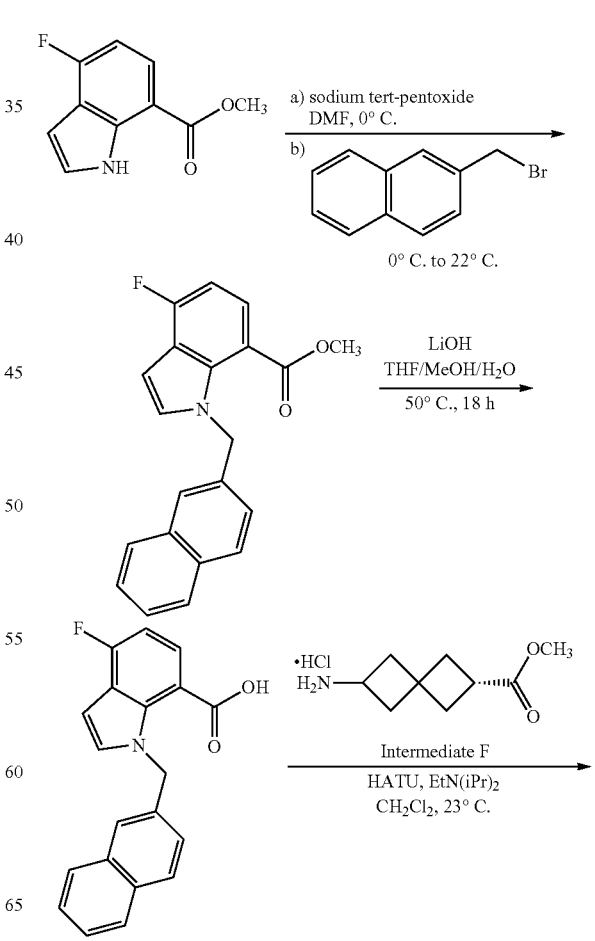

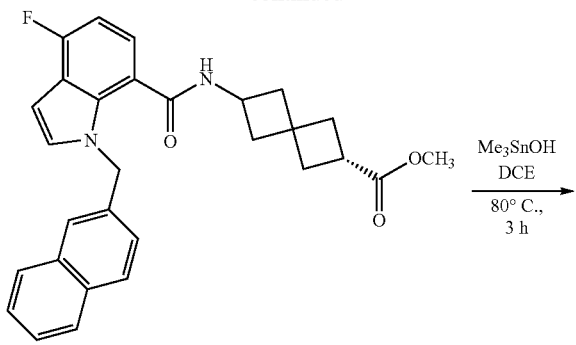

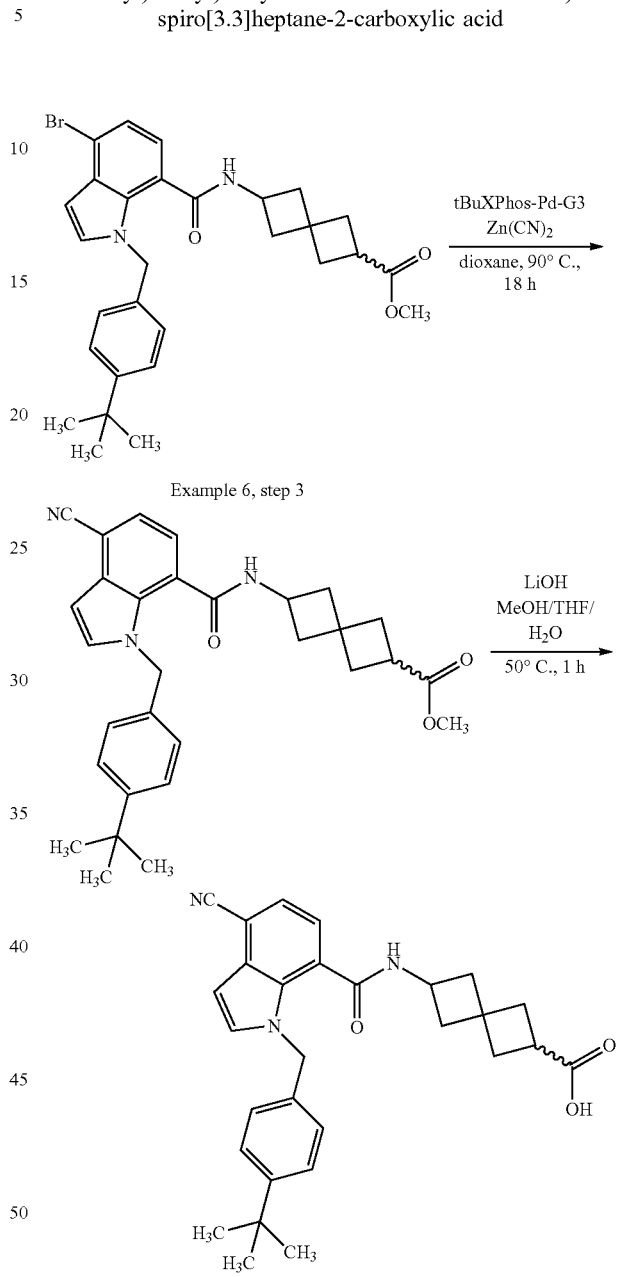

Example 27

Preparation of Example 27: (racemic)-6-(1-(4-(tert-Butyl)benzyl)-4-cyano-1H-indole-7-carboxamido)spiro[3.3]heptane-2-carboxylic acid Steps 1 and 2: Preparation of 4-fluoro-1-(naphthalen-2-ylmethyl)-1H-indole-7-carboxylic acid Prepared in a similar manner to Intermediate A replacing 1-(bromomethyl)-4-(trifluoromethoxy)benzene with 2-(bromomethyl)naphthalene (Combi-Blocks, CAS #939-26-4).

Steps 3 and 4: Preparation of $(S_a)$-6-(4-fluoro-1-(naphthalen-2-ylmethyl)-1H-indole-7-carboxamido)spiro[3.3]heptane-2-carboxylic acid Prepared in a similar manner to alternate procedure of Example 8 replacing 4-fluoro-1-(4-(trifluoromethoxy)benzyl)-1H-indole-7-carboxylic acid with 4-fluoro-1-(naphthalen-2-ylmethyl)-1H-indole-7-carboxylic acid. LCMS (ESI+): 457 (M+1)+.

Step 1: Preparation of (racemic)-methyl 6-(1-(4-(tert-butyl)benzyl)-4-cyano-1H-indole-7-carboxamido)spiro[3.3]heptane-2-carboxylate To a degassed mixture of compound from Example 6, Step 3 (methyl 2-[[4-bromo-1-[(4-tert-butylphenyl)methyl]indole-7-carbonyl]amino]spiro[3.3]heptane-6-carboxylate, 1 equiv) and zinc cyanide (1 equiv) in dioxane (0.19 M) was added tBuXPhos-Pd-G3 (0.15 equiv, Strem CAS #1447963-75-8) and the mixture was heated to 90° C. for 18 hours. The mixture was acidified with formic acid and directly purified by reverse-phase column chromatography using a C18 cartridge on an automated Teledyne ISCO Rf machine, eluting with 0% to 100% acetonitrile in water+0.1% formic acid as a gradient over 20 minutes. The desired product fractions eluting at 95% ACN were combined and lyophilized to provide the title compound.

Step 2: Preparation of (racemic)-6-(1-(4-(tert-butyl)benzyl)-4-cyano-1H-indole-7-carboxamido)spiro[3.3]heptane-2-carboxylic acid To a solution of (racemic)-methyl 2-[[1-[(4-tert-butylphenyl)methyl]-4-cyano-indole-7-carbonyl]amino]spiro[3.3]heptane-6-carboxylate (1 equiv) in MeOH (0.11 M) and THF (0.11 M) was added 1.0 M aqueous LiOH solution (2 equiv) and the reaction was heated to 50° C. for 1 hour. The mixture was concentrated under vacuum to remove the organic solvents and then acidified with the drop-wise addition of formic acid (4 equiv). This mixture was dissolved in DMSO and purified by reverse-phase column chromatography using a C18 cartridge on an automated Teledyne ISCO Rf machine, eluting with 0% to 80% acetonitrile in water+0.1% formic acid as a gradient. The desired fractions eluting at 65% acetonitrile were combined and lyophilized to provide the title compound as a white solid (73% yield). LCMS (ESI+): 470 (M+1)⁺.

Example 28

Preparation of (racemic)-6-(1-(4-(cyclopentyloxy)benzyl)-4-fluoro-1H-indole-7-carboxamido)spiro[3.3]heptane-2-carboxylic acid

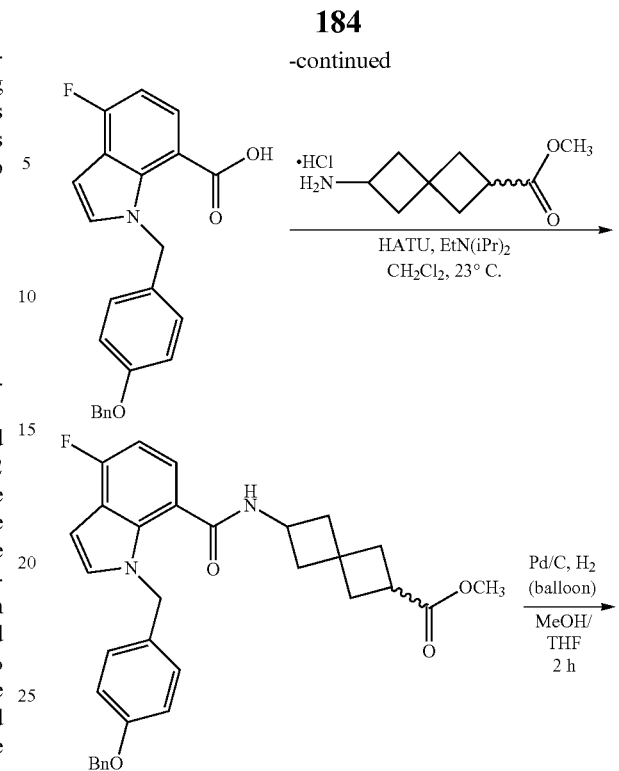

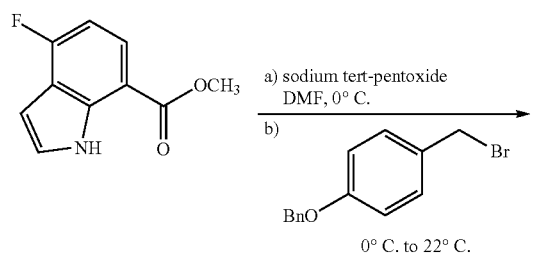

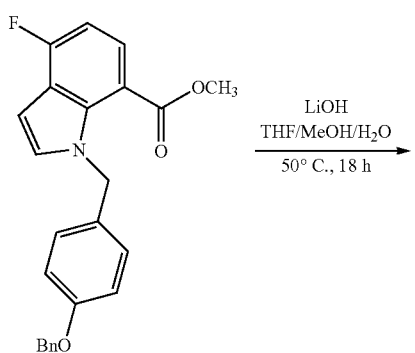

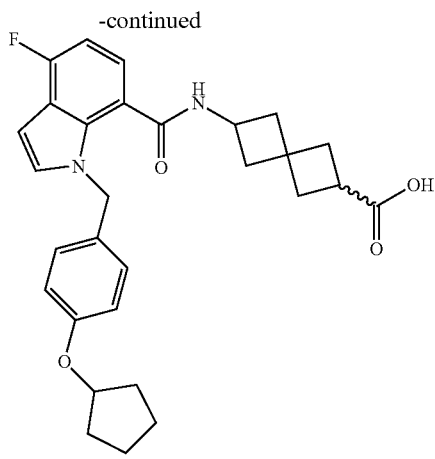

Example 28

Step 1 to 3: Preparation of (racemic)-methyl 6-(1-(4-(benzyloxy)benzyl)-4-fluoro-1H-indole-7-carboxamido)spiro[3.3]heptane-2-carboxylate The title compound was prepared as in Intermediate A, replacing 1-(bromomethyl)-4-(trifluoromethoxy)benzene with 1-(benzyloxy)-4-(bromomethyl)benzene (Enamine, CAS #5544-60-5) in Step 1 of Intermediate B synthesis.

Step 4: Preparation of (racemic)-methyl 6-(4-fluoro-1-(4-hydroxybenzyl)-1H-indole-7-carboxamido)spiro[3.3]heptane-2-carboxylate To a degassed solution of methyl 2-[[1-[(4-benzyloxyphenyl)methyl]-4-fluoro-indole-7-carbonyl]amino]spiro[3.3]heptane-6-carboxylate (1 equiv) in MeOH (0.1 M) and THF (0.05 M) was added 10% palladium on carbon (10% weight). This mixture was evacuated and purged with nitrogen 3 times and then evacuated and then stirred under a balloon of hydrogen for 2 hours. This mixture was degassed and filtered through a pad of celite and this pad was rinsed with additional MeOH and CH$_2$Cl$_2$. The combined filtrates were concentrated under vacuum. This crude residue was pre-absorbed onto a silica gel pre-cartridge and then purified by column chromatography through silica gel on the Teledyne ISCO Rf eluting with 0% to 80% EtOAc in hexanes as a gradient over 25 minutes. The fractions from the major peak which elutes at 75% EtOAc were combined and concentrated under vacuum to provide the title compound as a white foam (79% yield).

Step 5: Preparation of (racemic)-methyl 6-(1-(4-(cyclopentyloxy)benzyl)-4-fluoro-1H-indole-7-carboxamido)spiro[3.3]heptane-2-carboxylate To a cold (−80° C.) solution of (racemic)-methyl 6-(4-fluoro-1-(4-hydroxybenzyl)-1H-indole-7-carboxamido)spiro[3.3]heptane-2-carboxylate (1 equiv), cyclopentanol (1 equiv) and triphenylphosphine (2 equiv) in THF (0.1 M) was added DIAD (2 equiv. Aldrich, CAS #2446-83-5) and the mixture was then stirred at 22° C. for 16 hours. After this time, the reaction mixture was directly pre-absorbed onto a silica gel pre-cartridge and then purified by column chromatography through silica gel on the Teledyne ISCO Rf eluting with 0% to 100% EtOAc in hexanes as a gradient. The fractions from the major peak were combined and concentrated under vacuum to provide the title compound as a white solid (80% yield).

Step 6: Preparation of (racemic)-6-(1-(4-(cyclopentyloxy)benzyl)-4-fluoro-1H-indole-7-carboxamido)spiro[3.3]heptane-2-carboxylic acid To a solution of (racemic)-methyl 6-(1-(4-(cyclopentyloxy)benzyl)-4-fluoro-1H-indole-7-carboxamido)spiro[3.3]heptane-2-carboxylate (1 equiv) in MeOH (0.2 M) and THF (0.2 M) was added 1.0 M aqueous LiOH solution (2 equiv) and the reaction was heated to 50° C. for 18 hour. The mixture was concentrated under vacuum and the resulting solid was dissolved in DMSO with formic acid (4 equiv). This mixture was purified by reverse-phase column chromatography using a C18 cartridge on an automated Teledyne ISCO Rf machine, eluting with 0% to 100% acetonitrile in water+0.1% formic acid as a gradient. The desired fractions eluting at 85% acetonitrile in water were combined and lyophilized to provide the title compound as a white solid (80% yield). LCMS (ESI+): 513 (M+Na)$^+$.

The following compounds were prepared as in a similar manner to Example 28 replacing cyclopentanol in Step 5 with commercially available alcohols.

| Example | Structure and Name | MW | MS (ESI+) |
|---|---|---|---|
| Example 29 | (racemic)-6-(1-(4-(cyclohexyloxy)benzyl)-4-fluoro-1H-indole-7-carboxamido)spiro[3.3]heptane-2-carboxylic acid | 504.6 | 527 (M + Na)$^+$ |

| Example | Structure and Name | MW | MS (ESI+) |
|---|---|---|---|
| Example 30 | 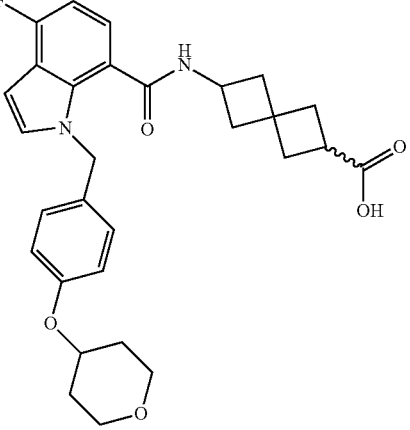<br>(racemic)-6-(4-fluoro-1-(4-((tetrahydro-2H-pyran-4-yl)oxy)benzyl)-1H-indole-7-carboxamido)spiro[3.3]heptane-2-carboxylic acid | 506.57 | 529 (M + Na)+ |

Example 31

Preparation of (racemic)-6-(4-Fluoro-1-(4-morpholinobenzyl)-1H-indole-7-carboxamido)spiro[3.3]heptane-2-carboxylic acid

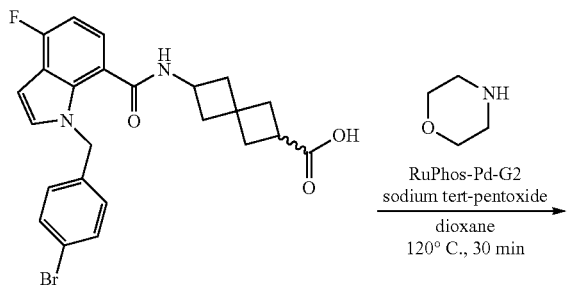

Intermediate C

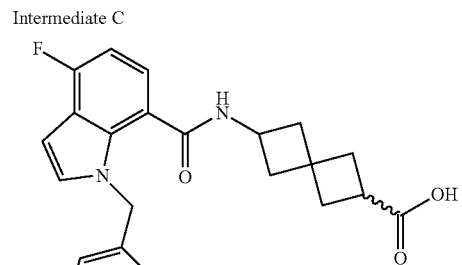

Example 31

Into a microwave reaction vial equipped with a magnetic stir bar and under nitrogen was added Intermediate C (1.0 equiv), RuPhos-Pd-G2 (0.05 equiv, Strem, CAS #1375325-68-0), sodium tert-pentoxide (2.5 equiv), morpholine (2.0 equiv) and dioxane (anhydrous, 0.1 M). The resulting mixture was purged with nitrogen for 10 minutes before it was sealed and stirred at 120° C. for 30 minutes in a microwave reactor. LCMS analysis revealed conversion to product. The reaction mixture was loaded onto a silica gel pre-cartridge, rinsing with MeOH. Purification by reverse-phase column chromatography using a C18 cartridge on an automated Teledyne ISCO Rf machine, eluting with 0% to 100% acetonitrile in water+0.1% formic acid as a gradient over 20 minutes. The desired fractions were combined and lyophilized to afford the title compound as a white solid (90% yield). $^1$H NMR (400 MHz, CDCl$_3$) δ 7.13 (d, J=3.5 Hz, 1H), 7.08 (dd, J=8.0, 5.0 Hz, 1H), 6.88-6.73 (m, 4H), 6.72-6.68 (m, 1H), 6.68-6.64 (m, 1H), 5.73 (d, J=8.0 Hz, 1H), 5.53-5.35 (m, 2H), 4.31 (apparent pentet, J=8.0 Hz, 1H), 3.82 (t, J=5.0 Hz, 4H), 3.15-2.97 (m, 5H), 2.50-2.47 (m, 1H), 2.36 (d, J=8.5 Hz, 3H), 2.28-2.23 (m, 1H), 2.13 (t, J=10.5 Hz, 1H), 1.76-1.73 (m, 1H), 1.69-1.66 (m, 1H). LCMS (ESI+): 492 (M+1)+.

Example 32

Preparation of (racemic)-6-(1-(4-(Trifluoromethoxy)benzyl)-1H-indazole-7-carboxamido)spiro[3.3]heptane-2-carboxylic acid

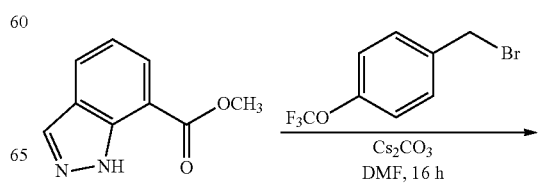

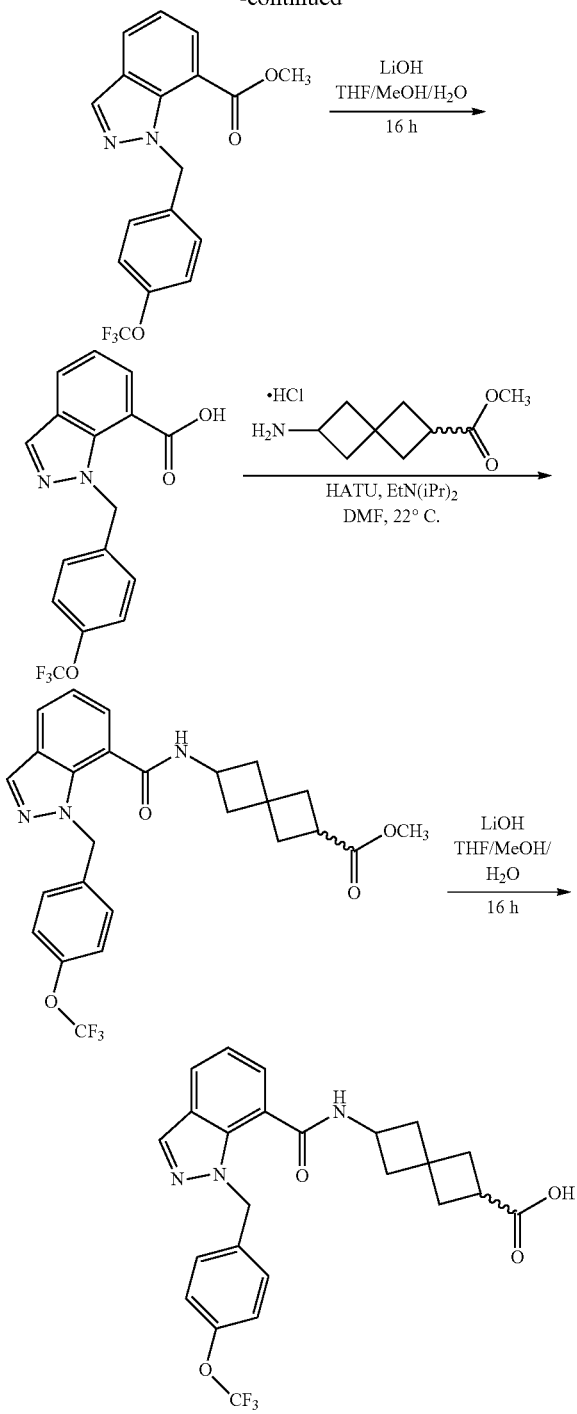

Example 32

Step 1: Preparation of methyl 1-(4-(trifluoromethoxy)benzyl)-1H-indazole-7-carboxylate In a round-bottom flask equipped with a magnetic stir bar was suspended methyl 1H-indazole-7-carboxylate (1.0 equiv, Combi-Blocks, CAS #755752-82-0) and cesium carbonate (3 equiv) in DMF (0.71 M). This suspension was cooled to 0° C. and treated with neat 4-(trifluoromethoxy)benzyl bromide (1.2 equiv, Aldrich, CAS #50824-05-0) drop-wise over a period of 5 minutes. The resulting reaction mixture was allowed to 22° C. over 16 hours. The reaction was then carefully quenched with the addition of ice-water and extracted with tert-butyl methyl ether. The combined organic extracts were washed further with water and brine, dried over MgSO₄, and filtered. Concentration of the filtrate thus obtained under vacuum furnished the crude reaction product as a golden yellow oil. Purification by column chromatography through silica gel on the Teledyne ISCO Rf eluting with 10% to 100% EtOAc in hexanes as a gradient afforded the title compound.

Step 2: Preparation of 1-(4-(trifluoromethoxy)benzyl)-1H-indazole-7-carboxylic acid Into a glass round-bottom flask equipped with a magnetic stir bar was dissolved methyl 1-(4-(trifluoromethoxy)benzyl)-1H-indazole-7-carboxylate (1 equiv) in a 3:2 (v/v) solution (0.11 M) of THF and MeOH. To this was then added 2.0 M aqueous LiOH solution (3 equiv) and the resulting solution was stirred at 22° C. for 16 hours. The reaction mixture was then carefully neutralized with the drop-wise addition of 1 M aqueous HCl solution (3 equiv). The resulting suspension was extracted with EtOAc. The combined organic extracts were washed further with water and brine, dried over MgSO₄, and filtered. Concentration of the filtrate thus obtained under vacuum furnished the crude reaction product as a viscous oil that solidified upon standing. Trituration of the crude product in tert-butyl methyl ether and hexanes then afforded the title compound as a white, crystalline solid.

Step 3: Preparation of (racemic)-methyl 6-(1-(4-(trifluoromethoxy)benzyl)-1H-indazole-7-carboxamido)spiro[3.3]heptane-2-carboxylate In a round-bottom flask equipped with a magnetic stir bar was dissolved 1-(4-(trifluoromethoxy)benzyl)-1H-indazole-7-carboxylic acid (1 equiv), methyl 6-aminospiro[3.3]heptane-2-carboxylate hydrochloride (1.5 equiv, Enamine, CAS #1808249-67-3) and HATU (1.5 equiv) in DMF (0.19 M). To this was then added Hünig's base (5 equiv) and the resulting yellow solution was allowed to stir at 22° C. for 4 hours. The crude reaction mixture was diluted with EtOAc and washed sequentially with water, 10% aqueous NaHCO₃, 10% aqueous NH₄Cl, water and brine. The organic extract was then dried over MgSO₄, filtered and the filtrate concentrated under vacuum. Purification by column chromatography through silica gel on the Teledyne ISCO Rf luting with 50% to 100% EtOAc in hexanes as a gradient furnished the title compound.

Step 4: Preparation of (racemic)-6-(1-(4-(trifluoromethoxy)benzyl)-1H-indazole-7-carboxamido)spiro[3.3]heptane-2-carboxylic acid Into a round-bottom flask equipped with a magnetic stir bar was dissolved (racemic)-methyl 6-(1-(4-(trifluoromethoxy)benzyl)-1H-indazole-7-carboxamido)spiro[3.3]heptane-2-carboxylate (1 equiv) in a 3:2 (v/v) solution (0.03 M) of THF and MeOH. To this was then added 2.0 M aqueous LiOH solution (3 equiv) and the resulting solution was stirred at 22° C. for 16 hours. The reaction mixture was then carefully neutralized with the drop-wise addition of 1 M aqueous HCl solution (3 equiv). The resulting suspension was extracted with EtOAc. The combined organic extracts were washed further with water and brine, dried over MgSO₄, and filtered. Concentration of the filtrate thus obtained under vacuum furnished the crude reaction product as a viscous oil that solidified upon standing. Trituration of the crude product in toluene afforded the title compound as a white, crystalline solid. ¹H NMR (400 MHz, CDCl₃) δ 8.14 (s, 1H), 7.86 (dd. J=8.0, 1.0 Hz, 1H), 7.38 (dd, J=7.0, 1.0 Hz, 1H), 7.23-6.94 (m, 5H), 5.91-5.83 (m, 3H), 4.37-4.35 (m, 1H), 3.08-3.06 (m, 1H), 2.52-2.49 (m, 1H), 2.48-2.33 (m, 3H), 2.29 (dd, J=12, 8.0 Hz, 1H), 2.21-2.08 (m, 1H), 1.74 (dt, J=12.0, 8.5 Hz, 2H). LCMS (ESI+): 474 (M+1)⁺.

The following compounds were prepared in a similar manner to Example 32, replacing 4-(trifluoromethoxy)benzyl bromide in Step 1 with commercially available benzylbromides and/or the methyl 1H-indazole-7-carboxylate with an alternative available indazole in Step 1.

| Example | Structure and Name | MW | MS(ESI+) |
|---|---|---|---|
| Example 33 | 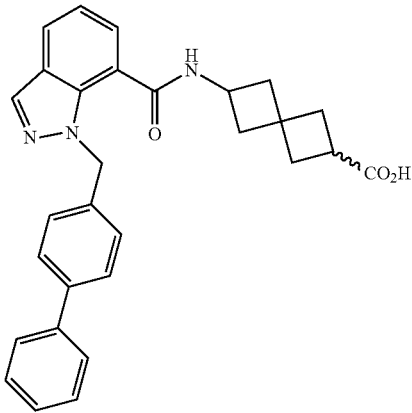 [SMILES: O=C(NC1CC2(C1)CC(C(=O)O)C2)c1cccc2cnn(Cc3ccc(-c4ccccc4)cc3)c12]<br>(racemic)-6-(1-([1,1'-biphenyl]-4-ylmethyl)-1H-indazole-7-carboxamido)spiro[3.3]heptane-2-carboxylic acid | 465.21 | 466 (M + 1)⁺ |
| Example 34 | 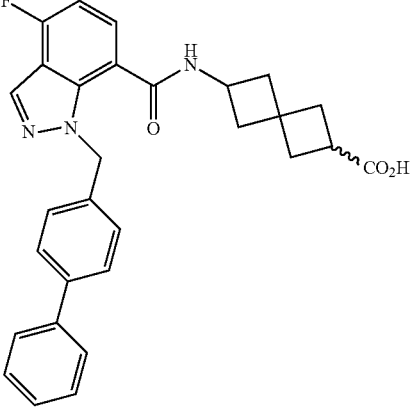<br>(racemic)-6-(1-([1,1'-biphenyl]-4-ylmethyl)-4-fluoro-1H-indazole-7-carboxamido)spiro[3.3]heptane-2-carboxylic acid | 483.54 | 485 (M + 1)⁺ |

Example 35

Preparation of (Racemic)-6-(4-Fluoro-1-((3'-fluoro-[1,1'-biphenyl]-4-yl)methyl)-1H-indole-7-carboxamido)spiro[3.3]heptane-2-carboxylic acid

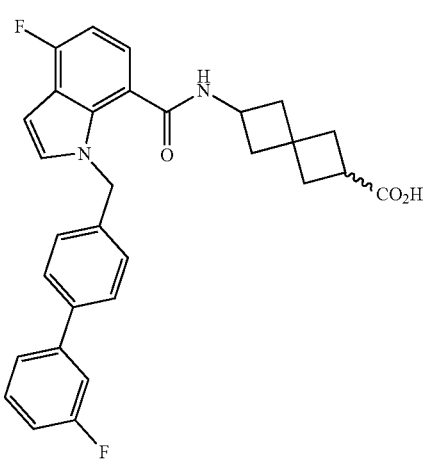 [SMILES: O=C(NC1CC2(C1)CC(C(=O)O)C2)c1ccc(F)c2ccn(Cc3ccc(-c4cccc(F)c4)cc3)c12]

The title compound was made in a similar manner to Example 17, but replacing (5-chloro-6-methoxypyridin-3-yl)boronic acid with 3-fluorophenyl boronic acid (Combi-Blocks CAS #768-35-4). LCMS (ESI+): 501 (M+1)+.

Example 36

Preparation of (Racemic)-6-(1-(4-(2-ethoxypyridin-4-yl)benzyl)-4-fluoro-1H-indole-7-carboxamido)spiro[3.3]heptane-2-carboxylic acid

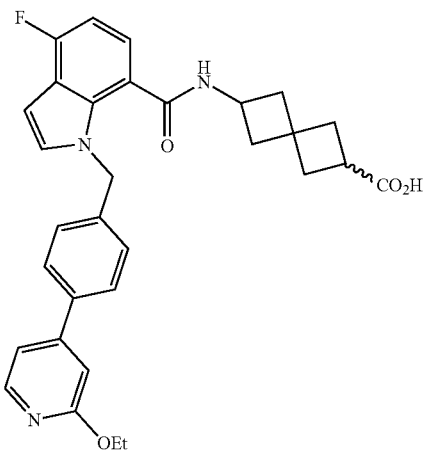 [SMILES: CCOc1cc(-c2ccc(Cn3ccc4c(F)ccc(C(=O)NC5CC6(C5)CC(C(=O)O)C6)c43)cc2)ccn1]

The title compound was made in a similar manner to Example 17, but replacing (5-chloro-6-methoxypyridin-3-yl)boronic acid with 4-ethoxypyridine-4-boronic acid (Combi-Blocks CAS #1072946-58-7). LCMS (ESI+): 528 (M+1)+.

Examples 37-44

The following compounds were prepared as in a similar manner to Example 26 replacing 2-(bromomethyl)naphthalene in Step 1 with the appropriately functionalized 2-(bromomethyl)naphthalene.

| Example | Structure and Name | MW | MS (ESI+) |
|---|---|---|---|
| Example 37 | ![structure] ($S_a$)-6-(4-fluoro-1-((6-fluoronaphthalen-2-yl)methyl)-1H-indole-7-carboxamido)spiro[3.3]heptane-2-carboxylic acid | 474.50 | 475 (M + 1)+ |

| Example | Structure and Name | MW | MS (ESI+) |
|---|---|---|---|
| Example 38 | 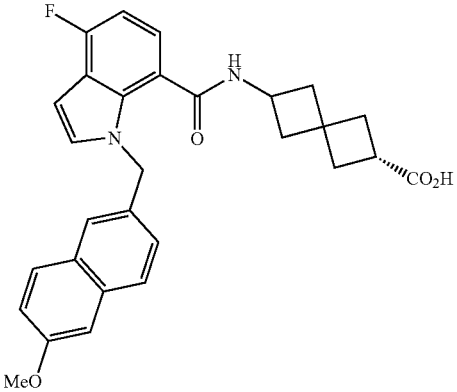<br>(S$_a$)-6-(4-fluoro-1-((6-methoxynaphthalen-2-yl)methyl)-1H-indole-7-carboxamido)spiro[3.3]heptane-2-carboxylic acid | 486.54 | 487 (M + 1)$^+$ |
| Example 39 | 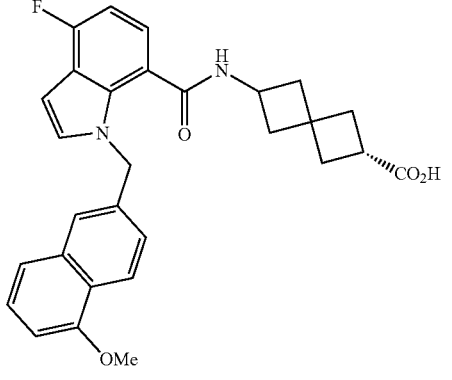<br>(S$_a$)-6-(4-fluoro-1-((5-methoxynaphthalen-2-yl)methyl)-1H-indole-7-carboxamido)spiro[3.3]heptane-2-carboxylic acid | 486.54 | 487 (M + 1)$^+$ |
| Example 40 | 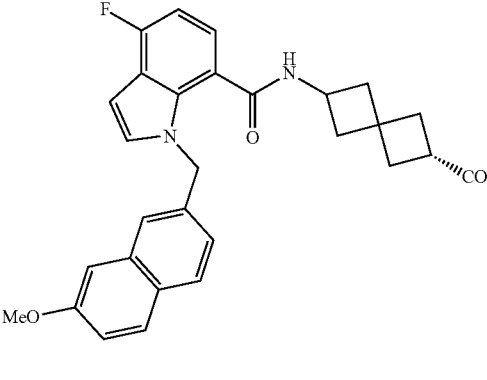<br>(S$_a$)-6-(4-fluoro-1-((7-methoxynaphthalen-2-yl)methyl)-1H-indole-7-carboxamido)spiro[3.3]heptane-2-carboxylic acid | 486.54 | 487 (M + 1)$^+$ |

| Example | Structure and Name | MW | MS (ESI+) |
|---|---|---|---|
| Example 41 | 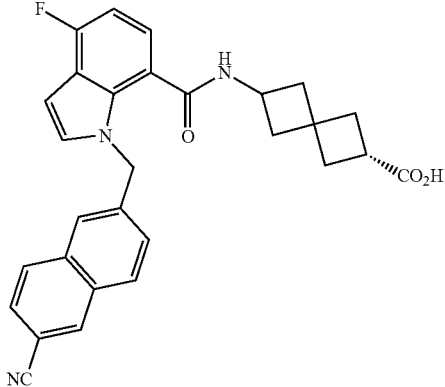<br>($S_a$)-6-(1-(((6-cyanonaphthalen-2-yl)methyl)-4-fluoro-1H-indole-7-carboxamido)spiro[3.3]heptane-2-carboxylic acid | 481.52 | 482 (M + 1)+ |
| Example 42 | 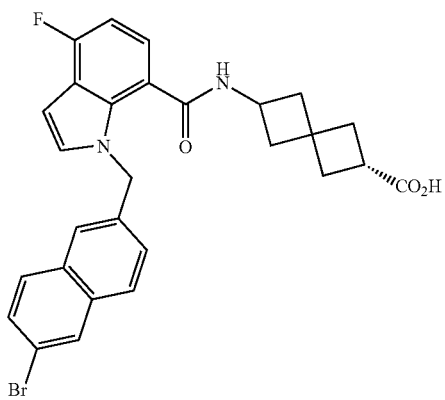<br>($S_a$)-6-(1-(((6-bromonaphthalen-2-yl)methyl)-4-fluoro-1H-indole-7-carboxamido)spiro[3.3]heptane-2-carboxylic acid | 535.41 | 537 (M + 1)+ |

-continued

| Example | Structure and Name | MW | MS (ESI+) |
|---|---|---|---|
| Example 43 | 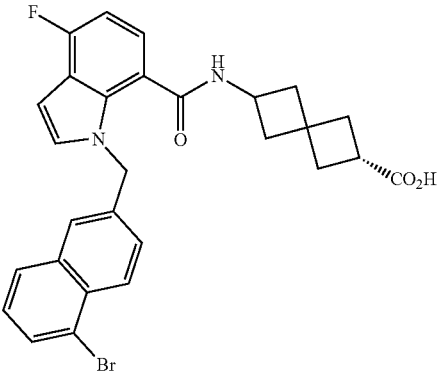<br>($S_a$)-6-(1-((5-bromonaphthalen-2-yl)methyl])-4-fluoro-1H-indole-7-carboxamido)spiro[3.3]heptane-2-carboxylic acid | 535.41 | 537 (M + 1)$^+$ |
| Example 44 | 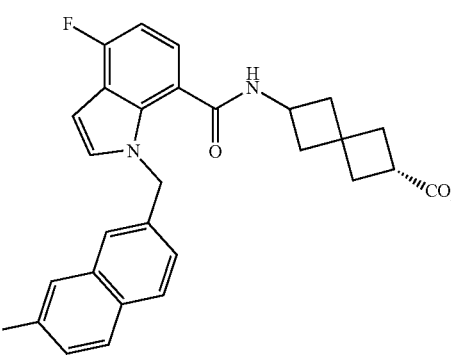<br>($S_a$)-6-(1-((7-bromonaphthalen-2-yl)methyl)-4-fluoro-1H-indole-7-carboxamido)spiro[3.3]heptane-2-carboxylic acid | 535.41 | 537 (M + 1)$^+$ |

Example 45

Preparation of ($S_a$)-6-(4-Fluoro-1-((3'-fluoro-[1,1'-biphenyl]-4-yl)methyl)-1H-indole-7-carboxamido)spiro[3.3]heptane-2-carboxylic acid

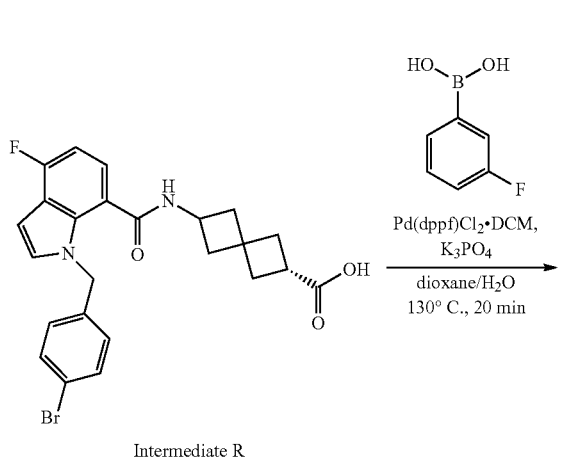

Intermediate R

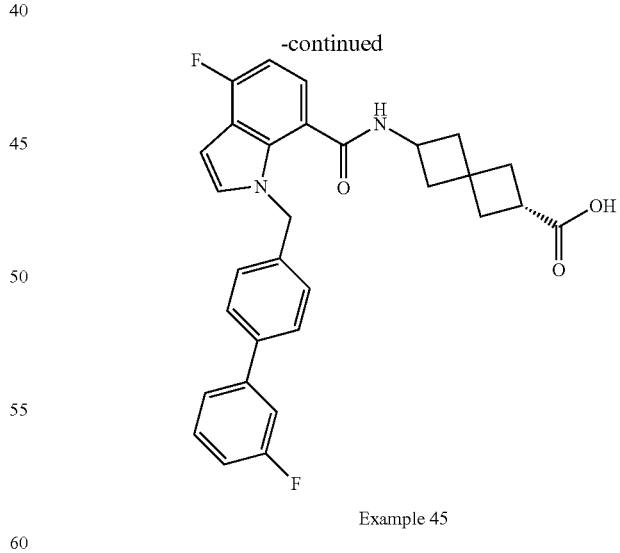

Example 45

In a microwave vial equipped with a magnetic stir bar was added Intermediate R (1.0 equiv), 3-fluorophenylboronic acid (1.2 equiv, Combi-Blocks, CAS #768-35-4) and Pd(dppf)Cl$_2$ dichloromethane adduct (0.1 equiv. Strem CASS #95464-05-4). The vial was sealed with a Teflon cap. The vial was evacuated and back-filled with a N$_2$ atmosphere three times. The vial was then placed under vacuum before the addition of a 2 M aqueous solution of $K_3PO_4$ (3.0 equiv) and dioxane (0.14 M). The vial was heated to 130° C. for 20 min in a microwave reactor. The resulting reaction mixture was allowed to cool to 22° C. and then directly subjected to purification by reverse-phase column chromatography using a C18 cartridge on an automated Teledyne ISCO Rf machine, eluting with 10% to 100% acetonitrile in water+0.1% formic acid as a gradient over 20 minutes.

Fractions with the desired product were combined and lyophilized to afford the title compound as a white powder. LCMS (ESI+): 501 (M+1)$^+$.

Compounds in the following table were made in a similar manner to Example 45. Reactions were run using the Intermediate R and the corresponding commercially available boronic acid at temperatures ranging from 100-130° C. for durations ranging from 10-30 min in a microwave reactor.

| Example | Structure and Name | MW | MS (ESI+) |
|---|---|---|---|
| Example 46 | 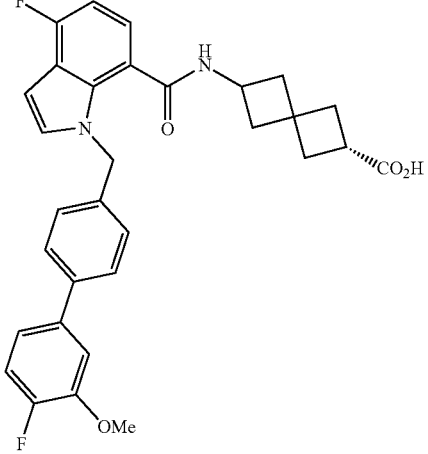<br>$(S_a)$-6-(4-fluoro-1-((4'-fluoro-3'-methoxy-[1,1'-biphenyl]-4-yl)methyl)-1H-indole-7-carboxamido)spiro[3.3]heptane-2-carboxylic acid | 530.57 | 531 (M + 1)$^+$ |
| Example 47 | 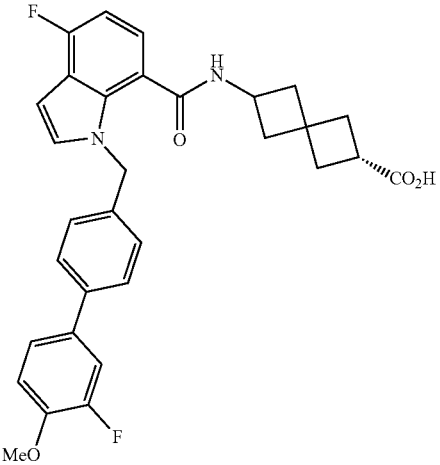<br>$(S_a)$-6-(4-fluoro-1-((3'-fluoro-4'-methoxy-[1,1'-biphenyl]-4-yl)methyl)-1H-indole-7-carboxamido)spiro[3.3]heptane-2-carboxylic acid | 530.57 | 531 (M + 1)$^+$ |

-continued

| Example | Structure and Name | MW | MS (ESI+) |
|---|---|---|---|
| Example 48 | 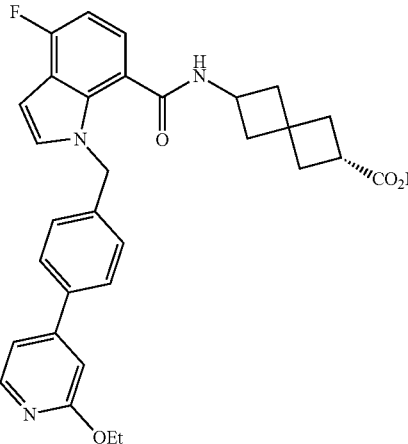<br>($S_a$)-6-(1-(4-(2-ethoxypyridin-4-yl)benzyl)-4-fluoro-1H-indole-7-carboxamido)spiro[3.3]heptane-2-carboxylic acid | 527.59 | 528 (M + 1)+ |
| Example 49 | 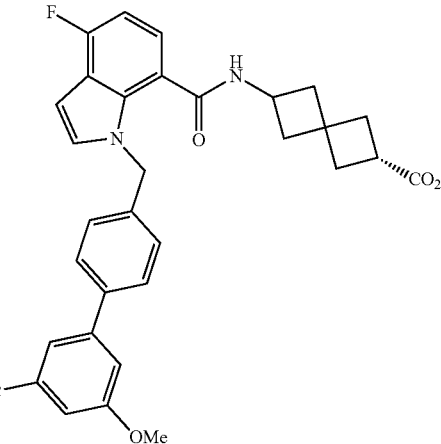<br>($S_a$)-6-(1-((3'-cyano-5'-methoxy-[1,1'-biphenyl]-4-yl)methyl)-4-fluoro-1H-indole-7-carboxamido)spiro[3.3]heptane-2-carboxylic acid | 537.58 | 538 (M + 1)+ |
| Example 50 | 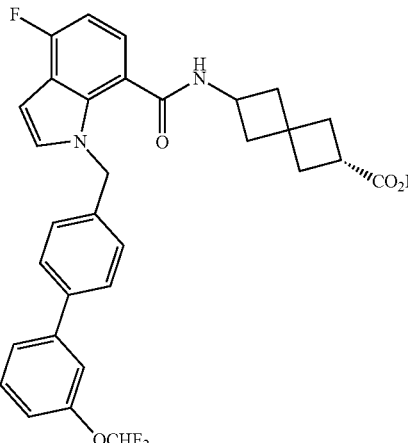<br>($S_a$)-6-(1-((3'-(difluoromethoxy)-[1,1'-biphenyl]-4-yl)methyl)-4-fluoro-1H-indole-7-carboxamido)spiro[3.3]heptane-2-carboxylic acid | 548.56 | 549 (M + 1)+ |

| Example | Structure and Name | MW | MS (ESI+) |
|---|---|---|---|
| Example 51 | 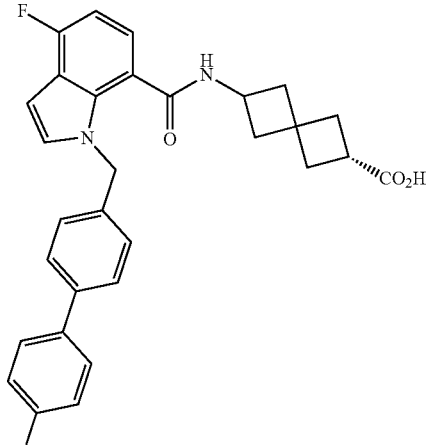<br>($S_a$)-6-(4-fluoro-1-((4'-methoxy-[1,1'-biphenyl]-4-yl)methyl)-1H-indole-7-carboxamido)spiro[3.3]heptane-2-carboxylic acid | 512.57 | 513 (M + 1)+ |
| Example 52 | 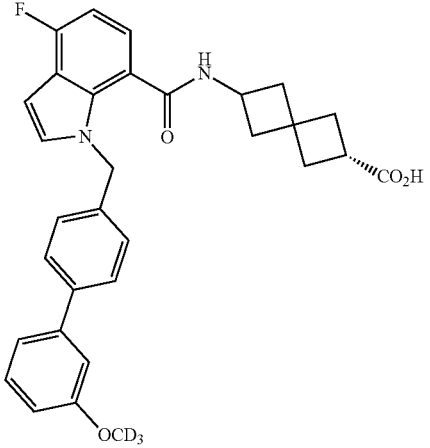<br>($S_a$)-6-(4-fluoro-1-((3'-methoxy-$d_3$-[1,1'-biphenyl]-4-yl)methyl)-1H-indole-7-carboxamido)spiro[3.3]heptane-2-carboxylic acid | 515.59 | 516 (M + 1)+ |
| Example 53 | 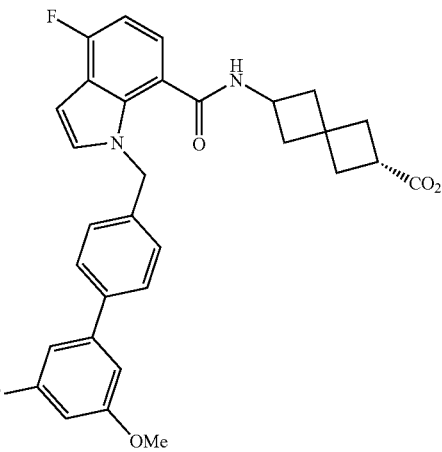<br>($S_a$)-6-(4-fluoro-1-((3'-fluoro-5'-methoxy-[1,1'-biphenyl]-4-yl)methyl)-1H-indole-7-carboxamido)spiro[3.3]heptane-2-carboxylic acid | 530.57 | 531 (M + 1)+ |

| Example | Structure and Name | MW | MS (ESI+) |
|---|---|---|---|
| Example 54 | 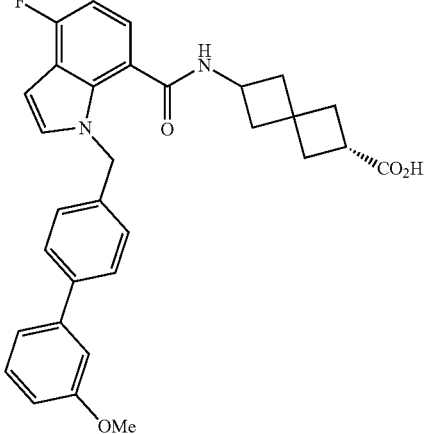<br>(S$_a$)-6-(1-((3'-ethoxy-[1,1'-biphenyl]-4-yl)methyl)-4-fluoro-1H-indole-7-carboxamido)spiro[3.3]heptane-2-carboxylic acid | 526.60 | 527 (M + 1)$^+$ |
| Example 55 | 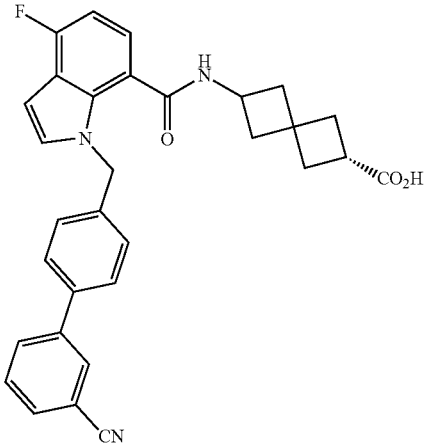<br>(S$_a$)-6-(1-((3'-cyano-[1,1'-biphenyl]-4-yl)methyl)-4-fluoro-1H-indole-7-carboxamido)spiro[3.3]heptane-2-carboxylic acid | 507.56 | 508 (M + 1)$^+$ |

Example 56

Preparation of (S$_a$)-6-(1-(4-(6-Ethoxypyridin-2-yl)benzyl)-4-fluoro-1H-indole-7-carboxamido)spiro[3.3]heptane-2-carboxylic acid

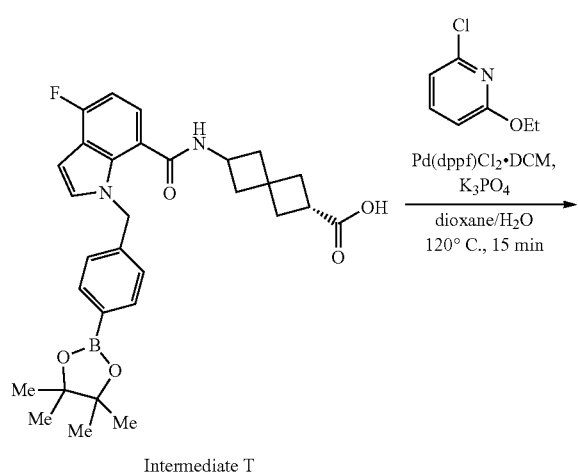

Intermediate T

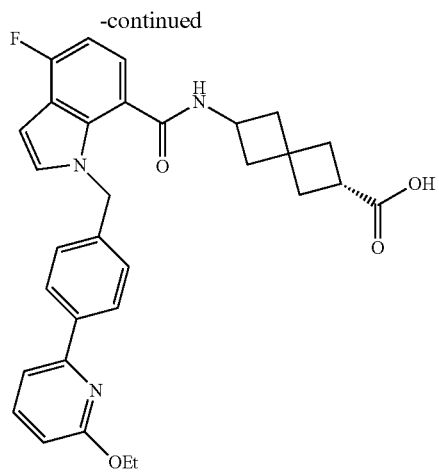

Example 56

In a microwave vial equipped with a magnetic stir bar was added Intermediate T (1.0 equiv), 2-chloro-6-ethoxypyridine (1.5 equiv. Combi-Blocks, CAS #42144-78-5) and Pd(dppf)Cl$_2$ dichloromethane adduct (0.1 equiv. Strem CAS #95464-05-4). The vial was sealed with a Teflon cap. The vial was evacuated and back-filled with a N$_2$ atmosphere three times. The vial was then placed under vacuum before the addition of a 2 M aqueous solution of K$_3$PO$_4$ (3.0 equiv) and dioxane (0.06 M). The vial was heated to 120° C. for 15 min in a microwave reactor. The resulting reaction mixture was allowed to cool to 22° C. and then directly subjected to purification by reverse-phase column chromatography using a C18 cartridge on an automated Teledyne ISCO Rf machine, eluting with 10% to 100% acetonitrile in water+ 0.1% formic acid as a gradient over 20 minutes. Fractions with the desired product were combined and lyophilized to afford the title compound as a white powder. LCMS (ESI+): 528 (M+1)$^+$.

Compounds in the following table were made in a similar manner to Example 56. Reactions were run using the Intermediate T and the corresponding commercially available (hetero)aryl halide at temperatures ranging from 100-130° C. for durations ranging from 10-30 min in a microwave reactor.

| Example | Structure and Name | MW | MS (ESI+) |
|---|---|---|---|
| Example 57 | ![structure] (S$_a$)-6-(4-fluoro-1-((3'-(oxetane-3-yloxy)-[1,1'-biphenyl]-4-yl)methyl)-1H-indole-7-carboxamido)spiro[3.3]heptane-2-carboxylic acid | 554.61 | 555 (M + 1)$^+$ |

| Example | Structure and Name | MW | MS (ESI+) |
|---|---|---|---|
| Example 58 | 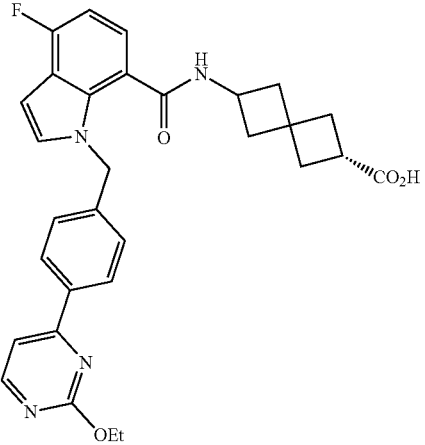<br>($S_a$)-6-(1-(4-(2-ethoxypyrimidin-4-yl)benzyl)-4-fluoro-1H-indole-7-carboxamido)spiro[3.3]heptane-2-carboxylic acid | 528.59 | 529 (M + 1)$^+$ |
| Example 59 | 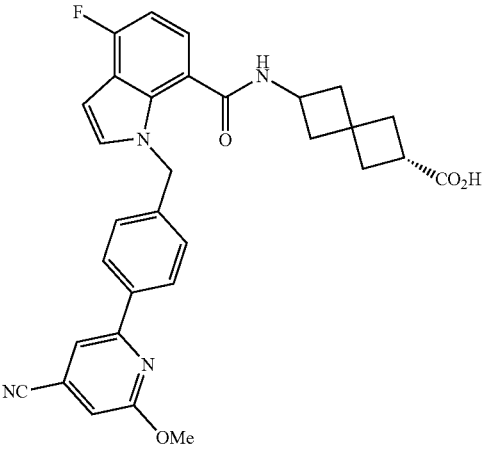<br>($S_a$)-6-(1-(4-(4-cyano-6-methoxypyridin-2-yl)benzyl)-4-fluoro-1H-indole-7-carboxamido)spiro[3.3]heptane-2-carboxylic acid | 538.57 | 539 (M + 1)$^+$ |
| Example 60 | 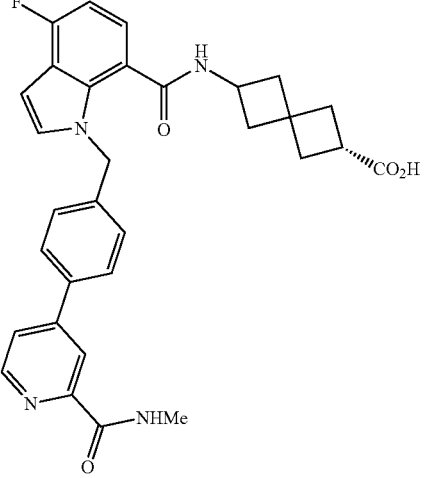<br>($S_a$)-6-(4-fluoro-1-(4-(2-(methylcarbamoyl)pyridin-4-yl)benzyl)-1H-indole-7-carboxamido)spiro[3.3]heptane-2-carboxylic acid | 540.59 | 541 (M + 1)$^+$ |

-continued
| Example | Structure and Name | MW | MS (ESI+) |
|---|---|---|---|
| Example 61 | 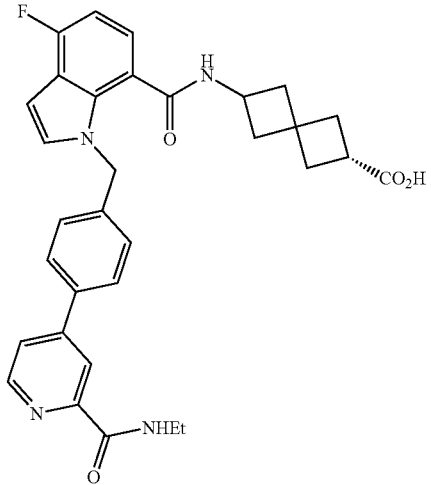<br>($S_a$)-6-(1-(4-(2-(ethylcarbamoyl)pyridin-4-yl)benzyl)-4-fluoro-1H-indole-7-carboxamido)spiro[3.3]heptane-2-carboxylic acid | 554.61 | 555 (M + 1)+ |
| Example 62 | 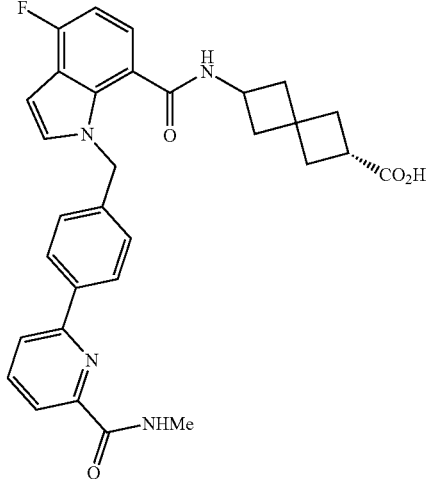<br>($S_a$)-6-(4-fluoro-1-(4-(6-(methylcarbamoyl)pyridin-2-yl)benzyl)-1H-indole-7-carboxamido)spiro[3.3]heptane-2-carboxylic acid | 540.59 | 541 (M + 1)+ |

-continued
| Example | Structure and Name | MW | MS (ESI+) |
|---|---|---|---|
| Example 63 | 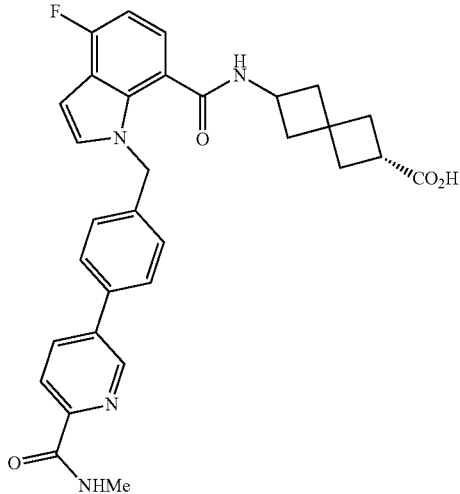<br>(S$_a$)-6-(4-fluoro-1-(4-(6-(methylcarbamoyl)pyridin-3-yl)benzyl)-1H-indole-7-carboxamido)spiro[3.3]heptane-2-carboxylic acid | 540.59 | 541 (M + 1)$^+$ |
| Example 64 | 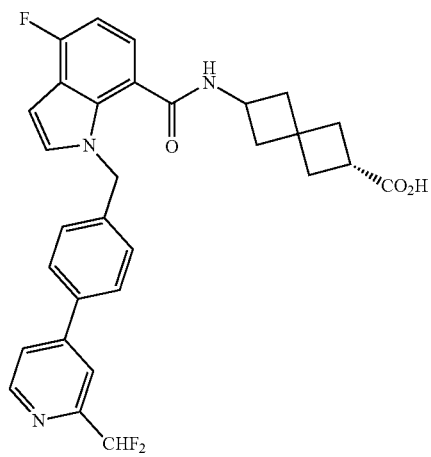<br>(S$_a$)-6-(1-(4-(2-(difluoromethyl)pyridin-4-yl)benzyl)-4-fluoro-1H-indole-7-carboxamido)spiro[3.3]heptane-2-carboxylic acid | 533.54 | 534 (M + 1)$^+$ |

Example 65

Preparation of (S$_a$)-6-(4-Fluoro-1-((2-fluoro-[1,1'-biphenyl]-4-yl)methyl)-1H-indole-7-carboxamido)spiro[3.3]heptane-2-carboxylic acid

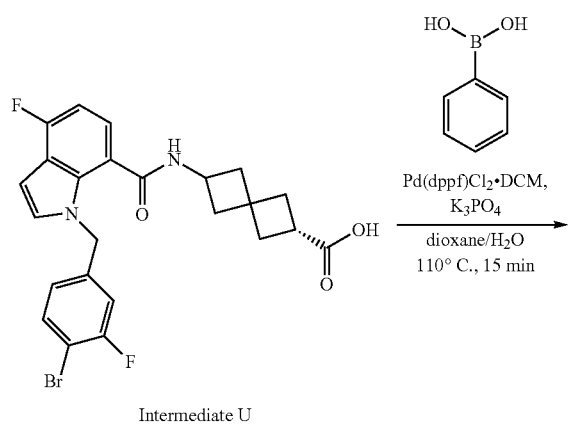

Intermediate U

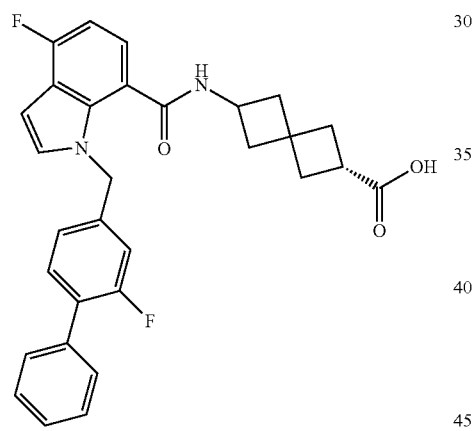

Example 65

In a microwave vial equipped with a magnetic stir bar was added Intermediate U (1.0 equiv), phenylboronic acid (1.2 equiv, Combi-Blocks, CAS #768-35-4) and Pd(dppf)Cl$_2$ dichloromethane adduct (0.1 equiv, Strem CAS #98-80-6). The vial was sealed with a Teflon cap. The vial was evacuated and back-filled with a N$_2$ atmosphere three times. The vial was then placed under vacuum before the addition of a 2 M aqueous solution of K$_3$PO$_4$ (3.0 equiv) and dioxane (0.14 M). The vial was heated to 110° C. for 15 min in a microwave reactor. The resulting reaction mixture was allowed to cool to 22° C. and then directly subjected to purification by reverse-phase column chromatography using a C18 cartridge on an automated Teledyne ISCO Rf machine, eluting with 10% to 100% acetonitrile in water+ 0.1% formic acid as a gradient over 20 minutes. Fractions with the desired product were combined and lyophilized to afford the title compound as a white powder. LCMS (ESI+): 501 (M+1)$^+$.

Example 66

Preparation of (S$_a$)-6-(4-Fluoro-1-((3-fluoro-[1,1'-biphenyl]-4-yl)methyl)-1H-indole-7-carboxamido)spiro[3.3]heptane-2-carboxylic acid

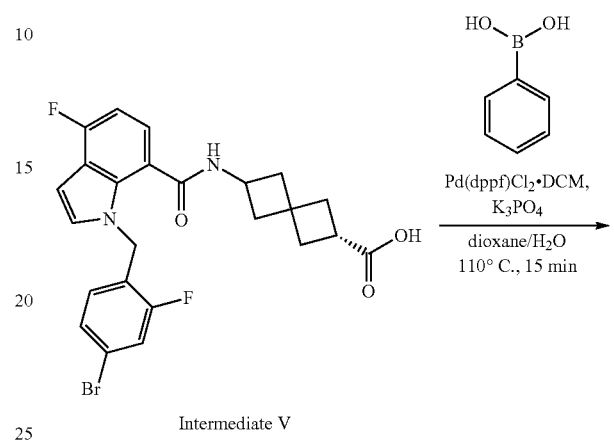

Intermediate V

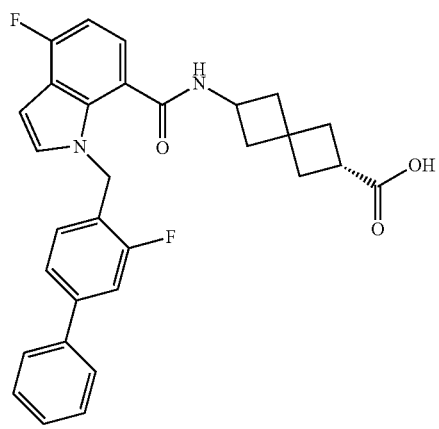

Example 66

In a microwave vial equipped with a magnetic stir bar was added Intermediate V (1.0 equiv), phenylboronic acid (1.2 equiv, Combi-Blocks, CAS #768-35-4) and Pd(dppf)Cl$_2$ dichloromethane adduct (0.1 equiv, Strem CAS #98-80-6). The vial was sealed with a Teflon cap. The vial was evacuated and back-filled with a N$_2$ atmosphere three times. The vial was then placed under vacuum before the addition of a 2 M aqueous solution of K$_3$PO$_4$ (3.0 equiv) and dioxane (0.14 M). The vial was heated to 110° C. for 15 min in a microwave reactor. The resulting reaction mixture was allowed to cool to 22° C. and then directly subjected to purification by reverse-phase column chromatography using a C18 cartridge on an automated Teledyne ISCO Rf machine, eluting with 10% to 100% acetonitrile in water+ 0.1% formic acid as a gradient over 20 minutes. Fractions with the desired product were combined and lyophilized to afford the title compound as a white powder. LCMS (ESI+): 501 (M+1)$^+$.

Example 67

Preparation of (S$_a$)-6-(4-Chloro-1-(4-(pyridin-4-yl)benzyl)-1H-indole-7-carboxamido)spiro[3.3]heptane-2-carboxylic acid

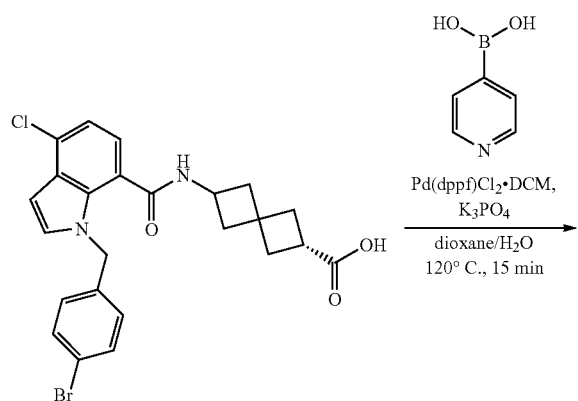

Intermediate W

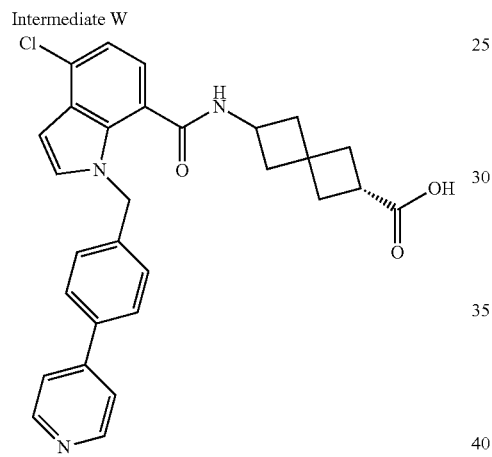

Example 67

In a microwave vial equipped with a magnetic stir bar was added Intermediate W (1.0 equiv), pyridine-4-boronic acid (1.2 equiv. Combi-Blocks, CAS #1692-15-5) and Pd(dppf)Cl$_2$ dichloromethane adduct (0.1 equiv, Strem CAS #98-80-6). The vial was sealed with a Teflon cap. The vial was evacuated and back-filled with a N$_2$ atmosphere three times. The vial was then placed under vacuum before the addition of a 2 M aqueous solution of K$_3$PO$_4$ (3.0 equiv) and dioxane (0.11 M). The vial was heated to 120° C. for 15 min in a microwave reactor. The resulting reaction mixture was allowed to cool to 22° C. and then directly subjected to purification by reverse-phase column chromatography using a C18 cartridge on an automated Teledyne ISCO Rf machine, eluting with 10% to 100% acetonitrile in water+ 0.1% formic acid as a gradient over 20 minutes. Fractions with the desired product were combined and lyophilized to afford the title compound as a white powder. LCMS (ESI+): 500 (M+1)$^+$.

Compounds in the following table were made in a similar manner to Example 67. Reactions were run using the Intermediate W and the corresponding commercially available boronic acid at temperatures ranging from 100-130° C. for durations ranging from 10-30 min in a microwave reactor.

| Example | Structure and Name | MW | MS (ESI+) |
|---|---|---|---|
| Example 68 | ![structure] (S$_a$)-6-(1-([1,1'-biphenyl]-4-ylmethyl)-4-chloro-1H-indole-7-carboxamido)spiro[3.3]heptane-2-carboxylic acid | 499.00 | 499 (M + 1)$^+$ |

-continued
| Example | Structure and Name | MW | MS (ESI+) |
|---|---|---|---|
| Example 69 | 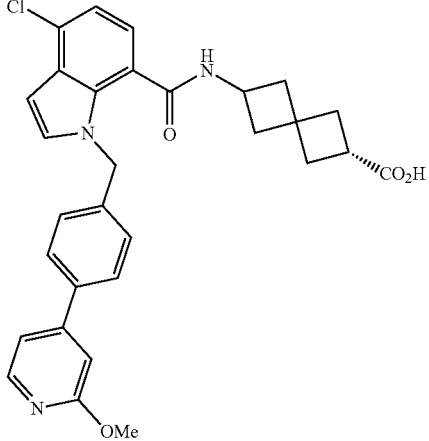
($S_a$)-6-(4-chloro-1-(4-(2-methoxypyridin-4-yl)benzy))-1H-indole-7-carboxamido)spiro[3.3]heptane-2-carboxylic acid | 530.02 | 530 (M + 1)+ |
| Example 70 | 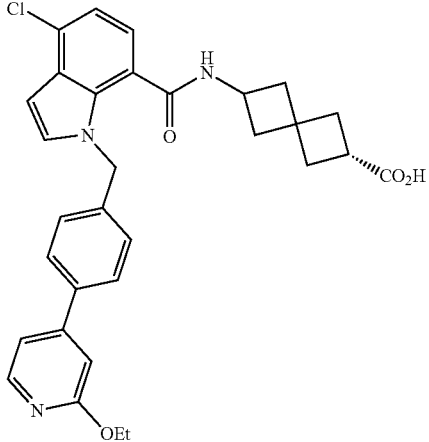
($S_a$)-6-(4-chloro-1-(4-(2-ethoxypyridin-4-yl)benzyl)-1H-indole-7-carboxamido)spiro[3.3]heptane-2-carboxylic acid | 544.04 | 544 (M + 1)+ |

Example 71

Preparation of (S$_a$)-6-(4-Chloro-1-(4-morpholinobenzyl)-1H-indole-7-carboxamido)spiro[3.3]heptane-2-carboxylic acid

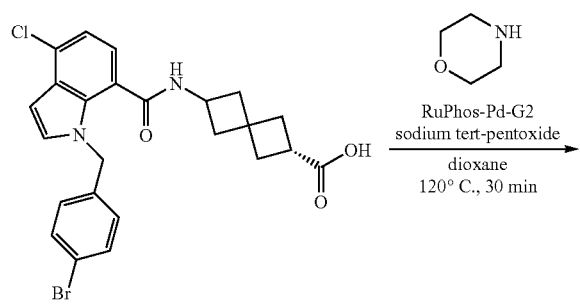

Intermediate W

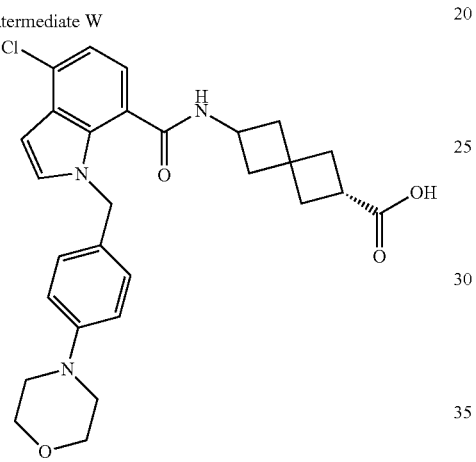

Example 71

Into a microwave reaction vial equipped with a magnetic stir bar and under nitrogen was added Intermediate W (1.0 equiv), RuPhos-Pd-G2 (0.05 equiv, Strem, CAS #1375325-68-0), sodium tert-pentoxide (2.5 equiv), morpholine (2.0 equiv) and dioxane (anhydrous, 0.1 M). The resulting mixture was purged with nitrogen for 10 minutes before it was sealed and stirred at 120° C. for 30 minutes in a microwave reactor. LCMS analysis revealed conversion to product. The reaction mixture was loaded onto a silica gel pre-cartridge, rinsing with MeOH. Purification by reverse-phase column chromatography using a C18 cartridge on an automated Teledyne ISCO Rf machine, eluting with 0% to 100% acetonitrile in water+0.1% formic acid as a gradient over 20 minutes. The desired fractions were combined and lyophilized to afford the title compound as a white solid. LCMS (ESI+): 508 (M+1)$^+$.

Compounds in the following table were made in a similar manner to Example 71. Reactions were run using the appropriate aryl halide (Intermediate X for Examples 72, 73, and 74; Intermediate Y for Examples 75 and 76; Intermediate JJ for Example 77) and the corresponding commercially available secondary amine at temperatures ranging from 80-180° C. for durations ranging from 10-30 min in a microwave reactor.

| Example | Structure and Name | MW | MS (ESI+) |
|---|---|---|---|
| Example 72 | ![structure] (S$_a$)-6-(1-(4-((1R,5S)-3-azabicyclo[3.1.0]hexan-3-yl)benzyl)-4-chloro-1H-indazole-7-carboxamido)spiro[3.3]heptane-2-carboxylic acid | 505.01 | 505 (M + 1)$^+$ |

| Example | Structure and Name | MW | MS (ESI+) |
|---|---|---|---|
| Example 73 | (S$_a$)-6-(1-(4-(1H-pyrazol-1-yl)benzyl)-4-chloro-1H-indazole-7-carboxamido)spiro[3.3]heptane-2-carboxylic acid | 489.96 | 490 (M + 1)$^+$ |
| Example 74 | (S$_a$)-6-(4-chloro-1-(4-(3,3-difluoropyrrolidin-1-yl)benzyl)-1H-indazole-7-carboxamido)spiro[3.3]heptane-2-carboxylic acid | 528.98 | 529 (M + 1)$^+$ |
| Example 75 | (S$_a$)-6-(1-(4-((1R,5S)-3-azabicyclo[3.1.0]hexan-3-yl)-3-fluorobenzyl)-4-chloro-1H-indazole-7-carboxamido)spiro[3.3]heptane-2-carboxylic acid | 523.00 | 523 (M + 1)$^+$ |

| Example | Structure and Name | MW | MS (ESI+) |
|---|---|---|---|
| Example 76 | 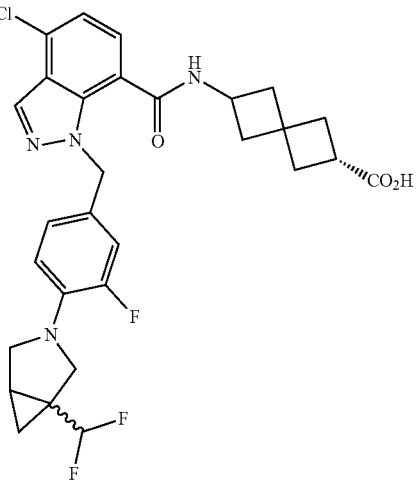<br>($S_a$)-6-(4-chloro-1-(4-((racemic)-1-(difluoromethyl)-3-azabicyclo[3.1.0]hexan-3-yl)-3-fluorobenzyl)-1H-indazole-7-carboxamido)spiro[3.3]heptane-2-carboxylic acid | 573.01 | 573 (M + 1)+ |
| Example 77 | 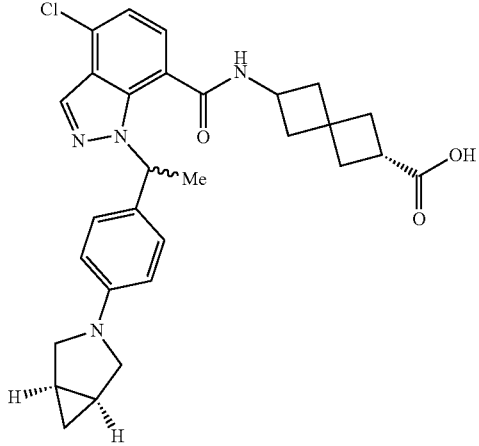<br>($S_a$)-6-(1-((racemic)-1-(4-((1R,5S)-3-azabicyclo[3.1.0]hexan-3-yl)phenyl)ethyl)-4-chloro-1H-indazole-7-carboxamido)spiro[3.3]heptane-2-carboxylic acid | 519.04 | 519 (M + 1)+ |

Example 78

Preparation of (S$_a$)-6-(4-Chloro-1-(4-(2-methoxypyridin-4-yl)benzyl)-1H-indazole-7-carboxamido)spiro[3.3]heptane-2-carboxylic acid

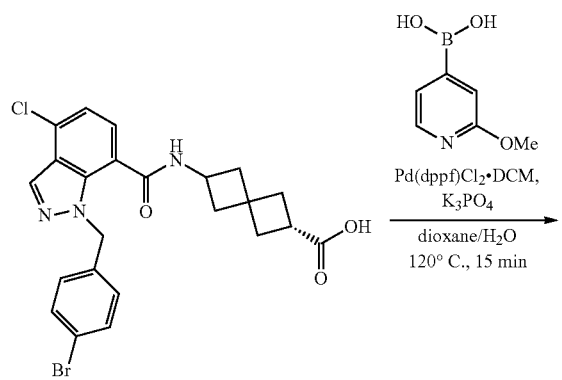

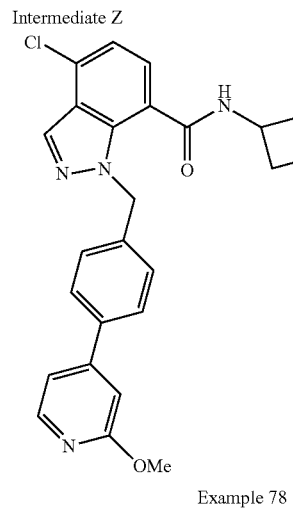

Example 78

In a microwave vial equipped with a magnetic stir bar was added Intermediate Z (1.0 equiv), 2-methoxypyridine-4-boronic acid (1.2 equiv, Combi-Blocks. CAS #762262-09-9) and Pd(dppf)Cl$_2$ dichloromethane adduct (0.1 equiv, Strem CAS #98-80-6). The vial was sealed with a Teflon cap. The vial was evacuated and back-filled with a N$_2$ atmosphere three times. The vial was then placed under vacuum before the addition of a 2 M aqueous solution of K$_3$PO$_4$ (3.0 equiv) and dioxane (0.09 M). The vial was heated to 120° C. for 15 min in a microwave reactor. The resulting reaction mixture was allowed to cool to 22° C. and then directly subjected to purification by reverse-phase column chromatography using a C18 cartridge on an automated Teledyne ISCO Rf machine, eluting with 10% to 100% acetonitrile in water+0.1% formic acid as a gradient over 20 minutes. Fractions with the desired product were combined and lyophilized to afford the title compound as a white powder. LCMS (ESI+): 531 (M+1)$^+$.

Compounds in the following table were made in a similar manner to Example 78. Reactions were run using either Intermediate Z (Examples 79 and 80) or Intermediate Y (Examples 81 and 82) and the corresponding commercially available boronic acid or boron pinacolate ester.

| Example | Structure and Name | MW | MS (ESI+) |
|---|---|---|---|
| Example 79 | (S$_a$)-6-(4-chloro-1-(4-(2-ethoxypyridin-4-yl)benzyl)-1H-indazole-7-carboxamido)spiro[3.3]heptane-2-carboxylic acid | 545.03 | 545 (M + 1)$^+$ |

-continued

| Example | Structure and Name | MW | MS (ESI+) |
|---|---|---|---|
| Example 80 | 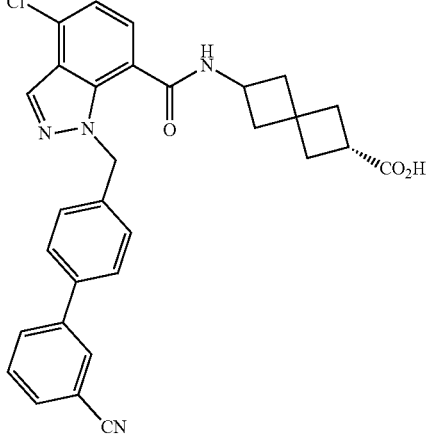<br>(S$_a$)-6-(4-chloro-1-((3'-cyano-[1,1'-biphenyl]-4-yl)methyl)-1H-indazole-7-carboxamido)spiro[3.3]heptane-2-carboxylic acid | 525.00 | 525 (M + 1)$^+$ |
| Example 81 | 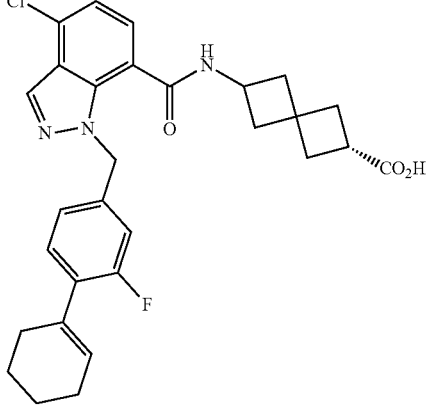<br>(S$_a$)-6-(4-chloro-1-((2-fluoro-2'3'4'5'-tetrahydro-[1,1'-biphenyl]-4-yl)methyl)-1H-indazole-7-carboxamido)spiro[3.3]heptane-2-carboxylic acid | 522.01 | 522 (M + 1)$^+$ |
| Example 82 | 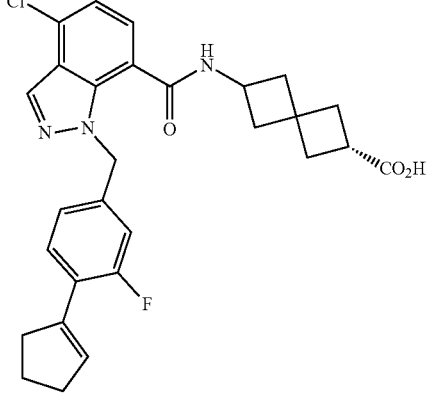<br>(S$_a$)-6-(4-chloro-1-(4-(cyclopent-1-en-1-yl)-3-fluorobenzyl)-1H-indazole-7-carboxamido)spiro[3.3]heptane-2-carboxylic acid | 507.99 | 508 (M + 1)$^+$ |

Example 83

Preparation of (S$_a$)-6-(4-Chloro-1-(4-(6-ethoxypyridin-2-yl)benzyl)-1H-indazole-7-carboxamido)spiro[3.3]heptane-2-carboxylic acid

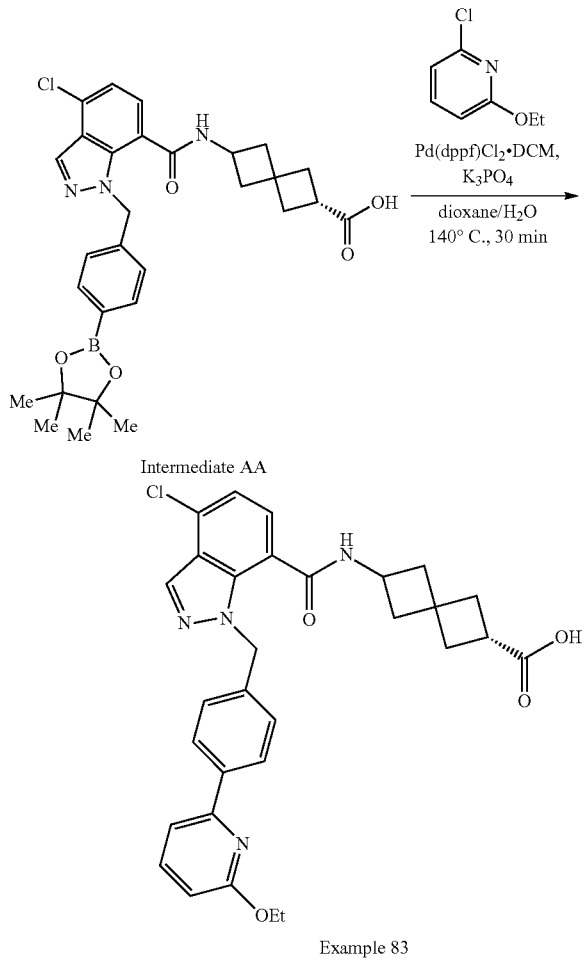

Intermediate AA

Example 83

In a microwave vial equipped with a magnetic stir bar was added Intermediate AA (1.0 equiv), 2-chloro-6-ethoxypyridine (1.2 equiv, Combi-Blocks, CAS #42144-78-5) and Pd(dppf)Cl$_2$ dichloromethane adduct (0.1 equiv, Strem CASS #95464-05-4). The vial was sealed with a Teflon cap. The vial was evacuated and back-filled with a N$_2$ atmosphere three times. The vial was then placed under vacuum before the addition of a 2 M aqueous solution of K$_3$PO$_4$ (3.0 equiv) and dioxane (0.11 M). The vial was heated to 140° C. for 30 min in a microwave reactor. The resulting reaction mixture was allowed to cool to 22° C. and then directly subjected to purification by reverse-phase column chromatography using a C18 cartridge on an automated Teledyne ISCO Rf machine, eluting with 10% to 100% acetonitrile in water+0.1% formic acid as a gradient over 20 minutes. Fractions with the desired product were combined and lyophilized to afford the title compound as a white powder. LCMS (ESI+): 545 (M+1)$^+$.

Compounds in the following table were made in a similar manner to Example 83. Reactions were run using the Intermediate AA and the corresponding commercially available (hetero)aryl halide at temperatures ranging from 100-150° C. for durations ranging from 10-30 min in a microwave reactor.

| Example | Structure and Name | MW | MS (ESI+) |
|---|---|---|---|
| Example 84 | (S$_a$)-6-(4-chloro-1-(4-(2-ethoxypyrimidin-6-yl)benzyl)-1H-indazole-7-carboxamido)spiro[3.3]heptane-2-carboxylic acid | 546.02 | 546 (M + 1)$^+$ |

| Example | Structure and Name | MW | MS (ESI+) |
|---|---|---|---|
| Example 85 | 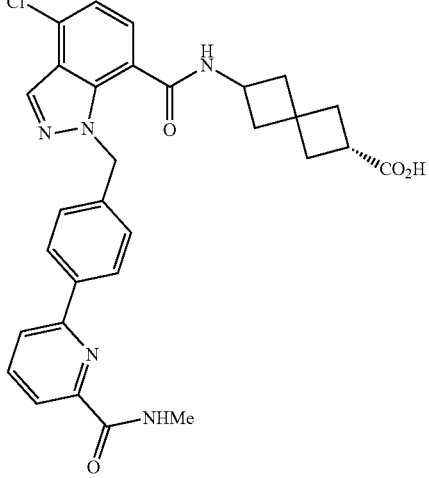<br>($S_a$)-6-(4-chloro-1-(4-(6-(methylcarbamoyl)pyridin-2-yl)benzyl)-1H-indazole-7-carboxamido)spiro[3.3]heptane-2-carboxylic acid | 558.03 | 558 (M + 1)⁺ |
| Example 86 | 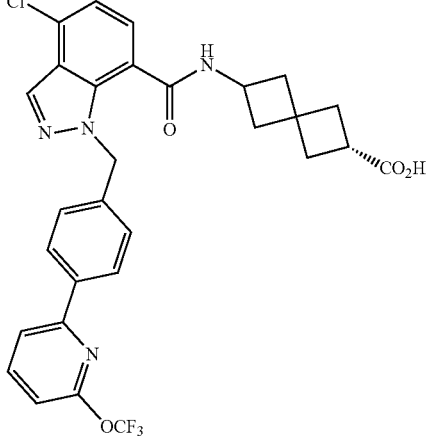<br>($S_a$)-6-(4-chloro-1-(4-(6-(trifluoromethoxy)pyridin-2-yl)benzy))-1H-indazole-7-carboxamido)spiro[3.3]heptane-2-carboxylic acid | 584.98 | 585 (M + 1)⁺ |

| Example | Structure and Name | MW | MS (ESI+) |
|---|---|---|---|
| Example 87 | 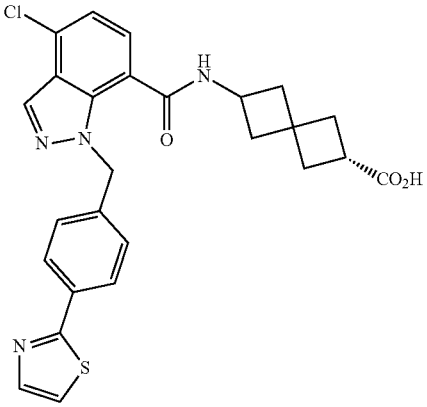<br>($S_a$)-6-(4-chloro-1-(4-(thiazol-2-yl)benzyl)-1H-indazole-7-carboxamido)spiro[3.3]heptane-2-carboxylic acid | 507.01 | 507 (M + 1)+ |

Example 88

Preparation of ($S_a$)-6(1-([1,1'-Biphenyl]-4-ylmethyl)-4-methoxy-1H-pyrrolo[3,2-c]pyridine-7-carboxamido)spiro[3.3]heptane-2-carboxylic acid

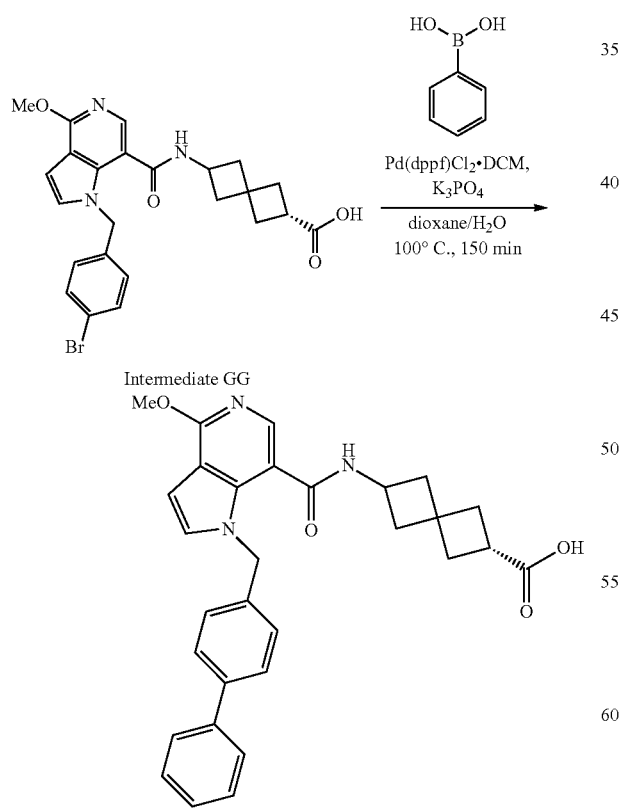

Example 88

In a sealable reaction vial equipped with a magnetic stir bar was added Intermediate GG (1.0 equiv), phenylboronic acid (1.5 equiv, Combi-Blocks, CAS #768-35-4) and Pd(dppf)Cl$_2$ dichloromethane adduct (0.1 equiv, Strem CAS #98-80-6). The vial was sealed with a Teflon cap. The vial was evacuated and back-filled with a N$_2$ atmosphere three times. The vial was then placed under vacuum before the addition of a 2 M aqueous solution of K$_3$PO$_4$ (3.0 equiv) and dioxane (0.05 M). The vial was heated to 100° C. for 150 min in a stainless steel heating block. The resulting reaction mixture was allowed to cool to 22° C. and then directly subjected to purification by reverse-phase column chromatography using a C18 cartridge on an automated Teledyne ISCO Rf machine, eluting with 10% to 100% acetonitrile in water+0.1% formic acid as a gradient over 20 minutes. Fractions with the desired product were combined and concentrated to afford the title compound as a white powder. LCMS (ESI+): 496 (M+1)+.

Compounds in the following table were made in a similar manner to Example 88. Reactions were run using either Intermediate GG (Examples 89 and 91) or Intermediate HH (Examples 90) and the corresponding commercially available boronic acid.

| Example | Structure and Name | MW | MS (ESI+) |
|---|---|---|---|
| Example 89 | (S$_a$)-6-(1-(4-(2-ethoxypyridin-4-yl)benzyl)-4-methoxy-1H-pyrrolo[3,2-c]pyridine-7-carboxamido)spiro[3.3]heptane-2-carboxylic acid | 540.61 | 541 (M + 1)$^+$ |
| Example 90 | (S$_a$)-6-(1-([1,1'-biphenyl]-4-ylmethyl)-4-ethoxy-1H-pyrrolo[3,2-c]pyridine-7-carboxamido)spiro[3.3]heptane-2-carboxylic acid | 509.60 | 510 (M + 1)$^+$ |
| Example 91 | (S$_a$)-6-(1-(4-(6-ethoxypyridin-3-yl)benzyl)-4-methoxy-1H-pyrrolo[3,2-c]pyridine-7-carboxamido)spiro[3.3]heptane-2-carboxylic acid | 540.61 | 541 (M + 1)$^+$ |

Example 92

Preparation of (S$_a$)-6-(4-Methoxy-1-(4-(6-methoxy-pyridin-2-yl)benzyl)-1H-pyrrolo[3,2-c]pyridine-7-carboxamido)spiro[3.3]heptane-2-carboxylic acid

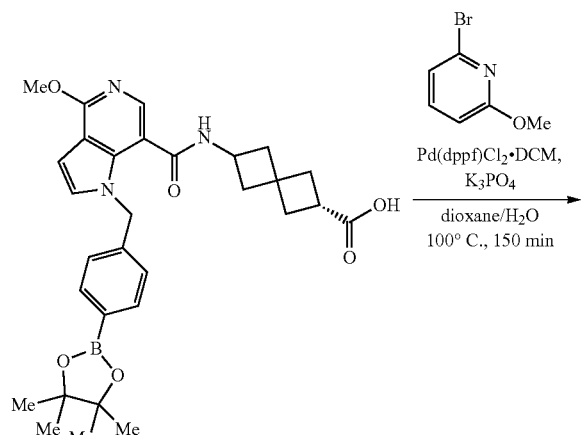

Intermediate II

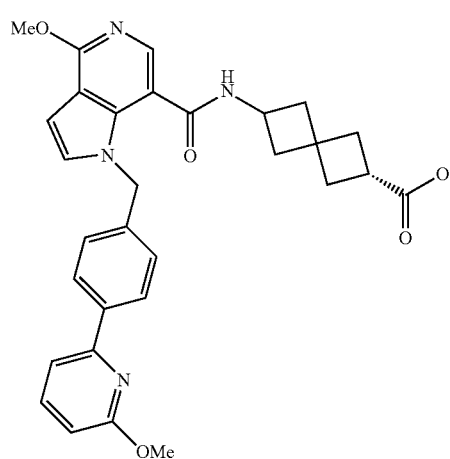

Example 92

In a sealable reaction vial equipped with a magnetic stir bar was added Intermediate II (1.0 equiv), 2-bromo-6-methoxypyridine (1.4 equiv, Combi-Blocks, CAS #40473-07-2) and Pd(dppf)Cl$_2$ dichloromethane adduct (0.1 equiv, Strem CAS #95464-054). The vial was sealed with a Teflon cap. The vial was evacuated and back-filled with a N$_2$ atmosphere three times. The vial was then placed under vacuum before the addition of a 2 M aqueous solution of K$_3$PO$_4$ (3.0 equiv) and dioxane (0.05 M). The vial was heated to 100° C. for 150 min in a stainless steel heating block. The resulting reaction mixture was allowed to cool to 22° C. and then directly subjected to purification by reverse-phase column chromatography using a C18 cartridge on an automated Teledyne ISCO Rf machine, eluting with 10% to 100% acetonitrile in water+0.1% formic acid as a gradient over 20 minutes. Fractions with the desired product were combined and concentrated to afford the title compound as a white powder. LCMS (ESI+): 527 (M+1)$^+$.

Example 93

Preparation of (S$_a$)-6-(1-([1,1'-Biphenyl]-4-ylmethyl)-5-chloro-1H-indazole-7-carboxamido)spiro[3.3]heptane-2-carboxylic acid

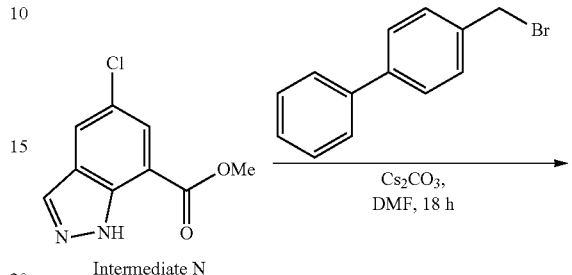

Intermediate N

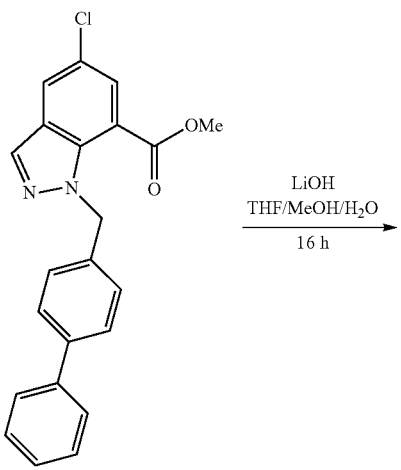

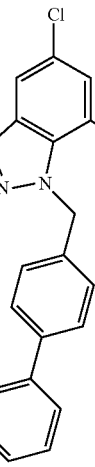 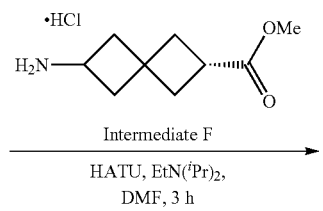

Intermediate F

HATU, EtN($^i$Pr)$_2$, DMF, 3 h

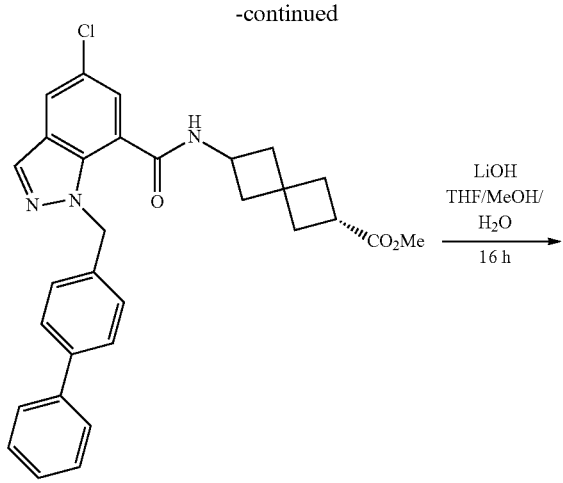

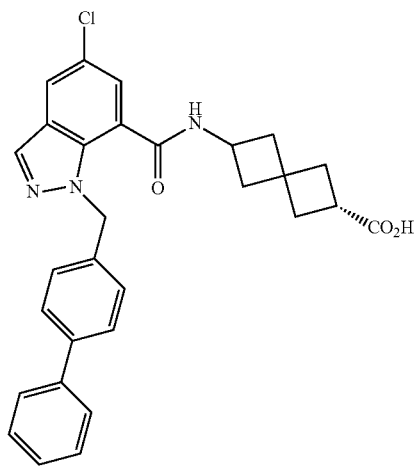

Example 93

Step 1: Preparation of methyl 1-([1,1'-biphenyl]-4-ylmethyl)-5-chloro-1H-indazole-7-carboxylate In a round-bottom flask equipped with a magnetic stir bar was suspended Intermediate N (1.0 equiv) and cesium carbonate (3 equiv) in DMF (0.71 M). This suspension was cooled to 0° C. and then added 4-(bromomethyl)-1,1'-biphenyl (1.2 equiv, Combi-Blocks, CAS #2567-29-5) portion-wise over a period of 5 minutes. The resulting reaction mixture was allowed to warm to 22° C. over 18 hours. The reaction was then carefully quenched with the addition of ice-water and extracted with tert-butyl methyl ether. The combined organic extracts were washed further with water and brine, dried over MgSO$_4$, and filtered. Concentration of the filtrate thus obtained in vacuo furnished the crude reaction product as a golden yellow oil. Purification by column chromatography through silica gel on the Teledyne ISCO Rf (gradient elution with 10% to 100% EtOAc in hexanes) afforded the title compound as a colorless oil that solidified upon standing.

Step 2: Preparation of 1-([1,1'-biphenyl]-4-ylmethyl)-5-chloro-1H-indazole-7-carboxylic acid Into a glass round-bottom flask equipped with a magnetic stir bar was dissolved methyl 1-([1,1'-biphenyl]-4-ylmethyl)-5-chloro-1H-indazole-7-carboxylate (1 equiv) in a 3:2 (v/v) solution (0.11 M) of THF and MeOH. To this was then added 2.0 M aqueous LiOH solution (3 equiv) and the resulting solution was stirred at 22° C. for 16 hours. The reaction mixture was then carefully neutralized with the drop-wise addition of 1 M aqueous HCl solution (3 equiv). The resulting suspension was extracted with EtOAc. The combined organic extracts were washed further with water and brine, dried over MgSO$_4$, and filtered. Concentration of the filtrate thus obtained in vacuo furnished the crude reaction product as a white solid. Trituration of the crude product in tert-butyl methyl ether and hexanes then afforded the title compound as a white, crystalline solid.

Step 3: Preparation of (S$_a$)-methyl 6-(1-([1,1'-biphenyl]-4-ylmethyl)-5-chloro-1H-indazole-7-carboxamido)spiro[3.3]heptane-2-carboxylate In a round-bottom flask equipped with a magnetic stir bar was dissolved 1-([1,1'-biphenyl]-4-ylmethyl)-5-chloro-1H-indazole-7-carboxylic acid (1 equiv), Intermediate F (1.2 equiv) and HATU (1.5 equiv) in DMF (0.22 M). To this was then added Hünig's base (5 equiv) and the resulting yellow solution was allowed to stir at 22° C. for 3 hours. The crude reaction mixture was diluted with tert-butyl methyl ether and washed sequentially with water, 1 M aqueous HCl solution, 1 M aqueous NaOH solution, water and brine. The organic extract was then dried over MgSO$_4$ and filtered. Concentration of the filtrate thus obtained in vacuo furnished the crude reaction product as a yellow semi-solid. Trituration of the crude product in methanol then afforded the title compound as a white, crystalline solid.

Step 4: Preparation of (S$_a$)-6-(1-([1,1'-biphenyl]-4-ylmethyl)-5-chloro-1H-indazole-7-carboxamido)spiro[3.3]heptane-2-carboxylic acid Into a round-bottom flask equipped with a magnetic stir bar was dissolved (S$_a$)-methyl 6-(1-([1,1'-biphenyl]-4-ylmethyl)-5-chloro-1H-indazole-7-carboxamido)spiro[3.3]heptane-2-carboxylate (1 equiv) in a 3:2 (v/v) solution (0.1 M) of THF and MeOH. To this was then added 2.0 M aqueous LiOH solution (3 equiv) and the resulting solution was stirred at 22° C. for 16 hours. The reaction mixture was then carefully neutralized with the drop-wise addition of 1 M aqueous HCl solution (3 equiv). The resulting suspension was extracted with EtOAc. The combined organic extracts were washed further with water and brine, dried over MgSO$_4$, and filtered. Concentration of the filtrate thus obtained in vacuo furnished the crude reaction product as a white solid. Trituration of the crude product in tert-butyl methyl ether afforded the title compound as a white, crystalline solid. LCMS (ESI+): 500 (M+1)$^+$.

The following compounds were prepared in a similar manner to Example 93, replacing 4-(bromomethyl)-1,1'-biphenyl in Step 1 with an appropriate commercially available (bromomethyl)arene and Intermediate N in Step 1 with Intermediate M.

| Example | Structure and Name | MW | MS (ESI+) |
|---|---|---|---|
| Example 94 | ($S_a$)-6-(1-([1,1'-biphenyl]-4-ylmethyl)-4-chloro-1H-indazole-7-carboxamido)spiro[3.3]heptane-2-carboxylic acid | 499.99 | 500 (M + 1)+ |
| Example 95 | ($S_a$)-6-(4-chloro-1-(4-(trifluoromethoxy)benzyl)-1H-indazole-7-carboxamido)spiro[3.3]heptane-2-carboxylic acid | 507.89 | 508 (M + 1)+ |
| Example 96 | ($S_a$)-6-(4-chloro-1-(naphthalen-2-ylmethyl)-1H-indazole-7-carboxamido)spiro[3.3]heptane-2-carboxylic acid | 473.95 | 474 (M + 1)+ |

-continued

| Example | Structure and Name | MW | MS (ESI+) |
|---|---|---|---|
| Example 97 | 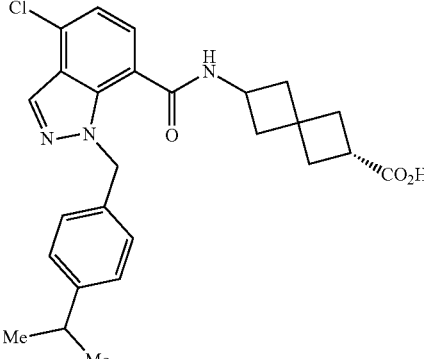<br>($S_a$)-6-(4-chloro-1-(4-isopropylbenzyl)-1H-indazole-7-carboxamido)spiro[3.3]heptane-2-carboxylic acid | 465.97 | 466 (M + 1)$^+$ |
| Example 98 | 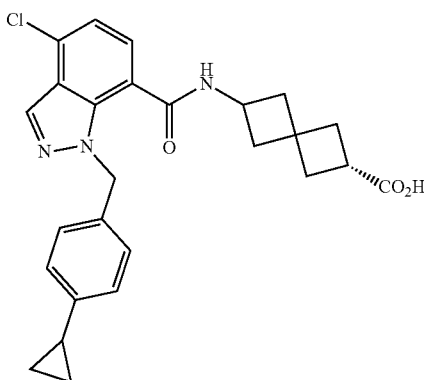<br>($S_a$)-6-(4-chloro-1-(4-cyclopropylbenzyl)-1H-indazole-7-carboxamido)spiro[3.3]heptane-2-carboxylic acid | 463.96 | 464 (M + 1)$^+$ |
| Example 99 | 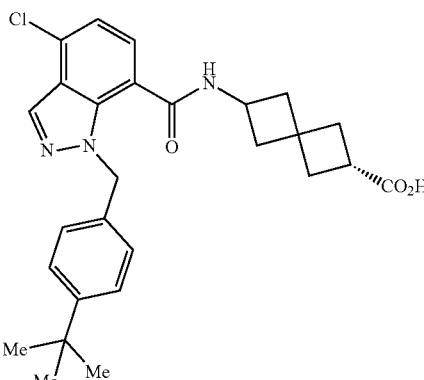<br>($S_a$)-6-(4-chloro-1-(4-(er-butyl)benzyl)-1H-indazole-7-carboxamido)spiro[3.3]heptane-2-carboxylic acid | 480.00 | 480 (M + 1)$^+$ |

Example 100

Preparation of (Racemic)-6-(1-([1,1'-Biphenyl]-4-ylmethyl)-4-fluoro-1H-indole-7-carboxamido)-2-methylspiro[3.3]heptane-2-carboxylic acid

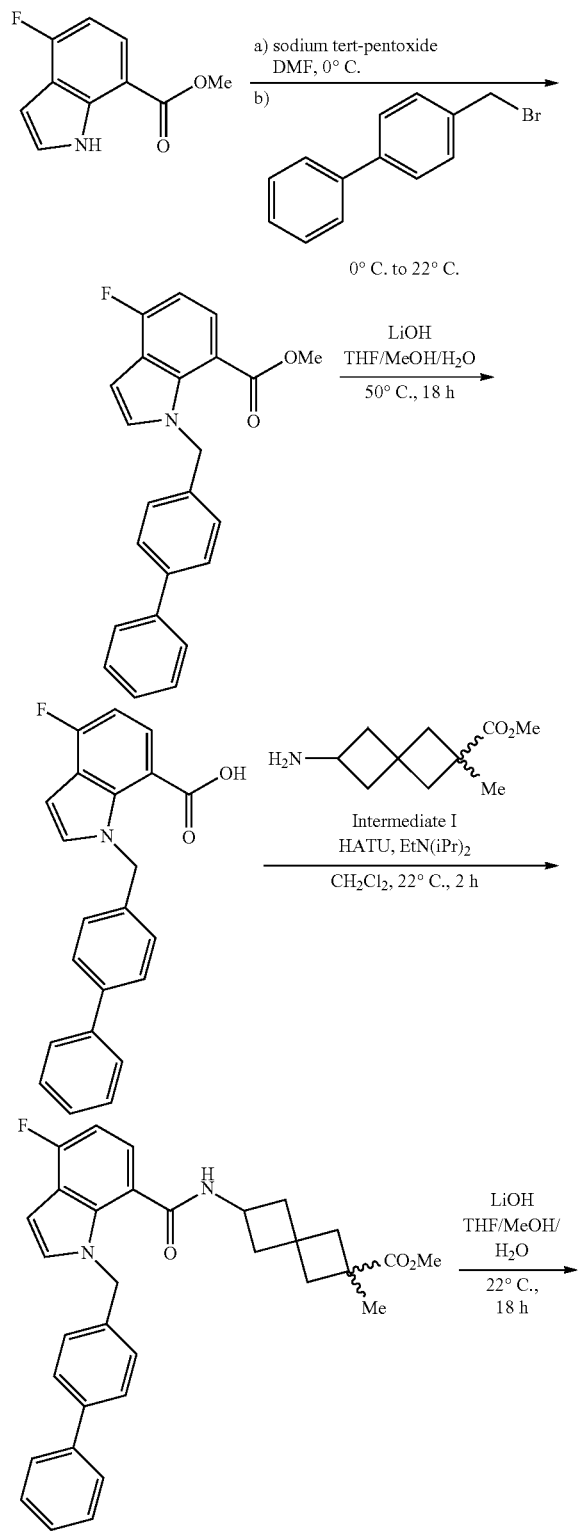

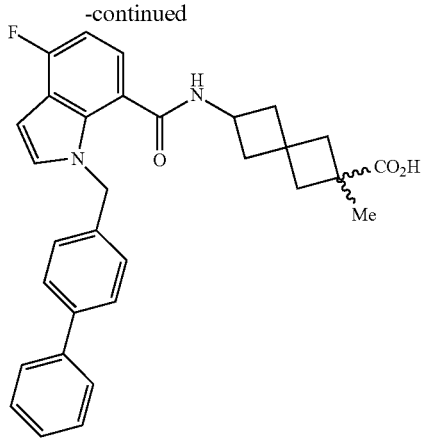

Example 100

Step 1: Preparation of methyl 1-([1,1'-biphenyl]-4-ylmethyl)-4-fluoro-1H-indole-7-carboxylate Into a sample vial equipped with a magnetic stir bar and under $N_2$ was added methyl 4-fluoro-1H-indole-7-carboxylate (1.0 equiv, PharmaBlock, CAS #313337-35-8), sodium tert-pentoxide (1.5 equiv) and DMF (0.4 M). The solution was cooled to 0° C. in an ice bath and treated with 4-(bromomethyl)-1,1'-biphenyl (1.2 equiv, Combi-Blocks, CAS #2567-29-5) and the mixture was allowed to warm to 22° C. for 18 hours overnight. The reaction mixture was quenched with sat. aqueous $NH_4Cl$ solution and poured into a Cl-phase separatory cartridge and extracted with $CH_2Cl_2$ (3×). The combined organic layers were concentrated and loaded directly onto a silica gel pre-cartridge and dried. Purification by column chromatography through silica gel, using an automated Teledyne ISCO Rf machine, eluting with 0% to 50% EtOAc in hexanes as a gradient over 25 minutes. The desired fractions were combined, concentrated under reduced pressure and dried under vacuum to afford the title compound.

Step 2: Preparation of 1-([1,1'-biphenyl]-4-ylmethyl)-4-fluoro-H-indole-7-carboxylic acid A solution of methyl 1-([1,1'-biphenyl]-4-ylmethyl)-4-fluoro-1H-indole-7-carboxylate (1.0 equiv) in a mixture of THF (0.4 M) and MeOH (0.4 M) was treated with 1.0 M aqueous LiOH solution (2.5 equiv) and heated on an aluminum block to 50° C. for 18 hours. The resulting solution was cooled to 22° C. and quenched with 10% aqueous citric acid solution (5 mL) and poured into a Cl-phase separatory cartridge. The aqueous layer was extracted with $CH_2Cl_2$ (3×) and the combined organic layers were concentrated under reduced pressure. Purification by reverse-phase column chromatography using a C18 cartridge on an automated Teledyne ISCO Rf machine, eluting with 5% to 70% acetonitrile in water+0.1% formic acid as a gradient over 25 minutes. The desired fractions were combined, concentrated and dried under vacuum to afford the tide compound as a white solid.

Step 3: Preparation of (racemic)-methyl 6-(1-([1,1'-biphenyl]-4-ylmethyl)-4-fluoro-1H-indole-7-carboxamido)-2-methylspiro[3.3]heptane-2-carboxylate Into a reaction vial equipped with a magnetic stir and under $N_2$ was added 1-([1,1'-biphenyl]-4-ylmethyl)-4- fluoro-1H-indole-7-carboxylic acid (1.0 equiv), HATU (1.2 equiv) and dichloromethane (0.3 M). The solution was stirred at 22° C. for 10 minutes and then treated with Intermediate I (1.1 equiv) and then Hunig's base (3.0 equiv) and stirred at 22° C. for 2 hours. LCMS analysis after this time revealed complete conversion of starting material. The reaction mixture was quenched with sat. aqueous NH₄Cl solution and poured into a Cl-phase separatory cartridge and extracted with CH₂Cl₂ (3×). The combined organic layers were concentrated and loaded directly onto a silica gel pre-cartridge and dried. Purification by column chromatography through silica gel, using an automated Teledyne ISCO Rf machine, eluting with 0% to 40% EtOAc in hexanes as a gradient over 25 minutes. The desired fractions were combined, concentrated under reduced pressure and dried under vacuum to afford the title compound as a white solid.

Step 4: Preparation of (racemic)-6-(1-([1,1'-biphenyl]-4-ylmethyl)-4-fluoro-1H-indole-7-carboxamido)-2-methylspiro[3.3]heptane-2-carboxylic acid Into a reaction vial equipped with a magnetic stir bar and under N₂ was added (racemic)-methyl 6-(1-([1,1'-biphenyl]-4-ylmethyl)-4-fluoro-1H-indole-7-carboxamido)-2-methylspiro[3.3]heptane-2-carboxylate (1.0 equiv), THF (0.4 M) and MeOH (0.4 M). The solution was treated with 1.0 M aqueous LiOH solution (2.5 equiv) and stirred at 22° C. for 18 h. The reaction mixture was quenched with 10% aqueous citric acid solution (2 mL) and concentrated under reduced pressure. The residue was loaded onto a C18 pre-cartridge and dried under vacuum. Purification by reverse-phase column chromatography using a C18 cartridge on an automated Teledyne ISCO Rf machine, eluting with 5% to 70% acetonitrile in water+0.1% formic acid as a gradient over 20 minutes. The desired fractions were combined, concentrated and dried under vacuum to afford the title compound as a white solid. LCMS (ESI+): 497 (M+1)⁺.

The following compounds were prepared in a similar manner to Example 100, replacing Intermediate I in Step 3 with an appropriate amine.

| Example | Structure and Name | MW | MS (ESI+) |
|---|---|---|---|
| Example 101 | 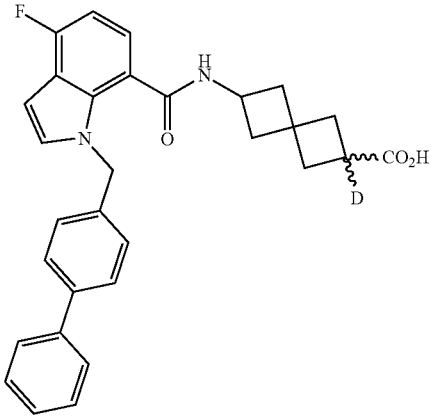<br>(racemic)-6-(1-([1,1'-biphenyl]-4-ylmethyl)-4-fluoro-1H-indole-7-carboxamido)-2-deuterospiro[3.3]heptane-2-carboxylic acid | 483.55 | 484 (M + 1)⁺ |
| Example 102 | 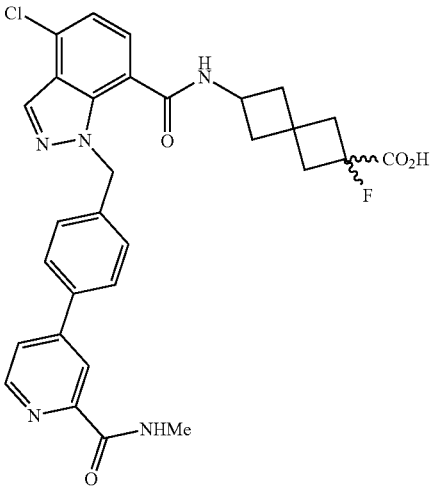<br>(racemic)-6-(4-chloro-1-(4-(2-(methylcarbamoyl)pyridin-4-yl)benzyl)-1H-indazole-7-carboxamido)-2-fluorospiro[3.3]heptane-2-carboxylic acid | 576.02 | 576 (M + 1)⁺ |

| Example | Structure and Name | MW | MS (ESI+) |
|---|---|---|---|
| Example 103 | 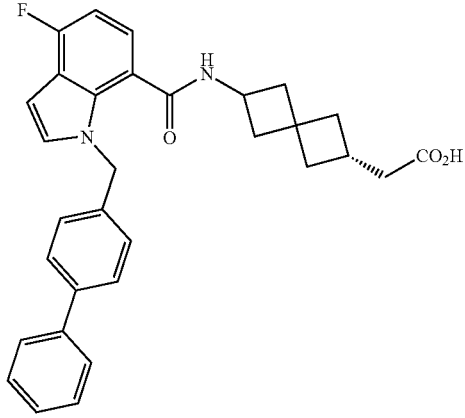<br>(S)-2-(6-(1([1,1'-biphenyl]-4-ylmethyl)-4-fluoro-1H-indole-7-carboxamido)spiro[3.3]heptan-2-yl)acetic acid | 496.58 | 497 (M + 1)+ |
| Example 104 | 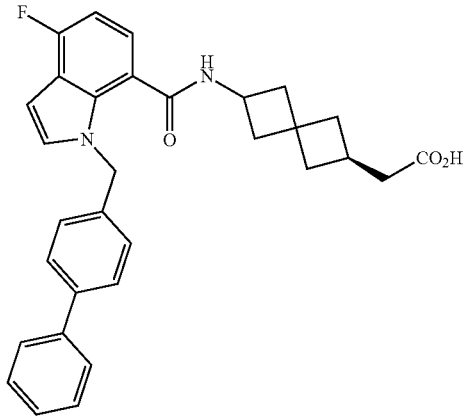<br>($R_a$)-2-(6-(1-([1,1'-biphenyl]-4-ylmethyl)-4-fluoro-1H-indole-7-carboxamido)spiro[3.3]heptan-2-yl)acetic acid | 496.58 | 497 (M + 1)+ |

Example 105

Preparation of (S$_a$)-6-(1-([1,1'-Biphenyl]-4-ylmethyl)-4-fluoro-1H-indole-7-carboxamido)-2-deuterospiro[3.3]heptane-2-carboxylic acid (Second Eluting Enantiomer)

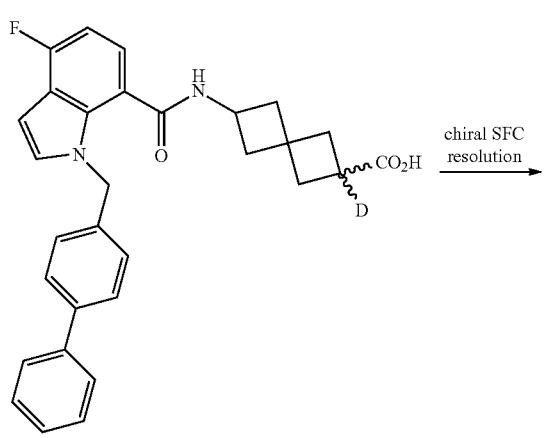

Example 101

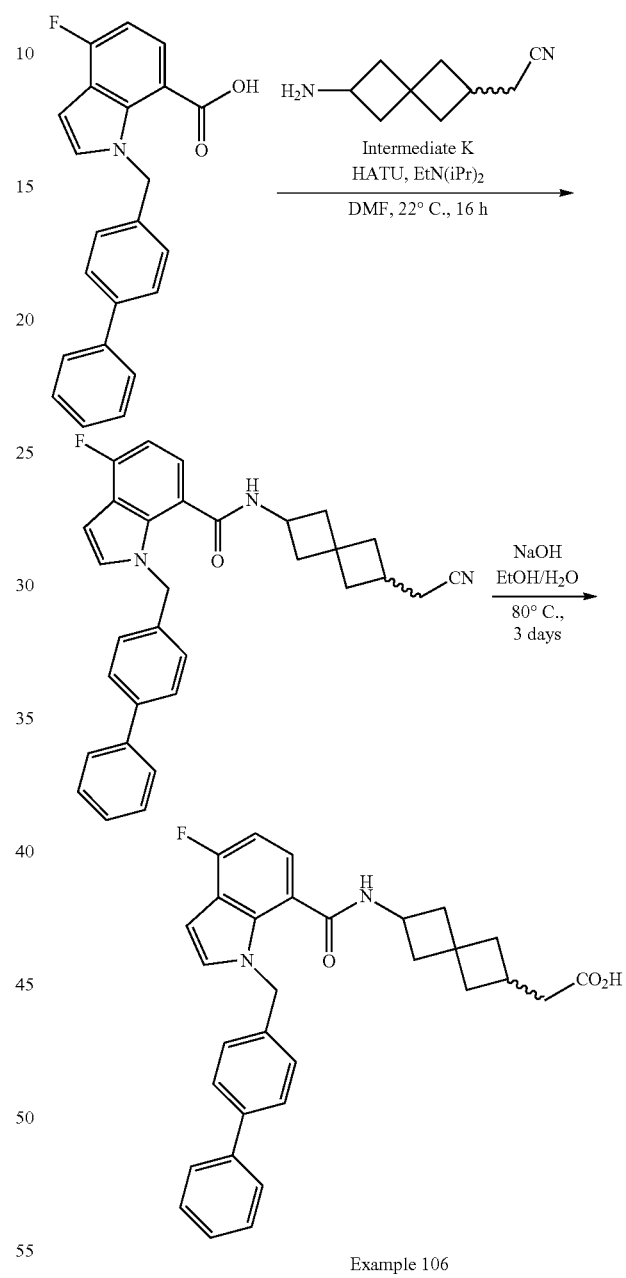

The racemic compound, Example 101, was resolved into both enantiomers using chiral SFC. The enantiomers were separated using a 5 μm ChiralPac OJ column (10×250 mm), eluting on a gradient from 5% to 55% MeOH at a flow rate of 5 mL/min over 5 minutes, maintaining a column temperature of 35° C. The first eluting peak had a retention time of 3.3 minutes and the second eluting enantiomer at 3.5 minutes. The second eluting enantiomer, Example 105, was determined to be the more active enantiomer. LCMS (ESI+): 484 (M+1)$^+$.

Example 106

Preparation of (Racemic)-2-(6-(1-([1,1'-Biphenyl]-4-ylmethyl)-4-fluoro-1H-indole-7-carboxamido)spiro[3.3]heptan-2-yl)acetic acid Example 106

Step 1: Preparation of (racemic)-1-([1,1'-biphenyl]-4-ylmethyl)-N-(6-(cyanomethyl)spiro[3.3]heptan-2-yl)-4-fluoro-1H-indole-7-carboxamide Into a reaction vial equipped with a magnetic stir and under N$_2$ was added 1-([1,1'-biphenyl]-4-ylmethyl)-4-fluoro-1H-indole-7-carboxylic acid (1.0 equiv, Example 100, Step 2), HATU (1.3 equiv) and DMF (0.05 M). The solution was stirred at 22° C. for 10 minutes and then treated with Intermediate K (1.5 equiv) and then Hunig's base (4.0 equiv) and stirred at 22° C. for 16 hours. LCMS analysis after this time revealed complete conversion of starting material. The reaction mixture was loaded directly onto a C18 pre-cartridge and dried under vacuum. Purification by reverse-phase column chromatography using a C18 cartridge on an automated Teledyne ISCO Rf machine, eluting with 5% to 70% acetonitrile in water+0.1% formic acid as a gradient over 20 minutes. The desired fractions were combined, concentrated and dried under vacuum to afford the title compound as a white solid.

Step 2: Preparation of (racemic)-2-(6-(1-([1,1'-biphenyl]-4-ylmethyl)-4-fluoro-1H-indole-7-carboxamido)spiro[3.3]heptan-2-yl)acetic acid Into a reaction vial equipped with a magnetic stir and under $N_2$ was added (racemic)-1-([1,1'-biphenyl]4-ylmethyl)-N-(6-(cyanomethyl)spiro[3.3]heptan-2yl)-4-fluoro-1H-indole-7-carboxamide (1.0 equiv) and ethanol (0.03 M). To this solution was then added 6 M aqueous solution of sodium hydroxide (170 equiv) and the resulting mixture was heated at 80° C. for 3 days. LCMS analysis after this time revealed the successful formation of the desired product. The reaction mixture was then neutralized with 6 M aqueous HCl solution, diluted with water and extracted with dichloromethane. The combined organic extracts were concentrated in vacuo and loaded directly onto a C18 pre-cartridge and dried under vacuum. Purification by reverse-phase column chromatography using a C18 cartridge on an automated Teledyne ISCO Rf machine, eluting with 5% to 70% acetonitrile in water+0.1% formic acid as a gradient over 20 minutes. The desired fractions were combined, concentrated and dried under vacuum to afford the title compound as a white solid. LCMS (ESI+): 497 (M+1)$^+$.

Compounds in the following table were made in a similar manner to Example 106. Reactions were run using Intermediate K in Step 1 and an appropriate indole or indazole intermediate which was altered as shown below.

| Example | Structure and Name | MW | MS (ESI+) |
|---|---|---|---|
| Example 107 | 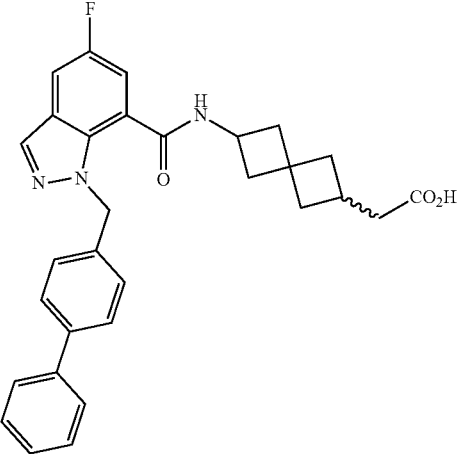 [SMILES: O=C(O)CC1CC2(C1)CC(NC(=O)c1cc(F)cc3cnn(Cc4ccc(-c5ccccc5)cc4)c13)C2]<br>(racemic)-2-(6-(1-([1,1'-biphenyl]-4-ylmethyl)-5-fluoro-1H-indazole-7-carboxamido)spiro[3.3]heptan-2-yl)acetic acid | 497.56 | 498 (M + 1)$^+$ |
| Example 108 | 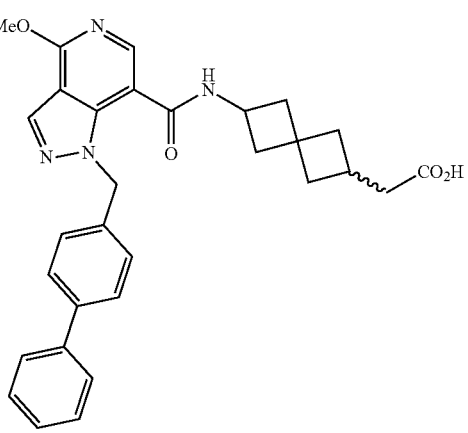<br>(racemic)-2-(6-(1-([1,1'-biphenyl]-4-ylmethyl)-4-methoxy-1H-pyrrolo[3,2-c]pyridine-7-carboxamido)spiro[3.3]heptan-2-yl)acetic acid | 509.60 | 510 (M + 1)$^+$ |

| Example | Structure and Name | MW | MS (ESI+) |
|---|---|---|---|
| Example 109 | 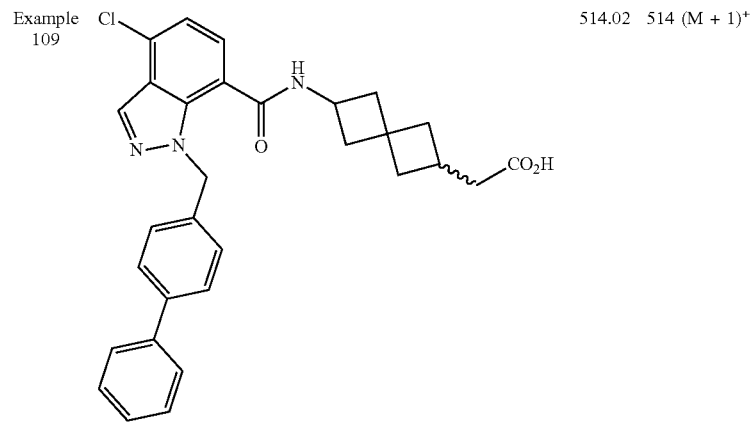<br>(racemic)-2-(6-(1-([1,1'-biphenyl]-4-ylmethyl)-4-chloro-1H-indazole-7-carboxamido)spiro[3.3]heptan-2-yl)acetic acid | 514.02 | 514 (M + 1)+ |
| Example 110 | 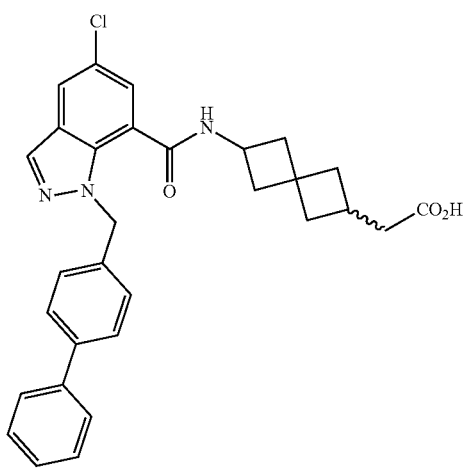 [SMILES: O=C(O)CC1CC2(C1)CC(NC(=O)c1cc(Cl)cc3cnn(Cc4ccc(-c5ccccc5)cc4)c13)C2]<br>(racemic)-2-(6-(1-([1,1'-biphenyl]-4-ylmethyl)-5-chloro-1H-indazole-7-carboxamido)spiro[3.3]heptan-2-yl)acetic acid | 514.02 | 514 (M + 1)+ |

Example 111

Preparation of (S$_a$)-4-Fluoro-N-(6-((methylsulfonyl)carbamoyl)spiro[3.3]heptan-2-yl)-1-(4-(trifluoromethoxy)benzyl)-1H-indole-7-carboxamide

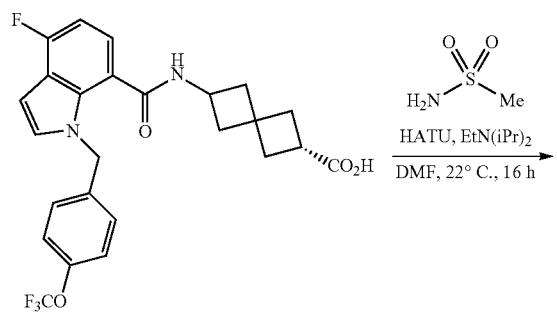

Example 8

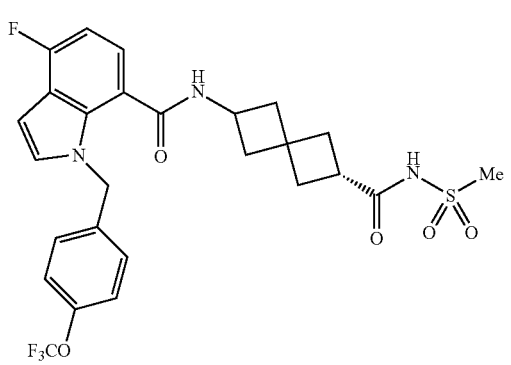

Example 111

Into a reaction vial equipped with a magnetic stir and under N$_2$ was added Example 8 (1.0 equiv), HATU (1.5 equiv), methanesulfonamide (1.2 equiv) and DMF (0.11 M). The solution was stirred at 22° C. for 2 minutes and then treated with Hünig's base (4.5 equiv). The resulting solution was stirred at 22° C. for 16 hours. The reaction mixture was then quenched with 1 M aqueous HCl solution, diluted further with water and extracted with EtOAc (3×). The combined organic extracts were then washed with brine, dried over Na$_2$SO$_4$, filtered and the filtrate concentrated in vacuo. The crude product thus obtained was first purified by regular-phase column chromatography through silica gel on an automated Teledyne ISCO Rf machine, eluting with 5% to 100% EtOAc in Hexanes as a gradient. Further purification by reverse-phase column chromatography using a C18 cartridge, eluting with 20% to 100% acetonitrile in water+ 0.1% formic acid as a gradient furnished the title compound. LCMS (ESI+): 568 (M+1)$^+$.

Example 112

Preparation of (S$_a$)-6-(1-((racemic)-1-([1,1'-Biphenyl]-4-yl)-ethyl)-1H-indazole-7-carboxamido)spiro[3.3]heptane-2-carboxylic acid

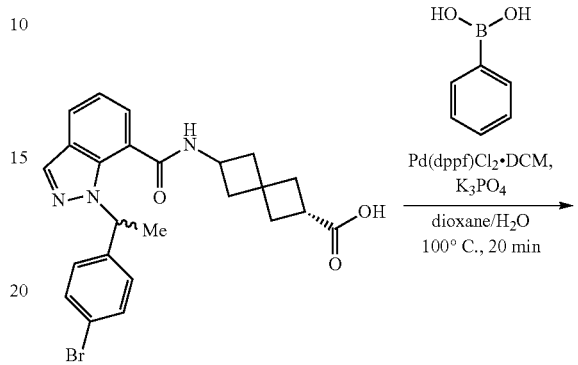

Intermediate BB

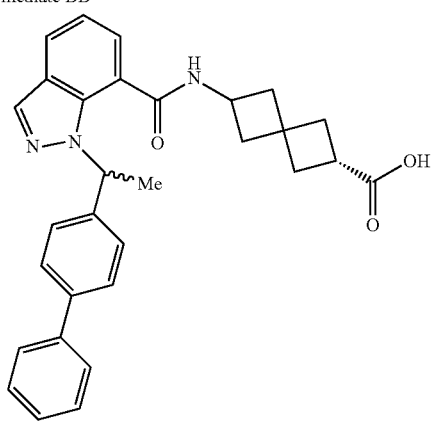

Example 112

In a microwave vial equipped with a magnetic stir bar was added Intermediate BB (1.0 equiv), phenylboronic acid (1.2 equiv, Combi-Blocks, CAS #768-35-4) and Pd(dppf)Cl$_2$ dichloromethane adduct (0.1 equiv. Strem CAS #98-80-6). The vial was sealed with a Teflon cap. The vial was evacuated and back-filled with a N$_2$ atmosphere three times. The vial was then placed under vacuum before the addition of a 2 M aqueous solution of K$_3$PO$_4$ (3.0 equiv) and dioxane (0.1 M). The vial was heated to 100° C. for 20 min in a microwave reactor. The resulting reaction mixture was allowed to cool to 22° C. and then directly subjected to purification by reverse-phase column chromatography using a C18 cartridge on an automated Teledyne ISCO Rf machine, eluting with 10% to 100% acetonitrile in water+ 0.1% formic acid as a gradient over 20 minutes. Fractions with the desired product were combined and lyophilized to afford the title compound as a white powder. LCMS (ESI+): 480 (M+1)$^+$.

Compounds in the following table were made in a similar manner to Example 112. Reactions were run using either Intermediate BB (Examples 113, 114, and 115) or Intermediate CC (Examples 121, 122, 123 and 124) or Intermediate DD (Examples 116, 117, 118, 119 and 120) and the corresponding commercially available boronic acid.

| Example | Structure and Name | MW | MS (ESI+) |
|---|---|---|---|
| Example 113 | (S_a)-6-(1-((racemic)-1-(3'-methoxy-[1,1'-biphenyl]-4-yl)-ethyl)-1H-indazole-7-carboxamido)spiro[3.3]heptane-2-carboxylic acid | 509.60 | 510 (M + 1)+ |
| Example 114 | (S_a)-6-(1-((racemic)-1-(3'-cyano-5'-methoxy-[1,1'-biphenyl]-4-yl)-ethyl)-1H-indazole-7-carboxamido)spiro[3.3]heptane-2-carboxylic acid | 534.61 | 535 (M + 1)+ |
| Example 115 | (S_a)-6-(1-((racemic)-1-(4-(2-ethoxypyridin-4-yl)phenyl)-ethyl)-1H-indazole-7-carboxamido)spiro[3.3]heptane-2-carboxylic acid | 524.61 | 525 (M + 1)+ |

| Example | Structure and Name | MW | MS (ESI+) |
|---|---|---|---|
| Example 116 | 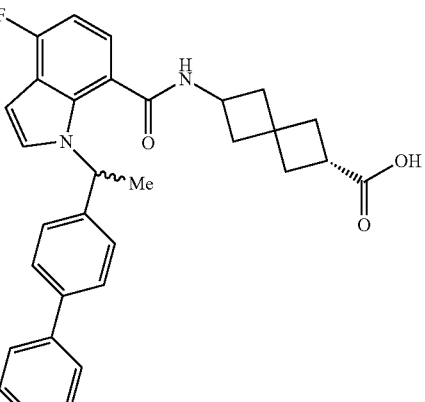<br>(S)-6-(1-(racemic)-1-([1,1'-biphenyl]-4-yl)-ethyl)-4-fluoro-1H-indole-7-carboxamido)spiro[3.3]heptane-2-carboxylic acid | 496.58 | 519 (M + Na)+ |
| Example 117 | 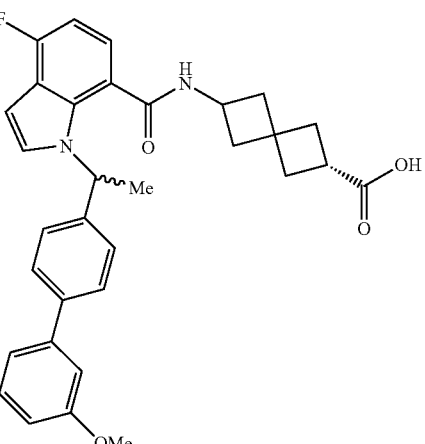<br>(S$_a$)-6-(4-fluoro-1-((racemic)-1-(3'-methoxy-[1,1'-biphenyl]-4-yl)-ethyl)-1H-indole-7-carboxamido)spiro[3.3]heptane-2-carboxylic acid | 526.60 | 549 (M + Na)+ |
| Example 118 | 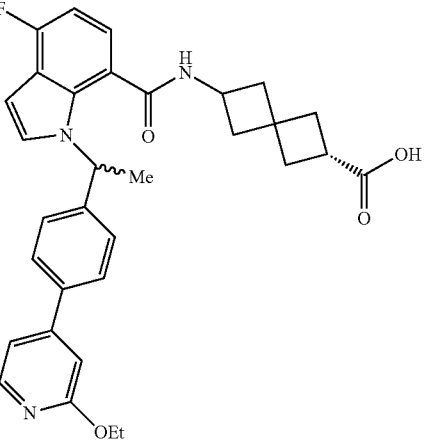<br>(S$_a$)-6-(1-((racemic)-1-(4-(2-ethoxypyridin-4-yl)phenyl)-ethyl)-4-fluoro-1H-indole-7-carboxamido)spiro[3.3]heptane-2-carboxylic acid | 541.62 | 542 (M + 1)+ |

-continued

| Example | Structure and Name | MW | MS (ESI+) |
|---|---|---|---|
| Example 119 | 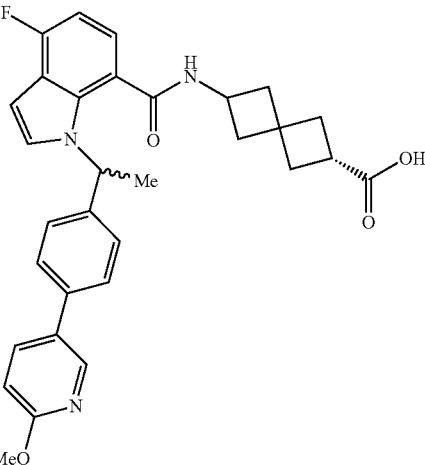<br>($S_a$)-6-(4-fluoro-1-((racemic)-1-(4-(6-methoxypyridin-3-yl)phenyl)-ethyl)-1H-indole-7-carboxamido)spiro[3.3]heptane-2-carboxylic acid | 527.59 | 528 (M + 1)+ |
| Example 120 | 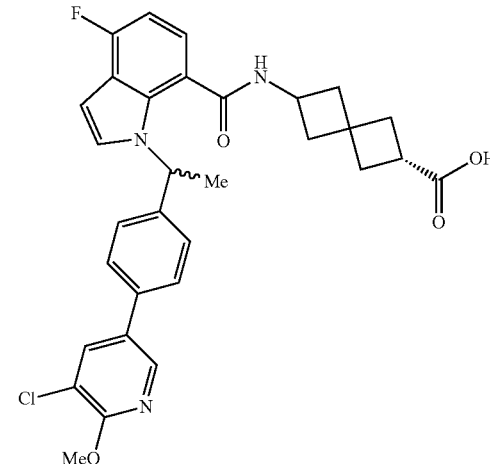<br>($S_a$)-6-(1-((racemic)-1-(4-(5-chloro-6-methoxypyridin-3-yl)phenyl)-ethyl)-4-fluoro-1H-indole-7-carboxamido)spiro[3.3]heptane-2-carboxylic acid | 562.03 | 562 (M + 1)+ |
| Example 121 | 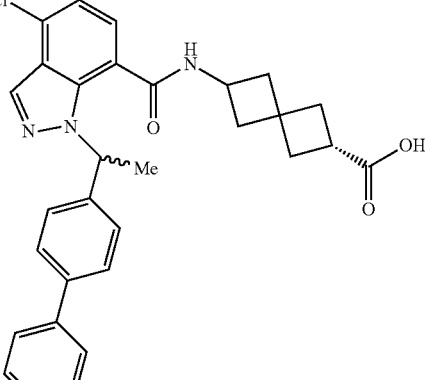<br>($S_a$)-6-(1-((racemic)-1-([1,1'-biphenyl]-4-yl)-ethyl)-4-chloro-1H-indazole-7-carboxamido)spiro[3.3]heptane-2-carboxylic acid | 514.02 | 537 (M + Na)+ |

| Example | Structure and Name | MW | MS (ESI+) |
|---|---|---|---|
| Example 122 | 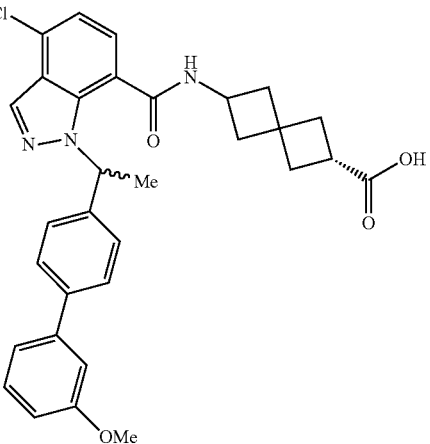<br>($S_a$)-6-(4-chloro-1-((racemic)-1-(3'-methoxy-[1,1'-biphenyl]-4-yl)-ethyl)-1H-indazole-7-carboxamido)spiro[3.3]heptane-2-carboxylic acid | 544.04 | 566 (M + Na)+ |
| Example 123 | 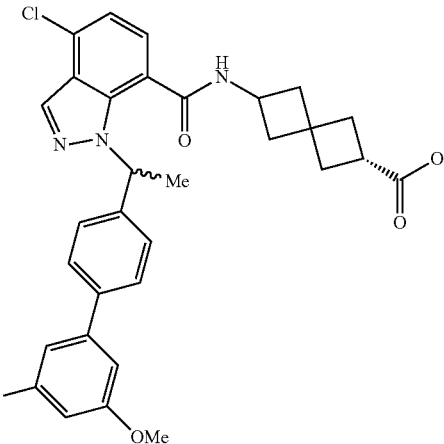<br>($S_a$)-6-(4-chloro-1-((racemic)-1-(3'-cyano-5'-methoxy-[1,1'-biphenyl]-4-yl)-ethyl)-1H-indazole-7-carboxamido)spiro[3.3]heptane-2-carboxylic acid | 569.05 | 569 (M + 1)+ |
| Example 124 | 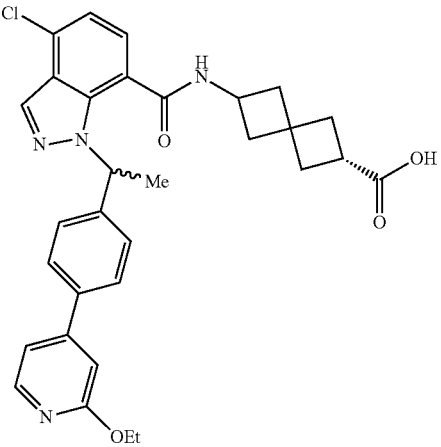<br>($S_a$)-6-(4-chloro-1-((racemic)-1-(4-(2-ethoxypyridin-4-yl)phenyl)-ethyl)-1H-indazole-7-carboxamido)spiro[3.3]heptane-2-carboxylic acid | 559.06 | 559 (M + 1)+ |

Example 125

Preparation of (S$_a$)-6-(1-((R) or (S)-1-([1,1'-Biphenyl]-4-yl)-ethyl)-1H-indazole-7-carboxamido)spiro[3.3]heptane-2-carboxylic acid (First Eluting Diastereomer)

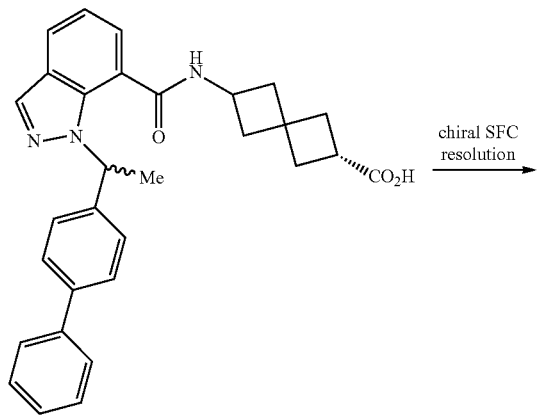

Example 112 chiral SFC resolution →

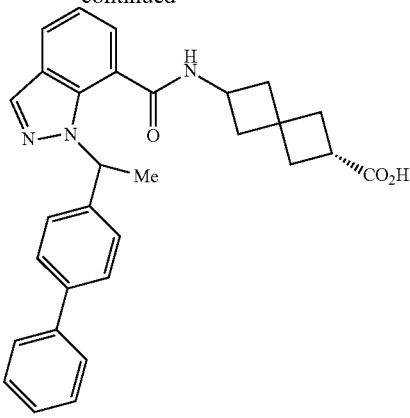

Example 125

The diastereomeric compound, Example 112, was resolved into both diastereomers using chiral SFC. The enantiomers were separated using a 5 μm ChiralPac IA column (10×250 mm), eluting on 55% isopropanol at a flow rate of 10 mL/min over 10 minutes, maintaining a column temperature of 35° C. The first eluting peak had a retention time of 2.8 minutes and the second eluting peak at 6.2 minutes. The first eluting diastereomer, Example 125, was determined to be the more active diastereomer. LCMS (ESI+): 480 (M+1)$^+$.

Compounds in the following table were resolved using chiral SFC in a similar manner to Example 125. In these cases, the more active diastereomer was the first eluting peak.

| Example | Structure and Name | MW | MS (ESI+) |
|---|---|---|---|
| Example 126 | (S$_a$)-6-(1-((R) or (S)-1-(3'-cyano-5'-methoxy-[1,1'-biphenyl]-4-yl)-ethyl)-1H-indazole-7-carboxamido)spiro[3.3]heptane-2-carboxylic acid | 534.61 | 535 (M + 1)$^+$ |

| Example | Structure and Name | MW | MS (ESI+) |
|---|---|---|---|
| Example 127 | 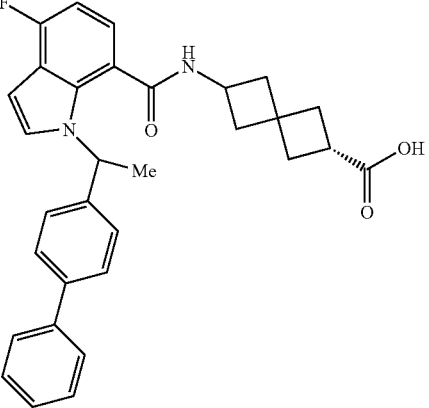<br>(S_a)-6-(1-((R) or (S)-1-([1,1'-biphenyl]-4-yl)-ethyl)-4-fluoro-1H-indole-7-carboxamido)spiro[3.3]heptane-2-carboxylic acid | 496.58 | 519 (M + Na)+ |
| Example 128 | 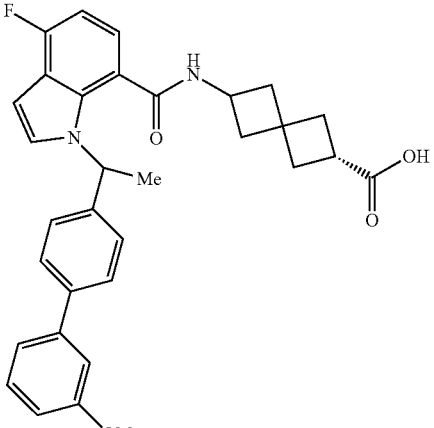<br>(S_a)-6-(4-fluoro-1-((R) or (S)-1-(3'-methoxy-[1,1'-biphenyl]-4-yl)-ethyl)-1H-indole-7-carboxamido)spiro[3.3]heptane-2-carboxylic acid | 526.60 | 549 (M + Na)+ |
| Example 129 | 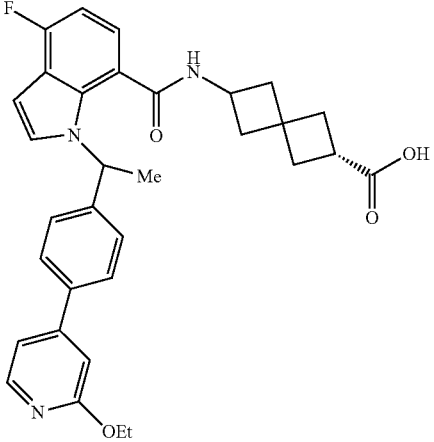<br>(S_a)-6-(1-((R) or (S)-1-(4-(2-ethoxypyridin-4-yl)phenyl)-ethyl)-4-fluoro-1H-indole-7-carboxamido)spiro[3.3]heptane-2-carboxylic acid | 541.62 | 542 (M + 1)+ |

-continued

| Example | Structure and Name | MW | MS (ESI+) |
|---|---|---|---|
| Example 130 | 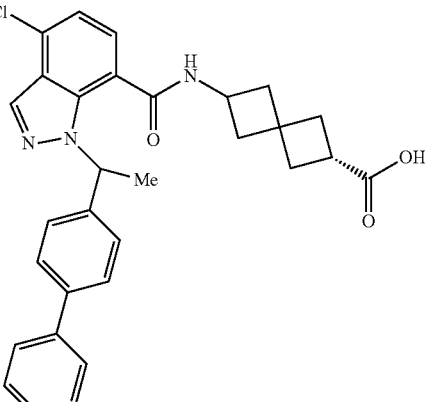<br>(S$_a$)-6-(1-((R) or (S)-1-([1,1'-biphenyl]-4-yl)-ethyl)-4-chloro-1H-indazole-7-carboxamido)spiro[3.3]heptane-2-carboxylic acid | 514.02 | 537 (M + Na)+ |
| Example 131 | 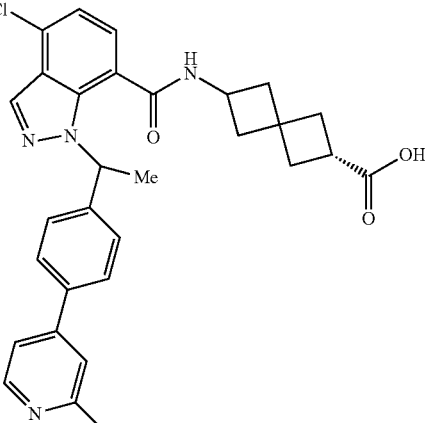<br>(S$_a$)-6-(4-chloro-1-((R) or (S)-1-(4-(2-ethoxypyridin-4-yl)phenyl)-ethyl)-1H-indazole-7-carboxamido)spiro[3.3]heptane-2-carboxylic acid | 559.06 | 559 (M + 1)+ |
| Example 132 | 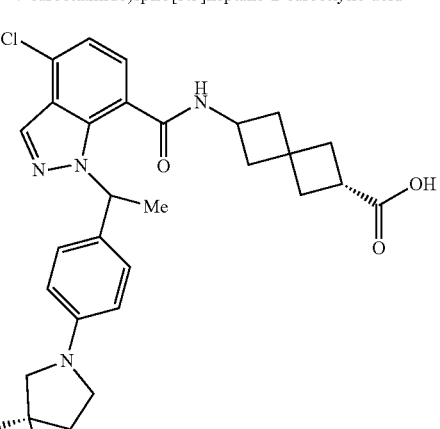<br>(S$_a$)-6-(1-((R) or (S)-1-(4-((1R, 5S)-3-azabicyclo[3.1.0]hexan-3-yl)phenyl)ethyl)-4-chloro-1H-indazole-7-carboxamido)spiro[3.3]heptane-2-carboxylic acid | 519.04 | 519 (M + 1)+ |

Example 133

Preparation of (S$_a$)-6-(1-((racemic)-1-(4-(6-Ethoxy-pyridin-2-yl)phenyl)-ethyl)-1H-indazole-7-carboxamido)spiro[3.3]heptane-2-carboxylic acid

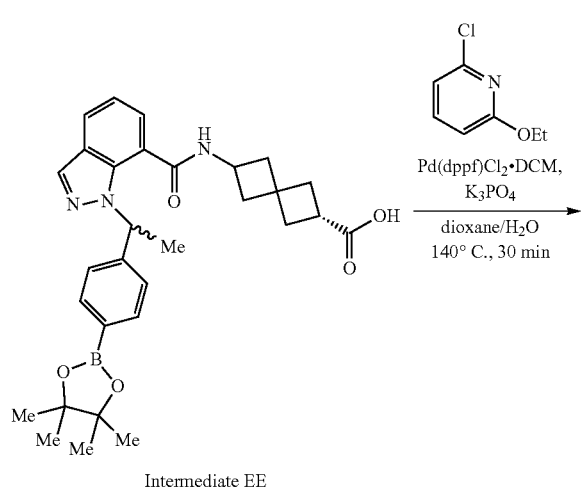

Intermediate EE

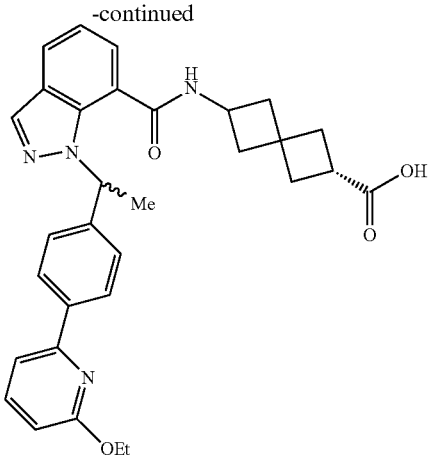

Example 133

In a microwave vial equipped with a magnetic stir bar was added Intermediate EE (1.0 equiv), 2-chloro-6-ethoxypyridine (1.5 equiv, Combi-Blocks, CAS #42144-78-5) and Pd(dppf)Cl$_2$ dichloromethane adduct (0.1 equiv, Strem CAS #95464-054). The vial was sealed with a Teflon cap. The vial was evacuated and back-filled with a N$_2$ atmosphere three times. The vial was then placed under vacuum before the addition of a 2 M aqueous solution of K$_3$PO$_4$ (3.0 equiv) and dioxane (0.10 M). The vial was heated to 140° C. for 30 min in a microwave reactor. The resulting reaction mixture was allowed to cool to 22° C. and then directly subjected to purification by reverse-phase column chromatography using a C18 cartridge on an automated Teledyne ISCO Rf machine, eluting with 10% to 100% acetonitrile in water+ 0.1% formic acid as a gradient over 20 minutes. Fractions with the desired product were combined and lyophilized to afford the title compound as a white powder. LCMS (ESI+): 525 (M+1)$^+$.

Compounds in the following table were made in a similar manner to Example 133. Reactions were run using the Intermediate FF in place of Intermediate EE

| Example | Structure and Name | MW | MS (ESI+) |
|---|---|---|---|
| Example 134 | ![structure] (S$_a$)-6-(4-chloro-1-((racemic)-1-(4-(6-ethoxypyridin-2-yl)phenyl)-ethyl)-1H-indazole-7-carboxamido)spiro[3.3]heptane-2-carboxylic acid | 559.06 | 559 (M + 1)$^+$ |

Example 135
Preparation of (S<sub>a</sub>)-6-(5-Chloro-1-(4-(2-methoxy-pyridin-4-yl)benzyl)-1H-indazole-7-carboxamido)spiro[3.3]heptane-2-carboxylic acid
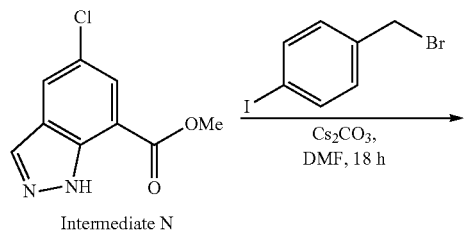
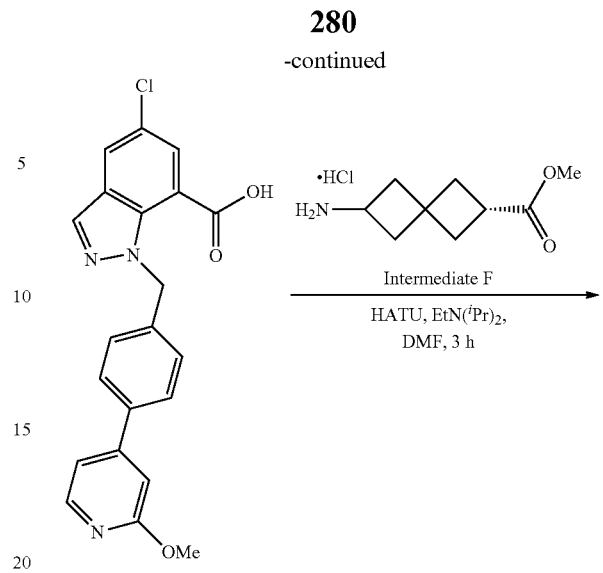
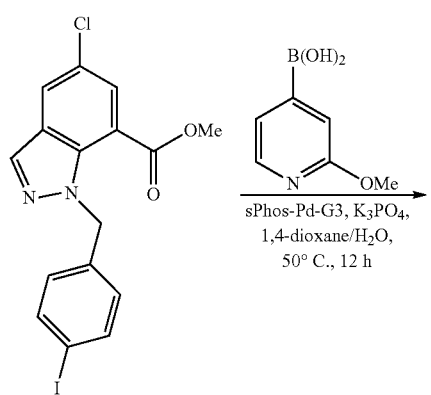
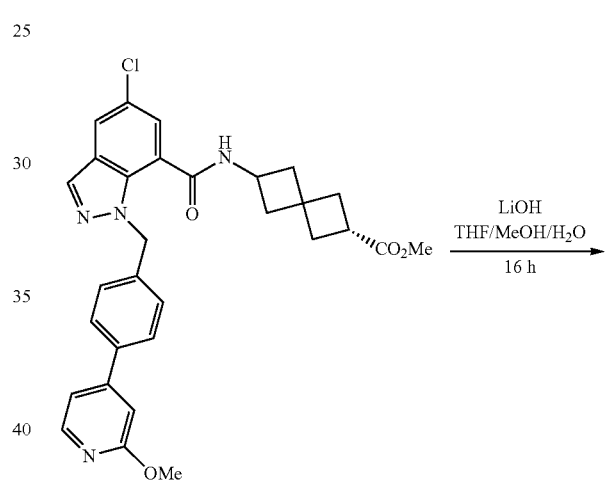
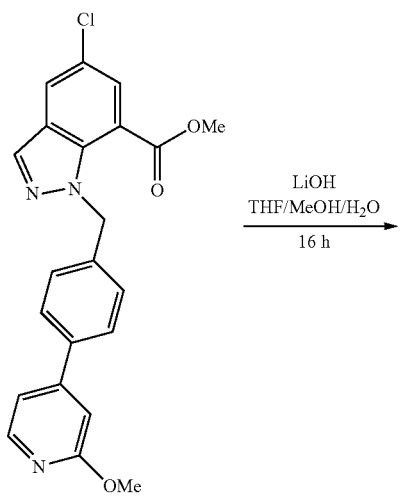
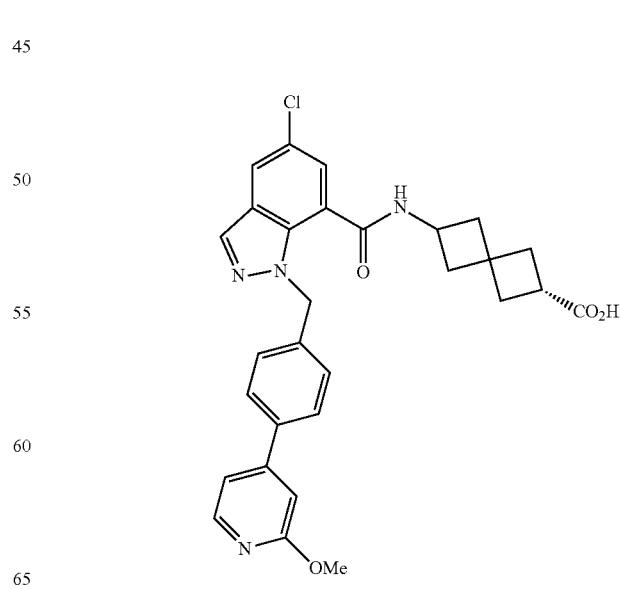
Example 135

Step 1: Preparation of methyl 5-chloro-1-(4-iodo-benzyl)-1H-indazole-7-carboxylate In a round-bottom flask equipped with a magnetic stir bar was suspended Intermediate N (1.0 equiv) and cesium carbonate (3 equiv) in DMF (0.63 M). This suspension was cooled to 0° C. and then added 1-(bromomethyl)-4-iodobenzene (1.2 equiv) portion-wise over a period of 5 minutes. The resulting reaction mixture was allowed to warm to 22° C. over 18 hours. The reaction was then carefully quenched with the addition of ice-water and extracted with tert-butyl methyl ether. The combined organic extracts were washed further with water and brine, dried over MgSO$_4$, treated with activated charcoal and filtered through a pad of celite. Concentration of the filtrate thus obtained in vacuo furnished the crude reaction product as a red oil. Purification by column chromatography through silica gel on the Teledyne ISCO Rf (gradient elution with 10% to 70% EtOAc in hexanes) afforded the title compound as a pale yellow oil that solidified upon standing.

Step 2: Preparation of methyl 5-chloro-1-(4-(2-methoxypyridin-4-yl)benzyl)-1H-indazole-7-carboxylate In a thick-walled reaction flask equipped with a magnetic stir bar and a Teflon screw cap was added methyl 5-chloro-1-(4-iodobenzyl)-1H-indazole-7-carboxylate (1 equiv), (2-methoxypyridin-4-yl)boronic acid (1.2 equiv) and sPhos-Pd-G2 catalyst (0.1 equiv. Strem, CAS #1375325-64-6). The vessel was then evacuated and back-filled with N$_2$. 2 M aqueous K$_3$PO$_4$ solution (4 equiv) and dioxane (0.14 M) were added. The vessel was tightly sealed and heated at 50° C. for 12 hours. The resulting reaction mixture was cooled to 22° C., poured into water and extracted with tert-butyl methyl ether (3×). The combined organic extracts were washed further with brine, dried over MgSO$_4$, filtered and the filtrate concentrated in vacuo. Purification by column chromatography through silica gel on the Teledyne ISCO Rf (gradient elution with 10% to 70% EtOAc in hexanes) afforded the title compound as a pale yellow oil.

Step 3: Preparation of 5-chloro-1-(4-(2-methoxypyridin-4-yl)benzyl)-1H-indazole-7-carboxylic acid Into a glass round-bottom flask equipped with a magnetic stir bar was dissolved methyl 5-chloro-1-(4-(2-methoxypyridin-4-yl)benzyl)-1H-indazole-7-carboxylate (1 equiv) in a 3:2 (v/v) solution (0.15 M) of THF and MeOH. To this was then added 2.0 M aqueous LiOH solution (3 equiv) and the resulting solution was stirred at 22° C. for 16 hours. The reaction mixture was then carefully neutralized with the drop-wise addition of 1 M aqueous HCl solution (3 equiv). The resulting suspension was extracted with EtOAc. The combined organic extracts were washed further with water and brine, dried over MgSO$_4$ and filtered. Concentration of the filtrate thus obtained in vacuo furnished the crude reaction product as a pale yellow semi-solid. Trituration of the crude product in tert-butyl methyl ether and hexanes afforded the title compound as an off-white solid.

Step 4: Preparation of (S$_a$)-methyl 6-(5-chloro-1-(4-(2-methoxypyridin-4-yl)benzyl)-1H-indazole-7-carboxamido)spiro[3.3]heptane-2-carboxylate In a round-bottom flask equipped with a magnetic stir bar was dissolved 5-chloro-1-(4-(2-methoxypyridin-4-yl)benzyl)-1H-indazole-7-carboxylic acid (1 equiv), Intermediate F (1.2 equiv) and HATU (1.5 equiv) in DMF (0.22 M). To this was then added Hünig's base (5 equiv) and the resulting yellow solution was allowed to stir at 22° C. for 3 hours. The crude reaction mixture was diluted with tert-butyl methyl ether and washed sequentially with water, 1 M aqueous HCl solution, 1 M aqueous NaOH solution, water and brine. The organic extract was dried over MgSO$_4$, filtered and the filtrate concentrated in vacuo. Purification by column chromatography through silica gel on the Teledyne ISCO Rf (gradient elution with 10% to 70% EtOAc in hexanes) afforded the title compound as a pale yellow oil that solidified upon standing.

Step 5: Preparation of (S$_a$)-6-(5-chloro-1-(4-(2-methoxypyridin-4-yl)benzyl)-1H-indazole-7-carboxamido)spiro[3.3]heptane-2-carboxylic acid Into a round-bottom flask equipped with a magnetic stir bar was dissolved (S$_a$)-methyl 6-(5-chloro-1-(4-(2-methoxypyridin-4-yl)benzyl)-1H-indazole-7-carboxamido)spiro[3.3]heptane-2-carboxylate (1 equiv) in a 3:2 (v/v) solution (0.1 M) of THF and MeOH. To this was then added 2.0 M aqueous LiOH (3 equiv) and the resulting solution was stirred at 22° C. for 16 hours. The reaction mixture was then carefully neutralized with the drop-wise addition of 1 M aqueous HCl solution (3 equiv). The resulting suspension was extracted with EtOAc. The combined organic extracts were washed further with water and brine, dried over MgSO$_4$, and filtered. Concentration of the filtrate thus obtained in vacuo furnished the crude reaction product as a beige solid. Trituration of the crude product in tert-butyl methyl ether afforded the title compound as an off-white, solid. LCMS (ESI+): 531 (M+1)$^+$.

The following compounds were prepared in a similar manner to Example 135, replacing (2-methoxypyridin-4-yl)boronic acid in Step 2 with commercially available boronic acids.

| Example | Structure and Name | MW | MS (ESI+) |
|---|---|---|---|
| Example 136 | 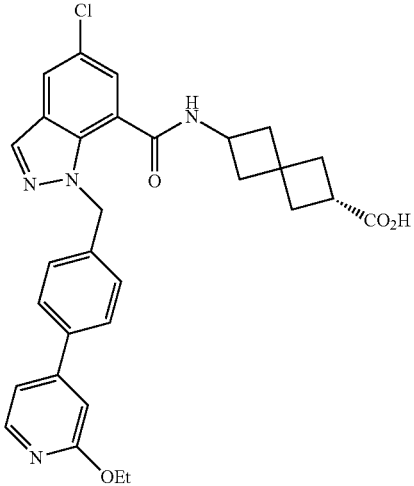<br>($S_a$)-6-(5-chloro-1-(4-(2-ethoxypyridin-4-yl)benzyl)-1H-indazole-7-carboxamido)spiro[3.3]heptane-2-carboxylic acid | 545.03 | 545 $(M + 1)^+$ |

Example 137

Preparation of ($S_a$)-2-(6-(4-Fluoro-1-(4-(2-methoxyquinolin-6-yl)benzyl)-1H-indole-7-carboxamido)spiro[3.3]heptan-2-yl)acetic acid

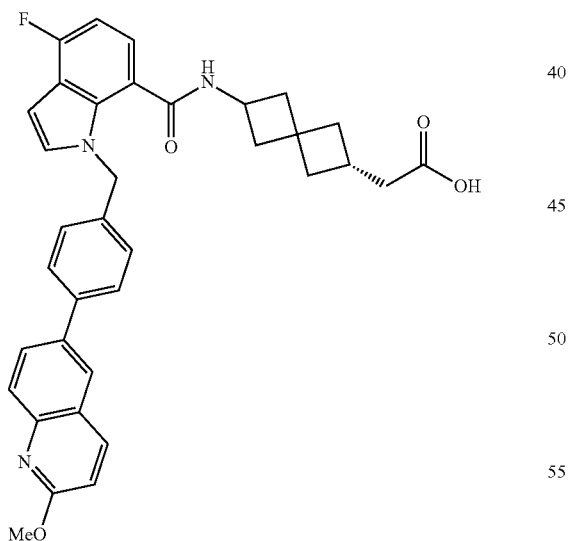

The title compound was made in a similar manner to Example 45 using Intermediate KK in place of Intermediate R and the corresponding commercially available boronic acid at temperatures ranging from 100-130° C. for durations ranging from 10-30 min in a microwave reactor. LCMS (ESI+): 578 $(M+1)^+$.

Compounds in the following table were made in a similar manner using Intermediate LL in place of Intermediate KK and the corresponding commercially available boronic acid.

| Example | Structure and Name | MW | MS (ESI+) |
|---|---|---|---|
| Example 138 | 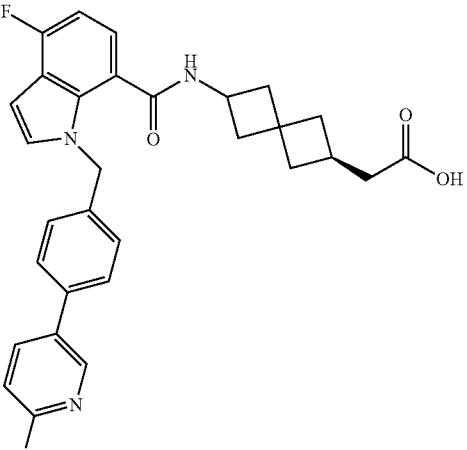<br>($R_a$)-2-(6-(4-Fluoro-1-(4-(6-methoxypyridin-3-yl)benzyl)-1H-indole-7-carboxamido)spiro[3.3]heptan-2-yl)acetic acid | 527.59 | 528 (M + 1)$^+$ |
| Example 139 | 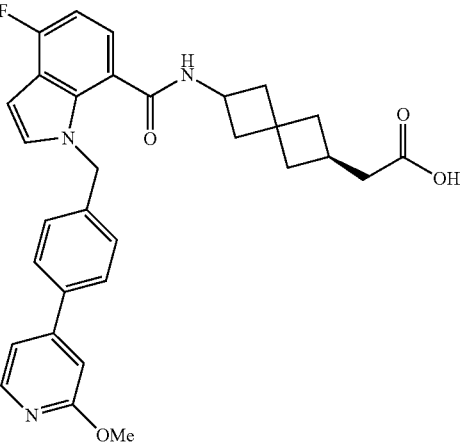<br>($R_a$)-2-(6-(4-Fluoro-1-(4-(2-methoxypyridin-4-yl)benzyl)-1H-indole-7-carboxamido)spiro[3.3]heptan-2-yl)acetic acid | 527.59 | 528 (M + 1)$^+$ |
| Example 140 | 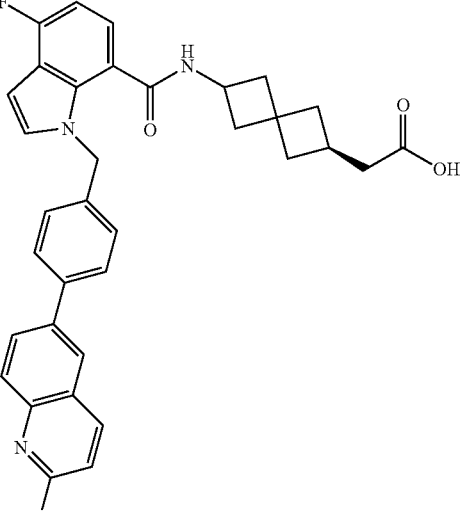 | 577.65 | 578 (M + 1)$^+$ |

| Example | Structure and Name | MW | MS (ESI+) |
|---|---|---|---|
| | ($R_a$)-2-(6-(4-Fluoro-1-(4-(2-methoxyquinolin-6-yl)benzyl)-1H-indole-7-carboxamido)spiro[3.3]heptan-2-yl)acetic acid | | |

Example 141

Preparation of ($S_a$)-2-(6-(1-([1,1'-Biphenyl]-4-ylmethyl)-4-chloro-1H-indazole-7-carboxamido)spiro[3.3]heptan-2-yl)acetic acid

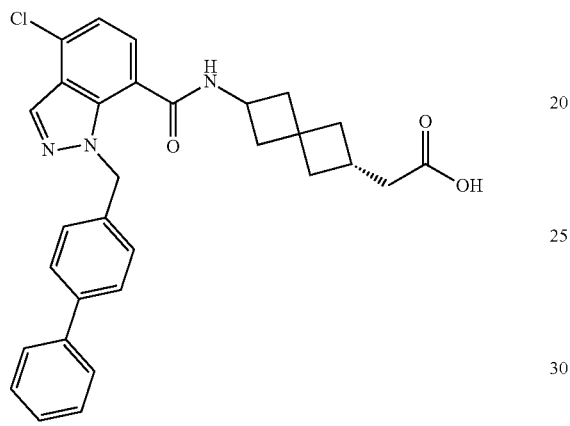

Compounds in the following table were made in a similar manner to Example 78. Reactions were run using Intermediate MM and the corresponding commercially available boronic acid or boron pinacolate ester. LCMS (ESI+): 514 (M+1)$^+$ The compounds in the table below were prepared in a similar manner using Intermediate NN, Intermediate OO or Intermediate PP in place of Intermediate MM.

| Example | Structure and Name | MW | MS (ESI+) |
|---|---|---|---|
| Example 142 | ($R_a$)-2-(6-(1-([1,1'-Biphenyl]-4-ylmethyl)-4-chloro-1H-indazole-7-carboxamido)spiro[3.3]heptan-2-yl)acetic acid | 514.02 | 514 (M + 1)$^+$ |

-continued

| Example | Structure and Name | MW | MS (ESI+) |
|---|---|---|---|
| Example 143 | 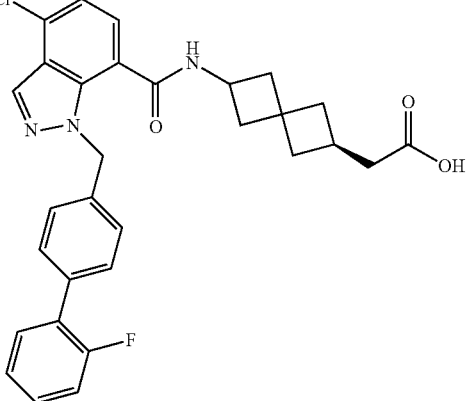(R$_a$)-2-(6-(4-Chloro-1-((2'-fluoro-[1,1'-biphenyl]-4-yl)methyl)-1H-indazole-7-carboxamido)spiro[3.3]heptan-2-yl)acetic acid | 532.01 | 532 (M + 1)$^+$ |
| Example 144 | 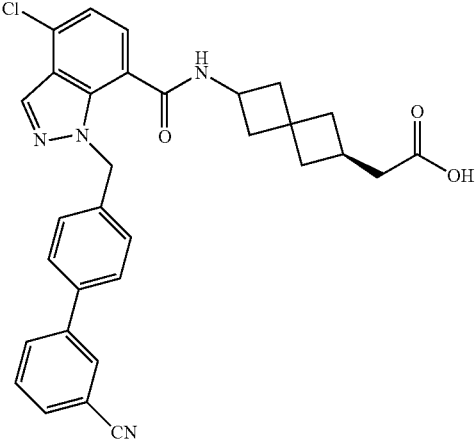(R$_a$)-2-(6-(4-Chloro-1-((3'-cyano-[1,1-biphenyl]-4-yl)methyl)-1H-indazole-7-carboxamido)spiro[3.3]heptan-2-yl)acetic acid | 539.03 | 539 (M + 1)$^+$ |
| Example 145 | 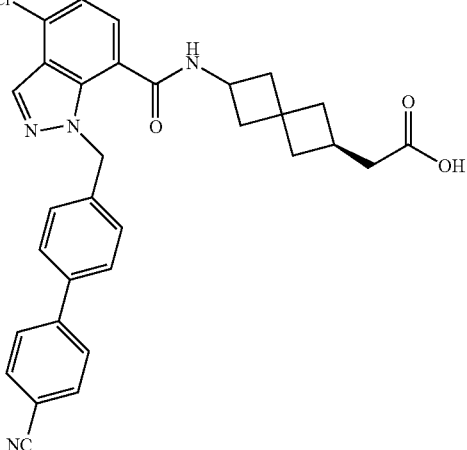(R$_a$)-2-(6-(4-Chloro-1-((4'-cyano-[1,1'-biphenyl]-4-yl)methyl)-1H-indazole-7-carboxamido)spiro[3.3]heptan-2-yl)acetic acid | 539.03 | 539 (M + 1)$^+$ |

| Example | Structure and Name | MW | MS (ESI+) |
|---|---|---|---|
| Example 146 | 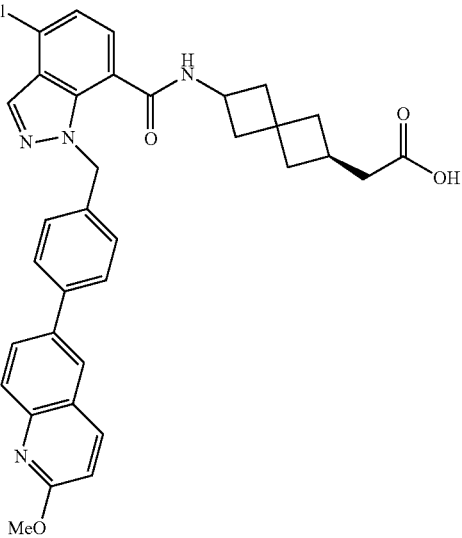<br>($R_a$)-2-(6-(4-Chloro-1-(4-(2-methoxyquinolin-6-yl)benzyl)-1H-indazole-7-carboxamido)spiro[3.3]heptan-2-yl)acetic acid | 595.09 | 595 (M + 1)+ |
| Example 147 | 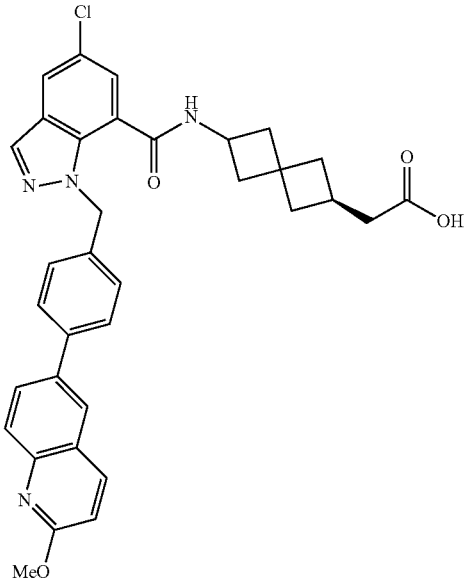<br>($R_a$)-2-(6-(5-Chloro-1-(4-(2-methoxyquinolin-6-yl)benzyl)-1H-indazole-7-carboxamido)spiro[3.3]heptan-2-yl)acetic acid | 595.09 | 595 (M + 1)+ |

-continued

| Example | Structure and Name | MW | MS (ESI+) |
|---|---|---|---|
| Example 148 | 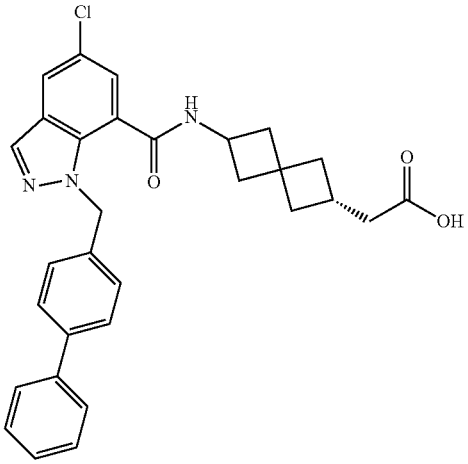<br>($S_a$)-2-(6-(1-([1,1'-Biphenyl]-4-ylmethyl)-5-chloro-1H-indazole-7-carboxamido)spiro[3.3]heptan-2-yl)acetic acid | 514.02 | 514 (M + 1)$^+$ |

Example 149

Preparation of (R)-2-(6-(4-Chloro-1-(4-(6-methoxypyridin-2-yl)benzyl)-1H-indazole-7-carboxamido)spiro[3.3]heptan-2-yl)acetic acid

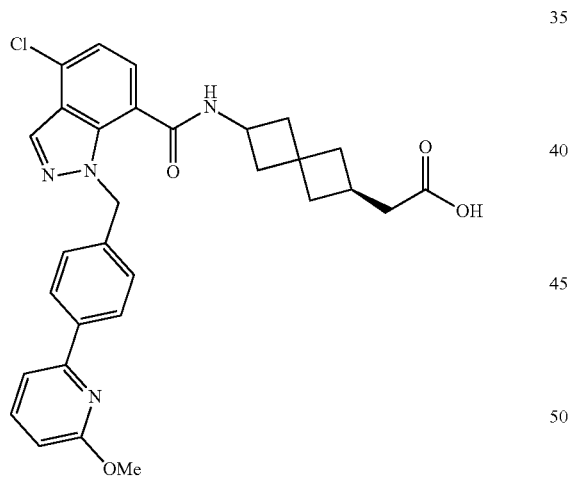

The title compound was prepared a similar manner to Example 83 using Intermediate QQ in place of Intermediate AA and the corresponding commercially available (hetero) aryl halide at temperatures ranging from 100-150° C. for durations ranging from 10-30 min in a microwave reactor. LCMS (ESI+): 545 (M+1)$^+$ The compound in the table below was prepared in a similar manner using Intermediate RR in place of Intermediate QQ.

| Example | Structure and Name | MW | MS (ESI+) |
|---|---|---|---|
| Example 150 | 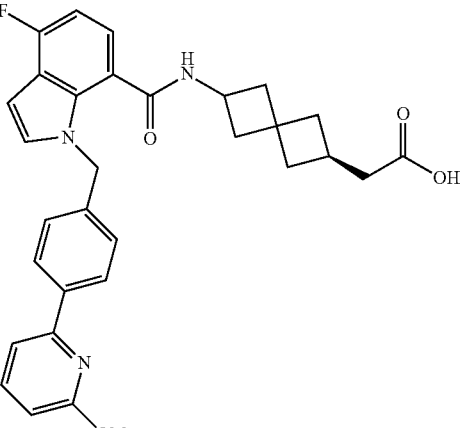<br>($R_a$)-2-(6-(4-Fluoro-1-(4-(6-methoxypyridin-2-yl)benzyl)-1H-indole-7-carboxamido)spiro[3.3]heptan-2-yl)acetic acid | 527.59 | 528 (M + 1)+ |

Example 151

Preparation of ($R_a$)-2-(6-(5-Chloro-1-((2-fluoro-[1,1'-biphenyl]-4-yl)methyl)-1H-indazole-7-carboxamido)spiro[3.3]heptan-2-yl)acetic acid

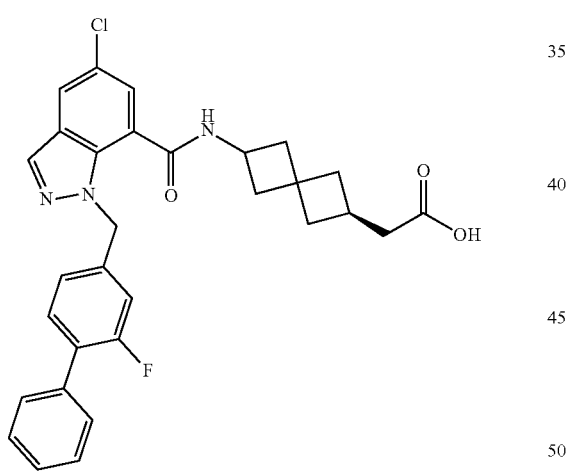

The title compound was prepared in a similar manner to Example 141 using Intermediate SS in place of Intermediate MM and the corresponding commercially available boronic acid or boron pinacolate ester. LCMS (ESI): 532 (M+1)+.

The compounds in the table below were made in a similar manner using Intermediate TT, Intermediate UU, Intermediate VV or Intermediate XX in place of Intermediate SS.

| Example | Structure and Name | MW | MS (ESI+) |
|---|---|---|---|
| Example 152 | 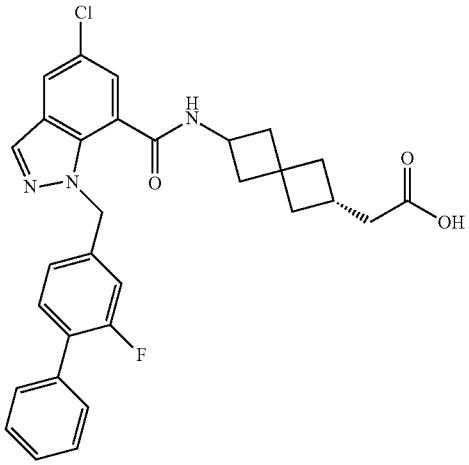<br>($S_a$)-2-(6-(5-Chloro-1-((2-fluoro-[1,1'-biphenyl]-4-yl)methyl)-1H-indazole-7-carboxamido)spiro[3.3]heptan-2-yl)acetic acid | 532.01 | 532 (M + 1)+ |
| Example 153 | 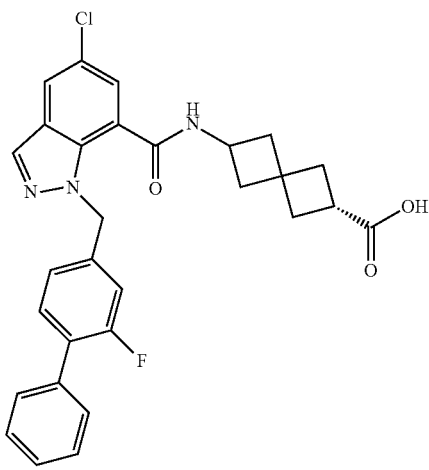<br>($S_a$)-6-(5-Chloro-1-((2fluoro-[1,1'-biphenyl]-4-yl)methyl)-1H-indazole-7-carboxamido)spiro[3.3]heptane-2-carboxylic acid | 517.98 | 518 (M + 1)+ |
| Example 154 | 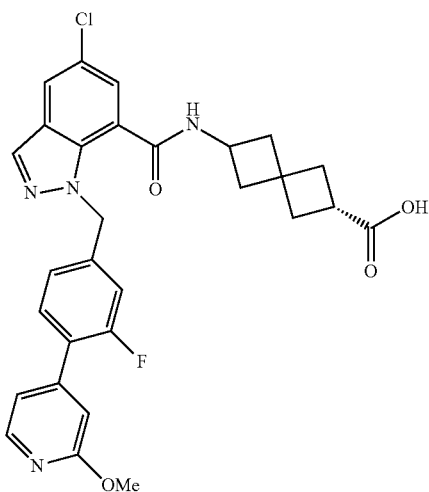 | 549.00 | 549 (M + 1)+ |

| Example | Structure and Name | MW | MS (ESI+) |
|---|---|---|---|
| | ($S_a$)-6-(5-Chloro-1-(3-fluoro-4-(2-methoxypyridin-4-yl)benzyl)-1H-indazole-7-carboxamido)spiro[3.3]heptane-2-carboxylic acid | | |
| Example 155 | 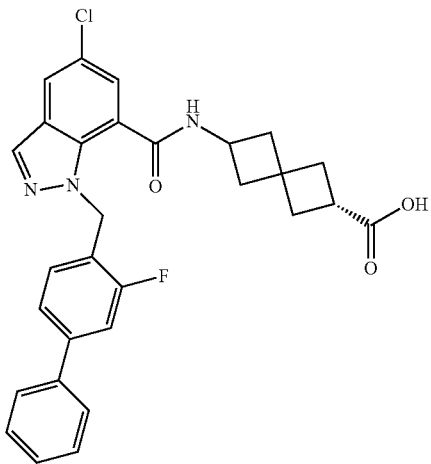<br>($S_a$)-6-(5-Chloro-1-((3-fluoro-[1,1-biphenyl]-4-yl)methyl)-1H-indazole-7-carboxamido)spiro[3.3]heptane-2-carboxylic acid | 517.98 | 518 (M + 1)+ |
| Example 156 | 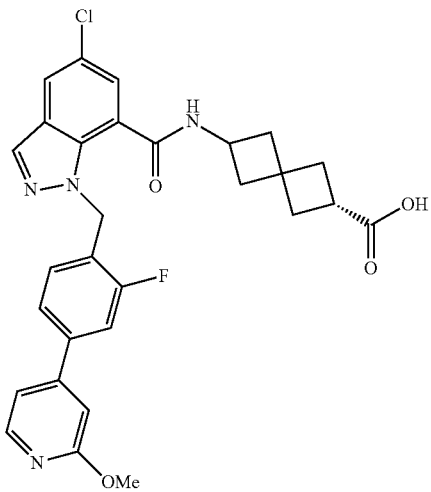<br>($S_a$)-6-(5-Chloro-1-(2-fluoro-4-(2-methoxypyridin-4-yl)benzyl)-1H-indazole-7-carboxamido)spiro[3.3]heptane-2-carboxylic acid | 549.00 | 549 (M + 1)+ |

| Example | Structure and Name | MW | MS (ESI+) |
|---|---|---|---|
| Example 157 | (S$_a$)-6-(1-((([1,1'-Biphenyl]-4-yl-2,3,5,6-d$_4$)methyl-d$_2$)-4-chloro-1H-indazole-7-carboxamido)spiro[3.3]heptane-2-carboxylic acid | 506.03 | 506 (M + 1)$^+$ |

Example 158

Preparation of (S$_a$)-6-(1-([1,1'-Biphenyl]-4-ylmethyl)-5-bromo-1H-indazole-7-carboxamido)spiro[3.3]heptane-2-carboxylic acid

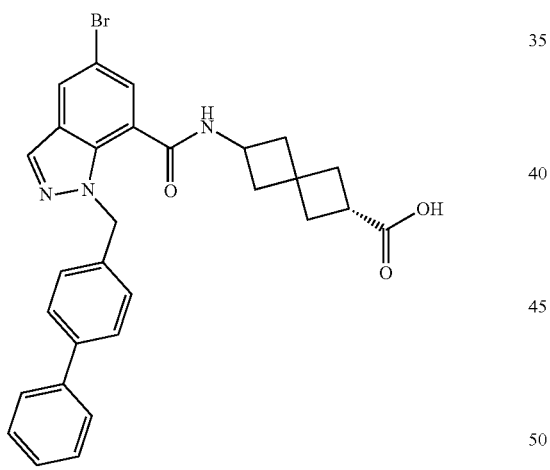

The title compound was prepared as described in Example 93 beginning at Step 3 using Intermediate YY in place of 1-([1,1'-biphenyl]-4-ylmethyl)-5-chloro-1H-indazole-7-carboxylic acid and using the appropriate amine. LCMS (ESI+): 544 (M+1)$^+$ The compounds in the table below were prepared in a similar manner, using Intermediate ZZ, Intermediate aaa or Intermediate bbb in place of Intermediate YY and using the appropriate amine.

| Example | Structure and Name | MW | MS (ESI+) |
|---|---|---|---|
| Example 159 | (S$_a$)-6-(1-([1,1'-Biphenyl]-4-ylmethyl)-5-methoxy-1H-indazole-7-carboxamido)spiro[3.3]heptane-2-carboxylic acid | 495.6 | 496 (M + 1)+ |
| Example 160 | (S$_a$)-6-(1-([1,1'-Biphenyl]-4-ylmethyl)-5-methyl-1H-indazole-7-carboxamido)spiro[3.3]heptane-2-carboxylic acid | 479.6 | 480 (M + 1)+ |
| Example 161 | (R$_a$)-2-(6-(1-([1,1'-Biphenyl]-4-ylmethyl)-4-methoxy-1H-indazole-7-carboxamido)spiro[3.3]heptan-2-yl)acetic acid | 509.6 | 510 (M + 1)+ |

-continued

| Example | Structure and Name | MW | MS (ESI+) |
|---|---|---|---|
| Example 162 | (R$_a$)-2-(6-(1-([1,1'-Biphenyl]-4-ylmethyl)-4-(difluoromethoxy)-1H-indazole-7-carboxamido)spiro[3.3]heptan-2-yl)acetic acid | 545.48 | 546 (M + 1)+ |
| Example 163 | (S$_a$)-6-(1-(1,1'-Biphenyl]-4-ylmethyl)-5-(difluoromethoxy)-1H-indazole-7-carboxamido)spiro[3.3]heptane-2-carboxylic acid | 531.55 | 532 (M + 1)+ |
| Example 164 | (R$_a$)-2-(6-(1-([1,1'-Biphenyl]-4-ylmethyl)-5-methoxy-1H-indazole-7-carboxamido)spiro[3.3]heptan-2-yl)acetic acid | 509.60 | 510 (M + 1)+ |

| Example | Structure and Name | MW | MS (ESI+) |
|---|---|---|---|
| Example 165 | 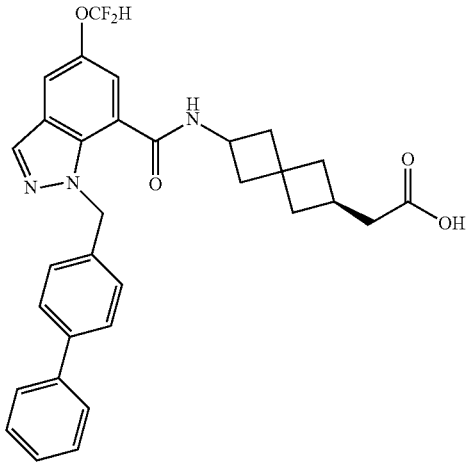<br>(R$_a$)-2-(6-(1-([1,1'-Biphenyl]-4-ylmethyl)-5-(difluoromethoxy)-1H-indazole-7-carboxamido)spiro[3.3]heptan-2-yl)acetic acid | 545.58 | 546 (M + 1)$^+$ |
| Example 166 | 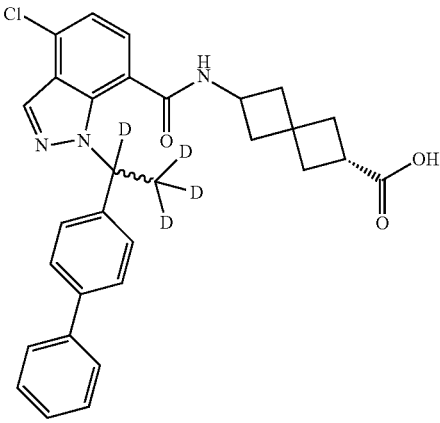<br>(S$_a$)-6-(1-((racemic)-1-([1,1'-Biphenyl]-4-yl)ethyl-1,2,2,2-d$_4$)-4-chloro-1H-indazole-7-carboxamido)spiro[3.3]heptane-2-carboxylic acid | 518.04 | 540 (M + 23)$^+$ |
| Example 167 | 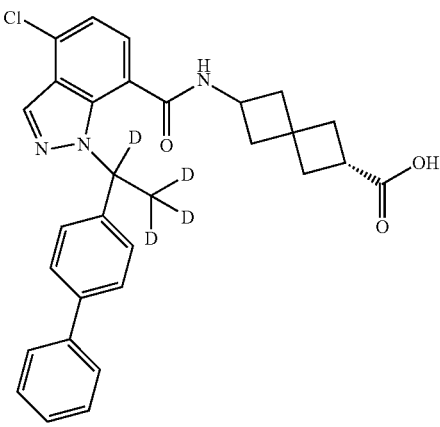<br>(S$_a$)-6-(1-((R) or (S)-1-([1,1'-Biphenyl]-4-yl)ethyl-1,2,2,2-d$_4$)-4-chloro-1H-indazole-7-carboxamido)spiro[3.3]heptane-2-carboxylic acid | 518.04 | 516 (M − 1)$^-$ |

| Example | Structure and Name | MW | MS (ESI+) |
|---|---|---|---|
| Example 168 | 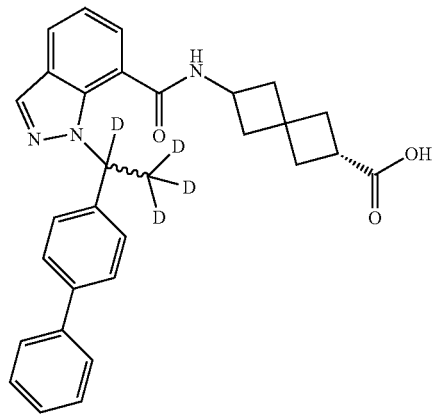<br>(S$_a$)-6-(1-((racemic)-1-([1,1'-Biphenyl]-4-yl)ethyl-1,2,2,2-d$_4$)-1H-indazole-7-carboxamido)spiro[3.3]heptane-2-carboxylic acid | 483.6 | 506 (M + 23)$^+$ |
| Example 169 | 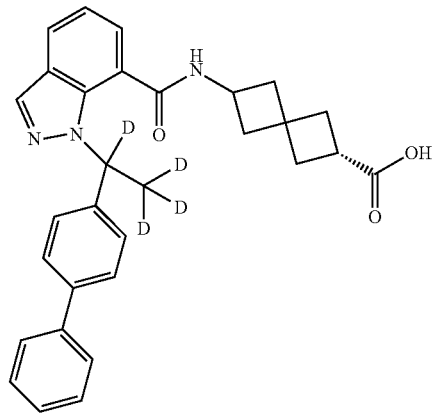<br>(S$_a$)-6-(1-((R) or (S)-1-([1,1'-Biphenyl]-4-yl)ethyl-1,2,2,2-d$_4$)-1H-indazole-7-carboxamido)spiro[3.3]heptane-2-carboxylic acid | 483.6 | 516 (M + 23)$^+$ |

Example 170

Preparation of (R$_a$)-2-(6-(1-([1,1'-Biphenyl]-4-ylmethyl)-5-chloro-4-fluoro-1H-indazole-7-carboxamido)spiro[3.3]heptan-2-yl)acetic acid

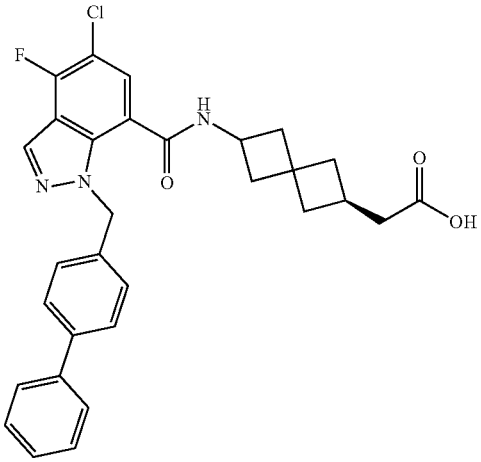

The title compound was prepared in a manner similar to Example 93, but using Intermediate eee in place of Intermediate N at Step 1 and Intermediate F in Step 3 with Intermediate (R$_a$)-L. LCMS (ESI+): 532 (M+1)$^+$

Example 171

Preparation of (R$_a$)-2-(6-(1-([1,1'-Biphenyl]-4-ylmethyl)-5-chloro-4-methoxy-1H-indazole-7-carboxamido)spiro[3.3]heptan-2-yl)acetic acid

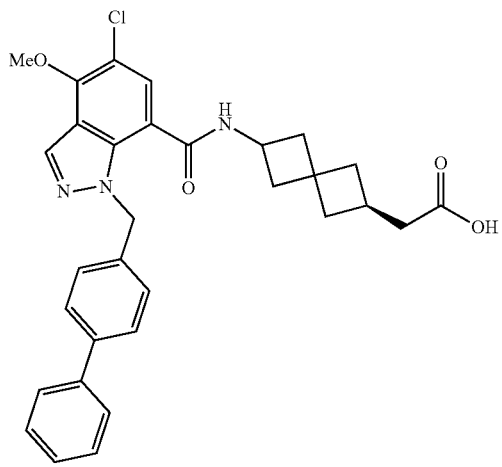

The title compound is a side product obtained during the hydrolysis in Step 2 of Example 170, from the incorporation of the methoxy group and displacement of chlorine during the synthesis of Example 170. LCMS (ESI+): 544 (M+1)$^+$.

Example 172

Preparation of (S$_a$)-6-(4-Chloro-1-(4-cyclobutyl-3-fluorobenzyl)-1H-indazole-7-carboxamido)spiro[3.3]heptane-2-carboxylic acid

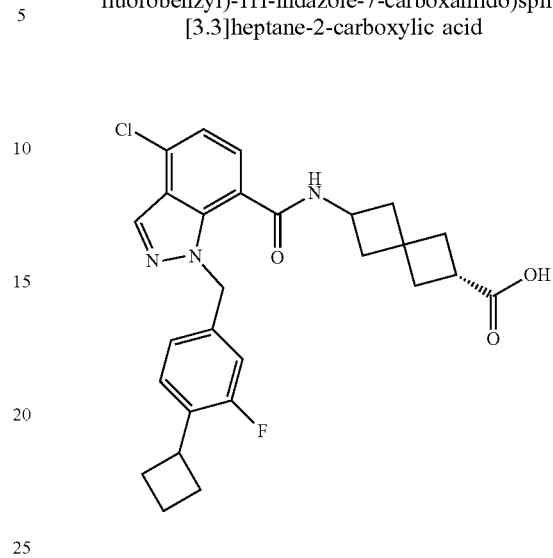

The following compounds were prepared in a similar manner to Example 93, replacing the product of Step 1, methyl 1-([1,1'-biphenyl]-4-ylmethyl)-5-chloro-1H-indazole-7-carboxylate with Intermediate fff. LCMS (ESI+): 496 (M+1)$^+$.

Example 173

Preparation of (S$_a$)-6-(1-((racemic)1-([1,1'-Biphenyl]-4-yl)ethyl)-5-chloro-1H-indazole-7-carboxamido)spiro[3.3]heptane-2-carboxylic acid

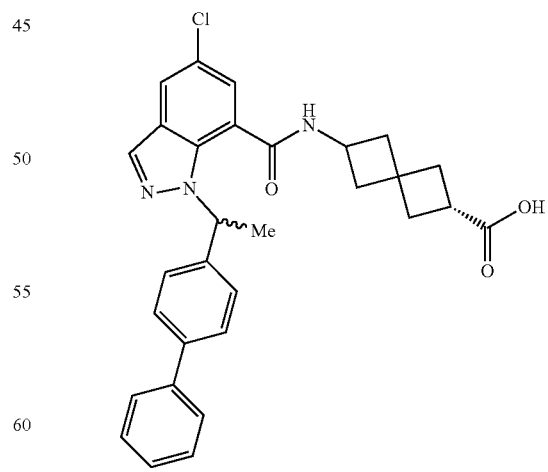

Compounds in the following table were made in a similar manner to Example 112 using Intermediate ggg in place of Intermediate BB and using the corresponding commercially available boronic acid. LCMS (ESI+): 514 (M+1)$^+$.

Example 174

Preparation of (S$_a$)-6-(1-((R) or (S))-1-([1,1'-Biphenyl]-4-yl)ethyl)-5-chloro-1H-indazole-7-carboxamido)spiro[3.3]heptane-2-carboxylic acid

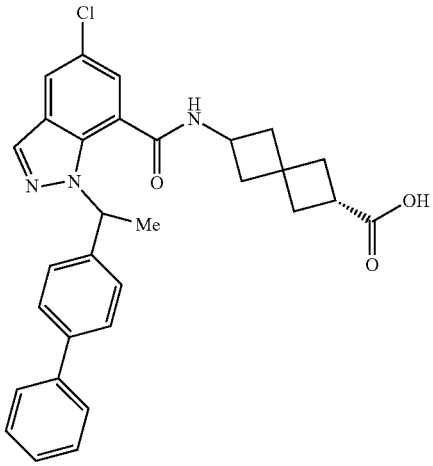

The racemic compound of Example 173 was resolved using chiral SFC in a similar manner to Example 125, to afford the title compound as the second eluting peak, which was determined to be the more active diastereomer. LCMS (ESI+): 514 (M+1)$^+$

Example 175

Preparation of (S$_a$)-6-(4-Chloro-1-((2-methoxyquinolin-6-yl)methyl)-1H-indazole-7-carboxamido)spiro[3.3]heptane-2-carboxylic acid

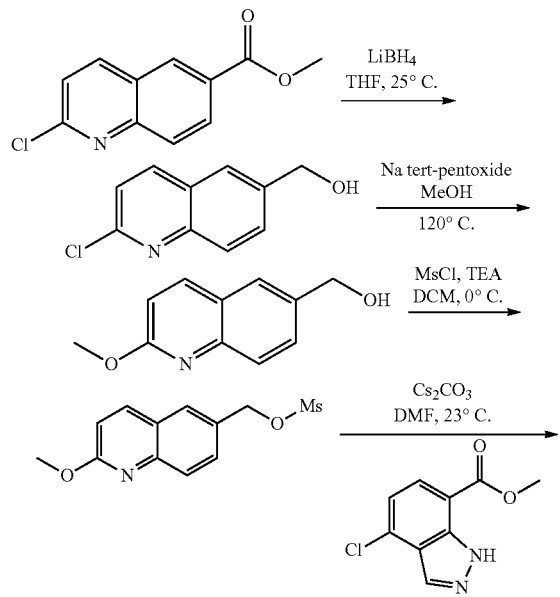

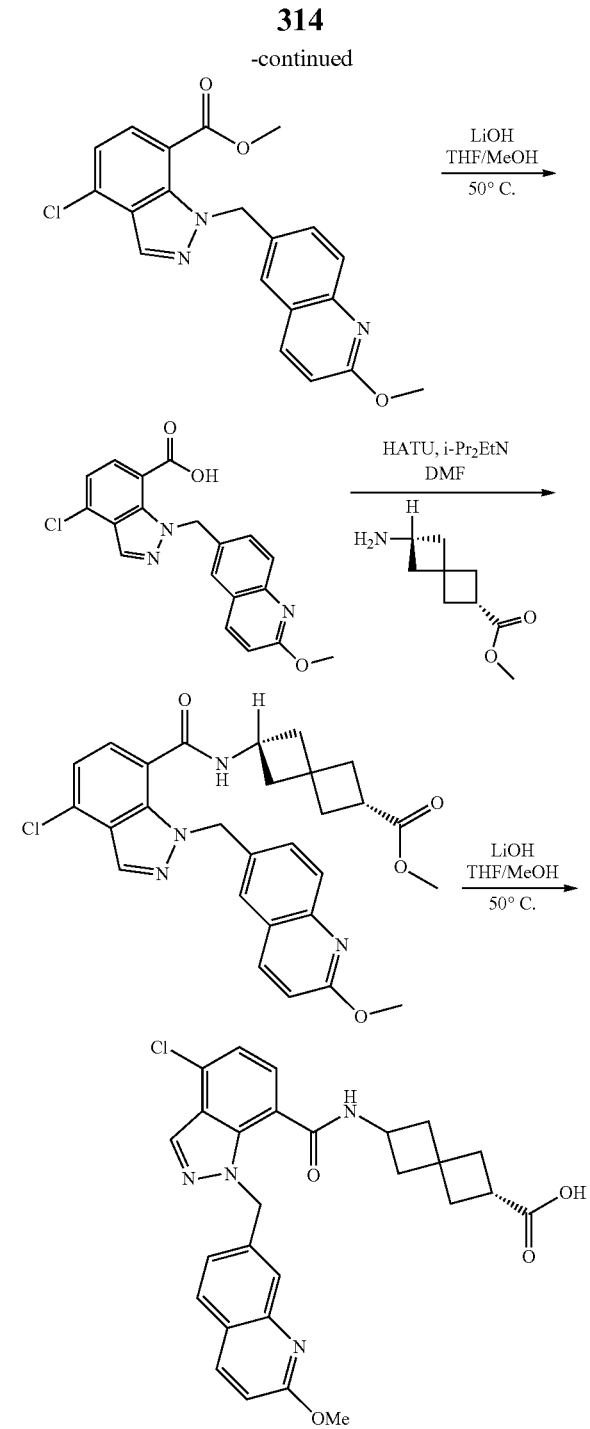

Step 1: Preparation of (2-chloroquinolin-6-yl)methanol

To a solution of methyl 2-chloroquinoline-6-carboxylate in THF (200 mM) cooled over an ice bath was added lithium borohydride, 95% (2 M, 2 eq.) and then stirred at 25° C. for 18 hours. This mixture was quenched with sat aq NH$_4$Cl and extracted with EtOAc (2×). The combined extracts were further washed with sat aq NaHCO$_3$, dried over MgSO$_4$, filtered and concentrated under vacuum to provide the title compound.

Step 2: Preparation of (2-methoxyquinolin-6-yl)methanol

To a solution of (2-chloro-6-quinolyl)methanol in MeOH (200 mM) in a microwave vial was added sodium t-pentoxide (1 eq.) and this mixture was irradiated to 120° C. for 30 minutes in a Biotage microwave reactor. The reaction mixture was concentrated under vacuum and the residue was applied to a precartridge using DCM. This material was purified by column chromatography using a Teledyne ISCO cartridge eluting with a 0-45% EtOAc/hexanes gradient. The fractions from the major peak eluting at 40% EtOAc were combined and concentrated under vacuum to the title compound as a white solid.

Step 3: Preparation of (2-methoxyquinolin-6-yl)methyl methanesulfonate

To a cold solution of (2-methoxy-6-quinolyl)methanol in DCM (300 mM) stirred over an ice bath was added mesyl chloride (1.1 eq.) and TEA (1.14 eq.) and stirred over the cooling bath for 1 hour. After this time, the mixture was quenched with 0.1M HCl and partitioned with DCM (2×). The combined extracts were dried over MgSO$_4$, filtered and concentrated under vacuum to provide the title compound as a tan solid.

Step 4: Preparation of methyl 4-chloro-1-((2-methoxyquinolin-6-yl)methyl)-1H-indazole-7-carboxylate To a solution of (2-methoxy-6-quinolyl)methyl methanesulfonate and methyl 4-chloro-1H-indazole-7-carboxylate (1 eq.) in DMF (275 mM) cooled over an ice bath was added cesium carbonate (1 eq.) and stirred over the ice bath for 30 minutes and then at 23° C. for 18 hours. This mixture was diluted with water (3 volumes) and extracted with EtOAc (2×). The combined extracts were concentrated under vacuum and the resulting residue was applied to precartridge using DCM. This material was purified by column chromatography using a Teledyne ISCO silica cartridge eluting with a gradient of 5-40% EtOAc/hexanes. The fractions from the major peak which elutes at 25% EtOAc were combined and concentrated under vacuum to the title compound as a white solid.

Step 5: Preparation of 4-chloro-1-((2-methoxyquinolin-6-yl)methyl)-1H-indazole-7-carboxylic acid To a suspension of methyl 4-chloro-1-[(2-methoxy-6-quinolyl)methyl]indazole-7-carboxylate in THF/MeOH (1:1) (100 mM) was added lithium hydroxide (1 M, 2 eq.) and heated to 50° C. for 18 hours. This solution was concentrated under vacuum to remove organic solvents. This suspension was acidified with HCl (1 M, 2.9 eq.) and extracted with EtOAc (2×). The combined extracts were dried over MgSO$_4$, filtered and concentrated under vacuum to provide the title compound as a white solid.

Step 6: Preparation of methyl 6-(4-chloro-1-((2-methoxyquinolin-6-yl)methyl)-1H-indazole-7-carboxamido)spiro[3.3]heptane-2-carboxylate To a solution of 4-chloro-1-[(2-methoxy-6-quinolyl)methyl]indazole-7-carboxylic acid in DMF (230 mM) was added HATU (1.2 eq.) and stirred under nitrogen for 15 minutes. After this time, this solution was treated with methyl 2-aminospiro[3.3]heptane-6-carboxylate (1.1 eq., HCl) and Hunig's base (202.20 mg, 3 eq.) and stirred at 23° C. for 1 hour. The mixture precipitated out a white solid. This mixture was quenched with water and extracted with EtOAc (3×). The combined extracts were dried over MgSO$_4$, filtered and concentrated under vacuum. This residue was applied to precartridge using DCM and then purified by column chromatography using a Teledyne ISCO cartridge eluting with a 0-60% EtOAc/hexanes and then 100% EtOAc. The fractions from the main peak which elutes at 54% EtOAc and trails were combined and concentrated under vacuum to provide the title compound as a white solid.

Step 7: Preparation of 6-(4-chloro-1-((2-methoxyquinolin-6-yl)methyl)-1H-indazole-7-carboxamido)spiro[3.3]heptane-2-carboxylic acid To a solution of methyl 2-[[4-chloro-1-[(2-methoxy-6-quinolyl)methyl]indazole-7-carbonyl]amino]spiro[3.3]heptane-6-carboxylate in THF/MeOH (1:1) (50 mM) was added lithium hydroxide (1 M, 2 eq.) and then heated to 50° C. for 18 hours. This mixture was concentrated under vacuum to remove the organic solvent and diluted with water and then acidified to pH=1 with HCl (1 M) and extracted with EtOAc (2×). The combined extracts were dried over MgSO$_4$, filtered and concentrated under vacuum to the title compound as a white solid foam. LCMS (ESI+): 505 (M+1)$^+$.

Example 176

Preparation of (S$_a$)-6-(1-(3-([1,1'-Biphenyl]-4-yl)oxetan-3-yl)-4-chloro-1H-indazole-7-carboxamido)spiro[3.3]heptane-2-carboxylic acid

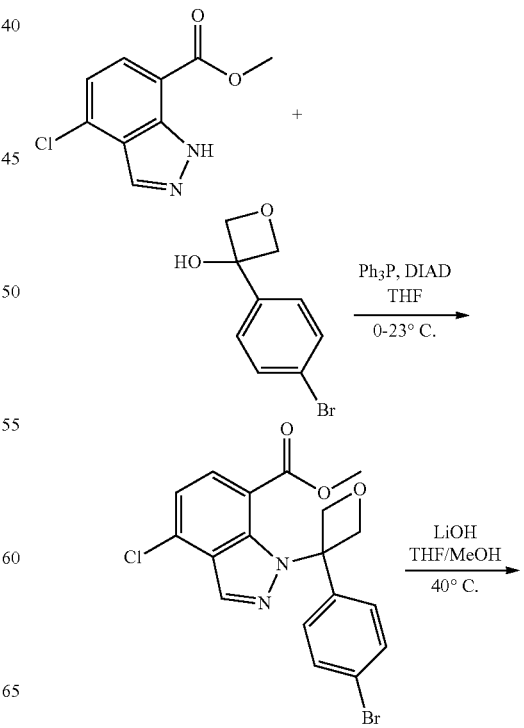

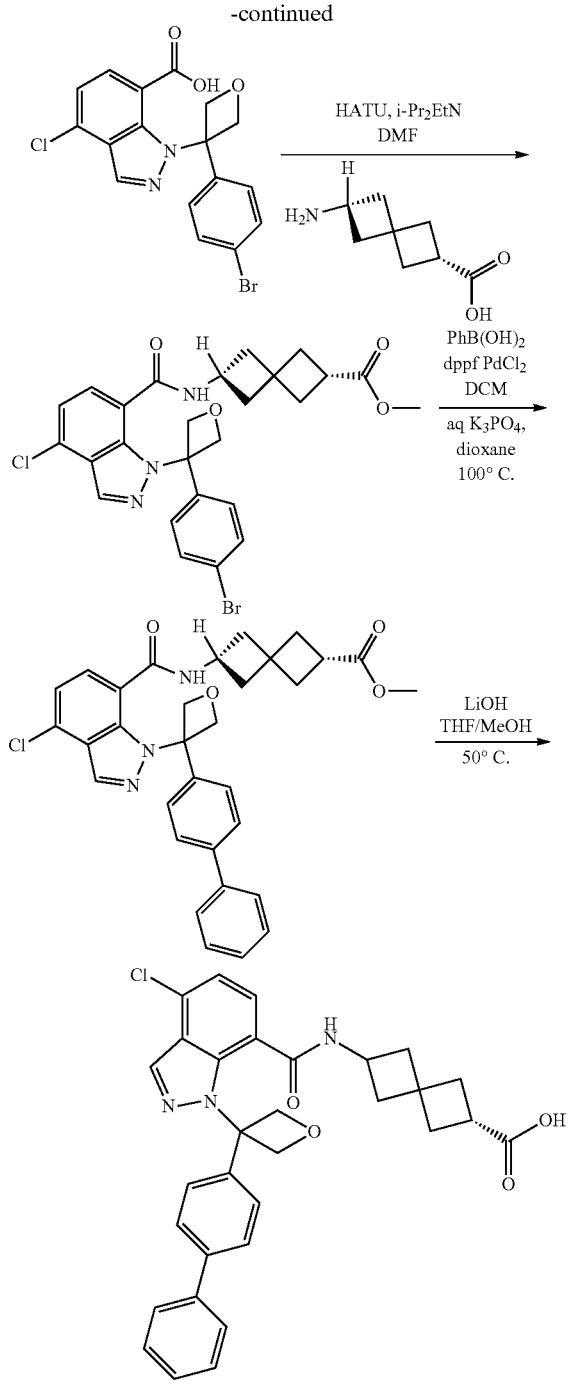

Step 2: Preparation of methyl 1-(3-(4-bromophenyl) oxetan-3-yl)-4-chloro-H-indazole-7-carboxylate To a solution of methyl 4-chloro-1H-indazole-7-carboxylate, 3-(4-bromophenyl)oxetan-3-ol (AstaTech, cat #32910, 2 eq.) and triphenylphosphine (2.25 eq.) in THF (200 mM) cooled over an ice bath was added diisopropylazodicarboxylate (2.1 eq.) and stirred cold for 10 minutes and then removed the cooling bath and stirred at 23° C. for hour. The crude mixture was purified by column chromatography using a Teledyne ISCO cartridge eluting with a 0-30% EtOAc/hexanes gradient. The fractions from the major peak which eluted at 13% EtOAc were combined and concentrated under vacuum to provide the title compound.

Step 2: Preparation of 1-(3-(4-bromophenyl)oxetan-3-yl)-4-chloro-1H-indazole-7-carboxylic acid To a solution of methyl 1-[3-(4-bromophenyl)oxetan-3-yl]-4-chloro-indazole-7-carboxylate in THF/MeOH (1:1) (70 mM) was added lithium hydroxide (1 M, 3 eq.) and stirred at 23° C. for 4 hours and then heated to 40° C. for 16 hours. This mixture was concentrated under vacuum. The resulting solid was acidified with HCl (1 M, 300 µL) and then partitioned between water and EtOAc (2×). The combined extracts were concentrated under vacuum to provide the title compound as a golden residue.

Step 3: Preparation of methyl 6-(1-(3-(4-bromophenyl)oxetan-3-yl)-4-chloro-1H-indazole-7-carboxamido)spiro[3.3]heptane-2-carboxylate To a solution of 1-[3-(4-bromophenyl)oxetan-3-yl]-4-chloro-indazole-7-carboxylic acid, methyl 2-aminospiro[3.3]heptane-6-carboxylate (1.4 eq.) and HATU (1.4 eq.) in DMF (130 mM) was added Hunig's base (3 eq.) and stirred at 23° C. for 2 hours. This mixture was partitioned between water and EtOAc (2×). The combined organic extracts were concentrated under vacuum. This residue was purified by column chromatography using a Teledyne ISCO silica gel cartridge eluting with a 0-50% EtOAc/hexanes gradient. The fractions from the major fraction which eluted at 42% EtOAc were combined and concentrated under vacuum to provide the title compound.

Step 4: Preparation of methyl 6-(1-(3-([1,1'-biphenyl]-4-yl)oxetan-3-yl)-4-chloro-1H-indazole-7-carboxamido)spiro[3.3]heptane-2-carboxylate To a degassed solution of methyl 2-[[1-[3-(4-bromophenyl)oxetan-3-yl]-4-chloro-indazole-7-carbonyl]amino]spiro[3.3]heptane-6-carboxylate, phenyl boronic acid (1 eq.) and dppf PdCl₂ DCM (0.1 eq.) in dioxane (70 mM) was added potassium phosphate (2 M, 3 eq.) and irradiated to 100° C. for 15 minutes on a Biotage Microwave reactor. This mixture was applied to a silica precartridge and then purified by reverse phase column chromatography using a C18 Teledyne ISCO cartridge eluting with a 10-80% ACN/water gradient containing 0.1% HCO₂H. The fractions from the main peak which eluted at 80% ACN were combined and concentrated under vacuum to provide the title compound.

Step 5: Preparation of 6-(1-(3-([1,1'-biphenyl]-4-yl)oxetan-3-yl)-4-chloro-1H-indazole-7-carboxamido)spiro[3.3]heptane-2-carboxylic acid To a solution of methyl 2-[[4-chloro-1-[3-(4-phenylphenyl)oxetan-3-yl]indazole-7-carbonyl]amino]spiro[3.3]heptane-6-carboxylate in THF/MeOH (1:1) (70 mM) was added lithium hydroxide (1 M, 4 eq.) and heated to 50° C. for 1 hour. This mixture was concentrated under vacuum to remove the organic solvent, acidified with HCl (1 M, 4 eq.) and then reconcentrated under vacuum to a solid. This solid was dissolved in DMSO and purified by reverse column chromatography using a C18 Teledyne ISCO cartridge eluting with a 10-100% ACN/water gradient containing 0.1% HCO₂H. The fractions from the major peak which eluted at 90% ACN were combined and lyophilized to provide the title compound as a white solid. LCMS (ESI+): 542 (M+1)⁺.

The embodiments described above are intended to be merely exemplary and those skilled in the art will recognize, or will be able to ascertain using no more than routine experimentation, numerous equivalents of specific compounds, materials, and procedures. All such equivalents are considered to be within the scope of the claimed subject matter and are encompassed by the appended claims.

While embodiments of the present disclosure have been shown and described herein, it will be obvious to those skilled in the art that such embodiments are provided by way of example only. Numerous variations, changes, and substitutions will now occur to those skilled in the art without departing from the present disclosure. It should be understood that various alternatives to the embodiments of the present disclosure described herein may be employed in practicing the present disclosure. It is intended that the following claims define the scope of the present disclosure and that methods and structures within the scope of these claims and their equivalents be covered thereby.

What is claimed is:

1. A method for the treatment of an EP4-mediated cancer in a patient comprising administering to the patient a compound that is selected from the group consisting of:

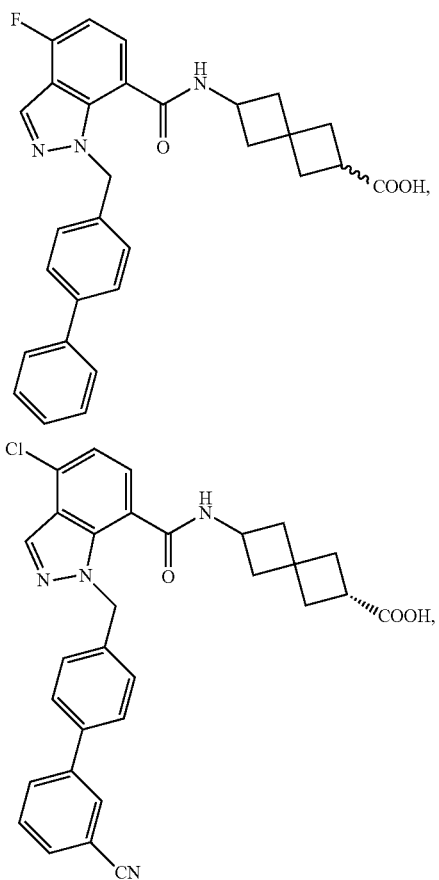

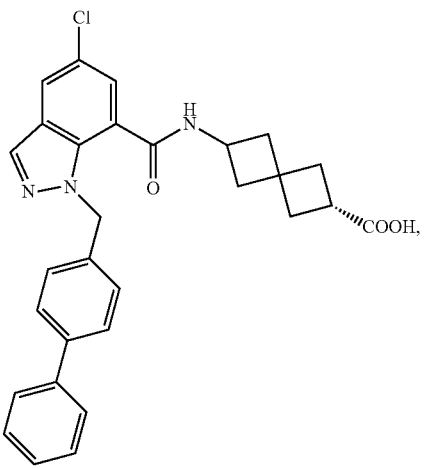

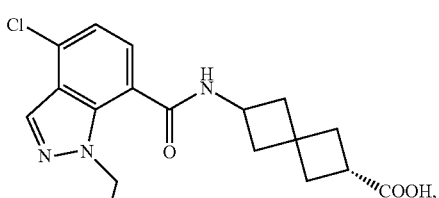

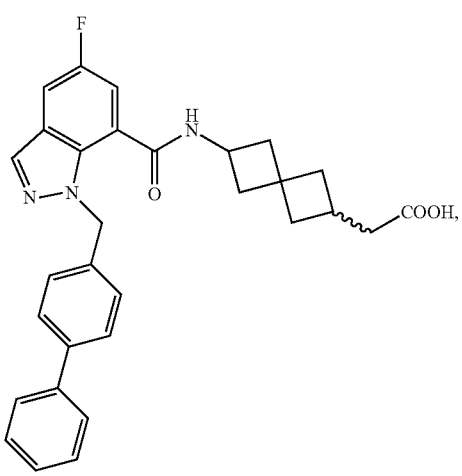

321
-continued
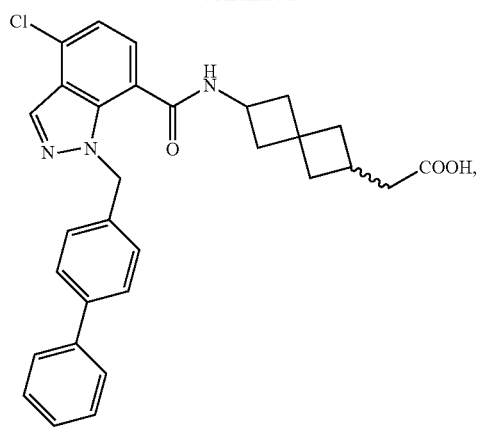
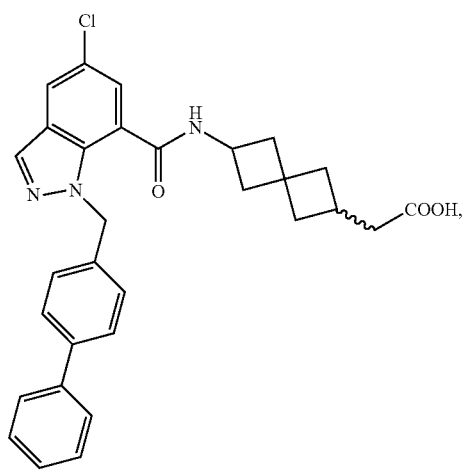
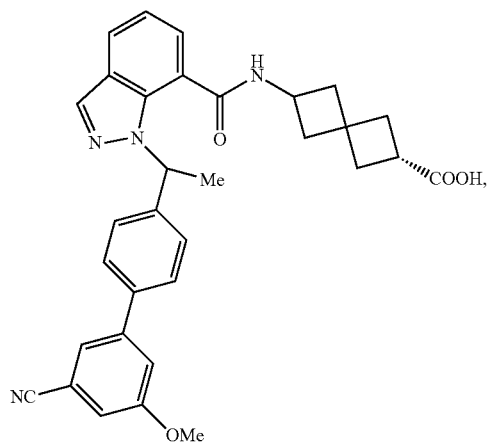
322
-continued
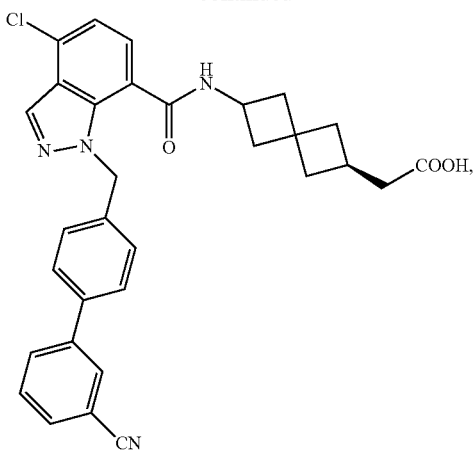
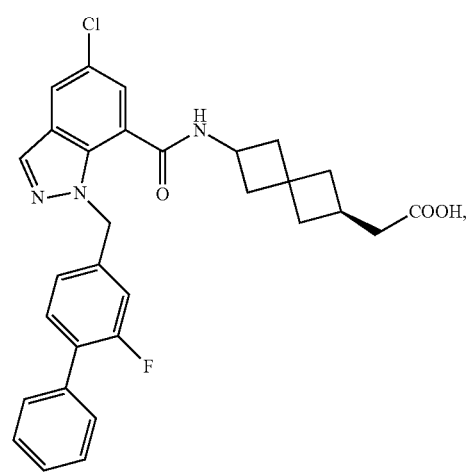
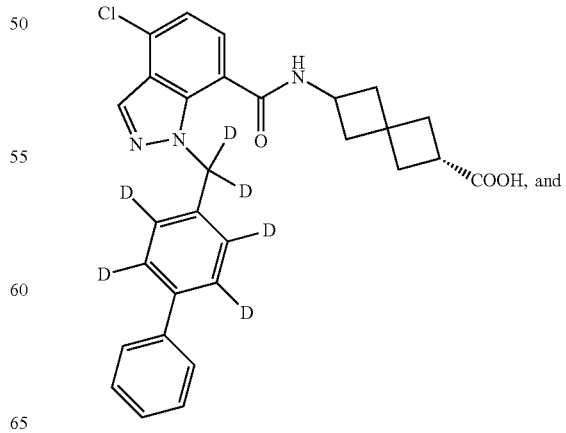

-continued

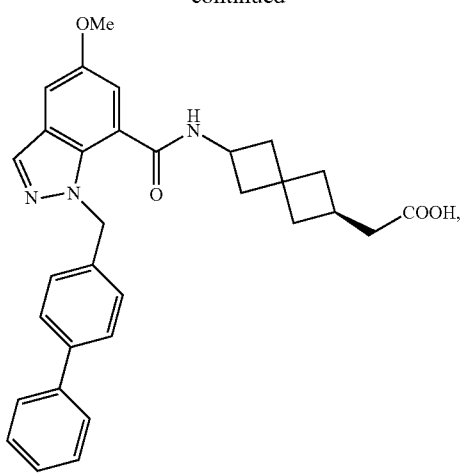

or a pharmaceutically acceptable salt thereof.

2. The method of claim 1, wherein the compound is:

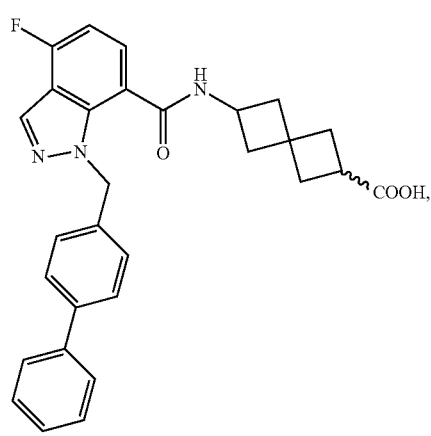 [SMILES: O=C(NC1CC2(C1)CC(C(=O)O)C2)c1ccc(F)c2cnn(Cc3ccc(-c4ccccc4)cc3)c12]

or a pharmaceutically acceptable salt thereof.

3. The method of claim 1, wherein the compound is:

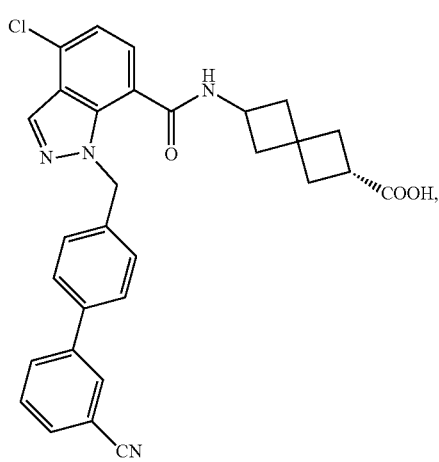

or a pharmaceutically acceptable salt thereof.

4. The method of claim 1, wherein the compound is:

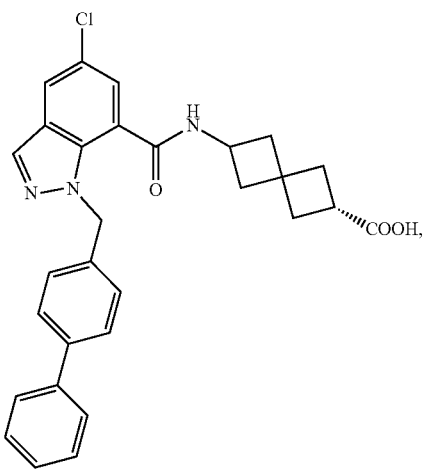

or a pharmaceutically acceptable salt thereof.

5. The method of claim 4, wherein the compound is:

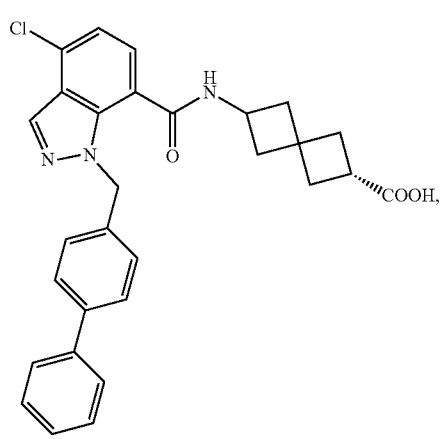

or a pharmaceutically acceptable salt thereof.

6. The method of claim 1, wherein the compound is:

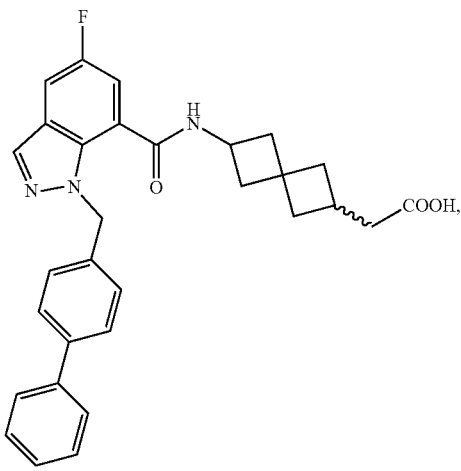 [SMILES: O=C(O)CC1CC2(C1)CC(NC(=O)c1cc(F)cc3cnn(Cc4ccc(-c5ccccc5)cc4)c13)C2]

or a pharmaceutically acceptable salt thereof.

7. The method of claim 1, wherein the compound is:

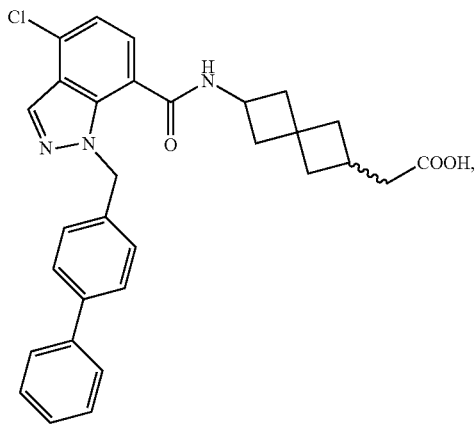 [SMILES: O=C(O)CC1CC2(C1)CC(NC(=O)c1ccc(Cl)c3cnn(Cc4ccc(-c5ccccc5)cc4)c13)C2]

or a pharmaceutically acceptable salt thereof.

8. The method of claim 1, wherein the compound is:

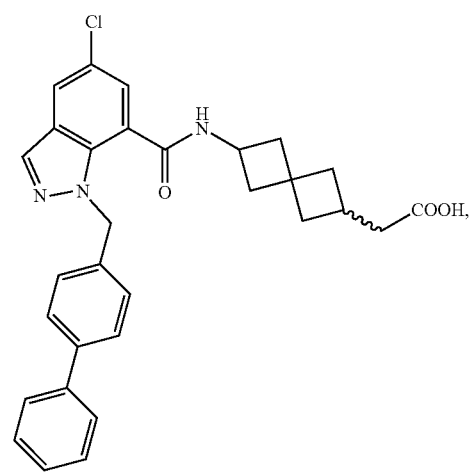 [SMILES: O=C(O)CC1CC2(C1)CC(NC(=O)c1cc(Cl)cc3cnn(Cc4ccc(-c5ccccc5)cc4)c13)C2]

or a pharmaceutically acceptable salt thereof.

9. The method of claim 1, wherein the compound is:

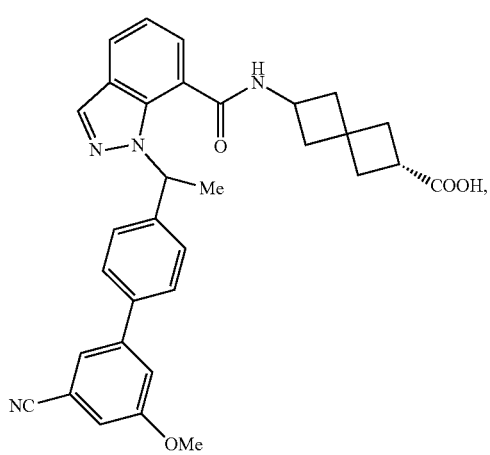

or a pharmaceutically acceptable salt thereof.

10. The method of claim 1, wherein the compound is:

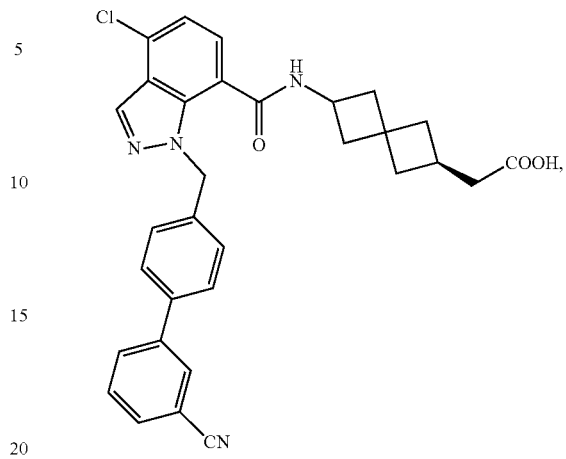

or a pharmaceutically acceptable salt thereof.

11. The method of claim 1, wherein the compound is:

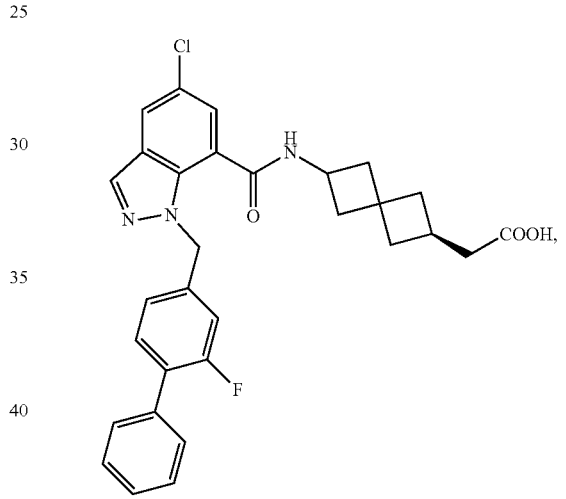

or a pharmaceutically acceptable salt thereof.

12. The method of claim 1, wherein the compound is:

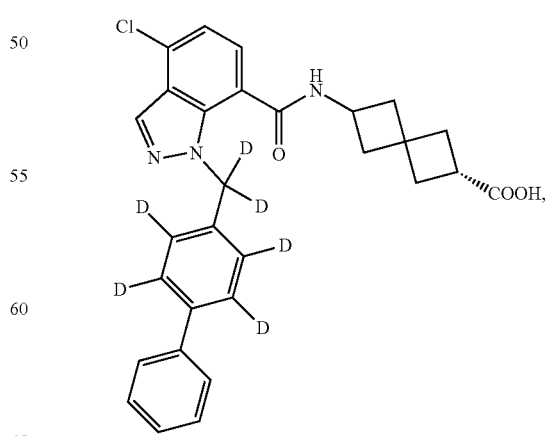

or a pharmaceutically acceptable salt thereof.

13. The method of claim 1, wherein the compound is:

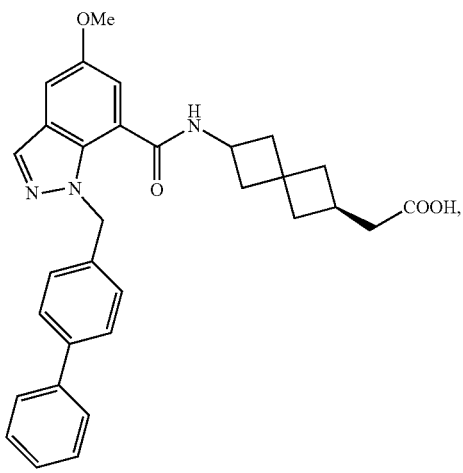

or a pharmaceutically acceptable salt thereof.

14. The method of claim 1, wherein the EP4-mediated cancer is selected from glioblastoma, bone cancer, head and neck cancer, melanoma, basal cell carcinoma, squamous cell carcinoma, adenocarcinoma, oral cancer, esophageal cancer, gastric cancer, intestinal cancer, colon cancer, bladder cancer, hepatocellular carcinoma, renal cell carcinoma, pancreatic cancer, ovarian cancer, cervical cancer, lung cancer, breast cancer and prostate cancer.

15. The method of claim 1, wherein the EP4-mediated cancer is selected from colon cancer, bladder cancer, hepatocellular carcinoma, pancreatic cancer, ovarian cancer, cervical cancer, lung cancer, breast cancer, and prostate cancer.

16. The method of claim 1, wherein the EP4-mediated cancer selected from colorectal cancer (CRC), lung cancer, squamous cell carcinoma of the head and neck (SCCHN), bladder cancer, endometrial cancer, and gastric cancer.

17. The method of claim 1, wherein the EP4-mediated cancer is colorectal cancer (CRC).

18. The method of claim 1, wherein the EP4-mediated cancer is endometrial cancer.

* * * * *